United States Patent
Gabant et al.

(10) Patent No.: US 11,932,672 B2
(45) Date of Patent: Mar. 19, 2024

(54) FERMENTATION PROCESS

(71) Applicants: Syngulon S.A., Seraing (BE); Université Libre de Bruxelles, Brussels (BE)

(72) Inventors: Philippe Gabant, Ottignies Louvain-la-Neuve (BE); Mohamed El Bakkoury, Brussels (BE); Laurence Van Melderen, Waterloo (BE)

(73) Assignees: Syngulon S.A., Seraing (BE); Université Libre de Bruxelles, Brussels (BE)

( * ) Notice: Subject to any disclaimer, the term of this patent is extended or adjusted under 35 U.S.C. 154(b) by 401 days.

(21) Appl. No.: 16/955,720

(22) PCT Filed: Dec. 19, 2018

(86) PCT No.: PCT/EP2018/085941
§ 371 (c)(1),
(2) Date: Jun. 18, 2020

(87) PCT Pub. No.: WO2019/121983
PCT Pub. Date: Jun. 27, 2019

(65) Prior Publication Data
US 2021/0070812 A1    Mar. 11, 2021

(30) Foreign Application Priority Data
Dec. 19, 2017   (EP) .................................... 17208600

(51) Int. Cl.
*C07K 14/245* (2006.01)
*C12N 15/113* (2010.01)
*C12N 15/70* (2006.01)

(52) U.S. Cl.
CPC .......... *C07K 14/245* (2013.01); *C12N 15/113* (2013.01); *C12N 15/70* (2013.01); *C12N 2800/101* (2013.01); *C12N 2800/204* (2013.01)

(58) Field of Classification Search
CPC .... C07K 14/245; C12N 15/113; C12N 15/70; C12N 2800/101; C12N 2800/204
See application file for complete search history.

(56) References Cited

U.S. PATENT DOCUMENTS

| | | | |
|---|---|---|---|
| 5,300,431 A | 4/1994 | Pierce et al. | |
| 5,549,895 A | 8/1996 | Lyon et al. | |
| 5,631,153 A | 5/1997 | Capecchi | |
| 5,670,370 A | 9/1997 | Molin et al. | |
| 5,855,732 A | 1/1999 | Yoshida | |
| 5,888,732 A | 3/1999 | Hartley et al. | |
| 5,910,438 A | 6/1999 | Bernard et al. | |
| 5,922,583 A | 7/1999 | Morsey | |
| 6,143,557 A | 11/2000 | Hartley et al. | |
| 6,171,861 B1 | 1/2001 | Hartley et al. | |
| 6,180,407 B1 | 1/2001 | Bernard et al. | |
| 6,270,969 B1 | 8/2001 | Hartley et al. | |
| 6,271,359 B1 | 8/2001 | Norris et al. | |
| 6,528,285 B1 | 3/2003 | Biet et al. | |
| 7,176,029 B2 | 2/2007 | Bernard et al. | |
| 7,183,097 B1 | 2/2007 | Gerdes et al. | |
| 7,595,185 B2 | 9/2009 | Gerdes et al. | |
| 7,595,186 B2 | 9/2009 | Gerdes et al. | |
| 8,318,497 B2 | 11/2012 | Szpirer et al. | |
| 8,470,580 B2 | 6/2013 | Gabant et al. | |
| 8,476,048 B2 | 7/2013 | Caimi et al. | |
| 8,697,426 B2 | 4/2014 | Leana et al. | |
| 8,877,504 B2 | 11/2014 | Gabant et al. | |
| 9,333,227 B2 | 5/2016 | Gabant | |
| 10,188,114 B2 | 1/2019 | Gabant | |
| 11,427,800 B2 | 8/2022 | Gabant | |
| 11,492,651 B2 | 11/2022 | Gabant | |
| 2004/0115811 A1 | 6/2004 | Gabant | |
| 2005/0130308 A1 | 6/2005 | Bernard | |
| 2005/0260585 A1 | 11/2005 | Szpirer | |
| 2010/0330041 A1 | 12/2010 | Bayrock | |
| 2013/0115658 A1 | 5/2013 | Szpirer et al. | |
| 2013/0280810 A1 | 10/2013 | Gabant et al. | |
| 2014/0148379 A1 | 5/2014 | Liu et al. | |
| 2014/0178956 A1 | 6/2014 | Leana et al. | |
| 2015/0050253 A1 | 2/2015 | Gabant | |
| 2021/0238645 A1 | 8/2021 | Gabant | |
| 2022/0017573 A1 | 1/2022 | Mignolet et al. | |
| 2023/0193191 A1 | 6/2023 | Gabant | |

FOREIGN PATENT DOCUMENTS

| | | |
|---|---|---|
| DE | 10038573 | 2/2002 |
| EP | 1 111 061 | 6/2001 |
| EP | 2 543 255 | 1/2013 |
| JP | H05-56790 | 3/1993 |
| JP | 2014-502501 | 2/2014 |

(Continued)

OTHER PUBLICATIONS

International Search Report and Written Opinion dated Mar. 11, 2019 in International Application No. PCT/EP2018/085941.
Duquesne et al., Microcins, Gene-Encoded Antibacterial Peptides From Enterobacteria, The Journal Of The Royal Society Of Chemistry, vol. 24, pp. 708-734, 2007.
Takala et al., A Food-Grade Cloning Vector For Lactic Acid Bacteria Based On The Nisin Immunity Gene nisI, Appl Microbiology Biotechnology, vol. 59, pp. 467-471, 2002.
Fang et al., Use of mchI Encoding Immunity to the antimicrobial peptide microcin H47 as a Plasmid Selection Marker in Attenuated Bacterial Live Vectors, Infection and Immunity, vol. 76, No. 10, pp. 4422-4430, 2008.

(Continued)

*Primary Examiner* — Iqbal H Chowdhury
(74) *Attorney, Agent, or Firm* — KNOBBE, MARTENS, OLSON & BEAR, LLP

(57) ABSTRACT

Some embodiments relate to a method for producing a product of interest with a microbial host using an auto-replicative extra-chromosomal nucleic acid molecule comprising a first nucleic acid sequence whose genetic activity confers an advantage to the host, optionally wherein the genetic activity of said first nucleic acid molecule is controlled.

17 Claims, 11 Drawing Sheets

Specification includes a Sequence Listing.

(56) References Cited

FOREIGN PATENT DOCUMENTS

| | | |
|---|---|---|
| WO | WO 94/03616 | 2/1994 |
| WO | WO 97/13401 | 4/1997 |
| WO | WO 97/14805 | 4/1997 |
| WO | WO 99/02555 | 1/1999 |
| WO | WO 99/21977 | 5/1999 |
| WO | WO 99/58652 | 11/1999 |
| WO | WO 01/31039 | 5/2001 |
| WO | WO 01/42509 | 6/2001 |
| WO | WO 01/46444 | 6/2001 |
| WO | WO 02/12474 | 2/2002 |
| WO | WO 02/66657 | 8/2002 |
| WO | WO 2004/022745 | 3/2004 |
| WO | WO 2009/011940 | 1/2009 |
| WO | WO 2009/011940 A2 | 1/2009 |
| WO | WO 2010/060057 | 5/2010 |
| WO | WO 2019/046577 | 3/2019 |
| WO | WO 2019/121983 | 6/2019 |
| WO | WO 2019/236761 | 12/2019 |
| WO | WO 2022/104320 | 11/2021 |
| WO | WO 2022/104321 | 11/2021 |

OTHER PUBLICATIONS

Brede et al., Identification Of The Propionicin F Bacteriocin Immunity Gene (Pcfi) And Development Of A Food0Grade Cloning System For Propionibacterium Freudenreichii, Applied And Environmental Microbiology, vol. 73, No. 23, pp. 7542-7547, 2007.
Allison et al., Functional analysis of the Gene Encoding Immunity to Lactacin F, lafi, and its use as a Lactobacillus-Specific, Food-Grade Genetic Marker, Applied and Environmental Microbiology, vol. 62, No. 12, pp. 4450-4460, 1996.
(1992) Journal of Cellular Biochemistry, Keystone Symposia on Molecular & Cellular Biology, 104.
Abremski, et al. (1984) Bacteriophage P1 Site-specific Recombination. J. Bio. I. Chem. 259(3):1509-1514.
Acuna, et al., FEBS Open Bio, 2: 12-19, 2012.
Adetunji and Olaoye, Malaysian Journal of Microbiology 9: 130-13, 2013.
Aizenman, et al. (1996) An *Escherichia coli* chromosomal "addiction module" regulated by 3', 5'-bispyroohosohate: A modayk for programmed bacterial cell death. Proc. Nail. Acad. Sci. 93:6059-6063.
Altschul, S.F., et al., "Basic local alignment search tool", J. Mol. Biol. 215:403-410, 1990.
Backman, et al., (1983), "Tetracycline Resistance Determined by pBR322 is Mediated by one Polypeptide." Gene 26. pp. 197-203.
Bacteriocin, Wikipedia, http://en.wikpedia.org/wiki/Bacteriocin Printed on Oct. 3, 2014.
Bahassi, et al. (1995) F plasmid CcdB killer protein: ccd8 gene mutants coding for non-cylotoxic proteins which retain their regulatory functions. Molecular Microbiology 15(6\:1031-1037.
Basanta, A. et al. Developement of Bacteriocinogenic Strains of *Saccharomyces cerevisiae* Heterologously Expressing and Secreting the Leaderless Enterocin L50 Peptides L50A and L50B froln Enterococcz1s faeciurn L50, Applied And Environmental Microbiology, vol. 75, No. 8 p. 2382-2392, 200.
Baum, "Tn5401, a New Class II Transposable Element from Bacillus thuringiensis," Journal of Bacteriology, vol. 176. No. 10, May 1994, pp. 2835-2845.
Baunonis, et al. (1993) Genomic Targeting with Purified Cre Recombinase. Nucleic Acids Research 21 (9):2025-2029.
Bech et al., "Sequence of the reLB transcription unit from *Escherichia coli* and Identification of the reLB gene," The EMBO Journal, vol. 4, No. 4 00.1059-1066 1985.
Bernard (1996) Positive Selection of Recombinant DNA by CcdB. BioTechniques 21(2)320-323.
Bernard et al., 1992 "Cell killing, by the F plasmid CcdB protein involves poisoning of DNA-topoisomerase II complexes," J. Mol. Biol. 226:735-745.

Bernard, et al. (1991) The 41 carboxy-terminal residues of the miniF plasmid CcdA protein are sufficient to antagonize the killer activity of the CcdB protein. Mol. Gen Genet 226:297-304.
Bernard, P., et al. (1994) Positive-Selection Vectors Using the F Plasmid cedB Killer Gene. Gene 148, pp. 71-74.
Bex, et al. (1983) Mini-F encoded proteins: identification of a new 10.5 kilodalton species. The EMBO Journal,2(11):1853-1861.
Biswas, et al. (1993) High-Efficiency Gene Inactivation and Replacement System for Gram-Positive Bacteria. J. Bacteriology 175(11):3628-3635.
Bochner, et al. (1980) Positive Selection for loss of Tetracycline Resistance. J. Bacteriology 143(2):923-933.
Borrero J. et al., Cloning, Production, and Functional Expression of the Bacteriodn Enterocin A, Produced by Enterococcus faecium 'TI 36, by the Yeasts *Pichia pastoris*, *Kluyveromyces lactis*, *Flansenula polyn1orpha*, and *Arxula adeninivorans*, Applied and Environmental Mkrobiology, vol. 78, No. 16, p. 5956-5961, 2012.
Boyd (1993) Turbo Cloning: A Fast, Efficient Method for Cloning PCR Products and Other Blunt-Ended DNA Fragments into Plasmids. Nucleic Acids Research 21(4):817-821.
Bravo, et al. (1988) Killing of *Escherichia coli* cells modulated by components of the stability system ParD of plasmid R1. Mol. Gen. Genet. 215:146-151.
Bubeck, et al. (1993) Rapid Cloning by Homologous Recombination in vivo. Nucleic Acids Research 21(15):3601-3602.
Bult, "Complete Genome Sequence of the Methanogenic Archaeon, *Methanococcus jannaschii*," Science, vol. 273 Aug. 23, 1996.00. 1058-1073.
Burns, et al. (1984) Positive Selection Vectors: A Small Plasmid Vector Useful for the Direct Selection of Sau2A-aenerated overlapping DNA Fragments. Gene 27:323-325.
Campelo et al., "A bacteriocin gene cluster able to enhance plasmid maintenance in Lactococcus lactis", Microbial Cell Factories 2014, 13:77. Accessible on the world wide web at www.microbialcellfactories.com/content/13/1/77. 9 oaqes.
Cole et al., "Deciphering the Biology of *Mycobacterium tuberculosis* from the Complete Genome Sequence," Nature vol. 393, Jun. 11, 1998 Do.537-544.
Cotter, P. D. et al., "Bacteriocins-a viable alternative to antibiotics", Nature Reviews Microbiology 11:95-105, 2013.
Couturier, et al. (1998) Bacterial death by DNA gyrase poisoning. Trends in Microbiology 6(7):269-275.
Craine, (1982) Novel Selection for Tetracycline-or Chloramphenicol-Sensitive *Escherichia coli*. J. Bacteriology 151(1):487-490.
Cui et al., "Class IIa Bacteriocins: Diversity and New Developments", Int. J. Mol. Sci., vol. 13, pp. 16668-16707, 2012.
D'Souza, S.F., "Microbial biosensors", Biosensors & Bioelectronics, vol. 16, 2001, pp. 337-353.
Daw et al., "Bacteriocins: Nature, Function and Structure", Micron, vol. 27, No. 6, pp. 467-479, 1996.
Ebert et al. "A Moloney MLV-Rat Somatotropin Fusion Gene Produces Biologically Active Somatotropin in a transgenic pig." Molecular Endocrinology. 2:277-283, 1988.
Fleischmann et al., "Whole-Genome Random Sequencing and Assembly of Haemophilus Influenza Rd," Science, Vo1.269. 00.496-512 Jul. 28, 1995.
Gabant et al., 1997 "Bifunctional lacZ a-ccdB genes for selective cloning of PCR products," Biotechniques 23:938-941.
Gabant et al., 1998 "Direct selection cloning vectors adapted to the genetic analysis of gram-negative bacteria and their plasmids," Gene 207:87-92.
Gabant et al., 2000 "New positive selection system based on the parD (kislkid) system of the R1 plasmid," Biotechniques 28:784-788.
Gabant et al., 2001 "Use of poison/antidote systems for selective cloning," in Plasmid Biology 2000: International, Symposium on Molecular Bioloy of Bacterial Plasmids, Meeting Abstracts, 00.135-170, Plasmid 45:160-161.
Gajic et al., "Novel Mechanism of Bacteriocin Secretion and Immunity Carried Out by Lactococcal Multidrug Resistance Proteins*", The Journal of Biological Chemistry, Sep. 5, 2003, vol. 278, No. 36, DD. 34291-34298.

(56) References Cited

OTHER PUBLICATIONS

Gerard et al., Bactericidal Activity of Colicin V Is Mediated by an Inner Membrane Protein, SdaC, of *Escherichia coli*, Journal Of Bacteriology, vol. 187, No. 6, pp. 1945-1950, Mar. 2005.

Gerdes (2000) Toxin-Antitoxin modules may regulate synthesis of macromolecules during nutritional stress. Journal of Bacteriology 182:561-572.

Gerdes, et al. "RNA antitoxins." (2007) Current Opinion in Microbiology, vol. 10, p. 117-124.

Gibson et al., "Creation of a Bacterial Cell Controlled by a Chemically Synthesized Genome", Science, vol. 329, pp. 52-56, 2010.

Goni-Moreno, et al., "Multicellular Computing Using Conjugation for Wiring", PLoS One 8(6): e65986, 2013.

Gossen, J. A., et al. (1992) Application of Galactose-Sensitive *E.coli* Strains as Selective Hosts for LacZ Plasmids. Nucleic Acids Res. 20.0.3254.

Gotfredsen, et al., "The *Escherichia coli* relBE genes belong to a new toxin-antitoxin gene family" Molecular Microbiology (1998) 29(4): 1065-1076.

Green and Sambrook, "Molecular Cloning: a Laboratory Manual", Cold Spring Harbor Laboratory Press; 4th edition, 2012.

Gronenborn (1978) Methylation of single-stranded DNA in vitro introduces new restriction endonuclease cleavage sites. Nature, 272:375-377.

Gronlund et al., "Toxin-Antitoxin Systems Homologous with relBE of *Escherichia coli* Plasmid P307 are Ubiquitous in Prokaryotes," Journal of Molecular Biology, Vol.285, No. 4, Jan. 29, 1999, pp. 1401-1415.

Guilfoyle, R.A., and I.M. Smith (1994) "A Direct Selection Strategy for Stotgun Cloning and Sequencing in the Bacteriophage M13." Nucleic Acids Res.22, pp. 100-107.

Guzman et al. 1995 "Tight regulation, modulation, and high-level expression by vectors containing the arabinose PBAO promoter," J. Bacteriol. 177:4121-4130.

Hammer et al. "Genetic Engineering of Mammalian Embryos." J. Anim. Sci. 63:269-278, 1986.

Hartley et al., DNA cloning using in vitro site-specific recombination: Genome Res. 10:1788-1795, 2000.

Hasan et al., Gene, vol. 56, pp. 145, 1987.

Hebsgaard, S.M., et al. (1996) "Splice Site Prediction in *Arabidopsis thaliana* Pre-mRNA by Combining Local and Global Sequence information." Nucleic Acids Research, 24(17) 3439-3452.

Henrich et al. 1986 "Use of the lysis gene of bacteriophage X174 for the construction of a positive selection vector," Gene 42:345-349.

Herrero, M., et al., (1990) "Transposon Vectors Containing Non-Antibiotic Resistance Selection markers for Cloning and Stable Chromosomal Insertion of Foreign Genes in Gram-Negative Bacteria." J. Bact. 172,11, pp. 6557-6567.

Holt, et al. (1993) A Novel Phage λ Replacement Cre-lox Vector that has Automatic Subcloning Capabilities, Gene 133:95-97.

Inglis, et al., "The Role of Bacteriocins as Selfish Genetic Elements". Biology Letters, Issue 9, vol. Jun. 3, 2013. Published Apr. 24, 2013, DOI: 10.1098/rsbl.2012.1173. 6 pages.

Ioannou, et al. (1994) A new bacteriophage P1-derived vector for the propagation of large human DNA fragments, Nature Genetics 6:84-89.

Jaramillo, A., "Synthetic Biology—Engineered stable ecosystems". Nature Microbiology, vol. 2, No. 17119, pp. 1-2, Jul. 25, 2017.

Jensen et al., 1995 "Comparison of ccd of F, parDE of RP4, and parD of R1 using a novel conditional replication control system of plasmid R1," Molecular Microbiology 17:211-220.

Jensen et al., 1995 Programmed cell death in bacteria: protect plasmid stabilization systems, Molecular Microbiology 17:205-210.

Kaneko et al., "Sequence Analysis of the Genome of the Unicellular Cyanobacterium *synechocystis* sp. Strain PCC6803. II. Sequence Determination of the Entire Genome and Assignment of Potential Protein-Coding Regions " DNA Research, vol. 3, 00.109-136.1996.

Karoui, et al. (1983) Ham22, a mini-F mutation which is lethal to host cell and promotes recA-dependent induction of lambdoid prophage. The EMBO Journal. 2(11): 1863-1868.

Kristoffersen et al. "Bacterial Toxin-Antitoxin Gene Systems as Containment Control in Yeast Cells" Applied and Environmental Microbiology, vol. 66 No. 12, Dec. 2000, p. 5524-5526.

Kuhn et al. 1986 "Positive-selection vectors utilizing lethality of the EcoRI endonuclease," Gene 44:253-263.

Landy, Arthur, 1989 Dynamic, structural, and regulatory aspects of A site-specific recombination: Annu. Rev. Biochem 58:913-949.

Lehnherr, et al. (1993) Plasmid Addiction Genes of Bacteriophage P1: doc, which cause cell death on curing of prophage, and phd, which prevents host death when prophage is retained. J. Mol. Biol. 233:414-428.

LIU (1989) DNA Topoisomerase poisons as antitumor drugs. Annu. Rev. Biochem. 58:351-375.

Maki, et al.(1992) Modulation of DNA Supercoiling Activity of *Escherichia coli* DNA Gyrase by F Plasmid Proteins, The Journal of Biological Chemistry vol. 267(17):12244-12251.

Maloy, et al. (1981) Selection for Loss of Tetracycline Resistance by *Escherichia coli*, Journal of Bacteriology, 145(2):1110-1112.

Manning, P.A., "Nucleotide Sequence encoding the Mannose-fucose-resistant Hemagglutinin of Vibrio Cholerae 01 and Construction of a Mutant," EMBL Sequence Database, Aug. 7, 1993. pp.1-7.

Maxwell, et al. (1986) Mechanistic aspects of DNA Topoisomerases. Advan. Protein Chem. 38:69-107.

McAuliffe et al., "Identification and overexpression of Itnl, a novel gene which confers immunity to the two-component lantibiotic lacticin 3147", Microbiology, 2000, vol. 146, pp. 129-138.

McBride, et al., "Contamination management in Low Cost Open Algae Ponds for Biofuels Production", Industrial Biotechnology, vol. 10, pp. 221-227, 2014.

Messing, et al. (1977) Filamentous coliphage M13 as a cloning vehicle: Insertion of a HindII Fragment of the lac regulatory region in M13 replicative form in vitro. Proc Nail. Acad. Sci. 74(9):3642-3646.

Miki, et al. (1984) Control of Cell Division by Sex Factor F in *Escherichia coli*. J. Mol. Bioi. 174:627-646.

Moreadith et al. "Gene Targeting in Embryonic Stem Cells: The new Physiology and metabolism." J. Mol. Med. 75:208-216 1997.

Mori, Hirotada, et al., "Prophage A Induction Caused by Mini-F Plasmid Genes." (1984) Mol Gen Genet 196:185-193.

Mullins et al. "Perspective Series: Molecular Medicine in Genetically Engineered Animals." J. Clin. Invest. 98 (Suppl.): 837-S40, 1996.

Murphy, et al. (1991), pAZd39: A New Type of cDNA Expression Vector for Low Background, High Efficiency Directional Cloning. Nucleic Acids Research 19(12):3403-3408.

Muyrers et al. 2001 "Techniques: recombinogenic engineering—new 'options for cloning and manipulating DNA," Trends in Biochem. Sci. 26:325-331.

Nilsson, et al. (1983) An Improved Positive Selection Plasmid Vector Constructed by Oligonucleotide Mediated Mutagenesis. Nucleic Acids Research 11 (22):8019-8029.

Nomura M., "Colicins and Related Bacteriocins", Annual Review of Microbiology, vol. 21, pp. 257-284, Oct. 1967.

Norrander, et al. (1983) Construction of improved M13 vectors using oligodeoxynucleotide-directed mutagenesis. Gene 26:101-106.

Ogura, et al. (1983) Mini-F plasmid genes that couple host cell division to plasmid proliferation. Proc. Natl. Acad. Sci. USA 80:4784-4788.

Opinion of the Scientific Panel on Food Additives, Flavourings, Processing Aids and Materials in Contact with Food on a Request from the Commission Related to the use of Nisin (E 234) as a food additive. Question No. EFSA-Q-2005-031. Adopted on Jan. 26, 2006. The EFSA Journal (2006) 314, pp. 1-16.

Pag et al., "Molecular Analysis of Expression of the Lantibiotic Pep5 Immunity Phenotype", Applied and Environmental Microbiology, Feb. 1999, vol. 65, No. 2, pp. 591-598.

Peakman, et al. (1992) Highly Efficient Generation of Recombinant Baculoviruses by Enzymatically Mediated Site-Specific in vitro Recombination. Nucleic Acids Research 20(3):495-500.

(56) References Cited

OTHER PUBLICATIONS

Pecota, et al. "Combining the hok/sok, parDE, and pnd Postsegregational Killer Loci to Enhance Plasmid Stability." (1997) Applied and Environmental Microbiology, vol. 63, p. 1917-1924.
PGT-N28 Vector DNA (catalog #N3728) New England Biolabs Online Catalog, Jun. 2, 1999, p. 1, www.neb.comlneb/products/nucleicJ307-28.html the whole document.
Pierce et al. 1992 "A positive selection vector for cloning high molecular weight DNA by the bacteriophage P1 system: improved cloning efficacy," PNAS USA 89:2056-2060.
PKO Scrambler Series Gene Targeting Vectors for Knockout Mice. Stratagene Online Catalog, Jan. 1998, pp. 1-3; www.stratagene.com/cellbio/toxicology/pko.htm, the whole document.
Pomares et al., "Potential Applicability of Chymotrypsin-Susceptible Microcin J25 Derivatives to Food Preservation", Applied and Environmental Microbiology, vol. 75, No. 17, pp. 5734-5738, Sep. 2009.
Reeves et al., Engineering *Escherichia coli* into a Protein Delivery Systemn for Mammalian Cells ACS Synth. Biol. 2015, 4 ,644-654.
Riley et al., "Bacteriocins: Evolution, Ecology, and Application", Annu. Rev. Microbiol., 2002, vol. 56, pp. 117-137.
Roberts, et al. (1992) Definition of a Minimal Plasmid Stabilization System from the Broad-Host-Range Plasmid RK2. Journal of Bacteriology Dec. 1992:8119-8132.
Roberts, et al. (1994) The parDE operon of the broad-host-range plasmid RK2 specifies growth inhibition associated with plasmid loss. J. Mol. Biol. 18; 237 (1): 35-51.
Roca, et al. (1992) A Hit-and-Run System for Targeted Genetic Manipulations in Yeast. Nucleic Acid Research 20(17):4671-4672.
Ruiz-Echevarria et al. (1991) Structural and functional comparison between the stability systems ParD of plasmid R1 and Ccd of plasmid. F. Mol. Gen. Genet 225:355-362.
Ruiz-Echevarria et al. 1995 A mutation that decreases the efficiency of plasmid R1 replication leads to the activation of parD, a killer stability system of the plasmid: FEMS Microb. Letters 130: 129-136.
Ruiz-Echevarria, et al. (1991) The kis and kid genes of the parD maintenance system of plasmid R1 form an operon that is autoregulated at the level of transcription by the co-ordinated action of the Kis and Kid proteins. Molecular Microbiology 5(11):2685-2693.
Sadler, et al. (1980) Plasmids containing many tandem copies of a synthetic lactose operator. Gene 8:279-300.
Salmon et al., "The Antidote and Autoregulatory Functions of the F Plasmid CcdA Protein: a Genetic and biochemical Survey" Molecular and General Genetics vol. 244, pp. 530-538. 1994.
Sambrook, et al. (1989) Molecular Cloning: A Laboratory Manual. Cold Spring Harbor Laboratory Press, Cold Spring Harbor, NY, pp. 4.12 A.9-A.13.
Saul, et al., "Nucleotide Sequence and Replication Characteristics of RepFIB, a Basic Replicon of IncF Plasmids," Journal of Bacteriology. vol. 171 No. 5 00.2697-2707, May 1989.
Schlieper et al. 1998 "A positive selection vector for cloning of long polymerase chain reaction fragments based on a lethal mutant of the crp gene of *Escherichia coli*," Anal. Biochem. 257:203-209.
Schoeman, H. et al., the Development of Bactericidal Yeast Strains by Expressing the Pediococcus acidilactici Pediocin Gene (pedA) in *Saccharolnyces cerevisiae*, Yeast, vol. 15, 647-656, 1999.
Seamark R.F. "Progress and Emerging Problems in Livestock Transgenesis: a Summary perspective." Repod. Fert. Dev. 6:653-657, 1994.
Shalani and Srivastava (2008) The Internet Journal of Microbiology. vol. 5 No. 2. DOI: 10.5580127dd—accessible on the worldwide web at archive.ispub.comljournallthe-internet-journal-of-microbiology/volume-5-number-2/screening-for-antifungal-activity-of-pseudomonas-fluorescens-against-phytopathogenic-fungi.html#sthash.dOYs03UO.1DKuT1US.dpuf.
Shekh and Roy, BMC Microbiology 12: 132, 2012.
Shenin et al., "Characteristics of Alirin B1, the major component of a fungicidal substance produced by Bacillus subtilis 10-VIZR". Antibiot Khimioter 1995 vol. 50: pp. 3-7.
Sierra et al. 1998 "Functional interactions between chpB and parD, two homologous conditional killer systems found in the *Escherichia coli* chromosome and in plasmid R1," FEMS Microb. Letters 168:51-58.
Simons, R. W., et al. (1987) "Improved Single and Multicopy Lac-Based Cloning Vectors for Protein and Operon Fusions." Gene 53 Do.85-96.
Smith, et al. (1985) Modification and Selection of Human Interleukin 2 Produced in Insect Cells by Baculovirus Expression Vector. Nalt Acad. Sci. 82:8404-8408.
Smith, et al. (1997) The poison-antidote stability system of the broad-host-range Thiobacilus ferroxidans plasmid pTF-FC2. Molecular Microbioloav 26(5):961-970.
Thisted, et al., "Mechanism of Post-segregational Killing by the hok/sok System of Plasmid R1; Sok Antisense RNA Regulates hok Gene Expression Indirectly Through the Overlapping mok Gene." (1992) J. Mol. Biol., vol. 223, p. 41-54.
Tomb et al., "The Complete Genome Sequence of the Gastric Pathogen Helicobacter Pylori," Nature. vol. 388 Aug. 7, 1997 pp. 539-547.
Trudel et al., (1996), pGATA: a positive selection vector based on the toxicity of the transcription factor GATA-1 to bacteria: BioTechniques 20:684-693.
Tsuchimoto et al. (1988) Two Genes, pelK and peml, responsible for stable maintenance of resistance plasmid R100. J. of Bateriol., 170(4):1461-1466.
Tsuchimoto et al., "The Stable Maintenance System pem of Plasmid R100: Degradation of Peml Protein May Allow PemK Protein To Inhibit Cell Growth." Journal of Bacteriology, vol. 174, No. 13, pp. 4205-4211 Jul. 1992.
Tsuchimoto, et al. (1993) Autoregulation by cooperative binding of the Peml and PemK proteins to the promoter region of the pem operon. 237:81-88.
Union Nationale des Groupements de Distillateurs D'Alcool, "Kamoran", 2005.
Van Melderen, et al., "Bacterial Toxin-Antitoxin Systems: More Than Selfish Entities?", PLoS Genetics, vol. 5, No. 3, Mar. 2009, pp. 1-6.
Van Reeth, T., et al. (1998) "Positive Selection Vectors to Generate Fused Genes for the Expression of His-Tagged Proteins." BioTechniques. 25(5):898-904.
Vernet, T., et al. (1985) "A Direct-Selection Vector Derived from pColE3-CA38 and adapted for Foreign Gene Expression." Gene 34:87-93.
Wang et al., Genome Mining Demonstrates the Widespread Occurrence of Gene Clusters Encoding Bacteriocins in Cyanobacteria. PLoS One 6(7): e22384, 2011.
Wang, (1985), DNA Topoisomerases. Ann. Rev. Biochem. 54:665-697.
Wright et al., "Building-in biosafety for synthetic biology", Microbiology, vol. 159, pp. 1221-1235, 2013.
Yanisch-Perron, et al. (1985) Improved M13 phage closing vectors and host strains: Nucleotide sequence of the M13mp18 and DUC19 vectors. Gen, 33:103-119.
Yarmolinsky (1995) Programmed cell death in bacterial populations. Science, 267:836-837.
Yu et al. 2000 "An efficient recombination system for chromosome engineering in *Escherichia coli*," PNAS USA 97:5978-5983.
Zuber, P et al., "Peptide Antibiotics", in Sonenshein ed, "Bacillus subtilis and Other Gram-Positive Bacteria", 1993 American Society for Microbiology, Washington D.C. pp. 897-916.
Office Action with English Translation in Japanese Patent Application No. 2020-535048, dated May 17, 2023 in 19 pages.
Kobayashi, M., et al., Promoter selectivity of *Escherichia coli* RNA polymerase: effect of base substitutions in the promoter-35 region on promoter strength. Nucleic Acids Res. 18:7367-7372, 1990.

FERMENTATION PROCESS

CROSS REFERENCE TO RELATED APPLICATIONS

This application is a U.S. national phase application under 35 U.S.C. § 371 of International Application No. PCT/EP2018/085941, filed on Dec. 19, 2018, which claims the benefit of European Application No. EP17208600, filed Dec. 19, 2017. The content of each of the aforementioned applications is expressly incorporated herein by reference in its entirety.

FIELD

Embodiments herein relate to a method for producing a product of interest with a microbial host using an auto-replicative extra-chromosomal nucleic acid molecule comprising a first nucleic acid sequence whose genetic activity confers an advantage to the host, optionally wherein the genetic activity of said first nucleic acid molecule is controlled.

BACKGROUND

Antibiotics are widely used as selection agents for the production of a product of interest in microbial cells. However, there are several drawbacks associated with the use of antibiotics such as large-scale spreading of antibiotics in the environment. In addition the sequence coding for the resistance of the antibiotic in the DNA constructs represent an energetic burden for the cell and therefore negatively affects the yield of the product. This energetic burden is particularly relevant when the resistance-conferring gene is a large gene, when it is expressed at a high level and/or when it is expressed constitutively.

Therefore, there is still a need for an alternative and even improved method, which does not have all the drawbacks of existing methods.

DESCRIPTION

In a first aspect, there is provided a method for producing a product of interest with a microbial host, said method comprising the steps of:
  a) Providing the microbial host comprising an auto-replicative extra-chromosomal nucleic acid molecule comprising a first nucleic acid sequence, optionally wherein the genetic activity of said first nucleic acid sequence is controlled;
  b) Optionally said auto-replicative extra-chromosomal nucleic acid molecule comprises a second nucleic acid sequence that is involved in the production of said product of interest, wherein the genetic activity of said second nucleic acid sequence is controlled independently from the first sequence;
  c) Culturing said microbial host under conditions allowing said microbial host to express the first nucleic acid sequence to a given level to maintain the auto-replicative extra-chromosomal molecule into the growing microbial population and simultaneously genetically controlling the second sequence coding for said product of interest.

Step a)

Step a) comprises providing a microbial host comprising an auto-replicative extra-chromosomal nucleic acid molecule comprising a first nucleic acid sequence whose genetic activity confers an advantage to the host, optionally wherein the genetic activity of said first nucleic acid sequence is controlled. The auto-replicative extra-chromosomal nucleic acid molecule can be provided in a microbial host (e.g., a microbial cell as described herein). For example, the host or a predecessor of the host may have been previously transformed with the auto-replicative extra-chromosomal nucleic acid molecule. As such, in some embodiments, step a) comprises providing a microbial cell host comprising an auto-replicative extra-chromosomal nucleic acid molecule comprising a first nucleic acid sequence whose genetic activity confers an advantage to the host, optionally wherein the genetic activity of said first nucleic acid sequence is controlled.

Optional Transforming Step

In some embodiments, the microbial host is transformed with the auto-replicative extra-chromosomal nucleic acid molecule under conditions allowing only host that has received said auto-replicative extra-chromosomal nucleic acid molecule to survive, thus providing a microbial host comprising an auto-replicative extra-chromosomal nucleic acid molecule. As such, in some embodiments, the method further comprises transforming the microbial host with said auto-replicative extra-chromosomal nucleic acid molecule prior to or during step a) under conditions allowing only host that has received said auto-replicative extra-chromosomal nucleic acid molecule to survive, thus providing the microbial host comprising the auto-replicative extra-chromosomal nucleic acid molecule.

The auto-replicative extra-chromosomal nucleic acid molecule transformed into the microbial host optionally comprises the second nucleic acid sequence of step b). The microbial host comprising the auto-replicative extra-chromosomal nucleic acid molecule can subsequently be cultured according to step c).

Within the context of methods, uses, compositions, hosts, and nucleic acids of embodiments herein, an auto-replicative extra-chromosomal nucleic acid molecule comprising a first nucleic acid sequence is provided. An auto-replicative extra-chromosomal nucleic acid molecule can exist free of the genome and may be derived from or comprise, consist essentially of, or consist of a plasmid, or episome, minichromosome, or alike. This feature is attractive as a higher number (from one to hundreds of copies or from 10 to 50 copies depending on the plasmid used) of copies of such nucleic acid molecule can be introduced and maintained into the microbial cell host. In addition, any host can be used in the methods of embodiments herein. In some embodiments, there is no need to modify the genome of the host. The genetic elements needed to carry out the methods of embodiments herein are present in the auto-replicative extra-chromosomal nucleic acid molecule. Such an auto-replicative extra-chromosomal nucleic acid molecule usually comprises an origin of replication, a first nucleic acid sequence which is of interest and a regulatory region. In some embodiments, without being limited by theory, a first nucleic acid sequence encoding an immunity modulator acts as a selectable marker to maintain the presence and function of the auto-replicative extra-chromosomal nucleic acid in the host cell. In some embodiments, the first nucleic acid sequence encoding the immunity modulator maintains the presence of the auto-replicative extra-chromosomal nucleic acid so that a product can be produced. The product can alter the environment in which the host is present, for example by fermenting a substance in the environment to produce one or more new substances. In some embodiments, genetic drift is minimized by providing selective pressure against auto-replicative extra-chromosomal nucleic acids that have acquired mutations, and do not produce a functional immunity modulator, produce an immunity modulator with reduced function, and/or produced lower levels of immunity modulator than an auto-replicative extra-chromosomal nucleic acid that has not acquired the mutation(s).

Within the context of methods, uses compositions, hosts, and nucleic acids of embodiments herein, the first nucleic acid molecule represented by the first nucleic acid sequence is able to exhibit a genetic activity, said genetic activity confering an selective advantage to the microbial host cell wherein it is present and wherein this genetic activity is expressed. This genetic activity is provided by the product encoded by the first nucleic acid molecule. Moreover this genetic activity can be controlled or is expressed constitutively at a low level or is tunable or is under the control of a weak constitutive promoter. The control of said activity is believed to provide an advantage to limit the burden of energy for the host. Similarly, an advantage to limit the energy burden of the host may be obtained when the genetic activity is expressed constitutively at a low level or is tunable or is under the control of a weak constitutive promoter. Throughout the application text, the concept "conferring an advantage" may be replaced by "conferring immunity to a bacteriocin" or "conferring resistance to a bacteriocin". In some embodiments, the first nucleic acid sequence encodes an immunity modulator as described herein, and thereby confers an advantage to the host.

A second nucleic acid sequence encodes directly or indirectly for a product of interest. The same description holds for the genetic activity of the second nucleic acid molecule described herein. In some embodiments, the product of interest comprises an enzyme that is useful in an industrial process, for example a fermentation process. The fermentation process can ferment at least one compound in the culture medium. In some embodiments, the product of interest comprises an industrially useful molecule, for example a carbohydrate, a lipid, an organic molecule, a nutrient, a fertilizer, a biofuel, a cosmetic (or precursor thereof), a pharmaceutical or biopharmaceutical product (or precursor thereof), or two or more of any of the listed items.

Within the context of methods, uses, compositions, hosts, and nucleic acids of embodiments herein, a genetic activity may mean any activity that is caused by or linked with the presence of the first nucleic acid molecule in a microbial host. The advantage of said activity may be the ability to survive or survive and grow under given conditions (pH, temperature, presence of a given molecule such as a bacteriocin or combination of two or more bacteriocins as described herein, . . . ). Accordingly the advantage of said activity may be assessed by determining the number of microbial cells/hosts comprising the auto-replicative extra-chromosomal nucleic acid molecule. The assessment may be carried out at the end of and/or during the optional transforming step (but prior to culturing step c), or prior to steps a) and culturing step c)) and/or prior to culturing step c). In an embodiment, the number of microbial host cells comprising the auto-replicative extra-chromosomal nucleic acid molecule present has not been decreased and may be increased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more compared to the number of initial microbial cells/host when the cells are being cultured under conditions allowing the microbial host that has received said auto-replicative extra-chromosomal nucleic acid molecule to survive (e.g., by possessing immunity to one or more bacteriocins as described herein, and which are present in the given conditions). This assessment step may have a duration of at least 6 hours, 12 hours, 24 hours, 36 hours, 48 hours, 60 hours, 72 hours, 84 hours, 96 hours, 108 hours, 120 hours or more, including ranges between any two of the listed values.

Within the context of methods, uses, compositions, hosts, and nucleic acids of embodiments herein, the control of a genetic activity may mean either an increase or decrease of activity of a nucleic acid molecule (i.e. first and/or second nucleic acid molecule). Accordingly, the control of a genetic activity can be controlled or is expressed constitutively at a low level or is tunable or is under the control of a weak constitutive promoter. In some embodiments, the coding product for which genetic activity is regulated/controlled comprises, consists essentially of, or consists of an immunity modulator or is involved in the production of a product of interest. In some embodiments, genetic activity is regulated/controlled at the level of gene expression. In some embodiments, genetic activity is regulated at the transcriptional level, for example by activating or repressing a promoter. In some embodiments, promoters in this context are inducible promoters. In some embodiments, promoters in this context are weak promoters. Without being limited by theory, weak promoters of some embodiments can be amendable to up- or down-regulating the level of transcription so that the advantage conferred to the host (e g immunity modulator activity) is sensitive to changes in levels and/or activity of the gene product(s) under the control of the promoter. In some embodiments, the promoter comprises, consists of, or consists essentially of the P24 promoter represented by SEQ ID NO:707 and/or the ProC promoter represented by SEQ ID NO: 708 and/or the P24 LacO hybrid promoter. The P24LacO hybrid promoter is a tunable/controlled promoter. In some embodiments, gene activity is regulated/controlled at the post-transcriptional level, for example through regulation of RNA stability. In some embodiments, genetic activity is regulated/controlled at the translational level, for example through regulation of initiation of translation. In some embodiments, genetic activity is regulated/controlled at the post-translational level, for example through regulation of polypeptide stability, post-translational modifications to the polypeptide, or binding of an inhibitor to the polypeptide.

In some embodiments, genetic activity is increased. In some embodiments, activity of at least one of an immunity modulator and/or the coding product of the second nucleic acid molecule is involved in the production of a product of interest is increased. Conceptually, genetic activity can be increased by directly activating genetic activity, or by decreasing the activity of an inhibitor of genetic activity. In some embodiments, genetic activity is activated by at least one of: inducing promoter activity, inhibiting a transcriptional repressor, increasing RNA stability, inhibiting a post-transcriptional inhibitor (for example, inhibiting a ribozyme or antisense oligonucleotide), inducing translation (for example, via a regulatable tRNA), making a desired post-translational modification, or inhibiting a post-translational inhibitor (for example a protease directed to a polypeptide encoded by the gene). In some embodiments, a compound present in a desired environment induces a promoter. For example, the presence of iron in culture medium can induce transcription by an iron-sensitive promoter as described herein. In some embodiments, a compound present in a desired culture medium inhibits a transcriptional repressor. For example, the presence of tetracycline in an environment can inhibit the tet repressor, and thus allow activity from the tetO promoter. In some embodiments, a compound found only outside of a desired culture medium induces transcription.

In some embodiments, genetic activity is decreased. Conceptually, genetic activity can be decreased by directly inhibiting genetic activity, or by decreasing the activity of an activator of genetic activity. In some embodiments, genetic activity is reduced, but some level of activity remains. In some embodiments, genetic activity is fully inhibited. In some embodiments, genetic activity is decreased by at least one of inhibiting promoter activity, activating a transcriptional repressor, decreasing RNA stability, activating a post-transcriptional inhibitor (for example, expressing a ribozyme or antisense oligonucleotide), inhibiting translation (for example, via a regulatable tRNA), failing to make a required post-translational modification, inactivating a polypeptide (for example by binding an inhibitor or via a polypeptide-specific protease), or failing to properly localize a polypeptide. In some embodiments, genetic activity is decreased by removing a gene from a desired location, for example by excising a gene using a FLP-FRT or cre-lox cassette, homologous recombination or CRIPR-CAS9 activity or through loss or degradation of a plasmid. In some embodiments, a gene product (e.g. a polypeptide) or a product produced by a gene product (e.g. the product of an enzymatic reaction) inhibits further gene activity (e.g. a negative feedback loop).

In some embodiments, the advantage conferred to a microbial host by the genetic activity of the first nucleic acid molecule is the ability to survive or survive and grow in a medium comprising a bacteriocin (or a mix of bacteriocins). As used herein, "bacteriocin" encompasses a cell-free or chemically synthesized version of such a polypeptide. A "bacteriocin," and variations of this root term, may also refer to a polypeptide that had been secreted by a host cell. A bacteriocin therefore encompasses a proteinaceous toxin produced by bacteria to inhibit the growth of similar or closely related bacterial strain(s). They are similar to yeast and paramecium killing factors, and are structurally, functionally, and ecologically diverse. A bacteriocin also encompasses a synthetic variant of a bacteriocin secreted by a host cell. Synthetic variant of a bacteriocin may be derived from the bacteriocin secreted by a host cell in any way as long as the synthetic variant still exhibits at least 10%, 20%, 30%, 40%, 50%, 60%, 70%, 80%, 901© of the activity of the corresponding bacteriocin secreted by a host cell A detailed description of an antibiotic is provided in the part dedicated to general descriptions at the end of the specification.

A "bacteriocin" can neutralize at least one cell other than the individual host cell in which the polypeptide is made, including cells clonally related to the host cell and other microbial cells.

A cell that expresses a particular "immunity modulator" (discussed in more detail herein) is immune to the neutralizing effects of a particular bacteriocin or group of bacteriocins. As such, bacteriocins can neutralize a cell producing the bacteriocin and/or other microbial cells, so long as these cells do not produce an appropriate immunity modulator. As such, a bacteriocin can exert cytotoxic or growth-inhibiting effects on a plurality of other microbial organisms. In an embodiment, a bacteriocin is produced by the translational machinery (e.g. a ribosome, etc.) of a microbial cell. In another embodiment, a bacteriocin is chemically synthesized. Some bacteriocins can be derived from a polypeptide precursor. The polypeptide precursor can undergo cleavage (for example processing by a protease) to yield the polypeptide of the bacteriocin itself. As such, in some embodiments, a bacteriocin is produced from a precursor polypeptide. In some embodiments, a bacteriocin comprises, consists essentially of, or consists of a polypeptide that has undergone post-translational modifications, for example cleavage, or the addition of one or more functional groups.

Neutralizing activity of bacteriocins can include arrest of microbial reproduction, or cytotoxicity. Some bacteriocins have cytotoxic activity (e.g. "bacteriocide" effects), and thus can kill microbial organisms, for example bacteria, yeast, algae, synthetic micoorganisms, and the like. Some bacteriocins can inhibit the reproduction of microbial organisms (e.g. "bacteriostatic" effects), for example bacteria, yeast, algae, synthetic micoorganisms, and the like, for example by arresting the cell cycle.

A number of bacteriocins have been identified and characterized (see tables 1.1 and 1.2.). Without being limited by any particular theory, exemplary bacteriocins can be classified as "class I" bacteriocins, which typically undergo post-translational modification, and "class II" bacteriocins, which are typically unmodified. Additionally, exemplary bacteriocins in each class can be categorized into various subgroups, as summarized in Table 1.1, which is adapted from Cotter, P. D. et al. "Bacteriocins—a viable alternative to antibiotics" Nature Reviews Microbiology 11: 95-105, hereby incorporated by reference in its entirety.

Without being limited by any particular theory, bacteriocins can effect neutralization of a target microbial cell in a variety of ways. For example, a bacteriocin can permeabilize a cell wall, thus depolarizing the cell wall and interfering with respiration. Table 1.1: Classification of Exemplary Bacteriocins.

TABLE 1.1

| Group | Distinctive feature | Examples |
|---|---|---|
| Classification of Exemplary Bacteriocins | | |
| Class I (typically modified) | | |
| MccC7-C51-type bacteriocins | Is covalently attached to a carboxy-terminal aspartic acid | MccC7-051 |
| Lasso peptides | Have a lasso structure | MccJ25 |
| Linear azole- or azoline-containing peptides | Possess heterocycles but not other modifications | MccB17 |
| Lantibiotics | Possess lanthionine bridges | Nisin, planosporicin, mersacidin, actagardine, mutacin 1140 |
| Linaridins | Have a linear structure and contain dehydrated amino acids | Cypemycin |

TABLE 1.1-continued

Classification of Exemplary Bacteriocins

| Group | Distinctive feature | Examples |
|---|---|---|
| Proteusins | Contain multiple hydroxylations, epimerizations and methylations | Polytheonamide A |
| Sactibiotics | Contain sulphur-α-carbon linkages | Subtilosin A, thuricin CD |
| Patellamide-like cyanobactins | Possess heterocycles and undergo macrocyclization | Patellamide A |
| Anacyclamide-like cyanobactins | Cyclic peptides consisting of proteinogenic amino acids with prenyl attachments | Anacyclamide A10 |
| Thiopeptides | Contain a central pyridine, dihydropyridine or piperidine ring as well as heterocycles | Thiostrepton, nocathiacin I, GE2270 A, philipimycin |
| Bottromycins | Contain macrocyclic amidine, a decarboxylated carboxy-terminal thiazole and carbon-methylated amino acids | Bottromycin A2 |
| Glycocins | Contain S-linked glycopeptides | Sublancin 168 |
| Class II (typically unmodified or cyclic) | | |
| IIa peptides (pediocin PA-1-like bacteriocins) | Possess a conserved YGNGV motif (in which N represents any amino acid) | Pediocin PA-1, enterocin CRL35, carnobacteriocin BM1 |
| IIb peptides | Two unmodified peptides are required for activity | ABP118, lactacin F |
| IIc peptides | Cyclic peptides | Enterocin AS-48 |
| IId peptides | Unmodified, linear, non-pediocin-like, single-peptide bacteriocins | MccV, MccS, epidermicin NI01, lactococcin A |
| IIe peptides | Contain a serine-rich carboxy-terminal region with a non-ribosomal siderophore-type modification | MccE492, MccM |

A number of bacteriocins can be used in accordance with embodiments herein. Exemplary bacteriocins are shown in Table 1.2. In some embodiments, at least one bacteriocin comprising, consisting essentially of, or consisting of a polypeptide sequence of Table 1.2 is provided. As shown in Table 1.2, some bacteriocins function as pairs of molecules. As such, it will be understood that unless explicity stated otherwise, when a functional "bacteriocin" or "providing a bacteriocin," or the like is discussed herein, functional bacteriocin pairs are included along with bacteriocins that function individually. With reference to Table 1.2, "organisms of origin" listed in parentheses indicate alternative names and/or strain information for organisms known to produce the indicated bacteriocin.

Embodiments herein also include peptides and proteins with identity to bacteriocins described in Table 1.2. The term "identity" is meant to include nucleic acid or protein sequence homology or three-dimensional homology. Several techniques exist to determine nucleic acid or polypeptide sequence homology and/or three-dimensional homology to polypeptides. These methods are routinely employed to discover the extent of identity that one sequence, domain, or model has to a target sequence, domain, or model. A vast range of functional bacteriocins can incorporate features of bacteriocins disclosed herein, thus providing for a vast degree of identity to the bacteriocins in Table 1.2. In some embodiments, a bacteriocin has at least 50% identity, for example, at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of the polypeptides of Table 1.2. Percent identity may be determined using the BLAST software (Altschul, S. F., et al. (1990) "Basic local alignment search tool." J. Mol. Biol. 215:403-410, accessible on the world wide web at blast.ncbi.nlm.nih.gov) with the default parameters.

While the bacteriocins in Table 1.2 are naturally-occurring, the skilled artisan will appreciate that variants of the bacteriocins of Table 1.2, naturally-occurring bacteriocins other than the bacteriocins of Table 1.2 or variants thereof, or synthetic bacteriocins can be used according to some embodiments herein. In some embodiments, such variants have enhanced or decreased levels of cytotoxic or growth inhibition activity on the same or a different microorganism or species of microorganism relative to the wild type protein. Several motifs have been recognized as characteristic of bacteriocins. For example, the motif YGXGV (SEQ ID NO: 2), wherein X is any amino acid residue, is a N-terminal consensus sequence characteristic of class IIa bacteriocins. Accordingly, in some embodiments, a synthetic bacteriocin comprises an N-terminal sequence with at least 50% identity to SEQ ID NO: 2, for example at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2. In some embodiments, a synthetic bacteriocin comprises a N-terminal sequence comprising SEQ ID NO: 2. Additionally, some class IIb bacteriocins comprise a GxxxG motif (x means any amino acid). Without being limited by any particular theory, it is believed that the GxxxG motif can mediate association between helical proteins in the cell membrane, for example to facilitate bacteriocin-mediated neutralization through cell membrane interactions. As such, in some embodiments, the bacteriocin comprises a motif that facilitates interactions with the cell membrane. In some embodiments, the bacteriocin comprises a GxxxG motif. Optionally, the bacteriocin comprising a GxxxG motif can comprise a helical structure. In addition to structures described herein, "bacteriocin" as used herein also encompasses structures that have substantially the same effect on microbial cells as any of the bacteriocins explicitly provided herein.

It has been shown that fusion polypeptides comprising, consisting essentially of, or consisting of two or more bacteriocins or portions thereof can have neutralizing activity against a broader range of microbial organisms than either individual bacteriocin. For example, it has been shown that a hybrid bacteriocin, Ent35-MccV (GKYYGNGVSCNKKGCSVDWGRAIGIIGNNSAANLATGGAAGWKSGGGASGR DIAMAIGTLSGQFVAGGIGAAAGGVAGGAIYDYASTHKPNPAMSPSGLGGTIK QKPEGIPSE AWNYAAGRLCNWSPNNLSDVCL, SEQ ID NO: 3), displays antimicrobial activity against pathogenic Gram-positive and Gram-negative bacteria (Acuna et al. (2012), FEBS Open Bio, 2: 12-19). It is noted that that Ent35-MccV fusion bacteriocin comprises, from N-terminus to C-terminus, an N-terminal glycine, Enterocin CRL35, a linker comprising three glycines, and a C-terminal Microcin V. It is contemplated herein that bacteriocins can comprise fusions of two or more polypeptides having bacteriocin activity. In some embodiments, a fusion polypeptide of two or more bacteriocins is provided. In some embodiments, the two or more bacteriocins comprise, consist essentially of, or consist of polypeptides from Table 1.2, or modifications thereof. In some embodiments, the fusion polypeptide comprising of two or more bacteriocins has a broader spectrum of activity than either individual bacteriocin, for example having neutralizing activity against more microbial organisms, neutralizing activity under a broader range of environmental conditions, and/or a higher efficiency of neutralization activity. In some embodiments, a fusion of two or more bacteriocins is provided, for example two, three, four, five, six, seven, eight, nine, or ten bacteriocins. In some embodiments, two or more bacteriocin polypeptides are fused to each other via a covalent bond, for example a peptide linkage. In some embodiments, a linker is positioned between the two bacteriocin polypeptides. In some embodiments, the linker comprises, consists essentially of, or consists of one or more glycines, for example about 1, 2, 3, 4, 5, 6, 7, 8, 9, 10, 11, 12, 13, 14, 15, 16, 17, 18, 19, or 20 glycines. In some embodiments, the linker is cleaved within the cell to produce the individual bacteriocins included in the fusion protein. In some embodiments, a bacteriocin as provided herein is modified to provide a desired spectrum of activity relative to the unmodified bacteriocin. For example, the modified bacteriocin may have enhanced or decreased activity against the same organisms as the unmodified bacteriocin. Alternatively, the modified bacteriocin may have enhanced activity against an organism against which the unmodified bacteriocin has less activity or no activity.

TABLE 1.2

Exemplary Bacteriocins

| Polypeptide SEQ ID NO: | Name | Class | Organism of origin | Polynucleotide SEQ ID NO: |
|---|---|---|---|---|
| 4 | Acidocin 8912 | Unclassified | *Lactobacillus acidophilus* | 5 |
| 6 | Acidocin A | class IIA/YGNGV | *Lactobacillus acidophilus* | 7 |
| 8 | Acidocin B (AcdB) | Unclassified | *Lactobacillus acidophilus* | 9 |
| 10 | Acidocin LF221B (Gassericin K7 B) | Unclassified | *Lactobacillus gasseri* | 11 |
| 12 | Aureocin A53 | Unclassified | *Staphylococcus aureus* | 13 |
| 14 | Avicin A | class IIA/YGNGV | *Enterococcus avium* (*Streptococcus avium*) | 15 |
| 16 | Bacteriocin 31 | Unclassified | *Enterococcus faecalis* (*Streptococcus faecalis*) | 17 |
| 18 | Bacteriocin J46 | Unclassified | *Lactococcus lactis* | 19 |
| 20 | Bacteriocin T8 | class IIa | *Enterococcus faecium* (*Streptococcus faecium*) | 21 |
| 22 | Boticin B | Unclassified | *Clostridium botulinum* | 23 |
| 24 | Bovicin HJ50 | Lantibiotic | *Streptococcus equinus* (*Streptococcus bovis*) | 25 |
| 26 | Brochocin-c | Unclassified | *Brochothrix campestris* | 27 |
| 28 | Butyrivibriocin AR10 | Unclassified | *Butyrivibrio fibrisolvens* | 29 |
| 30 | Butyrivibriocin OR79 | Lantibiotic | *Butyrivibrio fibrisolvens* | 31 |
| 32 | Carnobacteriocin B2 (Carnocin CP52) | class IIA/YGNGV | *Carnobacterium maltaromaticum* (*Carnobacterium piscicola*) | 33 |
| 34 | Carnobacteriocin BM1 (Carnobacteriocin B1) | class IIA/YGNGV | *Carnobacterium maltaromaticum* (*Carnobacterium piscicola*) | 35 |
| 36 | Carnobacteriocin-A (Piscicolin-61) | class IIc, non subgrouped bacteriocins (problematic) | *Carnobacterium maltaromaticum* (*Carnobacterium piscicola*) | 37 |
| 38 | Carnocyclin-A | Unclassified | *Carnobacterium maltaromaticum* (*Carnobacterium piscicola*) | 39 |

TABLE 1.2-continued

Exemplary Bacteriocins

| Polypeptide SEQ ID NO: | Name | Class | Organism of origin | Polynucleotide SEQ ID NO: |
|---|---|---|---|---|
| 40 | Carocin D | Unclassified | *Pectobacterium carotovorum* subsp. *carotovorum* (*Erwinia carotovora* subsp. *carotovora*) | 41 |
| 42 | Cerein 7B | Unclassified | *Bacillus cereus* | 43 |
| 44 | Cinnamycin (Lanthiopeptin) | Lantibiotic | *Streptoverticillium griseoverticillatum* | 45 |
| 46 | Circularin A | Unclassified | *Geobacillus kaustophilus* (strain HTA426) | 47 |
| 48 | Closticin 574 | Unclassified | *Clostridium tyrobutyricum* | 49 |
| 50 | Coagulin A | Unclassified | *Bacillus coagulans* | 51 |
| 52 | Colicin-10 | Unclassified | *Escherichia coli* | 53 |
| 54 | Colicin-E1 | Unclassified | *Escherichia coli* | 55 |
| 56 | Colicin-Ia | Unclassified | *Escherichia coli* | 57 |
| 58 | Colicin-Ib | Unclassified | *Escherichia coli* | 59 |
| 60 | Colicin-M | Unclassified | *Escherichia coli* | 61 |
| 62 | Colicin-N | Unclassified | *Escherichia coli* | 63 |
| 64 | Colicin-V (Microcin-V) | Unclassified | *Escherichia coli* | 65 |
| 66 | Columbicin A | Lantibiotic | *Enterococcus columbae* | 69 |
| 68 | Curvacin-A | class IIA/YGNGV | *Lactobacillus curvatus* | 69 |
| 70 | Cypemycin | Unclassified | *Streptomyces* sp. | 71 |
| 72 | Cytolysin | Lantibiotic | *Bacillus halodurans* (strain ATCC BAA-125/DSM 18197/FERM 7344/JCM 9153/C-125) | 73 |
| 74 | Divercin V41 | class IIa/YGNGV | *Carnobacterium divergens* (*Lactobacillus divergens*) | 75 |
| 76 | Divergicin 750 | Unclassified | *Carnobacterium divergens* (*Lactobacillus divergens*) | 77 |
| 78 | Divergicin A | Class IIc | *Carnobacterium divergens* (*Lactobacillus divergens*) | 79 |
| 80 | Durancin Q | Unclassified | *Enterococcus durans* | 81 |
| 82 | Durancin TW-49M | Unclassified | *Enterococcus durans* | 83 |
| 84 | Dysgalacticin | Unclassified | *Streptococcus dysgalactiae* subsp. *equisimilis* (*Streptococcus equisimilis*) | 85 |
| 86 | Enterocin 1071A | Unclassified | *Enterococcus faecalis* (*Streptococcus faecalis*) | 87 |
| 88 | Enterocin 7A (Enterocin L50A) | bacteriocins without sequence leader | *Enterococcus faecalis* (*Streptococcus faecalis*) | 89 |
| 90 | Enterocin 7B | Unclassified | *Enterococcus faecalis* (*Streptococcus faecalis*) | 91 |
| 92 | Enterocin 96 | Class II | *Enterococcus faecalis* (strain ATCC 700802/V583) | 93 |
| 94 | Enterocin A | Class IIa, IIc (problematic) | *Enterococcus faecium* (*Streptococcus faecium*) | 95 |
| 96 | Enterocin AS-48 (BACTERIOCIN AS-48) | Unclassified | *Enterococcus faecalis* (*Streptococcus faecalis*) | 97 |
| 98 | Enterocin B | class IIc, non subgrouped bacteriocins (problematic) | *Enterococcus faecium* (*Streptococcus faecium*) | 99 |
| 100 | Enterocin CRL35 (Mundticin KS) | Class IIa | *Enterococcus mundtii* | 101 |
| 102 | Enterocin EJ97 | Unclassified | *Enterococcus faecalis* (*Streptococcus faecalis*) | 103 |
| 104 | Enterocin P | Class IIa, IIb and IIc (problematic) | *Enterococcus faecium* (*Streptococcus faecium*) | 105 |
| 106 | Enterocin Q | Class IIc | *Enterococcus faecium* (*Streptococcus faecium*) | 107 |
| 108 | Enterocin SE-K4 | Class IIa | *Enterococcus faecalis* (*Streptococcus faecalis*) | 109 |
| 110 | Enterocin W alfa | Class IIb | *Enterococcus faecalis* (*Streptococcus faecalis*) | 111 |
| 112 | Enterocin W beta | Class IIb | *Enterococcus faecalis* (*Streptococcus faecalis*) | 113 |
| 114 | Enterocin Xalpha | Class IIb | *Enterococcus faecium* (*Streptococcus faecium*) | 115 |

TABLE 1.2-continued

Exemplary Bacteriocins

| Polypeptide SEQ ID NO: | Name | Class | Organism of origin | Polynucleotide SEQ ID NO: |
|---|---|---|---|---|
| 116 | Enterocin Xbeta | Class IIb | *Enterococcus faecium* (*Streptococcus faecium*) | 117 |
| 118 | Enterolysin A | class III | *Enterococcus faecalis* (*Streptococcus faecalis*) | 119 |
| 120 | Epicidin 280 | Lantibiotic | *Staphylococcus epidermidis* | 121 |
| 122 | Epidermicin NI01 | Unclassified | *Staphylococcus epidermidis* | 123 |
| 124 | Epidermin | Lantibiotic | *Staphylococcus epidermidis* | 125 |
| 126 | Epilancin K7 | Lantibiotic | *Staphylococcus epidermidis* | 127 |
| 128 | Gallidermin | Lantibiotic | *Staphylococcus gallinarum* | 129 |
| 130 | Garvicin A | IId | *Lactococcus garvieae* | 131 |
| 132 | Garvicin ML | Unclassified | *Lactococcus garvieae* | 133 |
| 134 | Gassericin A | Unclassified | *Lactobacillus gasseri* | 135 |
| 136 | Gassericin T (gassericin K7 B) | Unclassified | *Lactobacillus gasseri* | 137 |
| 138 | Glycocin F | Unclassified | *Lactobacillus plantarum* | 139 |
| 140 | Halocin H4 | Unclassified | *Haloferax mediterranei* (strain ATCC 33500/DSM 1411/JCM 8866/NBRC 14739/NCIMB 2177/R-4) (*Halobacterium mediterranei*) | 141 |
| 142 | Halocin-S8 | Unclassified | *Haloarchaeon* S8a | 143 |
| 144 | Helveticin-J | Unclassified | *Lactobacillus helveticus* (*Lactobacillus suntoryeus*) | 145 |
| 146 | Hiracin JM79 | Class II sec-dependent | *Enterococcus hirae* | 147 |
| 148 | Lactacin-F (lafA) | class IIB | *Lactobacillus johnsonii* (strain CNCM I-12250/La1/NCC 533) | 149 |
| 150 | Lactacin-F (lafX) | class IIB | *Lactobacillus johnsonii* (strain CNCM I-12250/La1/NCC 533) | 151 |
| 152 | Lacticin 3147 A1 | Lantibiotic | *Lactococcus lactis* subsp. *lactis* (*Streptococcus lactis*) | 153 |
| 154 | Lacticin 3147 A2 | Lantibiotic | *Lactococcus lactis* subsp. *lactis* (*Streptococcus lactis*) | 155 |
| 156 | Lacticin 481 (Lactococcin DR) | Lantibiotic | *Lactococcus lactis* subsp. *lactis* (*Streptococcus lactis*) | 157 |
| 158 | Lacticin Q | Unclassified | *Lactococcus lactis* | 159 |
| 160 | Lacticin Z | Unclassified | *Lactococcus lactis* | 161 |
| 162 | Lactobin-A (Amylovorin-L471) | class IIB | *Lactobacillus amylovorus* | 163 |
| 164 | Lactocin-S | Lantibiotic | *Lactobacillus sakei* L45 | 165 |
| 166 | Lactococcin 972 | Unclassified | *Lactococcus lactis* subsp. *lactis* (*Streptococcus lactis*) | 167 |
| 168 | Lactococcin-A | Unclassified | *Lactococcus lactis* subsp. *cremoris* (*Streptococcus cremoris*) | 169 |
| 170 | Lactococcin-B | Unclassified | *Lactococcus lactis* subsp. *cremoris* (*Streptococcus cremoris*) | 171 |
| 172 | Lactocyclicin Q | Unclassified | *Lactococcus* sp. QU 12 | 173 |
| 174 | Laterosporulin | Unclassified | *Brevibacillus* sp. GI-9 | 175 |
| 176 | Leucocin N | Class IId | *Leuconostoc pseudomesenteroides* | 177 |
| 178 | Leucocin Q | Class IId | *Leuconostoc pseudomesenteroides* | 179 |
| 180 | Leucocin-A (Leucocin A-UAL 187) | class IIA/YGNGV | *Leuconostoc gelidum* | 181 |
| 182 | Leucocin-B (Leucocin B-Ta11a) | class IIA/YGNGV | *Leuconostoc carnosum* | 183 |
| 184 | Leucocyclicin Q | Unclassified | *Leuconostoc mesenteroides* | 185 |
| 186 | Lichenicidin A1 | Lantibiotic (two-peptide) | *Bacillus licheniformis* (strain DSM 13/ATCC 14580) | 187 |
| 188 | Linocin M18 | Unclassified | *Brevibacterium linens* | 189 |
| 190 | Listeriocin 743A | Class IIa | *Listeria innocua* | 191 |
| 192 | Mersacidin | Lantibiotic, type B | *Bacillus* sp. (strain HIL-Y85/54728) | 193 |
| 194 | Mesentericin Y105 | class IIA/YGNGV | *Leuconostoc mesenteroides* | 195 |
| 196 | Michiganin-A | Lantibiotic | *Clavibacter michiganensis* subsp. *michiganensis* | 197 |

TABLE 1.2-continued

Exemplary Bacteriocins

| Polypeptide SEQ ID NO: | Name | Class | Organism of origin | Polynucleotide SEQ ID NO: |
|---|---|---|---|---|
| 198 | Microcin B17 (MccB17) | Unclassified | *Escherichia coli* | 199 |
| 200 | Microcin C7 | Unclassified | *Escherichia coli* | 201 |
| 202 | Microcin E492 | Unclassified | *Klebsiella pneumoniae* | 203 |
| 204 | Microcin H47 | Unclassified | *Escherichia coli* | 205 |
| 206 | Microcin J25 | Unclassified | *Escherichia coli* | 207 |
| 208 | Microcin-24 | Unclassified | *Escherichia coli* | 209 |
| 210 | Mundticin KS | Unclassified | *Enterococcus mundtii* | 211 |
| 212 | Mundticin L | class IIA/YGNGV | *Enterococcus mundtii* | 213 |
| 214 | Mutacin 1140 (Mutacin III) | Lantibiotic | *Streptococcus mutans* | 215 |
| 216 | Mutacin-2 | Lantibiotic | *Streptococcus mutans* | 217 |
| 218 | Nisin A | Lantibiotic | *Lactococcus lactis* subsp. *lactis* (*Streptococcus lactis*) | 219 |
| 220 | Nisin F | Lantibiotic | *Lactococcus lactis* | 221 |
| 222 | Nisin Q | Lantibiotic | *Lactococcus lactis* | 223 |
| 224 | Nisin U | Lantibiotic | *Streptococcus uberis* | 225 |
| 226 | Nisin Z | Lantibiotic | *Lactococcus lactis* subsp. *lactis* (*Streptococcus lactis*) | 227 |
| 228 | Nukacin ISK-1 | Lantibiotic | *Staphylococcus warneri* | 229 |
| 230 | Paenicidin A | Lantibiotic | *Paenibacillus polymyxa* (*Bacillus polymyxa*) | 231 |
| 232 | Pediocin PA-1 (Pediocin ACH) | class IIA/YGNGV | *Pediococcus acidilactici* | 233 |
| 234 | Penocin A | class IIA/YGNGV | *Pediococcus pentosaceus* (strain ATCC 25745/183-1w) | 235 |
| 236 | Pep5 | Lantibiotic | *Staphylococcus epidermidis* | 237 |
| 238 | Piscicolin 126 | class IIA/YGNGV | *Carnobacterium maltaromaticum* (*Carnobacterium piscicola*) | 239 |
| 240 | Plantaricin 1.25 β | Unclassified | *Lactobacillus plantarum* | 241 |
| 242 | Plantaricin 423 | class IIa | *Lactobacillus plantarum* | 243 |
| 244 | Plantaricin ASM1 | Unclassified | *Lactobacillus plantarum* | 245 |
| 246 | Plantaricin E | Unclassified | *Lactobacillus plantarum* | 247 |
| 248 | Plantaricin F | Class IIb | *Lactobacillus plantarum* | 249 |
| 250 | Plantaricin J | Class IIb | *Lactobacillus plantarum* | 251 |
| 252 | Plantaricin K | Unclassified | *Lactobacillus plantarum* | 253 |
| 254 | Plantaricin NC8 α | Unclassified | *Lactobacillus plantarum* | 255 |
| 256 | Plantaricin NC8 β | Unclassified | *Lactobacillus plantarum* | 257 |
| 258 | Plantaricin S α | Unclassified | *Lactobacillus plantarum* | 259 |
| 260 | Plantaricin S β | Unclassified | *Lactobacillus plantarum* | 261 |
| 262 | Plantaricin W α | Lantibiotic (two-peptide) | *Lactobacillus plantarum* | 263 |
| 264 | Plantaricin W β | Lantibiotic (two-peptide) | *Lactobacillus plantarum* | 265 |
| 266 | Plantaricin-A | Unclassified | *Lactobacillus plantarum* (strain ATCC BAA-793/NCIMB 8826/WCFS1) | 267 |
| 268 | Propionicin SM1 | Unclassified | *Propionibacterium jensenii* | 269 |
| 270 | Propionicin T1 | Unclassified | *Propionibacterium thoenii* | 271 |
| 272 | Propionicin-F | Unclassified | *Propionibacterium freudenreichii* subsp. *freudenreichii* | 273 |
| 274 | Pyocin S1 | Unclassified | *Pseudomonas aeruginosa* | 275 |
| 276 | Pyocin S2 | colicin/pyosin nuclease family | *Pseudomonas aeruginosa* (strain ATCC 15692/PAO1/1C/PRS 101/LMG 12228) | 277 |
| 278 | Ruminococcin-A | Lantibiotic | *Ruminococcus gnavus* | 279 |
| 280 | Sakacin G | Class IIa | *Lactobacillus sakei* | 281 |
| 282 | Sakacin-A | class IIA/YGNGV | *Lactobacillus sakei* | 283 |
| 284 | Sakacin-P (Sakacin 674) | class IIA/YGNGV | *Lactobacillus sakei* | 285 |
| 286 | Salivaricin 9 | lantibiotic | *Streptococcus salivarius* | 287 |
| 288 | Salivaricin A | Lantibiotic | *Streptococcus pyogenes* serotype M28 (strain MGAS6180) | 289 |
| 290 | Salivaricin A3 | Lantibiotic | *Streptococcus salivarius* | 291 |
| 292 | Salivaricin-A sa | Lantibiotic | *Streptococcus salivarius* | 293 |
| 294 | Staphylococcin C55 alpha | Lantibiotic (two-peptide) | *Staphylococcus aureus* | 295 |
| 296 | Staphylococcin C55 beta | Lantibiotic (two-peptide) | *Staphylococcus aureus* | 297 |

TABLE 1.2-continued

Exemplary Bacteriocins

| Polypeptide SEQ ID NO: | Name | Class | Organism of origin | Polynucleotide SEQ ID NO: |
|---|---|---|---|---|
| 298 | Streptin | lantibiotic | *Streptococcus pyogenes* | 299 |
| 300 | Streptococcin A-FF22 | Lantibiotic | *Streptococcus pyogenes* | 301 |
| 302 | Streptococcin A-M49 | Lantibiotic | *Streptococcus pyogenes* serotype M49 | 303 |
| 304 | Sublancin 168 | Lantibiotic | *Bacillus subtilis* (strain 168) | 305 |
| 306 | Subtilin | Lantibiotic | *Bacillus subtilis* | 307 |
| 308 | Subtilosin | Unclassified | *Bacillus subtilis* (strain 168) | 309 |
| 310 | Subtilosin-A | Unclassified | *Bacillus subtilis* (strain 168) | 311 |
| 312 | Thermophilin 1277 | Lantibiotic | *Streptococcus thermophilus* | 313 |
| 314 | Thermophilin 13 | Unclassified | *Streptococcus thermophilus* | 315 |
| 316 | Thermophilin A | Unclassified | *Streptococcus thermophilus* | 317 |
| 318 | Thiocillin (Micrococcin P1) (Micrococcin P2) (Thiocillin I) (Thiocillin II) (Thiocillin III) (Thiocillin IV) (Antibiotic YM-266183) (Antibiotic YM-266184) | Unclassified | *Bacillus cereus* (strain ATCC 14579/DSM 31) | 319 |
| 320 | Thuricin CD alpha | two-peptide lantibiotic | *Bacillus cereus* 95/8201 | 321 |
| 322 | Thuricin CD beta | two-peptide lantibiotic | *Bacillus cereus* 95/8201 | 323 |
| 324 | Thuricin-17 | Class IId | *Bacillus thuringiensis* | 325 |
| 326 | Trifolitoxin | Unclassified | *Rhizobium leguminosarum* bv. *trifolii* | 327 |
| 328 | Ubericin A | Class IIa | *Streptococcus uberis* | 329 |
| 330 | Uberoly sin | Unclassified | *Streptococcus uberis* | 331 |
| 332 | UviB | Unclassified | *Clostridium perfringens* | 333 |
| 334 | Variacin | Lantibiotic, Type A | *Micrococcus varians* | 335 |
| 336 | Zoocin A | Unclassified | *Streptococcus equi* subsp. *zooepidemicus* | 337 |
| 338 | Fulvocin-C | Unclassified | *Myxococcus fulvus* | 339 |
| 340 | Duramycin-C | Lantibiotic | *Streptomyces griseoluteus* | 341 |
| 342 | Duramycin (duramycin-B) (Leucopeptin) | Lantibiotic B | *Streptoverticillium griseoverticillatum* | 343 |
| 344 | Carnocin UI49 | lantibiotic | *Carnobacterium* sp. (strain UI49) | 345 |
| 346 | Lactococcin-G α | Unclassified | *Lactococcus lactis* subsp. *lactis* (*Streptococcus lactis*) | 347 |
| 348 | Lactococcin-G β | Unclassified | *Lactococcus lactis* subsp. *lactis* (*Streptococcus lactis*) | 349 |
| 350 | Ancovenin | Lantibiotic | *Streptomyces* sp. (strain A647P-2) | 351 |
| 352 | Actagardine (Gardimycin) | Lantibiotic | *Actinoplanes liguriae* | 353 |
| 354 | Curvaticin FS47 | Unclassified | *Lactobacillus curvatus* | 355 |
| 356 | Bavaricin-MN | class IIA/YGNGV | *Lactobacillus sakei* | 357 |
| 358 | Mutacin B-Ny266 | Lantibiotic | *Streptococcus mutans* | 359 |
| 360 | Mundticin | class IIA/YGNGV | *Enterococcus mundtii* | 361 |
| 362 | Bavaricin-A | class IIA/YGNGV | *Lactobacillus sakei* | 363 |
| 364 | Lactocin-705 | Class IIb | *Lactobacillus paracasei* | 365 |
| 366 | Leucocin-B | Unclassified | *Leuconostoc mesenteroides* | 367 |
| 368 | Leucocin C | class IIA/YGNGV | *Leuconostoc mesenteroides* | 369 |
| 370 | LCI | Unclassified | *Bacillus subtilis* | 371 |
| 372 | Lichenin | Unclassified | *Bacillus licheniformis* | 373 |
| 374 | Lactococcin MMFII | class IIA/YGNGV | *Lactococcus lactis* subsp. *lactis* (*Streptococcus lactis*) | 375 |
| 376 | Serracin-P | Phage-Tail-Like | *Serratia plymuthica* | 377 |
| 378 | Halocin-C8 | Unclassified | *Halobacterium* sp. (strain A57092) | 379 |
| 380 | Subpeptin JM4-B | Unclassified | *Bacillus subtilis* | 381 |
| 382 | Curvalicin-28a | Unclassified | *Lactobacillus curvatus* | 383 |
| 384 | Curvalicin-28b | Unclassified | *Lactobacillus curvatus* | 385 |
| 386 | Curvalicin-28c | Unclassified | *Lactobacillus curvatus* | 387 |
| 388 | Thuricin-S | Unclassified | *Bacillus thuringiensis* subsp. *entomocidus* | 389 |

TABLE 1.2-continued

Exemplary Bacteriocins

| Polypeptide SEQ ID NO: | Name | Class | Organism of origin | Polynucleotide SEQ ID NO: |
|---|---|---|---|---|
| 390 | Curvaticin L442 | Unclassified | *Lactobacillus curvatus* | 391 |
| 392 | Divergicin M35 | class IIa/YGNGV | *Carnobacterium divergens* (*Lactobacillus divergens*) | 393 |
| 394 | Enterocin E-760 | class IIb | *Enterococcus* sp. | 395 |
| 396 | Bacteriocin E50-52 | Unclassified | *Enterococcus faecium* (*Streptococcus faecium*) | 397 |
| 398 | Paenibacillin | Unclassified | *Paenibacillus polymyxa* (*Bacillus polymyxa*) | 399 |
| 400 | Epilancin 15x | Unclassified | *Staphylococcus epidermidis* | 401 |
| 402 | Enterocin-HF | class IIa | *Enterococcus faecium* (*Streptococcus faecium*) | 403 |
| 404 | Bacillocin 602 | Class IIa | *Paenibacillus polymyxa* (*Bacillus polymyxa*) | 405 |
| 406 | Bacillocin 1580 | Class IIa | *Bacillus circulans* | 407 |
| 408 | Bacillocin B37 | Unclassified | *Paenibacillus polymyxa* (*Bacillus polymyxa*) | 409 |
| 410 | Rhamnosin A | Unclassified | *Lactobacillus rhamnosus* | 411 |
| 412 | Lichenicidin A2 | Lantibiotic (two-peptide) | *Bacillus licheniformis* (strain DSM 13/ATCC 14580) | 413 |
| 414 | Plantaricin C19 | Class IIa | *Lactobacillus plantarum* | 415 |
| 416 | Acidocin J1132 β | Class IIb | *Lactobacillus acidophilus* | 417 |
| 418 | factor with anti-*Candida* activity | Unclassified | *Enterococcus faecalis* | 419 |
| 420 | Ava_1098 (putative heterocyst differentiation protein) | Unclassified | *Anabaena variabilis* ATCC 29413 | 421 |
| 422 | alr2818 (putative heterocyst differentiation protein) | Unclassified | *Nostoc* sp 7120 | 423 |
| 424 | Aazo_0724 (putative heterocyst differentiation protein) | Unclassified | *Nostoc azollae* 0708 | 425 |
| 426 | AM1_4010 (putative heterocyst differentiation protein) | Unclassified | *Acaryochloris marina* MBIC11017 | 427 |
| 428 | PCC8801_3266 (putative heterocyst differentiation protein) | Unclassified | *Cyanothece* PCC 8801 | 429 |
| 430 | Cyan8802_2855 (putative heterocyst differentiation protein) | Unclassified | *Cyanothece* PCC 8802 | 431 |
| 432 | PCC7424_3517 | Unclassified | *Cyanothece* PCC 7424 | 433 |
| 434 | cce_2677(putative HetP protein) | Unclassified | *Cyanothece* ATCC 51142 | 435 |
| 436 | CY0110_11572 (putative heterocyst differentiation protein) | Unclassified | *Cyanothece* CCY0110 | 437 |
| 438 | MC7420_4637 | Unclassified | *Microcoleus chthonoplastes* PCC 7420 | 439 |
| 440 | asr1611 (putative DUF37 family protein) | Unclassified | *Nostoc* sp 7120 | 441 |
| 442 | Ava_4222 (putative DUF37 family protein) | Unclassified | *Anabaena variabilis* ATCC 29413 | 443 |

TABLE 1.2-continued

Exemplary Bacteriocins

| Polypeptide SEQ ID NO: | Name | Class | Organism of origin | Polynucleotide SEQ ID NO: |
|---|---|---|---|---|
| 444 | N9414_07129 (putative DUF37 family protein) | Unclassified | *Nodularia spumigena* CCY9414 | 445 |
| 446 | Aazo_0083 (putative DUF37 family protein) | Unclassified | *Nostoc azollae* 0708 | 447 |
| 448 | S7335_3409 (putative DUF37 family protein) | Unclassified | *Synechococcus* PCC 7335 | 449 |
| 450 | P9303_21151 (putative DUF37 family protein) | Unclassified | *Prochlorococcus marinus* MIT 9303 | 451 |
| 720 | Curvalicin-28c | Unclassified | *Lactobacillus curvatus* | 721 |
| 722 | thruicin-S | Unclassified | *Bacillus thuringiensis* | 723 |
| 724 | curvaticin L442 | Unclassified | *Lactobacillus curvatus* L442 | 725 |
| 726 | Bacteriocin divergicin M35 | P84962 | *Carnobacterium divergens* (*Lactobacillus divergens*) | 727 |
| 728 | Lantibiotic 107891 | P85065 | *Microbispora* sp. (strain 107891) | 729 |
| 730 | Enterocin E-760 (Bacteriocin E-760) | P85147 | *Enterococcus* sp. | 731 |
| 732 | Bacteriocin E50-52 | P85148 | *Enterococcus faecium* (*Streptococcus faecium*) | 733 |
| 734 | Lantibiotic paenibacillin | P86013 | *Paenibacillus polymyxa* (*Bacillus polymyxa*) | 735 |
| 736 | Lantibiotic epilancin 15X | P86047 | *Staphylococcus epidermidis* | 737 |
| 738 | Enterocin-HF | P86183 | *Enterococcus faecium* (*Streptococcus faecium*) | 739 |
| 740 | Bacteriocin SRCAM 602 | P86393 | *Paenibacillus polymyxa* (*Bacillus polymyxa*) | 741 |
| 742 | Bacteriocin SRCAM 1580 | P86394 | *Bacillus circulans* | 743 |
| 744 | Bacteriocin SRCAM 37 | P86395 | *Paenibacillus polymyxa* (*Bacillus polymyxa*) | 745 |
| 746 | Bacteriocin rhamno sin A (Fragment) | P86526 | *Lactobacillus rhamnosus* | 747 |
| 748 | Lantibiotic lichenicidin A2 (LchA2) (BliA2) | P86720 | *Bacillus licheniformis* (strain ATCC 14580/DSM 13/JCM 2505/NBRC 12200/NCIMB 9375/NRRL NRS-1264/Gibson 46) | 749 |
| 750 | Pyocin-52 (EC 3.1.-.-) (Killer protein) | | *Pseudomonas aeruginosa* (strain ATCC 15692/DSM 22644/CIP 104116/JCM 14847/LMG 12228/1C/PRS 101/PAO1) | 751 |
| 752 | Plantaricin C19 (Fragment) | | *Lactobacillus plantarum* | 753 |
| 754 | LsbB | | *Lactococcus lactis* subsp. *lactis* (*Streptococcus lactis*) | 755 |
| 756 | ACIDOCIN J1132 beta peptide (Fragment) | | *Lactobacillus acidophilus* | 757 |
| 758 | Uncharacterized protein | | *Lactobacillus salivarius* cp400 | 759 |

For example, in some embodiments, an anti-fungal activity (such as anti-yeast activity) is desired. A number of bacteriocins with anti-fungal activity have been identified. For example, bacteriocins from *Bacillus* have been shown to have neutralizing activity against yeast strains {see Adetunji and Olaoye (2013) Malaysian Journal of Microbiology 9: 130-13, hereby incorporated by reference in its entirety), an *Enterococcus faecalis* peptide (WLPPAGLL-GRCGRWFRPWLLWLQ SGAQY KWLGNLFGLGPK, SEQ ID NO: 1) has been shown to have neutralizing activity against *Candida* species {see Shekh and Roy (2012) BMC Microbiology 12: 132, hereby incorporated by reference in its entirety), and bacteriocins from *Pseudomonas* have been shown to have neutralizing activity against fungi such as

*Curvularia lunata, Fusarium* species, *Helminthosporium* species, and *Biopolaris* species (Shalani and Srivastava (2008) The Internet Journal of Microbiology. Volume 5 Number 2. DOI: 10.5580/27dd—accessible on the worldwide web at archive, ispub.com/journal/the-internet-journal-of-micro biology/volume-5-number-2/screening-for-antifungal-activity-of-pseudomonas-fluorescens-against-phytopathogenic-fungi.html #sthash.d0Ys03UO.1DKuT1US.dpuf, hereby incorporated by reference in its entirety). By way of example, botrycidin AJ1316 {see Zuber, P et al. (1993) Peptide Antibiotics. In *Bacillus subtilis* and Other Gram-Positive Bacteria: Biochemistry, Physiology, and Molecular Genetics ed Sonenshein et al., pp. 897-916, American Society for Microbiology, hereby incorporated by reference in its entirety) and alirin B1 {see Shenin et al. (1995) Antibiot Khimioter 50: 3-7, hereby incorporated by reference in its entirety) from *S. subtilis* have been shown to have antifungal activities. As such, in some embodiments, for example embodiments in which neutralization of a fungal microbial organism is desired, a bacteriocin comprises at least one of botrycidin AJ1316 or alirin B1.

For example, in some embodiments, bacteriocin activity in a culture of cyanobacteria is desirable. In some embodiments, bacteriocins are provided to neutralize cyanobacteria. In some embodiments, bacteriocins are provided to neutralize invading microbial organisms typically found in a cyanobacteria culture environment. Clusters of conserved bacteriocin polypeptides have been identified in a wide variety of cyanobacteria species. For example, at least 145 putative bacteriocin gene clusters have been identified in at least 43 cyanobacteria species, as reported in Wang et al. (2011), Genome Mining Demonstrates the Widespread Occurrence of Gene Clusters Encoding Bacteriocins in Cyanobacteria. PLoS ONE 6(7): e22384, hereby incorporated by reference in its entirety. Exemplary cyanobacteria bacteriocins are shown in Table 1.2 as SEQ ID NO's 420, 422, 424, 426, 428, 30, 432, 434, 436, 438, 440, 442, 444, 446, 448, and 450.

Within the context of methods, uses, compositions, hosts, and nucleic acids of embodiments herein, although a bacteriocin may work via different mechanisms on a microbial cell as explained herein, a bacteriocin may be said to be active when the number of microbial host has decreased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more compared to the number of initial microbial host when the microbial hosts are being cultured with a medium comprising a bacteriocin. This culture step may have a duration of at least 12 hours, 24 hours, 36 hours, 48 hours, 60 hours, 72 hours or more before assessing the activity of the bacteriocin by counting the number of microbial hosts present. The activity may be assessed by counting the cells under the microscope or by any known microbial techniques. In some embodiments, a bacteriocin is active when the growth has been arrested in at least a specified number or percentage of microbial hosts, for example at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the microbial hosts arrested compared to the initial population of microbial hosts when the microbial hosts are being cultured with a medium comprising a bacteriocin.

Within the context of methods, uses, compositions, hosts, and nucleic acids of some embodiments herein, the bacteriocin is B17 or C7 represented by an amino acid sequence comprising or consisting of SEQ ID NO: 198 or 200 respectively. B17 and C7 have been experimentally confirmed to be selection agents simple to produce, easy to use and stable in culture medium in accordance with some embodiments herein (See Example 1). Some of methods, uses, compositions, hosts, and nucleic acids of embodiments herein also encompass the use a bacteriocin having at least 50% identity to SEQ ID NO: 198 or 200, for example at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 198 or 200. Such variants of B17 or C7 may be used in methods, uses, compositions, hosts, and nucleic acids of embodiments herein as long as they exhibit at least a substantial activity of B17 or C7. In this context, "substantial" means, for example, at least 50%, at least 60%, at least 705, at least 80%, at least 90%, or at least 100% or more of the activity of B17 or C7 having SEQ ID NO: 198 or 200. The activity of a bacteriocin has been described earlier herein.

Within the context of methods, uses, compositions, hosts, and nucleic acids of embodiments herein, and depending on the microbial host targeted and the bacteriocin used, the skilled person will know which concentration of bacteriocin is to be used in a medium or in an agar petri plate. Using bacteriocin B17 or C7 inventors were able to prepare culture medium comprising said bacteriocin in a concentration which allows one to carry out the methods and uses of embodiments herein, i.e. to observe or visualize an advantage of the expression of said genetic activity. If an advantage of said activity is to allow the growth of the host comprising the auto-replicative extra-chromosomal nucleic acid molecule, then the quantity of bacteriocin in said medium or agar plate is such that the number of host that does not comprise said auto-replicative extra-chromosomal has been decreased by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more compared to the number of initial microbial cells/host when the cells are being cultured under conditions allowing the microbial host that has received said auto-replicative extra-chromosomal nucleic acid molecule to survive and to grow. This assessment step may have a duration of at least 6 hours, 12 hours, 24 hours, 36 hours, 48 hours, 60 hours, 72 hours, 84 hours, 96 hours, 108 hours, 120 hours or more. Said culture medium may be sterilized without losing substantial bacteriocin activity. In this context "substantial" means, for example, more than 50%, more than 60%, more than 70%, more than 80%, more than 90% of the bacteriocin activity present in the culture medium before sterilization.

First nucleic acid sequences suitable for methods, uses, compositions, hosts, and nucleic acids of some embodiments herein, and whose product provides immunity to a bacteriocin are shown in Table 2.

TABLE 2

Exemplary nucleic acid sequences whose provide immunity to a bacteriocin

| Poly-peptide SEQ ID NO: | Name | Organism of origin | Poly-nucleotide SEQ ID NO: |
|---|---|---|---|
| 452 | Microcin H47 immunity modulator MchI | Escherichia coli | 453 |
| 454 | Colicin-E3 immunity modulator (Colicin-E3 chain B) (ImmE3) (Microcin-E3 immunity modulator) | Escherichia coli | 455 |
| 456 | Colicin-E1 immunity modulator (ImmE1) (Microcin-E1 immunity modulator) | Escherichia coli | 457 |
| 458 | Cloacin immunity modulator | Escherichia coli | 459 |
| 460 | Colicin-E2 immunity modulator (ImmE2) (Microcin-E2 immunity modulator) | Escherichia coli | 461 |
| 462 | Colicin-A immunity modulator (Microcin-A immunity modulator) | Citrobacter freundii | 463 |
| 464 | Colicin-Ia immunity modulator | Escherichia coli | 465 |
| 466 | Colicin-Ib immunity modulator | Escherichia coli | 467 |
| 468 | Colicin-N immunity modulator (Microcin-N immunity modulator) | Escherichia coli | 469 |
| 470 | Colicin-E8 immunity modulator (ImmE8) (Microcin-E8 immunity modulator) | Escherichia coli | 471 |
| 472 | Lactococcin-A immunity modulator | Lactococcus lactis subsp. lactis (Streptococcus lactis) | 473 |
| 474 | Lactococcin-A immunity modulator | Lactococcus lactis subsp. cremoris (Streptococcus cremoris) | 475 |
| 476 | Colicin-D immunity modulator (Microcin-D immunity modulator) | Escherichia coli | 477 |
| 478 | Colicin-E5 immunity modulator (ImmE5) (Microcin-E5 immunity modulator) | Escherichia coli | 479 |
| 480 | Colicin-E6 immunity modulator (ImmE6) (Microcin-E6 immunity modulator) | Escherichia coli | 481 |
| 482 | Colicin-E8 immunity modulator in ColE6 (E8Imm[E6]) | Escherichia coli | 483 |
| 484 | Colicin-E9 immunity modulator (ImmE9) (Microcin-E9 immunity modulator) | Escherichia coli | 485 |
| 486 | Colicin-M immunity modulator (Microcin-M immunity modulator) | Escherichia coli | 487 |
| 488 | Colicin-B immunity modulator (Microcin-B immunity modulator) | Escherichia coli | 489 |
| 490 | Colicin-V immunity modulator (Microcin-V immunity modulator) | Escherichia coli | 491 |
| 492 | Colicin-E1* immunity modulator (ImmE1) (Microcin-E1* immunity modulator) | Shigella sonnei | 493 |
| 494 | Colicin-E1 immunity modulator (ImmE1) (Microcin-E1 immunity modulator) | Escherichia coli | 495 |
| 496 | Probable leucocin-A immunity modulator | Leuconostoc gelidum | 497 |
| 498 | Lactococcin-B immunity modulator | Lactococcus lactis subsp. cremoris (Streptococcus cremoris) | 499 |
| 500 | Pediocin PA-1 immunity modulator (Pediocin ACH immunity modulator) | Pediococcus acidilactici | 501 |
| 502 | Putative carnobacteriocin-BM1 immunity modulator | Carnobacterium maltaromaticum (Carnobacterium piscicola) | 503 |
| 504 | Putative carnobacteriocin-B2 immunity modulator (Carnocin-CP52 immunity modulator) | Carnobacterium maltaromaticum (Carnobacterium piscicola) | 505 |
| 506 | Nisin immunity modulator | Lactococcus lactis subsp. lactis (Streptococcus lactis) | 507 |
| 508 | Trifolitoxin immunity modulator | Rhizobium leguminosarum bv. trifolii | 509 |
| 510 | Antilisterial bacteriocin subtilosin biosynthesis protein AlbD | Bacillus subtilis (strain 168) | 511 |
| 512 | Putative ABC transporter ATP-binding protein AlbC (Antilisterial bacteriocin subtilosin biosynthesis protein AlbC) | Bacillus subtilis (strain 168) | 513 |
| 514 | Antilisterial bacteriocin subtilosin biosynthesis protein AlbB | Bacillus subtilis (strain 168) | 515 |
| 516 | Colicin-E7 immunity modulator (ImmE7) (Microcin-E7 immunity modulator) | Escherichia coli | 517 |
| 518 | Pyocin-S1 immunity modulator | Pseudomonas aeruginosa | 519 |
| 520 | Pyocin-S2 immunity modulator | Pseudomonas aeruginosa (strain ATCC 15692 /PAO1 / 1C / PRS 101 / LMG 12228) | 521 |
| 522 | Hiracin-JM79 immunity factor | Enterococcus hirae | 523 |
| 524 | Probable mesentericin-Y105 immunity modulator | Leuconostoc mesenteroides | 525 |
| 526 | Microcin-24 immunity modulator | Escherichia coli | 527 |
| 528 | Colicin-K immunity modulator | Escherichia coli | 529 |
| 530 | Microcin C7 self-immunity modulator MccF | Escherichia coli | 531 |
| 532 | Sakacin-A immunity factor | Lactobacillus sakei | 533 |
| 534 | Colicin-E5 immunity modulator in ColE9 (E5Imm[E9]) | Escherichia coli | 535 |
| 536 | Antilisterial bacteriocin subtilosin biosynthesis protein AlbD | Bacillus subtilis | 537 |

TABLE 2-continued

Exemplary nucleic acid sequences whose provide immunity to a bacteriocin

| Poly-peptide SEQ ID NO: | Name | Organism of origin | Poly-nucleotide SEQ ID NO: |
|---|---|---|---|
| 538 | Microcin-J25 export ATP-binding/permease protein McjD (Microcin-J25 immunity modulator) (Microcin-J25 secretion ATP-binding protein McjD) | *Escherichia coli* | 539 |
| 540 | Microcin E492 immunity modulator | *Klebsiella pneumoniae* | 541 |
|  | McbG | *Escherichia coli* | 699 |
|  | MccE | *Escherichia coli* | 700 |
| 706 | C-terminal part of MccE | Derived from *E. coli* and considered as artificial | 701 |
|  | Cvi | *Escherichia coli* | 709 |
|  | McbG-MccE | Derived from *E. coli* and considered as artificial | 715 |
|  | McbG-Cter part MccE (Cter could be replaced by C-terminal) | Derived from *E. coli* and considered as artificial | 716 |
|  | Cvi-MccE | Derived from *E. coli* and considered as artificial | 717 |
|  | Cvi-Cter part MccE (Cter could be replaced by C-terminal) | Derived from *E. coli* and considered as artificial | 718 |

While the sequence providing immunity to a bacteriocin of Table 2 are naturally-occurring, the skilled artisan will appreciate that variants of such molecules, naturally-occurring molecules other than the ones of Table 2, or synthetic ones can be used according to some embodiments herein. In some embodiments, a particular molecule conferring immunity or particular combination of molecules conferring immunity to a particular bacteriocin, particular class or category of bacteriocins, or particular combination of bacteriocins. Exemplary bacteriocins to which molecules can confer immunity are identified in Table 2. While Table 2 identifies an "organism of origin" for a molecule conferring immunity, these molecules conferring immunity can readily be expressed in other naturally-occurring, genetically modified, or synthetic microorganisms to provide a desired bacteriocin immunity activity in accordance with some embodiments herein. As such, as used herein "immunity modulator" or "molecule conferring or providing immunity to a bacteriocin" encompasses not only to structures expressly provided herein, but also structures that have substantially the same effect as the "immunity modulator" structures described herein, including fully synthetic immunity modulators, and immunity modulators that provide immunity to bacteriocins that are functionally equivalent to the bacteriocins disclosed herein.

Exemplary polynucleotide sequences encoding the polypeptides of Table 2 are indicated in Table 2. The skilled artisan will readily understand that the genetic code is degenerate, and moreover, codon usage can vary based on the particular organism in which the gene product is being expressed, and as such, a particular polypeptide can be encoded by more than one polynucleotide. In some embodiments, a polynucleotide encoding a bacteriocin immunity modulator is selected based on the codon usage of the organism expressing the bacteriocin immunity modulator. In some embodiments, a polynucleotide encoding a bacteriocin immunity modulator is codon optimized based on the particular organism expressing the bacteriocin immunity modulator. A vast range of functional immunity modulators can incorporate features of immunity modulators disclosed herein, thus providing for a vast degree of identity to the immunity modulators in Table 2. In some embodiments, an immunity modulator has at least about 50% identity, for example, at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to any one of the polypeptides of Table 2.

Within the context of methods, uses, compositions, hosts, and nucleic acids of embodiments herein, resistance or immunity to a bacteriocin may mean the number of microbial cells at the end of a culturing step with a bacteriocin has not been decreased, and in some embodiments has been increased of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more compared to the number of initial microbial cells when the cells are being cultured with a medium comprising a bacteriocin. This culture step may have a duration of at least 12 hours, 24 hours, 36 hours, 48 hours, 60 hours, 72 hours, 84 hours, 96 hours, 108 hours, 120 hours or more before assessing the activity of the bacteriocin by counting the number of microbial cells present.

A nucleic acid molecule suitable for methods, uses, compositions, hosts, and nucleic acids of some embodiments herein and whose encoding product confers immunity is McbG (Immunity to the bacteriocin B17), which is represented by SEQ ID NO: 699. McbG has been experimentally confirmed to be useful as a selectable marker either constitutively or inducibly in accordance with some embodiments herein (See Example 3). Another suitable nucleic acid is the MccE (Immunity to the bacteriocin C7) which is represented by SEQ ID NO: 700 or its c-terminal portion, represented by SEQ ID NO: 701. MccE had been used as a vector selection marker in strains sensitive to microcines/bacteriocins (See Example 2). Methods, uses, compositions, hosts, and nucleic acids of some embodiments also encompass the use of a nucleic acid molecule whose encoding product confers immunity to bacteriocin B17 and/or C7 and having at least 50% identity to SEQ ID NO: 699, 700, or 701, for example at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 699, 700 or 701. Such variants of McbG and/or MccE may be used in methods, uses, compositions, hosts, and nucleic acids of embodiments herein as long as they exhibit at least a substantial activity of McbG (respectively MccE). In this context, "substantial" means, for example, at least 50%, at least 60%, at least 70%, at least 80%, at least 90%, or at least 100% or more of the activity of McbG (respectively MccE) having SEQ ID NO: 699, 700 or 701. The immunity conferred by the encoding product of McbG (respectively MccE) has been described earlier herein.

Surprisingly it has been found that the C-terminal part of MccE which is represented by SEQ ID NO: 701 is sufficient to confer resistance to bacteriocin C7. Part means in this context, for example, at least 50%, at least 60%, at least 70%, at least 80%, at least 90% or more of the original nucleic acid molecule. This is quite attractive and surprising that such a short nucleic acid molecule can confer resistance to a bacteriocin. It is expected that an auto-replicative extra-chromosomal nucleic acid molecule comprising such short nucleic acid molecule does not form any burden for the microbial cell.

A further suitable nucleic acid molecule for methods, uses, compositions, hosts, and nucleic acids of some embodiments herein, and whose product provides immunity to a bacteriocin is a single nucleic acid molecule whose single product provides immunity to at least two distinct bacteriocins. In some embodiments, such product of such nucleic acid molecule provides immunity to B17 and C7 or to ColV and C7 or to ColV and B17 or to B17, C7 and ColV. A nucleic acid encoding ColV is identified as SEQ ID NO: 65 and a corresponding coding amino acid sequence is identified as SEQ ID NO: 64.

In some embodiments, a nucleic acid molecule whose product provides immunity to B17 and C7 is represented by a sequence having at least 50% identity to SEQ ID NO: 715 or 716 for example at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 715 or 716. SEQ ID NO: 715 is a nucleic acid molecule of McbG fused to MccE. SEQ ID NO: 716 is a nucleic acid molecule of McbG fused to the C-terminal part of MccE as earlier described herein.

In some embodiments, a nucleic acid molecule whose product provides immunity to ColV and C7 is represented by a sequence having at least 50% identity to SEQ ID NO: 717 or 718 for example at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 717 or 718. SEQ ID NO: 717 is a nucleic acid molecule of Cvi fused to MccE. SEQ ID NO: 718 is a nucleic acid molecule of Cvi fused to the C-terminal part of MccE as earlier described herein.

Such identity variants of the core sequence may be used in methods, uses, compositions, hosts, and nucleic acids of embodiments herein as long as they exhibit at least a substantial activity of the molecule they derived from as earlier described herein.

In methods, uses, compositions, hosts, and nucleic acids of some embodiments herein, each of these nucleic acid molecules described herein whose product confers immunity to a single or to more than one or to at least two bacteriocins may be operably linked to a promoter as described herein. In some embodiments, the promoter is a weak promoter. In some embodiments, the weak promoter is the proC promoter represented by SEQ ID NO: 708 or the P24 promoter represented by SEQ ID NO: 707, which has been experimentally confirmed (See, e.g. Example 3).

Suitable constructs useful in methods, uses, compositions, hosts, and nucleic acids of embodiments herein can comprise a first nucleic acid molecule whose product confers immunity to a bacteriocin, and these constructs may comprise, consist essentially of, or consist of SEQ ID NO: 702, 703, 710, 711, 704, 705, 712, 713 or 714. Each of these constructs has been extensively described in the experimental part of the application, which notes that each of these constructs was actually constructed and confirmed to be suitable in accordance with some embodiments herein (See, e.g., Examples 1 and 2 and 3).

In a method of some embodiments, the bacteriocin added to the culture medium is a B17 and/or a C7 and/or a ColV as identified herein The method may allow the production of any product of interest. In a method of some embodiments, the product of interest is a microbial biomass, the auto-replicative extra-chromosomal nucleic acid molecule, the transcript of said second nucleic sequence, a polypeptide encoded by said second sequence or a metabolite produced directly or indirectly by said polypeptide.

In a method of some embodiments, the product of interest is purified at the end of the culturing step c). This may be carried out using techniques known to the skilled person. Since the energetic burden associated with the presence of the auto-replicative extra-chromosomal nucleic acid molecule has been minimized, the yield of the product of interest is expected to be optimal.

The method may use any suitable microbial cells, for example as hosts. Suitable microbial cells are listed in the part of the specification entitled general descriptions. Suitable microbial cells per se and for use in methods, uses, compositions, and hosts of embodiments herein include, but are not limited to: a bacterium (for example, a Gram negative bacterium, for example an *E. coli* species), a yeast, a filamentous fungus or an algae. In some embodiments, the microbial cell is a synthetic microbial cell.

In a method, the first nucleic acid sequence present on the auto-replicative extra-chromosomal nucleic acid molecule may be operably linked to a promoter. In some embodiments, said promoter is a weak promoter. In some embodiments, said promoter is a constitutive promoter. In some embodiments, said promoter is inducible. In some embodiments, said promoter is a weak constitutive promoter. In some embodiments, said promoter is a weak inducible promoter. The inducibility of said promoter is a way of controlling the presence of the genetic activity of the first nucleic acid sequence. Promoters are well known in the art. A detailed description is provided in the part of the specification dedicated to the general descriptions. A promoter can be used to drive the transcription of one or more coding sequences. Optionally said auto-replicative extra-chromosomal nucleic acid molecule comprises a second nucleic acid sequence that is involved in the production of a product of interest, wherein the genetic activity of said second nucleic acid sequence is controlled independently from the one of the first sequence.

In an embodiment, the control of the genetic activity of said second nucleic acid sequence is not independent from the control of the genetic activity of the first sequence.

In some embodiments, a second promoter drives expression of said second nucleic acid sequence being involved in the production of a product of interest as described herein. In an embodiment, a first promoter drives expression of an immunity modulator polynucleotide as described herein.

A promoter that could be used herein may be not native to a nucleic acid molecule to which it is operably linked, i.e. a promoter that is heterologous to the nucleic acid molecule (coding sequence) to which it is operably linked. Although a promoter of some embodiments is heterologous to a coding sequence to which it is operably linked, in some embodiments, a promoter is homologous, e.g., endogenous to a microbial cell. In some embodiments, a heterologous promoter (to the nucleotide sequence) is capable of producing a higher steady state level of a transcript comprising a coding sequence (or is capable of producing more transcript molecules, i.e. mRNA molecules, per unit of time) than is a promoter that is native to a coding sequence. Some promoters can drive transcription at all times ("constitutive promoters"). Some promoters can drive transcription under only select circumstances ("conditional promoters" or "inducible promoter"), for example depending on the presence or absence of an environmental condition, chemical compound, gene product, stage of the cell cycle, or the like.

The skilled artisan will appreciate that depending on the desired expression activity, an appropriate promoter can be selected, and placed in cis (i.e. or is operably linked with) with a sequence to be expressed. Exemplary promoters with exemplary activities are provided in Table 3.1-3.11 herein. The skilled artisan will appreciate that some promoters are compatible with particular transcriptional machinery (e.g. RNA polymerases, general transcription factors, and the like). As such, while compatible "species" are identified for some promoters described herein, it is contemplated that according to some embodiments herein, these promoters can readily function in microorganisms other than the identified species, for example in species with compatible endogenous transcriptional machinery, genetically modified species comprising compatible transcriptional machinery, or fully synthetic microbial organisms comprising compatible transcriptional machinery.

The promoters of Tables 3.1-3.11 herein are publicly available from the Biobricks foundation. It is noted that the Biobricks foundation encourages use of these promoters in accordance with BioBrick™ Public Agreement (BPA).

It should be appreciated that any of the "coding" polynucleotides described herein (for example a first nucleic acid sequence and/or a second nucleic acid sequence involved in the production of a product of interest) is generally amenable to being expressed under the control of a desired promoter. In an embodiment, a first nucleic acid sequence is under the control of a first promoter. In an embodiment, a second nucleic acid sequence involved in the production of a product of interest is under the control of a second promoter.

Generally, translation initiation for a particular transcript is regulated by particular sequences at 5' end of the coding sequence of a transcript. For example, a coding sequence can begin with a start codon configured to pair with an initiator tRNA. While naturally-occurring translation systems typically use Met (AUG) as a start codon, it will be readily appreciated that an initiator tRNA can be engineered to bind to any desired triplet or triplets, and accordingly, triplets other than AUG can also function as start codons in certain embodiments. Additionally, sequences near the start codon can facilitate ribosomal assembly, for example a Kozak sequence ((gcc)gccNccAUGG, SEQ ID NO: 542, in which N represents "A" or "G") or Internal Ribosome Entry Site (IRES) in typical eukaryotic translational systems, or a Shine-Dalgarno sequence (GGAGGU, SEQ ID NO: 543) in typical prokaryotic translation systems. As such in some embodiments, a transcript comprising a "coding" polynucleotide sequence, for example a first nucleic acid sequence, or second nucleic acid sequence involved in the production of a fermentation product, comprises an appropriate start codon and translational initiation sequence. In some embodiments, for example if two or more "coding" polynucleotide sequences are positioned in cis on a transcript, each polynucleotide sequence comprises an appropriate start codon and translational initiation sequence(s).

In some embodiments, for example if two or more "coding" polynucleotide sequences are positioned in cis on a transcript, the two sequences are under control of a single translation initiation sequence, and either provide a single polypeptide that can function with both encoded polypeptides in cis, or provide a means for separating two polypeptides encoded in cis, for example a 2A sequence or the like. In some embodiments, a translational intiator tRNA is regulatable, so as to regulate initiation of translation of an immunity modulator or industrially useful molecule.

TABLE 3.1

Exemplary Metal-Sensitive Promoters

| SEQ ID NO: | Name | Description |
|---|---|---|
| 544 | BBa_I721001 | Lead Promoter |
| 545 | BBa_I731004 | FecA promoter |
| 546 | BBa_I760005 | Cu-sensitive promoter |
| 547 | BBa_I765000 | Fe promoter |
| 548 | BBa_I765007 | Fe and UV promoters |
| 549 | BBa_J3902 | PrFe (PI + PII rus operon) |

TABLE 3.2

Exemplary Cell-Signaling-Responsive Promoters

| SEQ ID NO: | Name | Description |
|---|---|---|
| 550 | BBa_I1051 | Lux cassette right promoter |
| 551 | BBa_I14015 | P(Las) TetO |
| 552 | BBa_I14016 | P(Las) CIO |
| 553 | BBa_I14017 | P(Rhl) |
| 554 | BBa_I739105 | Double Promoter (LuxR/HSL, positive / cI, negative) |
| 555 | BBa_I746104 | P2 promoter in agr operon from *S. aureus* |
| 556 | BBa_I751501 | plux-cI hybrid promoter |
| 557 | BBa_I751502 | plux-lac hybrid promoter |
| 558 | BBa_I761011 | CinR, CinL and glucose controlled promotor |
| 559 | BBa_J06403 | RhIR promoter repressible by CI |
| 560 | BBa_J102001 | Reverse Lux Promoter |

TABLE 3.2-continued

Exemplary Cell-Signaling-Responsive Promoters

| SEQ ID NO: | Name | Description |
| --- | --- | --- |
| 561 | BBa_J64000 | rhlI promoter |
| 562 | BBa_J64010 | lasI promoter |
| 563 | BBa_J64067 | LuxR + 3OC6HSL independent R0065 |
| 564 | BBa_J64712 | LasR/LasI Inducible & RHLR/RHLI repressible Promoter |
| 565 | BBa_K091107 | pLux/cI Hybrid Promoter |
| 566 | BBa_K091117 | pLas promoter |
| 567 | BBa_K091143 | pLas/cI Hybrid Promoter |
| 568 | BBa_K091146 | pLas/Lux Hybrid Promoter |
| 569 | BBa_K091156 | pLux |
| 570 | BBa_K091157 | pLux/Las Hybrid Promoter |
| 571 | BBa_K145150 | Hybrid promoter: HSL-LuxR activated, P22 C2 repressed |
| 572 | BBa_K266000 | PAI + LasR → LuxI (AI) |
| 573 | BBa_K266005 | PAI + LasR → LasI & AI + LuxR --∣ LasI |
| 574 | BBa_K266006 | PAI + LasR → LasI + GFP & AI + LuxR --∣ LasI + GFP |
| 575 | BBa_K266007 | Complex QS → LuxI & LasI circuit |
| 576 | BBa_K658006 | position 3 mutated promoter lux pR-3 (luxR & HSL regulated) |
| 577 | BBa_K658007 | position 5 mutated promoter lux pR-5 (luxR & HSL regulated) |
| 578 | BBa_K658008 | position 3&5 mutated promoter lux pR-3/5 (luxR & HSL regulated) |
| 579 | BBa_R0061 | Promoter (HSL-mediated luxR repressor) |
| 580 | BBa_R0062 | Promoter (luxR & HSL regulated -- lux pR) |
| 581 | BBa_R0063 | Promoter (luxR & HSL regulated -- lux pL) |
| 582 | BBa_R0071 | Promoter (Rh1R & C4-HSL regulated) |
| 583 | BBa_R0078 | Promoter (cinR and HSL regulated) |
| 584 | BBa_R0079 | Promoter (LasR & PAI regulated) |
| 585 | BBa_R1062 | Promoter, Standard (luxR and HSL regulated -- lux pR) |

TABLE 3.3

Exemplary Constitutive E. coli $\sigma^{70}$ Promoters

| SEQ ID NO: | Name | Description |
| --- | --- | --- |
| 586 | BBa_I14018 | P(Bla) |
| 587 | BBa_I14033 | P(Cat) |
| 588 | BBa_I14034 | P(Kat) |
| 589 | BBa_I732021 | Template for Building Primer Family Member |
| 590 | BBa_I742126 | Reverse lambda cI-regulated promoter |
| 591 | BBa_J01006 | Key Promoter absorbs 3 |
| 592 | BBa_J23100 | constitutive promoter family member |
| 593 | BBa_J23101 | constitutive promoter family member |
| 594 | BBa_J23102 | constitutive promoter family member |
| 595 | BBa_J23103 | constitutive promoter family member |
| 596 | BBa_J23104 | constitutive promoter family member |
| 597 | BBa_J23105 | constitutive promoter family member |
| 598 | BBa_J23106 | constitutive promoter family member |
| 599 | BBa_J23107 | constitutive promoter family member |
| 600 | BBa_J23108 | constitutive promoter family member |
| 601 | BBa_J23109 | constitutive promoter family member |
| 602 | BBa_J23110 | constitutive promoter family member |
| 603 | BBa_J23111 | constitutive promoter family member |
| 604 | BBa_J23112 | constitutive promoter family member |
| 605 | BBa_J23113 | constitutive promoter family member |
| 606 | BBa_J23114 | constitutive promoter family member |
| 607 | BBa_J23115 | constitutive promoter family member |
| 608 | BBa_J23116 | constitutive promoter family member |
| 609 | BBa_J23117 | constitutive promoter family member |
| 610 | BBa_J23118 | constitutive promoter family member |
| 611 | BBa_J23119 | constitutive promoter family member |
| 612 | BBa_J23150 | 1bp mutant from J23107 |
| 613 | BBa_J23151 | 1bp mutant from J23114 |
| 614 | BBa_J44002 | pBAD reverse |
| 615 | BBa_J48104 | NikR promoter, a protein of the ribbon helix-helix family of trancription factors that repress expre |
| 616 | BBa_J54200 | lacq_Promoter |
| 617 | BBa_J56015 | lacIQ - promoter sequence |
| 618 | BBa_J64951 | E. Coli CreABCD phosphate sensing operon promoter |
| 619 | BBa_K088007 | GlnRS promoter |
| 620 | BBa_K119000 | Constitutive weak promoter of lacZ |
| 621 | BBa_K119001 | Mutated LacZ promoter |
| 622 | BBa_K137029 | constitutive promoter with (TA)10 between −10 and −35 elements |
| 623 | BBa_K137030 | constitutive promoter with (TA)9 between −10 and −35 elements |
| 624 | BBa_K137031 | constitutive promoter with (C)10 between −10 and −35 elements |
| 625 | BBa_K137032 | constitutive promoter with (C)12 between −10 and −35 elements |

TABLE 3.3-continued

Exemplary Constitutive E. coli σ⁷⁰ Promoters

| SEQ ID NO: | Name | Description |
|---|---|---|
| 626 | BBa_K137085 | optimized (TA) repeat constitutive promoter with 13 bp between −10 and −35 elements |
| 627 | BBa_K137086 | optimized (TA) repeat constitutive promoter with 15 bp between −10 and −35 elements |
| 628 | BBa_K137087 | optimized (TA) repeat constitutive promoter with 17 bp between −10 and −35 elements |
| 629 | BBa_K137088 | optimized (TA) repeat constitutive promoter with 19 bp between −10 and −35 elements |
| 630 | BBa_K137089 | optimized (TA) repeat constitutive promoter with 21 bp between −10 and −35 elements |
| 631 | BBa_K137090 | optimized (A) repeat constitutive promoter with 17 bp between −10 and −35 elements |
| 632 | BBa_K137091 | optimized (A) repeat constitutive promoter with 18 bp between −10 and −35 elements |
| 633 | BBa_K256002 | J23101:GFP |
| 634 | BBa_K256018 | J23119:IFP |
| 635 | BBa_K256020 | J23119:HO1 |
| 636 | BBa_K256033 | Infrared signal reporter (J23119:IFP:J23119:HO1) |
| 637 | BBa_K292000 | Double terminator + constitutive promoter |
| 638 | BBa_K292001 | Double terminator + Constitutive promoter + Strong RBS |
| 639 | BBa_K418000 | IPTG inducible Lac promoter cassette |
| 640 | BBa_K418002 | IPTG inducible Lac promoter cassette |
| 641 | BBa_K418003 | IPTG inducible Lac promoter cassette |
| 642 | BBa_M13101 | M13K07 gene I promoter |
| 643 | BBa_M13102 | M13K07 gene II promoter |
| 644 | BBa_M13103 | M13K07 gene III promoter |
| 645 | BBa_M13104 | M13K07 gene IV promoter |
| 646 | BBa_M13105 | M13K07 gene V promoter |
| 647 | BBa_M13106 | M13K07 gene VI promoter |
| 648 | BBa_M13108 | M13K07 gene VIII promoter |
| 649 | BBa_M13110 | M13110 |
| 650 | BBa_M31519 | Modified promoter sequence of g3. |
| 651 | BBa_R1074 | Constitutive Promoter I |
| 652 | BBa_R1075 | Constitutive Promoter II |
| 653 | BBa_S03331 | Constitutive promoter |

TABLE 3.4

Exemplary Constitutive E. coli σ⁸ Promoters

| SEQ ID NO: | Name | Description |
|---|---|---|
| 654 | BBa_J45992 | Full-length stationary phase osmY promoter |
| 655 | BBa_J45993 | Minimal stationary phase osmY promoter |

TABLE 3.5

Exemplary Constitutive E. coli σ³² Promoters

| SEQ ID NO: | Name | Description |
|---|---|---|
| 656 | BBa_J45504 | htpG Heat Shock Promoter |

TABLE 3.6

Exemplary Constitutive B. subtilis σ⁴ Promoters

| SEQ ID NO: | Name | Description |
|---|---|---|
| 657 | BBa_K143012 | Promoter veg a constitutive promoter for B. subtilis |
| 658 | BBa_K143013 | Promoter 43 a constitutive promoter for B. subtilis |
| 659 | BBa_K780003 | Strong constitutive promoter for Bacillus subtilis |
| 660 | BBa_K823000 | PliaG |
| 661 | BBa_K823002 | PlepA |
| 662 | BBa_K823003 | Pveg |

TABLE 3.7

Exemplary Constitutive B. subtilis σᴮ Promoters

| SEQ ID NO: | Name | Description |
|---|---|---|
| 663 | BBa_K143010 | Promoter etc for B. subtilis |
| 664 | BBa_K143011 | Promoter gsiB for B. subtilis |
| 665 | BBa_K143013 | Promoter 43 a constitutive promoter for B. subtilis |

TABLE 3.8

Exemplary Constitutive Promoters from miscellaneous prokaryotes

| SEQ ID NO: | Name | Description |
|---|---|---|
| 666 | a_K112706 | Pspv2 from Salmonella |
| 667 | BBa_K112707 | Pspv from Salmonella |

TABLE 3.9

Exemplary Constitutive Promoters from bacteriophage T7

| SEQ ID NO: | Name | Description |
|---|---|---|
| 668 | BBa_I712074 | T7 promoter (strong promoter from T7 bacteriophage) |
| 669 | BBa_I719005 | T7 Promoter |
| 670 | BBa_J34814 | T7 Promoter |
| 671 | BBa_J64997 | T7 consensus −10 and rest |
| 672 | BBa_K113010 | overlapping T7 promoter |

TABLE 3.9-continued

Exemplary Constitutive Promoters from bacteriophage T7

| SEQ ID NO: | Name | Description |
|---|---|---|
| 673 | BBa_K113011 | more overlapping T7 promoter |
| 674 | BBa_K113012 | weaken overlapping T7 promoter |
| 675 | BBa_R0085 | T7 Consensus Promoter Sequence |
| 676 | BBa_R0180 | T7 RNAP promoter |
| 677 | BBa_R0181 | T7 RNAP promoter |
| 678 | BBa_R0182 | T7 RNAP promoter |
| 679 | BBa_R0183 | T7 RNAP promoter |
| 680 | BBa_Z0251 | T7 strong promoter |
| 681 | BBa_Z0252 | T7 weak binding and processivity |
| 682 | BBa_Z0253 | T7 weak binding promoter |

TABLE 3.10

Exemplary Constitutive Promoters from yeast

| SEQ ID NO: | Name | Description |
|---|---|---|
| 683 | BBa_I766555 | pCyc (Medium) Promoter |
| 684 | BBa_I766556 | pAdh (Strong) Promoter |
| 685 | BBa_I766557 | pSte5 (Weak) Promoter |
| 686 | BBa_J63005 | yeast ADH1 promoter |
| 687 | BBa_K105027 | cyc100 minimal promoter |
| 688 | BBa_K105028 | cyc70 minimal promoter |
| 689 | BBa_K105029 | cyc43 minimal promoter |
| 690 | BBa_K105030 | cyc28 minimal promoter |
| 691 | BBa_K105031 | cyc16 minimal promoter |
| 692 | BBa_K122000 | pPGK1 |
| 693 | BBa_K124000 | pCYC Yeast Promoter |
| 694 | BBa_K124002 | Yeast GPD (TDH3) Promoter |
| 695 | BBa_K319005 | yeast mid-length ADH1 promoter |
| 696 | BBa_M31201 | Yeast CLB1 promoter region, G2/M cell cycle specific |

TABLE 3.11

Exemplary Constitutive Promoters from miscellaneous eukaryotes

| SEQ ID NO: | Name | Description |
|---|---|---|
| 697 | BBa_I712004 | CMV promoter |
| 698 | BBa_K076017 | Ubc Promoter |

The above-referenced promoters are provided by way of non-limiting example only. A promoter may be a synthetic promoter. Suitable promoters for methods, uses, compositions, hosts, and nucleic acids of some embodiments herein have been described earlier herein e.g., proC represented by SEQ ID NO: 708 which has been experimentally confirmed in accordance with some embodiments herein (See Example 2) and P24 represented by SEQ ID NO: 707 which has been experimentally confirmed in accordance with some embodiments herein (See Example 3). In some embodiments, a suitable inducible promoter is the P24 LacO hybrid promoter, which is repressed in the presence of LacI and active in presence of IPTG. This promoter has been experimentally confirmed in accordance with some embodiments herein (See Example 3).

The skilled artisan will readily recognize that many variants of the above-referenced promoters, and many other promoters (including promoters isolated from naturally existing organisms, variations thereof, and fully synthetic or engineered promoters) can readily be used in accordance with some embodiments herein. A variant, fully synthetic or synthetic or engineer promoter is said to be active or functional and can therefore be used in methods, uses, compositions, hosts, and nucleic acids of embodiments herein when tested in a control or reference plasmid being operably linked with a nucleic acid molecule encoding a transcript, a detectable amount of said transcript molecule is present when said plasmid is present in a cell. A variant, fully synthetic or synthetic or engineer promoter may have at least 50%, at least 60%, at least 70%, at least 80%, at least 90%, or at least 100% of the activity of the promoter it derives from.

Optionally, the method comprises transforming said microbial host with said auto-replicative extra-chromosomal nucleic acid molecule under conditions allowing the host that has received said auto-replicative extra-chromosomal nucleic acid molecule to survive. It is noted that in some embodiments, the auto-replicative extra-chromosomal nucleic acid molecule can be provided in a microbial cell (e.g., if the microbial cell, or a predecessor thereof was transformed with the auto-replicative extra-chromosomal nucleic acid molecule), and as such, in some embodiments, the transformation step is not needed in the method. The transforming step can be performed prior to the culturing of step c). In some embodiments, the transforming step is provided prior to step a) so as to provide the host cell comprising the auto-replicative extra-chromosomal nucleic acid molecule. In some embodiments, the auto-replicative extra-chromosomal nucleic acid molecule used in the transforming step further comprises the second nucleic acid of optional step b).

Techniques of genetically modifying microbial organisms are well known in the art (for example see Molecular Cloning Fourth edition, 2012 Cold Spring Harbor Laboratory Press, A laboratory manual, by M. R. Green and J Sambrook, which is herein incorporated by reference in its entirety). In some embodiments, a microorganism is genetically modified to comprise said auto-replicative extra-chromosomal nucleic acid molecule comprising a first nucleic acid sequence and optionally a molecule involved in the production of a product of interest. Polynucleotides or nucleic acid molecules can be delivered to microorganisms.

In an embodiment a microbial cell is positively selected for by the genetic activity of the first nucleic acid sequence corresponding to at least one given condition allowing the cell that has received the said auto-replicative extra-chromosomal nucleic acid molecule to survive and said conditions can be environmental conditions. Environmental conditions may be a culture medium.

It can be useful to flexibly genetically modify a microbial cell, for example to engineer or reengineer a microbial cell to have a desired type and/or spectrum of genetic activities. In some embodiments, a cassette for inserting one or more desired distinct first nucleic acid sequences is provided. Exemplary cassettes include, but are not limited to, a Cre/lox cassette or FLP/FRT cassette.

In an embodiment, a microbial cell comprises more than one (more than two, more than three, . . . ) different auto-replicative extra-chromosomal nucleic acid molecule comprising a first nucleic acid sequence as described herein, meaning that said cell can exhibit more than one (more than two, more than three, . . . ) genetic activity, each genetic activity conferring an advantage to the cell. If a first promoter is present in each of the different auto-replicative extra-chromosomal nucleic acid molecule, each of said first promoters may be different or identical. It is therefore within the scope of the of methods, uses, compositions, hosts, and nucleic acids of embodiments herein to use one, two, three, four or more distinct bacteriocins in a method for producing a product of interest wherein the microbial host comprises one, two, three, four or more distinct extra-chromosomal nucleic acid molecule, each conferring a distinct genetic activity to said microbial host. Alternatively, it is within the scope of methods, uses, compositions, hosts, and nucleic acids of embodiments herein that a single nucleic acid molecule whose product provides immunity to at least distinct bacteriocins is used. Such a nucleic acid molecule has been described herein.

In some embodiments, plasmid conjugation can be used to introduce a desired plasmid from a "donor" microbial cell to a recipient microbial cell. Goni-Moreno, et al. (2013) Multicellular Computing Using Conjugation for Wiring. PLoS ONE 8(6): e65986, hereby incorporated by reference in its entirety. In some embodiments, plasmid conjugation can genetically modify a recipient microbial cell by introducing a conjugation plasmid from a donor microbial cell to a recipient microbial cell. Without being limited by any particular theory, conjugation plasmids that comprise the same or functionally same set of replication genes typically cannot coexist in the same microbial cell. As such, in some embodiments, plasmid conjugation "reprograms" a recipient microbial cell by introducing a new conjugation plasmid to supplant another conjugation plasmid that was present in the recipient cell. In some embodiments, plasmid conjugation is used to engineer (or reengineer) a microbial cell with a particular combination of first nucleic acid molecules (which can code for immunity modulators in some embodiments). According to some embodiments, a variety of conjugation plasmids comprising different combinations of first acid sequence (which can code for immunity modulators in some embodiments) is provided. The plasmids can comprise additional genetic elements as described herein, for example promoters, translational initiation sites, and the like. In some embodiments the variety of conjugation plasmids is provided in a collection of donor cells, so that a donor cell comprising the desired plasmid can be selected for plasmid conjugation. In some embodiments, a particular combination of immunity modulators is selected, and an appropriate donor cell is conjugated with a microbial cell of interest to introduce a conjugation plasmid comprising that combination into a recipient cell. In some embodiments, the recipient cell is a "newly engineered" cell, for example to be introduced into or for initiating a culture.

Step b)

In addition to step a), in some embodiments the method further comprises optional step b) wherein said auto-replicative extra-chromosomal nucleic acid molecule comprises a second nucleic acid sequence that is involved in the production of said product of interest, wherein the genetic activity of said second nucleic acid sequence is controlled independently from the one of the first sequence.

In the context of methods, uses, compositions, hosts, and nucleic acids of embodiments herein, the expression "controlled independently" has its customary and ordinary meanings as understood by one of skill in the art in view of this disclosure, including meaning that distinct ways are used for controlling the genetic activity of the first and the second nucleic acid sequences. Ways of controlling the genetic activity of a nucleic acid sequence have been already described in detail herein.

Step c)

In some embodiments, step a) (which optionally includes transforming as described herein) and optional step b) is followed by step c), which comprises culturing said transformed microbial host under conditions allowing said transformed microbial host to express the first nucleic acid sequence to a given level to maintain the auto-replicative extra-chromosomal molecule into the growing microbial population. In some embodiments, optionally controlling the second sequence coding for said product of interest.

In a method of some embodiments, at least part of step c) conditions are such that the first nucleic acid sequence does not exhibit said genetic activity. "Part of step c)" means, for example, at least 20%, 30%, 40%, 50%, 60%, 70%, 80% or 90% or up to 100% of the duration of step c). This embodiment of the method is quite attractive as part of step c) is carried out without the presence of the genetic activity of the first nucleic acid sequence. The presence of said genetic activity forms an energetic burden for the microbial host cell and is not always needed in order to keep a suitable production level of a product of interest. It is envisaged in some embodiments to have part of step c) without genetic activity of the first nucleic acid sequence followed by a part with said activity. These two parts may be repeated one or more time during step c).

A microbial cell may be cultured in any suitable microbial culture environment. Microbial culture environments can comprise a wide variety of culture media, for example feedstocks. The selection of a particular culture medium can depend upon the desired application. Conditions of a culture medium include not only chemical composition, but also temperature, amounts of light, pH, $CO_2$ levels, and the like. The culture medium can comprise a bacteriocin. In an embodiment, a compound that induces the activity of the bacteriocin is present outside of the feedstock, but not in the feedstock.

In an embodiment, a genetically engineered or transformed microorganism as described herein is added to a culture medium that comprises at least one feedstock. In an embodiment, the culture medium comprises a compound that induces the activity or expression of an immunity modulator.

The term "feedstock" has is customary and ordinary meaning as understood by one of skill in the art in view of this disclosure, and encompasses material that can be consumed, fermented, purified, modified, or otherwise processed by microbial organisms, for example in the context of industrial processes. As such, "feedstock" is not limited to food or food products. As used herein a "feedstock" is a category of culture medium. Accordingly, as used herein "culture medium" includes, but it is not limited to feedstock. As such, whenever a "culture medium" is referred to herein, feedstocks are also expressly contemplated.

Before culturing a transformed microbial cell, it can be useful to determine the effects, if any, or optimize the conditions allowing the host that has received said auto-replicative extra-chromosomal nucleic acid molecule to survive and optionally to grow.

In some embodiments, a microbial cell or microbial host or microbial host cell or synthetic microbial host cell comprising an auto-replicative extra-chromosomal nucleic acid molecule is provided, comprising a first nucleic acid sequence whose genetic activity confers an advantage to a microbial host wherein the genetic activity of said first nucleic acid sequence is controlled, and optionally comprising a second nucleic acid sequence that is directly or indirectly involved in the production of a product of interest.

In some embodiments, there is provided an auto-replicative extra-chromosomal nucleic acid molecule, comprising a first nucleic acid sequence whose genetic activity confers an advantage to a microbial host wherein the genetic activity of said first nucleic acid sequence is controlled, and optionally comprising a second nucleic acid sequence that is directly or indirectly involved in the production of a product of interest.

Each feature of this microbial host and of this auto-replicative extra-chromosomal nucleic acid molecule have already been described herein.

General Descriptions

The terms used herein have the customary and ordinary meaning understood by one of skill in the art when read in view of this disclosure, and can include the following general descriptions.

Microorganism

As used herein, "microbial organism," "microorganism," "microbial cell" or "microbial host" and variations of these root terms (such as pluralizations and the like) have their customary and ordinary meanings as understood by one of skill in the art in view of this disclosure, including any naturally-occurring species or synthetic or fully synthetic prokaryotic or eukaryotic unicellular organism, as well as Archae species. Thus, this expression can refer to cells of bacterial species, fungal species, and algae. Exemplary microorganisms that can be used in accordance with embodiments herein include, but are not limited to, bacteria, yeast, filamentous fungi, and algae, for example photosynthetic microalgae. Furthermore, fully synthetic microorganism genomes can be synthesized and transplanted into single microbial cells, to produce synthetic microorganisms capable of continuous self-replication (see Gibson et al. (2010), "Creation of a Bacterial Cell Controlled by a Chemically Synthesized Genome," Science 329: 52-56, hereby incorporated by reference in its entirety). As such, in some embodiments, the microorganism is fully synthetic. A desired combination of genetic elements, including elements that regulate gene expression, and elements encoding gene products (for example immunity modulators, poison, antidote, and industrially useful molecules also called product of interest) can be assembled on a desired chassis into a partially or fully synthetic microorganism. Description of genetically engineered microbial organisms for industrial applications can also be found in Wright, et al. (2013) "Building-in biosafety for synthetic biology" Microbiology 159: 1221-1235. Suitable embodiments of genetic elements will be described later herein.

A variety of bacterial species and strains can be used in accordance with embodiments herein, and genetically modified variants, or synthetic bacteria based on a "chassis" of a known species can be provided. Exemplary bacteria with industrially applicable characteristics, which can be used in accordance with embodiments herein include, but are not limited to, *Bacillus* species (for example *Bacillus coagulans, Bacillus subtilis*, and *Bacillus licheniformis*), *Paenibacillus* species, *Streptomyces* species, *Micrococcus* species, *Corynebacterium* species, *Acetobacter* species, *Cyanobacteria* species, *Salmonella* species, *Rhodococcus* species, *Pseudomonas* species, *Lactobacillus* species, *Enterococcus* species, *Alcaligenes* species, *Klebsiella* species, *Paenibacillus* species, *Arthrobacter* species, *Corynebacterium* species, *Brevibacterium* species, *Thermus aquaticus, Pseudomonas stutzeri, Clostridium thermocellus*, and *Escherichia coli*. A variety of yeast species and strains can be used in accordance with embodiments herein, and genetically modified variants, or synthetic yeast based on a "chassis" of a known species can be provided. Exemplary yeast with industrially applicable characteristics, which can be used in accordance with embodiments herein include, but are not limited to *Saccharomyces* species (for example, *Saccharomyces cerevisiae, Saccharomyces bayanus, Saccharomyces boulardii*), *Candida* species (for example, *Candida utilis, Candida krusei*), *Schizosaccharomyces* species (for example *Schizosaccharomyces pombe, Schizosaccharomyces japonicas*), *Pichia* or *Hansenula* species (for example, *Pichia pastoris* or *Hansenula polymorphd*) species, and *Brettanomyces* species (for example, *Brettanomyces claussenii*).

A variety of algae species and strains can be used in accordance with embodiments herein, and genetically modified variants, or synthetic algae based on a "chassis" of a known species can be created. In some embodiments, the algae comprises, consists essentially of, or consists of photosynthetic microalgae. Exemplary algae species that can be useful for biofuels, and can be used in accordance with embodiments herein, include *Botryococcus braunii, Chlorella* species, *Dunaliella tertiolecta, Gracilaria* species, *Pleurochrysis carterae*, and *Sargassum* species. Additionally, many algaes can be useful for food products, fertilizer products, waste neutralization, environmental remediation, and carbohydrate manufacturing (for example, biofuels).

A variety of filamentous fungal species and strains can be used in accordance with embodiments herein, and genetically modified variants, or synthetic filamentous fungi based on a "chassis" of a known species can be provided. Exemplary filamentous fungi with industrially applicable characteristics, which can be used in accordance with embodiments herein include, but are not limited to an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocaffimastix, Neurospora, Paecilomyces, Penicifflum, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria*.

Species include *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zona turn, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenaturn, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride*.

Antibiotic

"Antibiotic," and variations of this root term, have their customary and ordinary meanings as understood by one of skill in the art in view of this disclosure, including a metabolite, or an intermediate of a metabolic pathway which can kill or arrest the growth of at least one microbial cell. Some antibiotics can be produced by microbial cells, for example bacteria. Some antibiotics can be synthesized chemically. It is understood that bacteriocins are distinct from antibiotics, at least in that bacteriocins refer to gene products (which, in some embodiments, undergo additional post-translational processing) or synthetic analogs of the same, while antibiotics refer to intermediates or products of metabolic pathways or synthetic analogs of the same.

Sequence Identity and Similarity

Sequence identity has its customary and ordinary meanings as understood by one of skill in the art in view of this disclosure, including a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" can also refer to the degree of sequence relatedness between amino acid or nucleic acid sequences, as the case may be, as determined by the match between strings of such sequences. "Similarity" between two amino acid sequences can be determined by comparing the amino acid sequence and its conserved amino acid substitutes of one polypeptide to the sequence of a second polypeptide. "Identity" and "similarity" can be readily calculated by various methods, known to those skilled in the art. In some embodiments, sequence identity is determined by comparing the whole length of the sequences as identified herein.

Some methods to determine identity are designed to give the largest match between the sequences tested. Methods to determine identity and similarity are codified in publicly available computer programs. Computer program methods to determine identity and similarity between two sequences include e.g. the BestFit, BLASTP, BLASTN, and FASTA (Altschul, S. F. et al., J. Mol. Biol. 215:403-410 (1990), publicly available from NCBI and other sources (BLAST Manual, Altschul, S., et al., NCBI NLM NIH Bethesda, MD 20894). An algorithm used can be EMBOSS (accessible on the world wide web at www(dot)ebi(dot)ac(dot)uk/emboss/align). Parameters for amino acid sequences comparison using EMBOSS can include gap open 10.0, gap extend 0.5, Blosum 62 matrix. Parameters for nucleic acid sequences comparison using EMBOSS can include gap open 10.0, gap extend 0.5, DNA full matrix (DNA identity matrix).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Suitable conservative amino acids substitution groups include: valine-leucine-isoleucine, phenylalanine-tyrosine, lysine-arginine, alanine-valine, and asparagine-glutamine Substitutional variants of the amino acid sequence disclosed herein are those in which at least one residue in the disclosed sequences has been removed and a different residue inserted in its place. In some embodiments, the amino acid change is conservative. Suitable conservative substitutions for each of the naturally occurring amino acids include: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Homologous

The term "homologous" has its customary and ordinary meanings as understood by one of skill in the art in view of this disclosure, including when used to indicate the relation between a given (recombinant) nucleic acid or polypeptide molecule and a given host organism or host cell, it can be understood to mean that in nature the nucleic acid or polypeptide molecule is produced by a host cell or organisms of the same species, optionally of the same variety or strain. If homologous to a host cell, a nucleic acid sequence encoding a polypeptide will typically be operably linked to another promoter sequence than in its natural environment. When used to indicate the relatedness of two nucleic acid sequences the term "homologous" has its customary and ordinary meanings as understood by one of skill in the art in view of this disclosure, and can refer to one single-stranded nucleic acid sequence that may hybridize to a complementary single-stranded nucleic acid sequence. The degree of hybridization may depend on a number of factors including the amount of identity between the sequences and the hybridization conditions such as temperature and salt concentration as earlier presented. The region of identity can be greater than about 5 bp, the region of identity can be greater than 10 bp. In some embodiments, two nucleic acid or polypeptides sequences are said to be homologous when they have more than 80% identity.

Heterologous

The term "heterologous" has its customary and ordinary meanings as understood by one of skill in the art in view of this disclosure, including when used with respect to a nucleic acid (DNA or RNA) or protein, it can refer to a nucleic acid or protein (also named polypeptide or enzyme) that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

Operably Linked

As used herein, the term "operably linked" has its customary and ordinary meanings as understood by one of skill in the art in view of this disclosure, and can refer to a linkage of polynucleotide elements (or coding sequences or nucleic acid sequence or nucleic acid molecule) in a functional relationship. A nucleic acid sequence is "operably linked"

when it is placed into a functional relationship with another nucleic acid sequence. For instance, a promoter or enhancer is operably linked to a coding sequence if it affects the transcription of the coding sequence. Operably linked means that the nucleic acid sequences being linked are typically contiguous and, where necessary to join two protein coding regions, contiguous and in reading frame.

Promoter

As used herein, the term "promoter" has its customary and ordinary meanings as understood by one of skill in the art in view of this disclosure, and can refer to a nucleic acid fragment that functions to control the transcription of one or more nucleic acid molecules, located upstream with respect to the direction of transcription of the transcription initiation site of the nucleic acid molecule, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate/control the amount of transcription from the promoter. A "constitutive" promoter is a promoter that is active under most environmental and developmental conditions. An "inducible" promoter is a promoter that is active under environmental or developmental regulation.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that an auto-replicative extra-chromosomal nucleic acid molecule, a microbial host (or a method) as defined herein may comprise additional component(s) (or additional steps) than the ones specifically identified, said additional component(s) (or additional steps) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety. The following examples are offered for illustrative purposes only, and are not intended to limit the scope of the present invention in any way

SEQUENCE LISTING (DNA UNLESS OTHERWISE INDICATED)

SEQ ID NO: 1 Enterococcus faecalis peptide
SEQ ID NO: 2 motif characteristic of bacteriocin
SEQ ID NO: 3 hybrid bacteriocin, Ent35-MccV
SEQ ID NO: 4-698, 720-759: Sequences in tables 1-3 (half DNA/half protein as indicated in the tables)
SEQ ID NO: 699 McbG
SEQ ID NO: 700 MccE
SEQ ID NO: 701 C terminal part of MccE
SEQ ID NO: 702 pSyn2-McbG
SEQ ID NO: 703 pSyn2-McbE/F
SEQ ID NO: 704 pMcbG1.0
SEQ ID NO: 705 pMcbG.1.1.
SEQ ID NO: 706 C-terminal part of MccE (amino acid)
SEQ ID NO: 707 P24 promoter
SEQ ID NO: 708 proC promoter
SEQ ID NO: 709 Cvi
SEQ ID NO: 710 proC-McbG-CterMccE(proc) (Cter could be replaced by C-terminal)
SEQ ID NO: 711 proC-Cvi-Cter-MccE (proc) (Cter could be replaced by C-terminal)
SEQ ID NO: 712 pBACT5.0
SEQ ID NO: 713 pBACT2.0
SEQ ID NO: 714 pBACT5.0-mcherry
SEQ ID NO: 715 McbG-MccE
SEQ ID NO: 716 McbG-Cter part MccE (Cter could be replaced by C-terminal)
SEQ ID NO: 717 Cvi-MccE
SEQ ID NO: 718 Cvi-Cter part MccE (Cter could be replaced by C-terminal)
SEQ ID NO: 719: vector pUC-ColV

EXAMPLES

Example 1: Use of Bacteriocin B17 and C7 as Selection Agent

1. Production of Bacteriocin B17, C7 and ColV

Strain used: C600: F⁻ tonA21 thi-1 thr-1 leuB6 lacY1 glnV44 rfbC1 fhuA1λ⁻

Described in Appleyard Genetics 39 (1954), 440-452.

The vector used for producing Mic B17 is described in the table below.

TABLE X

| Vector used for producing Mic B17 | |
| --- | --- |
| Construct used pCID909 | pACYC184 containing the mccB17-producing genes (mcbABCDEFG), chloramphenicol resistance |

These constructs were described in detail in Rodriguez-Sainz, M. C., C. et al. 1990. Mol. Microbiol. 4:1921-1932.

The vector used for producing Mic C7 is Pp70. This vector is based on pBR322 and bears a ~6000 bp DNA fragment with the mcc gene cluster (as described in Zukher I et al, *Nucleic Acids Research*, 2014, Vol. 42, No. 19 11891-11902).

The vector used for producing ColV is pUC-ColV (SEQ ID NO: 719). This vector is based on pUC57 and bear a ~5000 bp DNA fragment with the ColV gene cluster. The strains harbouring these recombinant vectors were grown in LB medium at 37° C.

After an overnight culture the fermented medium was centrifuged and the supernatant flit red on a 0.2 micron filter.

The bacteriocin activity present in the supernatant was estimated by the size of the diffusion inhibition growth on a plate containing a sensitive strain.

2. Results

We demonstrated that we can use the supernatants that exhibit B17, C7 or ColV activities as classical antibiotics such as Amp, Kan or Chlo added in culture medium. Supernatant presenting such a bacteriocin activity were stored for several months (at least 12 months) at −20° C. and we did not observe a significant decrease of activity. Petri plates containing medium with such a bacteriocin activity were stored at +4° C. for several weeks (at least 4 weeks). We did not observe a decrease of activity. Therefore we demonstrated that such B17, C7 or ColV activities as present in culture medium are stable.

3. Conclusion

Bacteriocins B17, C7 and ColV produced by fermentation in laboratory are selection agents simple to produce, easy to use and stable in culture medium. These properties are similar to the ones of antibiotics used as classical selection agent.

Example 2: Identification of the Minimum Genetic Elements Necessary to Confer Resistance to C7 and B17

1. Construction of Needed Vectors

The literature has made it possible to determine the elements necessary for the production of the host against the production of its own bacteriocin, also in the case of B17 bacteriocin: McbG for B17, represented by SEQ ID NO: 699 and pumps (McbE and McbF for B17, represented by SEQ ID NO: 703). These genes are known to be necessary (or more precisely involved in protection against the action of bacteriocin B17). The literature for the B17 locus does not identify which is or is the sufficient element to give resistance.

We have separated genes from B17 immunity structures and cloned these into vectors behind an inducible promoter (Ptac).

Figure 1:
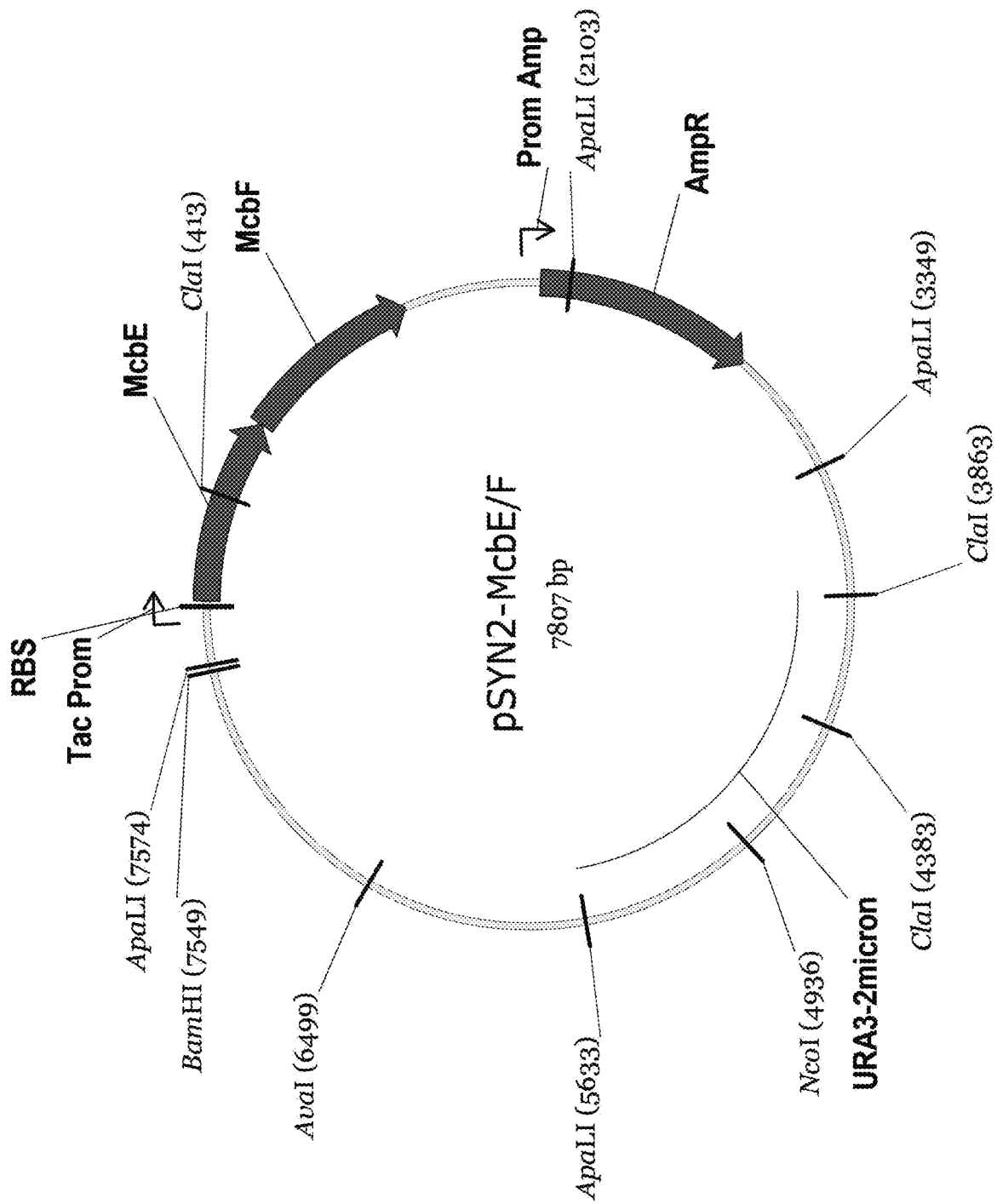
FIG. 1: Construction: pSyn2-McbE/F: containing the gene McbE and F under Ptac.
Figure 2:
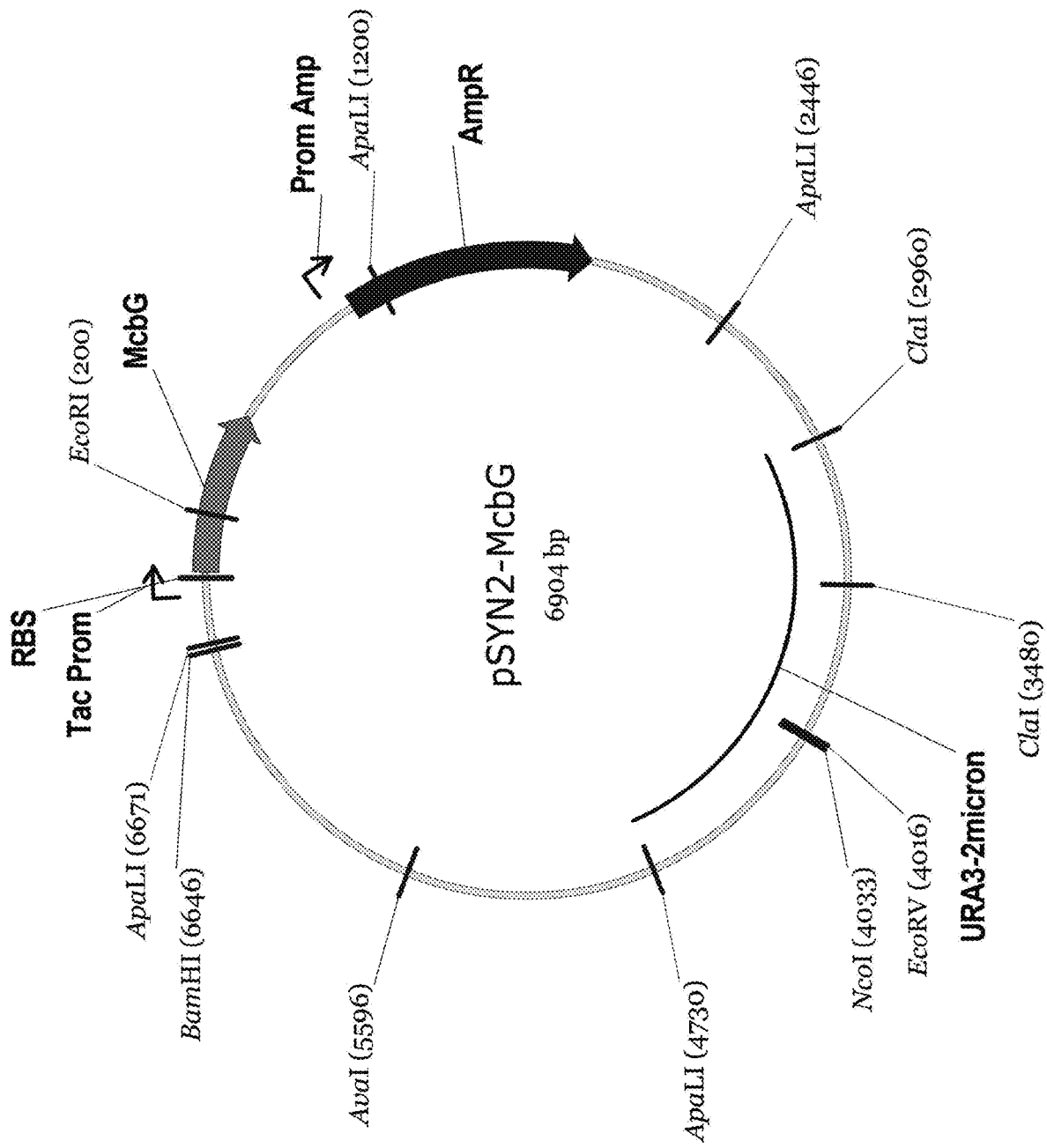
FIG. 2: Construction: pSyn2-McbG: containing the gene McbG under Ptac.

Construction: pSyn2-McbG (FIG. 2, SEQ ID NO: 702): containing the gene McbG under Ptac Construction: pSyn2-McbE/F (FIG. 1, SEQ ID NO: 703): containing the gene McbE and F under Ptac We have separated the genes from B17 immunity structures and cloned them into vectors behind an inducible promoter (Ptac).

We have shown that low McbG expression (Ptac not induced) is sufficient to give the phenotype of resistance to the strain on the other hand the presence of McbE/F is toxic and did not allow to give a response As to the protection provided in relation to the presence of B17.

2. Results

Surprisingly it has been found that the C-terminal part of MccE which is represented by SEQ ID NO: 701 is sufficient to confer resistance to bacteriocin C7.

Figure 6:
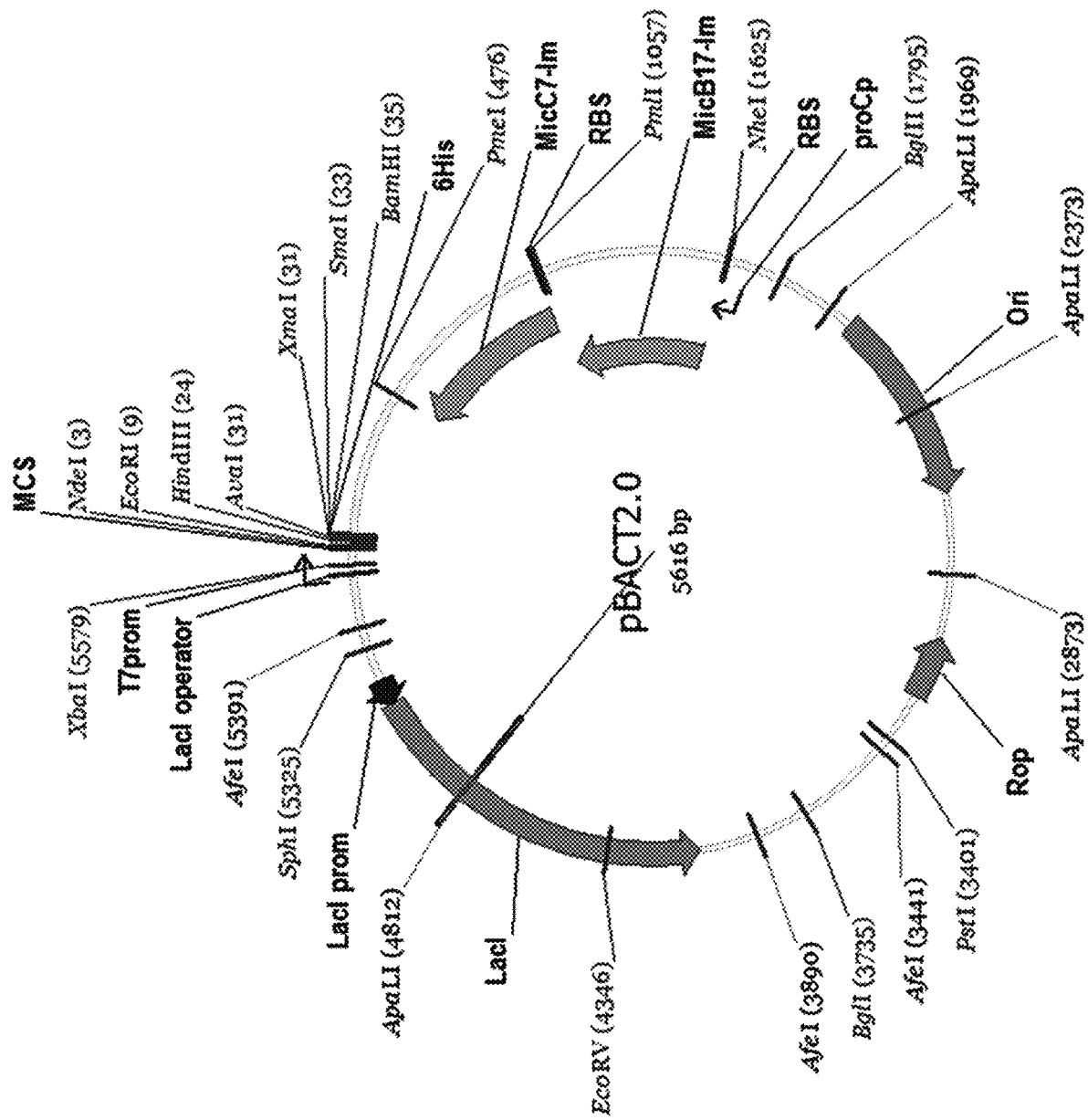
FIG. 6: pBACT2.0 vector

We have demonstrated that expression from a plasmid of the McbG and MccE genes (or truncated MccE, represented by SEQ ID NO: 701) are capable when cloned into a vector to give resistance to B17 and C7 respectively and that these proteins can be used as a vector selection marker in strains sensitive to these microcines/bacteriocins. The vector used is pBACT2.0 (FIG. 6, SEQ ID NO: 713).

SEQ ID NO: 710 represents the construct proC-McbG-CterMccE

Figure 5:
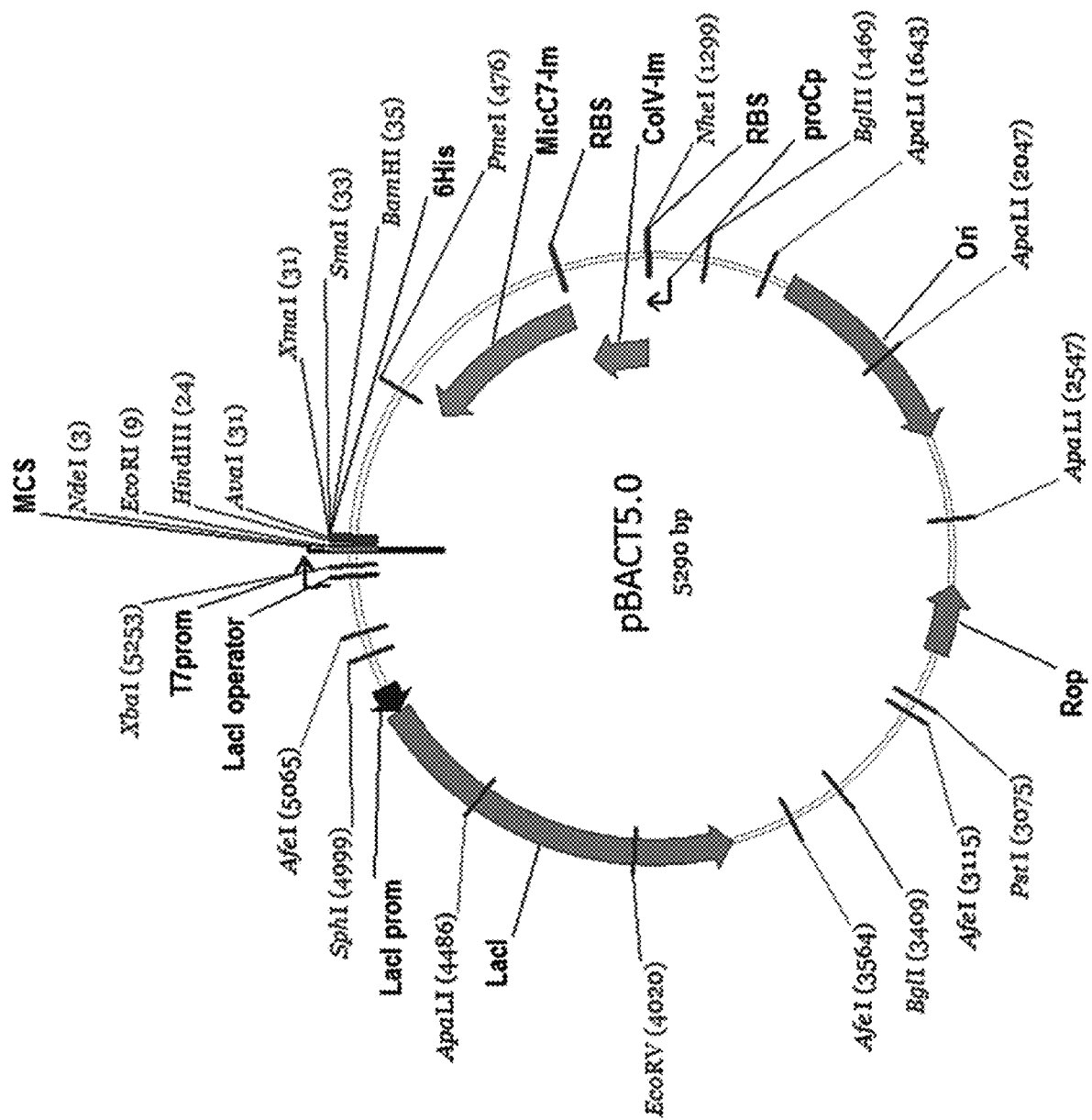
FIG. 5: pBACT5.0 vector

We have demonstrated that expression from a plasmid of the Cvi and C-terminal part of MccE genes are capable when cloned into a vector to give resistance to ColV and C7 respectively and that these proteins can be used as a vector selection marker in strains sensitive to these microcines/bacteriocins. The vector used is pBACT5.0 (FIG. 5, SEQ ID NO: 712).

SEQ ID NO: 711 represents the construct proC-Cvi-CterMccE

3. Conclusion

It is therefore possible to use a single segment of small size represented by SEQ ID NO: 701 as a selection marker against C7.

Example 3: Can we Generate a Selectable Marker Using Little or No Energy from the Bacteria from McbG?

1. Vectors Constructed

To answer this question the McbG gene was cloned under a weak promoter P24 (SEQ ID NO: 707). The P24 promoter was described in Braatsch S et al, Biotechniques. 2008 Sep.; 45(3):335-7.

We inserted the B17 McbG immunity structure gene and cloned the latter into vectors behind the weak constitutive promoter (P24). A second construct was generated with a P24 LacO hybrid promoter which is an inducible promoter repressed in the presence of lad and active in presence of IPTG.

Construction: pMcbG 1.0 (FIG. 4, SEQ ID NO: 704) containing the gene McbG under P24 LacO.

Construction: pMcbG 1.1 (FIG. 3, SEQ ID NO: 705) containing the gene McbG under P24.

The strains used are the following:

BL21(DE3): fhuA2 [lon] ompT gal (λ DE3) [dcm] ΔhsdS

λ DE3=λ sBamHIo ΔEcoRI-B int::(lacI::PlacUV5::T7 gene1) i21 Δnin5

Figure 3:
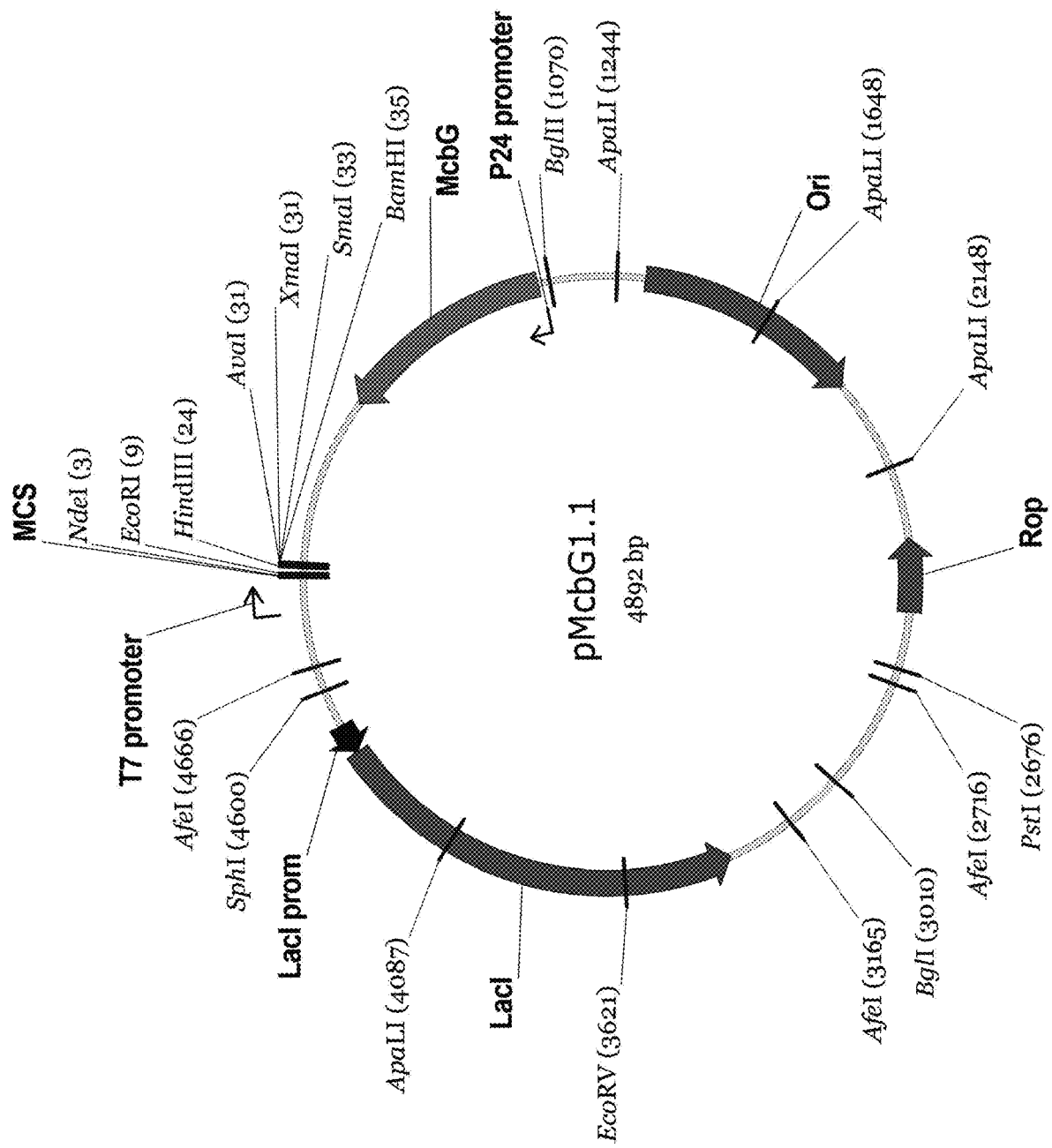
FIG. 3: Construction: pMcbG 1.1: containing the gene McbG under P24.
Figure 4:
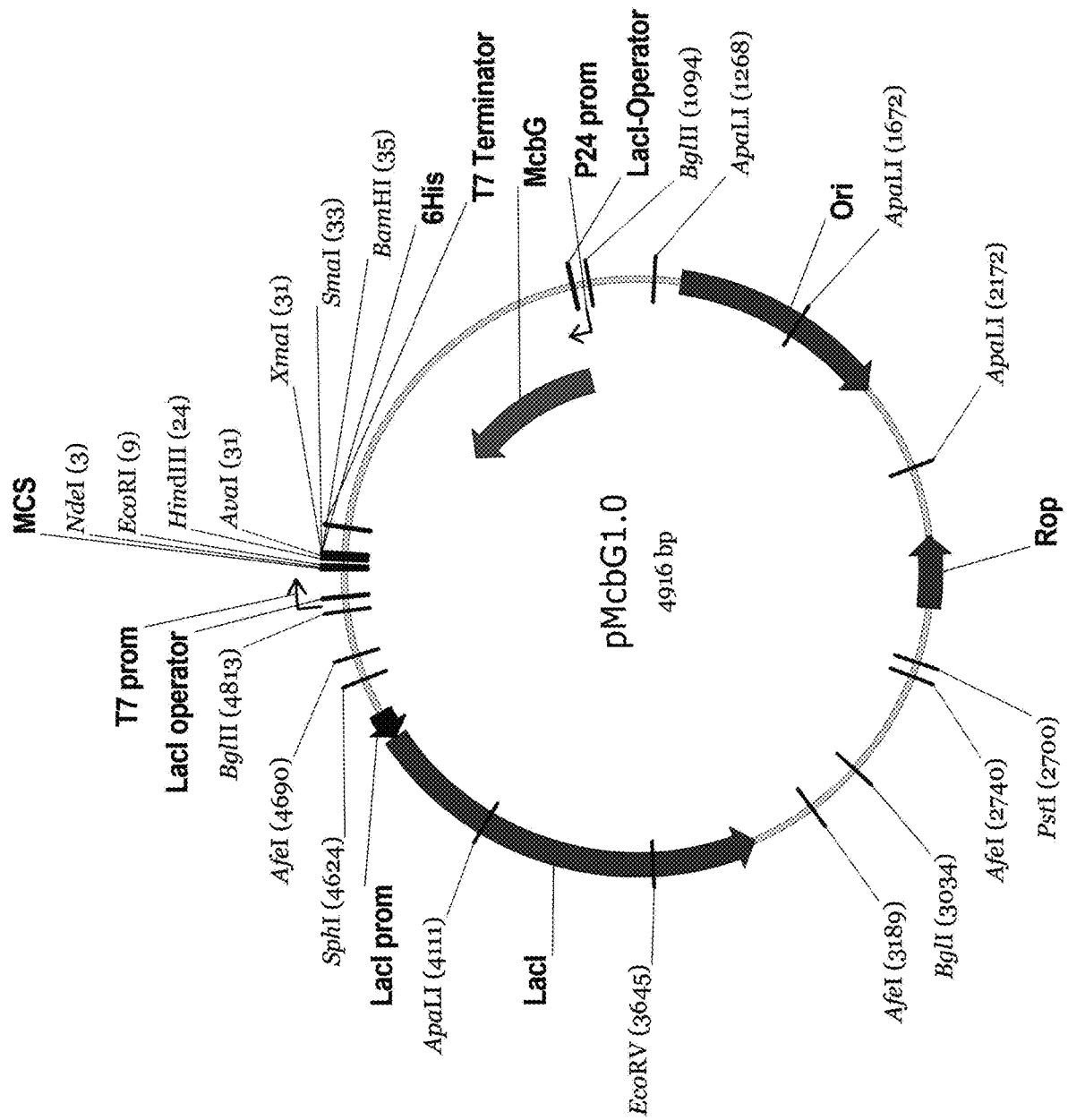
FIG. 4: Construction: pMcbG 1.0: containing the gene McbG under P24 LacO.

The BL21(DE3) strain was transformed with vector pMcbG1.0 or pMcbG1.1 (see FIG. 3 or 4). After transformation, transformants were selected on plates containing B17. Isolated colonies were re-grown and the plasmid they contained was analyzed by gel electrophoresis after treatment with relevant restriction enzymes.

2. Results

We showed that a weak transcription of McbG is sufficient to give the resistance to B17. In addition, we have shown that this selection marker is inducible via the P24 LacO promoter and that the vectors containing this gene gives the phenotype of resistance only in presence of IPTG.

3. Conclusions

It is possible to use the McbG gene as a selectable marker either constitutively or inducibly. Thus, it is shown that constitutive expression at a low level and inducible expression according to the need during the process, allows to

49 reduce the energy burden for the producing cell, without loss of the plasmid from the producing cell.

Example 4: Production of m-Cherry Protein

Figure 7:
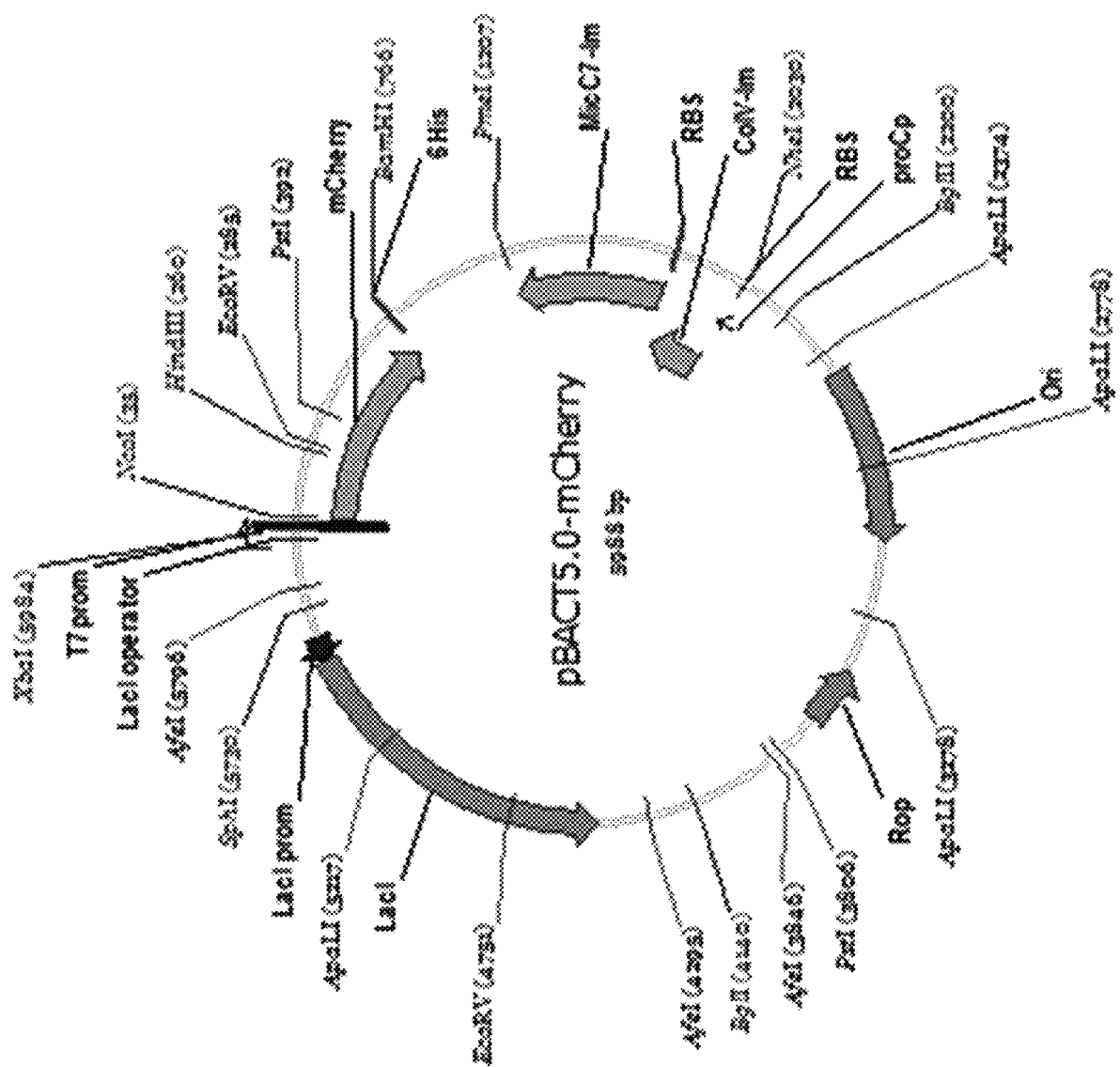
FIG. 7: pBACT5.0-mcherry vector

SEQ ID NO: 714 represents the construct used for producing the m-cherry protein. This construct is depicted in FIG. 7.

The m-cherry protein was produced and visualised as the bacterial colony turns red on petri dish in the presence of IPTG.

Example 5: Tuning Promoter

Figure 8:
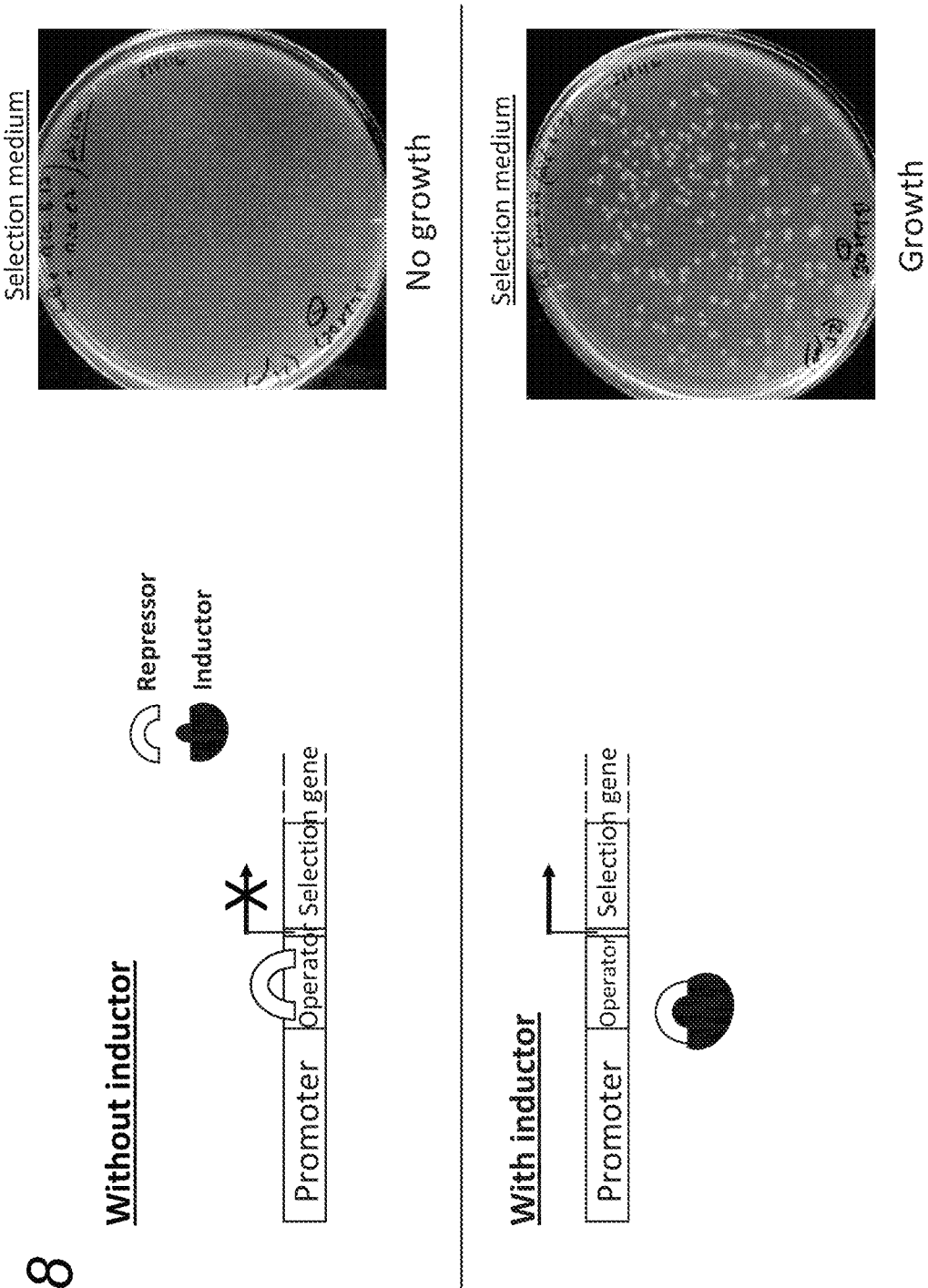
FIG. 8: Tuning promoter. In the absence of inductor (upper part), repressor can bind to operator and prevent expression of selection gene. In the presence of inductor (lower part), repressor cannot bind to operator allowing expression of selection gene.

We have prepared vectors with immunity selection that is tunable (see FIG. 8). Tuning the promoter allows us to switch the selection "on" or "off". For the first time this allows to adapt the selective pressure to the need during the fermentation process, for example according to the loss by the host of the recombinant plasmid. This will provide an advantage by limiting the burden of energy for the host. Thus, such vectors improve the industrial outcome (recombinant product). Moreover, they are easy to use in any strain (no requirement for a special feature in the host genome) and require no antibiotics.

Example 6: Comparison of Antibiotic (Kanamycin) Selection with Immunity Selection We have applied immunity selection on different recombinant proteins.

Figure 9:
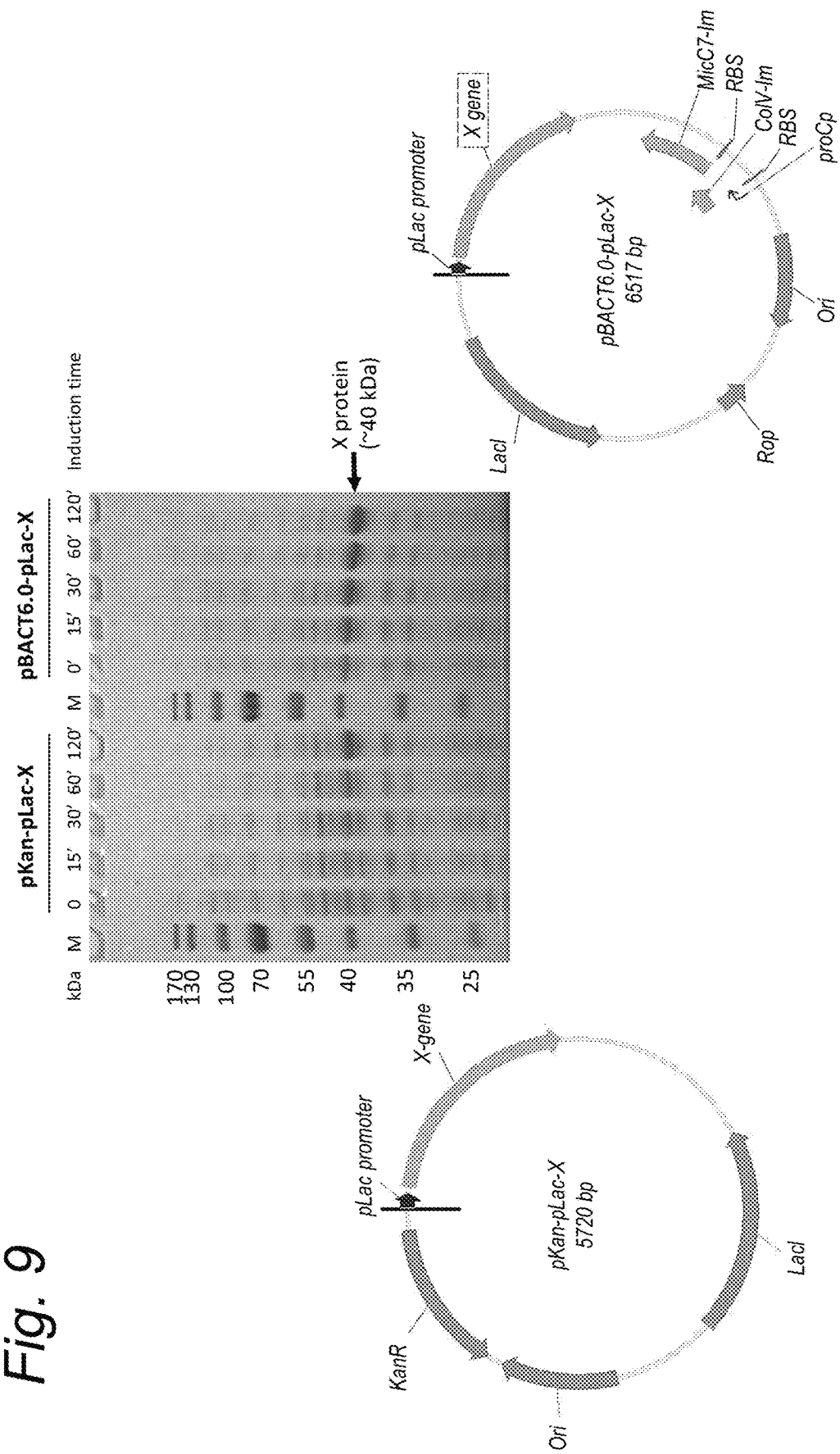
FIG. 9: Comparison of overexpression of protein X in E. coli with KanR (pKan-pLac) and with 2 immunities against microcines C7 and ColV (pBACT6.0-pLac). 5 mg of total extract was analysed in SDS-PAGE.

FIG. 9 shows the comparison of overexpression of protein X in *E. coli* with KanR (pKan-pLac) and with 2 immunities against microcines C7 and ColV (pBACT6.0-pLac). 5 mg of total extract was analysed in SDS-PAGE.

Figure 10:
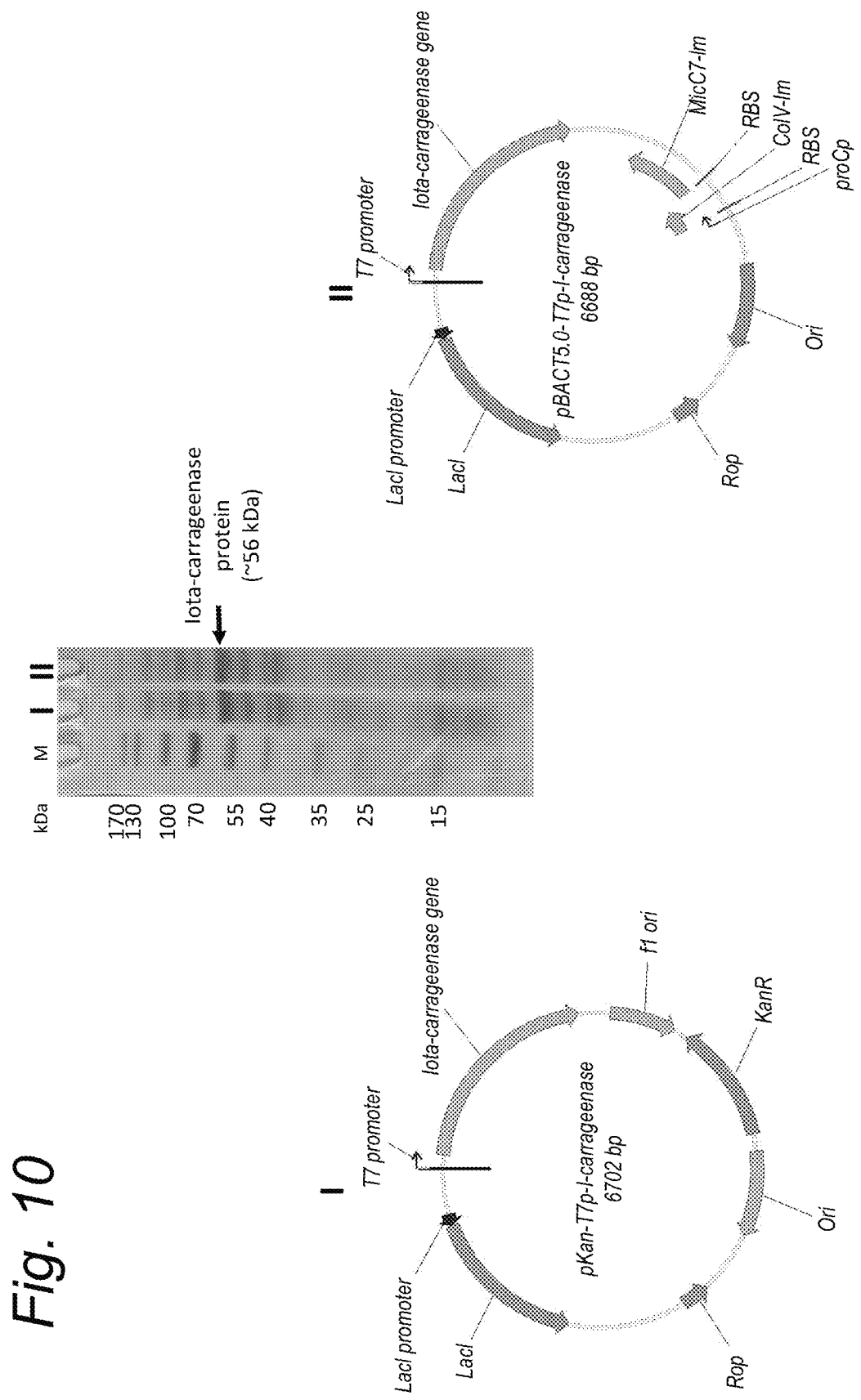
FIG. 10: Comparison of overexpression of iota-carrageenase protein in E. coli with KanR (pKan-T7prom) and with 2 immunities against microcines C7 and ColV (pBACT5.0-T7prom). 5 mg of total extract was analysed in SDS-PAGE.

FIG. 10 shows the comparison of overexpression of iota-carrageenase protein in *E. coli* with KanR (pKan-T7prom) and with 2 immunities against microcines C7 and ColV (pBACT5.0-T7prom). 5 mg of total extract was analysed in SDS-PAGE. The vector used is based on the pBACT5.0 vector (SEQ ID NO: 712).

Figure 11:
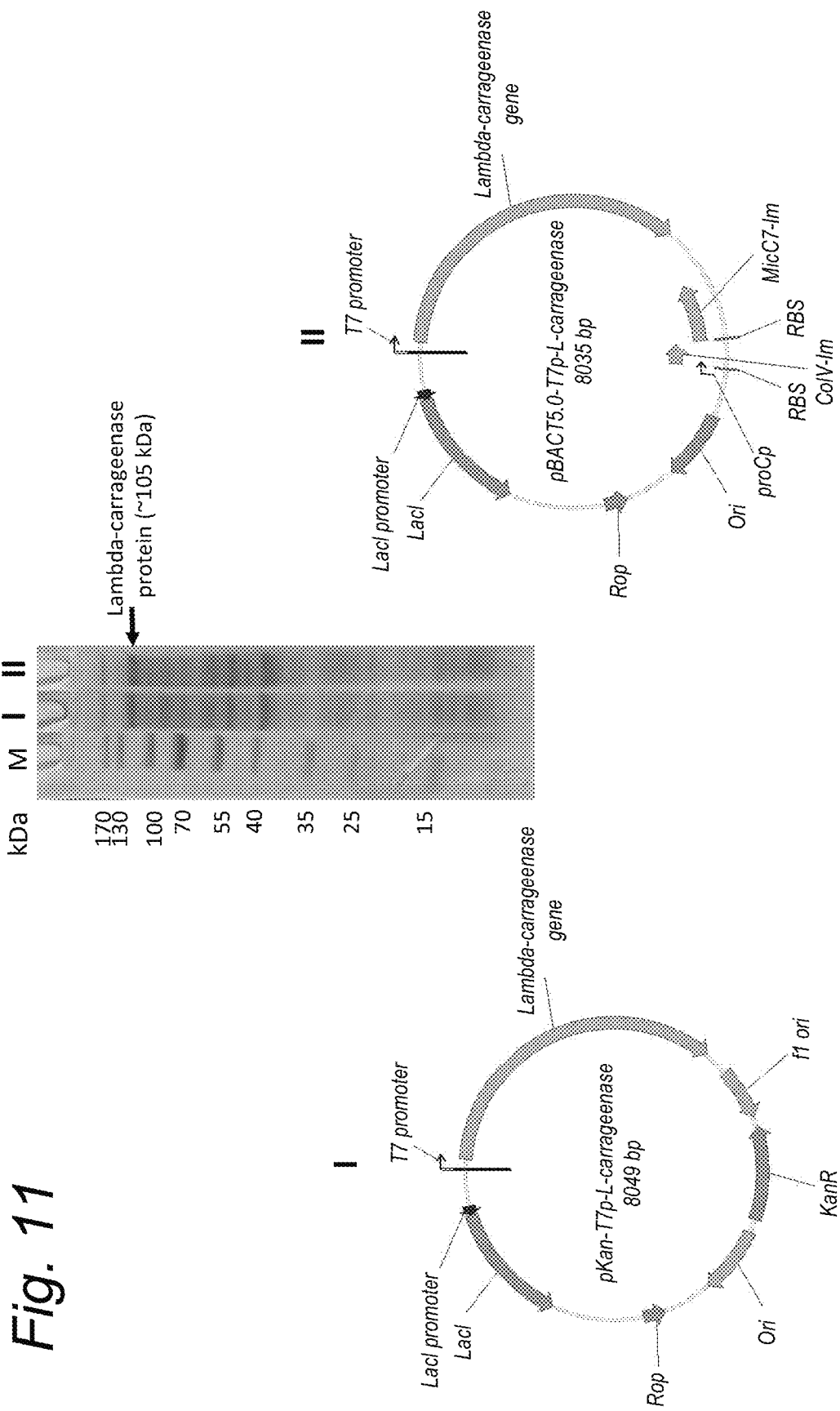
FIG. 11: Comparison of overexpression of lambda-carrageenase protein in E. coli with KanR (pKan-T7prom) and with 2 immunities against microcines C7 and ColV (pBACT5.0-T7prom). 5 mg of total extract was analysed in SDS-PAGE.

FIG. 11 shows the comparison of overexpression of lambda-carrageenase protein in *E. coli* with KanR (pKan-T7prom) and with 2 immunities against microcines C7 and ColV (pBACT5.0-T7prom). 5 mg of total extract was analysed in SDS-PAGE. The vector used is based on the pBACT5.0 vector (SEQ ID NO: 712).

The weak constitutive proC promoter used in this example allows to reduce the energy burden for the host.

The invention claimed is:

1. A method for producing a product of interest with a microbial host, said method comprising the steps of:
   a) providing the microbial host comprising i) an auto-replicative extra-chromosomal nucleic acid molecule comprising a first nucleic acid sequence whose genetic activity confers immunity or resistance to a bacteriocin to the microbial host, wherein the genetic activity of said first nucleic acid sequence is controlled and ii) a second nucleic acid sequence coding for said product of interest; and
   b) culturing said transformed microbial host under conditions allowing said transformed microbial host to express the first nucleic acid sequence to a given level such that the genetic activity of the first nucleic acid sequence confers a selective advantage to the microbial host during the culturing, to thereby maintain the auto-replicative extra-chromosomal molecule in the growing microbial population, and simultaneously genetically controlling the second nucleic acid sequence to produce said product of interest,
   wherein during at least a portion of the culturing of step b) conditions are such that the first nucleic acid sequence does not exhibit said genetic activity thereby reducing the energetic burden for the microbial host cell during the production of the product of interest.

2. The method of claim 1, further comprising transforming the microbial host with said auto-replicative extra-chromosomal nucleic acid molecule prior to or during step a), thereby providing the microbial host comprising the auto-replicative extra-chromosomal nucleic acid molecule.

3. The method of claim 1, wherein the product of interest is purified at the end of the culturing step b).

4. The method of claim 1, wherein the product of interest is a microbial biomass, the auto-replicative extra-chromosomal nucleic acid molecule, the transcript of said second nucleic sequence, a polypeptide encoded by said second sequence or a metabolite produced directly or indirectly by said polypeptide.

5. The method of claim 1, wherein the microbial host is a bacterium, yeast, filamentous fungus or an algae.

6. The method of claim 1, wherein the first nucleic acid sequence is operably linked to an inducible promoter.

7. The method of claim 1, wherein the first nucleic acid sequence comprises an immunity gene whose expression confers to its microbial host a resistance to the presence of a specific bacteriocin in the medium.

8. The method of claim 7, wherein the sequence encoded by the first nucleic acid sequence confers to its microbial host a resistance to the presence of at least two distinct bacteriocins in the medium.

9. The method of claim 8, wherein the bacteriocin is B17, C7 or Colicin-V (ColV) and the immunity conferring resistance to a B17 is McbG, to C7 is either MccE or C-terminal MccE and to a ColV is Colicin-V immunity modulator (Cvi).

10. The method of claim 1, wherein the auto-replicative extra-chromosomal nucleic acid molecule is a plasmid.

11. The method of claim 1, wherein the genetic activity of said second nucleic acid sequence is controlled independently from the genetic activity of said first nucleic acid sequence.

12. The method of claim 1, wherein said auto-replicative extra-chromosomal nucleic acid molecule comprises said second nucleic acid sequence.

13. The method of claim 2, wherein the auto-replicative extra-chromosomal nucleic acid molecule comprises said second nucleic acid sequence.

14. The method of claim 1, wherein the first nucleic acid sequence is operably linked to a weak constitutive promoter.

15. The method of claim 1, wherein the method is a fermentation method.

16. The method of claim 1, wherein the product of interest comprises an industrially useful molecule.

17. The method of claim 16, wherein the industrially useful molecule is a carbohydrate, a lipid, an organic molecule, a nutrient, a biofuel, or precursor thereof, a pharmaceutical or biopharmaceutical product or precursor thereof, or two or more of said molecules.

* * * * *

SEQUENCE LISTING

```
<160> NUMBER OF SEQ ID NOS: 759

<210> SEQ ID NO 1
<211> LENGTH: 40
<212> TYPE: PRT
<213> ORGANISM: Enterococcus faecalis

<400> SEQUENCE: 1

Trp Leu Pro Pro Ala Gly Leu Leu Gly Arg Cys Gly Arg Trp Phe Arg
1               5                   10                  15

Pro Trp Leu Leu Trp Leu Gln Ser Gly Ala Gln Tyr Lys Trp Leu Gly
            20                  25                  30

Asn Leu Phe Gly Leu Gly Pro Lys
        35                  40

<210> SEQ ID NO 2
<211> LENGTH: 5
<212> TYPE: PRT
<213> ORGANISM: Artificial Sequence
<220> FEATURE:
<223> OTHER INFORMATION: N-terminal motif of class terminal IIa
<220> FEATURE:
<221> NAME/KEY: VARIANT
<222> LOCATION: (3)..(3)
<223> OTHER INFORMATION: Xaa = any amino acid

<400> SEQUENCE: 2

Tyr Gly Xaa Gly Val
1               5

<210> SEQ ID NO 3
<211> LENGTH: 135
<212> TYPE: PRT
<213> ORGANISM: Artificial Sequence
<220> FEATURE:
<223> OTHER INFORMATION: Hybrid bacteriocin Ent35-MccV

<400> SEQUENCE: 3

Gly Lys Tyr Tyr Gly Asn Gly Val Ser Cys Asn Lys Lys Gly Cys Ser
```

```
1               5                   10                  15
Val Asp Trp Gly Arg Ala Ile Gly Ile Ile Gly Asn Asn Ser Ala Ala
                    20                  25                  30

Asn Leu Ala Thr Gly Gly Ala Ala Gly Trp Lys Ser Gly Gly Gly Ala
                35                  40                  45

Ser Gly Arg Asp Ile Ala Met Ala Ile Gly Thr Leu Ser Gly Gln Phe
        50                  55                  60

Val Ala Gly Gly Ile Gly Ala Ala Gly Gly Val Ala Gly Gly Ala
65                  70                  75                  80

Ile Tyr Asp Tyr Ala Ser Thr His Lys Pro Asn Pro Ala Met Ser Pro
                    85                  90                  95

Ser Gly Leu Gly Gly Thr Ile Lys Gln Lys Pro Glu Gly Ile Pro Ser
                100                 105                 110

Glu Ala Trp Asn Tyr Ala Ala Gly Arg Leu Cys Asn Trp Ser Pro Asn
                115                 120                 125

Asn Leu Ser Asp Val Cys Leu
            130                 135

<210> SEQ ID NO 4
<211> LENGTH: 46
<212> TYPE: PRT
<213> ORGANISM: Lactobacillus acidophilus

<400> SEQUENCE: 4

Met Ile Ser Ser His Gln Lys Thr Leu Thr Asp Lys Glu Leu Ala Leu
1               5                   10                  15

Ile Ser Gly Gly Lys Thr His Tyr Pro Thr Asn Ala Trp Lys Ser Leu
                20                  25                  30

Trp Lys Gly Phe Trp Glu Ser Leu Arg Tyr Thr Asp Gly Phe
            35                  40                  45

<210> SEQ ID NO 5
<211> LENGTH: 141
<212> TYPE: DNA
<213> ORGANISM: Lactobacillus acidophilus

<400> SEQUENCE: 5
atgatttcat ctcatcaaaa aacgttaact gataaagaat tagcattaat ttctgggggg    60
aaaacgcact acccgactaa tgcatggaaa agtctttgga aggtttctg ggaaagcctt    120 cgttatactg acggttttta g                                              141

<210> SEQ ID NO 6
<211> LENGTH: 81
<212> TYPE: PRT
<213> ORGANISM: Lactobacillus acidophilus

<400> SEQUENCE: 6

Met Ile Ser Met Ile Ser Ser His Gln Lys Thr Leu Thr Asp Lys Glu
1               5                   10                  15

Leu Ala Leu Ile Ser Gly Gly Lys Thr Tyr Tyr Gly Thr Asn Gly Val
                20                  25                  30

His Cys Thr Lys Lys Ser Leu Trp Gly Lys Val Arg Leu Lys Asn Val
            35                  40                  45

Ile Pro Gly Thr Leu Cys Arg Lys Gln Ser Leu Pro Ile Lys Gln Asp
        50                  55                  60

Leu Lys Ile Leu Leu Gly Trp Ala Thr Gly Ala Phe Gly Lys Thr Phe
65                  70                  75                  80
```

His

<210> SEQ ID NO 7
<211> LENGTH: 246
<212> TYPE: DNA
<213> ORGANISM: Lactobacillus acidophilus

<400> SEQUENCE: 7

```
atgatttcaa tgatttcatc tcatcaaaaa acgttaactg ataaagaatt agcattaatt        60
tctgggggga aaacgtacta tggtactaat ggtgtgcatt gtactaaaaa gagtctttgg       120
ggtaaagtac gcttaaaaaa cgtgattcct ggaactcttt gtcgtaagca atcgttgccg       180
atcaaacagg atttaaaaat tttactgggc tgggctacag gtgcttttgg caagacattt       240
cattaa                                                                  246
```

<210> SEQ ID NO 8
<211> LENGTH: 60
<212> TYPE: PRT
<213> ORGANISM: Lactobacillus acidophilus

<400> SEQUENCE: 8

```
Met Asp Lys Lys Thr Lys Ile Leu Phe Glu Val Leu Tyr Ile Ile Cys
1               5                   10                  15

Ile Ile Gly Pro Gln Phe Ile Leu Phe Val Thr Ala Lys Asn Asn Met
            20                  25                  30

Tyr Gln Leu Val Gly Ser Phe Val Gly Ile Val Trp Phe Ser Tyr Ile
        35                  40                  45

Phe Trp Tyr Ile Phe Phe Lys Gln His Lys Lys Met
    50                  55                  60
```

<210> SEQ ID NO 9
<211> LENGTH: 183
<212> TYPE: DNA
<213> ORGANISM: Lactobacillus acidophilus

<400> SEQUENCE: 9

```
atggataaga aaacaaaaat attatttgaa gtattataca tcatctgtat aataggccct        60
caatttatat tatttgtgac tgcaaaaaac aatatgtatc agttggtggg ttcgtttgtt       120
ggaatagtat ggttttcgta tattttttgg tatattttt tcaaacaaca taaaaaaatg       180
tag                                                                     183
```

<210> SEQ ID NO 10
<211> LENGTH: 65
<212> TYPE: PRT
<213> ORGANISM: Lactobacillus gasseri

<400> SEQUENCE: 10

```
Met Ala Leu Lys Thr Leu Glu Lys His Glu Leu Arg Asn Val Met Gly
1               5                   10                  15

Gly Asn Lys Trp Gly Asn Ala Val Ile Gly Ala Ala Thr Gly Ala Thr
            20                  25                  30

Arg Gly Val Ser Trp Cys Arg Gly Phe Gly Pro Trp Gly Met Thr Ala
        35                  40                  45

Cys Ala Leu Gly Gly Ala Ala Ile Gly Gly Tyr Leu Gly Tyr Lys Ser
    50                  55                  60

Asn
65
```

<210> SEQ ID NO 11
<211> LENGTH: 198
<212> TYPE: DNA
<213> ORGANISM: Lactobacillus gasseri

<400> SEQUENCE: 11

```
atggctttaa aaacattaga aaaacatgaa ttaagaaatg taatgggtgg aaacaagtgg      60
gggaatgctg taataggagc tgctacggga gctactcgcg gagtaagttg gtgcagagga     120
ttcggaccat ggggaatgac tgcctgtgcg ttaggaggtg ctgcaattgg aggatatctg     180
ggatataaga gtaattaa                                                   198
```

<210> SEQ ID NO 12
<211> LENGTH: 51
<212> TYPE: PRT
<213> ORGANISM: Staphylococcus aureus

<400> SEQUENCE: 12

```
Met Ser Trp Leu Asn Phe Leu Lys Tyr Ile Ala Lys Tyr Gly Lys Lys
1               5                   10                  15

Ala Val Ser Ala Ala Trp Lys Tyr Lys Gly Lys Val Leu Glu Trp Leu
            20                  25                  30

Asn Val Gly Pro Thr Leu Glu Trp Val Trp Gln Lys Leu Lys Lys Ile
        35                  40                  45

Ala Gly Leu
    50
```

<210> SEQ ID NO 13
<211> LENGTH: 156
<212> TYPE: DNA
<213> ORGANISM: Staphylococcus aureus

<400> SEQUENCE: 13

```
atgagttggt taaatttttt aaaatacatc gctaaatatg gcaaaaaagc ggtatctgct      60
gcttggaagt acaaaggtaa agtattagaa tggcttaatg ttggtcctac tcttgaatgg     120
gtatggcaaa aattaaagaa aattgctgga ttataa                               156
```

<210> SEQ ID NO 14
<211> LENGTH: 61
<212> TYPE: PRT
<213> ORGANISM: Enterococcus avium

<400> SEQUENCE: 14

```
Met Thr Arg Ser Lys Lys Leu Asn Leu Arg Glu Met Lys Asn Val Val
1               5                   10                  15

Gly Gly Thr Tyr Tyr Gly Asn Gly Val Ser Cys Asn Lys Lys Gly Cys
            20                  25                  30

Ser Val Asp Trp Gly Lys Ala Ile Ser Ile Ile Gly Asn Asn Ser Ala
        35                  40                  45

Ala Asn Leu Ala Thr Gly Gly Ala Ala Gly Trp Lys Ser
    50                  55                  60
```

<210> SEQ ID NO 15
<211> LENGTH: 186
<212> TYPE: DNA
<213> ORGANISM: Enterococcus avium

<400> SEQUENCE: 15

```
atgacaagat caaaaaaatt aaatttacgc gaaatgaaga atgttgttgg tggtacctac      60
tatggaaatg gtgtatcttg taacaagaaa ggctgttcag ttgactgggg caaagccatc     120
agtattatag gaaataattc cgcagcaaac ttagcaactg gtggtgctgc tggttggaag     180
tcataa                                                                186
```

```
<210> SEQ ID NO 16
<211> LENGTH: 67
<212> TYPE: PRT
<213> ORGANISM: Enterococcus faecalis

<400> SEQUENCE: 16

Met Lys Lys Leu Val Ile Cys Gly Ile Ile Gly Ile Gly Phe Thr
1               5                   10                  15

Ala Leu Gly Thr Asn Val Glu Ala Ala Thr Tyr Tyr Gly Asn Gly Leu
            20                  25                  30

Tyr Cys Asn Lys Gln Lys Cys Trp Val Asp Trp Asn Lys Ala Ser Arg
        35                  40                  45

Glu Ile Gly Lys Ile Ile Val Asn Gly Trp Val Gln His Gly Pro Trp
    50                  55                  60

Ala Pro Arg
65
```

```
<210> SEQ ID NO 17
<211> LENGTH: 204
<212> TYPE: DNA
<213> ORGANISM: Enterococcus faecalis

<400> SEQUENCE: 17
atgaaaaaga aattagttat ttgtggcatt attgggattg gttttacagc attaggaaca      60
aatgtagaag ctgctacgta ttacggaaat ggtttatatt gtaataagca aaaatgttgg     120
gtagactgga ataaagcttc aagggaaatt ggaaaaatta ttgttaatgg ttgggtacaa     180
catggccctt gggctcctag atag                                            204
```

```
<210> SEQ ID NO 18
<211> LENGTH: 51
<212> TYPE: PRT
<213> ORGANISM: Lactococcus lactis

<400> SEQUENCE: 18

Met Lys Glu Gln Asn Ser Phe Asn Leu Leu Gln Glu Val Thr Glu Ser
1               5                   10                  15

Glu Leu Asp Leu Ile Leu Gly Ala Lys Gly Gly Ser Gly Val Ile His
            20                  25                  30

Thr Ile Ser His Glu Val Ile Tyr Asn Ser Trp Asn Phe Val Phe Thr
        35                  40                  45

Cys Cys Ser
    50
```

```
<210> SEQ ID NO 19
<211> LENGTH: 156
<212> TYPE: DNA
<213> ORGANISM: Lactococcus lactis

<400> SEQUENCE: 19
atgaaagaac aaaactcttt taatcttctt caagaagtga cagaaagtga attggacctt      60
attttaggtg caaaaggcgg cagtggagtt attcatacaa tttctcatga agtaatatat     120
```
aatagctgga actttgtatt tacttgctgc tcttaa 156

<210> SEQ ID NO 20
<211> LENGTH: 74
<212> TYPE: PRT
<213> ORGANISM: Enterococcus faecium

<400> SEQUENCE: 20

```
Met Lys Lys Lys Val Leu Lys His Cys Val Ile Leu Gly Ile Leu Gly
1               5                   10                  15

Thr Cys Leu Ala Gly Ile Gly Thr Gly Ile Lys Val Asp Ala Ala Thr
            20                  25                  30

Tyr Tyr Gly Asn Gly Leu Tyr Cys Asn Lys Glu Lys Cys Trp Val Asp
        35                  40                  45

Trp Asn Gln Ala Lys Gly Glu Ile Gly Lys Ile Ile Val Asn Gly Trp
    50                  55                  60

Val Asn His Gly Pro Trp Ala Pro Arg Arg
65                  70
```

<210> SEQ ID NO 21
<211> LENGTH: 225
<212> TYPE: DNA
<213> ORGANISM: Enterococcus faecium

<400> SEQUENCE: 21
atgaaaaaga aagtattaaa acattgtgtt attctaggaa tattaggaac ttgtctagct 60
ggcatcggta caggaataaa agttgatgca gctacttact atggaaatgg tctttattgt 120
aacaaagaaa aatgttgggt agattggaat caagctaaag gagaaattgg aaaaattatt 180
gttaatggtt gggttaatca tggtccatgg gcacctagaa ggtag 225

<210> SEQ ID NO 22
<211> LENGTH: 50
<212> TYPE: PRT
<213> ORGANISM: Clostridium botulinum

<400> SEQUENCE: 22

```
Met Gln Lys Pro Glu Ile Ile Ser Ala Asp Leu Gly Leu Cys Ala Val
1               5                   10                  15

Asn Glu Phe Val Ala Leu Ala Ala Ile Pro Gly Gly Ala Ala Thr Phe
            20                  25                  30

Ala Val Cys Gln Met Pro Asn Leu Asp Glu Ile Val Ser Asn Ala Ala
        35                  40                  45

Tyr Val
    50
```

<210> SEQ ID NO 23
<211> LENGTH: 153
<212> TYPE: DNA
<213> ORGANISM: Clostridium botulinum

<400> SEQUENCE: 23
atgcaaaaac cagaaattat tagtgctgat ttagggcttt gtgcagttaa tgaatttgta 60
gctcttgctg ccattcctgg tggtgctgct acatttgcag atgccaaat gccaaacttg 120 gatgagattg ttagtaatgc agcatatgtt taa 153

<210> SEQ ID NO 24
<211> LENGTH: 58
<212> TYPE: PRT

<213> ORGANISM: Streptococcus equinus

<400> SEQUENCE: 24

```
Met Met Asn Ala Thr Glu Asn Gln Ile Phe Val Glu Thr Val Ser Asp
1               5                   10                  15

Gln Glu Leu Glu Met Leu Ile Gly Gly Ala Asp Arg Gly Trp Ile Lys
            20                  25                  30

Thr Leu Thr Lys Asp Cys Pro Asn Val Ile Ser Ser Ile Cys Ala Gly
        35                  40                  45

Thr Ile Ile Thr Ala Cys Lys Asn Cys Ala
    50                  55
```

<210> SEQ ID NO 25
<211> LENGTH: 177
<212> TYPE: DNA
<213> ORGANISM: Streptococcus equinus

<400> SEQUENCE: 25

```
atgatgaatg ctactgaaaa ccaaattttt gttgagactg tgagtgacca agaattagaa    60
atgttaattg gtggtgcaga tcgtggatgg attaagactt taacaaaaga ttgtccaaat   120
gtaatttctt caatttgtgc aggtacaatt attacagctt gtaaaaattg tgcttaa     177
```

<210> SEQ ID NO 26
<211> LENGTH: 77
<212> TYPE: PRT
<213> ORGANISM: Brochothrix campestris

<400> SEQUENCE: 26

```
Met His Lys Val Lys Lys Leu Asn Asn Gln Glu Leu Gln Gln Ile Val
1               5                   10                  15

Gly Gly Tyr Ser Ser Lys Asp Cys Leu Lys Asp Ile Gly Lys Gly Ile
            20                  25                  30

Gly Ala Gly Thr Val Ala Gly Ala Ala Gly Gly Leu Ala Ala Gly
        35                  40                  45

Leu Gly Ala Ile Pro Gly Ala Phe Val Gly Ala His Phe Gly Val Ile
    50                  55                  60

Gly Gly Ser Ala Ala Cys Ile Gly Gly Leu Leu Gly Asn
65                  70                  75
```

<210> SEQ ID NO 27
<211> LENGTH: 234
<212> TYPE: DNA
<213> ORGANISM: Brochothrix campestris

<400> SEQUENCE: 27

```
atgcacaagg taaaaaaatt aaacaatcaa gagttacaac agatcgtggg aggttacagt    60
tcaaaagatt gtctaaaaga tattggtaaa ggaattggtg ctggtacagt agctggggca   120
gccggcggtg gcctagctgc aggattaggt gctatcccag gagcattcgt tggagcacat   180
tttggagtaa tcggcggatc tgccgcatgc attggtggat tattaggtaa ctag         234
```

<210> SEQ ID NO 28
<211> LENGTH: 80
<212> TYPE: PRT
<213> ORGANISM: Butyrivibrio fibrisolvens

<400> SEQUENCE: 28

```
Met Ser Lys Lys Gln Ile Met Ser Asn Cys Ile Ser Ile Ala Leu Leu
1               5                   10                  15
```

Ile Ala Leu Ile Pro Asn Ile Tyr Phe Ile Ala Asp Lys Met Gly Ile
            20                  25                  30

Gln Leu Ala Pro Ala Trp Tyr Gln Asp Ile Val Asn Trp Val Ser Ala
        35                  40                  45

Gly Gly Thr Leu Thr Thr Gly Phe Ala Ile Ile Val Gly Val Thr Val
    50                  55                  60

Pro Ala Trp Ile Ala Glu Ala Ala Ala Phe Gly Ile Ala Ser Ala
65                  70                  75                  80

<210> SEQ ID NO 29
<211> LENGTH: 243
<212> TYPE: DNA
<213> ORGANISM: Butyrivibrio fibrisolvens

<400> SEQUENCE: 29
atgagtaaaa aacaaattat gagtaactgt atatcaattg cattattaat agcactaatt      60
cctaatatct attttattgc agataaaatg ggaattcagt tagcacctgc ttggtatcaa     120
gatattgtga attgggtatc tgctggtgga acacttacta ctggttttgc gattattgta     180
ggagttacag taccggcatg gatagcagaa gcagctgcag cttttggtat agcttcagca     240
tga                                                                   243

<210> SEQ ID NO 30
<211> LENGTH: 48
<212> TYPE: PRT
<213> ORGANISM: Butyrivibrio fibrisolvens

<400> SEQUENCE: 30

Met Asn Lys Glu Leu Asn Ala Leu Thr Asn Pro Ile Asp Glu Lys Glu
1               5                   10                  15

Leu Glu Gln Ile Leu Gly Gly Gly Asn Gly Val Ile Lys Thr Ile Ser
            20                  25                  30

His Glu Cys His Met Asn Thr Trp Gln Phe Ile Phe Thr Cys Cys Ser
        35                  40                  45

<210> SEQ ID NO 31
<211> LENGTH: 147
<212> TYPE: DNA
<213> ORGANISM: Butyrivibrio fibrisolvens

<400> SEQUENCE: 31
atgaacaaag aacttaatgc acttacaaat cctattgacg agaaggagct tgagcagatc      60
ctcggtggtg gcaatggtgt catcaagaca atcagccacg agtgccacat gaacacatgg     120
cagttcattt tcacatgttg ctcttaa                                         147

<210> SEQ ID NO 32
<211> LENGTH: 66
<212> TYPE: PRT
<213> ORGANISM: Carnobacterium maltaromaticum

<400> SEQUENCE: 32

Met Asn Ser Val Lys Glu Leu Asn Val Lys Glu Met Lys Gln Leu His
1               5                   10                  15

Gly Gly Val Asn Tyr Gly Asn Gly Val Ser Cys Ser Lys Thr Lys Cys
            20                  25                  30

Ser Val Asn Trp Gly Gln Ala Phe Gln Glu Arg Tyr Thr Ala Gly Ile
        35                  40                  45

Asn Ser Phe Val Ser Gly Val Ala Ser Gly Ala Gly Ser Ile Gly Arg
        50                  55                  60

Arg Pro
65

<210> SEQ ID NO 33
<211> LENGTH: 201
<212> TYPE: DNA
<213> ORGANISM: Carnobacterium maltaromaticum

<400> SEQUENCE: 33
atgaatagcg taaaagaatt aaacgtgaaa gaaatgaaac aattcacgg tggagtaaat    60 tatggtaatg gtgtttcttg cagtaaaaca aaatgttcag ttaactgggg acaagccttt   120
caagaaagat acacagctgg aattaactca tttgtaagtg agtcgcttc tggggcagga   180 tccattggta ggagaccgta a                                            201

<210> SEQ ID NO 34
<211> LENGTH: 61
<212> TYPE: PRT
<213> ORGANISM: Carnobacterium maltaromaticum

<400> SEQUENCE: 34

Met Lys Ser Val Lys Glu Leu Asn Lys Lys Glu Met Gln Gln Ile Asn
1               5                   10                  15

Gly Gly Ala Ile Ser Tyr Gly Asn Gly Val Tyr Cys Asn Lys Glu Lys
            20                  25                  30

Cys Trp Val Asn Lys Ala Glu Asn Lys Gln Ala Ile Thr Gly Ile Val
        35                  40                  45

Ile Gly Gly Trp Ala Ser Ser Leu Ala Gly Met Gly His
    50                  55                  60

<210> SEQ ID NO 35
<211> LENGTH: 186
<212> TYPE: DNA
<213> ORGANISM: Carnobacterium maltaromaticum

<400> SEQUENCE: 35
atgaaaagcg ttaagaaact aaataaaaaa gaaatgcaac aaattaatgg tggagctatc    60
tcttatggca atggtgttta ttgtaacaaa gagaaatgtt gggtaaacaa ggcagaaaac   120
aaacaagcta ttactggaat agttatcggt ggatgggctt ctagtttagc aggaatggga   180
cattaa                                                              186

<210> SEQ ID NO 36
<211> LENGTH: 71
<212> TYPE: PRT
<213> ORGANISM: Carnobacterium maltaromaticum

<400> SEQUENCE: 36

Met Asn Asn Val Lys Glu Leu Ser Ile Lys Glu Met Gln Gln Val Thr
1               5                   10                  15

Gly Gly Asp Gln Met Ser Asp Gly Val Asn Tyr Gly Lys Gly Ser Ser
            20                  25                  30

Leu Ser Lys Gly Gly Ala Lys Cys Gly Leu Gly Ile Val Gly Gly Leu
        35                  40                  45

Ala Thr Ile Pro Ser Gly Pro Leu Gly Trp Leu Ala Gly Ala Ala Gly
    50                  55                  60

Val Ile Asn Ser Cys Met Lys

-continued

<210> SEQ ID NO 37
<211> LENGTH: 216
<212> TYPE: DNA
<213> ORGANISM: Carnobacterium maltaromaticum

<400> SEQUENCE: 37

```
atgaataatg taaaagagtt aagtattaaa gaaatgcaac aagttactgg tggagaccaa      60
atgtcagatg gtgtaaatta tggaaaaggc tctagcttat caaaaggtgg tgccaaatgt     120
ggtttaggga tcgtcggcgg attagctact atcccttcag gtcctttagg ctggttagcc     180
ggagcagcag gtgtaattaa tagctgtatg aaataa                                216
```

<210> SEQ ID NO 38
<211> LENGTH: 64
<212> TYPE: PRT
<213> ORGANISM: Carnobacterium maltaromaticum

<400> SEQUENCE: 38

```
Met Leu Tyr Glu Leu Val Ala Tyr Gly Ile Ala Gln Gly Thr Ala Glu
1               5                   10                  15

Lys Val Val Ser Leu Ile Asn Ala Gly Leu Thr Val Gly Ser Ile Ile
            20                  25                  30

Ser Ile Leu Gly Gly Val Thr Val Gly Leu Ser Gly Val Phe Thr Ala
        35                  40                  45

Val Lys Ala Ala Ile Ala Lys Gln Gly Ile Lys Lys Ala Ile Gln Leu
    50                  55                  60
```

<210> SEQ ID NO 39
<211> LENGTH: 195
<212> TYPE: DNA
<213> ORGANISM: Carnobacterium maltaromaticum

<400> SEQUENCE: 39

```
atgttatatg aattagttgc atatggtatc gcacaaggta cagctgaaaa ggttgtaagt      60
ctaattaacg caggtttaac agtagggtct attatttcaa ttttgggtgg ggtcacagtc     120
ggtttatcag gtgtcttcac agcagttaaa gcagcaattg ctaaacaagg aataaaaaaa     180
gcaattcaat ataa                                                       195
```

<210> SEQ ID NO 40
<211> LENGTH: 836
<212> TYPE: PRT
<213> ORGANISM: Pectobacterium carotovorum subsp. carotovorum

<400> SEQUENCE: 40

```
Met Ile Lys Tyr Arg Leu Tyr Ala Pro Asn Asp Gly Asp Thr Met Thr
1               5                   10                  15

Val Ser Gly Gly Gly Gly Trp Val Ser Asn Asp Asp Arg Lys Gly Gly
            20                  25                  30

Asn Asp Arg Asp Asn Gly Lys Gly Gly Ser Ala Val Asp Phe Ser Lys
        35                  40                  45

Asn Pro Glu Lys Gln Ala Ile Val Asn Pro Tyr Leu Ala Ile Ala Ile
    50                  55                  60

Pro Met Pro Val Tyr Pro Leu Tyr Gly Lys Leu Gly Phe Thr Ile Asn
65                  70                  75                  80

Thr Thr Ala Ile Glu Thr Glu Leu Ala Asn Val Arg Ala Ala Ile Asn
                85                  90                  95
```

```
Thr Lys Leu Ala Thr Leu Ser Ala Val Ile Gly Arg Ser Leu Pro Val
            100                 105                 110

Val Gly Arg Val Phe Gly Val Thr Ala Ala Gly Met Trp Pro Ser Ser
            115                 120                 125

Thr Ala Pro Ser Ser Leu Asp Ser Ile Tyr Asn Gln Ala His Gln Gln
            130                 135                 140

Ala Leu Ala Gln Leu Ala Ala Gln Gln Gly Val Leu Asn Lys Gly Tyr
145                 150                 155                 160

Asn Val Thr Ala Met Pro Ala Gly Phe Val Ser Ser Leu Pro Val Ser
                    165                 170                 175

Glu Ile Lys Ser Leu Pro Thr Ala Pro Ala Ser Leu Leu Ala Gln Ser
            180                 185                 190

Val Ile Asn Thr Glu Leu Ser Gln Arg Gln Leu Ala Leu Thr Gln Pro
            195                 200                 205

Thr Thr Asn Ala Pro Val Ala Asn Ile Pro Val Val Lys Ala Glu Lys
210                 215                 220

Thr Ala Met Pro Gly Val Tyr Ser Ala Lys Ile Ile Ala Gly Glu Pro
225                 230                 235                 240

Ala Phe Gln Ile Lys Val Asp Asn Thr Lys Pro Ala Leu Ala Gln Asn
                245                 250                 255

Pro Pro Lys Val Lys Asp Asp Ile Gln Val Ser Ser Phe Leu Ser Ser
            260                 265                 270

Pro Val Ala Asp Thr His His Ala Phe Ile Asp Phe Gly Ser Asp His
            275                 280                 285

Glu Pro Val Tyr Val Ser Leu Ser Lys Ile Val Thr Ala Glu Glu Glu
            290                 295                 300

Lys Lys Gln Val Glu Glu Ala Lys Arg Arg Glu Gln Glu Trp Leu Leu
305                 310                 315                 320

Arg His Pro Ile Thr Ala Ala Glu Arg Lys Leu Thr Glu Ile Arg Gln
                325                 330                 335

Val Ile Ser Phe Ala Gln Gln Leu Lys Glu Ser Ser Val Ala Thr Ile
            340                 345                 350

Ser Glu Lys Thr Lys Thr Val Ala Val Tyr Gln Glu Gln Val Asn Thr
            355                 360                 365

Ala Ala Lys Asn Arg Asp Asn Phe Tyr Asn Gln Asn Arg Gly Leu Leu
            370                 375                 380

Ser Ala Gly Ile Thr Gly Gly Pro Gly Tyr Pro Ile Tyr Leu Ala Leu
385                 390                 395                 400

Trp Gln Thr Met Asn Asn Phe His Gln Ala Tyr Phe Arg Ala Asn Asn
                405                 410                 415

Ala Leu Glu Gln Glu Ser His Val Leu Asn Leu Ala Arg Ser Asp Leu
            420                 425                 430

Ala Lys Ala Glu Gln Leu Leu Ala Glu Asn Asn Arg Leu Gln Val Glu
            435                 440                 445

Thr Glu Arg Thr Leu Ala Glu Glu Lys Glu Ile Lys Arg Asn Arg Val
            450                 455                 460

Asn Val Ser Thr Phe Gly Thr Val Gln Thr Gln Leu Ser Lys Leu Leu
465                 470                 475                 480

Ser Asp Phe Tyr Ala Val Thr Ser Leu Ser Gln Ser Val Pro Ser Gly
                485                 490                 495

Ala Leu Ala Ser Phe Ser Tyr Asn Pro Gln Gly Met Ile Gly Ser Gly
            500                 505                 510
```

```
Lys Ile Val Gly Lys Asp Val Asp Val Leu Phe Ser Ile Pro Val Lys
                515                 520                 525

Asp Ile Pro Gly Tyr Lys Ser Pro Ile Asn Leu Asp Asp Leu Ala Lys
            530                 535                 540

Lys Asn Gly Ser Leu Asp Leu Pro Ile Arg Leu Ala Phe Ser Asp Glu
545                 550                 555                 560

Asn Gly Glu Arg Val Leu Arg Ala Phe Lys Ala Asp Ser Leu Arg Ile
                565                 570                 575

Pro Ser Ser Val Arg Gly Val Ala Gly Ser Tyr Asp Lys Asn Thr Gly
            580                 585                 590

Ile Phe Ser Ala Glu Ile Asp Gly Val Ser Ser Arg Leu Val Leu Glu
        595                 600                 605

Asn Pro Ala Phe Pro Pro Thr Gly Asn Val Gly Asn Thr Gly Asn Thr
    610                 615                 620

Ala Pro Asp Tyr Lys Ala Leu Leu Asn Thr Gly Val Asp Val Lys Pro
625                 630                 635                 640

Val Asp Lys Ile Thr Val Thr Val Thr Pro Val Ala Asp Pro Val Asp
                645                 650                 655

Ile Asp Asp Tyr Ile Ile Trp Leu Pro Thr Ala Ser Gly Ser Gly Val
            660                 665                 670

Glu Pro Ile Tyr Val Val Phe Asn Ser Asn Pro Tyr Gly Gly Thr Glu
        675                 680                 685

Lys Gly Lys Tyr Ser Lys Arg Tyr Tyr Asn Pro Asp Lys Ala Gly Gly
    690                 695                 700

Pro Ile Leu Glu Leu Asp Trp Lys Asn Val Lys Ile Asp His Ala Gly
705                 710                 715                 720

Val Asp Asn Val Lys Leu His Thr Gly Arg Phe Lys Ala Ser Val Glu
                725                 730                 735

Asn Lys Val Met Ile Glu Arg Leu Glu Asn Ile Leu Asn Gly Gln Ile
            740                 745                 750

Thr Ala Thr Asp Thr Asp Lys Arg Phe Tyr Thr His Glu Leu Arg Glu
        755                 760                 765

Leu Asn Arg Tyr Arg Asn Leu Gly Ile Lys Asp Gly Glu Val Pro Ser
    770                 775                 780

Ser Ile Gln Glu Glu Ser Ala Val Trp Asn Asp Thr His Thr Ala Thr
785                 790                 795                 800

Leu Glu Asp Tyr Lys Ile Asn Glu Lys Glu Gln Pro Leu Tyr Thr Asp
                805                 810                 815

Ala Ala Leu Gln Ala Ala Tyr Glu Gln Glu Leu Lys Asp Ala Leu Gly
            820                 825                 830

Gly Lys His Gly
        835

<210> SEQ ID NO 41
<211> LENGTH: 2511
<212> TYPE: DNA
<213> ORGANISM: Pectobacterium carotovorum subsp. carotovorum

<400> SEQUENCE: 41
atgattaaat accgtttata tgctccaaat gatggagaca ccatgacagt gagtggtggt    60
ggtggttggg tttcaaacga tgatcgcaaa ggtggtaatg acagggacaa tggcaaaggt   120
ggttctgccg ttgattttag taaaaatcca gaaaagcagg ctatcgttaa tccctatttg   180
gcaatcgcga taccgatgcc ggtctaccct ctttatggaa agctaggggtt cacaataaat   240
```

```
acgacggcaa ttgagactga actcgcaaat gtcagagcag caattaacac taaacttgca      300
acactcagtg cagtgattgg cagatcactt ccggtcgttg ggcgggtatt tggtgttact      360
gccgccggaa tgtggccttc tagtaccgct cccagtagtc tcgattctat atacaatcaa      420
gcacatcagc aggctttagc ccagttagct gctcaacagg gagtattaaa taagggtat       480
aacgttacag caatgcctgc aggtttcgtc agcagtttgc ctgttagtga aatcaaatca      540
ttgccaacag ctcccgccag tttactggca caaagtgtga ttaataccga actttcccag      600
cgtcaactgg ctcttactca gcccacgacg aatgcaccag tcgcgaatat tcccgtagtt      660
aaagcagaga aaacagcaat gccaggtgtg tattcagcga aaattattgc tggtgagcct      720
gcattccaaa tcaaggtcga taataccaaa cctgctttgg cacagaatcc gccgaaagta      780
aaagatgata ttcaggtatc ttctttcctt tcctcgccag tagctgatac gcaccatgca      840
tttattgatt ttggcagcga tcatgaaccg gtatacgtgt ctctttcaaa gatcgtgaca      900
gccgaggagg agaaaaaaca ggttgaagag gccaagcgcc gtgagcagga gtggttgttg      960
cgtcatccaa ttacagctgc ggagcgaaaa ttaactgaaa tccgccaagt gatctctttt     1020
gctcaacagc taaagaaaag ctctgtcgca accatttcag aaaaaactaa aactgttgcg     1080
gtttaccaag aacaggtgaa taccgctgca aaaaatcgcg acaattttta taatcaaaat     1140
agaggtctgt taagtgcggg tataactggg ggaccgggat atcctattta tcttgcttta     1200
tggcaaacga tgaataactt tcatcaggct tatttcagag caataatgc attggaacaa      1260
gagagtcatg ttctgaacct ggctcgttct gatctggcta aggctgagca attgcttgct     1320
gagaataatc gacttcaggt tgaaacggag cgaacgcttg ccgaagaaaa agagataaaa     1380
cgcaacaggg ttaatgtatc aacatttggc acagtgcaaa ctcaacttag taaattgctg     1440
tcagattttt atgctgttac atcacttttcc caaagtgttc cttcgggggc attagcctct     1500
ttttcatata atccacaagg gatgattggc agcggtaaga ttgttgggaa ggatgtcgat     1560
gttttatttt ccatcccagt aaaagatatt ccgggatata aatctcctat taacttggac     1620
gatttagcca agaaaaatgg aagtctggat cttcccattc gtctggcatt ttctgatgag     1680
aatggagaaa gggttcttcg ggcattcaaa gcggatagtc tgcgaatccc ttcgagtgtc     1740
agaggtgtag cggcagtta tgacaaaaat acgggtattt ttagtgcaga aattgatggt     1800
gtttcatctc gccttgtact ggaaaaccca gcgtttcctc cgaccggaaa tgtcggtaat     1860
acgggtaata ctgcacctga ctataaagca ttactgaata ctggtgttga tgttaaacct     1920
gttgataaaa tcacagttac ggtaacacca gttgctgatc cagtggatat tgatgactat     1980
ataatctggt tgccaactgc gtctggttct ggcgtggaac ccatttatgt cgtgtttaac     2040
agtaatccgt atggtgggac ggaaaaagga aaatatagca aacgttatta taatccagat     2100
aaggcaggcg gtccgatctt ggagctggat tggaaaaacg ttaagattga ccatgcaggt     2160
gtggacaatt ttaaattaca cacagggcgt ttcaaagcgt cggttgaaaa caaagtgatg     2220
attgaacgtt tggaaaacat actgaatggt caaatcacgg ccacggatac tgacaagcga     2280
ttctatacgc atgaattaag agagttaaac cgctacagaa atttaggcat caaagacggt     2340
gaagtgccta gtagcattca agaagaaagc gctgtttgga acgacacaca cacagcgacg     2400
cttgaagact acaaaattaa tgagaaagag caaccgttgt acactgatgc tgctttgcag     2460
gcagcctacg aacaggaact caaagacgca ttaggaggga aacatggcta a             2511
```

<210> SEQ ID NO 42
<211> LENGTH: 74

<212> TYPE: PRT
<213> ORGANISM: Bacillus cereus

<400> SEQUENCE: 42

```
Met Glu Asn Leu Gln Met Leu Thr Glu Glu Leu Met Glu Ile Glu
1               5                   10                  15

Gly Gly Gly Trp Trp Asn Ser Trp Gly Lys Cys Val Ala Thr Ile
            20                  25                  30

Gly Gly Ala Gly Thr Gly Gly Leu Gly Gly Ala Ala Gly Ser Ala
            35                  40                  45

Val Pro Val Ile Gly Thr Gly Ile Gly Ala Ile Gly Val Ser
    50                  55                  60

Gly Gly Leu Thr Gly Ala Ala Thr Phe Cys
65                  70
```

<210> SEQ ID NO 43
<211> LENGTH: 225
<212> TYPE: DNA
<213> ORGANISM: Bacillus cereus

<400> SEQUENCE: 43

| | |
|---|---|
| atggaaaact tacaaatgtt aactgaagaa gaattaatgg aaattgaagg tggaggctgg | 60 |
| tggaatagct ggggtaaatg tgttgctgga actatcggtg gagctggaac tggtggttta | 120 |
| ggtggagctg ctgcaggttc agctgttccg gttattggta ctggtattgg tggcgctatt | 180 |
| ggtggagtta gcggtggcct tacaggtgca gctacttttt gctaa | 225 |

<210> SEQ ID NO 44
<211> LENGTH: 78
<212> TYPE: PRT
<213> ORGANISM: Streptoverticillium griseoverticillatum

<400> SEQUENCE: 44

```
Met Thr Ala Ser Ile Leu Gln Gln Ser Val Val Asp Ala Asp Phe Arg
1               5                   10                  15

Ala Ala Leu Leu Glu Asn Pro Ala Ala Phe Gly Ala Ser Ala Ala Ala
                20                  25                  30

Leu Pro Thr Pro Val Glu Ala Gln Asp Gln Ala Ser Leu Asp Phe Trp
            35                  40                  45

Thr Lys Asp Ile Ala Ala Thr Glu Ala Phe Ala Cys Arg Gln Ser Cys
        50                  55                  60

Ser Phe Gly Pro Phe Thr Phe Val Cys Asp Gly Asn Thr Lys
65                  70                  75
```

<210> SEQ ID NO 45
<211> LENGTH: 237
<212> TYPE: DNA
<213> ORGANISM: Streptoverticillium griseoverticillatum

<400> SEQUENCE: 45

| | |
|---|---|
| atgaccgctt ccattcttca gcagtccgtc gtggacgccg acttccgcgc ggcgctgctt | 60 |
| gagaacccg ccgccttcgg cgcttccgcc gcggccctgc ccacgcccgt cgaggcccag | 120 |
| gaccaggcgt cccttgactt ctggaccaag gacatcgccg ccacggaagc cttcgcctgc | 180 |
| cgccagagct gcagcttcgg cccgttcacc ttcgtgtgcg acggcaacac caagtaa | 237 |

<210> SEQ ID NO 46
<211> LENGTH: 76
<212> TYPE: PRT

<213> ORGANISM: Geobacillus kaustophilus

<400> SEQUENCE: 46

Met Ser Leu Leu Ala Leu Val Ala Gly Thr Leu Gly Val Ser Gln Ser
1 5 10 15

Ile Ala Thr Thr Val Val Ser Ile Val Leu Thr Gly Ser Thr Leu Ile
20 25 30

Ser Ile Ile Leu Gly Ile Thr Ala Ile Leu Ser Gly Gly Val Asp Ala
35 40 45

Ile Leu Glu Ile Gly Trp Ser Ala Phe Val Ala Thr Val Lys Lys Ile
50 55 60

Val Ala Glu Arg Gly Lys Ala Ala Ala Ile Ala Trp
65 70 75

<210> SEQ ID NO 47
<211> LENGTH: 231
<212> TYPE: DNA
<213> ORGANISM: Geobacillus kaustophilus

<400> SEQUENCE: 47
atgagtttgc tggcgcttgt tgccgggacg ctcggcgtgt cacagtcaat cgcgacgacg 60
gttgtttcga ttgtgttgac cggctccact ctcatttcta ttattcttgg gatcaccgct 120
attttgtcag gtggagtcga cgccattttg gaaattgggt ggtcagcttt tgtcgcgacg 180
gtgaaaaaaa tagtggcgga acgaggaaaa gcggcagcga ttgcatggta a 231

<210> SEQ ID NO 48
<211> LENGTH: 309
<212> TYPE: PRT
<213> ORGANISM: Clostridium tyrobutyricum

<400> SEQUENCE: 48

Met Arg Lys Val Phe Leu Arg Ser Ile Ile Ser Thr Leu Val Met Cys
1 5 10 15

Ala Phe Val Ser Ser Ser Phe Ser Val Asn Ala Asp Glu Ser Lys Pro
20 25 30

Asn Asp Glu Lys Ile Ile Asn Asn Ile Glu Asn Val Thr Thr Thr Lys
35 40 45

Asp Ile Val Lys Ser Asn Lys Asn Asn Ile Val Tyr Leu Asp Glu Gly
50 55 60

Val Met Ser Ile Pro Leu Ser Gly Arg Lys Pro Ile Ala Ile Lys Asp
65 70 75 80

Asp Asn Asn Lys Glu Asp Leu Thr Val Thr Leu Pro Ile Lys Asn Thr
85 90 95

Gly Asp Ile Ser Lys Ile Ser Ser Asn Gly Thr Ile Leu Tyr Lys Asn
100 105 110

Asn Ser Ser Asn Ser Ser Asn Ile Ala Leu Gln Pro Lys Asn Asp Gly
115 120 125

Phe Lys Ala Leu Ile Asn Ile Asn Asp Lys Leu Ala Asn Lys Glu Tyr
130 135 140

Glu Phe Thr Phe Asn Leu Pro Lys Asn Ser Lys Leu Ile Ser Ala Ala
145 150 155 160

Thr Tyr Leu Gly Lys Glu Tyr Asp Thr Lys Glu Val Phe Val Val Asp
165 170 175

Lys Asn Asn Ile Ile Thr Ser Ile Ile Ser Pro Ala Trp Ala Lys Asp
180 185 190

```
Ala Asn Gly His Asn Val Ser Thr Tyr Tyr Lys Ile Val Ser Asn Asn
        195                 200                 205

Lys Leu Val Gln Val Val Glu Phe Thr Glu Asn Thr Ala Phe Pro Val
    210                 215                 220

Val Ala Asp Pro Asn Trp Thr Lys Ile Gly Lys Cys Ala Gly Ser Ile
225                 230                 235                 240

Ala Trp Ala Ile Gly Ser Gly Leu Phe Gly Gly Ala Lys Leu Ile Lys
                245                 250                 255

Ile Lys Lys Tyr Ile Ala Glu Leu Gly Gly Leu Gln Lys Ala Ala Lys
            260                 265                 270

Leu Leu Val Gly Ala Thr Thr Trp Glu Glu Lys Leu His Ala Gly Gly
        275                 280                 285

Tyr Ala Leu Ile Asn Leu Ala Ala Glu Leu Thr Gly Val Ala Gly Ile
    290                 295                 300

Gln Ala Asn Cys Phe
305

<210> SEQ ID NO 49
<211> LENGTH: 930
<212> TYPE: DNA
<213> ORGANISM: Clostridium tyrobutyricum

<400> SEQUENCE: 49
ttgagaaaag tatttttaag atcaataatt tcaacattag ttatgtgtgc atttgtttca      60
agcagctttt cagtaaatgc ggatgaaagc aaaccaaatg atgaaaaaat aattaataac     120
atagaaaacg ttactactac taaagatatt gtaaaaagta ataaaaataa tattgtatat     180
ttagatgaag gtgtaatgag tattccattg tctgggagaa aacccattgc tattaaagat     240
gataataata aagaagattt aactgttaca ttacctatta agaatactgg agatatatct     300
aaaattagta gtaatggtac tattctgtat aaaaataata gtagtaattc atctaatata     360
gctttacaac ctaaaaatga tggatttaag gctttaataa atattaatga taagttagct     420
aataaagaat atgaatttac atttaattta cccaaaaaca gtaaattaat tagtgctgcc     480
acatatttgg gtaaagaata tgatacaaaa gaagtatttg tagtagacaa aaataatata     540
attacgagta ttattagtcc agcttgggct aaagatgcaa atggacataa tgtttctact     600
tattataaga tagtatcgaa taataaatta gtacaagttg ttgaattcac agaaaatact     660
gcattcccgg tggtagctga tcctaattgg actaaaattg ggaaatgcgc tgggtcaata     720
gcatgggcta taggttctgg cctttttggt ggagcaaagc taattaaaat aaaaaaatat     780
atagcagagc ttggaggact tcaaaaagca gctaaattat tagttggtgc aaccacttgg     840
gaagaaaaat tacacgcagg cggttatgca ttaattaact tagctgctga gctaacaggt     900
gtagcaggta tacaagcaaa ttgtttttaa                                      930

<210> SEQ ID NO 50
<211> LENGTH: 62
<212> TYPE: PRT
<213> ORGANISM: Bacillus coagulans

<400> SEQUENCE: 50

Met Lys Lys Ile Glu Lys Leu Thr Glu Lys Glu Met Ala Asn Ile Ile
1               5                   10                  15

Gly Gly Lys Tyr Tyr Gly Asn Gly Val Thr Cys Gly Lys His Ser Cys
            20                  25                  30

Ser Val Asp Trp Gly Lys Ala Thr Thr Cys Ile Ile Asn Asn Gly Ala
```

```
                35                  40                  45
Met Ala Trp Ala Thr Gly Gly His Gln Gly Thr His Lys Cys
         50                  55                  60

<210> SEQ ID NO 51
<211> LENGTH: 189
<212> TYPE: DNA
<213> ORGANISM: Bacillus coagulans

<400> SEQUENCE: 51
atgaaaaaaa ttgaaaaatt aactgaaaaa gaaatggcca atatcattgg tggtaaatac      60
tacggtaatg gggttacttg tggcaaacat tcctgctctg ttgactgggg taaggctacc     120
acctgcataa tcaataatgg agctatggca tgggctactg gtggacatca aggtactcat     180
aaatgctag                                                             189

<210> SEQ ID NO 52
<211> LENGTH: 490
<212> TYPE: PRT
<213> ORGANISM: Escherichia coli

<400> SEQUENCE: 52

Met Asp Lys Val Thr Asp Asn Ser Pro Asp Val Glu Ser Thr Glu Ser
1               5                   10                  15

Thr Glu Gly Ser Phe Pro Thr Val Gly Val Asp Thr Gly Asp Thr Ile
            20                  25                  30

Thr Ala Thr Leu Ala Thr Gly Thr Glu Asn Val Gly Gly Gly Gly
        35                  40                  45

Ala Phe Gly Gly Ala Ser Glu Ser Ser Ala Ala Ile His Ala Thr Ala
    50                  55                  60

Lys Trp Ser Thr Ala Gln Leu Lys Lys His Gln Ala Glu Gln Ala Ala
65                  70                  75                  80

Arg Ala Ala Ala Glu Ala Ala Leu Ala Lys Ala Lys Ser Gln Arg
                85                  90                  95

Asp Ala Leu Thr Gln Arg Leu Lys Asp Ile Val Asn Asp Ala Leu Arg
            100                 105                 110

Ala Asn Ala Ala Arg Ser Pro Ser Val Thr Asp Leu Ala His Ala Asn
        115                 120                 125

Asn Met Ala Met Gln Ala Glu Ala Glu Arg Leu Arg Leu Ala Lys Ala
    130                 135                 140

Glu Gln Lys Ala Arg Glu Gly Ala Ala Glu Lys Ala Leu Arg
145                 150                 155                 160

Glu Ala Glu Arg Gln Arg Asp Glu Ile Ala Arg Gln Ala Glu Thr
                165                 170                 175

Ala His Leu Leu Ala Met Ala Glu Ala Glu Ala Glu Lys Asn Arg
            180                 185                 190

Gln Asp Ser Leu Asp Glu Glu His Arg Ala Val Glu Val Ala Glu Lys
        195                 200                 205

Lys Leu Ala Glu Ala Lys Ala Glu Leu Ala Lys Ala Glu Ser Asp Val
    210                 215                 220

Gln Ser Lys Gln Ala Ile Val Ser Arg Val Ala Gly Glu Leu Glu Asn
225                 230                 235                 240

Ala Gln Lys Ser Val Asp Val Lys Val Thr Gly Phe Pro Gly Trp Arg
                245                 250                 255

Asp Val Gln Lys Lys Leu Glu Arg Gln Leu Gln Asp Lys Lys Asn Glu
            260                 265                 270
```

```
Tyr Ser Ser Val Thr Asn Ala Leu Asn Ser Ala Val Ser Ile Arg Asp
            275                 280                 285

Ala Lys Lys Thr Glu Val Gln Asn Ala Glu Ile Lys Leu Lys Glu Ala
        290                 295                 300

Lys Asp Ala Leu Glu Lys Ser Gln Val Lys Asp Ser Val Asp Thr Met
305                 310                 315                 320

Val Gly Phe Tyr Gln Tyr Ile Thr Glu Gln Tyr Gly Glu Lys Tyr Ser
                325                 330                 335

Arg Ile Ala Gln Asp Leu Ala Glu Lys Ala Lys Gly Ser Lys Phe Asn
            340                 345                 350

Ser Val Asp Glu Ala Leu Ala Ala Phe Glu Lys Tyr Lys Asn Val Leu
        355                 360                 365

Asp Lys Lys Phe Ser Lys Val Asp Arg Asp Asp Ile Phe Asn Ala Leu
    370                 375                 380

Glu Ser Ile Thr Tyr Asp Glu Trp Ala Lys His Leu Glu Lys Ile Ser
385                 390                 395                 400

Arg Ala Leu Lys Val Thr Gly Tyr Leu Ser Phe Gly Tyr Asp Val Trp
                405                 410                 415

Asp Gly Thr Leu Lys Gly Leu Lys Thr Gly Asp Trp Lys Pro Leu Phe
            420                 425                 430

Val Thr Leu Glu Lys Ser Ala Val Asp Phe Gly Val Ala Lys Ile Val
        435                 440                 445

Ala Leu Met Phe Ser Phe Ile Val Gly Ala Pro Leu Gly Phe Trp Gly
    450                 455                 460

Ile Ala Ile Ile Thr Gly Ile Val Ser Ser Tyr Ile Gly Asp Asp Glu
465                 470                 475                 480

Leu Asn Lys Leu Asn Glu Leu Leu Gly Ile
                485                 490

<210> SEQ ID NO 53
<211> LENGTH: 1473
<212> TYPE: DNA
<213> ORGANISM: Escherichia coli

<400> SEQUENCE: 53
atggataaag tcactgataa ttctccagat gtggagagca cagaatctac tgaggggtca        60
ttcccaactg ttggggttga tactggcgat acgattacag cgacgcttgc aactggaact       120
gaaaatgttg gtggaggcgg tggagcattt ggtgggcca gtgaaagttc tgctgcgata        180
catgcaaccg ctaaatggtc taccgcgcag ttgaaaaaac atcaggctga acaggctgcc       240
cgtgctgctg cggctgaggc agcattggca aaagcgaaat ctcagcgtga tgccctgact       300
caacgtctca aggatattgt taatgacgct ttacgtgcta atgccgctcg tagtccatca       360
gtaactgacc ttgctcatgc caataatatg gcaatgcagg cagaggctga gcgtttgcgc       420
cttgcgaagg cagagcaaaa agcccgtgaa aagctgaag cagcagaaaa agcgctccgg        480
gaagcagaac gccaacgtga tgagattgcc cgccaacagg ctgaaaccgc gcatttgtta       540
gcaatggcgg aggcagcaga ggctgagaaa atcgacagg attctcttga tgaagagcat        600
cgggctgtgg aagtggcaga agaagctg gctgaggcta agctgaact ggcgaaggcc          660 gaaagcgatg tacagagtaa gcaagcgatt gtttccagag ttgcagggga gcttgaaaac       720
gctcaaaaaa gtgttgatgt gaaggttacc ggatttcctg atggcgtga tgttcagaaa        780 aaactggaga acaattgca ggataagaag aatgaatatt cgtcagtgac gaatgctctt       840
```

```
aattctgctg ttagcattag agatgctaaa aaaacagaag ttcagaatgc tgagataaaa    900
ttaaaagaag ctaaggatgc tcttgagaag agtcaggtaa aagactctgt tgatactatg    960
gttgggtttt atcaatatat aaccgaacaa tatggggaaa aatattccag aatagctcag   1020
gatttagctg aaaaggcgaa gggtagtaaa tttaatagtg ttgatgaagc acttgctgca   1080
tttgaaaagt ataaaaatgt actggataag aaattcagta aggttgatag ggatgatatt   1140
tttaatgctt tagagtctat tacttatgat gagtgggcca agcatctaga aaagatctct   1200
agggctctta aggttactgg atatttgtct ttcgggtatg atgtatggga tggtacccta   1260 aaggattaa aaacaggaga ctggaagcct ttatttgtca ctctggagaa gagcgcggta   1320
gatttcggcg tggcaaaaat tgtggcatta atgtttagtt ttattgttgg tgcgcctctt   1380
ggcttctggg gaattgcaat tatcacaggt attgtttctt cttacatagg ggatgatgag   1440
ttgaacaagc ttaatgaatt actaggtatt taa                                1473
```

<210> SEQ ID NO 54
<211> LENGTH: 522
<212> TYPE: PRT
<213> ORGANISM: Escherichia coli

<400> SEQUENCE: 54

```
Met Glu Thr Ala Val Ala Tyr Tyr Lys Asp Gly Val Pro Tyr Asp Asp
1               5                   10                  15

Lys Gly Gln Val Ile Ile Thr Leu Leu Asn Gly Thr Pro Asp Gly Ser
            20                  25                  30

Gly Ser Gly Gly Gly Gly Gly Lys Gly Gly Ser Lys Ser Glu Ser Ser
        35                  40                  45

Ala Ala Ile His Ala Thr Ala Lys Trp Ser Thr Ala Gln Leu Lys Lys
    50                  55                  60

Thr Gln Ala Glu Gln Ala Ala Arg Ala Lys Ala Ala Glu Ala Gln
65                  70                  75                  80

Ala Lys Ala Lys Ala Asn Arg Asp Ala Leu Thr Gln Arg Leu Lys Asp
                85                  90                  95

Ile Val Asn Glu Ala Leu Arg His Asn Ala Ser Arg Thr Pro Ser Ala
            100                 105                 110

Thr Glu Leu Ala His Ala Asn Asn Ala Ala Met Gln Ala Glu Asp Glu
        115                 120                 125

Arg Leu Arg Leu Ala Lys Ala Glu Glu Lys Ala Arg Lys Glu Ala Glu
    130                 135                 140

Ala Ala Glu Lys Ala Phe Gln Glu Ala Glu Gln Arg Arg Lys Glu Ile
145                 150                 155                 160

Glu Arg Glu Lys Ala Glu Thr Glu Arg Gln Leu Lys Leu Ala Glu Ala
                165                 170                 175

Glu Glu Lys Arg Leu Ala Ala Leu Ser Glu Ala Lys Ala Val Glu
            180                 185                 190

Ile Ala Gln Lys Lys Leu Ser Ala Ala Gln Ser Glu Val Val Lys Met
        195                 200                 205

Asp Gly Glu Ile Lys Thr Leu Asn Ser Arg Leu Ser Ser Ser Ile His
    210                 215                 220

Ala Arg Asp Ala Glu Met Lys Thr Leu Ala Gly Lys Arg Asn Glu Leu
225                 230                 235                 240

Ala Gln Ala Ser Ala Lys Tyr Lys Glu Leu Asp Glu Leu Val Lys Lys
                245                 250                 255

Leu Ser Pro Arg Ala Asn Asp Pro Leu Gln Asn Arg Pro Phe Phe Glu
```

|  |  | 260 |  |  |  | 265 |  |  |  | 270 |  |
|---|---|---|---|---|---|---|---|---|---|---|---|

Ala Thr Arg Arg Val Gly Ala Gly Lys Ile Arg Glu Glu Lys Gln
                275                 280                 285

Lys Gln Val Thr Ala Ser Glu Thr Arg Ile Asn Arg Ile Asn Ala Asp
            290                 295                 300

Ile Thr Gln Ile Gln Lys Ala Ile Ser Gln Val Ser Asn Asn Arg Asn
305                 310                 315                 320

Ala Gly Ile Ala Arg Val His Glu Ala Glu Asn Leu Lys Lys Ala
                325                 330                 335

Gln Asn Asn Leu Leu Asn Ser Gln Ile Lys Asp Ala Val Asp Ala Thr
            340                 345                 350

Val Ser Phe Tyr Gln Thr Leu Thr Glu Lys Tyr Gly Glu Lys Tyr Ser
            355                 360                 365

Lys Met Ala Gln Glu Leu Ala Asp Lys Ser Lys Gly Lys Lys Ile Gly
            370                 375                 380

Asn Val Asn Glu Ala Leu Ala Ala Phe Glu Lys Tyr Lys Asp Val Leu
385                 390                 395                 400

Asn Lys Lys Phe Ser Lys Ala Asp Arg Asp Ala Ile Phe Asn Ala Leu
                405                 410                 415

Ala Ser Val Lys Tyr Asp Asp Trp Ala Lys His Leu Asp Gln Phe Ala
                420                 425                 430

Lys Tyr Leu Lys Ile Thr Gly His Val Ser Phe Gly Tyr Asp Val Val
            435                 440                 445

Ser Asp Ile Leu Lys Ile Lys Asp Thr Gly Asp Trp Lys Pro Leu Phe
450                 455                 460

Leu Thr Leu Glu Lys Lys Ala Ala Asp Ala Gly Val Ser Tyr Val Val
465                 470                 475                 480

Ala Leu Leu Phe Ser Leu Leu Ala Gly Thr Thr Leu Gly Ile Trp Gly
                485                 490                 495

Ile Ala Ile Val Thr Gly Ile Leu Cys Ser Tyr Ile Asp Lys Asn Lys
                500                 505                 510

Leu Asn Thr Ile Asn Glu Val Leu Gly Ile
            515                 520

<210> SEQ ID NO 55
<211> LENGTH: 1569
<212> TYPE: DNA
<213> ORGANISM: Escherichia coli

<400> SEQUENCE: 55
atggaaaccg cggtagcgta ctataaagat ggtgttcctt atgatgataa gggacaggta     60
attattactc ttttgaatgg tactcctgac gggagtggct ctggcggcgg aggtggaaaa    120
ggaggcagta aaagtgaaag ttctgcagct attcatgcaa ctgctaaatg gtctactgct    180
caattaaaga aaacacaggc agagcaggct gcccgggcaa aagctgcagc ggaagcacag    240
gcgaaagcaa aggcaaacag ggatgcgctg actcagcgcc tgaaggatat cgtgaatgag    300
gctcttcgtc acaatgcctc acgtacgcct tcagcaacag agcttgctca tgctaataat    360
gcagctatgc aggcggaaga cgagcgtttg cgccttgcga aagcagaaga aaaagcccgt    420
aaagaagcgg aagcagcaga aaaggctttt caggaagcag aacaacgacg taaagagatt    480
gaacgggaga aggctgaaac agaacgccag ttgaaactgg ctgaagctga gagaaacga    540 ctggctgcat tgagtgaaga agctaaagct gttgagatcg cccaaaaaaa acttctgct    600 gcacaatctg aagtggtgaa aatggatgga gagattaaga ctctcaattc tcgtttaagc    660

```
tccagtatcc atgcccgtga tgcagaaatg aaaacgctcg ctggaaaacg aaatgaactg    720
gctcaggcat ccgctaaata taagaactg atgagctgg tcaaaaaact atcaccaaga    780
gccaatgatc cgcttcagaa ccgtcctttt tttgaagcaa ccagacgacg ggttggggcc    840
ggtaagatta gagaagaaaa acaaaaacag gtaacagcat cagaaacacg tattaaccgg    900
ataaatgctg atataactca gatccagaag gctatttctc aggtcagtaa taatcgtaat    960
gccggtatcg ctcgtgttca tgaagctgaa gaaaatttga aaaagcaca gaataatctc   1020 cttaattcac agattaagga tgctgttgat gcaacagtta gctttatca aacgctgact    1080 gaaaaatatg gtgaaaaata ttcgaaaatg gcacaggaac ttgctgataa gtctaaaggt   1140
aagaaaatcg gcaatgtgaa tgaagctctc gctgcttttg aaaaatacaa ggatgtttta   1200
aataagaaat tcagcaaagc cgatcgtgat gctatttta atgcgttggc atcggtgaag   1260
tatgatgact gggctaaaca tttagatcag tttgccaagt acttgaagat tacggggcat   1320 gtttctttg gatatgatgt ggtatctgat atcctaaaaa ttaaggatac aggtgactgg   1380
aagccactat ttcttacatt agagaagaaa gctgcagatg caggggtgag ttatgttgtt   1440
gctttacttt ttagcttgct tgctggaact acattaggta tttggggtat tgctattgtt   1500
acaggaattc tatgctccta tattgataag aataaactta atactataaa tgaggtgtta   1560
gggattaa                                                             1569
```

<210> SEQ ID NO 56
<211> LENGTH: 626
<212> TYPE: PRT
<213> ORGANISM: Escherichia coli

<400> SEQUENCE: 56

```
Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Ala Trp Ser Ser
        35                  40                  45

Phe Gly Asn Lys Thr Ile Trp Gly Gly Asn Glu Trp Val Asp Asp Ser
    50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Glu Leu Arg Glu Tyr
    130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Glu Lys Arg Gln Lys Asp
            180                 185                 190

Ala Gln Asn Ala Asp Lys Lys Ala Ala Asp Met Leu Ala Glu Tyr Glu
        195                 200                 205
```

Arg Arg Lys Gly Ile Leu Asp Thr Arg Leu Ser Glu Leu Glu Lys Asn
    210                 215                 220
Gly Gly Ala Ala Leu Ala Val Leu Asp Ala Gln Gln Ala Arg Leu Leu
225                 230                 235                 240
Gly Gln Gln Thr Arg Asn Asp Arg Ala Ile Ser Glu Ala Arg Asn Lys
                245                 250                 255
Leu Ser Ser Val Thr Glu Ser Leu Asn Thr Ala Arg Asn Ala Leu Thr
            260                 265                 270
Arg Ala Glu Gln Gln Leu Thr Gln Gln Lys Asn Thr Pro Asp Gly Lys
        275                 280                 285
Thr Ile Val Ser Pro Glu Lys Phe Pro Gly Arg Ser Ser Thr Asn His
    290                 295                 300
Ser Ile Val Val Ser Gly Asp Pro Arg Phe Ala Gly Thr Ile Lys Ile
305                 310                 315                 320
Thr Thr Ser Ala Val Ile Asp Asn Arg Ala Asn Leu Asn Tyr Leu Leu
                325                 330                 335
Ser His Ser Gly Leu Asp Tyr Lys Arg Asn Ile Leu Asn Asp Arg Asn
            340                 345                 350
Pro Val Val Thr Glu Asp Val Glu Gly Asp Lys Lys Ile Tyr Asn Ala
        355                 360                 365
Glu Val Ala Glu Trp Asp Lys Leu Arg Gln Arg Leu Leu Asp Ala Arg
    370                 375                 380
Asn Lys Ile Thr Ser Ala Glu Ser Ala Val Asn Ser Ala Arg Asn Asn
385                 390                 395                 400
Leu Ser Ala Arg Thr Asn Glu Gln Lys His Ala Asn Asp Ala Leu Asn
                405                 410                 415
Ala Leu Leu Lys Glu Lys Glu Asn Ile Arg Asn Gln Leu Ser Gly Ile
            420                 425                 430
Asn Gln Lys Ile Ala Glu Glu Lys Arg Lys Asp Glu Leu Lys Ala
        435                 440                 445
Thr Lys Asp Ala Ile Asn Phe Thr Thr Glu Phe Leu Lys Ser Val Ser
    450                 455                 460
Glu Lys Tyr Gly Ala Lys Ala Glu Gln Leu Ala Arg Glu Met Ala Gly
465                 470                 475                 480
Gln Ala Lys Gly Lys Lys Ile Arg Asn Val Glu Glu Ala Leu Lys Thr
                485                 490                 495
Tyr Glu Lys Tyr Arg Ala Asp Ile Asn Lys Lys Ile Asn Ala Lys Asp
            500                 505                 510
Arg Ala Ala Ile Ala Ala Ala Leu Glu Ser Val Lys Leu Ser Asp Ile
        515                 520                 525
Ser Ser Asn Leu Asn Arg Phe Ser Arg Gly Leu Gly Tyr Ala Gly Lys
    530                 535                 540
Phe Thr Ser Leu Ala Asp Trp Ile Thr Glu Phe Gly Lys Ala Val Arg
545                 550                 555                 560
Thr Glu Asn Trp Arg Pro Leu Phe Val Lys Thr Glu Thr Ile Ile Ala
                565                 570                 575
Gly Asn Ala Ala Thr Ala Leu Val Ala Leu Val Phe Ser Ile Leu Thr
            580                 585                 590
Gly Ser Ala Leu Gly Ile Ile Gly Tyr Gly Leu Leu Met Ala Val Thr
        595                 600                 605
Gly Ala Leu Ile Asp Glu Ser Leu Val Glu Lys Ala Asn Lys Phe Trp
    610                 615                 620

Gly Ile
625

<210> SEQ ID NO 57
<211> LENGTH: 1881
<212> TYPE: DNA
<213> ORGANISM: Escherichia coli

<400> SEQUENCE: 57

| | | | | | |
|---|---|---|---|---|---|
| atgtctgacc | ctgtacgtat | tacaaatccc | ggtgcagaat | cgctggggta | tgattcagat | 60 |
| ggccatgaaa | ttatggccgt | tgatatttat | gtaaaccctc | cacgtgtcga | tgtctttcat | 120 |
| ggtaccccgc | ctgcatggag | ttccttcggg | aacaaaacca | tctggggcgg | aaacgagtgg | 180 |
| gttgatgatt | ccccaacccg | aagtgatatc | gaaaaaggg | acaaggaaat | cacagcgtac | 240 |
| aaaaacacgc | tcagcgcgca | gcagaaagag | aatgagaata | agcgtactga | agccggaaaa | 300 |
| cgcctctctg | cggcgattgc | tgcaagggaa | aaagatgaaa | acacactgaa | aacactccgt | 360 |
| gccggaaacg | cagatgccgc | tgatattaca | cgacaggagt | tcagactcct | gcaggcagag | 420 |
| ctgagagaat | acggattccg | tactgaaatc | gccggatatg | acgccctccg | gctgcataca | 480 |
| gagagccgga | tgctgtttgc | tgatgctgat | tctcttcgta | tatctccccg | ggaggccagg | 540 |
| tcgttaatcg | aacaggctga | aaaacggcag | aaggatgcgc | agaacgcaga | caagaaggcc | 600 |
| gctgatatgc | ttgctgaata | cgagcgcaga | aaagtattc | tggacacccg | gttgtcagag | 660 |
| ctggaaaaaa | atggcggggc | agcccttgcc | gttcttgatg | cacaacaggc | ccgtctgctc | 720 |
| gggcagcaga | cacggaatga | cagggccatt | tcagaggccc | ggaataaact | cagttcagtg | 780 |
| acggaatcgc | ttaacacggc | ccgtaatgca | ttaaccagag | ctgaacaaca | gctgacgcaa | 840 |
| cagaaaaaca | cgcctgacgg | caaaacgata | gtttccctg | aaaattccc | ggggcgttca | 900 |
| tcaacaaatg | attctattgt | tgtgagcggt | gatccgagat | ttgccggtac | gataaaaatc | 960 |
| acaaccagcg | cagtcatcga | taaccgtgca | aacctgaatt | atcttctgag | ccattccggt | 1020 |
| ctggactata | aacgcaatat | tctgaatgac | cggaatccgg | tggtgacaga | ggatgtggaa | 1080 |
| ggtgacaaga | aaatttataa | tgctgaagtt | gctgaatggg | ataagttacg | gcaaagattg | 1140 |
| cttgatgcca | gaaataaaat | cacctctgct | gaatctgcgg | taaattcggc | gagaaataac | 1200 |
| ctcagtgcca | gaacaaatga | gcaaaagcat | gcaaatgacg | ctcttaatgc | cctgttgaag | 1260 |
| gaaaaagaga | atatccgtaa | ccagcttttcc | ggcatcaatc | agaagatagc | ggaagagaaa | 1320 |
| agaaaacagg | atgaactgaa | ggcaacgaaa | gacgcaatta | atttcacaac | agagttcctg | 1380 |
| aaatcagttt | cagaaaaata | tggtgcaaaa | gctgagcagt | tagccagaga | gatggccggg | 1440 |
| caggctaaag | ggaagaaaat | acgtaatgtt | gaagaggcat | taaaaacgta | tgaaaagtac | 1500 |
| cgggctgaca | ttaacaaaaa | aattaatgca | aagatcgtg | cagcgattgc | cgcagccctt | 1560 |
| gagtctgtga | agctgtctga | tatatcgtct | aatctgaaca | gattcagtcg | gggactggga | 1620 |
| tatgcaggaa | aatttacaag | tcttgctgac | tggatcactg | agtttggtaa | ggctgtccgg | 1680 |
| acagagaact | ggcgtcctct | ttttgttaaa | acagaaacca | tcatagcagg | caatgccgca | 1740 |
| acggctcttg | tggcactggt | cttcagtatt | cttaccggaa | gcgctttagg | cattatcggg | 1800 |
| tatggtttac | tgatggctgt | caccggtgcg | ctgattgatg | aatcgcttgt | ggaaaaagcg | 1860 |
| aataagttct | ggggtatttta | a | | | | 1881 |

<210> SEQ ID NO 58
<211> LENGTH: 626
<212> TYPE: PRT

<213> ORGANISM: Escherichia coli

<400> SEQUENCE: 58

Met Ser Asp Pro Val Arg Ile Thr Asn Pro Gly Ala Glu Ser Leu Gly
1               5                   10                  15

Tyr Asp Ser Asp Gly His Glu Ile Met Ala Val Asp Ile Tyr Val Asn
            20                  25                  30

Pro Pro Arg Val Asp Val Phe His Gly Thr Pro Pro Ala Trp Ser Ser
        35                  40                  45

Phe Gly Asn Lys Thr Ile Trp Gly Gly Asn Glu Trp Val Asp Asp Ser
    50                  55                  60

Pro Thr Arg Ser Asp Ile Glu Lys Arg Asp Lys Glu Ile Thr Ala Tyr
65                  70                  75                  80

Lys Asn Thr Leu Ser Ala Gln Gln Lys Glu Asn Glu Asn Lys Arg Thr
                85                  90                  95

Glu Ala Gly Lys Arg Leu Ser Ala Ala Ile Ala Ala Arg Glu Lys Asp
            100                 105                 110

Glu Asn Thr Leu Lys Thr Leu Arg Ala Gly Asn Ala Asp Ala Ala Asp
        115                 120                 125

Ile Thr Arg Gln Glu Phe Arg Leu Leu Gln Ala Glu Leu Arg Glu Tyr
130                 135                 140

Gly Phe Arg Thr Glu Ile Ala Gly Tyr Asp Ala Leu Arg Leu His Thr
145                 150                 155                 160

Glu Ser Arg Met Leu Phe Ala Asp Ala Asp Ser Leu Arg Ile Ser Pro
                165                 170                 175

Arg Glu Ala Arg Ser Leu Ile Glu Gln Ala Glu Lys Arg Gln Lys Asp
            180                 185                 190

Ala Gln Asn Ala Asp Lys Lys Ala Ala Asp Met Leu Ala Glu Tyr Glu
        195                 200                 205

Arg Arg Lys Gly Ile Leu Asp Thr Arg Leu Ser Glu Leu Glu Lys Asn
210                 215                 220

Gly Gly Ala Ala Leu Ala Val Leu Asp Ala Gln Gln Ala Arg Leu Leu
225                 230                 235                 240

Gly Gln Gln Thr Arg Asn Asp Arg Ala Ile Ser Glu Ala Arg Asn Lys
                245                 250                 255

Leu Ser Ser Val Thr Glu Ser Leu Lys Thr Ala Arg Asn Ala Leu Thr
            260                 265                 270

Arg Ala Glu Gln Gln Leu Thr Gln Gln Lys Asn Thr Pro Asp Gly Lys
        275                 280                 285

Thr Ile Val Ser Pro Glu Lys Phe Pro Gly Arg Ser Ser Thr Asn His
290                 295                 300

Ser Ile Val Val Ser Gly Asp Pro Arg Phe Ala Gly Thr Ile Lys Ile
305                 310                 315                 320

Thr Thr Ser Ala Val Ile Asp Asn Arg Ala Asn Leu Asn Tyr Leu Leu
                325                 330                 335

Thr His Ser Gly Leu Asp Tyr Lys Arg Asn Ile Leu Asn Asp Arg Asn
            340                 345                 350

Pro Val Val Thr Glu Asp Val Glu Gly Asp Lys Lys Ile Tyr Asn Ala
        355                 360                 365

Glu Val Ala Glu Trp Asp Lys Leu Arg Gln Arg Leu Leu Asp Ala Arg
370                 375                 380

Asn Lys Ile Thr Ser Ala Glu Ser Ala Ile Asn Ser Ala Arg Asn Asn
385                 390                 395                 400

| | | | | | | | | | | | |
|---|---|---|---|---|---|---|---|---|---|---|---|
|Val|Ser|Ala|Arg|Thr|Asn|Glu|Gln|Lys|His|Ala|Asn|Asp|Ala|Leu|Asn|
| | | | |405| | | |410| | | |415| | | |

Ala Leu Leu Lys Glu Lys Glu Asn Ile Arg Ser Gln Leu Ala Asp Ile
                420                 425                 430

Asn Gln Lys Ile Ala Glu Lys Arg Lys Arg Asp Glu Ile Asn Met
            435                 440                 445

Val Lys Asp Ala Ile Lys Leu Thr Ser Asp Phe Tyr Arg Thr Ile Tyr
450                 455                 460

Asp Glu Phe Gly Lys Gln Ala Ser Glu Leu Ala Lys Glu Leu Ala Ser
465                 470                 475                 480

Val Ser Gln Gly Lys Gln Ile Lys Ser Val Asp Asp Ala Leu Asn Ala
                485                 490                 495

Phe Asp Lys Phe Arg Asn Asn Leu Asn Lys Lys Tyr Asn Ile Gln Asp
                500                 505                 510

Arg Met Ala Ile Ser Lys Ala Leu Glu Ala Ile Asn Gln Val His Met
            515                 520                 525

Ala Glu Asn Phe Lys Leu Phe Ser Lys Ala Phe Gly Phe Thr Gly Lys
            530                 535                 540

Val Ile Glu Arg Tyr Asp Val Ala Val Glu Leu Gln Lys Ala Val Lys
545                 550                 555                 560

Thr Asp Asn Trp Arg Pro Phe Phe Val Lys Leu Glu Ser Leu Ala Ala
                565                 570                 575

Gly Arg Ala Ala Ser Ala Val Thr Ala Trp Ala Phe Ser Val Met Leu
            580                 585                 590

Gly Thr Pro Val Gly Ile Leu Gly Phe Ala Ile Ile Met Ala Ala Val
            595                 600                 605

Ser Ala Leu Val Asn Asp Lys Phe Ile Glu Gln Val Asn Lys Leu Ile
610                 615                 620

Gly Ile
625

<210> SEQ ID NO 59
<211> LENGTH: 1881
<212> TYPE: DNA
<213> ORGANISM: Escherichia coli

<400> SEQUENCE: 59

```
atgtctgacc ctgtacgtat tacaaatccc ggtgcagaat cgctgggata tgattcagat      60
ggccatgaaa ttatggccgt tgatatttat gtaaaccctc cacgtgtcga tgtctttcat     120
ggtaccccgc ctgcatggag ttccttcggg aacaaaacca tctggggtgg aaacgagtgg    180
gtcgatgatt ccccaacccg aagtgatatc gaaaaaaggg acaaggaaat cacagcgtac    240
aaaaacacgc tcagcgcgca gcagaaagag aatgagaata gcgtactga agctggaaaa    300
cgcctttctg cggcaattgc tgcaagggaa aaagatgaaa cacactgaa aacactccgt    360
gccggaaacg cagatgccgc tgatattaca cgacaggagt tcagactcct gcaggcagag    420
ctgagagaat acggattccg tactgaaatc gccggatatg atgccctccg gctgcataca    480
gagagccgga tgctgtttgc tgatgctgat tctcttcgta tatctccccg cgaggccagg    540
tcgttaatcg aacaggctga aaacggcag aaggatcgc agaacgcaga caagaaggcc    600
gctgatatgc ttgctgaata cgagcgcaga aaaggtattc tggacacgcg gttgtcagag    660
ctggaaaaaa atggcgggc agcccttgcc gttcttgatg cacaacaggc ccgtctgctc    720
gggcagcaga cacggaatga cagggccatt tcagaggccc ggaataaact cagttcggtg    780
```

```
acggaatcgc ttaagacggc ccgtaatgca ttaaccagag ctgaacaaca gctgacgcaa    840
cagaaaaaca cgcctgacgg caaaacgata gtttcccctg aaaaattccc ggggcgttca    900
tcaacaaatc attctattgt tgtgagtggt gatccgaggt ttgccggtac gataaaaatc    960
acaaccagcg cggtcatcga taaccgtgca aacctgaatt atcttctgac ccattccggt   1020
ctggactata aacgcaatat tctgaatgac cggaatccgg tggtgacaga ggatgtggaa   1080
ggtgacaaga aaatttataa tgctgaagtt gctgaatggg ataagttacg caacgattg    1140
cttgatgcca gaaataaaat cacctctgct gaatctgcga taaattcggc gagaaataac   1200
gtcagtgcca gaacaaatga acaaaagcat gcaaatgacg ctcttaatgc cctgttgaag   1260
gaaaagaga atatccgtag ccagcttgct gacatcaatc agaaaatagc tgaagagaaa    1320
agaaaaaggg atgaaataaa tatggtaaag gatgccataa aactcacctc tgatttctac   1380
agaacgatat atgatgagtt cggtaaacaa gcatccgaac ttgctaagga gctggcttct   1440
gtatctcaag ggaaacagat taagagtgtg gatgatgcac tgaacgcttt tgataaattc   1500
cgtaataatc tgaacaagaa atataacata caagatcgca tggccatttc taaagccctg   1560
gaagctatta atcaggtcca tatggcggag aatttttaagc tgttcagtaa ggcatttggt   1620
tttaccggaa aagttattga acgttatgat gttgctgtgg agttacaaaa ggctgtaaaa   1680
acggacaact ggcgtccatt tttttgtaaaa cttgaatcac tggcagcagg aagagctgct   1740
tcagcagtta cagcatgggc gttttccgtc atgctgggaa cccctgtagg tattctgggt   1800
tttgcaatta ttatggcggc tgtgagtgcg cttgttaatg ataagtttat tgagcaggtc   1860
aataaactta ttggtatctg a                                              1881
```

<210> SEQ ID NO 60
<211> LENGTH: 271
<212> TYPE: PRT
<213> ORGANISM: Escherichia coli

<400> SEQUENCE: 60

Met Glu Thr Leu Thr Val His Ala Pro Ser Pro Ser Thr Asn Leu Pro
1               5                   10                  15

Ser Tyr Gly Asn Gly Ala Phe Ser Leu Ser Ala Pro His Val Pro Gly
            20                  25                  30

Ala Gly Pro Leu Leu Val Gln Val Tyr Ser Phe Phe Gln Ser Pro
        35                  40                  45

Asn Met Cys Leu Gln Ala Leu Thr Gln Leu Glu Asp Tyr Ile Lys Lys
    50                  55                  60

His Gly Ala Ser Asn Pro Leu Thr Leu Gln Ile Ser Thr Asn Ile
65                  70                  75                  80

Gly Tyr Phe Cys Asn Ala Asp Arg Asn Leu Val Leu His Pro Gly Ile
                85                  90                  95

Ser Val Tyr Asp Ala Tyr His Phe Ala Lys Pro Ala Pro Ser Gln Tyr
            100                 105                 110

Asp Tyr Arg Ser Met Asn Met Lys Gln Met Ser Gly Asn Val Thr Thr
        115                 120                 125

Pro Ile Val Ala Leu Ala His Tyr Leu Trp Gly Asn Gly Ala Glu Arg
    130                 135                 140

Ser Val Asn Ile Ala Asn Ile Gly Leu Lys Ile Ser Pro Met Lys Ile
145                 150                 155                 160

Asn Gln Ile Lys Asp Ile Ile Lys Ser Gly Val Val Gly Thr Phe Pro
                165                 170                 175

```
Val Ser Thr Lys Phe Thr His Ala Thr Gly Asp Tyr Asn Val Ile Thr
            180                 185                 190

Gly Ala Tyr Leu Gly Asn Ile Thr Leu Lys Thr Glu Gly Thr Leu Thr
            195                 200                 205

Ile Ser Ala Asn Gly Ser Trp Thr Tyr Asn Gly Val Val Arg Ser Tyr
210                 215                 220

Asp Asp Lys Tyr Asp Phe Asn Ala Ser Thr His Arg Gly Ile Ile Gly
225                 230                 235                 240

Glu Ser Leu Thr Arg Leu Gly Ala Met Phe Ser Gly Lys Glu Tyr Gln
            245                 250                 255

Ile Leu Leu Pro Gly Glu Ile His Ile Lys Glu Ser Gly Lys Arg
            260                 265                 270

<210> SEQ ID NO 61
<211> LENGTH: 816
<212> TYPE: DNA
<213> ORGANISM: Escherichia coli

<400> SEQUENCE: 61
atggaaacct taactgttca tgcaccatca ccatcaacta acttaccaag ttatggcaat      60
ggtgcatttt ctctttcagc accacatgtg cctggtgctg ccctcttttt agtccaggtt    120
gtttatagtt ttttccagag tccaaacatg tgtcttcagg ctttaactca acttgaggat    180
tacatcaaaa acatggggc cagcaaccct ctcacattgc agatcatatc gacaaatatt    240
ggttacttct gtaacgccga ccgaaatctg gttcttcacc ctggaataag cgtttatgac    300
gcttaccact tcgcaaaacc agcgccaagt caatatgact atcgctcaat gaatatgaaa    360
caaatgagcg gtaatgtcac tacaccaatt gtggcgcttg ctcactattt atggggtaat    420
ggcgctgaaa ggagcgttaa tatcgccaac attggtctta aaatttcccc tatgaaaatt    480
aatcagataa aagacattat aaaatctggt gtagtaggca cattccctgt ttctacaaag    540
ttcacacatg ccactggtga ttataatgtt attaccggtg catatcttgg taatatcaca    600
ctgaaaacag aaggtacttt aactatctct gccaatggct cctggactta caatggcgtt    660
gttcgttcat atgatgataa atacgatttt aacgccagca ctcaccgtgg cattatcgga    720
gagtcgctca aaggctcgg ggcgatgttt tctggtaaag agtaccagat actgcttcct    780
ggtgaaattc acattaaaga aagtggtaag cgataa                              816

<210> SEQ ID NO 62
<211> LENGTH: 387
<212> TYPE: PRT
<213> ORGANISM: Escherichia coli

<400> SEQUENCE: 62

Met Gly Ser Asn Gly Ala Asp Asn Ala His Asn Asn Ala Phe Gly Gly
1               5                   10                  15

Gly Lys Asn Pro Gly Ile Gly Asn Thr Ser Gly Ala Gly Ser Asn Gly
            20                  25                  30

Ser Ala Ser Ser Asn Arg Gly Asn Ser Asn Gly Trp Ser Trp Ser Asn
        35                  40                  45

Lys Pro His Lys Asn Asp Gly Phe His Ser Asp Gly Ser Tyr His Ile
    50                  55                  60

Thr Phe His Gly Asp Asn Asn Ser Lys Pro Lys Pro Gly Gly Asn Ser
65                  70                  75                  80

Gly Asn Arg Gly Asn Asn Gly Asp Gly Ala Ser Ala Lys Val Gly Glu
                85                  90                  95
```

Ile Thr Ile Thr Pro Asp Asn Ser Lys Pro Gly Arg Tyr Ile Ser Ser
            100                 105                 110

Asn Pro Glu Tyr Ser Leu Leu Ala Lys Leu Ile Asp Ala Glu Ser Ile
            115                 120                 125

Lys Gly Thr Glu Val Tyr Thr Phe His Thr Arg Lys Gly Gln Tyr Val
        130                 135                 140

Lys Val Thr Val Pro Asp Ser Asn Ile Asp Lys Met Arg Val Asp Tyr
145                 150                 155                 160

Val Asn Trp Lys Gly Pro Lys Tyr Asn Asn Lys Leu Val Lys Arg Phe
                165                 170                 175

Val Ser Gln Phe Leu Leu Phe Arg Lys Glu Lys Glu Lys Asn Glu
            180                 185                 190

Lys Glu Ala Leu Leu Lys Ala Ser Glu Leu Val Ser Gly Met Gly Asp
            195                 200                 205

Lys Leu Gly Glu Tyr Leu Gly Val Lys Tyr Lys Asn Val Ala Lys Glu
            210                 215                 220

Val Ala Asn Asp Ile Lys Asn Phe His Gly Arg Asn Ile Arg Ser Tyr
225                 230                 235                 240

Asn Glu Ala Met Ala Ser Leu Asn Lys Val Leu Ala Asn Pro Lys Met
                245                 250                 255

Lys Val Asn Lys Ser Asp Lys Asp Ala Ile Val Asn Ala Trp Lys Gln
            260                 265                 270

Val Asn Ala Lys Asp Met Ala Asn Lys Ile Gly Asn Leu Gly Lys Ala
            275                 280                 285

Phe Lys Val Ala Asp Leu Ala Ile Lys Val Glu Lys Ile Arg Glu Lys
            290                 295                 300

Ser Ile Glu Gly Tyr Asn Thr Gly Asn Trp Gly Pro Leu Leu Leu Glu
305                 310                 315                 320

Val Glu Ser Trp Ile Ile Gly Val Val Ala Gly Val Ala Ile Ser
                325                 330                 335

Leu Phe Gly Ala Val Leu Ser Phe Leu Pro Ile Ser Gly Leu Ala Val
            340                 345                 350

Thr Ala Leu Gly Val Ile Gly Ile Met Thr Ile Ser Tyr Leu Ser Ser
            355                 360                 365

Phe Ile Asp Ala Asn Arg Val Ser Asn Ile Asn Asn Ile Ile Ser Ser
            370                 375                 380

Val Ile Arg
385

<210> SEQ ID NO 63
<211> LENGTH: 1171
<212> TYPE: DNA
<213> ORGANISM: Escherichia coli

<400> SEQUENCE: 63
atgggtagta atggcgcaga taatgcacat aacaatgctt ttggtggagg gaaaaatccg      60
ggcattggta taccagtgg cgcaggaagt aatggtagtg catcaagtaa ccgaggaaat     120
tccaatggat ggtcatggag taataagcct cataaaaatg atggcttcca cagtgatggt     180
tcttaccata ttacatttca tggggacaat aattcaaagc ctaaacctgg agggaatagt     240
ggaaatcgag gtaataacgg tgatggagcg agtgctaagg ttggagagat aacaatcaca     300
cctgacaact cgaaaccagg tcgttatatt tcgtcaaatc ctgaatattc attgttggca     360
aaattaattg atgcggaatc aattaaaggt acagaggtat atacttttca caccagaaaa     420

```
ggtcagtatg ttaaggttac tgttccagat agtaatattg ataaaatgag agttgattat      480
gtgaactgga agggaccgaa atataacaat aaacttgtga agaggtttgt gagccagttt      540
ttattattta ggaaggaaga aaaagaaaaa aatgaaaaag aagccttgct aaaggctagt      600
gaacttgtgt ctggtatggg ggataagctt ggcgagtatc ttggagtaaa atataaaaat      660
gtagctaagg aagttgccaa tgatattaaa aacttccatg gtcgtaatat tcgtagctat      720
aatgaagcaa tggcttcact taataaagtg ttagcaaatc caaagatgaa agtaaacaaa      780
tctgataagg atgccattgt gaatgcctgg aaacaggtta atgctaagga catggctaat      840
aagattggta tcttggcaa ggcatttaag gttgctgatt tagctataaa ggttgagaaa       900
attagggaaa aaagcattga gggatacaat actggcaact ggggacctct cctgttggag      960
gttgaatcat ggatcattgg tggcgttgtt gctggagttg ctattagttt attcggggct     1020
gtgttgagtt ttctcccaat ctctggactt gcagttactg cgttgggggt aataggaata     1080
atgacgatta gttacttgtc atctttcata gatgcaaatc gagtttcgaa tataaataac     1140
attatatcta gtgttattcg agcaaatcga g                                    1171
```

<210> SEQ ID NO 64
<211> LENGTH: 103
<212> TYPE: PRT
<213> ORGANISM: Escherichia coli

<400> SEQUENCE: 64

```
Met Arg Thr Leu Thr Leu Asn Glu Leu Asp Ser Val Ser Gly Gly Ala
1               5                   10                  15

Ser Gly Arg Asp Ile Ala Met Ala Ile Gly Thr Leu Ser Gly Gln Phe
            20                  25                  30

Val Ala Gly Gly Ile Gly Ala Ala Gly Gly Val Ala Gly Gly Ala
        35                  40                  45

Ile Tyr Asp Tyr Ala Ser Thr His Lys Pro Asn Pro Ala Met Ser Pro
    50                  55                  60

Ser Gly Leu Gly Gly Thr Ile Lys Gln Lys Pro Glu Gly Ile Pro Ser
65                  70                  75                  80

Glu Ala Trp Asn Tyr Ala Ala Gly Arg Leu Cys Asn Trp Ser Pro Asn
                85                  90                  95

Asn Leu Ser Asp Val Cys Leu
            100
```

<210> SEQ ID NO 65
<211> LENGTH: 312
<212> TYPE: DNA
<213> ORGANISM: Escherichia coli

<400> SEQUENCE: 65

```
atgagaactc tgactctaaa tgaattagat tctgtttctg gtggtgcttc agggcgtgat       60
attgcgatgg ctataggaac actatccgga caatttgttg caggaggaat tggagcagct      120 gctggggggtg tggctggagg tgcaatatat gactatgcat ccactcacaa acctaatcct     180
gcaatgtctc catccggttt aggaggaaca attaagcaaa aacccgaagg gataccttca      240
gaagcatgga actatgctgc gggaagattg tgtaattgga gtccaaataa tcttagtgat      300
gtttgtttat aa                                                          312
```

<210> SEQ ID NO 66
<211> LENGTH: 58

-continued

```
<212> TYPE: PRT
<213> ORGANISM: Enterococcus columbae

<400> SEQUENCE: 66

Met Met Asn Ala Thr Glu Asn Gln Ile Phe Val Glu Thr Val Ser Asp
1               5                   10                  15

Gln Glu Leu Glu Met Leu Ile Gly Gly Ala Gly Arg Gly Trp Ile Lys
            20                  25                  30

Thr Leu Thr Lys Asp Cys Pro Asn Val Ile Ser Ser Ile Cys Ala Gly
        35                  40                  45

Thr Ile Ile Thr Ala Cys Lys Asn Cys Ala
    50                  55

<210> SEQ ID NO 67
<211> LENGTH: 177
<212> TYPE: DNA
<213> ORGANISM: Enterococcus columbae

<400> SEQUENCE: 67
atgatgaatg ctactgaaaa ccaaattttt gttgagactg tgagtgacca agaattagaa     60
atgttaattg gtggtgcagg tcgtggatgg attaagactt taacaaaaga ttgtccaaat    120
gtgatttctt caatttgtgc aggtacaatt attacagctt gtaaaaattg tgcttaa       177

<210> SEQ ID NO 68
<211> LENGTH: 59
<212> TYPE: PRT
<213> ORGANISM: Lactobacillus curvatus

<400> SEQUENCE: 68

Met Asn Asn Val Lys Glu Leu Ser Met Thr Glu Leu Gln Thr Ile Thr
1               5                   10                  15

Gly Gly Ala Arg Ser Tyr Gly Asn Gly Val Tyr Cys Asn Asn Lys Lys
            20                  25                  30

Cys Trp Val Asn Arg Gly Glu Ala Thr Gln Ser Ile Ile Gly Gly Met
        35                  40                  45

Ile Ser Gly Trp Ala Ser Gly Leu Ala Gly Met
    50                  55

<210> SEQ ID NO 69
<211> LENGTH: 180
<212> TYPE: DNA
<213> ORGANISM: Lactobacillus curvatus

<400> SEQUENCE: 69
atgaataatg taaagaatt aagtatgaca gaattacaaa caattaccgg cggtgctaga      60
tcatatggca acggtgttta ctgtaataat aaaaaatgtt gggtaaatcg gggtgaagca    120
acgcaaagta ttattggtgg tatgattagc ggctgggcta gtggtttagc tggaatgtaa    180

<210> SEQ ID NO 70
<211> LENGTH: 64
<212> TYPE: PRT
<213> ORGANISM: Streptomyces sp.

<400> SEQUENCE: 70

Met Arg Ser Glu Met Thr Leu Thr Ser Thr Asn Ser Ala Glu Ala Leu
1               5                   10                  15

Ala Ala Gln Asp Phe Ala Asn Thr Val Leu Ser Ala Ala Ala Pro Gly
            20                  25                  30
```

```
Phe His Ala Asp Cys Glu Thr Pro Ala Met Ala Thr Pro Ala Thr Pro
         35                  40                  45

Thr Val Ala Gln Phe Val Ile Gln Gly Ser Thr Ile Cys Leu Val Cys
 50                  55                  60

<210> SEQ ID NO 71
<211> LENGTH: 195
<212> TYPE: DNA
<213> ORGANISM: Streptomyces sp.

<400> SEQUENCE: 71
gtgcgatctg agatgactct tacgagcacg aattccgctg aggctctggc ggcgcaggac      60
tttgcgaaca ccgttctcag cgcggcggcc ccgggcttcc acgcggactg cgagacgccg     120
gccatggcca ccccggccac gccgaccgtc gcccagttcg tgatccaggg cagcacgatc     180
tgcctggtct gctga                                                      195

<210> SEQ ID NO 72
<211> LENGTH: 65
<212> TYPE: PRT
<213> ORGANISM: Bacillus halodurans

<400> SEQUENCE: 72

Met Val Asn Ser Lys Asp Leu Arg Asn Pro Glu Phe Arg Lys Ala Gln
 1               5                  10                  15

Gly Leu Gln Phe Val Asp Glu Val Asn Glu Lys Glu Leu Ser Ser Leu
                 20                  25                  30

Ala Gly Ser Gly Asp Val His Ala Gln Thr Thr Trp Pro Cys Ala Thr
             35                  40                  45

Val Gly Val Ser Val Ala Leu Cys Pro Thr Thr Lys Cys Thr Ser Gln
     50                  55                  60

Cys
 65

<210> SEQ ID NO 73
<211> LENGTH: 198
<212> TYPE: DNA
<213> ORGANISM: Bacillus halodurans

<400> SEQUENCE: 73
atggtaaatt caaaagattt gcgtaatcct gaattccgca aagcccaagg tctacaattc      60
gttgacgagg tgaacgagaa ggaactttcg tctctagctg gttcaggaga tgtgcatgca     120
caaacaactt ggccttgcgc tacagttggt gtctccgtag ccttgtgccc aactacaaag     180
tgtacaagcc agtgctaa                                                   198

<210> SEQ ID NO 74
<211> LENGTH: 66
<212> TYPE: PRT
<213> ORGANISM: Carnobacterium divergens

<400> SEQUENCE: 74

Met Lys Asn Leu Lys Glu Gly Ser Tyr Thr Ala Val Asn Thr Asp Glu
 1               5                  10                  15

Leu Lys Ser Ile Asn Gly Gly Thr Lys Tyr Tyr Gly Asn Gly Val Tyr
                 20                  25                  30

Cys Asn Ser Lys Lys Cys Trp Val Asp Trp Gly Gln Ala Ser Gly Cys
             35                  40                  45

Ile Gly Gln Thr Val Val Gly Gly Trp Leu Gly Gly Ala Ile Pro Gly
```

Lys Cys
65

<210> SEQ ID NO 75
<211> LENGTH: 201
<212> TYPE: DNA
<213> ORGANISM: Carnobacterium divergens

<400> SEQUENCE: 75

```
atgaaaaact taaagaagg ttcatacact gctgttaata ctgatgaatt aaaaagtatc    60
aatggtggaa caaatatta tgggaatggc gtttattgca attctaaaaa atgttgggta   120
gattggggac aagcttcagg ttgtatcggt caaactgttg ttggcggatg ctaggcgga   180
gctataccag gtaaatgcta a                                            201
```

<210> SEQ ID NO 76
<211> LENGTH: 63
<212> TYPE: PRT
<213> ORGANISM: Carnobacterium divergens

<400> SEQUENCE: 76

Met Ile Lys Arg Glu Lys Asn Arg Thr Ile Ser Ser Leu Gly Tyr Glu
1               5                   10                  15

Glu Ile Ser Asn His Lys Leu Gln Glu Ile Gln Gly Gly Lys Gly Ile
            20                  25                  30

Leu Gly Lys Leu Gly Val Val Gln Ala Gly Val Asp Phe Val Ser Gly
        35                  40                  45

Val Trp Ala Gly Ile Lys Gln Ser Ala Lys Asp His Pro Asn Ala
    50                  55                  60

<210> SEQ ID NO 77
<211> LENGTH: 192
<212> TYPE: DNA
<213> ORGANISM: Carnobacterium divergens

<400> SEQUENCE: 77

```
atgattaaaa gagaaaagaa cagaacaatt tcttcccttg gttatgaaga aatttctaat    60
cataaattgc aagaaataca aggtggaaaa ggaattcttg gtaaactagg agtagtacag   120
gcaggagtgg attttgtatc aggagtgtgg gctggaataa aacagtctgc caagatcat   180
cctaatgcgt aa                                                       192
```

<210> SEQ ID NO 78
<211> LENGTH: 75
<212> TYPE: PRT
<213> ORGANISM: Carnobacterium divergens

<400> SEQUENCE: 78

Met Lys Lys Gln Ile Leu Lys Gly Leu Val Ile Val Cys Leu Ser
1               5                   10                  15

Gly Ala Thr Phe Phe Ser Thr Pro Gln Gln Ala Ser Ala Ala Ala Pro
            20                  25                  30

Lys Ile Thr Gln Lys Gln Lys Asn Cys Val Asn Gly Gln Leu Gly Gly
        35                  40                  45

Met Leu Ala Gly Ala Leu Gly Gly Pro Gly Gly Val Val Leu Gly Gly
    50                  55                  60

Ile Gly Gly Ala Ile Ala Gly Gly Cys Phe Asn
65                  70                  75

-continued

<210> SEQ ID NO 79
<211> LENGTH: 228
<212> TYPE: DNA
<213> ORGANISM: Carnobacterium divergens

<400> SEQUENCE: 79

```
atgaaaaaac aaattttaaa agggttggtt atagttgttt gtttatctgg ggcaacattt      60
ttctcaacac acaacaagc ttctgctgct gcaccgaaaa ttactcaaaa acaaaaaaat     120
tgtgttaatg acaattagg tggaatgctt gctggagctt gggtggacc tggcggagtt     180
gtgttaggtg gtataggtgg tgcaatagca ggaggttgtt ttaattaa                228
```

<210> SEQ ID NO 80
<211> LENGTH: 72
<212> TYPE: PRT
<213> ORGANISM: Enterococcus durans

<400> SEQUENCE: 80

Met Gln Thr Ile Lys Glu Leu Asn Thr Met Glu Leu Gln Glu Ile Ile
1               5                   10                  15

Gly Gly Glu Asn Asp His Arg Met Pro Tyr Glu Leu Asn Arg Pro Asn
            20                  25                  30

Asn Leu Ser Lys Gly Gly Ala Lys Cys Ala Ala Gly Ile Leu Gly Ala
        35                  40                  45

Gly Leu Gly Ala Val Gly Gly Pro Gly Gly Phe Ile Ser Ala Gly
    50                  55                  60

Ile Ser Ala Val Leu Gly Cys Met
65                  70

<210> SEQ ID NO 81
<211> LENGTH: 219
<212> TYPE: DNA
<213> ORGANISM: Enterococcus durans

<400> SEQUENCE: 81

```
atgcaaacga tcaaagaatt gaacacgatg gaattacaag aaataattgg aggtgaaaat      60
gaccatcgga tgccttacga attgaaccgt ccaaataatt tatccaaagg tggggctaag     120
tgtgctgctg gaatacttgg cgctggacta ggcgcagtag gcggtggacc tggcggattt     180
attagtgccg gaatcagtgc tgttcttggt tgtatgtaa                           219
```

<210> SEQ ID NO 82
<211> LENGTH: 72
<212> TYPE: PRT
<213> ORGANISM: Enterococcus durans

<400> SEQUENCE: 82

Met Gln Thr Ile Lys Glu Leu Asn Thr Met Glu Leu Gln Lys Ile Ile
1               5                   10                  15

Gly Gly Glu Asn Asp His Arg Met Pro Tyr Glu Leu Asn Arg Pro Asn
            20                  25                  30

Asn Leu Ser Lys Gly Gly Ala Lys Cys Ala Ala Gly Ile Leu Gly Ala
        35                  40                  45

Gly Leu Gly Ala Val Gly Gly Pro Gly Gly Phe Ile Ser Ala Gly
    50                  55                  60

Ile Ser Ala Val Leu Gly Cys Met
65                  70

<210> SEQ ID NO 83
<211> LENGTH: 219
<212> TYPE: DNA
<213> ORGANISM: Enterococcus durans

<400> SEQUENCE: 83

```
atgcaaacga tcaaagaatt gaacacgatg gaattacaaa aaataattgg aggtgaaaat      60
gaccatcgga tgccttacga attgaaccgt ccaaataatt tatccaaagg tggagctaag     120
tgcgctgccg gaatacttgg tgctggatta ggcgcagtag gcggtggacc tggcggattt     180
attagtgccg gaatcagtgc tgttcttggt tgtatgtaa                           219
```

<210> SEQ ID NO 84
<211> LENGTH: 220
<212> TYPE: PRT
<213> ORGANISM: Streptococcus dysgalactiae subsp. equisimilis

<400> SEQUENCE: 84

```
Met Lys Lys Leu Lys Arg Leu Val Ile Ser Leu Val Thr Ser Leu Leu
1               5                   10                  15

Val Ile Ser Ser Thr Val Pro Ala Leu Val Tyr Ala Asn Glu Thr Asn
            20                  25                  30

Asn Phe Ala Glu Thr Gln Lys Glu Ile Thr Thr Asn Ser Glu Ala Thr
        35                  40                  45

Leu Thr Asn Glu Asp Tyr Thr Lys Leu Thr Ser Glu Val Lys Thr Ile
    50                  55                  60

Tyr Thr Asn Leu Ile Gln Tyr Asp Gln Thr Lys Asn Lys Phe Tyr Val
65                  70                  75                  80

Asp Glu Asp Lys Thr Glu Gln Tyr Tyr Asn Tyr Asp Asp Glu Ser Ile
                85                  90                  95

Lys Gly Val Tyr Leu Met Lys Asp Ser Leu Asn Asp Glu Leu Asn Asn
            100                 105                 110

Asn Asn Ser Ser Asn Tyr Ser Glu Ile Ile Asn Gln Lys Ile Ser Glu
        115                 120                 125

Ile Asp Tyr Val Leu Gln Gly Asn Asp Ile Asn Asn Leu Ile Pro Ser
    130                 135                 140

Asn Thr Arg Val Lys Arg Ser Ala Asp Phe Ser Trp Ile Gln Arg Cys
145                 150                 155                 160

Leu Glu Glu Ala Trp Gly Tyr Ala Ile Ser Leu Val Thr Leu Lys Gly
                165                 170                 175

Ile Ile Asn Leu Phe Lys Ala Gly Lys Phe Glu Ala Ala Ala Ala Lys
            180                 185                 190

Leu Ala Ser Ala Thr Ala Gly Arg Ile Ala Gly Met Ala Ala Leu Phe
        195                 200                 205

Ala Phe Val Ala Thr Cys Gly Ala Thr Thr Val Ser
    210                 215                 220
```

<210> SEQ ID NO 85
<211> LENGTH: 663
<212> TYPE: DNA
<213> ORGANISM: Streptococcus dysgalactiae subsp. equisimilis

<400> SEQUENCE: 85

```
atgaaaaaat taaaacgtct tgttatctct cttgttactt cattactagt aatttcaagt      60
acagttccag cacttgttta cgctaatgaa acaaataact ttgcagaaac tcaaaaagaa     120
attacaacaa attcagaagc aacattaacc aatgaagact acactaaatt aacttccgaa     180
```

```
gtaaaaacaa tttatacaaa tctgattcaa tacgaccaaa caaaaaacaa attttacgtc      240
gatgaagaca aaactgaaca atattataac tacgatgatg aaagtataaa aggggttat       300 ctcatgaaag atagtttgaa cgatgagtta acaataata actcttcaaa ctattctgaa       360
ataattaatc aaaaaatctc tgaaattgac tatgtccttc aaggaaacga tataaataat      420
ttaattccta gcaataccag agtaaaaaga tcagcagatt tttcttggat tcaaagatgt      480
ctagaagaag catggggata tgctattagt ctagttactc taaaaggaat aatcaatcta      540
tttaaagcag gaaaatttga agctgctgct gctaaattag cttctgctac agcaggtaga      600
atcgctggaa tggctgcctt atttgctttc gtagcaactt gcggtgcgac aactgtatca      660
taa                                                                   663
```

<210> SEQ ID NO 86
<211> LENGTH: 57
<212> TYPE: PRT
<213> ORGANISM: Enterococcus faecalis

<400> SEQUENCE: 86

```
Met Lys Gln Tyr Lys Val Leu Asn Glu Lys Glu Met Lys Lys Pro Ile
1               5                   10                  15

Gly Gly Glu Ser Val Phe Ser Lys Ile Gly Asn Ala Val Gly Pro Ala
            20                  25                  30

Ala Tyr Trp Ile Leu Lys Gly Leu Gly Asn Met Ser Asp Val Asn Gln
        35                  40                  45

Ala Asp Arg Ile Asn Arg Lys Lys His
    50                  55
```

<210> SEQ ID NO 87
<211> LENGTH: 174
<212> TYPE: DNA
<213> ORGANISM: Enterococcus faecalis

<400> SEQUENCE: 87

```
atgaagcaat ataaagtatt gaatgaaaaa gaaatgaaaa aacctattgg gggagagtcg       60 gttttttagta aataggtaa tgctgtaggt ccagctgctt attggatttt aaaaggatta      120
ggtaatatga gtgatgtaaa ccaagctgat agaattaata gaaagaaaca ttaa            174
```

<210> SEQ ID NO 88
<211> LENGTH: 44
<212> TYPE: PRT
<213> ORGANISM: Enterococcus faecalis

<400> SEQUENCE: 88

```
Met Gly Ala Ile Ala Lys Leu Val Ala Lys Phe Gly Trp Pro Ile Val
1               5                   10                  15

Lys Lys Tyr Tyr Lys Gln Ile Met Gln Phe Ile Gly Glu Gly Trp Ala
            20                  25                  30

Ile Asn Lys Ile Ile Asp Trp Ile Lys Lys His Ile
        35                  40
```

<210> SEQ ID NO 89
<211> LENGTH: 135
<212> TYPE: DNA
<213> ORGANISM: Enterococcus faecalis

<400> SEQUENCE: 89

```
atgggagcaa tcgcaaaatt agtagcaaag tttggatggc caattgttaa aaagtattac       60
```
aaacaaatta tgcaatttat tggagaagga tgggcaatta acaaaattat tgattggatc    120
aaaaaacata tttaa                                                    135

<210> SEQ ID NO 90
<211> LENGTH: 43
<212> TYPE: PRT
<213> ORGANISM: Enterococcus faecalis

<400> SEQUENCE: 90

Met Gly Ala Ile Ala Lys Leu Val Ala Lys Phe Gly Trp Pro Phe Ile
1               5                   10                  15

Lys Lys Phe Tyr Lys Gln Ile Met Gln Phe Ile Gly Gln Gly Trp Thr
            20                  25                  30

Ile Asp Gln Ile Glu Lys Trp Leu Lys Arg His
        35                  40

<210> SEQ ID NO 91
<211> LENGTH: 132
<212> TYPE: DNA
<213> ORGANISM: Enterococcus faecalis

<400> SEQUENCE: 91
atgggagcaa tcgcaaaatt agtagcaaag tttggatggc catttattaa aaaattctac    60
aaacaaatta tgcagtttat cggacaagga tggacaatag atcaaattga aaatggtta    120 aaaagacatt ga                                                       132

<210> SEQ ID NO 92
<211> LENGTH: 74
<212> TYPE: PRT
<213> ORGANISM: Enterococcus faecalis

<400> SEQUENCE: 92

Met Leu Asn Lys Lys Leu Leu Glu Asn Gly Val Val Asn Ala Val Thr
1               5                   10                  15

Ile Asp Glu Leu Asp Ala Gln Phe Gly Gly Met Ser Lys Arg Asp Cys
            20                  25                  30

Asn Leu Met Lys Ala Cys Cys Ala Gly Gln Ala Val Thr Tyr Ala Ile
        35                  40                  45

His Ser Leu Leu Asn Arg Leu Gly Gly Asp Ser Ser Asp Pro Ala Gly
    50                  55                  60

Cys Asn Asp Ile Val Arg Lys Tyr Cys Lys
65                  70

<210> SEQ ID NO 93
<211> LENGTH: 225
<212> TYPE: DNA
<213> ORGANISM: Enterococcus faecalis

<400> SEQUENCE: 93
atgttaaata aaaaattatt agaaaatggt gtagtaaatg ctgtaacaat tgatgaactt    60
gatgctcaat tggtggaat gagcaaacgt gattgtaact tgatgaaggc gtgttgtgct    120
ggacaagcag taacatatgc tattcatagt cttttaaatc gattaggtgg agactctagt    180
gatccagctg gttgtaatga tattgtaaga aaatattgta aataa                   225

<210> SEQ ID NO 94
<211> LENGTH: 65
<212> TYPE: PRT

<213> ORGANISM: Enterococcus faecium

<400> SEQUENCE: 94

| Met | Lys | His | Leu | Lys | Ile | Leu | Ser | Ile | Lys | Glu | Thr | Gln | Leu | Ile | Tyr |
|---|---|---|---|---|---|---|---|---|---|---|---|---|---|---|---|
| 1 | | | | 5 | | | | | 10 | | | | | 15 | |

| Gly | Gly | Thr | Thr | His | Ser | Gly | Lys | Tyr | Tyr | Gly | Asn | Gly | Val | Tyr | Cys |
|---|---|---|---|---|---|---|---|---|---|---|---|---|---|---|---|
| | | | 20 | | | | | 25 | | | | | 30 | | |

| Thr | Lys | Asn | Lys | Cys | Thr | Val | Asp | Trp | Ala | Lys | Ala | Thr | Thr | Cys | Ile |
|---|---|---|---|---|---|---|---|---|---|---|---|---|---|---|---|
| | | | 35 | | | | | 40 | | | | | 45 | | |

| Ala | Gly | Met | Ser | Ile | Gly | Gly | Phe | Leu | Gly | Gly | Ala | Ile | Pro | Gly | Lys |
|---|---|---|---|---|---|---|---|---|---|---|---|---|---|---|---|
| 50 | | | | | 55 | | | | | 60 | | | | | |

Cys
65

<210> SEQ ID NO 95
<211> LENGTH: 195
<212> TYPE: DNA
<213> ORGANISM: Enterococcus faecium

<400> SEQUENCE: 95

```
atgaaacatt taaaaatttt gtctattaaa gagacacaac ttatctatgg gggtaccact      60
catagtggaa aatattatgg aaatggagtg tattgcacta aaaataaatg tacggtcgat     120
tgggccaagg caactacttg tattgcagga atgtctatag gtggtttttt aggtggagca     180
attccaggga agtgc                                                      195
```

<210> SEQ ID NO 96
<211> LENGTH: 105
<212> TYPE: PRT
<213> ORGANISM: Enterococcus faecalis

<400> SEQUENCE: 96

| Met | Val | Lys | Glu | Asn | Lys | Phe | Ser | Lys | Ile | Phe | Ile | Leu | Met | Ala | Leu |
|---|---|---|---|---|---|---|---|---|---|---|---|---|---|---|---|
| 1 | | | | 5 | | | | | 10 | | | | | 15 | |

| Ser | Phe | Leu | Gly | Leu | Ala | Leu | Phe | Ser | Ala | Ser | Leu | Gln | Phe | Leu | Pro |
|---|---|---|---|---|---|---|---|---|---|---|---|---|---|---|---|
| | | | 20 | | | | | 25 | | | | | 30 | | |

| Ile | Ala | His | Met | Ala | Lys | Glu | Phe | Gly | Ile | Pro | Ala | Ala | Val | Ala | Gly |
|---|---|---|---|---|---|---|---|---|---|---|---|---|---|---|---|
| | | 35 | | | | | 40 | | | | | 45 | | | |

| Thr | Val | Leu | Asn | Val | Val | Glu | Ala | Gly | Gly | Trp | Val | Thr | Thr | Ile | Val |
|---|---|---|---|---|---|---|---|---|---|---|---|---|---|---|---|
| | 50 | | | | | 55 | | | | | 60 | | | | |

| Ser | Ile | Leu | Thr | Ala | Val | Gly | Ser | Gly | Gly | Leu | Ser | Leu | Leu | Ala | Ala |
|---|---|---|---|---|---|---|---|---|---|---|---|---|---|---|---|
| 65 | | | | | 70 | | | | | 75 | | | | | 80 |

| Ala | Gly | Arg | Glu | Ser | Ile | Lys | Ala | Tyr | Leu | Lys | Lys | Glu | Ile | Lys | Lys |
|---|---|---|---|---|---|---|---|---|---|---|---|---|---|---|---|
| | | | | 85 | | | | | 90 | | | | | 95 | |

| Lys | Gly | Lys | Arg | Ala | Val | Ile | Ala | Trp |
|---|---|---|---|---|---|---|---|---|
| | | | 100 | | | | | 105 |

<210> SEQ ID NO 97
<211> LENGTH: 318
<212> TYPE: DNA
<213> ORGANISM: Enterococcus faecalis

<400> SEQUENCE: 97

```
atggttaaag aaaataaatt ttctaagatt tttattttaa tggctttgag ttttttgggg      60
ttagccttgt ttagtgcaag tcttcagttt ttgcccattg cacatatggc taaagagttc     120
ggtataccag cagcagttgc aggaactgtg cttaatgtag ttgaagctgg tggatgggtc     180
actactattg tatcaattct tactgctgta ggtagcggag gtctttcttt actcgctgca     240
```
gcaggaagag agtcaattaa agcatacctt aagaaagaaa ttaagaaaaa aggaaaaaga    300
gcagttattg cttggtaa                                                 318

<210> SEQ ID NO 98
<211> LENGTH: 71
<212> TYPE: PRT
<213> ORGANISM: Enterococcus faecium

<400> SEQUENCE: 98

Met Gln Asn Val Lys Glu Leu Ser Thr Lys Glu Met Lys Gln Ile Ile
1               5                   10                  15

Gly Gly Glu Asn Asp His Arg Met Pro Asn Glu Leu Asn Arg Pro Asn
            20                  25                  30

Asn Leu Ser Lys Gly Gly Ala Lys Cys Gly Ala Ala Ile Ala Gly Gly
        35                  40                  45

Leu Phe Gly Ile Pro Lys Gly Pro Leu Ala Trp Ala Ala Gly Leu Ala
    50                  55                  60

Asn Val Tyr Ser Lys Cys Asn
65                  70

<210> SEQ ID NO 99
<211> LENGTH: 216
<212> TYPE: DNA
<213> ORGANISM: Enterococcus faecium

<400> SEQUENCE: 99
atgcaaaatg taaagaatt aagtacgaaa gagatgaaac aaattatcgg tggagaaaat    60
gatcacagaa tgcctaatga gttaaataga cctaacaact tatctaaagg tggagcaaaa   120
tgtggtgctg caattgctgg gggattattt ggaatcccaa aaggaccact agcatgggct   180
gctgggttag caaatgtata ctctaaatgc aactaa                             216

<210> SEQ ID NO 100
<211> LENGTH: 58
<212> TYPE: PRT
<213> ORGANISM: Enterococcus mundtii

<400> SEQUENCE: 100

Met Lys Lys Leu Thr Ser Lys Glu Met Ala Gln Val Val Gly Gly Lys
1               5                   10                  15

Tyr Tyr Gly Asn Gly Val Ser Cys Asn Lys Lys Gly Cys Ser Val Asp
            20                  25                  30

Trp Gly Lys Ala Ile Gly Ile Ile Gly Asn Asn Ser Ala Ala Asn Leu
        35                  40                  45

Ala Thr Gly Gly Ala Ala Gly Trp Lys Ser
    50                  55

<210> SEQ ID NO 101
<211> LENGTH: 177
<212> TYPE: DNA
<213> ORGANISM: Enterococcus mundtii

<400> SEQUENCE: 101
ttgaagaaat taacatcaaa agaaatggca caagtagtag gtggaaaata ctacggtaat    60
ggagtctcat gtaataaaaa agggtgcagt gttgattggg gaaaagctat tggcattatt   120
ggaaataatt ctgctgcgaa tttagctact ggtggagcag ctggttggaa aagttaa      177

<210> SEQ ID NO 102
<211> LENGTH: 44
<212> TYPE: PRT
<213> ORGANISM: Enterococcus faecalis

<400> SEQUENCE: 102

Met Leu Ala Lys Ile Lys Ala Met Ile Lys Lys Phe Pro Asn Pro Tyr
1               5                   10                  15

Thr Leu Ala Ala Lys Leu Thr Thr Tyr Glu Ile Asn Trp Tyr Lys Gln
            20                  25                  30

Gln Tyr Gly Arg Tyr Pro Trp Glu Arg Pro Val Ala
        35                  40

<210> SEQ ID NO 103
<211> LENGTH: 135
<212> TYPE: DNA
<213> ORGANISM: Enterococcus faecalis

<400> SEQUENCE: 103
atgttagcaa aaattaaagc gatgattaag aagtttccga acccttatac tttagcagct      60
aagctaacga cttacgaaat taattggtat aaacaacaat acggtcgtta tccttgggag     120
cgccctgtag cataa                                                      135

<210> SEQ ID NO 104
<211> LENGTH: 71
<212> TYPE: PRT
<213> ORGANISM: Enterococcus faecium

<400> SEQUENCE: 104

Met Arg Lys Lys Leu Phe Ser Leu Ala Leu Ile Gly Ile Phe Gly Leu
1               5                   10                  15

Val Val Thr Asn Phe Gly Thr Lys Val Asp Ala Ala Thr Arg Ser Tyr
            20                  25                  30

Gly Asn Gly Val Tyr Cys Asn Asn Ser Lys Cys Trp Val Asn Trp Gly
        35                  40                  45

Glu Ala Lys Glu Asn Ile Ala Gly Ile Val Ile Ser Gly Trp Ala Ser
    50                  55                  60

Gly Leu Ala Gly Met Gly His
65                  70

<210> SEQ ID NO 105
<211> LENGTH: 216
<212> TYPE: DNA
<213> ORGANISM: Enterococcus faecium

<400> SEQUENCE: 105
atgagaaaaa aattatttag tttagctctt attggaatat tgggttagt tgtgacaaat       60 tttggtacaa aagttgatgc agctacgcgt tcatatggta atggtgttta ttgtaataat     120
agtaaatgct gggttaactg gggagaagct aaagagaata ttgcaggaat cgttattagt     180
ggctgggctt ctggtttggc aggtatggga cattaa                              216

<210> SEQ ID NO 106
<211> LENGTH: 34
<212> TYPE: PRT
<213> ORGANISM: Enterococcus faecium

<400> SEQUENCE: 106

Met Asn Phe Leu Lys Asn Gly Ile Ala Lys Trp Met Thr Gly Ala Glu
1               5                   10                  15

Leu Gln Ala Tyr Lys Lys Tyr Gly Cys Leu Pro Trp Glu Lys Ile
            20                  25                  30

Ser Cys

<210> SEQ ID NO 107
<211> LENGTH: 105
<212> TYPE: DNA
<213> ORGANISM: Enterococcus faecium

<400> SEQUENCE: 107
atgaattttc ttaaaaatgg tatcgcaaaa tggatgaccg gtgctgaatt gcaagcgtat      60
aaaaagaaat atggatgctt gccatgggaa aaaatttctt gttaa                    105

<210> SEQ ID NO 108
<211> LENGTH: 76
<212> TYPE: PRT
<213> ORGANISM: Enterococcus faecalis

<400> SEQUENCE: 108

Met Lys Lys Lys Leu Val Lys Gly Leu Val Ile Cys Gly Met Ile Gly
1               5                   10                  15

Ile Gly Phe Thr Ala Leu Gly Thr Asn Val Glu Ala Ala Thr Tyr Tyr
            20                  25                  30

Gly Asn Gly Val Tyr Cys Asn Lys Gln Lys Cys Trp Val Asp Trp Ser
        35                  40                  45

Arg Ala Arg Ser Glu Ile Ile Asp Arg Gly Val Lys Ala Tyr Val Asn
    50                  55                  60

Gly Phe Thr Lys Val Leu Gly Gly Ile Gly Gly Arg
65                  70                  75

<210> SEQ ID NO 109
<211> LENGTH: 231
<212> TYPE: DNA
<213> ORGANISM: Enterococcus faecalis

<400> SEQUENCE: 109
atgaaaaaga aattagttaa aggcttagtt atttgtggca tgattgggat tggttttaca      60
gcattaggaa caaatgtaga agccgccacg tattacggaa atggtgtcta ttgcaataag     120
caaaaatgtt gggtagattg gagtagagca cgttctgaaa ttatagacag aggcgtaaaa     180
gcatacgtca atggatttac gaaagtgtta ggtggtatag gtggaagata a              231

<210> SEQ ID NO 110
<211> LENGTH: 60
<212> TYPE: PRT
<213> ORGANISM: Enterococcus faecalis

<400> SEQUENCE: 110

Met Lys Lys Glu Glu Leu Val Gly Met Ala Lys Glu Asp Phe Leu Asn
1               5                   10                  15

Val Ile Cys Glu Asn Asp Asn Lys Leu Glu Asn Ser Gly Ala Lys Cys
            20                  25                  30

Pro Trp Trp Asn Leu Ser Cys His Leu Gly Asn Asp Gly Lys Ile Cys
        35                  40                  45

Thr Tyr Ser His Glu Cys Thr Ala Gly Cys Asn Ala
    50                  55                  60

<210> SEQ ID NO 111

```
<211> LENGTH: 183
<212> TYPE: DNA
<213> ORGANISM: Enterococcus faecalis

<400> SEQUENCE: 111
atgaaaaaag aagaattagt aggaatggct aaggaagact ttttaaatgt tatttgtgaa      60
aatgacaaca aactagaaaa tagtggagca aaatgtcctt ggtggaatct ttcttgtcat     120
ttaggcaatg atggtaaaat ttgcacttat tcacatgaat gtaccgcagg ttgtaatgca     180
taa                                                                   183

<210> SEQ ID NO 112
<211> LENGTH: 61
<212> TYPE: PRT
<213> ORGANISM: Enterococcus faecalis

<400> SEQUENCE: 112

Met Thr Glu Leu Asn Lys Arg Leu Gln Leu Lys Arg Asp Val Ser Thr
1               5                   10                  15

Glu Asn Ser Leu Lys Lys Ile Ser Asn Thr Asp Glu Thr His Gly Gly
            20                  25                  30

Val Thr Thr Ser Ile Pro Cys Thr Val Met Val Ser Ala Ala Val Cys
        35                  40                  45

Pro Thr Leu Val Cys Ser Asn Lys Cys Gly Gly Arg Gly
    50                  55                  60

<210> SEQ ID NO 113
<211> LENGTH: 186
<212> TYPE: DNA
<213> ORGANISM: Enterococcus faecalis

<400> SEQUENCE: 113
atgactgaac ttaacaaaag attacaatta aaaagagatg tttcaacaga aaatagtttg      60
aaaaaaattt ctaatactga tgaaacacat gggggagtta ctacatcaat tccatgtaca     120
gtaatggtta gtgcggcagt atgtcctacc cttgtttgct cgaataaatg tggcggtaga     180
ggctag                                                                186

<210> SEQ ID NO 114
<211> LENGTH: 58
<212> TYPE: PRT
<213> ORGANISM: Enterococcus faecium

<400> SEQUENCE: 114

Met Gln Asn Val Lys Glu Val Ser Val Lys Glu Met Lys Gln Ile Ile
1               5                   10                  15

Gly Gly Ser Asn Asp Ser Leu Trp Tyr Gly Val Gly Gln Phe Met Gly
            20                  25                  30

Lys Gln Ala Asn Cys Ile Thr Asn His Pro Val Lys His Met Ile Ile
        35                  40                  45

Pro Gly Tyr Cys Leu Ser Lys Ile Leu Gly
    50                  55

<210> SEQ ID NO 115
<211> LENGTH: 177
<212> TYPE: DNA
<213> ORGANISM: Enterococcus faecium

<400> SEQUENCE: 115
atgcaaaatg taaagaaagt ttctgtaaaa gagatgaaac aaattatcgg tggttctaat      60
```

```
gatagtcttt ggtatggtgt aggacaattt atgggtaaac aagcaaactg tataacaaac      120
catcctgtta aacacatgat aattcctgga tattgtttat cgaaaatttt agggtaa         177
```

<210> SEQ ID NO 116
<211> LENGTH: 55
<212> TYPE: PRT
<213> ORGANISM: Enterococcus faecium

<400> SEQUENCE: 116

```
Met Lys Lys Tyr Asn Glu Leu Ser Lys Lys Glu Leu Leu Gln Ile Gln
1               5                   10                  15

Gly Gly Ile Ala Pro Ile Ile Val Ala Gly Leu Gly Tyr Leu Val Lys
            20                  25                  30

Asp Ala Trp Asp His Ser Asp Gln Ile Ile Ser Gly Phe Lys Lys Gly
        35                  40                  45

Trp Asn Gly Gly Arg Lys
    50                  55
```

<210> SEQ ID NO 117
<211> LENGTH: 168
<212> TYPE: DNA
<213> ORGANISM: Enterococcus faecium

<400> SEQUENCE: 117

```
atgaaaaaat ataatgagtt atctaaaaaa gaacttctac agattcaagg aggaatagca      60
cctattatag ttgctggcct tggctattta gtaaaagatg catgggatca ctcagatcaa     120
ataatctcag gatttaaaaa aggttggaat ggtggacgta gaaaataa                  168
```

<210> SEQ ID NO 118
<211> LENGTH: 343
<212> TYPE: PRT
<213> ORGANISM: Enterococcus faecalis

<400> SEQUENCE: 118

```
Met Lys Asn Ile Leu Leu Ser Ile Leu Gly Val Leu Ser Ile Val Val
1               5                   10                  15

Ser Leu Ala Phe Ser Ser Tyr Ser Val Asn Ala Ala Ser Asn Glu Trp
            20                  25                  30

Ser Trp Pro Leu Gly Lys Pro Tyr Ala Gly Arg Tyr Glu Glu Gly Gln
        35                  40                  45

Gln Phe Gly Asn Thr Ala Phe Asn Arg Gly Thr Tyr Phe His Asp
    50                  55                  60

Gly Phe Asp Phe Gly Ser Ala Ile Tyr Gly Asn Gly Ser Val Tyr Ala
65                  70                  75                  80

Val His Asp Gly Lys Ile Leu Tyr Ala Gly Trp Asp Pro Val Gly Gly
                85                  90                  95

Gly Ser Leu Gly Ala Phe Ile Val Leu Gln Ala Gly Asn Thr Asn Val
            100                 105                 110

Ile Tyr Gln Glu Phe Ser Arg Asn Val Gly Asp Ile Lys Val Ser Thr
        115                 120                 125

Gly Gln Thr Val Lys Lys Gly Gln Leu Ile Gly Lys Phe Thr Ser Ser
    130                 135                 140

His Leu His Leu Gly Met Thr Lys Lys Glu Trp Arg Ser Ala His Ser
145                 150                 155                 160

Ser Trp Asn Lys Asp Asp Gly Thr Trp Phe Asn Pro Ile Pro Ile Leu
                165                 170                 175
```

```
Gln Gly Gly Ser Thr Pro Thr Pro Pro Asn Pro Gly Pro Lys Asn Phe
            180                 185                 190
Thr Thr Asn Val Arg Tyr Gly Leu Arg Val Leu Gly Gly Ser Trp Leu
        195                 200                 205
Pro Glu Val Thr Asn Phe Asn Asn Thr Asn Asp Gly Phe Ala Gly Tyr
    210                 215                 220
Pro Asn Arg Gln His Asp Met Leu Tyr Ile Lys Val Asp Lys Gly Gln
225                 230                 235                 240
Met Lys Tyr Arg Val His Thr Ala Gln Ser Gly Trp Leu Pro Trp Val
                245                 250                 255
Ser Lys Gly Asp Lys Ser Asp Thr Val Asn Gly Ala Ala Gly Met Pro
            260                 265                 270
Gly Gln Ala Ile Asp Gly Val Gln Leu Asn Tyr Ile Thr Pro Lys Gly
        275                 280                 285
Glu Lys Leu Ser Gln Ala Tyr Tyr Arg Ser Thr Thr Lys Arg Ser
    290                 295                 300
Gly Trp Leu Lys Val Ser Ala Asp Asn Gly Ser Ile Pro Gly Leu Asp
305                 310                 315                 320
Ser Tyr Ala Gly Ile Phe Gly Glu Pro Leu Asp Arg Leu Gln Ile Gly
                325                 330                 335
Ile Ser Gln Ser Asn Pro Phe
            340
```

<210> SEQ ID NO 119
<211> LENGTH: 1032
<212> TYPE: DNA
<213> ORGANISM: Enterococcus faecalis

<400> SEQUENCE: 119

```
atgaaaaata ttttactttc tattctaggg gtattatcta tcgttgtttc tttggcgttt      60
tcttcttatt ctgtcaacgc agcttctaat gagtggtcgt ggccactggg caaaccatat     120
gcgggaagat atgaagaagg acaacaattc ggaacactg catttaaccg aggaggtact     180
tatttccatg atgggtttga ctttggttct gctatttatg gaaatggcag tgtgtatgct     240
gtgcatgatg gtaaaatttt atatgctggt tgggatcctg taggtggagg ctcattaggt     300
gcatttattg tactacaagc gggaaacaca aatgtgattt atcaagaatt agccgaaat     360
gttggagata ttaaagttag cactggacaa actgttaaaa aggacagct gataggaaag     420
tttacttcta gtcatttaca tttaggaatg acaaaaaaag aatggcgttc tgctcattct     480
tcttggaata aagatgatgg cacttggttt aacccaattc ctatacttca aggaggatct     540
acgcctacgc ctccaaatcc aggaccaaaa aatttcacaa caatgttcg ttacggattg     600
cgggtcctcg gaggttcatg gttaccagaa gtaaccaact ttaacaatac caatgatggt     660
ttcgcaggtt accctaatcg tcaacatgat atgctttata taaggtaga taaagggcaa     720
atgaaatatc gtgttcacac ggctcaaagt ggatggttgc cttgggtaag taagggggat     780
aagagcgata cagtaaatgg agcggcaggt atgcctggac aagcaattga tggtgttcag     840
ctaaactata taactcctaa gggagaaaaa ttatcacagg cttactatcg ttcacaaact     900
acgaaacgat caggctggtt aaaagtaagt gcagataatg gttctattcc tggactagac     960
agttatgcag gaatctttgg agaaccgttg gatcgcttgc aaataggtat ttcacagtca    1020
aatccatttt aa                                                        1032
```

```
<210> SEQ ID NO 120
<211> LENGTH: 56
<212> TYPE: PRT
<213> ORGANISM: Staphylococcus epidermidis

<400> SEQUENCE: 120

Met Glu Asn Lys Lys Asp Leu Phe Asp Leu Glu Ile Lys Lys Asp Asn
1               5                   10                  15

Met Glu Asn Asn Asn Glu Leu Glu Ala Gln Ser Leu Gly Pro Ala Ile
            20                  25                  30

Lys Ala Thr Arg Gln Val Cys Pro Lys Ala Thr Arg Phe Val Thr Val
        35                  40                  45

Ser Cys Lys Lys Ser Asp Cys Gln
    50                  55

<210> SEQ ID NO 121
<211> LENGTH: 171
<212> TYPE: DNA
<213> ORGANISM: Staphylococcus epidermidis

<400> SEQUENCE: 121
atggaaaaca aaaagatttt atttgattta gaaatcaaaa aagataatat ggaaaataat     60
aatgaattag aagctcaatc tcttggtcct gcaattaagg caactagaca ggtatgtcct    120
aaagcaacac gttttgttac agtttcttgt aaaaaaagtg attgtcaata g             171

<210> SEQ ID NO 122
<211> LENGTH: 51
<212> TYPE: PRT
<213> ORGANISM: Staphylococcus epidermidis

<400> SEQUENCE: 122

Met Ala Ala Phe Met Lys Leu Ile Gln Phe Leu Ala Thr Lys Gly Gln
1               5                   10                  15

Lys Tyr Val Ser Leu Ala Trp Lys His Lys Gly Thr Ile Leu Lys Trp
            20                  25                  30

Ile Asn Ala Gly Gln Ser Phe Glu Trp Ile Tyr Lys Gln Ile Lys Lys
        35                  40                  45

Leu Trp Ala
    50

<210> SEQ ID NO 123
<211> LENGTH: 156
<212> TYPE: DNA
<213> ORGANISM: Staphylococcus epidermidis

<400> SEQUENCE: 123
atggcagcat ttatgaagtt aattcagttc ttagcaacta aaggtcaaaa gtatgtttca     60
cttgcatgga acataaagg tactatttta aaatggatta acgccggtca agtttttgaa    120
tggatttata acaaatcaa aaaattatgg gcataa                              156

<210> SEQ ID NO 124
<211> LENGTH: 52
<212> TYPE: PRT
<213> ORGANISM: Staphylococcus epidermidis

<400> SEQUENCE: 124

Met Glu Ala Val Lys Glu Lys Asn Asp Leu Phe Asn Leu Asp Val Lys
1               5                   10                  15

Val Asn Ala Lys Glu Ser Asn Asp Ser Gly Ala Glu Pro Arg Ile Ala
```

```
                20              25              30

Ser Lys Phe Ile Cys Thr Pro Gly Cys Ala Lys Thr Gly Ser Phe Asn
        35                  40                  45

Ser Tyr Cys Cys
    50

<210> SEQ ID NO 125
<211> LENGTH: 159
<212> TYPE: DNA
<213> ORGANISM: Staphylococcus epidermidis

<400> SEQUENCE: 125
atggaagcag taaaagaaaa aaatgatctt tttaatcttg atgttaaagt taatgcaaaa        60
gaatctaacg attcaggagc tgaaccaaga attgctagta aatttatatg tactcctgga       120
tgtgcaaaaa caggtagttt taacagttat tgttgttaa                              159

<210> SEQ ID NO 126
<211> LENGTH: 55
<212> TYPE: PRT
<213> ORGANISM: Staphylococcus epidermidis

<400> SEQUENCE: 126

Met Asn Asn Ser Leu Phe Asp Leu Asn Leu Asn Lys Gly Val Glu Thr
1               5                   10                  15

Gln Lys Ser Asp Leu Ser Pro Gln Ser Ala Ser Val Leu Lys Thr Ser
            20                  25                  30

Ile Lys Val Ser Lys Lys Tyr Cys Lys Gly Val Thr Leu Thr Cys Gly
        35                  40                  45

Cys Asn Ile Thr Gly Gly Lys
    50                  55

<210> SEQ ID NO 127
<211> LENGTH: 168
<212> TYPE: DNA
<213> ORGANISM: Staphylococcus epidermidis

<400> SEQUENCE: 127
atgaataact cattattcga tttaaaccta acaaaggtg tagaaactca aaagagtgat         60
ttaagtccgc aatctgctag tgtcttgaag acttctatta agtatctaa aaaatattgt       120 aaaggtgtta ctttaacatg cggttgcaat attactggtg gtaaataa                   168

<210> SEQ ID NO 128
<211> LENGTH: 52
<212> TYPE: PRT
<213> ORGANISM: Staphylococcus gallinarum

<400> SEQUENCE: 128

Met Glu Ala Val Lys Glu Lys Asn Glu Leu Phe Asp Leu Asp Val Lys
1               5                   10                  15

Val Asn Ala Lys Glu Ser Asn Asp Ser Gly Ala Glu Pro Arg Ile Ala
            20                  25                  30

Ser Lys Phe Leu Cys Thr Pro Gly Cys Ala Lys Thr Gly Ser Phe Asn
        35                  40                  45

Ser Tyr Cys Cys
    50

<210> SEQ ID NO 129
<211> LENGTH: 159
```

```
<212> TYPE: DNA
<213> ORGANISM: Staphylococcus gallinarum

<400> SEQUENCE: 129
atggaagcag taaaagagaa aaatgaactt tttgatcttg acgttaaagt aaatgcaaaa      60
gagtctaatg attcaggcgc agaaccacga attgctagta aatttttatg tactcctgga     120
tgtgccaaaa caggtagctt caatagctac tgttgttaa                            159

<210> SEQ ID NO 130
<211> LENGTH: 63
<212> TYPE: PRT
<213> ORGANISM: Lactococcus garvieae

<400> SEQUENCE: 130

Met Glu Asn Asn Tyr Thr Val Leu Ser Asp Glu Glu Leu Gln Lys
1               5                  10                  15

Ile Asp Gly Gly Ile Gly Gly Ala Leu Gly Asn Ala Leu Asn Gly Leu
            20                  25                  30

Gly Thr Trp Ala Asn Met Met Asn Gly Gly Phe Val Asn Gln Trp
        35                  40                  45

Gln Val Tyr Ala Asn Lys Gly Lys Ile Asn Gln Tyr Arg Pro Tyr
    50                  55                  60

<210> SEQ ID NO 131
<211> LENGTH: 192
<212> TYPE: DNA
<213> ORGANISM: Lactococcus garvieae

<400> SEQUENCE: 131
atggaaaaca acaattacac agtactttca gatgaagaac tacaaaaaat tgatggtgga      60
atcggcgggg ctcttggtaa tgctctcaac ggattaggta cctgggcaaa catgatgaac     120
ggtggaggat tgttaatca gtggcaagtt tatgctaata aggaaaaat aaatcaatac       180 cgtccgtatt aa                                                          192

<210> SEQ ID NO 132
<211> LENGTH: 63
<212> TYPE: PRT
<213> ORGANISM: Lactococcus garvieae

<400> SEQUENCE: 132

Met Phe Asp Leu Val Ala Thr Gly Met Ala Ala Gly Val Ala Lys Thr
1               5                  10                  15

Ile Val Asn Ala Val Ser Ala Gly Met Asp Ile Ala Thr Ala Leu Ser
            20                  25                  30

Leu Phe Ser Gly Ala Phe Thr Ala Ala Gly Gly Ile Met Ala Leu Ile
        35                  40                  45

Lys Lys Tyr Ala Gln Lys Lys Leu Trp Lys Gln Leu Ile Ala Ala
    50                  55                  60

<210> SEQ ID NO 133
<211> LENGTH: 192
<212> TYPE: DNA
<213> ORGANISM: Lactococcus garvieae

<400> SEQUENCE: 133
atgtttgatt tagtcgcgac tggaatggct gcaggtgtag caaaaactat tgttaatgcc      60
gttagtgctg gtatggatat tgccactgct ttatcattgt tctcaggagc ttttactgca     120
```

```
gctgggggaa ttatggcact cattaaaaaa tatgctcaaa agaaattatg gaaacagctt      180
attgctgcat aa                                                          192
```

<210> SEQ ID NO 134
<211> LENGTH: 91
<212> TYPE: PRT
<213> ORGANISM: Lactobacillus gasseri

<400> SEQUENCE: 134

```
Met Val Thr Lys Tyr Gly Arg Asn Leu Gly Leu Asn Lys Val Glu Leu
1               5                   10                  15

Phe Ala Ile Trp Ala Val Leu Val Val Ala Leu Leu Leu Thr Thr Ala
            20                  25                  30

Asn Ile Tyr Trp Ile Ala Asp Gln Phe Gly Ile His Leu Ala Thr Gly
        35                  40                  45

Thr Ala Arg Lys Leu Leu Asp Ala Met Ala Ser Gly Ala Ser Leu Gly
    50                  55                  60

Thr Ala Phe Ala Ala Ile Leu Gly Val Thr Leu Pro Ala Trp Ala Leu
65                  70                  75                  80

Ala Ala Ala Gly Ala Leu Gly Ala Thr Ala Ala
                85                  90
```

<210> SEQ ID NO 135
<211> LENGTH: 276
<212> TYPE: DNA
<213> ORGANISM: Lactobacillus gasseri

<400> SEQUENCE: 135

```
atggttacta agtacggacg taatttaggt ttgaacaagg tagagttgtt tgcaatttgg      60
gcggttttag tagttgctct tttattgacc acagcgaaca tttattggat tgctgatcaa     120
ttcgggattc atttagcgac tggaacagcc cgtaagttat tagatgcaat ggcttctggt     180
gcctcattgg gaactgcctt tgctgctatt ttgggcgtga cattacctgc atgggctttg     240
gcagctgcag gagcattggg agcgactgca gcctag                              276
```

<210> SEQ ID NO 136
<211> LENGTH: 75
<212> TYPE: PRT
<213> ORGANISM: Lactobacillus gasseri

<400> SEQUENCE: 136

```
Met Lys Asn Phe Asn Thr Leu Ser Phe Glu Thr Leu Ala Asn Ile Val
1               5                   10                  15

Gly Gly Arg Asn Asn Trp Ala Ala Asn Ile Gly Gly Val Gly Gly Ala
            20                  25                  30

Thr Val Ala Gly Trp Ala Leu Gly Asn Ala Val Cys Gly Pro Ala Cys
        35                  40                  45

Gly Phe Val Gly Ala His Tyr Val Pro Ile Ala Trp Ala Gly Val Thr
    50                  55                  60

Ala Ala Thr Gly Gly Phe Gly Lys Ile Arg Lys
65                  70                  75
```

<210> SEQ ID NO 137
<211> LENGTH: 228
<212> TYPE: DNA
<213> ORGANISM: Lactobacillus gasseri

<400> SEQUENCE: 137

-continued

```
atgaaaaatt ttaatacatt atcatttgaa acattggcta acatagttgg tgggagaaat      60
aattgggctg ctaatatagg tggagtaggt ggagcgacag tcgctggatg ggctcttgga     120
aatgcagttt gcggtcctgc ttgtggcttt gttggagcac actatgttcc aatagcatgg     180
gctggcgtaa cggcagctac tggtggattc ggaaagataa gaaagtag                 228
```

<210> SEQ ID NO 138
<211> LENGTH: 64
<212> TYPE: PRT
<213> ORGANISM: Lactobacillus plantarum

<400> SEQUENCE: 138

```
Met Ser Lys Leu Val Lys Thr Leu Thr Ile Ser Glu Ile Ser Lys Ala
1               5                   10                  15

Gln Asn Asn Gly Gly Lys Pro Ala Trp Cys Trp Tyr Thr Leu Ala Met
            20                  25                  30

Cys Gly Ala Gly Tyr Asp Ser Gly Thr Cys Asp Tyr Met Tyr Ser His
        35                  40                  45

Cys Phe Gly Ile Lys His His Ser Ser Gly Ser Ser Ser Tyr His Cys
    50                  55                  60
```

<210> SEQ ID NO 139
<211> LENGTH: 195
<212> TYPE: DNA
<213> ORGANISM: Lactobacillus plantarum

<400> SEQUENCE: 139

```
atgagtaaat tggttaagac acttactata agtgaaattt ctaaggctca aaacaacggt      60
ggaaaacctg catggtgttg gtatacttta gcaatgtgtg gtgctggtta tgattcggga    120
acctgtgatt atatgtattc gcattgtttt ggtataaagc atcatagtag tggtagtagc    180
agttatcatt gttag                                                     195
```

<210> SEQ ID NO 140
<211> LENGTH: 359
<212> TYPE: PRT
<213> ORGANISM: Haloferax mediterranei

<400> SEQUENCE: 140

```
Met Ser Lys Asp Arg Asp Gly Arg Arg Thr Ser Arg Arg Gly Thr Leu
1               5                   10                  15

Lys Lys Ile Gly Gly Phe Ser Leu Gly Ala Leu Ser Phe Gly Ala Val
            20                  25                  30

Gly Arg Thr Gln Ala Ala Thr Gly Ser Ser Val Thr Thr Ala Asp Ile
        35                  40                  45

Ala Pro Pro Gly Pro Asn Gly Asp Pro Lys Ser Val Gln Ile Asp Asp
    50                  55                  60

Lys Tyr Thr Gly Ala Glu Met Tyr Gly Glu Gly Asp Phe Arg Val Gly
65                  70                  75                  80

Leu Gly Thr Asp Leu Thr Met Tyr Pro Pro Val Tyr Arg Glu Ser Leu
                85                  90                  95

Gly Asn Gly Ser Gly Gly Trp Glu Phe Asp Phe Thr Val Cys Gly Ser
            100                 105                 110

Thr Ala Cys Arg Phe Val Asp Ser Asn Gly Asp Val Lys Glu Asp Asp
        115                 120                 125

Lys Ala Lys Glu Met Trp Trp Gln Glu Ile Asn Phe Asn Asp Ile Asn
    130                 135                 140
```

```
Gln Asp Leu Tyr Ser Arg Asn Asp Ser Asp Trp Val Gly Ser Thr Pro
145                 150                 155                 160

Ala Asp Thr Gln Pro Glu Phe Asp Tyr Thr Glu Phe Ala Leu Ala Arg
                165                 170                 175

Asp Gly Val Thr Leu Ala Leu Thr Ala Leu Asn Pro Ala Met Gly Ser
            180                 185                 190

Leu Ala Leu Gly Ala Thr Tyr Phe Leu Ser Asp Met Val Asn Trp Ile
        195                 200                 205

Ala Ser Gln His Glu Asp Ser Ser Leu Lys Arg Lys Trp Asp Tyr
        210                 215                 220

Asp Gly Leu Ser Gly Pro Leu Tyr Ala Asp Ser Ser Thr Tyr Leu Leu
225                 230                 235                 240

Ala Arg Asp Glu Met Thr Ser Asn Ser Tyr Glu Ser Phe Thr Ile Asp
                245                 250                 255

Asn Ile Ala Val Ala Phe Pro Glu Phe Pro Val Arg Thr Lys Tyr Tyr
            260                 265                 270

Val Thr Phe Thr Ala Pro Asp Asp Pro Ser Thr Gln Ser Ile Ser Thr
        275                 280                 285

Leu Glu Glu Glu Gly Ile Tyr Arg Val Pro Ala Thr Glu Val Ala Ala
290                 295                 300

Ala Arg Pro Pro Gly Ser Arg Arg Ser Lys Ser Ala Ala Asp Glu Met
305                 310                 315                 320

Val Tyr Val Ala Asp Pro Lys Lys Phe Ile Glu Val Glu Pro Val Lys
                325                 330                 335

Asn Pro Ser Ile Pro Asp Arg Ile Tyr Glu Glu Ile Glu Gln Lys Lys
            340                 345                 350

Lys Gln Arg Ser Arg Lys Gln
        355

<210> SEQ ID NO 141
<211> LENGTH: 1080
<212> TYPE: DNA
<213> ORGANISM: Haloferax mediterranei

<400> SEQUENCE: 141
atgtcgaaag acagagatgg gagaaggaca agtcggcgag gcacgttaaa gaaaatcggc      60
ggtttcagtc tcggagcgct tagtttcggg gcagtcggac gaactcaagc ggcgaccggc     120
tcatcggtta cgaccgctga tatcgcacct cccggaccga acggagaccc gaagagtgtt     180
cagatagatg ataaatacac cggagccgag atgtacggcg agggtgactt cagagtcggt     240
ctcggaactg acctgacgat gtatccgccc gtgtaccgtg agagtcttgg aaatggaagc     300
gggggttggg aattcgactt caccgttgt gggtccactg cctgtcgatt tgtggacagt     360
aacggtgacg tcaaagagga cgacaaggcg aaagaaatgt ggtggcagga aattaacttc     420
aacgacataa atcaggattt atacagtcgg aacgattccg actgggtcgg tcgaccccct     480 gccgatacccc aaccggagtt cgattacacc gactttgcgc tcgctcggga cggagtgacg     540
ctcgctctca cggcactcaa ccccgcaatg ggagtcttga cactcggtgc cacgtacttc     600
ctcagcgaca tggtgaactg gattgcgagc cagcacgaag acgacagttc gctcaagaga     660
aaatgggatt acgacgggct aagtgggccg ttgtacgccg attcgtcgac gtacctactg     720
gcacgcgacg agatgacttc gaactcgtac gaatcattca cgatcgataa catcgccgtt     780
gccttcccag agttccccgt ccggaccaag tactacgtca cattcactgc gccggatgac     840
ccgtcaacgc agtcgatatc tacgctcgaa gaggagggaa tctaccgagt gcccgctacg     900
```

```
gaagtggctg cggccagacc accggggtcc cgacgttcca aatcggcagc cgacgagatg    960
gtgtacgttg ccgatccgaa gaagttcata gaggtcgagc cggtgaagaa cccaagtatc   1020
ccggaccgaa tctacgagga gatagagcaa aaaagaaac aacggagtag gaaacagtag   1080
```

<210> SEQ ID NO 142
<211> LENGTH: 311
<212> TYPE: PRT
<213> ORGANISM: Haloarchaeon S8a

<400> SEQUENCE: 142

Met Ser Asp Lys Asp Ser Ile Asn Arg Arg Asn Val Leu Arg Lys Ile
1               5                   10                  15

Gly Gly Ile Gly Val Ala Ser Ala Val Gly Phe Ser Gly Leu Ala Ser
            20                  25                  30

Gly Glu Ser Leu Ser Asp Asp Glu Lys Gln Asp Val Ile Asp Thr Ile
        35                  40                  45

Tyr Lys Ser Gln Arg Val Glu Gln Ile Lys Lys Phe Gly Gly Val
    50                  55                  60

Asn Ile Glu Pro Lys Lys Val Gln Ser Val Thr Thr Asn Gln Ser Gly
65                  70                  75                  80

Asp Leu Val Thr Ala Lys Leu Ser Val Ser Asp Gly Asp Leu Val Tyr
                85                  90                  95

Ser Ser Val Lys Asp Thr Thr Val Ile Val Gln Phe Asp Arg Ser Ala
            100                 105                 110

Ser Glu Ile Gly Glu Ser Trp Pro Lys Asn Thr Glu Ala Phe Ile Lys
        115                 120                 125

Ser Thr Ser Ser Gly Val Asp Leu Leu Arg Thr Ala Thr Asp Glu Glu
    130                 135                 140

Ile Lys Asp Val Thr Glu Gly Val Asn Thr Ser Glu Ile Glu Ser Ala
145                 150                 155                 160

Asp Ala Val Asn Ile Phe Ile Asp Pro Glu Ser Gln Thr Tyr Tyr Met
                165                 170                 175

Glu Lys Tyr Asp Phe Asn Asn Lys Val Leu Glu Met Phe Glu Leu Ala
            180                 185                 190

Thr Gly Gly Thr Ser Ser Gly Lys Ile Ser Pro Thr Arg Glu Asp Gln
        195                 200                 205

Asn His Glu Tyr Asn Val Arg Glu His Lys Val Phe Asn Ser Glu Lys
    210                 215                 220

Gln Asn Ile Gln Leu Gln Ser Asp Cys Asn Ile Asn Ser Asn Thr Ala
225                 230                 235                 240

Ala Asp Val Ile Leu Cys Phe Asn Gln Val Gly Ser Cys Ala Leu Cys
                245                 250                 255

Ser Pro Thr Leu Val Gly Gly Pro Val Pro Thr Val Ala Cys Leu Leu
            260                 265                 270

Val Val Cys Phe Gly Thr Pro Asn Ala Val Ser Ala Ile Leu Glu Glu
        275                 280                 285

Val Asp Asn Ser Cys Phe Asn Leu Ile Lys Val Ile Ser Cys Trp
    290                 295                 300

Asp Glu Trp Thr Ser Phe Trp
305                 310

<210> SEQ ID NO 143
<211> LENGTH: 936
<212> TYPE: DNA

<213> ORGANISM: Haloarchaeon S8a

<400> SEQUENCE: 143

```
atgtcggata aagacagcat taacagaaga aatgtattaa gaaaaattgg cggtatcggt      60
gtggcttcag ctgtcggatt ttctggtttg gcaagcgggg aaagtcttag cgatgatgag     120
aaacaagatg ttattgacac aatttacaaa tcacaaagag ttgaacagat aaagaaaaag     180
ttcggaggag tgaatattga gccgaaaaag gttcaatctg taacgaccaa tcagagcgga     240
gatcttgtta cggcgaagct gtcggttagt gatggggatt tggtatattc gagtgtcaaa     300
gatacaactg taatagttca gttcgataga tcggcttctg aaattggtga agttggccc      360
aagaatactg aggcattcat caaatcgacg tcctctgggg tcgatcttct acgtacagca     420
actgatgaag aaataaagga cgttactgag ggagtcaaca catctgaaat tgaatctgcg     480
gatgctgtta acatatttat tgatcctgaa tcacagacat actatatgga aaatatgac      540
tttaataata aggtacttga gatgtttgaa ttagcgacag gtgggacaag tagtggtaaa     600
atctccccca cacgtgaaga ccagaatcac gaatataatg ttagggaaca taaagtattt     660
aactcagaaa aacagaatat acaacttcag agtgactgta atataaacag taacaccgct     720
gctgatgtta ttctatgctt caaccaggtt ggttcttgtg cactctgctc cccgactta      780
gtcggaggtc cagtccctac agttgcatgt ctcttagtcg tctgtttcgg cactccaaat     840
gctgtgtccg cgatacttga agaagtcgat aattcttgct ttaacttgat caaggatgta     900
atttcgtgtt gggatgaatg gactagcttc tggtga                               936
```

<210> SEQ ID NO 144
<211> LENGTH: 333
<212> TYPE: PRT
<213> ORGANISM: Lactobacillus helveticus

<400> SEQUENCE: 144

```
Met Lys His Leu Asn Glu Thr Thr Asn Val Arg Ile Leu Ser Gln Phe
  1               5                  10                  15

Asp Met Asp Thr Gly Tyr Gln Ala Val Val Gln Lys Gly Asn Val Gly
                 20                  25                  30

Ser Lys Tyr Val Tyr Gly Leu Gln Leu Arg Lys Gly Ala Thr Thr Ile
             35                  40                  45

Leu Arg Gly Tyr Arg Gly Ser Lys Ile Asn Asn Pro Ile Leu Glu Leu
         50                  55                  60

Ser Gly Gln Ala Gly Gly His Thr Gln Thr Trp Glu Phe Ala Gly Asp
 65                  70                  75                  80

Arg Lys Asp Ile Asn Gly Glu Glu Arg Ala Gly Gln Trp Phe Ile Gly
                 85                  90                  95

Val Lys Pro Ser Lys Ile Glu Gly Ser Lys Ile Ile Trp Ala Lys Gln
                100                 105                 110

Ile Ala Arg Val Asp Leu Arg Asn Gln Met Gly Pro His Tyr Ser Asn
            115                 120                 125

Thr Asp Phe Pro Arg Leu Ser Tyr Leu Asn Arg Ala Gly Ser Asn Pro
        130                 135                 140

Phe Ala Gly Asn Lys Met Thr His Ala Glu Ala Val Ser Pro Asp
145                 150                 155                 160

Tyr Thr Lys Phe Leu Ile Ala Thr Val Glu Asn Asn Cys Ile Gly His
                165                 170                 175

Phe Thr Ile Tyr Asn Leu Asp Thr Ile Asn Glu Lys Leu Asp Glu Lys
            180                 185                 190
```

Gly Asn Ser Glu Asp Val Asn Leu Glu Thr Val Lys Tyr Glu Asp Ser
            195                 200                 205

Phe Ile Ile Asp Asn Leu Tyr Gly Asp Asp Asn Ser Ile Val Asn
        210                 215                 220

Ser Ile Gln Gly Tyr Asp Leu Asp Asn Asp Gly Asn Ile Tyr Ile Ser
225                 230                 235                 240

Ser Gln Lys Ala Pro Asp Phe Asp Gly Ser Tyr Tyr Ala His His Lys
                245                 250                 255

Gln Ile Val Lys Ile Pro Tyr Tyr Ala Arg Ser Lys Glu Ser Glu Asp
            260                 265                 270

Gln Trp Arg Ala Val Asn Leu Ser Glu Phe Gly Gly Leu Asp Ile Pro
        275                 280                 285

Gly Lys His Ser Glu Val Glu Ser Ile Gln Ile Gly Glu Asn His
        290                 295                 300

Cys Tyr Leu Thr Val Ala Tyr His Ser Lys Lys Ala Gly Glu Asn
305                 310                 315                 320

Lys Thr Thr Leu Asn Glu Ile Tyr Glu Leu Ser Trp Asn
                325                 330

<210> SEQ ID NO 145
<211> LENGTH: 1002
<212> TYPE: DNA
<213> ORGANISM: Lactobacillus helveticus

<400> SEQUENCE: 145

| | | |
|---|---|---|
| atgaagcatt taaatgaaac aactaatgtt agaattttaa gtcaatttga tatggatact | 60 |
| ggctatcaag cagtagttca aaaaggcaat gtaggttcaa atatgtgata tggattacaa | 120 |
| cttcgcaaag gtgctactac tatcttgcgt ggttaccgtg aagtaaaat taataaccct | 180 |
| attcttgaat tatctggtca agcaggtggt cacacacaga catgggaatt tgctggtgat | 240 |
| cgtaaagaca ttaatggtga agaaagagca ggtcaatggt ttataggtgt taaaccatcg | 300 |
| aaaattgaag gaagcaaaat tatttgggca agcaaattg caagagttga tcttagaaat | 360 |
| caaatgggac ctcattattc aaatactgac tttcctcgat tatcctactt gaatcgcgcc | 420 |
| ggttctaatc catttgctgg taataagatg acgcatgccg aagccgcagt atcacctgat | 480 |
| tatactaagt ttttaattgc tactgttgaa ataactgta ttggtcattt tactatatac | 540 |
| aatttagata caattaatga aaaacttgat gaaaagggaa atagtgaaga tgttaatctc | 600 |
| gaaactgtta aatacgaaga tagttttatc attgataatt tatatggtga tgataataat | 660 |
| tctattgtaa attcaattca agggtatgat ttggataatg atggaaatat ttatatttcc | 720 |
| agtcaaaaag cgccagattt tgatggctct tattatgcac atcataagca gattgttaag | 780 |
| attccatatt atgctcggtc taaagaaagc gaagaccaat ggagagctgt aaatttaagc | 840 |
| gaattcggtg gcttggatat tccaggtaaa catagtgaag ttgaaagcat ccaaattatt | 900 |
| ggtgagaatc attgttactt aactgttgca tatcattcta aaaataaagc gggtgaaaat | 960 |
| aaaactactt tgaatgagat ttatgaatta tcttggaatt ag | 1002 |

<210> SEQ ID NO 146
<211> LENGTH: 74
<212> TYPE: PRT
<213> ORGANISM: Enterococcus hirae

<400> SEQUENCE: 146

Met Lys Lys Lys Val Leu Lys His Cys Val Ile Leu Gly Ile Leu Gly

```
                1               5                  10                  15
Thr Cys Leu Ala Gly Ile Gly Thr Gly Ile Lys Val Asp Ala Ala Thr
                20                  25                  30

Tyr Tyr Gly Asn Gly Leu Tyr Cys Asn Lys Glu Lys Cys Trp Val Asp
        35                  40                  45

Trp Asn Gln Ala Lys Gly Glu Ile Gly Lys Ile Ile Val Asn Gly Trp
    50                  55                  60

Val Asn His Gly Pro Trp Ala Pro Arg Arg
65                  70

<210> SEQ ID NO 147
<211> LENGTH: 225
<212> TYPE: DNA
<213> ORGANISM: Enterococcus hirae

<400> SEQUENCE: 147
atgaaaaaga aagtattaaa acattgtgtt attctaggaa tattaggaac ttgtctagct      60
ggcatcggta caggaataaa agttgatgca gctacttact atggaaatgg tctttattgt    120
aacaaagaaa atgttgggt agattggaat caagctaaag agaaattgg aaaaattatt     180 gttaatggtt gggttaatca tggtccatgg cacctagaa ggtag                    225

<210> SEQ ID NO 148
<211> LENGTH: 75
<212> TYPE: PRT
<213> ORGANISM: Lactobacillus johnsonii

<400> SEQUENCE: 148

Met Lys Gln Phe Asn Tyr Leu Ser His Lys Asp Leu Ala Val Val Val
1               5                  10                  15

Gly Gly Arg Asn Asn Trp Gln Thr Asn Val Gly Gly Ala Val Gly Ser
                20                  25                  30

Ala Met Ile Gly Ala Thr Val Gly Gly Thr Ile Cys Gly Pro Ala Cys
            35                  40                  45

Ala Val Ala Gly Ala His Tyr Leu Pro Ile Leu Trp Thr Ala Val Thr
        50                  55                  60

Ala Ala Thr Gly Gly Phe Gly Lys Ile Arg Lys
    65                  70                  75

<210> SEQ ID NO 149
<211> LENGTH: 228
<212> TYPE: DNA
<213> ORGANISM: Lactobacillus johnsonii

<400> SEQUENCE: 149
atgaaacaat ttaattattt atcacataaa gatttagcag tcgttgttgg tggaagaaat      60
aattggcaaa caaatgtggg aggagcagtg ggatcagcta tgattggggc tacagttggt    120
ggtacaattt gtggacctgc atgtgctgta gctggtgccc attatcttcc tattttatgg    180
acagcggtta cagctgcaac aggtggtttt ggcaagataa gaaagtag                 228

<210> SEQ ID NO 150
<211> LENGTH: 62
<212> TYPE: PRT
<213> ORGANISM: Lactobacillus johnsonii

<400> SEQUENCE: 150

Met Lys Leu Asn Asp Lys Glu Leu Ser Lys Ile Val Gly Gly Asn Arg
1               5                  10                  15
```

```
Trp Gly Asp Thr Val Leu Ser Ala Ala Ser Gly Ala Gly Thr Gly Ile
            20                  25                  30

Lys Ala Cys Lys Ser Phe Gly Pro Trp Gly Met Ala Ile Cys Gly Val
        35                  40                  45

Gly Gly Ala Ala Ile Gly Gly Tyr Phe Gly Tyr Thr His Asn
    50                  55                  60
```

<210> SEQ ID NO 151
<211> LENGTH: 189
<212> TYPE: DNA
<213> ORGANISM: Lactobacillus johnsonii

<400> SEQUENCE: 151

```
atgaaattaa atgacaaaga attatcaaag attgttggtg gaaatcgatg gggagatact      60
gttttatcag ctgctagtgg cgcaggaact ggtattaaag catgtaaaag ttttggccca     120
tggggaatgg caatttgtgg tgtaggaggt gcagcaatag gaggttattt tggctatact     180
cataattaa                                                              189
```

<210> SEQ ID NO 152
<211> LENGTH: 59
<212> TYPE: PRT
<213> ORGANISM: Lactococcus lactis subsp. lactis

<400> SEQUENCE: 152

```
Met Asn Lys Asn Glu Ile Glu Thr Gln Pro Val Thr Trp Leu Glu Glu
1               5                   10                  15

Val Ser Asp Gln Asn Phe Asp Glu Asp Val Phe Gly Ala Cys Ser Thr
            20                  25                  30

Asn Thr Phe Ser Leu Ser Asp Tyr Trp Gly Asn Asn Gly Ala Trp Cys
        35                  40                  45

Thr Leu Thr His Glu Cys Met Ala Trp Cys Lys
    50                  55
```

<210> SEQ ID NO 153
<211> LENGTH: 180
<212> TYPE: DNA
<213> ORGANISM: Lactococcus lactis subsp. lactis

<400> SEQUENCE: 153

```
atgaacaaaa atgaaattga aacacaacca gttacatggt tggaagaagt atctgatcaa      60
aattttgatg aagatgtatt tggtgcgtgt agtactaaca cattctcgct cagtgattac     120
tggggaaata acggggcttg gtgtacactc actcatgaat gtatggcttg gtgtaaataa     180
```

<210> SEQ ID NO 154
<211> LENGTH: 65
<212> TYPE: PRT
<213> ORGANISM: Lactococcus lactis subsp. lactis

<400> SEQUENCE: 154

```
Met Lys Glu Lys Asn Met Lys Lys Asn Asp Thr Ile Glu Leu Gln Leu
1               5                   10                  15

Gly Lys Tyr Leu Glu Asp Asp Met Ile Glu Leu Ala Glu Gly Asp Glu
            20                  25                  30

Ser His Gly Gly Thr Thr Pro Ala Thr Pro Ala Ile Ser Ile Leu Ser
        35                  40                  45

Ala Tyr Ile Ser Thr Asn Thr Cys Pro Thr Thr Lys Cys Thr Arg Ala
    50                  55                  60
```

-continued

Cys
65

<210> SEQ ID NO 155
<211> LENGTH: 198
<212> TYPE: DNA
<213> ORGANISM: Lactococcus lactis subsp. lactis

<400> SEQUENCE: 155
atgaaagaaa aaatatgaa aaagaatgac actattgaat tacaattggg aaaataccTt      60
gaagatgata tgattgaatt agctgaaggg gatgagtctc atggaggaac aacaccagca     120
actcctgcaa tctctattct cagtgcatat attagtacca atacttgtcc aacaacaaaa    180
tgtacacgtg cttgttaa                                                  198

<210> SEQ ID NO 156
<211> LENGTH: 51
<212> TYPE: PRT
<213> ORGANISM: Lactococcus lactis subsp. lactis

<400> SEQUENCE: 156

Met Lys Glu Gln Asn Ser Phe Asn Leu Leu Gln Glu Val Thr Glu Ser
1               5                   10                  15

Glu Leu Asp Leu Ile Leu Gly Ala Lys Gly Gly Ser Gly Val Ile His
            20                  25                  30

Thr Ile Ser His Glu Cys Asn Met Asn Ser Trp Gln Phe Val Phe Thr
        35                  40                  45

Cys Cys Ser
    50

<210> SEQ ID NO 157
<211> LENGTH: 156
<212> TYPE: DNA
<213> ORGANISM: Lactococcus lactis subsp. lactis

<400> SEQUENCE: 157
atgaaagaac aaaactcttt taatcttctt caagaagtga cagaaagtga attggacctt      60
attttaggtg caaaaggcgg cagtggagtt attcatacaa tttctcatga atgtaatatg     120
aatagctggc aatttgtatt tacttgctgc tcttaa                              156

<210> SEQ ID NO 158
<211> LENGTH: 53
<212> TYPE: PRT
<213> ORGANISM: Lactococcus lactis

<400> SEQUENCE: 158

Met Ala Gly Phe Leu Lys Val Val Gln Leu Leu Ala Lys Tyr Gly Ser
1               5                   10                  15

Lys Ala Val Gln Trp Ala Trp Ala Asn Lys Gly Lys Ile Leu Asp Trp
            20                  25                  30

Leu Asn Ala Gly Gln Ala Ile Asp Trp Val Val Ser Lys Ile Lys Gln
        35                  40                  45

Ile Leu Gly Ile Lys
    50

<210> SEQ ID NO 159
<211> LENGTH: 162
<212> TYPE: DNA
<213> ORGANISM: Lactococcus lactis

<400> SEQUENCE: 159

```
atggcagggt ttttaaaagt agttcaatta ctagctaaat atggttctaa agctgtacaa    60
tgggcttggg caaacaaggg taagatttta gattggctta atgcaggtca ggctattgat   120
tgggtagttt cgaaaattaa gcaaatttta ggtattaagt aa                      162
```

<210> SEQ ID NO 160
<211> LENGTH: 53
<212> TYPE: PRT
<213> ORGANISM: Lactococcus lactis

<400> SEQUENCE: 160

```
Met Ala Gly Phe Leu Lys Val Val Gln Ile Leu Ala Lys Tyr Gly Ser
1               5                   10                  15
Lys Ala Val Gln Trp Ala Trp Ala Asn Lys Gly Lys Ile Leu Asp Trp
            20                  25                  30
Ile Asn Ala Gly Gln Ala Ile Asp Trp Val Val Glu Lys Ile Lys Gln
        35                  40                  45
Ile Leu Gly Ile Lys
    50
```

<210> SEQ ID NO 161
<211> LENGTH: 162
<212> TYPE: DNA
<213> ORGANISM: Lactococcus lactis

<400> SEQUENCE: 161

```
atggcagggt ttttaaaagt agtccaaatt ttggctaagt atggttctaa agccgtacaa    60
tgggcatggg caaataaagg aaaaatctta gattggatta atgcaggtca agctattgac   120
tgggtagttg aaaagattaa gcaaattttg ggtattaaat aa                      162
```

<210> SEQ ID NO 162
<211> LENGTH: 65
<212> TYPE: PRT
<213> ORGANISM: Lactobacillus amylovorus

<400> SEQUENCE: 162

```
Met Lys Gln Leu Asn Ser Glu Gln Leu Gln Asn Ile Ile Gly Gly Asn
1               5                   10                  15
Arg Trp Thr Asn Ala Tyr Ser Ala Ala Leu Gly Cys Ala Val Pro Gly
            20                  25                  30
Val Lys Tyr Gly Lys Lys Leu Gly Gly Val Trp Gly Ala Val Ile Gly
        35                  40                  45
Gly Val Gly Gly Ala Ala Val Cys Gly Leu Ala Gly Tyr Val Arg Lys
    50                  55                  60
Gly
65
```

<210> SEQ ID NO 163
<211> LENGTH: 198
<212> TYPE: DNA
<213> ORGANISM: Lactobacillus amylovorus

<400> SEQUENCE: 163

```
atgaaacaat tgaattcaga acaattacaa aatattatcg gtggaaatag atggactaat    60
gcatacagcg cagctttggg atgcgctgtc cctggagtta aatatggaaa aaaacttggt   120
ggcgtatggg gtgctgtaat tggtggcgta ggcggtgcag cagtctgtgg cttggcgggt   180
```

-continued tatgttcgta aaggctaa                                                  198

<210> SEQ ID NO 164
<211> LENGTH: 68
<212> TYPE: PRT
<213> ORGANISM: Lactobacillus sakei L45

<400> SEQUENCE: 164

Met Lys Thr Glu Lys Lys Val Leu Asp Glu Leu Ser Leu His Ala Ser
1               5                   10                  15

Ala Lys Met Gly Ala Arg Asp Val Glu Ser Ser Met Asn Ala Asp Ser
            20                  25                  30

Thr Pro Val Leu Ala Ser Val Ala Val Ser Met Glu Leu Leu Pro Thr
        35                  40                  45

Ala Ser Val Leu Tyr Ser Asp Val Ala Gly Cys Phe Lys Tyr Ser Ala
    50                  55                  60

Lys His His Cys
65

<210> SEQ ID NO 165
<211> LENGTH: 207
<212> TYPE: DNA
<213> ORGANISM: Lactobacillus sakei L45

<400> SEQUENCE: 165
atgaaaacag aaaaaaaggt tttagatgaa ctgagcttac acgcttctgc aaaaatggga      60
gcacgtgatg ttgaatccag catgaatgca gactcaacac cagttttagc atcagtcgct    120
gtatccatgg aattattgcc aactgcgtct gttctttatt cggatgttgc aggttgcttc    180
aaatattctg caaacatca ttgttag                                         207

<210> SEQ ID NO 166
<211> LENGTH: 91
<212> TYPE: PRT
<213> ORGANISM: Lactococcus lactis subsp. lactis

<400> SEQUENCE: 166

Met Lys Thr Lys Ser Leu Val Leu Ala Leu Ser Ala Val Thr Leu Phe
1               5                   10                  15

Ser Ala Gly Gly Ile Val Ala Gln Ala Glu Gly Thr Trp Gln His Gly
            20                  25                  30

Tyr Gly Val Ser Ser Ala Tyr Ser Asn Tyr His His Gly Ser Lys Thr
        35                  40                  45

His Ser Ala Thr Val Val Asn Asn Asn Thr Gly Arg Gln Gly Lys Asp
    50                  55                  60

Thr Gln Arg Ala Gly Val Trp Ala Lys Ala Thr Val Gly Arg Asn Leu
65                  70                  75                  80

Thr Glu Lys Ala Ser Phe Tyr Tyr Asn Phe Trp
                85                  90

<210> SEQ ID NO 167
<211> LENGTH: 276
<212> TYPE: DNA
<213> ORGANISM: Lactococcus lactis subsp. lactis

<400> SEQUENCE: 167
atgaaaacca agtctctcgt attggcatta tctgcggtta cgttattctc tgccggagga      60
attgtagctc aagctgaagg aacatggcaa catggatatg gtgttagttc ggcatattca    120

```
aattatcatc atggtagcaa aactcattca gccacagttg taaataataa tactggccga      180
caaggtaagg atacacaacg tgccggtgtt tgggcaaaag ctactgttgg acgtaactta      240
actgaaaaag cttcatttta ttataacttt tggtaa                                276
```

<210> SEQ ID NO 168
<211> LENGTH: 75
<212> TYPE: PRT
<213> ORGANISM: Lactococcus lactis subsp. cremoris

<400> SEQUENCE: 168

```
Met Lys Asn Gln Leu Asn Phe Asn Ile Val Ser Asp Glu Glu Leu Ser
1               5                   10                  15
Glu Ala Asn Gly Gly Lys Leu Thr Phe Ile Gln Ser Thr Ala Ala Gly
                20                  25                  30
Asp Leu Tyr Tyr Asn Thr Asn Thr His Lys Tyr Val Tyr Gln Gln Thr
            35                  40                  45
Gln Asn Ala Phe Gly Ala Ala Ala Asn Thr Ile Val Asn Gly Trp Met
        50                  55                  60
Gly Gly Ala Ala Gly Gly Phe Gly Leu His His
65                  70                  75
```

<210> SEQ ID NO 169
<211> LENGTH: 228
<212> TYPE: DNA
<213> ORGANISM: Lactococcus lactis subsp. cremoris

<400> SEQUENCE: 169

```
atgaaaaatc aattaaattt taatattgtt tcagatgaag aactttcaga agctaacgga       60
ggaaaattaa catttattca atcgacagcg gctggagatt tatattacaa tactaataca      120
cacaaatatg tttaccaaca aactcaaaac gcttttgggg ctgctgctaa taccattgtt      180
aatggatgga tgggtggcgc tgctggaggt ttcgggttgc accattga                   228
```

<210> SEQ ID NO 170
<211> LENGTH: 68
<212> TYPE: PRT
<213> ORGANISM: Lactococcus lactis subsp. cremoris

<400> SEQUENCE: 170

```
Met Lys Asn Gln Leu Asn Phe Asn Ile Val Ser Asp Glu Glu Leu Ala
1               5                   10                  15
Glu Val Asn Gly Gly Ser Leu Gln Tyr Val Met Ser Ala Gly Pro Tyr
                20                  25                  30
Thr Trp Tyr Lys Asp Thr Arg Thr Gly Lys Thr Ile Cys Lys Gln Thr
            35                  40                  45
Ile Asp Thr Ala Ser Tyr Thr Phe Gly Val Met Ala Glu Gly Trp Gly
        50                  55                  60
Lys Thr Phe His
65
```

<210> SEQ ID NO 171
<211> LENGTH: 207
<212> TYPE: DNA
<213> ORGANISM: Lactococcus lactis subsp. cremoris

<400> SEQUENCE: 171

```
atgaaaaatc aattaaattt taatattgtt tctgatgaag aacttgcaga agttaatgga       60
```

```
ggaagcttgc agtatgttat gagtgctgga ccatatactt ggtataaaga tactagaaca      120
ggaaaaacaa tatgtaaaca gacaattgac acagcaagtt atacatttgg tgtaatggca      180
gaaggatggg gaaaaacatt ccactaa                                          207
```

```
<210> SEQ ID NO 172
<211> LENGTH: 63
<212> TYPE: PRT
<213> ORGANISM: Lactococcus sp. QU 12

<400> SEQUENCE: 172
```

Met Lys Leu Ile Asp His Leu Gly Ala Pro Arg Trp Ala Val Asp Thr
1               5                   10                  15

Ile Leu Gly Ala Ile Ala Val Gly Asn Leu Ala Ser Trp Val Leu Ala
            20                  25                  30

Leu Val Pro Gly Pro Gly Trp Ala Val Lys Ala Gly Leu Ala Thr Ala
        35                  40                  45

Ala Ala Ile Val Lys His Gln Gly Lys Ala Ala Ala Ala Trp
    50                  55                  60

```
<210> SEQ ID NO 173
<211> LENGTH: 192
<212> TYPE: DNA
<213> ORGANISM: Lactococcus sp. QU 12

<400> SEQUENCE: 173
atgaaattaa ttgatcattt aggtgctcca agatgggccg ttgatactat tttaggtgca       60
atcgcagttg gaacttagc aagttgggtt ctagcgcttg tccctggtcc agggtgggca      120
gtaaaagctg gtttagcaac tgctgctgcc atcgttaaac atcaaggtaa agctgccgct      180
gctgcttggt aa                                                          192
```

```
<210> SEQ ID NO 174
<211> LENGTH: 50
<212> TYPE: PRT
<213> ORGANISM: Brevibacillus sp. GI-9

<400> SEQUENCE: 174
```

Met Ala Cys Gln Cys Pro Asp Ala Ile Ser Gly Trp Thr His Thr Asp
1               5                   10                  15

Tyr Gln Cys His Gly Leu Glu Asn Lys Met Tyr Arg His Val Tyr Ala
            20                  25                  30

Ile Cys Met Asn Gly Thr Gln Val Tyr Cys Arg Thr Glu Trp Gly Ser
        35                  40                  45

Ser Cys
    50

```
<210> SEQ ID NO 175
<211> LENGTH: 153
<212> TYPE: DNA
<213> ORGANISM: Brevibacillus sp. GI-9

<400> SEQUENCE: 175
atggcttgcc aatgtccaga tgcgatctca ggttggacgc atacagatta ccagtgtcac       60
ggtttggaga ataaaatgta tagacatgtt tatgcaattt gcatgaacgg tactcaagta      120
tattgcagaa cagagtgggg tagcagctgc tag                                   153
```

```
<210> SEQ ID NO 176
<211> LENGTH: 57
```

```
<212> TYPE: PRT
<213> ORGANISM: Leuconostoc pseudomesenteroides

<400> SEQUENCE: 176

Met Asn Lys Glu Tyr Asn Ser Ile Ser Asn Phe Lys Lys Ile Thr Asn
1               5                   10                  15

Lys Asp Leu Gln Asn Ile Asn Gly Gly Phe Ile Gly Arg Ala Ile Gly
            20                  25                  30

Asp Phe Val Tyr Phe Gly Ala Lys Gly Leu Arg Glu Ser Gly Lys Leu
        35                  40                  45

Leu Asn Tyr Tyr Tyr Lys His Lys His
    50                  55

<210> SEQ ID NO 177
<211> LENGTH: 174
<212> TYPE: DNA
<213> ORGANISM: Leuconostoc pseudomesenteroides

<400> SEQUENCE: 177
atgaataaag aatataatag cattagcaat tttaaaaaaa ttactaataa agacttgcaa     60
aacataaatg gtggatttat tggtagggca ataggtgact tgtgtacttt tggagcgaag   120
ggactaagag aatctggtaa actacttaat tattactata agcataagca ttga         174

<210> SEQ ID NO 178
<211> LENGTH: 53
<212> TYPE: PRT
<213> ORGANISM: Leuconostoc pseudomesenteroides

<400> SEQUENCE: 178

Met Lys Asn Gln Leu Met Ser Phe Glu Val Ile Ser Glu Lys Glu Leu
1               5                   10                  15

Ser Thr Val Gln Gly Gly Lys Gly Leu Gly Lys Leu Ile Gly Ile Asp
            20                  25                  30

Trp Leu Leu Gly Gln Ala Lys Asp Ala Val Lys Gln Tyr Lys Lys Asp
        35                  40                  45

Tyr Lys Arg Trp His
    50

<210> SEQ ID NO 179
<211> LENGTH: 162
<212> TYPE: DNA
<213> ORGANISM: Leuconostoc pseudomesenteroides

<400> SEQUENCE: 179
atgaaaaatc agttaatgtc tttcgaagtg atatcagaaa aagaattgtc cacggtacaa     60
ggtggcaaag gcttaggtaa actcatagga attgattggc ttttgggtca agctaaggac   120
gctgttaaac agtacaagaa ggattacaaa cgttggcact aa                      162

<210> SEQ ID NO 180
<211> LENGTH: 61
<212> TYPE: PRT
<213> ORGANISM: Leuconostoc gelidum

<400> SEQUENCE: 180

Met Met Asn Met Lys Pro Thr Glu Ser Tyr Glu Gln Leu Asp Asn Ser
1               5                   10                  15

Ala Leu Glu Gln Val Val Gly Gly Lys Tyr Tyr Gly Asn Gly Val His
            20                  25                  30
```

```
Cys Thr Lys Ser Gly Cys Ser Val Asn Trp Gly Glu Ala Phe Ser Ala
            35                  40                  45

Gly Val His Arg Leu Ala Asn Gly Gly Asn Gly Phe Trp
        50                  55                  60

<210> SEQ ID NO 181
<211> LENGTH: 186
<212> TYPE: DNA
<213> ORGANISM: Leuconostoc gelidum

<400> SEQUENCE: 181
atgatgaaca tgaaacctac ggaaagctat gagcaattgg ataatagtgc tctcgaacaa    60
gtcgtaggag gtaagtatta tggtaacgga gttcattgca caaaaagtgg ttgttctgta   120
aactggggag aagccttttc agctggagta catcgtttag caaatggtgg aaatggtttc   180
tggtaa                                                              186

<210> SEQ ID NO 182
<211> LENGTH: 61
<212> TYPE: PRT
<213> ORGANISM: Leuconostoc carnosum

<400> SEQUENCE: 182

Met Asn Asn Met Lys Ser Ala Asp Asn Tyr Gln Gln Leu Asp Asn Asn
1               5                   10                  15

Ala Leu Glu Gln Val Val Gly Gly Lys Tyr Tyr Gly Asn Gly Val His
            20                  25                  30

Cys Thr Lys Ser Gly Cys Ser Val Asn Trp Gly Glu Ala Phe Ser Ala
            35                  40                  45

Gly Val His Arg Leu Ala Asn Gly Gly Asn Gly Phe Trp
        50                  55                  60

<210> SEQ ID NO 183
<211> LENGTH: 186
<212> TYPE: DNA
<213> ORGANISM: Leuconostoc carnosum

<400> SEQUENCE: 183
atgaataaca tgaaatctgc ggataattat cagcaattgg ataataatgc tctcgaacaa    60
gtcgtaggag gtaagtatta tggtaacgga gttcattgca caaaaagtgg ttgttctgta   120
aactggggag aagccttttc agctggagta catcgtttag caaatggtgg aaatggtttc   180
tggtaa                                                              186

<210> SEQ ID NO 184
<211> LENGTH: 63
<212> TYPE: PRT
<213> ORGANISM: Leuconostoc mesenteroides

<400> SEQUENCE: 184

Met Phe Leu Val Asn Gln Leu Gly Ile Ser Lys Ser Leu Ala Asn Thr
1               5                   10                  15

Ile Leu Gly Ala Ile Ala Val Gly Asn Leu Ala Ser Trp Leu Leu Ala
            20                  25                  30

Leu Val Pro Gly Pro Gly Trp Ala Thr Lys Ala Ala Leu Ala Thr Ala
            35                  40                  45

Glu Thr Ile Val Lys His Glu Gly Lys Ala Ala Ala Ile Ala Trp
        50                  55                  60
```

-continued

<210> SEQ ID NO 185
<211> LENGTH: 192
<212> TYPE: DNA
<213> ORGANISM: Leuconostoc mesenteroides

<400> SEQUENCE: 185

```
atgttcttgg taaatcagtt agggatttca aaatcgttag ctaatactat tcttggtgca      60
attgctgttg gtaatttggc cagttggtta ttagctttgg ttcctggtcc gggttgggca     120
acaaaagcag cacttgcgac agctgaaaca attgtgaagc atgaaggaaa agcagctgct     180
attgcgtggt aa                                                         192
```

<210> SEQ ID NO 186
<211> LENGTH: 74
<212> TYPE: PRT
<213> ORGANISM: Bacillus licheniformis

<400> SEQUENCE: 186

```
Met Ser Lys Lys Glu Met Ile Leu Ser Trp Lys Asn Pro Met Tyr Arg
1               5                   10                  15

Thr Glu Ser Ser Tyr His Pro Ala Gly Asn Ile Leu Lys Glu Leu Gln
            20                  25                  30

Glu Glu Glu Gln His Ser Ile Ala Gly Gly Thr Ile Thr Leu Ser Thr
        35                  40                  45

Cys Ala Ile Leu Ser Lys Pro Leu Gly Asn Asn Gly Tyr Leu Cys Thr
    50                  55                  60

Val Thr Lys Glu Cys Met Pro Ser Cys Asn
65                  70
```

<210> SEQ ID NO 187
<211> LENGTH: 225
<212> TYPE: DNA
<213> ORGANISM: Bacillus licheniformis

<400> SEQUENCE: 187

```
atgtcaaaaa aggaaatgat tctttcatgg aaaaatccta tgtatcgcac tgaatcttct      60
tatcatccag cagggaacat ccttaaagaa ctccaggaag aggaacagca cagcatcgcc     120
ggaggcacaa tcacgctcag cacttgtgcc atcttgagca agccgttagg aaataacgga     180
tacctgtgta cagtgacaaa agaatgcatg ccaagctgta actaa                     225
```

<210> SEQ ID NO 188
<211> LENGTH: 266
<212> TYPE: PRT
<213> ORGANISM: Brevibacterium linens

<400> SEQUENCE: 188

```
Met Asn Asn Leu Tyr Arg Glu Leu Ala Pro Ile Pro Gly Pro Ala Trp
1               5                   10                  15

Ala Glu Ile Glu Glu Glu Ala Arg Arg Thr Phe Lys Arg Asn Ile Ala
            20                  25                  30

Gly Arg Arg Ile Val Asp Val Ala Gly Pro Thr Gly Phe Glu Thr Ser
        35                  40                  45

Ala Val Thr Thr Gly His Ile Arg Asp Val Gln Ser Glu Thr Ser Gly
    50                  55                  60

Leu Gln Val Lys Gln Arg Ile Val Gln Glu Tyr Ile Glu Leu Arg Thr
65                  70                  75                  80

Pro Phe Thr Val Thr Arg Gln Ala Ile Asp Asp Val Ala Arg Gly Ser
                85                  90                  95
```

Gly Asp Ser Asp Trp Gln Pro Val Lys Asp Ala Ala Thr Thr Ile Ala
            100                 105                 110

Met Ala Glu Asp Arg Ala Ile Leu His Gly Leu Asp Ala Ala Gly Ile
        115                 120                 125

Gly Gly Ile Val Pro Gly Ser Ser Asn Ala Ala Val Ala Ile Pro Asp
    130                 135                 140

Ala Val Glu Asp Phe Ala Asp Ala Val Ala Gln Ala Leu Ser Val Leu
145                 150                 155                 160

Arg Thr Val Gly Val Asp Gly Pro Tyr Ser Leu Leu Leu Ser Ser Ala
                165                 170                 175

Glu Tyr Thr Lys Val Ser Glu Ser Thr Asp His Gly Tyr Pro Ile Arg
            180                 185                 190

Glu His Leu Ser Arg Gln Leu Gly Ala Gly Glu Ile Ile Trp Ala Pro
        195                 200                 205

Ala Leu Glu Gly Ala Leu Leu Val Ser Thr Arg Gly Gly Asp Tyr Glu
    210                 215                 220

Leu His Leu Gly Gln Asp Leu Ser Ile Gly Tyr Tyr Ser His Asp Ser
225                 230                 235                 240

Glu Thr Val Glu Leu Tyr Leu Gln Glu Thr Phe Gly Phe Leu Ala Leu
                245                 250                 255

Thr Asp Glu Ser Ser Val Pro Leu Ser Leu
            260                 265

<210> SEQ ID NO 189
<211> LENGTH: 801
<212> TYPE: DNA
<213> ORGANISM: Brevibacterium linens

<400> SEQUENCE: 189
gtgaataacc tctatcgcga gcttgccccc atccccggcc cggcctgggc ggagatcgag      60
gaggaggctc gacggacatt caaacgcaat atcgccggcc gccggatcgt cgatgtcgca     120
gggcccacgg gcttcgagac ctccgcggtg accactggcc acatccgaga cgtccagtcg     180
gagacgagcg gactgcaggt taagcagcgc atcgtgcagg aatacatcga gctgcggacc     240
ccattcaccg tgactcggca ggccatcgat gacgtggccc gcgggtccgg tgactcggac     300
tggcagcccg tcaaggatgc ggccacgacg atcgcgatgg ctgaagatcg gccattctc     360 cacgggctcg atgcggccgg gatcggcgga atcgttcccg gcagctcgaa tgccgcagtg     420
gccatccccg acgccgtcga ggacttcgcg gacgccgtcg cccaggcgct gagtgtgctg     480
cgcacggtgg gagtcgacgg gccctacagc ctgttgctct cctccgcgga gtacaccaag     540
gtctccgagt ccaccgacca cggctacccg atccgcgagc acctctcccg gcagctcggc     600
gccggagaga tcatctgggc gcccgcgctc gaagggcgc tgctcgtctc cacgcgcggg     660
ggtgactacg agctccacct cggccaggac ctgtcgatcg gttactacag ccacgacagc     720
gagaccgtcg aactctatct gcaggagacc ttcggattcc tcgcgctgac cgacgaatcc     780
agtgtgcctt tgagcctctg a                                              801

<210> SEQ ID NO 190
<211> LENGTH: 71
<212> TYPE: PRT
<213> ORGANISM: Listeria innocua

<400> SEQUENCE: 190

Met Lys Lys Ala Ala Leu Lys Phe Ile Ile Val Ile Ala Ile Leu Gly

```
                1               5                  10                  15
Phe Ser Phe Ser Phe Phe Ser Ile Gln Ser Glu Ala Lys Ser Tyr Gly
                20                  25                  30
Asn Gly Val Gln Cys Asn Lys Lys Cys Trp Val Asp Trp Gly Ser
        35                  40                  45
Ala Ile Ser Thr Ile Gly Asn Asn Ser Ala Ala Asn Trp Ala Thr Gly
    50                  55                  60
Gly Ala Ala Gly Trp Lys Ser
65                  70
```

<210> SEQ ID NO 191
<211> LENGTH: 216
<212> TYPE: DNA
<213> ORGANISM: Listeria innocua

<400> SEQUENCE: 191

```
ttgaagaagg cagcgttaaa atttattatt gttattgcta ttctaggttt cagttttct     60 ttctttagca tacaatctga agctaaatct tatggaaatg gagttcagtg taataagaaa   120
aaatgttggg tagattgggg tagtgctata agtactattg gaaataattc tgcagcgaat   180
tgggctacag gtggagcagc tggttggaaa agctga                             216
```

<210> SEQ ID NO 192
<211> LENGTH: 68
<212> TYPE: PRT
<213> ORGANISM: Bacillus sp.

<400> SEQUENCE: 192

```
Met Ser Gln Glu Ala Ile Ile Arg Ser Trp Lys Asp Pro Phe Ser Arg
1               5                   10                  15
Glu Asn Ser Thr Gln Asn Pro Ala Gly Asn Pro Phe Ser Glu Leu Lys
            20                  25                  30
Glu Ala Gln Met Asp Lys Leu Val Gly Ala Gly Asp Met Glu Ala Ala
        35                  40                  45
Cys Thr Phe Thr Leu Pro Gly Gly Gly Val Cys Thr Leu Thr Ser
    50                  55                  60
Glu Cys Ile Cys
65
```

<210> SEQ ID NO 193
<211> LENGTH: 207
<212> TYPE: DNA
<213> ORGANISM: Bacillus sp.

<400> SEQUENCE: 193

```
atgagtcaag aagctatcat tcgttcatgg aaagatcctt tttcccgtga aaattctaca    60
caaaatccag ctggtaaccc attcagtgag ctgaaagaag cacaaatgga taagttagta   120
ggtgcgggag acatggaagc agcatgtact tttacattgc ctggtggcgg cggtgttttgt  180 actctaactt ctgaatgtat ttgttaa                                       207
```

<210> SEQ ID NO 194
<211> LENGTH: 61
<212> TYPE: PRT
<213> ORGANISM: Leuconostoc mesenteroides

<400> SEQUENCE: 194

```
Met Thr Asn Met Lys Ser Val Glu Ala Tyr Gln Gln Leu Asp Asn Gln
1               5                   10                  15
```

-continued

```
Asn Leu Lys Lys Val Gly Gly Lys Tyr Tyr Gly Asn Gly Val His
            20                  25                  30

Cys Thr Lys Ser Gly Cys Ser Val Asn Trp Gly Glu Ala Ala Ser Ala
        35                  40                  45

Gly Ile His Arg Leu Ala Asn Gly Gly Asn Gly Phe Trp
    50                  55                  60
```

<210> SEQ ID NO 195
<211> LENGTH: 186
<212> TYPE: DNA
<213> ORGANISM: Leuconostoc mesenteroides

<400> SEQUENCE: 195

```
atgacgaata tgaagtctgt ggaagcatat cagcaattag ataaccagaa tctcaagaaa      60
gttgttggtg aaagtatta tgggaatggt gttcactgta caaaaagtgg atgctctgtt     120
aactggggag aagctgcctc agctggcata catcgtttgg ccaatggtgg aaatggattt     180
tggtaa                                                                186
```

<210> SEQ ID NO 196
<211> LENGTH: 68
<212> TYPE: PRT
<213> ORGANISM: Clavibacter michiganensis subsp. michiganensis

<400> SEQUENCE: 196

```
Met Asn Asp Ile Leu Glu Thr Glu Thr Pro Val Met Val Ser Pro Arg
1               5                   10                  15

Trp Asp Met Leu Leu Asp Ala Gly Glu Asp Thr Ser Pro Ser Val Gln
            20                  25                  30

Thr Gln Ile Asp Ala Glu Phe Arg Arg Val Val Ser Pro Tyr Met Ser
        35                  40                  45

Ser Ser Gly Trp Leu Cys Thr Leu Thr Ile Glu Cys Gly Thr Ile Ile
    50                  55                  60

Cys Ala Cys Arg
65
```

<210> SEQ ID NO 197
<211> LENGTH: 207
<212> TYPE: DNA
<213> ORGANISM: Clavibacter michiganensis subsp. michiganensis

<400> SEQUENCE: 197

```
atgaacgaca tcctcgagac ggagaccccc gtcatggtca gcccccggtg ggacatgctg      60
ctcgacgcgg gcgaggacac cagcccgtcc gtccagaccc agatcgacgc ggagttccgt     120
cgcgtcgtga gcccgtacat gtccagcagc ggctggctct gcacgctcac catcgaatgt     180
ggcaccatca tctgcgcgtg tcgctga                                          207
```

<210> SEQ ID NO 198
<211> LENGTH: 69
<212> TYPE: PRT
<213> ORGANISM: Escherichia coli

<400> SEQUENCE: 198

```
Met Glu Leu Lys Ala Ser Glu Phe Gly Val Val Leu Ser Val Asp Ala
1               5                   10                  15

Leu Lys Leu Ser Arg Gln Ser Pro Leu Gly Val Gly Ile Gly Gly Gly
            20                  25                  30
```

-continued

```
Gly Gly Gly Gly Gly Gly Ser Cys Gly Gly Gln Gly Gly Cys
            35                  40                  45

Gly Gly Cys Ser Asn Gly Cys Ser Gly Gly Asn Gly Gly Ser Gly Gly
 50                  55                  60

Ser Gly Ser His Ile
 65
```

```
<210> SEQ ID NO 199
<211> LENGTH: 207
<212> TYPE: DNA
<213> ORGANISM: Escherichia coli

<400> SEQUENCE: 199
atggaattaa aagcgagtga atttggtgta gttttgtccg ttgatgctct taaattatca      60
cgccagtctc cattaggtgt tggcattggt ggtggtggcg gcggcggcgg cggcggtagc     120
tgcggtggtc aaggtggcgg ttgtggtggt tgcagcaacg gttgtagtgg tggaaacggt     180
ggcagcggcg gaagtggttc acatatc                                          207
```

```
<210> SEQ ID NO 200
<211> LENGTH: 7
<212> TYPE: PRT
<213> ORGANISM: Escherichia coli

<400> SEQUENCE: 200

Met Arg Thr Gly Asn Ala Asn
 1               5
```

```
<210> SEQ ID NO 201
<211> LENGTH: 24
<212> TYPE: DNA
<213> ORGANISM: Escherichia coli

<400> SEQUENCE: 201
atgcgtactg gtaatgcaaa ctaa                                              24
```

```
<210> SEQ ID NO 202
<211> LENGTH: 99
<212> TYPE: PRT
<213> ORGANISM: Klebsiella pneumoniae

<400> SEQUENCE: 202

Met Arg Glu Ile Ser Gln Lys Asp Leu Asn Leu Ala Phe Gly Ala Gly
 1               5                  10                  15

Glu Thr Asp Pro Asn Thr Gln Leu Leu Asn Asp Leu Gly Asn Asn Met
            20                  25                  30

Ala Trp Gly Ala Ala Leu Gly Ala Pro Gly Gly Leu Gly Ser Ala Ala
        35                  40                  45

Leu Gly Ala Ala Gly Gly Ala Leu Gln Thr Val Gly Gln Gly Leu Ile
 50                  55                  60

Asp His Gly Pro Val Asn Val Pro Ile Pro Val Leu Ile Gly Pro Ser
 65                  70                  75                  80

Trp Asn Gly Ser Gly Ser Gly Tyr Asn Ser Ala Thr Ser Ser Ser Gly
                85                  90                  95

Ser Gly Ser
```

```
<210> SEQ ID NO 203
<211> LENGTH: 300
<212> TYPE: DNA
<213> ORGANISM: Klebsiella pneumoniae
```

<400> SEQUENCE: 203

```
atgagagaaa ttagtcaaaa ggacttaaat cttgcttttg gtgcaggaga gaccgatcca      60
aatactcaac ttctaaacga ccttggaaat aatatggcat ggggtgctgc tcttggcgct     120
cctggcggat taggatcagc agctttgggg gccgcgggag gtgcattaca aactgtaggg     180
caaggattaa ttgaccatgg tcctgtaaat gtccccatcc ctgtactcat cgggccaagc     240
tggaatggta gcggtagtgg ttataacagc gcaacatcca gttccggtag tggtagttaa     300
```

<210> SEQ ID NO 204
<211> LENGTH: 75
<212> TYPE: PRT
<213> ORGANISM: Escherichia coli

<400> SEQUENCE: 204

Met Arg Glu Ile Thr Glu Ser Gln Leu Arg Tyr Ile Ser Gly Ala Gly
1               5                   10                  15

Gly Ala Pro Ala Thr Ser Ala Asn Ala Ala Gly Ala Ala Ala Ile Val
            20                  25                  30

Gly Ala Leu Ala Gly Ile Pro Gly Gly Pro Leu Gly Val Val Val Gly
        35                  40                  45

Ala Val Ser Ala Gly Leu Thr Thr Ala Ile Gly Ser Thr Val Gly Ser
    50                  55                  60

Gly Ser Ala Ser Ser Ser Ala Gly Gly Gly Ser
65                  70                  75

<210> SEQ ID NO 205
<211> LENGTH: 228
<212> TYPE: DNA
<213> ORGANISM: Escherichia coli

<400> SEQUENCE: 205

```
atgcgagaaa taacagaatc acagttaaga tatatttccg gggcgggagg tgcgccagcg      60
acttcagcta atgccgcagg tgctgcagct attgttggag ctctcgccgg atacctggt     120 ggtccacttg gggttgtagt tggagccgta tctgccggtt tgacaacagc aattggctcg     180
accgtgggaa gtggtagtgc cagttcttct gctggtggcg gtagctaa                 228
```

<210> SEQ ID NO 206
<211> LENGTH: 58
<212> TYPE: PRT
<213> ORGANISM: Escherichia coli

<400> SEQUENCE: 206

Met Ile Lys His Phe His Phe Asn Lys Leu Ser Ser Gly Lys Lys Asn
1               5                   10                  15

Asn Val Pro Ser Pro Ala Lys Gly Val Ile Gln Ile Lys Lys Ser Ala
            20                  25                  30

Ser Gln Leu Thr Lys Gly Gly Ala Gly His Val Pro Glu Tyr Phe Val
        35                  40                  45

Gly Ile Gly Thr Pro Ile Ser Phe Tyr Gly
    50                  55

<210> SEQ ID NO 207
<211> LENGTH: 177
<212> TYPE: DNA
<213> ORGANISM: Escherichia coli

<400> SEQUENCE: 207

```
atgattaagc attttcattt taataaactg tcttctggta aaaaaaataa tgttccatct      60
cctgcaaagg gggttataca aataaaaaaa tcagcatcgc aactcacaaa aggtggtgca     120
ggacatgtgc ctgagtattt tgtggggatt ggtacaccta tatctttcta tggctga       177
```

<210> SEQ ID NO 208
<211> LENGTH: 90
<212> TYPE: PRT
<213> ORGANISM: Escherichia coli

<400> SEQUENCE: 208

```
Met Tyr Met Arg Glu Leu Asp Arg Glu Leu Asn Cys Val Gly Gly
1               5                   10                  15

Ala Gly Asp Pro Leu Ala Asp Pro Asn Ser Gln Ile Val Arg Gln Ile
                20                  25                  30

Met Ser Asn Ala Ala Trp Gly Pro Pro Leu Val Pro Glu Arg Phe Arg
            35                  40                  45

Gly Met Ala Val Gly Ala Ala Gly Gly Val Thr Gln Thr Val Leu Gln
        50                  55                  60

Gly Ala Ala Ala His Met Pro Val Asn Val Pro Ile Pro Lys Val Pro
65                  70                  75                  80

Met Gly Pro Ser Trp Asn Gly Ser Lys Gly
                85                  90
```

<210> SEQ ID NO 209
<211> LENGTH: 273
<212> TYPE: DNA
<213> ORGANISM: Escherichia coli

<400> SEQUENCE: 209

```
atgtatatga gagagttaga tagagaggaa ttaaattgcg ttggtggggc tggagatccg      60
cttgcagatc ctaattccca aattgtaaga cagataatgt ctaatgcggc atggggcccg     120
cctttggtgc cagagcggtt taggggaatg gctgttggag ccgcaggtgg ggttacgcag     180
acagttcttc aaggagcagc agctcatatg ccggttaatg tccctatacc taaagttccg     240
atgggaccct catggaacgg aagtaaagga taa                                  273
```

<210> SEQ ID NO 210
<211> LENGTH: 50
<212> TYPE: PRT
<213> ORGANISM: Enterococcus mundtii

<400> SEQUENCE: 210

```
Met Ser Gln Val Val Gly Gly Lys Tyr Tyr Gly Asn Gly Val Ser Cys
1               5                   10                  15

Asn Lys Lys Gly Cys Ser Val Asp Trp Gly Lys Ala Ile Gly Ile Ile
                20                  25                  30

Gly Asn Asn Ser Ala Ala Asn Leu Ala Thr Gly Gly Ala Ala Gly Trp
            35                  40                  45

Lys Ser
    50
```

<210> SEQ ID NO 211
<211> LENGTH: 153
<212> TYPE: DNA
<213> ORGANISM: Enterococcus mundtii

<400> SEQUENCE: 211

```
atgtcacagg tagtaggtgg aaaatactac ggtaatggag tctcatgtaa taaaaaggg      60 tgcagtgttg attggggaaa agcgattggc attattggaa ataattctgc tgcgaattta    120
gctactggtg gagcagctgg ttggaaaagt taa                                 153
```

<210> SEQ ID NO 212
<211> LENGTH: 58
<212> TYPE: PRT
<213> ORGANISM: Enterococcus mundtii

<400> SEQUENCE: 212

```
Met Lys Lys Leu Thr Ser Lys Glu Met Ala Gln Val Val Gly Gly Lys
1               5                   10                  15

Tyr Tyr Gly Asn Gly Leu Ser Cys Asn Lys Lys Gly Cys Ser Val Asp
            20                  25                  30

Trp Gly Lys Ala Ile Gly Ile Ile Gly Asn Asn Ser Ala Ala Asn Leu
        35                  40                  45

Ala Thr Gly Gly Ala Ala Gly Trp Lys Ser
    50                  55
```

<210> SEQ ID NO 213
<211> LENGTH: 177
<212> TYPE: DNA
<213> ORGANISM: Enterococcus mundtii

<400> SEQUENCE: 213

```
ttgaagaaat taacatcaaa agaaatggca caagtagtag gtgggaaata ctacggtaat     60
ggattatcat gtaataaaaa agggtgcagt gttgattggg gaaaagctat tggcattatt    120
ggaaataatt ctgctgcgaa tttagctact ggtggagcag ctggttggaa aagttaa       177
```

<210> SEQ ID NO 214
<211> LENGTH: 63
<212> TYPE: PRT
<213> ORGANISM: Streptococcus mutans

<400> SEQUENCE: 214

```
Met Ser Asn Thr Gln Leu Leu Glu Val Leu Gly Thr Glu Thr Phe Asp
1               5                   10                  15

Val Gln Glu Asp Leu Phe Ala Phe Asp Thr Thr Asp Thr Thr Ile Val
            20                  25                  30

Ala Ser Asn Asp Asp Pro Asp Thr Arg Phe Lys Ser Trp Ser Leu Cys
        35                  40                  45

Thr Pro Gly Cys Ala Arg Thr Gly Ser Phe Asn Ser Tyr Cys Cys
    50                  55                  60
```

<210> SEQ ID NO 215
<211> LENGTH: 192
<212> TYPE: DNA
<213> ORGANISM: Streptococcus mutans

<400> SEQUENCE: 215

```
atgtcaaaca cacaattatt agaagtcctt ggtactgaaa cttttgatgt tcaagaagat     60
ctctttgctt ttgatacaac agatactact attgtggcaa gcaacgacga tccagatact    120
cgtttcaaaa gttggagcct tgtacgcct ggttgtgcaa ggacaggtag tttcaatagt     180
tactgttgct ga                                                        192
```

<210> SEQ ID NO 216
<211> LENGTH: 53

```
<212> TYPE: PRT
<213> ORGANISM: Streptococcus mutans

<400> SEQUENCE: 216

Met Asn Lys Leu Asn Ser Asn Ala Val Val Ser Leu Asn Glu Val Ser
1               5                   10                  15

Asp Ser Glu Leu Asp Thr Ile Leu Gly Gly Asn Arg Trp Trp Gln Gly
            20                  25                  30

Val Val Pro Thr Val Ser Tyr Glu Cys Arg Met Asn Ser Trp Gln His
        35                  40                  45

Val Phe Thr Cys Cys
        50

<210> SEQ ID NO 217
<211> LENGTH: 162
<212> TYPE: DNA
<213> ORGANISM: Streptococcus mutans

<400> SEQUENCE: 217
atgaacaagt taaacagtaa cgcagtagtt tctttgaatg aagtttcaga ttctgaattg      60
gatactattt tgggtggtaa tcgttggtgg caaggtgttg tgccaacggt ctcatatgag     120
tgtcgcatga attcatggca acatgttttc acttgctgtt aa                        162

<210> SEQ ID NO 218
<211> LENGTH: 57
<212> TYPE: PRT
<213> ORGANISM: Lactococcus lactis subsp. lactis

<400> SEQUENCE: 218

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
        50                  55

<210> SEQ ID NO 219
<211> LENGTH: 174
<212> TYPE: DNA
<213> ORGANISM: Lactococcus lactis subsp. lactis

<400> SEQUENCE: 219
atgagtacaa aagattttaa cttggatttg gtatctgttt cgaagaaaga ttcaggtgca      60
tcaccacgca ttacaagtat ttcgctatgt acacccggtt gtaaaacagg agctctgatg     120
ggttgtaaca tgaaaacagc aacttgtcat tgtagtattc acgtaagcaa ataa            174

<210> SEQ ID NO 220
<211> LENGTH: 57
<212> TYPE: PRT
<213> ORGANISM: Lactococcus lactis

<400> SEQUENCE: 220

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30
```

```
Gly Cys Lys Thr Gly Ala Leu Met Gly Cys Asn Met Lys Thr Ala Thr
            35                  40                  45

Cys Asn Cys Ser Val His Val Ser Lys
            50                  55

<210> SEQ ID NO 221
<211> LENGTH: 171
<212> TYPE: DNA
<213> ORGANISM: Lactococcus lactis

<400> SEQUENCE: 221
atgagtacaa aagatttcaa cttggatttg gtatctgttt cgaagaaaga ttcaggtgca      60
tcaccacgca ttacaagtat ttcgctatgt acacccggtt gtaaaacagg agctctgatg    120
ggttgtaaca tgaaaacagc aacttgtaat tgtagcgttc acgtaagcaa a             171

<210> SEQ ID NO 222
<211> LENGTH: 57
<212> TYPE: PRT
<213> ORGANISM: Lactococcus lactis

<400> SEQUENCE: 222

Met Ser Thr Lys Asp Phe Asn Leu Asp Leu Val Ser Val Ser Lys Thr
1               5                   10                  15

Asp Ser Gly Ala Ser Thr Arg Ile Thr Ser Ile Ser Leu Cys Thr Pro
            20                  25                  30

Gly Cys Lys Thr Gly Val Leu Met Gly Cys Asn Leu Lys Thr Ala Thr
            35                  40                  45

Cys Asn Cys Ser Val His Val Ser Lys
            50                  55

<210> SEQ ID NO 223
<211> LENGTH: 174
<212> TYPE: DNA
<213> ORGANISM: Lactococcus lactis

<400> SEQUENCE: 223
atgagtacaa aagatttcaa cttagatttg gtatctgttt caaaaacaga ttctggcgct      60
tcaacacgta ttaccagcat ttcgctttgt acaccaggtt gtaaaacagg tgttctgatg    120
ggatgtaacc tgaaaacagc aacttgtaat tgtagcgttc acgtaagcaa ataa          174

<210> SEQ ID NO 224
<211> LENGTH: 55
<212> TYPE: PRT
<213> ORGANISM: Streptococcus uberis

<400> SEQUENCE: 224

Met Asn Asn Glu Asp Phe Asn Leu Asp Leu Ile Lys Ile Ser Lys Glu
1               5                   10                  15

Asn Asn Ser Gly Ala Ser Pro Arg Ile Thr Ser Lys Ser Leu Cys Thr
            20                  25                  30

Pro Gly Cys Lys Thr Gly Ile Leu Met Thr Cys Pro Leu Lys Thr Ala
            35                  40                  45

Thr Cys Gly Cys His Phe Gly
            50                  55

<210> SEQ ID NO 225
<211> LENGTH: 168
<212> TYPE: DNA
<213> ORGANISM: Streptococcus uberis
```

<400> SEQUENCE: 225

```
atgaacaatg aagatttta  tttggatctc atcaaaatct caaaggaaaa caactcagga    60
gcttcacctc gaataactag taaatcatta tgtactcctg gatgtaagac gggtatttg    120
atgacttgtc cactaaaaac tgcaacctgt ggttgtcatt ttggataa                 168
```

<210> SEQ ID NO 226
<211> LENGTH: 57
<212> TYPE: PRT
<213> ORGANISM: Lactococcus lactis subsp. lactis

<400> SEQUENCE: 226

```
Met Ser Thr Lys Asp Phe Asn Leu Asp Leu Val Ser Val Ser Lys Lys
1               5                   10                  15
Asp Ser Gly Ala Ser Pro Arg Ile Thr Ser Ile Ser Leu Cys Thr Pro
            20                  25                  30
Gly Cys Lys Thr Gly Ala Leu Met Gly Cys Asn Met Lys Thr Ala Thr
        35                  40                  45
Cys Asn Cys Ser Ile His Val Ser Lys
    50                  55
```

<210> SEQ ID NO 227
<211> LENGTH: 174
<212> TYPE: DNA
<213> ORGANISM: Lactococcus lactis subsp. lactis

<400> SEQUENCE: 227

```
atgagtacaa aagatttta  cttggatttg gtatctgttt cgaagaaaga ttcaggtgca    60
tcaccacgca ttacaagtat ttcgctatgt acacccggtt gtaaaacagg agctctgatg    120
ggttgtaaca tgaaaacagc aacttgtaat tgtagtattc acgtaagcaa ataa          174
```

<210> SEQ ID NO 228
<211> LENGTH: 57
<212> TYPE: PRT
<213> ORGANISM: Staphylococcus warneri

<400> SEQUENCE: 228

```
Met Glu Asn Ser Lys Val Met Lys Asp Ile Glu Val Ala Asn Leu Leu
1               5                   10                  15
Glu Glu Val Gln Glu Asp Glu Leu Asn Glu Val Leu Gly Ala Lys Lys
            20                  25                  30
Lys Ser Gly Val Ile Pro Thr Val Ser His Asp Cys His Met Asn Ser
        35                  40                  45
Phe Gln Phe Val Phe Thr Cys Cys Ser
    50                  55
```

<210> SEQ ID NO 229
<211> LENGTH: 174
<212> TYPE: DNA
<213> ORGANISM: Staphylococcus warneri

<400> SEQUENCE: 229

```
atggaaaatt ctaaagttat gaaggacatt gaagtagcaa atttattaga agaggttcaa    60
gaagatgaat tgaatgaagt cttaggagct aagaaaaagt caggagtaat cccaactgtg    120
tcacacgatt gccatatgaa ttctttccaa tttgtattta cttgttgttc ataa          174
```

<210> SEQ ID NO 230

```
<211> LENGTH: 58
<212> TYPE: PRT
<213> ORGANISM: Paenibacillus polymyxa

<400> SEQUENCE: 230
```

Met Ala Glu Asn Leu Phe Asp Leu Asp Ile Gln Val Asn Lys Ser Gln
1               5                   10                  15

Gly Ser Val Glu Pro Gln Val Leu Ser Ile Val Ala Cys Ser Ser Gly
            20                  25                  30

Cys Gly Ser Gly Lys Thr Ala Ala Ser Cys Val Glu Thr Cys Gly Asn
        35                  40                  45

Arg Cys Phe Thr Asn Val Gly Ser Leu Cys
    50                  55

```
<210> SEQ ID NO 231
<211> LENGTH: 177
<212> TYPE: DNA
<213> ORGANISM: Paenibacillus polymyxa

<400> SEQUENCE: 231
```
atggctgaaa acttatttga tctggacatt caagtaaaca aatctcaagg ttctgtagag     60
cctcaggttc tgagcattgt tgcatgttct agcggatgtg gtagcggtaa aacagctgcc    120
agttgtgttg aaacttgtgg caaccggtgc tttactaacg ttggttcact ctgctaa       177

```
<210> SEQ ID NO 232
<211> LENGTH: 62
<212> TYPE: PRT
<213> ORGANISM: Pediococcus acidilactici

<400> SEQUENCE: 232
```

Met Lys Lys Ile Glu Lys Leu Thr Glu Lys Glu Met Ala Asn Ile Ile
1               5                   10                  15

Gly Gly Lys Tyr Tyr Gly Asn Gly Val Thr Cys Gly Lys His Ser Cys
            20                  25                  30

Ser Val Asp Trp Gly Lys Ala Thr Thr Cys Ile Ile Asn Asn Gly Ala
        35                  40                  45

Met Ala Trp Ala Thr Gly Gly His Gln Gly Asn His Lys Cys
    50                  55                  60

```
<210> SEQ ID NO 233
<211> LENGTH: 189
<212> TYPE: DNA
<213> ORGANISM: Pediococcus acidilactici

<400> SEQUENCE: 233
```
atgaaaaaaa ttgaaaaatt aactgaaaaa gaaatggcca atatcattgg tggtaaatac     60
tacggtaatg gggttacttg tggcaaacat tcctgctctg ttgactgggg taaggctacc    120
acttgcataa tcaataatgg agctatggca tgggctactg gtggacatca aggtaatcat    180
aaatgctag                                                             189

```
<210> SEQ ID NO 234
<211> LENGTH: 60
<212> TYPE: PRT
<213> ORGANISM: Pediococcus pentosaceus

<400> SEQUENCE: 234
```

Met Thr Glu Ile Lys Val Leu Asn Asp Lys Glu Leu Lys Asn Val Val
1               5                   10                  15

Gly Gly Lys Tyr Tyr Gly Asn Gly Val His Cys Gly Lys Lys Thr Cys
                20                  25                  30

Tyr Val Asp Trp Gly Gln Ala Thr Ala Ser Ile Gly Lys Ile Ile Val
            35                  40                  45

Asn Gly Trp Thr Gln His Gly Pro Trp Ala His Arg
        50                  55                  60

<210> SEQ ID NO 235
<211> LENGTH: 183
<212> TYPE: DNA
<213> ORGANISM: Pediococcus pentosaceus

<400> SEQUENCE: 235
atgactgaaa ttaaagtact aaacgataag gaactaaaaa atgtcgtagg aggaaagtat      60
tacggtaacg gagtgcattg tggtaaaaag acttgctatg tggactgggg acaagctaca     120
gctagcattg gaaaaattat agtgaacgga tggacacaac acgggccttg ggcacataga     180
taa                                                                   183

<210> SEQ ID NO 236
<211> LENGTH: 60
<212> TYPE: PRT
<213> ORGANISM: Staphylococcus epidermidis

<400> SEQUENCE: 236

Met Lys Asn Asn Lys Asn Leu Phe Asp Leu Glu Ile Lys Lys Glu Thr
1               5                   10                  15

Ser Gln Asn Thr Asp Glu Leu Glu Pro Gln Thr Ala Gly Pro Ala Ile
            20                  25                  30

Arg Ala Ser Val Lys Gln Cys Gln Lys Thr Leu Lys Ala Thr Arg Leu
        35                  40                  45

Phe Thr Val Ser Cys Lys Gly Lys Asn Gly Cys Lys
    50                  55                  60

<210> SEQ ID NO 237
<211> LENGTH: 183
<212> TYPE: DNA
<213> ORGANISM: Staphylococcus epidermidis

<400> SEQUENCE: 237
atgaaaaata caaaaatttt atttgattta gaaattaaaa aagaaacaag tcaaaacact      60
gatgaacttg aacctcaaac tgctggacca gcgattagag cttctgtgaa acaatgtcag     120
aaaactttga agctacgcg tttatttaca gtgtcttgca aggaaaaaa cggatgtaaa      180 tag                                                                   183

<210> SEQ ID NO 238
<211> LENGTH: 62
<212> TYPE: PRT
<213> ORGANISM: Carnobacterium maltaromaticum

<400> SEQUENCE: 238

Met Lys Thr Val Lys Glu Leu Ser Val Lys Glu Met Gln Leu Thr Thr
1               5                   10                  15

Gly Gly Lys Tyr Tyr Gly Asn Gly Val Ser Cys Asn Lys Asn Gly Cys
            20                  25                  30

Thr Val Asp Trp Ser Lys Ala Ile Gly Ile Ile Gly Asn Asn Ala Ala
        35                  40                  45

Ala Asn Leu Thr Thr Gly Gly Ala Ala Gly Trp Asn Lys Gly

<210> SEQ ID NO 239
<211> LENGTH: 189
<212> TYPE: DNA
<213> ORGANISM: Carnobacterium maltaromaticum

<400> SEQUENCE: 239

```
atgaaaactg ttaaagaact tagcgttaaa gaaatgcaac taactacagg aggtaagtat      60
tacggaaatg gcgtttcctg taataaaaat ggttgtactg tagattggag caaagctatt     120
gggattatag gaaacaatgc agcagcaaat ttgactacag gtggagccgc tggttggaac     180
aaaggataa                                                             189
```

<210> SEQ ID NO 240
<211> LENGTH: 69
<212> TYPE: PRT
<213> ORGANISM: Lactobacillus plantarum
<220> FEATURE:
<221> NAME/KEY: VARIANT
<222> LOCATION: (40)..(40)
<223> OTHER INFORMATION: Xaa = any amino acid

<400> SEQUENCE: 240

```
Met Tyr Lys Glu Leu Thr Val Asp Glu Leu Ala Leu Ile Asp Gly Gly
1               5                   10                  15

Lys Lys Lys Lys Lys Val Ala Cys Thr Trp Gly Asn Ala Ala Thr
            20                  25                  30

Ala Ala Ala Ser Gly Ala Val Xaa Gly Ile Leu Gly Gly Pro Thr Gly
        35                  40                  45

Ala Leu Ala Gly Ala Ile Trp Gly Val Ser Gln Cys Ala Ser Asn Asn
    50                  55                  60

Leu His Gly Met His
65
```

<210> SEQ ID NO 241
<211> LENGTH: 210
<212> TYPE: DNA
<213> ORGANISM: Lactobacillus plantarum
<220> FEATURE:
<221> NAME/KEY: misc_feature
<222> LOCATION: (119)..(119)
<223> OTHER INFORMATION: n = a, c, t or g

<400> SEQUENCE: 241

```
atgtataaag aattaacagt tgatgaatta gcattgattg atggaggaaa aaagaagaag      60
aaaaaagtag cttgtacttg gggaaatgca gcaacagccg ctgcttctgg tgcagttang     120
ggtattcttg gtgggcctac tggtgcactg gctggagcta tctggggcgt ttcacaatgc     180
gcgtctaaca acttacacgg catgcactaa                                      210
```

<210> SEQ ID NO 242
<211> LENGTH: 56
<212> TYPE: PRT
<213> ORGANISM: Lactobacillus plantarum

<400> SEQUENCE: 242

```
Met Met Lys Lys Ile Glu Lys Leu Thr Glu Lys Glu Met Ala Asn Ile
1               5                   10                  15

Ile Gly Gly Lys Tyr Tyr Gly Asn Gly Val Thr Cys Gly Lys His Ser
            20                  25                  30
```

Cys Ser Val Asn Trp Gly Gln Ala Phe Ser Cys Ser Val Ser His Leu
             35                  40                  45

Ala Asn Phe Gly His Gly Lys Cys
         50                  55

<210> SEQ ID NO 243
<211> LENGTH: 171
<212> TYPE: DNA
<213> ORGANISM: Lactobacillus plantarum

<400> SEQUENCE: 243
atgatgaaaa aaattgaaaa attaactgaa aagaaatgg ccaatatcat tggtggtaaa      60
tactatggta atggggttac ttgtggtaaa cattcctgct ctgttaactg ggccaagca     120 ttttcttgta gtgtgtcaca tttagctaac ttcggtcatg gaaagtgcta a             171

<210> SEQ ID NO 244
<211> LENGTH: 64
<212> TYPE: PRT
<213> ORGANISM: Lactobacillus plantarum

<400> SEQUENCE: 244

Met Ser Lys Leu Val Lys Thr Leu Thr Val Asp Glu Ile Ser Lys Ile
1               5                   10                  15

Gln Thr Asn Gly Gly Lys Pro Ala Trp Cys Trp Tyr Thr Leu Ala Met
            20                  25                  30

Cys Gly Ala Gly Tyr Asp Ser Gly Thr Cys Asp Tyr Met Tyr Ser His
        35                  40                  45

Cys Phe Gly Val Lys His Ser Ser Gly Gly Gly Ser Tyr His Cys
    50                  55                  60

<210> SEQ ID NO 245
<211> LENGTH: 195
<212> TYPE: DNA
<213> ORGANISM: Lactobacillus plantarum

<400> SEQUENCE: 245
atgagtaaac tagttaaaac attaactgtc gatgaaatct ctaagattca aaccaatggt      60
ggaaaacctg catggtgttg gtacacattg gcaatgtgcg gtgctggtta tgattcaggc     120
acttgtgatt atatgtattc acactgcttt ggtgtaaaac actctagcgg tggtggcggt     180
agctaccatt gttag                                                     195

<210> SEQ ID NO 246
<211> LENGTH: 56
<212> TYPE: PRT
<213> ORGANISM: Lactobacillus plantarum

<400> SEQUENCE: 246

Met Leu Gln Phe Glu Lys Leu Gln Tyr Ser Arg Leu Pro Gln Lys Lys
1               5                   10                  15

Leu Ala Lys Ile Ser Gly Gly Phe Asn Arg Gly Gly Tyr Asn Phe Gly
            20                  25                  30

Lys Ser Val Arg His Val Val Asp Ala Ile Gly Ser Val Ala Gly Ile
        35                  40                  45

Arg Gly Ile Leu Lys Ser Ile Arg
    50                  55

<210> SEQ ID NO 247
<211> LENGTH: 171

```
<212> TYPE: DNA
<213> ORGANISM: Lactobacillus plantarum

<400> SEQUENCE: 247
atgctacagt ttgagaaatt acaatattcc aggttgccgc aaaaaaagct tgccaaaata    60
tctggtggtt ttaatcgggg cggttataac tttggtaaaa gtgttcgaca tgttgttgat   120
gcaattggtt cagttgcagg cattcgtggt attttgaaaa gtattcgtta a             171

<210> SEQ ID NO 248
<211> LENGTH: 52
<212> TYPE: PRT
<213> ORGANISM: Lactobacillus plantarum

<400> SEQUENCE: 248

Met Lys Lys Phe Leu Val Leu Arg Asp Arg Glu Leu Asn Ala Ile Ser
1               5                   10                  15

Gly Gly Val Phe His Ala Tyr Ser Ala Arg Gly Val Arg Asn Asn Tyr
            20                  25                  30

Lys Ser Ala Val Gly Pro Ala Asp Trp Val Ile Ser Ala Val Arg Gly
        35                  40                  45

Phe Ile His Gly
    50

<210> SEQ ID NO 249
<211> LENGTH: 159
<212> TYPE: DNA
<213> ORGANISM: Lactobacillus plantarum

<400> SEQUENCE: 249
atgaaaaaat ttctagtttt gcgtgaccgt gaattaaatg ctatttcagg tggcgttttc    60
catgcctata gcgcgcgtgg cgttcggaat aattataaaa gtgctgttgg gcctgccgat   120
tgggtcatta gcgctgtccg aggattcatc cacggatag                          159

<210> SEQ ID NO 250
<211> LENGTH: 55
<212> TYPE: PRT
<213> ORGANISM: Lactobacillus plantarum

<400> SEQUENCE: 250

Met Thr Val Asn Lys Met Ile Lys Asp Leu Asp Val Val Asp Ala Phe
1               5                   10                  15

Ala Pro Ile Ser Asn Asn Lys Leu Asn Gly Val Val Gly Gly Gly Ala
            20                  25                  30

Trp Lys Asn Phe Trp Ser Ser Leu Arg Lys Gly Phe Tyr Asp Gly Glu
        35                  40                  45

Ala Gly Arg Ala Ile Arg Arg
    50                  55

<210> SEQ ID NO 251
<211> LENGTH: 168
<212> TYPE: DNA
<213> ORGANISM: Lactobacillus plantarum

<400> SEQUENCE: 251
atgactgtga acaaaatgat taaggatttg gatgtagtag atgcatttgc acctatttct    60
aataataagt tgaacggggt tgttggggga ggcgcttgga aaaatttctg gtctagttta   120
agaaaaggat tttatgatgg cgaagctggc agagcaatcc gtcgttaa               168
```

<210> SEQ ID NO 252
<211> LENGTH: 57
<212> TYPE: PRT
<213> ORGANISM: Lactobacillus plantarum

<400> SEQUENCE: 252

Met Lys Ile Lys Leu Thr Val Leu Asn Glu Phe Glu Glu Leu Thr Ala
1               5                   10                  15
Asp Ala Glu Lys Asn Ile Ser Gly Gly Arg Arg Ser Arg Lys Asn Gly
            20                  25                  30
Ile Gly Tyr Ala Ile Gly Tyr Ala Phe Gly Ala Val Glu Arg Ala Val
        35                  40                  45
Leu Gly Gly Ser Arg Asp Tyr Asn Lys
    50                  55

<210> SEQ ID NO 253
<211> LENGTH: 174
<212> TYPE: DNA
<213> ORGANISM: Lactobacillus plantarum

<400> SEQUENCE: 253
atgaaaatta aattaactgt tttaaatgaa tttgaagaat taactgctga cgctgaaaag      60
aatatttctg gtggccgtcg gagtcgtaaa aatggaattg atacgctat tggttatgcg     120 tttggcgcgg ttgaacgggc cgtgcttggt ggttcaaggg attataataa gtga          174

<210> SEQ ID NO 254
<211> LENGTH: 47
<212> TYPE: PRT
<213> ORGANISM: Lactobacillus plantarum

<400> SEQUENCE: 254

Met Asp Lys Phe Glu Lys Ile Ser Thr Ser Asn Leu Glu Lys Ile Ser
1               5                   10                  15
Gly Gly Asp Leu Thr Thr Lys Leu Trp Ser Ser Trp Gly Tyr Tyr Leu
            20                  25                  30
Gly Lys Lys Ala Arg Trp Asn Leu Lys His Pro Tyr Val Gln Phe
        35                  40                  45

<210> SEQ ID NO 255
<211> LENGTH: 141
<212> TYPE: DNA
<213> ORGANISM: Lactobacillus plantarum

<400> SEQUENCE: 255
atggataaat ttgaaaaaat tagtacatct aacctagaaa agatctctgg cggtgattta      60
acaaccaagt tatggagctc ttggggatat tatcttggca agaaagcacg ttggaattta     120
aagcacccat atgttcaatt t                                               141

<210> SEQ ID NO 256
<211> LENGTH: 55
<212> TYPE: PRT
<213> ORGANISM: Lactobacillus plantarum

<400> SEQUENCE: 256

Met Asn Asn Leu Asn Lys Phe Ser Thr Leu Gly Lys Ser Ser Leu Ser
1               5                   10                  15
Gln Ile Glu Gly Gly Ser Val Pro Thr Ser Val Tyr Thr Leu Gly Ile
            20                  25                  30

Lys Ile Leu Trp Ser Ala Tyr Lys His Arg Lys Thr Ile Glu Lys Ser
                35                  40                  45

Phe Asn Lys Gly Phe Tyr His
    50                  55

<210> SEQ ID NO 257
<211> LENGTH: 168
<212> TYPE: DNA
<213> ORGANISM: Lactobacillus plantarum

<400> SEQUENCE: 257
atgaataact tgaataaatt ttctactcta ggcaagagta gcttgtctca aattgagggc     60
ggatcagtcc caacttcagt atatacgctt ggaattaaaa ttctatggtc tgcgtataag    120
catcgcaaaa cgattgaaaa aagtttaat aaaggctttt atcattaa                   168

<210> SEQ ID NO 258
<211> LENGTH: 55
<212> TYPE: PRT
<213> ORGANISM: Lactobacillus plantarum

<400> SEQUENCE: 258

Met Asn Asn Ala Leu Ser Phe Glu Gln Gln Phe Thr Asp Phe Ser Thr
1               5                   10                  15

Leu Ser Asp Ser Glu Leu Glu Ser Val Glu Gly Gly Arg Asn Lys Leu
                20                  25                  30

Ala Tyr Asn Met Gly His Tyr Ala Gly Lys Ala Thr Ile Phe Gly Leu
            35                  40                  45

Ala Ala Trp Ala Leu Leu Ala
        50                  55

<210> SEQ ID NO 259
<211> LENGTH: 168
<212> TYPE: DNA
<213> ORGANISM: Lactobacillus plantarum

<400> SEQUENCE: 259
atgaataacg cattaagttt tgaacaacaa tttacagact tcagcacctt atcggactct     60
gaattagaat ccgttgaggg tggccgaaat aagcttgcat ataatatggg cattacgct    120 ggtaaggcaa ccattttggg acttgcagca tgggcactcc ttgcatga                 168

<210> SEQ ID NO 260
<211> LENGTH: 47
<212> TYPE: PRT
<213> ORGANISM: Lactobacillus plantarum

<400> SEQUENCE: 260

Met Asp Lys Ile Ile Lys Phe Gln Gly Ile Ser Asp Asp Gln Leu Asn
1               5                   10                  15

Ala Val Ile Gly Gly Lys Lys Lys Lys Gln Ser Trp Tyr Ala Ala Ala
                20                  25                  30

Gly Asp Ala Ile Val Ser Phe Gly Glu Gly Phe Leu Asn Ala Trp
            35                  40                  45

<210> SEQ ID NO 261
<211> LENGTH: 144
<212> TYPE: DNA
<213> ORGANISM: Lactobacillus plantarum

<400> SEQUENCE: 261

```
atggataaga ttattaagtt tcaagggatt tctgatgatc aattaaatgc tgttatcggt    60
gggaaaaaga aaaaacaatc ttggtacgca gcagctggtg atgcaatcgt tagttttggt   120
gaaggatttt taaatgcttg gtaa                                          144
```

<210> SEQ ID NO 262
<211> LENGTH: 59
<212> TYPE: PRT
<213> ORGANISM: Lactobacillus plantarum

<400> SEQUENCE: 262

```
Met Lys Ile Ser Lys Ile Glu Ala Gln Ala Arg Lys Asp Phe Phe Lys
1               5                   10                  15

Lys Ile Asp Thr Asn Ser Asn Leu Leu Asn Val Asn Gly Ala Lys Cys
            20                  25                  30

Lys Trp Trp Asn Ile Ser Cys Asp Leu Gly Asn Gly His Val Cys
        35                  40                  45

Thr Leu Ser His Glu Cys Gln Val Ser Cys Asn
    50                  55
```

<210> SEQ ID NO 263
<211> LENGTH: 180
<212> TYPE: DNA
<213> ORGANISM: Lactobacillus plantarum

<400> SEQUENCE: 263

```
atgaaaattt ctaagattga agctcaggct cgtaaagatt tttttaaaaa aatcgatact    60
aactcgaact tattaaatgt aaatggtgcc aaatgcaagt ggtggaatat ttcgtgtgat   120
ttaggaaata atggccatgt ttgtaccttg tcacatgaat gccaagtatc ttgtaactaa   180
```

<210> SEQ ID NO 264
<211> LENGTH: 67
<212> TYPE: PRT
<213> ORGANISM: Lactobacillus plantarum

<400> SEQUENCE: 264

```
Met Thr Lys Thr Ser Arg Arg Lys Asn Ala Ile Ala Asn Tyr Leu Glu
1               5                   10                  15

Pro Val Asp Glu Lys Ser Ile Asn Glu Ser Phe Gly Ala Gly Asp Pro
            20                  25                  30

Glu Ala Arg Ser Gly Ile Pro Cys Thr Ile Gly Ala Ala Val Ala Ala
        35                  40                  45

Ser Ile Ala Val Cys Pro Thr Thr Lys Cys Ser Lys Arg Cys Gly Lys
    50                  55                  60

Arg Lys Lys
65
```

<210> SEQ ID NO 265
<211> LENGTH: 204
<212> TYPE: DNA
<213> ORGANISM: Lactobacillus plantarum

<400> SEQUENCE: 265

```
atgactaaaa ctagtcgtcg taagaatgct attgctaatt atttagaacc agtcgacgaa    60
aaaagtatta tgaatctttt tggggctggg gatccggaag caagatccgg aattccatgt   120
acaatcggcg cagctgtcgc agcatcaatt gcagtttgtc caactactaa gtgtagtaaa   180
cgttgtggca agcgtaagaa ataa                                          204
```

<210> SEQ ID NO 266
<211> LENGTH: 48
<212> TYPE: PRT
<213> ORGANISM: Lactobacillus plantarum

<400> SEQUENCE: 266

Met Lys Ile Gln Ile Lys Gly Met Lys Gln Leu Ser Asn Lys Glu Met
1               5                   10                  15

Gln Lys Ile Val Gly Gly Lys Ser Ser Ala Tyr Ser Leu Gln Met Gly
            20                  25                  30

Ala Thr Ala Ile Lys Gln Val Lys Lys Leu Phe Lys Lys Trp Gly Trp
        35                  40                  45

<210> SEQ ID NO 267
<211> LENGTH: 147
<212> TYPE: DNA
<213> ORGANISM: Lactobacillus plantarum

<400> SEQUENCE: 267
atgaaaattc aaattaaagg tatgaagcaa cttagtaata aggaaatgca aaaaatagta    60
ggtggaaaga gtagtgcgta ttctttgcag atgggggcaa ctgcaattaa acaggtaaag   120
aaactgttta aaaaatgggg atggtaa                                      147

<210> SEQ ID NO 268
<211> LENGTH: 207
<212> TYPE: PRT
<213> ORGANISM: Propionibacterium jensenii

<400> SEQUENCE: 268

Met Asn Lys Thr His Lys Met Ala Thr Leu Val Ile Ala Ala Ile Leu
1               5                   10                  15

Ala Ala Gly Met Thr Ala Pro Thr Ala Tyr Ala Asp Ser Pro Gly Asn
            20                  25                  30

Thr Arg Ile Thr Ala Ser Glu Gln Ser Val Leu Thr Gln Ile Leu Gly
        35                  40                  45

His Lys Pro Thr Gln Thr Glu Tyr Asn Arg Tyr Val Glu Thr Tyr Gly
    50                  55                  60

Ser Val Pro Thr Glu Ala Asp Ile Asn Ala Tyr Ile Glu Ala Ser Glu
65                  70                  75                  80

Ser Glu Gly Ser Ser Ser Gln Thr Ala Ala His Asp Asp Ser Thr Ser
                85                  90                  95

Pro Gly Thr Ser Thr Glu Ile Tyr Thr Gln Ala Ala Pro Ala Arg Phe
            100                 105                 110

Ser Met Phe Phe Leu Ser Gly Thr Trp Ile Thr Arg Ser Gly Val Val
        115                 120                 125

Ser Leu Ser Leu Lys Pro Arg Lys Gly Gly Ile Gly Asn Glu Gly Asp
    130                 135                 140

Glu Arg Thr Trp Lys Thr Val Tyr Asp Lys Phe His Asn Ala Gly Gln
145                 150                 155                 160

Trp Thr Arg Tyr Lys Asn Asn Gly Val Asp Ala Ser Met Lys Lys Gln
                165                 170                 175

Tyr Met Cys His Phe Lys Tyr Gly Met Val Lys Thr Pro Trp Asn Leu
            180                 185                 190

Glu Pro His Lys Lys Ala Ala Asp Val Ser Pro Val Lys Cys Asn
        195                 200                 205

<210> SEQ ID NO 269
<211> LENGTH: 624
<212> TYPE: DNA
<213> ORGANISM: Propionibacterium jensenii

<400> SEQUENCE: 269

| | |
|---|---|
| atgaacaaaa cacacaaaat ggcgacgctg gtaattgccg cgatcttggc cgccggaatg | 60 |
| accgcaccaa ctgcctatgc agattctcct ggaaacacca gaattacagc cagcgagcaa | 120 |
| agcgtcctta cccagatact cggccacaaa cctacacaaa ctgaatataa ccgatacgtt | 180 |
| gagacttacg gaagcgtacc gaccgaagca gacatcaacg catatataga agcgtctgaa | 240 |
| tctgagggat catcaagtca aacgctgct cacgatgact cgacatcacc cggcacgagt | 300 |
| accgaaatct acacgcaggc agcccctgcc aggttctcaa tgttttcct gtccggaact | 360 |
| tggatcacta ggagtggtgt agtatcgctc tccttgaagc caaggaaggg tggtattggc | 420 |
| aacgaggggg acgagcgtac ctggaagact gtatacgaca aattccataa cgctgggcaa | 480 |
| tggacacgat acaagaacaa cggcgtagac gccagcatga aaaagcagta catgtgccac | 540 |
| ttcaagtacg ggatggtgaa gacgccatgg aatctggagc cccacaagaa ggctgcagac | 600 |
| gtcagtccag tcaagtgcaa ctag | 624 |

<210> SEQ ID NO 270
<211> LENGTH: 96
<212> TYPE: PRT
<213> ORGANISM: Propionibacterium thoenii

<400> SEQUENCE: 270

Met Lys Lys Thr Leu Leu Arg Ser Gly Thr Ile Ala Leu Ala Thr Ala
1               5                   10                  15

Ala Ala Phe Gly Ala Ser Leu Ala Ala Ala Pro Ser Ala Met Ala Val
            20                  25                  30

Pro Gly Gly Cys Thr Tyr Thr Arg Ser Asn Arg Asp Val Ile Gly Thr
        35                  40                  45

Cys Lys Thr Gly Ser Gly Gln Phe Arg Ile Arg Leu Asp Cys Asn Asn
    50                  55                  60

Ala Pro Asp Lys Thr Ser Val Trp Ala Lys Pro Lys Val Met Val Ser
65                  70                  75                  80

Val His Cys Leu Val Gly Gln Pro Arg Ser Ile Ser Phe Glu Thr Lys
                85                  90                  95

<210> SEQ ID NO 271
<211> LENGTH: 291
<212> TYPE: DNA
<213> ORGANISM: Propionibacterium thoenii

<400> SEQUENCE: 271

| | |
|---|---|
| atgaagaaga ccctcctgcg aagtggaacg atcgcactgg cgaccgcggc tgcatttggc | 60 |
| gcatcattgg cagccgcccc atctgccatg gccgttcctg gtggttgcac gtacacaaga | 120 |
| agcaatcgcg acgtcatcgg tacctgcaag actggaagcg gccagttccg aatccgactt | 180 |
| gactgcaaca acgctccaga caaaacttca gtctgggcca gcccaaggt aatggtgtcg | 240 |
| gttcactgtc ttgttggtca accgaggtcc atctcgttcg agaccaagtg a | 291 |

<210> SEQ ID NO 272
<211> LENGTH: 255
<212> TYPE: PRT
<213> ORGANISM: Propionibacterium freudenreichii subsp freudenreii

<400> SEQUENCE: 272

| | | | | | | | | | | | | | | |
|---|---|---|---|---|---|---|---|---|---|---|---|---|---|---|
|Met|Asn|Thr|Lys|Ala|Val|Asn|Leu|Lys|Ser|Glu|Asn|Thr|Thr|Lys|Leu|
|1| | |5| | | | |10| | | | |15| | |

Val Ser Tyr Leu Thr Glu Asn Gln Leu Asp Glu Phe Ile Arg Arg Ile
           20                25              30

Arg Ile Asp Gly Ala Leu Val Glu Val Ser Gln Asn Ala Lys Gln
     35                  40               45

Ala Leu Asp Asn Thr Gly Leu Asn Gly Trp Ile Asn Thr Asp Cys Asp
50                55                   60

Glu Gly Leu Leu Ser Asp Phe Ile Ser Lys Ile Ala Ser Ala Arg Trp
65                70              75            80

Ile Pro Leu Ala Glu Ser Ile Arg Pro Ala Val Thr Asp Arg Asp Lys
           85                90             95

Tyr Arg Val Ser Cys Trp Phe Tyr Gln Gly Met Asn Ile Ala Ile Tyr
        100               105            110

Ala Asn Ile Gly Gly Val Ala Asn Ile Ile Gly Tyr Thr Glu Ala Ala
     115                120             125

Val Ala Thr Leu Leu Gly Ala Val Ala Val Ala Pro Val Val Pro
130                135               140

Gly Thr Pro Thr Pro Pro Lys Asp Lys Ser Ser Gln Tyr Lys Glu Val
145              150              155           160

Pro Leu Ala Val Arg Leu Ser Glu Thr Tyr His Glu Glu Gly Val Arg
        165             170            175

Gly Leu Phe Asp Glu Leu Asn Tyr Ser Glu Ser Arg Met Ile Ser Thr
         180            185            190

Leu Arg Arg Ala Ser Thr Asp Gly Val Leu Ile Asn Ser Trp Asn Asp
     195                200             205

Gly Gln Asp Thr Ile Leu Leu Lys Lys Tyr Asn Phe Gln Asp Leu Gln
210                215              220

Leu Thr Val Arg Ser Arg Ile Val Gly Asn Gln Thr Ile Ile Glu Glu
225              230              235           240

Cys Lys Ile Thr Asp Gly Arg Lys Thr Leu Ser Asp Glu Thr Val
        245             250            255

<210> SEQ ID NO 273
<211> LENGTH: 768
<212> TYPE: DNA
<213> ORGANISM: Propionibacterium freudenreichii subsp freudenreii

<400> SEQUENCE: 273

| | | | | |
|---|---|---|---|---|
|atgaatacca|aagctgtaaa|tctgaagtca|gaaaacacga|ctaagttggt gagctacctt|60|
|acggaaaatc|aattggatga|gtttattaga|aggattcgca|ttgatggcgc tcttgtggaa|120|
|gaggtcagtc|aaaatgctaa|gcaggcctta|gataatactg|gctcaatgg ctggataaat|180|
|actgattgcg|atgaaggcct|tctctctgat|ttcatttcaa|agatagcaag tgctagatgg|240|
|attccattag|ctgagtcaat|tcgacctgcg|gtgactgaca|gggataagta tcgagtaagt|300|
|tgctggttct|accaggggat|gaatatagca|atttacgcaa|atatcggtgg cgtggccaat|360|
|attatcggct|atacggaggc|cgcagtcgca|acactccttg|gtgcagttgt ggcggtagct|420|
|cctgtggtcc|ctggaactcc|aaccccctcca|aaggacaaga|gttcgcaata taaggaggtt|480|
|ccccttgccg|ttcgtctttc|cgaaacatac|cacgaagagg|gagtacgagg tctattcgac|540|
|gagctgaact|actccgagag|ccgtatgatc|tctactctaa|ggcgagcatc aaccgatgga|600|
|gtcctaatta|attcttggaa|cgatgggcag|gatacaattc|tgcttaagaa gtacaatttc|660|

```
caagacttgc aactgactgt caggagccgc attgttggga atcaaacaat aattgaagaa    720
tgcaaaatca ctgatggtag aaaaactctt tcagacgaga ctgtgtag                768
```

<210> SEQ ID NO 274
<211> LENGTH: 618
<212> TYPE: PRT
<213> ORGANISM: Pseudomonas aeruginosa

<400> SEQUENCE: 274

```
Met Ala Arg Pro Ile Ala Asp Leu Ile His Phe Asn Ser Thr Thr Val
1               5                   10                  15

Thr Ala Ser Gly Asp Val Tyr Tyr Gly Pro Gly Gly Thr Gly Ile
            20                  25                  30

Gly Pro Ile Ala Arg Pro Ile Glu His Gly Leu Asp Ser Ser Thr Glu
        35                  40                  45

Asn Gly Trp Gln Glu Phe Glu Ser Tyr Ala Asp Val Gly Val Asp Pro
    50                  55                  60

Arg Arg Tyr Val Pro Leu Gln Val Lys Glu Lys Arg Arg Glu Ile Glu
65                  70                  75                  80

Leu Gln Phe Arg Asp Ala Glu Lys Lys Leu Glu Ala Ser Val Gln Ala
                85                  90                  95

Glu Leu Asp Lys Ala Asp Ala Ala Leu Gly Pro Ala Lys Asn Leu Ala
            100                 105                 110

Pro Leu Asp Val Ile Asn Arg Ser Leu Thr Ile Val Gly Asn Ala Leu
        115                 120                 125

Gln Gln Lys Asn Gln Lys Leu Leu Asn Gln Lys Lys Ile Thr Ser
    130                 135                 140

Leu Gly Ala Lys Asn Phe Leu Thr Arg Thr Ala Glu Glu Ile Gly Glu
145                 150                 155                 160

Gln Ala Val Arg Glu Gly Asn Ile Asn Gly Pro Glu Ala Tyr Met Arg
                165                 170                 175

Phe Leu Asp Arg Glu Met Glu Gly Leu Thr Ala Ala Tyr Asn Val Lys
            180                 185                 190

Leu Phe Thr Glu Ala Ile Ser Ser Leu Gln Ile Arg Met Asn Thr Leu
        195                 200                 205

Thr Ala Ala Lys Ala Ser Ile Glu Ala Ala Ala Asn Lys Ala Arg
    210                 215                 220

Glu Gln Ala Ala Ala Glu Ala Lys Arg Lys Ala Glu Glu Gln Ala Arg
225                 230                 235                 240

Gln Gln Ala Ala Ile Arg Ala Ala Asn Thr Tyr Ala Met Pro Ala Asn
                245                 250                 255

Gly Ser Val Val Ala Thr Ala Gly Arg Gly Leu Ile Gln Val Ala
            260                 265                 270

Gln Gly Ala Ala Ser Leu Ala Gln Ala Ile Ser Asp Ala Ile Ala Val
        275                 280                 285

Leu Gly Arg Val Leu Ala Ser Ala Pro Ser Val Met Ala Val Gly Phe
    290                 295                 300

Ala Ser Leu Thr Tyr Ser Ser Arg Thr Ala Glu Gln Trp Gln Asp Gln
305                 310                 315                 320

Thr Pro Asp Ser Val Arg Tyr Ala Leu Gly Met Asp Ala Ala Lys Leu
                325                 330                 335

Gly Leu Pro Pro Ser Val Asn Leu Asn Ala Val Ala Lys Ala Ser Gly
            340                 345                 350
```

```
Thr Val Asp Leu Pro Met Arg Leu Thr Asn Glu Ala Arg Gly Asn Thr
            355                 360                 365

Thr Thr Leu Ser Val Val Ser Thr Asp Gly Val Ser Val Pro Lys Ala
        370                 375                 380

Val Pro Val Arg Met Ala Ala Tyr Asn Ala Thr Thr Gly Leu Tyr Glu
385                 390                 395                 400

Val Thr Val Pro Ser Thr Thr Ala Glu Ala Pro Pro Leu Ile Leu Thr
                405                 410                 415

Trp Thr Pro Ala Ser Pro Pro Gly Asn Gln Asn Pro Ser Ser Thr Thr
                420                 425                 430

Pro Val Val Pro Lys Pro Val Pro Val Tyr Glu Gly Ala Thr Leu Thr
                435                 440                 445

Pro Val Lys Ala Thr Pro Glu Thr Tyr Pro Gly Val Ile Thr Leu Pro
450                 455                 460

Glu Asp Leu Ile Ile Gly Phe Pro Ala Asp Ser Gly Ile Lys Pro Ile
465                 470                 475                 480

Tyr Val Met Phe Arg Asp Pro Arg Asp Val Pro Gly Ala Ala Thr Gly
                485                 490                 495

Lys Gly Gln Pro Val Ser Gly Asn Trp Leu Gly Ala Ala Ser Gln Gly
                500                 505                 510

Glu Gly Ala Pro Ile Pro Ser Gln Ile Ala Asp Lys Leu Arg Gly Lys
                515                 520                 525

Thr Phe Lys Asn Trp Arg Asp Phe Arg Glu Gln Phe Trp Ile Ala Val
        530                 535                 540

Ala Asn Asp Pro Glu Leu Ser Lys Gln Phe Asn Pro Gly Ser Leu Ala
545                 550                 555                 560

Val Met Arg Asp Gly Gly Ala Pro Tyr Val Arg Glu Ser Glu Gln Ala
                565                 570                 575

Gly Gly Arg Ile Lys Ile Glu Ile His His Lys Val Arg Val Ala Asp
                580                 585                 590

Gly Gly Gly Val Tyr Asn Met Gly Asn Leu Val Ala Val Thr Pro Lys
            595                 600                 605

Arg His Ile Glu Ile His Lys Gly Gly Lys
    610                 615

<210> SEQ ID NO 275
<211> LENGTH: 1857
<212> TYPE: DNA
<213> ORGANISM: Pseudomonas aeruginosa

<400> SEQUENCE: 275
atggcacgac ccattgctga ccttatccac ttcaactcta caactgtcac ggcaagcgga      60
gacgtttatt acggccctgg gggaggtacc ggcattggcc ccattgccag acctatagag     120
cacggcttgg attcgtccac tgaaaatggc tggcaagagt ttgaaagtta tgctgatgtg     180
ggcgttgacc ccagacgcta tgttcctctt caggttaaag aaaaacgcag ggagatcgag     240
cttcagttcc gagatgccga gaaaaaactt gaggcgtcgg tacaagccga gctggataag     300
gctgatgccg ctcttggtcc ggcaaagaat cttgcaccat ggacgtcat caaccgcagt      360 ctgaccatcg ttgaaacgc cctccagcaa agaatcaaa actactgct gaatcagaag      420 aagattacca gcctgggtgc aaagaatttc cttacccgta cggcggaaga gatcggtgaa     480
caagcggtgc gagaaggcaa tattaacggg cctgaagcct atatgcgctt cctcgacagg     540
gaaatggaag gtctcacggc agcttataac gtaaaactct tcaccgaagc gatcagtagt     600
```

-continued

```
ctccagatcc gcatgaatac gttgaccgcc gccaaagcaa gtattgaggc ggccgcagca    660
aacaaggcgc gtgaacaagc agcggctgag gccaaacgca aagccgaaga gcaggcccgc    720
cagcaagcgg cgataagagc tgccaatacc tatgccatgc cggccaatgg cagcgttgtc    780
gccaccgccg caggccgggg tctgatccag gtcgcacaag gcgccgcatc ccttgctcaa    840
gcgatctccg atgcgattgc cgtcctgggc cgggtcctgg cttcagcacc ctcggtgatg    900
gccgtgggct tgccagtct gacctactcc tcccggactg ccgagcaatg caggaccaa    960 acgcccgata gcgttcgtta cgccctgggc atggatgccg ctaaattggg gcttcccca   1020 agcgtaaacc tgaacgcggt tgcaaaagcc agcggtaccg tcgatctgcc gatgcgcctg   1080
accaacgagg cacgaggcaa cacgacgacc ctttcggtgg tcagcaccga tggtgtgagc   1140
gttccgaaag ccgttccggt ccggatggcg gcctacaatg ccacgacagg cctgtacgag   1200
gttacggttc cctctacgac cgcagaagcg ccgccactga tcctgacctg gacgccggcg   1260
agtcctccag gaaaccagaa cccttcgagt accactccgg tcgtaccgaa gccggtgccg   1320
gtatatgagg gagcgaccct tacaccggtg aaggctaccc ggaaaccta tcctggggtg   1380 attacactac cggaagacct gatcatcggc ttcccggccg actcggggat caagccgatc   1440
tatgtgatgt tcagggatcc gcgggatgta cctggtgctg cgactggcaa gggacagccc   1500
gtcagcggta attggctcgg cgccgcctct caaggtgagg gggctccaat tccaagccag   1560
attgcggata aactacgtgg taagacattc aaaaactggc gggactttcg ggaacaattc   1620
tggatagctg tggctaatga tcctgagtta agtaaacagt ttaatcctgg tagtttagct   1680
gtaatgagag atggaggggc tccttatgtc agagagtcag aacaggctgg cgggagaata   1740
aagatcgaaa tccaccacaa ggttcgagta gcagatggag gcggcgttta caatatgggg   1800
aaccttgttg cagtaacgcc aaaacgtcat atagaaatcc acaagggagg gaagtga     1857
```

<210> SEQ ID NO 276
<211> LENGTH: 689
<212> TYPE: PRT
<213> ORGANISM: Pseudomonas aeruginosa

<400> SEQUENCE: 276

```
Met Ala Val Asn Asp Tyr Glu Pro Gly Ser Met Val Ile Thr His Val
1               5                   10                  15

Gln Gly Gly Gly Arg Asp Ile Ile Gln Tyr Ile Pro Ala Arg Ser Ser
            20                  25                  30

Tyr Gly Thr Pro Pro Phe Val Pro Pro Gly Pro Ser Pro Tyr Val Gly
        35                  40                  45

Thr Gly Met Gln Glu Tyr Arg Lys Leu Arg Ser Thr Leu Asp Lys Ser
    50                  55                  60

His Ser Glu Leu Lys Lys Asn Leu Lys Asn Thr Leu Lys Glu Val
65                  70                  75                  80

Asp Glu Leu Lys Ser Glu Ala Gly Leu Pro Gly Lys Ala Val Ser Ala
                85                  90                  95

Asn Asp Ile Arg Asp Glu Lys Ser Ile Val Asp Ala Leu Met Asp Ala
            100                 105                 110

Lys Ala Lys Ser Leu Lys Ala Ile Glu Asp Arg Pro Ala Asn Leu Tyr
        115                 120                 125

Thr Ala Ser Asp Phe Pro Gln Lys Ser Glu Ser Met Tyr Gln Ser Gln
    130                 135                 140

Leu Leu Ala Ser Arg Lys Phe Tyr Gly Glu Phe Leu Asp Arg His Met
145                 150                 155                 160
```

```
Ser Glu Leu Ala Lys Ala Tyr Ser Ala Asp Ile Tyr Lys Ala Gln Ile
                165                 170                 175
Ala Ile Leu Lys Gln Thr Ser Gln Glu Leu Glu Asn Lys Ala Arg Ser
            180                 185                 190
Leu Glu Ala Glu Ala Gln Arg Ala Ala Glu Val Glu Ala Asp Tyr
        195                 200                 205
Lys Ala Arg Lys Ala Asn Val Glu Lys Val Gln Ser Glu Leu Asp
    210                 215                 220
Gln Ala Gly Asn Ala Leu Pro Gln Leu Thr Asn Pro Thr Pro Glu Gln
225                 230                 235                 240
Trp Leu Glu Arg Ala Thr Gln Leu Val Thr Gln Ala Ile Ala Asn Lys
                245                 250                 255
Lys Lys Leu Gln Thr Ala Asn Asn Ala Leu Ile Ala Lys Ala Pro Asn
                260                 265                 270
Ala Leu Glu Lys Gln Lys Ala Thr Tyr Asn Ala Asp Leu Leu Val Asp
            275                 280                 285
Glu Ile Ala Ser Leu Gln Ala Arg Leu Asp Lys Leu Asn Ala Glu Thr
    290                 295                 300
Ala Arg Arg Lys Glu Ile Ala Arg Gln Ala Ala Ile Arg Ala Ala Asn
305                 310                 315                 320
Thr Tyr Ala Met Pro Ala Asn Gly Ser Val Ala Thr Ala Ala Gly
                325                 330                 335
Arg Gly Leu Ile Gln Val Ala Gln Gly Ala Ala Ser Leu Ala Gln Ala
                340                 345                 350
Ile Ser Asp Ala Ile Ala Val Leu Gly Arg Val Leu Ala Ser Ala Pro
    355                 360                 365
Ser Val Met Ala Val Gly Phe Ala Ser Leu Thr Tyr Ser Ser Arg Thr
    370                 375                 380
Ala Glu Gln Trp Gln Asp Gln Thr Pro Asp Ser Val Arg Tyr Ala Leu
385                 390                 395                 400
Gly Met Asp Ala Ala Lys Leu Gly Leu Pro Pro Ser Val Asn Leu Asn
                405                 410                 415
Ala Val Ala Lys Ala Ser Gly Thr Val Asp Leu Pro Met Arg Leu Thr
            420                 425                 430
Asn Glu Ala Arg Gly Asn Thr Thr Thr Leu Ser Val Val Ser Thr Asp
            435                 440                 445
Gly Val Ser Val Pro Lys Ala Val Pro Val Arg Met Ala Ala Tyr Asn
    450                 455                 460
Ala Thr Thr Gly Leu Tyr Glu Val Thr Val Pro Ser Thr Thr Ala Glu
465                 470                 475                 480
Ala Pro Pro Leu Ile Leu Thr Trp Thr Pro Ala Ser Pro Gly Asn
                485                 490                 495
Gln Asn Pro Ser Ser Thr Thr Pro Val Val Pro Lys Pro Val Pro Val
            500                 505                 510
Tyr Glu Gly Ala Thr Leu Thr Pro Val Lys Ala Thr Pro Glu Thr Tyr
            515                 520                 525
Pro Gly Val Ile Thr Leu Pro Glu Asp Leu Ile Gly Phe Pro Ala
    530                 535                 540
Asp Ser Gly Ile Lys Pro Ile Tyr Val Met Phe Arg Asp Pro Arg Asp
545                 550                 555                 560
Val Pro Gly Ala Ala Thr Gly Lys Gly Gln Pro Val Ser Gly Asn Trp
                565                 570                 575
```

| | | | | | | | | | | | |
|---|---|---|---|---|---|---|---|---|---|---|---|
|Leu|Gly|Ala|Ala|Ser|Gln|Gly|Glu|Gly|Ala|Pro|Ile Pro Ser Gln Ile|
| | | |580| | | |585| | | |590|

Ala Asp Lys Leu Arg Gly Lys Thr Phe Lys Asn Trp Arg Asp Phe Arg
        595                 600                 605

Glu Gln Phe Trp Ile Ala Val Ala Asn Asp Pro Glu Leu Ser Lys Gln
    610                 615                 620

Phe Asn Pro Gly Ser Leu Ala Val Met Arg Asp Gly Ala Pro Tyr
625                 630                 635                 640

Val Arg Glu Ser Glu Gln Ala Gly Gly Arg Ile Lys Ile Glu Ile His
                645                 650                 655

His Lys Val Arg Ile Ala Asp Gly Gly Val Tyr Asn Met Gly Asn
            660                 665                 670

Leu Val Ala Val Thr Pro Lys Arg His Ile Glu Ile His Lys Gly Gly
        675                 680                 685

Lys

<210> SEQ ID NO 277
<211> LENGTH: 2070
<212> TYPE: DNA
<213> ORGANISM: Pseudomonas aeruginosa

<400> SEQUENCE: 277

```
atggctgtca atgattacga acctggttcg atggttatta cacatgtgca gggtggtggg      60
cgtgacataa tccagtatat tcctgctcga tcaagctacg gtactccacc atttgtccca     120
ccaggaccaa gtccgtatgt cggtactgga atgcaggagt acaggaagct aagaagtacg     180
cttgataagt cccattcaga actcaagaaa aacctgaaaa atgaaaccct gaaggaggtt     240
gatgaactca gagtgaagc ggggttgcca ggtaaagcgg tcagtgccaa tgacatccgc     300
gatgaaaaga gtatcgttga tgcactcatg gatgccaaag caaaatcgct aaaggccatt     360
gaggatcgcc cggccaatct ttatacggct tcagactttc ctcagaagtc agagtcgatg     420
taccagagtc agttgctggc cagccgaaaa ttctatggag agttcctgga tcgccatatg     480
agtgagctgg ccaaagcgta cagcgccgat atctataagg cgcaaatcgc tatcttgaaa     540
caaacgtctc aagagctgga gaataaagcc cggtcattgg aagcagaagc ccagcgagcc     600
gctgctgagg tggaggcgga ctacaaggcc aggaaggcaa atgtcgagaa aaaagtgcag     660
tccgagcttg accaggctgg gaatgctttg cctcaactga ccaatccaac gccagagcag     720
tggcttgaac gcgctactca actggttacg caggcgatcg ccaataagaa gaaattgcag     780
actgcaaaca tgccttgat tgccaaggca cccaatgcac tggagaaaca aaaggcaacc     840
tacaacgccg atctcctagt ggatgaaatc gccagcctgc aagcacggct ggacaagctg     900
aacgccgaaa cggcaaggcg caaggaaatc gctcgtcaag cggcgatcag ggctgccaat     960
acttatgcca tgccagccaa tggcagcgtt gtcgccaccg ccgcaggccg gggtctgatc    1020
caggtcgcac aaggcgccgc atcccttgct caagcgatct ccgatgcgat tgccgtcctg    1080
ggccgggtcc tggcttcagc accctcggtg atggccgtgg ctttgccag tctgacctac    1140
tcctcccgga ctgccgagca atggcaggac caaacgcccg atagcgttcg ttacgccctg    1200
ggcatggatg ccgctaaatt ggggcttccc ccaagcgtaa acctgaacgc ggttgcaaaa    1260
gccagcggta ccgtcgatct gccgatgcgc ctgaccaacg aggcacgagg caacacgacg    1320
acccttt cgg tggtcagcac cgatggtgtg agcgttccga aagccgttcc ggtccggatg    1380
gcggcctaca tgccacgac aggcctgtac gaggttacgg ttccctctac gaccgcagaa    1440
```

```
gcgccgccac tgatcctgac ctggacgccg gcgagtcctc caggaaacca gaaccttcg      1500 agtaccactc cggtcgtacc gaagccggtg ccggtatatg agggagcgac ccttacaccg     1560
gtgaaggcta ccccggaaac ctatcctggg gtgattacac taccggaaga cctgatcatc    1620
ggcttcccgg ccgactcggg gatcaagccg atctatgtga tgttcaggga tccgcgggat    1680
gtacctggtg ctgcgactgg caagggacag cccgtcagcg gtaattggct cggcgccgcc    1740
tctcaaggtg aggggctcc aattccaagc cagattgcgg ataaactacg tggtaagaca     1800
ttcaaaaact ggcgggactt tcgggaacaa ttctggatag ctgtggctaa tgatcctgag    1860
ttaagtaaac agtttaatcc tggtagttta gctgtaatga gagatggagg ggctccttat    1920
gtcagagagt cagaacaggc tggcgggaga ataaagatcg aaatccacca caaggttcga    1980
atagcagatg gaggcggcgt ttacaatatg gggaaccttg ttgcagtaac gccaaaacgt    2040
catatagaaa tccacaaggg agggaagtga                                     2070

<210> SEQ ID NO 278
<211> LENGTH: 47
<212> TYPE: PRT
<213> ORGANISM: Ruminococcus gnavus

<400> SEQUENCE: 278

Met Arg Asn Asp Val Leu Thr Leu Thr Asn Pro Met Glu Glu Lys Glu
1               5                   10                  15

Leu Glu Gln Ile Leu Gly Gly Gly Asn Gly Val Leu Lys Thr Ile Ser
            20                  25                  30

His Glu Cys Asn Met Asn Thr Trp Gln Phe Leu Phe Thr Cys Cys
        35                  40                  45

<210> SEQ ID NO 279
<211> LENGTH: 144
<212> TYPE: DNA
<213> ORGANISM: Ruminococcus gnavus

<400> SEQUENCE: 279
atgagaaatg acgtattaac attaacaaac ccaatggaag agaacgaact ggagcagatc      60
ttaggtggtg gcaatggtgt gttaaaaacg attagccacg aatgcaatat gaacacatgg     120
cagttcctgt ttacttgttg ctaa                                           144

<210> SEQ ID NO 280
<211> LENGTH: 55
<212> TYPE: PRT
<213> ORGANISM: Lactobacillus sakei

<400> SEQUENCE: 280

Met Lys Asn Ala Lys Ser Leu Thr Ile Gln Glu Met Lys Ser Ile Thr
1               5                   10                  15

Gly Gly Lys Tyr Tyr Gly Asn Gly Val Ser Cys Asn Ser His Gly Cys
            20                  25                  30

Ser Val Asn Trp Gly Gln Ala Trp Thr Cys Gly Val Asn His Leu Ala
        35                  40                  45

Asn Gly Gly His Gly Val Cys
    50                  55

<210> SEQ ID NO 281
<211> LENGTH: 168
<212> TYPE: DNA
<213> ORGANISM: Lactobacillus sakei
```

<400> SEQUENCE: 281

```
atgaaaaacg caaaaagcct aacaattcaa gaaatgaaat ctattacagg tggtaaatac    60
tatggtaatg cgttagctg taactctcac ggctgttcag taaattgggg gcaagcatgg   120
acttgtggag taaaccatct agctaatggc ggtcatggag tttgttaa              168
```

<210> SEQ ID NO 282
<211> LENGTH: 59
<212> TYPE: PRT
<213> ORGANISM: Lactobacillus sakei

<400> SEQUENCE: 282

```
Met Asn Asn Val Lys Glu Leu Ser Met Thr Glu Leu Gln Thr Ile Thr
1               5                   10                  15

Gly Gly Ala Arg Ser Tyr Gly Asn Gly Val Tyr Cys Asn Asn Lys Lys
            20                  25                  30

Cys Trp Val Asn Arg Gly Glu Ala Thr Gln Ser Ile Ile Gly Gly Met
        35                  40                  45

Ile Ser Gly Trp Ala Ser Gly Leu Ala Gly Met
    50                  55
```

<210> SEQ ID NO 283
<211> LENGTH: 180
<212> TYPE: DNA
<213> ORGANISM: Lactobacillus sakei

<400> SEQUENCE: 283

```
atgaataatg taaagaatt aagtatgaca gaattacaaa caattaccgg cggtgctaga    60
tcatatggca acggtgttta ctgtaataat aaaaaatgtt gggtaaatcg gggtgaagca   120
acgcaaagta ttattggtgg tatgattagc ggctgggcta gtggtttagc tggaatgtaa   180
```

<210> SEQ ID NO 284
<211> LENGTH: 61
<212> TYPE: PRT
<213> ORGANISM: Lactobacillus sakei

<400> SEQUENCE: 284

```
Met Glu Lys Phe Ile Glu Leu Ser Leu Lys Glu Val Thr Ala Ile Thr
1               5                   10                  15

Gly Gly Lys Tyr Tyr Gly Asn Gly Val His Cys Gly Lys His Ser Cys
            20                  25                  30

Thr Val Asp Trp Gly Thr Ala Ile Gly Asn Ile Gly Asn Asn Ala Ala
        35                  40                  45

Ala Asn Trp Ala Thr Gly Gly Asn Ala Gly Trp Asn Lys
    50                  55                  60
```

<210> SEQ ID NO 285
<211> LENGTH: 186
<212> TYPE: DNA
<213> ORGANISM: Lactobacillus sakei

<400> SEQUENCE: 285

```
atggaaaagt ttattgaatt atctttaaaa gaagtaacag caattacagg tggaaaatat    60
tatggtaacg gtgtacactg tggaaaacat tcatgtaccg tagactgggg aacagctatt   120
ggaaatatcg aaaataatgc agctgcaaac tgggccacag gcggaaacgc tggctggaat   180
aaataa                                                               186
```

-continued

<210> SEQ ID NO 286
<211> LENGTH: 56
<212> TYPE: PRT
<213> ORGANISM: Streptococcus salivarius

<400> SEQUENCE: 286

Met Lys Ser Thr Asn Asn Gln Ser Ile Ala Glu Ile Ala Ala Val Asn
1               5                   10                  15

Ser Leu Gln Glu Val Ser Met Glu Glu Leu Asp Gln Ile Ile Gly Ala
            20                  25                  30

Gly Asn Gly Val Val Leu Thr Leu Thr His Glu Cys Asn Leu Ala Thr
        35                  40                  45

Trp Thr Lys Lys Leu Lys Cys Cys
    50                  55

<210> SEQ ID NO 287
<211> LENGTH: 171
<212> TYPE: DNA
<213> ORGANISM: Streptococcus salivarius

<400> SEQUENCE: 287
atgaaatcaa caaataatca aagtatcgca gaaattgcag cagtaaactc actacaagaa      60
gtaagtatgg aggaactaga ccaaattatt ggtgccggaa acggagtggt tcttactctt     120
actcatgaat gtaacctagc aacttggaca aaaaaactaa atgttgcta a               171

<210> SEQ ID NO 288
<211> LENGTH: 51
<212> TYPE: PRT
<213> ORGANISM: Streptococcus pyogenes serotype M28

<400> SEQUENCE: 288

Met Ser Phe Met Lys Asn Ser Lys Asp Ile Leu Thr Asn Ala Ile Glu
1               5                   10                  15

Glu Val Ser Glu Lys Glu Leu Met Glu Val Ala Gly Gly Lys Lys Gly
            20                  25                  30

Ser Gly Trp Phe Ala Thr Ile Thr Asp Asp Cys Pro Asn Ser Val Phe
        35                  40                  45

Val Cys Cys
    50

<210> SEQ ID NO 289
<211> LENGTH: 156
<212> TYPE: DNA
<213> ORGANISM: Streptococcus pyogenes serotype M28

<400> SEQUENCE: 289
atgagtttta tgaaaaattc aaaggatatt ttgactaatg ctatcgaaga agttctgaa       60 aaagaactta tggaagtagc tggtggtaaa aaaggttccg gttggtttgc aactattact    120
gatgactgtc cgaactcagt attcgtttgt tgttaa                              156

<210> SEQ ID NO 290
<211> LENGTH: 48
<212> TYPE: PRT
<213> ORGANISM: Streptococcus salivarius

<400> SEQUENCE: 290

Met Lys Asn Ser Lys Asp Val Leu Asn Asn Ala Ile Glu Glu Val Ser
1               5                   10                  15

Glu Lys Glu Leu Met Glu Val Ala Gly Gly Lys Lys Gly Pro Gly Trp

Ile Ala Thr Ile Thr Asp Asp Cys Pro Asn Ser Ile Phe Val Cys Cys
            35                  40                  45

<210> SEQ ID NO 291
<211> LENGTH: 147
<212> TYPE: DNA
<213> ORGANISM: Streptococcus salivarius

<400> SEQUENCE: 291
atgaaaaact caaagatgt tttgaacaat gctatcgaag aggtttctga aaaagaactt    60
atggaagtag ctggtggtaa aaaaggtcca ggttggattg caactattac tgatgactgt   120
ccaaactcaa tattcgtttg ttgttaa                                       147

<210> SEQ ID NO 292
<211> LENGTH: 48
<212> TYPE: PRT
<213> ORGANISM: Streptococcus salivarius

<400> SEQUENCE: 292

Met Lys Asn Ser Lys Asp Ile Leu Asn Asn Ala Ile Glu Glu Val Ser
1               5                   10                  15

Glu Lys Glu Leu Met Glu Val Ala Gly Gly Lys Arg Gly Ser Gly Trp
            20                  25                  30

Ile Ala Thr Ile Thr Asp Asp Cys Pro Asn Ser Val Phe Val Cys Cys
            35                  40                  45

<210> SEQ ID NO 293
<211> LENGTH: 147
<212> TYPE: DNA
<213> ORGANISM: Streptococcus salivarius

<400> SEQUENCE: 293
atgaaaaact caaagatat tttgaacaat gctatcgaag aagtttctga aaaagaactt    60
atggaagtag ctggtggtaa aagaggttca ggttggattg caactattac tgatgactgt   120
ccaaactcag tattcgtttg ttgttaa                                       147

<210> SEQ ID NO 294
<211> LENGTH: 62
<212> TYPE: PRT
<213> ORGANISM: Staphylococcus aureus

<400> SEQUENCE: 294

Met Lys Ser Ser Phe Leu Glu Lys Asp Ile Glu Glu Gln Val Thr Trp
1               5                   10                  15

Phe Glu Glu Val Ser Glu Gln Glu Phe Asp Asp Asp Ile Phe Gly Ala
            20                  25                  30

Cys Ser Thr Asn Thr Phe Ser Leu Ser Asp Tyr Trp Gly Asn Lys Gly
            35                  40                  45

Asn Trp Cys Thr Ala Thr His Glu Cys Met Ser Trp Cys Lys
            50                  55                  60

<210> SEQ ID NO 295
<211> LENGTH: 189
<212> TYPE: DNA
<213> ORGANISM: Staphylococcus aureus

<400> SEQUENCE: 295
atgaaaagtt cttttttaga aaaagatata gaagaacaag tgacatggtt cgaggaagtt    60

```
tcagaacaag aatttgacga tgatattttt ggagcttgta gtacaaacac ttttctttg      120 agtgactatt ggggtaataa aggaaattgg tgtactgcta ctcacgaatg tatgtcttgg    180
tgtaaataa                                                             189
```

<210> SEQ ID NO 296
<211> LENGTH: 67
<212> TYPE: PRT
<213> ORGANISM: Staphylococcus aureus

<400> SEQUENCE: 296

```
Met Lys Asn Glu Leu Gly Lys Phe Leu Glu Glu Asn Glu Leu Glu Leu
1               5                   10                  15

Gly Lys Phe Ser Glu Ser Asp Met Leu Glu Ile Thr Asp Asp Glu Val
            20                  25                  30

Tyr Ala Ala Gly Thr Pro Leu Ala Leu Leu Gly Gly Ala Ala Thr Gly
        35                  40                  45

Val Ile Gly Tyr Ile Ser Asn Gln Thr Cys Pro Thr Thr Ala Cys Thr
    50                  55                  60

Arg Ala Cys
65
```

<210> SEQ ID NO 297
<211> LENGTH: 204
<212> TYPE: DNA
<213> ORGANISM: Staphylococcus aureus

<400> SEQUENCE: 297

```
atgaaaaatg aattaggtaa gttttagaa gaaaacgaat tagagttagg taaattttca     60
gaatcagaca tgctagaaat tactgatgat gaagtatatg cagctggaac acctttagcc   120
ttattgggtg gagctgccac cggggtgata ggttatattt ctaaccaaac atgtccaaca   180
actgcttgta cacgcgcttg ctag                                           204
```

<210> SEQ ID NO 298
<211> LENGTH: 46
<212> TYPE: PRT
<213> ORGANISM: Streptococcus pyogenes

<400> SEQUENCE: 298

```
Met Asn Asn Thr Ile Lys Asp Phe Asp Leu Asp Leu Lys Thr Asn Lys
1               5                   10                  15

Lys Asp Thr Ala Thr Pro Tyr Val Gly Ser Arg Tyr Leu Cys Thr Pro
            20                  25                  30

Gly Ser Cys Trp Lys Leu Val Cys Phe Thr Thr Thr Val Lys
        35                  40                  45
```

<210> SEQ ID NO 299
<211> LENGTH: 141
<212> TYPE: DNA
<213> ORGANISM: Streptococcus pyogenes

<400> SEQUENCE: 299

```
atgaataaca caattaaaga ctttgatctc gattgaaaa caaataaaaa agacactgct     60
acaccttatg ttggtagccg ttacctatgt acccctggtt cttgttggaa attagtttgc   120
tttacaacaa ctgttaaata a                                              141
```

<210> SEQ ID NO 300

```
<211> LENGTH: 51
<212> TYPE: PRT
<213> ORGANISM: Streptococcus pyogenes

<400> SEQUENCE: 300

Met Gln Lys Asn Asn Glu Val Ile Asn Ser Ile Gln Glu Val Ser Leu
1               5                   10                  15

Glu Glu Leu Asp Gln Ile Ile Gly Ala Gly Lys Asn Gly Val Phe Lys
            20                  25                  30

Thr Ile Ser His Glu Cys His Leu Asn Thr Trp Ala Phe Leu Ala Thr
        35                  40                  45

Cys Cys Ser
    50

<210> SEQ ID NO 301
<211> LENGTH: 156
<212> TYPE: DNA
<213> ORGANISM: Streptococcus pyogenes

<400> SEQUENCE: 301
atggaaaaaa ataatgaagt aatcaactct attcaagaag ttagtcttga agaactcgat      60
caaattatcg gtgctggaaa aaatggtgtg tttaaaacaa tttctcatga gtgtcatttg     120
aatacatggg cattccttgc tacttgttgt tcataa                              156

<210> SEQ ID NO 302
<211> LENGTH: 51
<212> TYPE: PRT
<213> ORGANISM: Streptococcus pyogenes serotype M49

<400> SEQUENCE: 302

Met Thr Lys Glu His Glu Ile Ile Asn Ser Ile Gln Glu Val Ser Leu
1               5                   10                  15

Glu Glu Leu Asp Gln Ile Ile Gly Ala Gly Lys Asn Gly Val Phe Lys
            20                  25                  30

Thr Ile Ser His Glu Cys His Leu Asn Thr Trp Ala Phe Leu Ala Thr
        35                  40                  45

Cys Cys Ser
    50

<210> SEQ ID NO 303
<211> LENGTH: 156
<212> TYPE: DNA
<213> ORGANISM: Streptococcus pyogenes serotype M49

<400> SEQUENCE: 303
atggaaaaaa ataatgaagt aatcaactct attcaagaag ttagtcttga agaactcgat      60
caaattatcg gtgctggaaa aaatggtgtg tttaaaacaa tttctcatga gtgtcatttg     120
aatacatggg cattccttgc tacttgttgc tcataa                              156

<210> SEQ ID NO 304
<211> LENGTH: 56
<212> TYPE: PRT
<213> ORGANISM: Bacillus subtilis

<400> SEQUENCE: 304

Met Glu Lys Leu Phe Lys Glu Val Lys Leu Glu Glu Leu Glu Asn Gln
1               5                   10                  15

Lys Gly Ser Gly Leu Gly Lys Ala Gln Cys Ala Ala Leu Trp Leu Gln
            20                  25                  30
```

Cys Ala Ser Gly Gly Thr Ile Gly Cys Gly Gly Ala Val Ala Cys
        35                  40                  45

Gln Asn Tyr Arg Gln Phe Cys Arg
    50                  55

<210> SEQ ID NO 305
<211> LENGTH: 171
<212> TYPE: DNA
<213> ORGANISM: Bacillus subtilis

<400> SEQUENCE: 305
atggaaaagc tatttaaaga agttaaacta gaggaactcg aaaaccaaaa aggtagtgga      60
ttaggaaaag ctcagtgtgc tgcgttgtgg ctacaatgtg ctagtggcgg tacaattggt     120
tgtggtggcg gagctgttgc ttgtcaaaac tatcgtcaat tctgcagata a              171

<210> SEQ ID NO 306
<211> LENGTH: 56
<212> TYPE: PRT
<213> ORGANISM: Bacillus subtilis

<400> SEQUENCE: 306

Met Ser Lys Phe Asp Asp Phe Asp Leu Asp Val Val Lys Val Ser Lys
1               5                   10                  15

Gln Asp Ser Lys Ile Thr Pro Gln Trp Lys Ser Glu Ser Leu Cys Thr
            20                  25                  30

Pro Gly Cys Val Thr Gly Ala Leu Gln Thr Cys Phe Leu Gln Thr Leu
        35                  40                  45

Thr Cys Asn Cys Lys Ile Ser Lys
    50                  55

<210> SEQ ID NO 307
<211> LENGTH: 171
<212> TYPE: DNA
<213> ORGANISM: Bacillus subtilis

<400> SEQUENCE: 307
atgtcaaagt tcgatgattt cgatttggat gttgtgaaag tctctaaaca agactcaaaa      60
atcactccgc aatggaaaag tgaatcactt tgtacaccag atgtgtaac tggtgcattg     120 caaacttgct tccttcaaac actaacttgt aactgcaaaa tctctaaata a              171

<210> SEQ ID NO 308
<211> LENGTH: 50
<212> TYPE: PRT
<213> ORGANISM: Bacillus subtilis

<400> SEQUENCE: 308

Met Lys Leu Pro Val Gln Gln Val Tyr Ser Val Tyr Gly Gly Lys Asp
1               5                   10                  15

Leu Pro Lys Gly His Ser His Ser Thr Met Pro Phe Leu Ser Lys Leu
            20                  25                  30

Gln Phe Leu Thr Lys Ile Tyr Leu Leu Asp Ile His Thr Gln Pro Phe
        35                  40                  45

Phe Ile
    50

<210> SEQ ID NO 309
<211> LENGTH: 153
<212> TYPE: DNA

<213> ORGANISM: Bacillus subtilis

<400> SEQUENCE: 309

```
ttgaaattgc cggtgcaaca ggtctattcg gtctatgggg gtaaggatct cccaaaaggg      60
catagtcatt ctactatgcc cttttttaagt aaattacaat ttttaactaa aatctacctc    120
ttggatatac atacacaacc gttttttcatt tga                                 153
```

<210> SEQ ID NO 310
<211> LENGTH: 43
<212> TYPE: PRT
<213> ORGANISM: Bacillus subtilis

<400> SEQUENCE: 310

```
Met Lys Lys Ala Val Ile Val Glu Asn Lys Gly Cys Ala Thr Cys Ser
1               5                   10                  15
Ile Gly Ala Ala Cys Leu Val Asp Gly Pro Ile Pro Asp Phe Glu Ile
            20                  25                  30
Ala Gly Ala Thr Gly Leu Phe Gly Leu Trp Gly
        35                  40
```

<210> SEQ ID NO 311
<211> LENGTH: 132
<212> TYPE: DNA
<213> ORGANISM: Bacillus subtilis

<400> SEQUENCE: 311

```
atgaaaaaag ctgtcattgt agaaaacaaa ggttgtgcaa catgctcgat cggagccgct      60
tgtctagtgg acggtcctat ccctgatttt gaaattgccg gtgcaacagg tctattcggt    120
ctatggggt aa                                                          132
```

<210> SEQ ID NO 312
<211> LENGTH: 58
<212> TYPE: PRT
<213> ORGANISM: Streptococcus thermophilus

<400> SEQUENCE: 312

```
Met Met Asn Ala Thr Glu Asn Gln Ile Phe Val Glu Thr Val Ser Asp
1               5                   10                  15
Gln Glu Leu Glu Met Leu Ile Gly Gly Ala Asp Arg Gly Trp Ile Lys
            20                  25                  30
Thr Leu Thr Lys Asp Cys Pro Asn Val Ile Ser Ser Ile Cys Ala Gly
        35                  40                  45
Thr Ile Ile Thr Ala Cys Lys Asn Cys Ala
    50                  55
```

<210> SEQ ID NO 313
<211> LENGTH: 177
<212> TYPE: DNA
<213> ORGANISM: Streptococcus thermophilus

<400> SEQUENCE: 313

```
atgatgaatg ctactgaaaa ccaaattttt gttgagactg tgagtgacca agaattagaa      60
atgttaattg gtggtgcaga tcgtggatgg attaagactt taacaaaaga ttgtccaaat    120
gtaatttctt caatttgtgc aggtacaatt attacagcct gtaaaaattg tgcttaa       177
```

<210> SEQ ID NO 314
<211> LENGTH: 64
<212> TYPE: PRT

<213> ORGANISM: Streptococcus thermophilus

<400> SEQUENCE: 314

Met Lys Gln Tyr Asn Gly Phe Glu Val Leu His Glu Leu Asp Leu Ala
1               5                   10                  15

Asn Val Thr Gly Gly Gln Ile Asn Trp Gly Ser Val Val Gly His Cys
            20                  25                  30

Ile Gly Gly Ala Ile Ile Gly Gly Ala Phe Ser Gly Gly Ala Ala Ala
        35                  40                  45

Gly Val Gly Cys Leu Val Gly Ser Gly Lys Ala Ile Ile Asn Gly Leu
    50                  55                  60

<210> SEQ ID NO 315
<211> LENGTH: 195
<212> TYPE: DNA
<213> ORGANISM: Streptococcus thermophilus

<400> SEQUENCE: 315
atgaagcagt ataatggttt tgaggttcta catgaacttg acttagcaaa tgtaactggc      60
ggtcaaatta attggggatc agttgtagga cactgtatag gtggagctat tatcggaggt    120
gcattttcag gaggtgcagc ggctggagta ggatgccttg ttgggagcgg aaaggcaatc    180
ataaatggat ataa                                                      195

<210> SEQ ID NO 316
<211> LENGTH: 85
<212> TYPE: PRT
<213> ORGANISM: Streptococcus thermophilus

<400> SEQUENCE: 316

Met Asn Thr Ile Thr Ile Cys Lys Phe Asp Val Leu Asp Ala Glu Leu
1               5                   10                  15

Leu Ser Thr Val Glu Gly Gly Tyr Ser Gly Lys Asp Cys Leu Lys Asp
            20                  25                  30

Met Gly Gly Tyr Ala Leu Ala Gly Ala Gly Ser Gly Ala Leu Trp Gly
        35                  40                  45

Ala Pro Ala Gly Gly Val Gly Ala Leu Pro Gly Ala Phe Val Gly Ala
    50                  55                  60

His Val Gly Ala Ile Ala Gly Gly Phe Ala Cys Met Gly Gly Met Ile
65                  70                  75                  80

Gly Asn Lys Phe Asn
                85

<210> SEQ ID NO 317
<211> LENGTH: 258
<212> TYPE: DNA
<213> ORGANISM: Streptococcus thermophilus

<400> SEQUENCE: 317
atgaatacaa taactatttg taaatttgat gttttagatg ctgaacttct ttcgacagtt      60
gagggtggat actctggtaa ggattgttta aaagacatgg gaggatatgc attggcagga    120
gctggaagtg gagctctgtg gggagctcca gcaggaggtg ttggagcact tccaggtgca    180
tttgtcggag ctcatgttgg ggcaattgca ggaggctttg catgtatggg tggaatgatt    240
ggtaataagt ttaactaa                                                  258

<210> SEQ ID NO 318
<211> LENGTH: 52

<212> TYPE: PRT
<213> ORGANISM: Bacillus cereus

<400> SEQUENCE: 318

```
Met Ser Glu Ile Lys Lys Ala Leu Asn Thr Leu Glu Ile Glu Asp Phe
1               5                   10                  15

Asp Ala Ile Glu Met Val Asp Val Asp Ala Met Pro Glu Asn Glu Ala
            20                  25                  30

Leu Glu Ile Met Gly Ala Ser Cys Thr Thr Cys Val Cys Thr Cys Ser
        35                  40                  45

Cys Cys Thr Thr
    50
```

<210> SEQ ID NO 319
<211> LENGTH: 159
<212> TYPE: DNA
<213> ORGANISM: Bacillus cereus

<400> SEQUENCE: 319

```
atgagtgaaa ttaaaaaagc attaaatacg cttgaaattg aagattttga tgcaattgaa     60
atggttgatg ttgatgctat gccagaaaac gaagcgcttg aaattatggg agcgtcatgt    120
acgacatgcg tatgtacatg cagttgttgt acaacttga                           159
```

<210> SEQ ID NO 320
<211> LENGTH: 47
<212> TYPE: PRT
<213> ORGANISM: Bacillus cereus

<400> SEQUENCE: 320

```
Met Glu Val Met Asn Asn Ala Leu Ile Thr Lys Val Asp Glu Glu Ile
1               5                   10                  15

Gly Gly Asn Ala Ala Cys Val Ile Gly Cys Ile Gly Ser Cys Val Ile
            20                  25                  30

Ser Glu Gly Ile Gly Ser Leu Val Gly Thr Ala Phe Thr Leu Gly
        35                  40                  45
```

<210> SEQ ID NO 321
<211> LENGTH: 144
<212> TYPE: DNA
<213> ORGANISM: Bacillus cereus

<400> SEQUENCE: 321

```
atggaagtta tgaacaatgc tttaattaca aaagtagatg aggagattgg aggaaacgct     60
gcttgtgtaa ttggttgtat tggcagttgc gtaattagtg aaggaattgg ttcacttgta    120
ggaacagcat ttactttagg ttaa                                           144
```

<210> SEQ ID NO 322
<211> LENGTH: 49
<212> TYPE: PRT
<213> ORGANISM: Bacillus cereus

<400> SEQUENCE: 322

```
Met Glu Val Leu Asn Lys Gln Asn Val Asn Ile Ile Pro Glu Ser Glu
1               5                   10                  15

Glu Val Gly Gly Trp Val Ala Cys Val Gly Ala Cys Gly Thr Val Cys
            20                  25                  30

Leu Ala Ser Gly Gly Val Gly Thr Glu Phe Ala Ala Ala Ser Tyr Phe
        35                  40                  45
```

Leu

<210> SEQ ID NO 323
<211> LENGTH: 150
<212> TYPE: DNA
<213> ORGANISM: Bacillus cereus

<400> SEQUENCE: 323
atggaagttt taaacaaaca aaatgtaaat attattccag aatctgaaga agtaggtgga 60
tgggtagcat gtgttggagc atgtggtaca gtatgtcttg ctagtggtgg tgttggaaca 120
gagtttgcag ctgcatctta tttcctataa 150

<210> SEQ ID NO 324
<211> LENGTH: 40
<212> TYPE: PRT
<213> ORGANISM: Bacillus thuringiensis

<400> SEQUENCE: 324

Met Glu Thr Pro Val Val Gln Pro Arg Asp Trp Thr Cys Trp Ser Cys
1 5 10 15

Leu Val Cys Ala Ala Cys Ser Val Glu Leu Leu Asn Leu Val Thr Ala
20 25 30

Ala Thr Gly Ala Ser Thr Ala Ser
35 40

<210> SEQ ID NO 325
<211> LENGTH: 123
<212> TYPE: DNA
<213> ORGANISM: Bacillus thuringiensis

<400> SEQUENCE: 325
atggaaacac cagtagtaca accaagggat tggacttgtt ggagttgctt agtatgtgca 60
gcatgttctg tggaattatt aaatttagtt actgcggcaa caggggctag tactgcaagc 120
taa 123

<210> SEQ ID NO 326
<211> LENGTH: 42
<212> TYPE: PRT
<213> ORGANISM: Rhizobium leguminosarum bv. trifolii

<400> SEQUENCE: 326

Met Asp Asn Lys Val Ala Lys Asn Val Glu Val Lys Lys Gly Ser Ile
1 5 10 15

Lys Ala Thr Phe Lys Ala Ala Val Leu Lys Ser Lys Thr Lys Val Asp
20 25 30

Ile Gly Gly Ser Arg Gln Gly Cys Val Ala
35 40

<210> SEQ ID NO 327
<211> LENGTH: 129
<212> TYPE: DNA
<213> ORGANISM: Rhizobium leguminosarum bv. trifolii

<400> SEQUENCE: 327
atggataaca aggttgcgaa gaatgtcgaa gtgaagaagg gctccatcaa ggcgaccttc 60
aaggctgctg ttctgaagtc gaagacgaag gtcgacatcg gaggtagccg tcagggctgc 120
gtcgcttaa 129

```
<210> SEQ ID NO 328
<211> LENGTH: 70
<212> TYPE: PRT
<213> ORGANISM: Streptococcus uberis

<400> SEQUENCE: 328

Met Asn Thr Ile Glu Lys Phe Glu Asn Ile Lys Leu Phe Ser Leu Lys
1               5                   10                  15

Lys Ile Ile Gly Gly Lys Thr Val Asn Tyr Gly Asn Gly Leu Tyr Cys
            20                  25                  30

Asn Gln Lys Lys Cys Trp Val Asn Trp Ser Glu Thr Ala Thr Thr Ile
        35                  40                  45

Val Asn Asn Ser Ile Met Asn Gly Leu Thr Gly Gly Asn Ala Gly Trp
    50                  55                  60

His Ser Gly Gly Arg Ala
65                  70

<210> SEQ ID NO 329
<211> LENGTH: 213
<212> TYPE: DNA
<213> ORGANISM: Streptococcus uberis

<400> SEQUENCE: 329
atgaatacaa ttgaaaaatt tgaaaatatt aaacttttttt cactaaagaa aattatcggt      60
ggcaaaactg taaattatgg taatggcctt tattgtaacc aaaaaaaatg ctgggtaaac     120
tggtcagaaa ctgctacaac aatagtaaat aattccatca tgaacgggct cacaggtggt     180
aatgcgggtt ggcactcagg cgggagagca taa                                  213

<210> SEQ ID NO 330
<211> LENGTH: 76
<212> TYPE: PRT
<213> ORGANISM: Streptococcus uberis

<400> SEQUENCE: 330

Met Asp Ile Leu Leu Glu Leu Ala Gly Tyr Thr Gly Ile Ala Ser Gly
1               5                   10                  15

Thr Ala Lys Lys Val Val Asp Ala Ile Asp Lys Gly Ala Ala Ala Phe
            20                  25                  30

Val Ile Ile Ser Ile Ile Ser Thr Val Ile Ser Ala Gly Ala Leu Gly
        35                  40                  45

Ala Val Ser Ala Ser Ala Asp Phe Ile Ile Leu Thr Val Lys Asn Tyr
    50                  55                  60

Ile Ser Arg Asn Leu Lys Ala Gln Ala Val Ile Trp
65                  70                  75

<210> SEQ ID NO 331
<211> LENGTH: 231
<212> TYPE: DNA
<213> ORGANISM: Streptococcus uberis

<400> SEQUENCE: 331
atggacattt tattagaact cgcaggatat actgggatag cctcaggtac tgcaaaaaaa      60
gttgttgatg ccattgataa aggagctgca gcctttgtta ttatttcaat tatctcaaca     120
gtaattagtg cgggagcatt gggagcagtt tcagcctcag ctgatttat tatttttaact     180 gtaaaaaatt acattagtag aaatttaaaa gcacaagctg tcatttggta a              231

<210> SEQ ID NO 332
```

```
<211> LENGTH: 64
<212> TYPE: PRT
<213> ORGANISM: Clostridium perfringens

<400> SEQUENCE: 332

Met Asp Ser Glu Leu Phe Lys Leu Met Ala Thr Gln Gly Ala Phe Ala
1               5                   10                  15

Ile Leu Phe Ser Tyr Leu Leu Phe Tyr Val Leu Lys Glu Asn Ser Lys
            20                  25                  30

Arg Glu Asp Lys Tyr Gln Asn Ile Ile Glu Glu Leu Thr Glu Leu Leu
        35                  40                  45

Pro Lys Ile Lys Glu Asp Val Glu Asp Ile Lys Glu Lys Leu Asn Lys
    50                  55                  60

<210> SEQ ID NO 333
<211> LENGTH: 195
<212> TYPE: DNA
<213> ORGANISM: Clostridium perfringens

<400> SEQUENCE: 333
atggatagtg aattatttaa gttaatggca acacaaggag cctttgcaat attattttcg      60
tatttattgt tttatgtttt aaaagagaat agtaaaagaa agataagta tcaaaatata     120 atagaggagc ttacagaatt attgccaaaa ataaaagaag atgtagaaga tataaaagaa     180
aaacttaata aatag                                                     195

<210> SEQ ID NO 334
<211> LENGTH: 47
<212> TYPE: PRT
<213> ORGANISM: Micrococcus varians

<400> SEQUENCE: 334

Met Thr Asn Ala Phe Gln Ala Leu Asp Glu Val Thr Asp Ala Glu Leu
1               5                   10                  15

Asp Ala Ile Leu Gly Gly Gly Ser Gly Val Ile Pro Thr Ile Ser His
            20                  25                  30

Glu Cys His Met Asn Ser Phe Gln Phe Val Phe Thr Cys Cys Ser
        35                  40                  45

<210> SEQ ID NO 335
<211> LENGTH: 144
<212> TYPE: DNA
<213> ORGANISM: Micrococcus varians

<400> SEQUENCE: 335
atgacgaacg catttcaggc actggacgaa gtcacggacg ccgagctcga cgccatcctt      60
ggcgggggca gtggtgttat tcccacgatc agccacgagt gccacatgaa ctccttccag     120
ttcgtgttca cctgctgctc ctga                                            144

<210> SEQ ID NO 336
<211> LENGTH: 285
<212> TYPE: PRT
<213> ORGANISM: Streptococcus equi subsp. zooepidemicus

<400> SEQUENCE: 336

Met Lys Arg Ile Phe Phe Ala Phe Leu Ser Leu Cys Leu Phe Ile Phe
1               5                   10                  15

Gly Thr Gln Thr Val Ser Ala Ala Thr Tyr Thr Arg Pro Leu Asp Thr
            20                  25                  30
```

Gly Asn Ile Thr Thr Gly Phe Asn Gly Tyr Pro Gly His Val Gly Val
                35                  40                  45

Asp Tyr Ala Val Pro Val Gly Thr Pro Val Arg Ala Val Ala Asn Gly
 50                  55                  60

Thr Val Lys Phe Ala Gly Asn Gly Ala Asn His Pro Trp Met Leu Trp
65                  70                  75                  80

Met Ala Gly Asn Cys Val Leu Ile Gln His Ala Asp Gly Met His Thr
                85                  90                  95

Gly Tyr Ala His Leu Ser Lys Ile Ser Val Ser Thr Asp Ser Thr Val
                100                 105                 110

Lys Gln Gly Gln Ile Ile Gly Tyr Thr Gly Ala Thr Gly Gln Val Thr
                115                 120                 125

Gly Pro His Leu His Phe Glu Met Leu Pro Ala Asn Pro Asn Trp Gln
130                 135                 140

Asn Gly Phe Ser Gly Arg Ile Asp Pro Thr Gly Tyr Ile Ala Asn Ala
145                 150                 155                 160

Pro Val Phe Asn Gly Thr Thr Pro Thr Glu Pro Thr Thr Pro Thr Thr
                165                 170                 175

Asn Leu Lys Ile Tyr Lys Val Asp Asp Leu Gln Lys Ile Asn Gly Ile
                180                 185                 190

Trp Gln Val Arg Asn Asn Ile Leu Val Pro Thr Asp Phe Thr Trp Val
                195                 200                 205

Asp Asn Gly Ile Ala Ala Asp Asp Val Ile Glu Val Thr Ser Asn Gly
                210                 215                 220

Thr Arg Thr Ser Asp Gln Val Leu Gln Lys Gly Gly Tyr Phe Val Ile
225                 230                 235                 240

Asn Pro Asn Asn Val Lys Ser Val Gly Thr Pro Met Lys Gly Ser Gly
                245                 250                 255

Gly Leu Ser Trp Ala Gln Val Asn Phe Thr Thr Gly Gly Asn Val Trp
                260                 265                 270

Leu Asn Thr Thr Ser Lys Asp Asn Leu Leu Tyr Gly Lys
                275                 280                 285

<210> SEQ ID NO 337
<211> LENGTH: 858
<212> TYPE: DNA
<213> ORGANISM: Streptococcus equi subsp. zooepidemicus

<400> SEQUENCE: 337
atgaaacgta tatttttgc tttcttaagt ttatgcttat ttatattcgg aacacaaacg      60
gtatctgcag ctacttatac tcggccatta gatacgggaa atatcactac agggtttaac     120 ggatacctg tcatgttgg agtcgattat gcagtacccg ttggaactcc ggttagagca      180
gttgcaaatg gtacagtcaa atttgcaggt aatggggcta atcacccatg gatgctttgg     240
atggctggaa actgtgttct aattcaacat gctgacggga tgcatactgg atatgcacac     300
ttatcaaaaa tttcagttag cacagatagt acagttaaac aaggacaaat cataggttat     360
actggtgcca ccggccaagt taccggtcca catttgcatt ttgaaatgtt gccagcaaat     420
cctaactggc aaaatggttt ttctggaaga atagatccaa ccggatacat cgctaatgcc     480
cctgtattta atggaacaac acctacagaa cctactactc ctacaacaaa tttaaaaatc     540
tataaagttg atgatttaca aaaaattaat ggtatttggc aagtaagaaa taacatactt     600
gtaccaactg atttcacatg ggttgataat ggaattgcag cagatgatgt aattgaagta     660
actagcaatg gaacaagaac ctctgaccaa gttcttcaaa aaggtggtta ttttgtcatc     720

```
aatcctaata atgttaaaag tgttggaact ccgatgaaag gtagtggtgg tctatcttgg        780
gctcaagtaa actttacaac aggtggaaat gtctggttaa atactactag caaagacaac        840
ttactttacg gaaaataa                                                      858
```

```
<210> SEQ ID NO 338
<211> LENGTH: 45
<212> TYPE: PRT
<213> ORGANISM: Myxococcus fulvus

<400> SEQUENCE: 338
```

```
Ala Asn Cys Ser Cys Ser Thr Ala Ser Asp Tyr Cys Pro Ile Leu Thr
1               5                   10                  15

Phe Cys Thr Thr Gly Thr Ala Cys Ser Tyr Thr Pro Thr Gly Cys Gly
            20                  25                  30

Thr Gly Trp Val Tyr Cys Ala Cys Asn Gly Asn Phe Tyr
        35                  40                  45
```

```
<210> SEQ ID NO 339
<211> LENGTH: 135
<212> TYPE: DNA
<213> ORGANISM: Artificial Sequence
<220> FEATURE:
<223> OTHER INFORMATION: Polynucleotide encoding the polypeptide of SEQ
      ID NO: 338

<400> SEQUENCE: 339
```

```
gcgaactgca gctgcagcac cgcgagcgat tattgcccga ttctgacctt ttgcaccacc        60
ggcaccgcgt gcagctatac cccgaccggc tgcggcaccg gctgggtgta ttgcgcgtgc       120
aacggcaact tttat                                                        135
```

```
<210> SEQ ID NO 340
<211> LENGTH: 19
<212> TYPE: PRT
<213> ORGANISM: Streptomyces griseoluteus

<400> SEQUENCE: 340
```

```
Cys Ala Asn Ser Cys Ser Tyr Gly Pro Leu Thr Trp Ser Cys Asp Gly
1               5                   10                  15

Asn Thr Lys
```

```
<210> SEQ ID NO 341
<211> LENGTH: 57
<212> TYPE: DNA
<213> ORGANISM: Artificial Sequence
<220> FEATURE:
<223> OTHER INFORMATION: Polynucleotide encoding the polypeptide of SEQ
      ID NO: 340

<400> SEQUENCE: 341
```

```
tgcgcgaaca gctgcagcta tggcccgctg acctggagct gcgatggcaa caccaaa          57
```

```
<210> SEQ ID NO 342
<211> LENGTH: 19
<212> TYPE: PRT
<213> ORGANISM: Streptoverticillium griseoverticillatum

<400> SEQUENCE: 342
```

```
Cys Lys Gln Ser Cys Ser Phe Gly Pro Phe Thr Phe Val Cys Asp Gly
1               5                   10                  15

Asn Thr Lys
```

<210> SEQ ID NO 343
<211> LENGTH: 57
<212> TYPE: DNA
<213> ORGANISM: Artificial Sequence
<220> FEATURE:
<223> OTHER INFORMATION: Polynucleotide encoding the polypeptide of SEQ
      ID NO: 342

<400> SEQUENCE: 343
tgcaaacaga gctgcagctt tggcccgttt acctttgtgt gcgatggcaa caccaaa      57

<210> SEQ ID NO 344
<211> LENGTH: 7
<212> TYPE: PRT
<213> ORGANISM: Carnobacterium sp.

<400> SEQUENCE: 344

Gly Ser Glu Ile Gln Pro Arg
1               5

<210> SEQ ID NO 345
<211> LENGTH: 21
<212> TYPE: DNA
<213> ORGANISM: Artificial Sequence
<220> FEATURE:
<223> OTHER INFORMATION: Polynucleotide encoding the polypeptide of SEQ
      ID NO: 344

<400> SEQUENCE: 345
ggcagcgaaa ttcagccgcg c                                              21

<210> SEQ ID NO 346
<211> LENGTH: 39
<212> TYPE: PRT
<213> ORGANISM: Lactococcus lactis subsp. lactis

<400> SEQUENCE: 346

Gly Thr Trp Asp Asp Ile Gly Gln Gly Ile Gly Arg Val Ala Tyr Trp
1               5                   10                  15

Val Gly Lys Ala Met Gly Asn Met Ser Asp Val Asn Gln Ala Ser Arg
            20                  25                  30

Ile Asn Arg Lys Lys Lys His
        35

<210> SEQ ID NO 347
<211> LENGTH: 117
<212> TYPE: DNA
<213> ORGANISM: Artificial Sequence
<220> FEATURE:
<223> OTHER INFORMATION: Polynucleotide encoding the polypeptide of SEQ
      ID NO: 346

<400> SEQUENCE: 347
ggcacctggg atgatattgg ccagggcatt ggccgcgtgg cgtattgggt gggcaaagcg      60
atgggcaaca tgagcgatgt gaaccaggcg agccgcatta accgcaaaaa aaaacat       117

<210> SEQ ID NO 348
<211> LENGTH: 35
<212> TYPE: PRT
<213> ORGANISM: Lactococcus lactis subsp. lactis

<400> SEQUENCE: 348

Lys Lys Trp Gly Trp Leu Ala Trp Val Asp Pro Ala Tyr Glu Phe Ile

```
                1               5                  10                  15
Lys Gly Phe Gly Lys Gly Ala Ile Lys Glu Gly Asn Lys Asp Lys Trp
                20                  25                  30
Lys Asn Ile
        35

<210> SEQ ID NO 349
<211> LENGTH: 105
<212> TYPE: DNA
<213> ORGANISM: Artificial Sequence
<220> FEATURE:
<223> OTHER INFORMATION: Polynucleotide encoding the polypeptide of SEQ
      ID NO: 348

<400> SEQUENCE: 349
aaaaaatggg gctggctggc gtgggtggat ccggcgtatg aatttattaa aggctttggc      60
aaaggcgcga ttaaagaagg caacaaagat aaatggaaaa acatt                    105

<210> SEQ ID NO 350
<211> LENGTH: 19
<212> TYPE: PRT
<213> ORGANISM: Streptomyces sp.

<400> SEQUENCE: 350

Cys Val Gln Ser Cys Ser Phe Gly Pro Leu Thr Trp Ser Cys Asp Gly
1               5                   10                  15

Asn Thr Lys

<210> SEQ ID NO 351
<211> LENGTH: 57
<212> TYPE: DNA
<213> ORGANISM: Artificial Sequence
<220> FEATURE:
<223> OTHER INFORMATION: Polynucleotide encoding the polypeptide of SEQ
      ID NO: 350

<400> SEQUENCE: 351
tgcgtgcaga gctgcagctt tggcccgctg acctggagct gcgatggcaa caccaaa        57

<210> SEQ ID NO 352
<211> LENGTH: 19
<212> TYPE: PRT
<213> ORGANISM: Actinoplanes liguriae

<400> SEQUENCE: 352

Ser Ser Gly Trp Val Cys Thr Leu Thr Ile Glu Cys Gly Thr Val Ile
1               5                   10                  15

Cys Ala Cys

<210> SEQ ID NO 353
<211> LENGTH: 57
<212> TYPE: DNA
<213> ORGANISM: Artificial Sequence
<220> FEATURE:
<223> OTHER INFORMATION: Polynucleotide encoding the polypeptide of SEQ
      ID NO: 352

<400> SEQUENCE: 353
agcagcggct gggtgtgcac cctgaccatt gaatgcggca ccgtgatttg cgcgtgc         57

<210> SEQ ID NO 354
<211> LENGTH: 38
<212> TYPE: PRT
```

<213> ORGANISM: Lactobacillus curvatus
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: VARIANT
<222> LOCATION: (37)..(37)
<223> OTHER INFORMATION: Xaa = any amino acid

<400> SEQUENCE: 354

Tyr Thr Ala Lys Gln Cys Leu Gln Ala Ile Gly Ser Cys Gly Ile Ala
1               5                   10                  15

Gly Thr Gly Ala Gly Ala Ala Gly Gly Pro Ala Gly Ala Phe Val Gly
            20                  25                  30

Ala Xaa Val Val Xaa Ile
        35

<210> SEQ ID NO 355
<211> LENGTH: 114
<212> TYPE: DNA
<213> ORGANISM: Artificial Sequence
<220> FEATURE:
<223> OTHER INFORMATION: Polynucleotide encoding the polypeptide of SEQ
      ID NO: 354
<220> FEATURE:
<221> NAME/KEY: misc_feature
<222> LOCATION: (100)..(102)
<223> OTHER INFORMATION: nnn = any amino acid-coding triplet
<220> FEATURE:
<221> NAME/KEY: misc_feature
<222> LOCATION: (109)..(111)
<223> OTHER INFORMATION: nnn = any amino acid-coding triplet

<400> SEQUENCE: 355
tataccgcga aacagtgcct gcaggcgatt ggcagctgcg gcattgcggg caccggcgcg    60
ggcgcggcgg gcggcccggc gggcgcgttt gtgggcgcgn nngtggtgnn natt          114

<210> SEQ ID NO 356
<211> LENGTH: 42
<212> TYPE: PRT
<213> ORGANISM: Lactobacillus sakei
<220> FEATURE:
<221> NAME/KEY: VARIANT
<222> LOCATION: (32)..(32)
<223> OTHER INFORMATION: Xaa = any amino acid

<400> SEQUENCE: 356

Thr Lys Tyr Tyr Gly Asn Gly Val Tyr Cys Asn Ser Lys Lys Cys Trp
1               5                   10                  15

Val Asp Trp Gly Gln Ala Ala Gly Gly Ile Gly Gln Thr Val Val Xaa
            20                  25                  30

Gly Trp Leu Gly Gly Ala Ile Pro Gly Lys
        35                  40

<210> SEQ ID NO 357
<211> LENGTH: 126
<212> TYPE: DNA
<213> ORGANISM: Artificial Sequence
<220> FEATURE:
<223> OTHER INFORMATION: Polynucleotide encoding the polypeptide of SEQ
      ID NO: 356
<220> FEATURE:
<221> NAME/KEY: misc_feature
<222> LOCATION: (94)..(96)
<223> OTHER INFORMATION: nnn = any amino acid-coding triplet

<400> SEQUENCE: 357

```
accaaatatt atggcaacgg cgtgtattgc aacagcaaaa aatgctgggt ggattggggc    60
caggcggcgg gcggcattgg ccagaccgtg gtgnnnggct ggctgggcgg cgcgattccg   120
ggcaaa                                                              126
```

<210> SEQ ID NO 358
<211> LENGTH: 22
<212> TYPE: PRT
<213> ORGANISM: Streptococcus mutans

<400> SEQUENCE: 358

```
Phe Lys Ser Trp Ser Phe Cys Thr Pro Gly Cys Ala Lys Thr Gly Ser
1               5                   10                  15

Phe Asn Ser Tyr Cys Cys
            20
```

<210> SEQ ID NO 359
<211> LENGTH: 132
<212> TYPE: DNA
<213> ORGANISM: Artificial Sequence
<220> FEATURE:
<223> OTHER INFORMATION: Polynucleotide encoding the polypeptide of SEQ
      ID NO: 358

<400> SEQUENCE: 359

```
tttaaaagct ggagcttttg cacccccgggc tgcgcgaaaa ccggcagctt taacagctat    60
tgctgcttta aaagctggag cttttgcacc ccgggctgcg cgaaaaccgg cagctttaac   120
agctattgct gc                                                       132
```

<210> SEQ ID NO 360
<211> LENGTH: 43
<212> TYPE: PRT
<213> ORGANISM: Enterococcus mundtii

<400> SEQUENCE: 360

```
Lys Tyr Tyr Gly Asn Gly Val Ser Cys Asn Lys Lys Gly Cys Ser Val
1               5                   10                  15

Asp Trp Gly Lys Ala Ile Gly Ile Ile Gly Asn Asn Ser Ala Ala Asn
            20                  25                  30

Leu Ala Thr Gly Gly Ala Ala Gly Trp Ser Lys
        35                  40
```

<210> SEQ ID NO 361
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 360

<400> SEQUENCE: 361

```
aaatattatg gcaacggcgt gagctgcaac aaaaaaggct gcagcgtgga ttggggcaaa    60
gcgattggca ttattggcaa caacagcgcg gcgaacctgg cgaccggcgg cgcggcgggc   120
tggagcaaa                                                           129
```

<210> SEQ ID NO 362
<211> LENGTH: 41
<212> TYPE: PRT
<213> ORGANISM: Lactobacillus sakei
<220> FEATURE:
<221> NAME/KEY: VARIANT

```
<222> LOCATION: (9)..(9)
<223> OTHER INFORMATION: Xaa = any amino acid
<220> FEATURE:
<221> NAME/KEY: VARIANT
<222> LOCATION: (14)..(14)
<223> OTHER INFORMATION: Xaa = any amino acid
<220> FEATURE:
<221> NAME/KEY: VARIANT
<222> LOCATION: (33)..(33)
<223> OTHER INFORMATION: Xaa = any amino acid
<220> FEATURE:
<221> NAME/KEY: VARIANT
<222> LOCATION: (37)..(37)
<223> OTHER INFORMATION: Xaa = any amino acid

<400> SEQUENCE: 362

Lys Tyr Tyr Gly Asn Gly Val His Xaa Gly Lys His Ser Xaa Thr Val
1               5                   10                  15

Asp Trp Gly Thr Ala Ile Gly Asn Ile Gly Asn Asn Ala Ala Ala Asn
            20                  25                  30

Xaa Ala Thr Gly Xaa Asn Ala Gly Gly
        35                  40

<210> SEQ ID NO 363
<211> LENGTH: 123
<212> TYPE: DNA
<213> ORGANISM: Artificial Sequence
<220> FEATURE:
<223> OTHER INFORMATION: Polynucleotide encoding the polypeptide of SEQ
      ID NO: 362
<220> FEATURE:
<221> NAME/KEY: misc_feature
<222> LOCATION: (25)..(27)
<223> OTHER INFORMATION: nnn = any amino acid-coding triplet
<220> FEATURE:
<221> NAME/KEY: misc_feature
<222> LOCATION: (40)..(42)
<223> OTHER INFORMATION: nnn = any amino acid-coding triplet
<220> FEATURE:
<221> NAME/KEY: misc_feature
<222> LOCATION: (97)..(99)
<223> OTHER INFORMATION: nnn = any amino acid-coding triplet
<220> FEATURE:
<221> NAME/KEY: misc_feature
<222> LOCATION: (109)..(111)
<223> OTHER INFORMATION: nnn = any amino acid-coding triplet

<400> SEQUENCE: 363
aaatattatg gcaacggcgt gcatnnnggc aaacatagcn nnaccgtgga ttggggcacc      60
gcgattggca acattggcaa caacgcggcg gcgaacnnng cgaccggcnn naacgcgggc     120
ggc                                                                   123

<210> SEQ ID NO 364
<211> LENGTH: 31
<212> TYPE: PRT
<213> ORGANISM: Lactobacillus paracasei

<400> SEQUENCE: 364

Gly Met Ser Gly Tyr Ile Gln Gly Ile Pro Asp Phe Leu Lys Gly Tyr
1               5                   10                  15

Leu His Gly Ile Ser Ala Ala Asn Lys His Lys Lys Gly Arg Leu
            20                  25                  30

<210> SEQ ID NO 365
<211> LENGTH: 93
<212> TYPE: DNA
<213> ORGANISM: Artificial Sequence
<220> FEATURE:
```

<223> OTHER INFORMATION: Polynucleotide encoding the polypeptide of SEQ
      ID NO: 364

<400> SEQUENCE: 365
ggcatgagcg gctatattca gggcattccg gatttctga aaggctatct gcatggcatt    60
agcgcggcga acaaacataa aaaaggccgc ctg                                93

<210> SEQ ID NO 366
<211> LENGTH: 31
<212> TYPE: PRT
<213> ORGANISM: Leuconostoc mesenteroides

<400> SEQUENCE: 366

Lys Gly Lys Gly Phe Trp Ser Trp Ala Ser Lys Ala Thr Ser Trp Leu
1               5                   10                  15

Thr Gly Pro Gln Gln Pro Gly Ser Pro Leu Leu Lys Lys His Arg
            20                  25                  30

<210> SEQ ID NO 367
<211> LENGTH: 93
<212> TYPE: DNA
<213> ORGANISM: Artificial Sequence
<220> FEATURE:
<223> OTHER INFORMATION: Polynucleotide encoding the polypeptide of SEQ
      ID NO: 366

<400> SEQUENCE: 367
aaaggcaaag gcttttggag ctgggcgagc aaagcgacca gctggctgac cggcccgcag    60
cagccgggca gcccgctgct gaaaaaacat cgc                                 93

<210> SEQ ID NO 368
<211> LENGTH: 43
<212> TYPE: PRT
<213> ORGANISM: Leuconostoc mesenteroides

<400> SEQUENCE: 368

Lys Asn Tyr Gly Asn Gly Val His Cys Thr Lys Lys Gly Cys Ser Val
1               5                   10                  15

Asp Trp Gly Tyr Ala Trp Thr Asn Ile Ala Asn Asn Ser Val Met Asn
            20                  25                  30

Gly Leu Thr Gly Gly Asn Ala Gly Trp His Asn
        35                  40

<210> SEQ ID NO 369
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 368

<400> SEQUENCE: 369
aaaaactatg gcaacggcgt gcattgcacc aaaaaaggct gcagcgtgga ttggggctat    60
gcgtggacca acattgcgaa caacagcgtg atgaacggcc tgaccggcgg caacgcgggc   120
tggcataac                                                           129

<210> SEQ ID NO 370
<211> LENGTH: 47
<212> TYPE: PRT
<213> ORGANISM: Bacillus subtilis

<400> SEQUENCE: 370

```
Ala Ile Lys Leu Val Gln Ser Pro Asn Gly Asn Phe Ala Ala Ser Phe
1               5                   10                  15

Val Leu Asp Gly Thr Lys Trp Ile Phe Lys Ser Lys Tyr Tyr Asp Ser
                20                  25                  30

Ser Lys Gly Tyr Trp Val Gly Ile Tyr Glu Val Trp Asp Arg Lys
            35                  40                  45
```

<210> SEQ ID NO 371
<211> LENGTH: 141
<212> TYPE: DNA
<213> ORGANISM: Artificial Sequence
<220> FEATURE:
<223> OTHER INFORMATION: Polynucleotide encoding the polypeptide of SEQ
      ID NO: 370

<400> SEQUENCE: 371

```
gcgattaaac tggtgcagag cccgaacggc aactttgcgg cgagctttgt gctggatggc    60
accaaatgga tttttaaaag caaatattat gatagcagca aaggctattg ggtgggcatt   120
tatgaagtgt gggatcgcaa a                                             141
```

<210> SEQ ID NO 372
<211> LENGTH: 12
<212> TYPE: PRT
<213> ORGANISM: Bacillus licheniformis
<220> FEATURE:
<221> NAME/KEY: VARIANT
<222> LOCATION: (7)..(7)
<223> OTHER INFORMATION: Xaa = any amino acid

<400> SEQUENCE: 372

```
Ile Ser Leu Glu Ile Cys Xaa Ile Phe His Asp Asn
1               5                   10
```

<210> SEQ ID NO 373
<211> LENGTH: 36
<212> TYPE: DNA
<213> ORGANISM: Artificial Sequence
<220> FEATURE:
<223> OTHER INFORMATION: Polynucleotide encoding the polypeptide of SEQ
      ID NO: 372
<220> FEATURE:
<221> NAME/KEY: misc_feature
<222> LOCATION: (19)..(21)
<223> OTHER INFORMATION: nnn = any amino acid-coding triplet

<400> SEQUENCE: 373

```
attagcctgg aaatttgcnn nattttcat gataac                               36
```

<210> SEQ ID NO 374
<211> LENGTH: 37
<212> TYPE: PRT
<213> ORGANISM: Lactococcus lactis subsp. lactis

<400> SEQUENCE: 374

```
Thr Ser Tyr Gly Asn Gly Val His Cys Asn Lys Ser Lys Cys Trp Ile
1               5                   10                  15

Asp Val Ser Glu Leu Glu Thr Tyr Lys Ala Gly Thr Val Ser Asn Pro
                20                  25                  30

Lys Asp Ile Leu Trp
            35
```

<210> SEQ ID NO 375
<211> LENGTH: 111

```
<212> TYPE: DNA
<213> ORGANISM: Artificial Sequence
<220> FEATURE:
<223> OTHER INFORMATION: Polynucleotide encoding the polypeptide of SEQ
      ID NO: 374

<400> SEQUENCE: 375
accagctatg gcaacggcgt gcattgcaac aaaagcaaat gctggattga tgtgagcgaa      60
ctggaaacct ataaagcggg caccgtgagc aacccgaaag atattctgtg g             111

<210> SEQ ID NO 376
<211> LENGTH: 9
<212> TYPE: PRT
<213> ORGANISM: Serratia plymuthica

<400> SEQUENCE: 376

Asp Tyr His His Gly Val Arg Val Leu
1               5

<210> SEQ ID NO 377
<211> LENGTH: 27
<212> TYPE: DNA
<213> ORGANISM: Artificial Sequence
<220> FEATURE:
<223> OTHER INFORMATION: Polynucleotide encoding the polypeptide of SEQ
      ID NO: 376

<400> SEQUENCE: 377
gattatcatc atggcgtgcg cgtgctg                                          27

<210> SEQ ID NO 378
<211> LENGTH: 15
<212> TYPE: PRT
<213> ORGANISM: Halobacterium sp.

<400> SEQUENCE: 378

Asp Ile Asp Ile Thr Gly Cys Ser Ala Cys Lys Tyr Ala Ala Gly
1               5                   10                  15

<210> SEQ ID NO 379
<211> LENGTH: 45
<212> TYPE: DNA
<213> ORGANISM: Artificial Sequence
<220> FEATURE:
<223> OTHER INFORMATION: Polynucleotide encoding the polypeptide of SEQ
      ID NO: 378

<400> SEQUENCE: 379
gatattgata ttaccggctg cagcgcgtgc aaatatgcgg cgggc                      45

<210> SEQ ID NO 380
<211> LENGTH: 12
<212> TYPE: PRT
<213> ORGANISM: Bacillus subtilis
<220> FEATURE:
<221> NAME/KEY: VARIANT
<222> LOCATION: (1)..(1)
<223> OTHER INFORMATION: Xaa = any amino acid
<220> FEATURE:
<221> NAME/KEY: VARIANT
<222> LOCATION: (2)..(2)
<223> OTHER INFORMATION: Xaa = any amino acid
<220> FEATURE:
<221> NAME/KEY: VARIANT
<222> LOCATION: (6)..(6)
<223> OTHER INFORMATION: Xaa = any amino acid

<400> SEQUENCE: 380
```

```
Xaa Xaa Lys Glu Ile Xaa His Ile Phe His Asp Asn
1               5                   10
```

<210> SEQ ID NO 381
<211> LENGTH: 36
<212> TYPE: DNA
<213> ORGANISM: Artificial Sequence
<220> FEATURE:
<223> OTHER INFORMATION: Polynucleotide encoding the polypeptide of SEQ
      ID NO: 380
<220> FEATURE:
<221> NAME/KEY: misc_feature
<222> LOCATION: (1)..(3)
<223> OTHER INFORMATION: nnn = any amino acid-coding triplet
<220> FEATURE:
<221> NAME/KEY: misc_feature
<222> LOCATION: (4)..(6)
<223> OTHER INFORMATION: nnn = any amino acid-coding triplet
<220> FEATURE:
<221> NAME/KEY: misc_feature
<222> LOCATION: (16)..(18)
<223> OTHER INFORMATION: nnn = any amino acid-coding triplet

<400> SEQUENCE: 381
nnnnnnaaag aaattnnnca tattttcat gataac                                    36

<210> SEQ ID NO 382
<211> LENGTH: 12
<212> TYPE: PRT
<213> ORGANISM: Lactobacillus curvatus

<400> SEQUENCE: 382

```
Thr Pro Val Val Asn Pro Pro Phe Leu Gln Gln Thr
1               5                   10
```

<210> SEQ ID NO 383
<211> LENGTH: 36
<212> TYPE: DNA
<213> ORGANISM: Artificial Sequence
<220> FEATURE:
<223> OTHER INFORMATION: Polynucleotide encoding the polypeptide of SEQ
      ID NO: 382

<400> SEQUENCE: 383
accccggtgg tgaacccgcc gtttctgcag cagacc                                   36

<210> SEQ ID NO 384
<211> LENGTH: 10
<212> TYPE: PRT
<213> ORGANISM: Lactobacillus curvatus
<220> FEATURE:
<221> NAME/KEY: VARIANT
<222> LOCATION: (10)..(10)
<223> OTHER INFORMATION: Xaa = any amino acid

<400> SEQUENCE: 384

```
Val Ala Pro Phe Pro Glu Gln Phe Leu Xaa
1               5                   10
```

<210> SEQ ID NO 385
<211> LENGTH: 30
<212> TYPE: DNA
<213> ORGANISM: Artificial Sequence
<220> FEATURE:
<223> OTHER INFORMATION: Polynucleotide encoding the polypeptide of SEQ
      ID NO: 384
<220> FEATURE:
<221> NAME/KEY: misc_feature
<222> LOCATION: (28)..(30)

```
<223> OTHER INFORMATION: nnn = any amino acid-coding triplet

<400> SEQUENCE: 385
gtggcgccgt ttccggaaca gtttctgnnn                                   30

<210> SEQ ID NO 386
<211> LENGTH: 9
<212> TYPE: PRT
<213> ORGANISM: Lactobacillus curvatus

<400> SEQUENCE: 386

Asn Ile Pro Gln Leu Thr Pro Thr Pro
1               5

<210> SEQ ID NO 387
<211> LENGTH: 27
<212> TYPE: DNA
<213> ORGANISM: Artificial Sequence
<220> FEATURE:
<223> OTHER INFORMATION: Polynucleotide encoding the polypeptide of SEQ
      ID NO: 386

<400> SEQUENCE: 387
aacattccgc agctgacccc gaccccg                                      27

<210> SEQ ID NO 388
<211> LENGTH: 18
<212> TYPE: PRT
<213> ORGANISM: Bacillus thuringiensis subsp. entomocidus
<220> FEATURE:
<221> NAME/KEY: VARIANT
<222> LOCATION: (4)..(4)
<223> OTHER INFORMATION: Xaa = any amino acid
<220> FEATURE:
<221> NAME/KEY: VARIANT
<222> LOCATION: (7)..(7)
<223> OTHER INFORMATION: Xaa = any amino acid
<220> FEATURE:
<221> NAME/KEY: VARIANT
<222> LOCATION: (10)..(10)
<223> OTHER INFORMATION: Xaa = any amino acid

<400> SEQUENCE: 388

Asp Trp Thr Xaa Trp Ser Xaa Leu Val Xaa Ala Ala Cys Ser Val Glu
1               5                   10                  15

Leu Leu

<210> SEQ ID NO 389
<211> LENGTH: 54
<212> TYPE: DNA
<213> ORGANISM: Artificial Sequence
<220> FEATURE:
<223> OTHER INFORMATION: Polynucleotide encoding the polypeptide of SEQ
      ID NO: 388
<220> FEATURE:
<221> NAME/KEY: misc_feature
<222> LOCATION: (10)..(12)
<223> OTHER INFORMATION: nnn = any amino acid-coding triplet
<220> FEATURE:
<221> NAME/KEY: misc_feature
<222> LOCATION: (19)..(21)
<223> OTHER INFORMATION: nnn = any amino acid-coding triplet
<220> FEATURE:
<221> NAME/KEY: misc_feature
<222> LOCATION: (28)..(30)
<223> OTHER INFORMATION: nnn = any amino acid-coding triplet

<400> SEQUENCE: 389
gattggaccn nntggagcnn nctggtgnnn gcggcgtgca gcgtggaact gctg          54
```

<210> SEQ ID NO 390
<211> LENGTH: 30
<212> TYPE: PRT
<213> ORGANISM: Lactobacillus curvatus

<400> SEQUENCE: 390

Ala Tyr Pro Gly Asn Gly Val His Cys Gly Lys Tyr Ser Cys Thr Val
1               5                   10                  15

Asp Lys Gln Thr Ala Ile Gly Asn Ile Gly Asn Asn Ala Ala
            20                  25                  30

<210> SEQ ID NO 391
<211> LENGTH: 90
<212> TYPE: DNA
<213> ORGANISM: Artificial Sequence
<220> FEATURE:
<223> OTHER INFORMATION: Polynucleotide encoding the polypeptide of SEQ
      ID NO: 390

<400> SEQUENCE: 391
gcgtatccgg gcaacggcgt gcattgcggc aaatatagct gcaccgtgga taaacagacc    60
gcgattggca acattggcaa caacgcggcg                                     90

<210> SEQ ID NO 392
<211> LENGTH: 43
<212> TYPE: PRT
<213> ORGANISM: Carnobacterium divergens

<400> SEQUENCE: 392

Thr Lys Tyr Tyr Gly Asn Gly Val Tyr Cys Asn Ser Lys Lys Cys Trp
1               5                   10                  15

Val Asp Trp Gly Thr Ala Gln Gly Cys Ile Asp Val Val Ile Gly Gln
            20                  25                  30

Leu Gly Gly Gly Ile Pro Gly Lys Gly Lys Cys
        35                  40

<210> SEQ ID NO 393
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 392

<400> SEQUENCE: 393
accaaatatt atggcaacgg cgtgtattgc aacagcaaaa aatgctgggt ggattggggc    60
accgcgcagg gctgcattga tgtggtgatt ggccagctgg cggcggcat tccgggcaaa    120 ggcaaatgc                                                           129

<210> SEQ ID NO 394
<211> LENGTH: 62
<212> TYPE: PRT
<213> ORGANISM: Enterococcus sp.

<400> SEQUENCE: 394

Asn Arg Trp Tyr Cys Asn Ser Ala Ala Gly Gly Val Gly Gly Ala Ala
1               5                   10                  15

Val Cys Gly Leu Ala Gly Tyr Val Gly Glu Ala Lys Glu Asn Ile Ala
            20                  25                  30

Gly Glu Val Arg Lys Gly Trp Gly Met Ala Gly Gly Phe Thr His Asn

Lys Ala Cys Lys Ser Phe Pro Gly Ser Gly Trp Ala Ser Gly
    50                  55                  60

<210> SEQ ID NO 395
<211> LENGTH: 186
<212> TYPE: DNA
<213> ORGANISM: Artificial Sequence
<220> FEATURE:
<223> OTHER INFORMATION: Polynucleotide encoding the polypeptide of SEQ
      ID NO: 394

<400> SEQUENCE: 395
aaccgctggt attgcaacag cgcggcgggc ggcgtgggcg cgcggcggt gtgcggcctg      60 gcgggctatg tgggcgaagc gaaagaaaac attgcgggcg aagtgcgcaa aggctggggc    120
atggcgggcg gctttacccc taacaaagcg tgcaaaagct tccgggcag cggctgggcg    180 agcggc                                                              186

<210> SEQ ID NO 396
<211> LENGTH: 39
<212> TYPE: PRT
<213> ORGANISM: Enterococcus faecium

<400> SEQUENCE: 396

Thr Thr Lys Asn Tyr Gly Asn Gly Val Cys Asn Ser Val Asn Trp Cys
1               5                   10                  15

Gln Cys Gly Asn Val Trp Ala Ser Cys Asn Leu Ala Thr Gly Cys Ala
            20                  25                  30

Ala Trp Leu Cys Lys Leu Ala
        35

<210> SEQ ID NO 397
<211> LENGTH: 117
<212> TYPE: DNA
<213> ORGANISM: Artificial Sequence
<220> FEATURE:
<223> OTHER INFORMATION: Polynucleotide encoding the polypeptide of SEQ
      ID NO: 396

<400> SEQUENCE: 397
accaccaaaa actatggcaa cggcgtgtgc aacagcgtga actggtgcca gtgcggcaac     60
gtgtgggcga gctgcaacct ggcgaccggc tgcgcggcgt ggctgtgcaa actggcg      117

<210> SEQ ID NO 398
<211> LENGTH: 30
<212> TYPE: PRT
<213> ORGANISM: Paenibacillus polymyxa

<400> SEQUENCE: 398

Ala Ser Ile Ile Lys Thr Thr Ile Lys Val Ser Lys Ala Val Cys Lys
1               5                   10                  15

Thr Leu Thr Cys Ile Cys Thr Gly Ser Cys Ser Asn Cys Lys
            20                  25                  30

<210> SEQ ID NO 399
<211> LENGTH: 90
<212> TYPE: DNA
<213> ORGANISM: Artificial Sequence
<220> FEATURE:
<223> OTHER INFORMATION: Polynucleotide encoding the polypeptide of SEQ
      ID NO: 398

<400> SEQUENCE: 399
gcgagcatta ttaaaaccac cattaaagtg agcaaagcgg tgtgcaaaac cctgacctgc    60
atttgcaccg gcagctgcag caactgcaaa                                    90

<210> SEQ ID NO 400
<211> LENGTH: 31
<212> TYPE: PRT
<213> ORGANISM: Staphylococcus epidermidis

<400> SEQUENCE: 400

Ser Ala Ser Ile Val Lys Thr Thr Ile Lys Ala Ser Lys Lys Leu Cys
1               5                   10                  15

Arg Gly Phe Thr Leu Thr Cys Gly Cys His Phe Thr Gly Lys Lys
            20                  25                  30

<210> SEQ ID NO 401
<211> LENGTH: 93
<212> TYPE: DNA
<213> ORGANISM: Artificial Sequence
<220> FEATURE:
<223> OTHER INFORMATION: Polynucleotide encoding the polypeptide of SEQ
      ID NO: 400

<400> SEQUENCE: 401
agcgcgagca ttgtgaaaac caccattaaa gcgagcaaaa aactgtgccg cggctttacc    60
ctgacctgcg gctgccattt taccggcaaa aaa                                 93

<210> SEQ ID NO 402
<211> LENGTH: 43
<212> TYPE: PRT
<213> ORGANISM: Enterococcus faecium

<400> SEQUENCE: 402

Lys Tyr Tyr Gly Asn Gly Val Ser Cys Asn Lys Lys Gly Cys Ser Val
1               5                   10                  15

Asp Trp Gly Lys Ala Ile Gly Ile Ile Gly Asn Asn Ala Ala Ala Asn
            20                  25                  30

Leu Thr Thr Gly Gly Lys Ala Ala Trp Ala Cys
        35                  40

<210> SEQ ID NO 403
<211> LENGTH: 129
<212> TYPE: DNA
<213> ORGANISM: Artificial Sequence
<220> FEATURE:
<223> OTHER INFORMATION: Polynucleotide encoding the polypeptide of SEQ
      ID NO: 402

<400> SEQUENCE: 403
aaatattatg gcaacggcgt gagctgcaac aaaaaaggct gcagcgtgga ttggggcaaa    60
gcgattggca ttattggcaa caacgcggcg gcgaacctga ccaccggcgg caaagcggcg   120
tgggcgtgc                                                          129

<210> SEQ ID NO 404
<211> LENGTH: 39
<212> TYPE: PRT
<213> ORGANISM: Paenibacillus polymyxa

<400> SEQUENCE: 404

Ala Thr Tyr Tyr Gly Asn Gly Leu Tyr Cys Asn Lys Gln Lys His Tyr
1               5                   10                  15

-continued

```
Thr Trp Val Asp Trp Asn Lys Ala Ser Arg Glu Ile Gly Lys Ile Thr
            20                  25                  30

Val Asn Gly Trp Val Gln His
        35

<210> SEQ ID NO 405
<211> LENGTH: 117
<212> TYPE: DNA
<213> ORGANISM: Artificial Sequence
<220> FEATURE:
<223> OTHER INFORMATION: Polynucleotide encoding the polypeptide of SEQ
      ID NO: 404

<400> SEQUENCE: 405
gcgacctatt atggcaacgg cctgtattgc aacaaacaga acattatac ctgggtggat      60 tggaacaaag cgagccgcga aattggcaaa attaccgtga acggctgggt gcagcat      117

<210> SEQ ID NO 406
<211> LENGTH: 35
<212> TYPE: PRT
<213> ORGANISM: Bacillus circulans

<400> SEQUENCE: 406

Val Asn Tyr Gly Asn Gly Val Ser Cys Ser Lys Thr Lys Cys Ser Val
1               5                   10                  15

Asn Trp Gly Ile Ile Thr His Gln Ala Phe Arg Val Thr Ser Gly Val
            20                  25                  30

Ala Ser Gly
        35

<210> SEQ ID NO 407
<211> LENGTH: 105
<212> TYPE: DNA
<213> ORGANISM: Artificial Sequence
<220> FEATURE:
<223> OTHER INFORMATION: Polynucleotide encoding the polypeptide of SEQ
      ID NO: 406

<400> SEQUENCE: 407
gtgaactatg gcaacggcgt gagctgcagc aaaaccaaat gcagcgtgaa ctggggcatt      60
attacccatc aggcgtttcg cgtgaccagc ggcgtggcga cggc                    105

<210> SEQ ID NO 408
<211> LENGTH: 30
<212> TYPE: PRT
<213> ORGANISM: Paenibacillus polymyxa

<400> SEQUENCE: 408

Phe Val Tyr Gly Asn Gly Val Thr Ser Ile Leu Val Gln Ala Gln Phe
1               5                   10                  15

Leu Val Asn Gly Gln Arg Arg Phe Phe Tyr Thr Pro Asp Lys
            20                  25                  30

<210> SEQ ID NO 409
<211> LENGTH: 90
<212> TYPE: DNA
<213> ORGANISM: Artificial Sequence
<220> FEATURE:
<223> OTHER INFORMATION: Polynucleotide encoding the polypeptide of SEQ
      ID NO: 408

<400> SEQUENCE: 409
```

```
tttgtgtatg gcaacggcgt gaccagcatt ctggtgcagg cgcagtttct ggtgaacggc    60
cagcgccgct ttttttatac cccggataaa                                    90
```

<210> SEQ ID NO 410
<211> LENGTH: 13
<212> TYPE: PRT
<213> ORGANISM: Lactobacillus rhamnosus

<400> SEQUENCE: 410

```
Ala Val Pro Ala Val Arg Lys Thr Asn Glu Thr Leu Asp
1               5                   10
```

<210> SEQ ID NO 411
<211> LENGTH: 39
<212> TYPE: DNA
<213> ORGANISM: Artificial Sequence
<220> FEATURE:
<223> OTHER INFORMATION: Polynucleotide encoding the polypeptide of SEQ
      ID NO: 410

<400> SEQUENCE: 411

```
gcggtgccgg cggtgcgcaa aaccaacgaa accctggat                          39
```

<210> SEQ ID NO 412
<211> LENGTH: 69
<212> TYPE: PRT
<213> ORGANISM: Bacillus licheniformis

<400> SEQUENCE: 412

```
Met Lys Asn Ser Ala Ala Arg Glu Ala Phe Lys Gly Ala Asn His Pro
1               5                   10                  15

Ala Gly Met Val Ser Glu Glu Glu Leu Lys Ala Leu Val Gly Gly Asn
                20                  25                  30

Asp Val Asn Pro Glu Thr Thr Pro Ala Thr Thr Ser Ser Trp Thr Cys
            35                  40                  45

Ile Thr Ala Gly Val Thr Val Ser Ala Ser Leu Cys Pro Thr Thr Lys
        50                  55                  60

Cys Thr Ser Arg Cys
65
```

<210> SEQ ID NO 413
<211> LENGTH: 207
<212> TYPE: DNA
<213> ORGANISM: Artificial Sequence
<220> FEATURE:
<223> OTHER INFORMATION: Polynucleotide encoding the polypeptide of SEQ
      ID NO: 412

<400> SEQUENCE: 413

```
atgaaaaaca gcgcggcgcg cgaagcgttt aaaggcgcga accatccggc gggcatggtg    60
agcgaagaag aactgaaagc gctggtgggc ggcaacgatg tgaacccgga aaccaccccg   120
gcgaccacca gcagctggac ctgcattacc gcgggcgtga ccgtgagcgc gagcctgtgc   180
ccgaccacca aatgcaccag ccgctgc                                      207
```

<210> SEQ ID NO 414
<211> LENGTH: 36
<212> TYPE: PRT
<213> ORGANISM: Lactobacillus plantarum

<400> SEQUENCE: 414

```
Lys Tyr Tyr Gly Asn Gly Leu Ser Cys Ser Lys Lys Gly Cys Thr Val
```

```
                1               5                   10                  15
Asn Trp Gly Gln Ala Phe Ser Cys Gly Val Asn Arg Val Ala Thr Ala
                20                  25                  30

Gly His Gly Lys
        35
```

<210> SEQ ID NO 415
<211> LENGTH: 108
<212> TYPE: DNA
<213> ORGANISM: Artificial Sequence
<220> FEATURE:
<223> OTHER INFORMATION: Polynucleotide encoding the polypeptide of SEQ
      ID NO: 414

<400> SEQUENCE: 415
aaatattatg gcaacggcct gagctgcagc aaaaaaggct gcaccgtgaa ctggggccag      60
gcgtttagct gcggcgtgaa ccgcgtggcg accgcgggcc atggcaaa                  108

<210> SEQ ID NO 416
<211> LENGTH: 24
<212> TYPE: PRT
<213> ORGANISM: Lactobacillus acidophilus

<400> SEQUENCE: 416

```
Gly Asn Pro Lys Val Ala His Cys Ala Ser Gln Ile Gly Arg Ser Thr
1               5                   10                  15

Ala Trp Gly Ala Val Ser Gly Ala
                20
```

<210> SEQ ID NO 417
<211> LENGTH: 72
<212> TYPE: DNA
<213> ORGANISM: Artificial Sequence
<220> FEATURE:
<223> OTHER INFORMATION: Polynucleotide encoding the polypeptide of SEQ
      ID NO: 416

<400> SEQUENCE: 417
ggcaacccga aagtggcgca ttgcgcgagc cagattggcc gcagcaccgc gtggggcgcg      60
gtgagcggcg cg                                                          72

<210> SEQ ID NO 418
<211> LENGTH: 40
<212> TYPE: PRT
<213> ORGANISM: Enterococcus faecalis

<400> SEQUENCE: 418

```
Trp Leu Pro Pro Ala Gly Leu Leu Gly Arg Cys Gly Arg Trp Phe Arg
1               5                   10                  15

Pro Trp Leu Leu Trp Leu Gln Ser Gly Ala Gln Tyr Lys Trp Leu Gly
                20                  25                  30

Asn Leu Phe Gly Leu Gly Pro Lys
        35                  40
```

<210> SEQ ID NO 419
<211> LENGTH: 120
<212> TYPE: DNA
<213> ORGANISM: Artificial Sequence
<220> FEATURE:
<223> OTHER INFORMATION: Polynucleotide encoding the polypeptide of SEQ
      ID NO: 418

<400> SEQUENCE: 419

```
tggctgccgc cggcgggcct gctgggccgc tgcggccgct ggtttcgccc gtggctgctg      60
tggctgcaga gcggcgcgca gtataaatgg ctgggcaacc tgtttggcct gggcccgaaa     120
```

<210> SEQ ID NO 420
<211> LENGTH: 40
<212> TYPE: PRT
<213> ORGANISM: Anabaena variabilis

<400> SEQUENCE: 420

Asn Leu Asp Gln Trp Leu Thr Glu Gln Val His Glu Phe Gln Asp Met
1               5                   10                  15

Tyr Leu Glu Pro Gln Ala Ile Ser Asn Gln Asp Ile Thr Phe Lys Leu
            20                  25                  30

Ser Asp Leu Asp Phe Ile His Asn
        35                  40

<210> SEQ ID NO 421
<211> LENGTH: 124
<212> TYPE: DNA
<213> ORGANISM: Anabaena variabilis

<400> SEQUENCE: 421

```
taatttagat cagtggttaa cagaacaagt tcatgagttt caagatatgt acttggaacc      60
acaagcaata tccaatcaag acattacctt caaactatct gacctagatt ttattcataa     120
ttga                                                                  124
```

<210> SEQ ID NO 422
<211> LENGTH: 40
<212> TYPE: PRT
<213> ORGANISM: Nostoc sp

<400> SEQUENCE: 422

Asn Leu Asp Gln Trp Leu Thr Glu Gln Val His Glu Phe Gln Asp Met
1               5                   10                  15

Tyr Leu Glu Pro Gln Ala Ile Ser Asn Gln Asp Ile Thr Phe Lys Leu
            20                  25                  30

Ser Asp Leu Asp Phe Ile His Asn
        35                  40

<210> SEQ ID NO 423
<211> LENGTH: 123
<212> TYPE: DNA
<213> ORGANISM: Nostoc sp

<400> SEQUENCE: 423

```
aatttagatc aatggttaac agaacaagtt catgagtttc aagatatgta cttggaacca      60
caagcaatat ccaatcaaga cattaccttc aaactgtcag acctagattt tattcataat     120
tga                                                                   123
```

<210> SEQ ID NO 424
<211> LENGTH: 7
<212> TYPE: PRT
<213> ORGANISM: Nostoc azollae

<400> SEQUENCE: 424

His Arg Glu Lys Lys Ser Ala
1               5

```
<210> SEQ ID NO 425
<211> LENGTH: 24
<212> TYPE: DNA
<213> ORGANISM: Nostoc azollae

<400> SEQUENCE: 425
cacagagaga aaaaatcagc atag                                          24

<210> SEQ ID NO 426
<211> LENGTH: 23
<212> TYPE: PRT
<213> ORGANISM: Acaryochloris marina

<400> SEQUENCE: 426

Thr Ser Asn Asn Trp Leu Ala Lys Asn Tyr Leu Ser Met Trp Asn Lys
1               5                   10                  15

Lys Ser Ser Asn Pro Asn Leu
            20

<210> SEQ ID NO 427
<211> LENGTH: 72
<212> TYPE: DNA
<213> ORGANISM: Acaryochloris marina

<400> SEQUENCE: 427
acaagcaata actggctagc caaaaactat ctttctatgt ggaataaaaa gagcagtaat   60
ccaaaccttt ag                                                      72

<210> SEQ ID NO 428
<211> LENGTH: 6
<212> TYPE: PRT
<213> ORGANISM: Cyanothece

<400> SEQUENCE: 428

Phe Arg Tyr Phe Trp Trp
1               5

<210> SEQ ID NO 429
<211> LENGTH: 21
<212> TYPE: DNA
<213> ORGANISM: Cyanothece

<400> SEQUENCE: 429
tttagatatt tttggtggta a                                             21

<210> SEQ ID NO 430
<211> LENGTH: 6
<212> TYPE: PRT
<213> ORGANISM: Cyanothece

<400> SEQUENCE: 430

Phe Arg Tyr Phe Trp Trp
1               5

<210> SEQ ID NO 431
<211> LENGTH: 21
<212> TYPE: DNA
<213> ORGANISM: Cyanothece

<400> SEQUENCE: 431
tttagatatt tttggtggta a                                             21

<210> SEQ ID NO 432
```

```
<211> LENGTH: 9
<212> TYPE: PRT
<213> ORGANISM: Cyanothece

<400> SEQUENCE: 432

Cys Gly Glu Lys Trp Arg Ile Phe Ser
1               5

<210> SEQ ID NO 433
<211> LENGTH: 27
<212> TYPE: DNA
<213> ORGANISM: Cyanothece

<400> SEQUENCE: 433
tgtggagaaa aatggagaat ttttagc                                         27

<210> SEQ ID NO 434
<211> LENGTH: 8
<212> TYPE: PRT
<213> ORGANISM: Cyanothece

<400> SEQUENCE: 434

Phe Arg Leu Gln Leu Trp Gln Phe
1               5

<210> SEQ ID NO 435
<211> LENGTH: 24
<212> TYPE: DNA
<213> ORGANISM: Cyanothece

<400> SEQUENCE: 435
tttcgcttac aactgtggca attt                                            24

<210> SEQ ID NO 436
<211> LENGTH: 16
<212> TYPE: PRT
<213> ORGANISM: Cyanothece

<400> SEQUENCE: 436

Leu Gly Cys Asn Gln Ser Ser Ile Trp Ser Ile Phe Phe Trp Asn His
1               5                   10                  15

<210> SEQ ID NO 437
<211> LENGTH: 51
<212> TYPE: DNA
<213> ORGANISM: Cyanothece

<400> SEQUENCE: 437
ctaggatgta accagagcag tatctggtca attttttttct ggaatcatta a             51

<210> SEQ ID NO 438
<211> LENGTH: 40
<212> TYPE: PRT
<213> ORGANISM: Microcoleus chthonoplastes

<400> SEQUENCE: 438

Tyr Asn Leu Gln Gly Leu Pro Ala Ile Glu Ser Glu Asp Cys Ile Pro
1               5                   10                  15

Asp Ser Val Ala Pro Ser Asp Trp Phe Ser Gly Val Ser Ser Leu
                20                  25                  30

Phe Asn Arg Leu Thr Gly Leu Gly
            35                  40
```

<210> SEQ ID NO 439
<211> LENGTH: 123
<212> TYPE: DNA
<213> ORGANISM: Microcoleus chthonoplastes

<400> SEQUENCE: 439

```
tataacctac aggggttgcc agcaattgag tcagaagact gtatcccaga ttctgtagcg    60
ccttcggatg attggttttc aggcgtatcg tctctgttta accgcttgac tgggttgggt   120
tag                                                                 123
```

<210> SEQ ID NO 440
<211> LENGTH: 37
<212> TYPE: PRT
<213> ORGANISM: Nostoc sp

<400> SEQUENCE: 440

Trp Met Ala Ile Arg Arg Ile Leu Arg Cys His Pro Phe His Pro Gly
 1               5                  10                  15

Gly Tyr Asp Pro Val Pro Glu Leu Gly Glu His Cys Cys His His Asp
                20                  25                  30

Ser Gly Asn Lys Gly
            35

<210> SEQ ID NO 441
<211> LENGTH: 114
<212> TYPE: DNA
<213> ORGANISM: Nostoc sp

<400> SEQUENCE: 441

```
tggatggcga ttcgccgcat tttgcgttgt catccattcc acccaggggg ttatgatcct    60
gtaccagagt tgggtgagca ttgttgtcat catgatagcg ggaataaggg gtga         114
```

<210> SEQ ID NO 442
<211> LENGTH: 35
<212> TYPE: PRT
<213> ORGANISM: Anabaena variabilis

<400> SEQUENCE: 442

Trp Met Gly Ile Arg Arg Ile Leu Arg Cys His Pro Phe His Pro Gly
 1               5                  10                  15

Gly Tyr Asp Pro Val Pro Glu Val Gly Glu His Cys Cys His His Asp
                20                  25                  30

Ser Gly Lys
        35

<210> SEQ ID NO 443
<211> LENGTH: 108
<212> TYPE: DNA
<213> ORGANISM: Anabaena variabilis

<400> SEQUENCE: 443

```
tggatgggga ttcgccgcat tttgcgttgt catccattcc acccaggcgg ttatgatcct    60
gtaccagagg tgggtgagca ttgttgtcat catgatagcg ggaagtag                108
```

<210> SEQ ID NO 444
<211> LENGTH: 48
<212> TYPE: PRT
<213> ORGANISM: Nodularia spumigena

<400> SEQUENCE: 444

```
Trp Met Ala Thr Arg Arg Ile Leu Arg Cys His Pro Phe His Pro Gly
1               5                   10                  15

Gly Tyr Asp Pro Val Pro Glu Val Lys His Asn Cys Cys Asp Gln His
                20                  25                  30

Leu Ser Asp Ser Gly Lys Gln Thr Thr Glu Asp His His Lys Gly Ser
            35                  40                  45

<210> SEQ ID NO 445
<211> LENGTH: 147
<212> TYPE: DNA
<213> ORGANISM: Nodularia spumigena

<400> SEQUENCE: 445
tggatggcga ctcggcggat tttgcgttgt catcccttcc atcctggtgg atatgatcca      60
gttccagagg taaaacacaa ttgctgcgat cagcatctgt ccgattctgg gaaacagacc     120
acagaagacc atcacaaagg ctcgtag                                         147

<210> SEQ ID NO 446
<211> LENGTH: 34
<212> TYPE: PRT
<213> ORGANISM: Nostoc azollae

<400> SEQUENCE: 446

Trp Met Ala Thr Leu Arg Ile Leu Arg Cys His Pro Phe His Pro Gly
1               5                   10                  15

Gly Tyr Asp Pro Val Pro Gly Leu Ala Glu Lys Ser Cys Cys Asp His
                20                  25                  30

His Asp

<210> SEQ ID NO 447
<211> LENGTH: 105
<212> TYPE: DNA
<213> ORGANISM: Nostoc azollae

<400> SEQUENCE: 447
tggatggcaa ctttgcggat tttacgctgt catcctttcc atcctggtgg ttatgatcct      60
gtaccaggac tagcggaaaa atcctgttgt gaccatcatg attga                     105

<210> SEQ ID NO 448
<211> LENGTH: 28
<212> TYPE: PRT
<213> ORGANISM: Synechococcus

<400> SEQUENCE: 448

Trp Leu Thr Ala Lys Arg Phe Cys Arg Cys His Pro Leu His Pro Gly
1               5                   10                  15

Gly Tyr Asp Pro Val Pro Glu Lys Lys Ser Val Leu
                20                  25

<210> SEQ ID NO 449
<211> LENGTH: 87
<212> TYPE: DNA
<213> ORGANISM: Synechococcus

<400> SEQUENCE: 449
tggctaacag ccaagcgctt tgtcgctgt catccgcttc atcctggcgg gtatgatccg       60
gtaccggaga agaaatcggt actctaa                                         87

<210> SEQ ID NO 450
```

```
<211> LENGTH: 23
<212> TYPE: PRT
<213> ORGANISM: Prochlorococcus marinus

<400> SEQUENCE: 450

Trp Leu Thr Leu Arg Arg Leu Ser Arg Cys His Pro Phe Thr Pro Cys
1               5                   10                  15

Gly Cys Asp Pro Val Pro Asp
            20

<210> SEQ ID NO 451
<211> LENGTH: 72
<212> TYPE: DNA
<213> ORGANISM: Prochlorococcus marinus

<400> SEQUENCE: 451
tggctcaccc tgcggcgcct gtctcgttgc catcctttta ccccctgtgg ttgcgacccg      60
gtgcctgatt aa                                                         72

<210> SEQ ID NO 452
<211> LENGTH: 69
<212> TYPE: PRT
<213> ORGANISM: Escherichia coli

<400> SEQUENCE: 452

Met Ser Tyr Lys Lys Leu Tyr Gln Leu Thr Ala Ile Phe Ser Leu Pro
1               5                   10                  15

Leu Thr Ile Leu Leu Val Ser Leu Ser Ser Leu Arg Ile Val Gly Glu
            20                  25                  30

Gly Asn Ser Tyr Val Asp Val Phe Leu Ser Phe Ile Ile Phe Leu Gly
        35                  40                  45

Phe Ile Glu Leu Ile His Gly Ile Arg Lys Ile Leu Val Trp Ser Gly
    50                  55                  60

Trp Lys Asn Gly Ser
65

<210> SEQ ID NO 453
<211> LENGTH: 210
<212> TYPE: DNA
<213> ORGANISM: Escherichia coli

<400> SEQUENCE: 453
atgagttata aaaaactgta ccaattgacg gctatattta gtttacctct tactatctta      60 ttggttttcac tttcatccct tcggattgtt ggcgaaggga attcttatgt tgacgttttt    120
ctaagcttta taatatttct tggttttatt gagctgattc atgggattcg aaagattttg    180
gtctggtcag gctggaaaaa cggaagttaa                                      210

<210> SEQ ID NO 454
<211> LENGTH: 85
<212> TYPE: PRT
<213> ORGANISM: Escherichia coli

<400> SEQUENCE: 454

Met Gly Leu Lys Leu Asp Leu Thr Trp Phe Asp Lys Ser Thr Glu Asp
1               5                   10                  15

Phe Lys Gly Glu Glu Tyr Ser Lys Asp Phe Gly Asp Asp Gly Ser Val
            20                  25                  30

Met Glu Ser Leu Gly Val Pro Phe Lys Asp Asn Val Asn Asn Gly Cys
        35                  40                  45
```

Phe Asp Val Ile Ala Glu Trp Val Pro Leu Leu Gln Pro Tyr Phe Asn
    50                  55                  60

His Gln Ile Asp Ile Ser Asp Asn Glu Tyr Phe Val Ser Phe Asp Tyr
 65                  70                  75                  80

Arg Asp Gly Asp Trp
                85

<210> SEQ ID NO 455
<211> LENGTH: 258
<212> TYPE: DNA
<213> ORGANISM: Escherichia coli

<400> SEQUENCE: 455
atgggactta aattggattt aacttggttt gataaaagta cagaagattt taagggtgag      60
gagtattcaa aagattttgg agatgacggt tcagttatgg aaagtctagg tgtgccttt     120 aaggataatg ttaataacgg ttgctttgat gttatagctg aatgggtacc tttgctacaa    180
ccatacttta atcatcaaat tgatatttcc gataatgagt attttgtttc gtttgattat    240
cgtgatggtg attggtga                                                  258

<210> SEQ ID NO 456
<211> LENGTH: 113
<212> TYPE: PRT
<213> ORGANISM: Escherichia coli

<400> SEQUENCE: 456

Met Ser Leu Arg Tyr Tyr Ile Lys Asn Ile Leu Phe Gly Leu Tyr Cys
 1               5                  10                  15

Thr Leu Ile Tyr Ile Tyr Leu Ile Thr Lys Asn Ser Glu Gly Tyr Tyr
                20                  25                  30

Phe Leu Val Ser Asp Lys Met Leu Tyr Ala Ile Val Ile Ser Thr Ile
            35                  40                  45

Leu Cys Pro Tyr Ser Lys Tyr Ala Ile Glu Tyr Ile Ala Phe Asn Phe
    50                  55                  60

Ile Lys Lys Asp Phe Phe Glu Arg Arg Lys Asn Leu Asn Asn Ala Pro
 65                  70                  75                  80

Val Ala Lys Leu Asn Leu Phe Met Leu Tyr Asn Leu Leu Cys Leu Val
                85                  90                  95

Leu Ala Ile Pro Phe Gly Leu Leu Gly Leu Phe Ile Ser Ile Lys Asn
            100                 105                 110

Asn

<210> SEQ ID NO 457
<211> LENGTH: 342
<212> TYPE: DNA
<213> ORGANISM: Escherichia coli

<400> SEQUENCE: 457
atgagcttaa gatactacat aaaaaatatt ttatttggcc tgtactgcac acttatatat      60 atataccta taacaaaaaa cagcgaaggg tattatttcc ttgtgtcaga taagatgcta     120
tatgcaatag tgataagcac tattctatgt ccatattcaa aatatgctat tgaatacata    180
gcttttaact tcataaagaa agattttttc gaaagaagaa aaaacctaaa taacgccccc    240
gtagcaaaat taaccctatt tatgctatat aatctacttt gtttggtcct agcaatccca    300
tttggattgc taggactttt tatatcaata aagaataatt aa                      342

<210> SEQ ID NO 458
<211> LENGTH: 85
<212> TYPE: PRT
<213> ORGANISM: Escherichia coli

<400> SEQUENCE: 458

Met Gly Leu Lys Leu His Ile His Trp Phe Asp Lys Lys Thr Glu Glu
1               5                   10                  15

Phe Lys Gly Gly Glu Tyr Ser Lys Asp Phe Gly Asp Asp Gly Ser Val
            20                  25                  30

Ile Glu Ser Leu Gly Met Pro Leu Lys Asp Asn Ile Asn Asn Gly Trp
        35                  40                  45

Phe Asp Val Glu Lys Pro Trp Val Ser Ile Leu Gln Pro His Phe Lys
    50                  55                  60

Asn Val Ile Asp Ile Ser Lys Phe Asp Tyr Phe Val Ser Phe Val Tyr
65                  70                  75                  80

Arg Asp Gly Asn Trp
                85

<210> SEQ ID NO 459
<211> LENGTH: 258
<212> TYPE: DNA
<213> ORGANISM: Escherichia coli

<400> SEQUENCE: 459
atggggctta aattacatat tcattggttt gataagaaaa ccgaagagtt taaaggcggt    60
gaatactcaa aagacttcgg tgatgatggt tctgtcattg aaagtctggg gatgcccttta   120 aaggataata ttaataatgg ttggtttgat gttgaaaaac catgggtttc gatattacag   180
ccacacttta aaaatgtaat cgatattagt aaatttgatt actttgtatc ctttgtttac   240
cgggatggta actggtaa                                                  258

<210> SEQ ID NO 460
<211> LENGTH: 86
<212> TYPE: PRT
<213> ORGANISM: Escherichia coli

<400> SEQUENCE: 460

Met Glu Leu Lys His Ser Ile Ser Asp Tyr Thr Glu Ala Glu Phe Leu
1               5                   10                  15

Glu Phe Val Lys Lys Ile Cys Arg Ala Glu Gly Ala Thr Glu Glu Asp
            20                  25                  30

Asp Asn Lys Leu Val Arg Glu Phe Glu Arg Leu Thr Glu His Pro Asp
        35                  40                  45

Gly Ser Asp Leu Ile Tyr Tyr Pro Arg Asp Asp Arg Glu Asp Ser Pro
    50                  55                  60

Glu Gly Ile Val Lys Glu Ile Lys Glu Trp Arg Ala Ala Asn Gly Lys
65                  70                  75                  80

Ser Gly Phe Lys Gln Gly
                85

<210> SEQ ID NO 461
<211> LENGTH: 261
<212> TYPE: DNA
<213> ORGANISM: Escherichia coli

<400> SEQUENCE: 461
atggaactga acatagtat tagtgattat accgaggctg aatttctgga gtttgtaaaa    60

```
aaaatatgta gagctgaagg tgctactgaa gaggatgaca ataaattagt gagagagttt    120
gagcgattaa ctgagcaccc agatggttca gatctgattt attatcctcg cgatgacagg    180
gaagatagtc ctgaagggat tgtcaaggaa attaagaat ggcgagctgc taacggtaag     240
tcaggattta aacagggctg a                                              261
```

<210> SEQ ID NO 462
<211> LENGTH: 178
<212> TYPE: PRT
<213> ORGANISM: Citrobacter freundii

<400> SEQUENCE: 462

```
Met Met Asn Glu His Ser Ile Asp Thr Asp Asn Arg Lys Ala Asn Asn
1               5                   10                  15

Ala Leu Tyr Leu Phe Ile Ile Gly Leu Ile Pro Leu Leu Cys Ile
            20                  25                  30

Phe Val Val Tyr Tyr Lys Thr Pro Asp Ala Leu Leu Leu Arg Lys Ile
        35                  40                  45

Ala Thr Ser Thr Glu Asn Leu Pro Ser Ile Thr Ser Ser Tyr Asn Pro
    50                  55                  60

Leu Met Thr Lys Val Met Asp Ile Tyr Cys Lys Thr Ala Pro Phe Leu
65                  70                  75                  80

Ala Leu Ile Leu Tyr Ile Leu Thr Phe Lys Ile Arg Lys Leu Ile Asn
                85                  90                  95

Asn Thr Asp Arg Asn Thr Val Leu Arg Ser Cys Leu Leu Ser Pro Leu
            100                 105                 110

Val Tyr Ala Ala Ile Val Tyr Leu Phe Cys Phe Arg Asn Phe Glu Leu
        115                 120                 125

Thr Thr Ala Gly Arg Pro Val Arg Leu Met Ala Thr Asn Asp Ala Thr
    130                 135                 140

Leu Leu Leu Phe Tyr Ile Gly Leu Tyr Ser Ile Ile Phe Phe Thr Thr
145                 150                 155                 160

Tyr Ile Thr Leu Phe Thr Pro Val Thr Ala Phe Lys Leu Leu Lys Lys
                165                 170                 175

Arg Gln
```

<210> SEQ ID NO 463
<211> LENGTH: 537
<212> TYPE: DNA
<213> ORGANISM: Citrobacter freundii

<400> SEQUENCE: 463

```
atgatgaatg aacactcaat agatacggac aacagaaagg ccaataacgc attgtattta     60
tttataataa tcggattaat accattattg tgcatttttg ttgtttacta caaaacgcca    120
gacgctttac ttttacgtaa aattgctaca agcactgaga atctcccgtc aataacatcc    180
tcctacaacc cattaatgac aaaggttatg gatatttatt gtaaaacagc cctttcctt    240 gccttaatac tatacatcct aacctttaaa atcagaaaat taatcaacaa caccgacagg    300
aacactgtac ttagatcttg tttattaagt ccattggtct atgcagcaat tgtttatcta    360
ttctgcttcc gaaattttga gttaacaaca gccggaaggc ctgtcagatt aatggccacc    420
aatgacgcaa cactattgtt attttatatt ggtctgtact caataatttt ctttacaacc    480
tatatcacgc tattcacacc agtcactgca tttaaattat taaaaaaaag gcagtaa      537
```

<210> SEQ ID NO 464
<211> LENGTH: 111
<212> TYPE: PRT
<213> ORGANISM: Escherichia coli

<400> SEQUENCE: 464

Met Asn Arg Lys Tyr Tyr Phe Asn Asn Met Trp Trp Gly Trp Val Thr
1               5                   10                  15

Gly Gly Tyr Met Leu Tyr Met Ser Trp Asp Tyr Glu Phe Lys Tyr Arg
                20                  25                  30

Leu Leu Phe Trp Cys Ile Ser Leu Cys Gly Met Val Leu Tyr Pro Val
            35                  40                  45

Ala Lys Trp Tyr Ile Glu Asp Thr Ala Leu Lys Phe Thr Arg Pro Asp
        50                  55                  60

Phe Trp Asn Ser Gly Phe Phe Ala Asp Thr Pro Gly Lys Met Gly Leu
65                  70                  75                  80

Leu Ala Val Tyr Thr Gly Thr Val Phe Ile Leu Ser Leu Pro Leu Ser
                85                  90                  95

Met Ile Tyr Ile Leu Ser Val Ile Ile Lys Arg Leu Ser Val Arg
                100                 105                 110

<210> SEQ ID NO 465
<211> LENGTH: 336
<212> TYPE: DNA
<213> ORGANISM: Escherichia coli

<400> SEQUENCE: 465
atgaacagaa aatattattt taataatatg tggtggggat gggtgacggg gggatatatg      60
ctgtatatgt catgggatta tgagtttaaa tacagattac tgttctggtg tatttctctc     120
tgcggaatgg ttttgtatcc ggttgcaaaa tggtatattg aagatacagc tctaaaattt     180
acccggcctg atttctggaa cagcggtttt tttgctgata cacctggaaa atgggggttg     240
cttgcggttt atacgggtac tgttttcata ttatctcttc cgttaagtat gatatatatt     300
ctttctgtta ttataaaaag gctgtctgta agatag                              336

<210> SEQ ID NO 466
<211> LENGTH: 115
<212> TYPE: PRT
<213> ORGANISM: Escherichia coli

<400> SEQUENCE: 466

Met Lys Leu Asp Ile Ser Val Lys Tyr Leu Leu Lys Ser Leu Ile Pro
1               5                   10                  15

Ile Leu Ile Ile Leu Thr Val Phe Tyr Leu Gly Trp Lys Asp Asn Gln
                20                  25                  30

Glu Asn Ala Arg Met Phe Tyr Ala Phe Ile Gly Cys Ile Ser Ala
            35                  40                  45

Ile Thr Phe Pro Phe Ser Met Arg Ile Ile Gln Lys Met Val Ile Arg
        50                  55                  60

Phe Thr Gly Lys Glu Phe Trp Gln Lys Asp Phe Thr Asn Pro Val
65                  70                  75                  80

Gly Gly Ser Leu Thr Ala Ile Phe Glu Leu Phe Cys Phe Val Ile Ser
                85                  90                  95

Val Pro Val Val Ala Ile Tyr Leu Ile Phe Ile Leu Cys Lys Ala Leu
                100                 105                 110

Ser Gly Lys
        115

<210> SEQ ID NO 467
<211> LENGTH: 348
<212> TYPE: DNA
<213> ORGANISM: Escherichia coli

<400> SEQUENCE: 467

```
atgaaactgg atatatctgt aaagtattta ctgaaaagcc tgataccaat cctcattatt      60
cttacagttt tttatctggg atggaaagat aaccaggaaa atgcaagaat gttttatgcg     120
ttcatcggat gcattatcag tgccattact tttccttttt caatgaggat aatacagaaa     180
atggtaataa ggtttacagg aaagaattc tggcaaaaag acttctttac aaatccagtt      240
ggcggaagct taactgcaat atttgaatta ttctgtttcg ttatatcagt tcctgtggtt     300
gccatttact taatttttat actctgcaaa gccctttcag gaaaatga                  348
```

<210> SEQ ID NO 468
<211> LENGTH: 131
<212> TYPE: PRT
<213> ORGANISM: Escherichia coli

<400> SEQUENCE: 468

```
Met His Asn Thr Leu Leu Glu Lys Ile Ile Ala Tyr Leu Ser Leu Pro
1               5                   10                  15

Gly Phe His Ser Leu Asn Asn Pro Pro Leu Ser Glu Ala Phe Asn Leu
            20                  25                  30

Tyr Val His Thr Ala Pro Leu Ala Ala Thr Ser Leu Phe Ile Phe Thr
        35                  40                  45

His Lys Glu Leu Glu Leu Lys Pro Lys Ser Ser Pro Leu Arg Ala Leu
    50                  55                  60

Lys Ile Leu Thr Pro Phe Thr Ile Leu Tyr Ile Ser Met Ile Tyr Cys
65                  70                  75                  80

Phe Leu Leu Thr Asp Thr Glu Leu Thr Leu Ser Ser Lys Thr Phe Val
                85                  90                  95

Leu Ile Val Lys Lys Arg Ser Val Phe Val Phe Phe Leu Tyr Asn Thr
            100                 105                 110

Ile Tyr Trp Asp Ile Tyr Ile His Ile Phe Val Leu Leu Val Pro Tyr
        115                 120                 125

Arg Asn Ile
    130
```

<210> SEQ ID NO 469
<211> LENGTH: 396
<212> TYPE: DNA
<213> ORGANISM: Escherichia coli

<400> SEQUENCE: 469

```
atgcacaata cactcctcga aaaaatcatc gcatacctat ccctaccagg atttcattca      60
ttaaacaacc cgcccctaag cgaagcattc aatctctatg ttcatacagc cccttttagct    120
gcaaccagct tattcatatt cacacacaaa gaattagagt taaaaccaaa gtcgtcacct    180
ctgcgggcac taaagatatt aactcctttc actattcttt atatatccat gatatactgt    240
ttcttgctaa ctgacacaga actaaccttg tcatcaaaaa catttgtatt aatagtcaaa    300
aaacgatctg tttttgtctt ttttctatat aacactatat attgggatat atatattcac    360
atatttgtac ttttggttcc ttataggaac atataa                               396
```

<210> SEQ ID NO 470
<211> LENGTH: 85
<212> TYPE: PRT
<213> ORGANISM: Escherichia coli

<400> SEQUENCE: 470

Met Glu Leu Lys Asn Ser Ile Ser Asp Tyr Thr Glu Thr Glu Phe Lys
1               5                   10                  15

Lys Ile Ile Glu Asp Ile Ile Asn Cys Glu Gly Asp Glu Lys Lys Gln
                20                  25                  30

Asp Asp Asn Leu Glu His Phe Ile Ser Val Thr Glu His Pro Ser Gly
            35                  40                  45

Ser Asp Leu Ile Tyr Tyr Pro Glu Gly Asn Asn Asp Gly Ser Pro Glu
    50                  55                  60

Ala Val Ile Lys Glu Ile Lys Glu Trp Arg Ala Ala Asn Gly Lys Ser
65                  70                  75                  80

Gly Phe Lys Gln Gly
                85

<210> SEQ ID NO 471
<211> LENGTH: 258
<212> TYPE: DNA
<213> ORGANISM: Escherichia coli

<400> SEQUENCE: 471
atggaactga aaacagcat tagtgattac actgaaactg aattcaaaaa aattattgaa      60
gacatcatca attgtgaagg tgatgaaaaa aaacaggatg ataacctcga gcatttata     120 agtgttactg agcatcctag tggttctgat ctgatttatt acccagaagg taataatgat    180
ggtagccctg aagctgttat taaagagatt aaagaatggc gagctgctaa cggtaagtca    240
ggatttaaac agggctga                                                  258

<210> SEQ ID NO 472
<211> LENGTH: 98
<212> TYPE: PRT
<213> ORGANISM: Lactococcus lactis subsp. lactis

<400> SEQUENCE: 472

Met Lys Lys Lys Gln Ile Glu Phe Glu Asn Glu Leu Arg Ser Met Leu
1               5                   10                  15

Ala Thr Ala Leu Glu Lys Asp Ile Ser Gln Glu Glu Arg Asn Ala Leu
                20                  25                  30

Asn Ile Ala Glu Lys Ala Leu Asp Asn Ser Glu Tyr Leu Pro Lys Ile
            35                  40                  45

Ile Leu Asn Leu Arg Lys Ala Leu Thr Pro Leu Ala Ile Asn Arg Thr
    50                  55                  60

Leu Asn His Asp Leu Ser Glu Leu Tyr Lys Phe Ile Thr Ser Ser Lys
65                  70                  75                  80

Ala Ser Asn Lys Asn Leu Gly Gly Gly Leu Ile Met Ser Trp Gly Arg
                85                  90                  95

Leu Phe

<210> SEQ ID NO 473
<211> LENGTH: 297
<212> TYPE: DNA
<213> ORGANISM: Lactococcus lactis subsp. lactis

<400> SEQUENCE: 473

```
atgaaaaaaa aacaaataga atttgaaaac gagctaagaa gtatgttggc taccgccctt    60
gaaaaagaca ttagtcaaga ggaaagaaat gctctgaata ttgcagaaaa ggcgcttgac   120
aattctgaat atttaccaaa aattatttta aacctcagaa aagccctaac tccattagct   180
ataaatcgaa cacttaacca tgatttatct gaactgtata aattcattac aagttccaaa   240
gcatcaaaca aaaatttagg tggtggttta attatgtcgt ggggacgact attctaa      297
```

<210> SEQ ID NO 474
<211> LENGTH: 98
<212> TYPE: PRT
<213> ORGANISM: Lactococcus lactis subsp. cremoris

<400> SEQUENCE: 474

```
Met Lys Lys Lys Gln Ile Glu Phe Glu Asn Glu Leu Arg Ser Met Leu
1               5                   10                  15

Ala Thr Ala Leu Glu Lys Asp Ile Ser Gln Glu Arg Asn Ala Leu
            20                  25                  30

Asn Ile Ala Glu Lys Ala Leu Asp Asn Ser Glu Tyr Leu Pro Lys Ile
        35                  40                  45

Ile Leu Asn Leu Arg Lys Ala Leu Thr Pro Leu Ala Ile Asn Arg Thr
50                  55                  60

Leu Asn His Asp Leu Ser Glu Leu Tyr Lys Phe Ile Thr Ser Ser Lys
65                  70                  75                  80

Ala Ser Asn Lys Asn Leu Gly Gly Gly Leu Ile Met Ser Trp Gly Arg
                85                  90                  95

Leu Phe
```

<210> SEQ ID NO 475
<211> LENGTH: 297
<212> TYPE: DNA
<213> ORGANISM: Lactococcus lactis subsp. cremoris

<400> SEQUENCE: 475

```
atgaaaaaaa aacaaataga atttgaaaac gagctaagaa gtatgttggc taccgccctt    60
gaaaaagaca ttagtcaaga ggaaagaaat gctctgaata ttgcagaaaa ggcgcttgac   120
aattctgaat atttaccaaa aattatttta aacctcagaa aagccctaac tccattagct   180
ataaatcgaa cacttaacca tgatttatct gaactgtata aattcattac aagttccaaa   240
gcatcaaaca aaaatttagg tggtggttta attatgtcgt ggggacgact attctaa      297
```

<210> SEQ ID NO 476
<211> LENGTH: 87
<212> TYPE: PRT
<213> ORGANISM: Escherichia coli

<400> SEQUENCE: 476

```
Met Asn Lys Met Ala Met Ile Asp Leu Ala Lys Leu Phe Leu Ala Ser
1               5                   10                  15

Lys Ile Thr Ala Ile Glu Phe Ser Glu Arg Ile Cys Val Glu Arg Arg
            20                  25                  30

Arg Leu Tyr Gly Val Lys Asp Leu Ser Pro Asn Ile Leu Asn Cys Gly
        35                  40                  45

Glu Glu Leu Phe Met Ala Ala Glu Arg Phe Glu Pro Asp Ala Asp Arg
    50                  55                  60

Ala Asn Tyr Glu Ile Asp Asp Asn Gly Leu Lys Val Glu Val Arg Ser
65                  70                  75                  80
```

Ile Leu Glu Lys Phe Lys Leu
            85

<210> SEQ ID NO 477
<211> LENGTH: 249
<212> TYPE: DNA
<213> ORGANISM: Escherichia coli

<400> SEQUENCE: 477
atgatcgatt tggcgaaatt attttagct tcgaaaatta cagtgattga gttttcagag      60
cgaatttgtg ttgaacggag aagattgtat ggtgttaagg atttgtctcc gaatatatta    120
aattgtgggg aagagttgtc tatggctgct gagcgatttg agcctgatgc agatagggct    180
aattatgaaa ttgatgataa tggacttaag gtcgaggtcc gatctatctt ggaaaaactt    240
aaatcataa                                                            249

<210> SEQ ID NO 478
<211> LENGTH: 83
<212> TYPE: PRT
<213> ORGANISM: Escherichia coli

<400> SEQUENCE: 478

Met Lys Leu Ser Pro Lys Ala Ala Ile Glu Val Cys Asn Glu Ala Ala
1               5                   10                  15

Lys Lys Gly Leu Trp Ile Leu Gly Ile Asp Gly Gly His Trp Leu Asn
            20                  25                  30

Pro Gly Phe Arg Ile Asp Ser Ser Ala Ser Trp Thr Tyr Asp Met Pro
        35                  40                  45

Glu Glu Tyr Lys Ser Lys Ile Pro Glu Asn Asn Arg Leu Ala Ile Glu
    50                  55                  60

Asn Ile Lys Asp Asp Ile Glu Asn Gly Tyr Thr Ala Phe Ile Ile Thr
65                  70                  75                  80

Leu Lys Met

<210> SEQ ID NO 479
<211> LENGTH: 243
<212> TYPE: DNA
<213> ORGANISM: Escherichia coli

<400> SEQUENCE: 479
atgaagttat caccaaaagc tgcaatagaa gtttgtaatg aagcagcgaa aaaaggctta     60
tggattttgg gcattgatgg tgggcattgg ctgaatcctg gattcaggat agatagttca    120
gcatcatgga catatgatat gccggagaat acaaatcaaa aatccctgaa ataataagat    180
tggctattga aaatattaaa gatgatattg agaatggata cactgctttc attatcacgt    240
taa                                                                  243

<210> SEQ ID NO 480
<211> LENGTH: 85
<212> TYPE: PRT
<213> ORGANISM: Escherichia coli

<400> SEQUENCE: 480

Met Gly Leu Lys Leu His Ile Asn Trp Phe Asp Lys Arg Thr Glu Glu
1               5                   10                  15

Phe Lys Gly Gly Glu Tyr Ser Lys Asp Phe Gly Asp Asp Gly Ser Val
            20                  25                  30

Ile Glu Arg Leu Gly Met Pro Phe Lys Asp Asn Ile Asn Asn Gly Trp

```
                35                  40                  45
Phe Asp Val Ile Ala Glu Trp Val Pro Leu Leu Gln Pro Tyr Phe Asn
             50                  55                  60

His Gln Ile Asp Ile Ser Asp Asn Glu Tyr Phe Val Ser Phe Asp Tyr
 65                  70                  75                  80

Arg Asp Gly Asp Trp
                85

<210> SEQ ID NO 481
<211> LENGTH: 258
<212> TYPE: DNA
<213> ORGANISM: Escherichia coli

<400> SEQUENCE: 481
atggggctta aattacatat taattggttt gataagacga ccgaggaatt taaaggtggt    60
gagtattcaa aagattttgg agatgatggc tcggtcattg aacgtcttgg aatgccttta   120
aaagataata tcaataatgg ttggtttgat gttatagctg aatgggtacc tttgctacaa   180
ccatacttta atcatcaaat tgatatttcc gataatgagt attttgtttc gtttgattat   240
cgtgatggtg attggtga                                                 258

<210> SEQ ID NO 482
<211> LENGTH: 85
<212> TYPE: PRT
<213> ORGANISM: Escherichia coli

<400> SEQUENCE: 482

Met Glu Leu Lys Lys Ser Ile Gly Asp Tyr Thr Glu Thr Glu Phe Lys
  1               5                  10                  15

Lys Ile Ile Glu Asn Ile Ile Asn Cys Glu Gly Asp Glu Lys Lys Gln
                 20                  25                  30

Asp Asp Asn Leu Glu His Phe Ile Ser Val Thr Glu His Pro Ser Gly
             35                  40                  45

Ser Asp Leu Ile Tyr Tyr Pro Glu Gly Asn Asn Asp Gly Ser Pro Glu
 50                  55                  60

Ala Val Ile Lys Glu Ile Lys Glu Trp Arg Ala Ala Asn Gly Lys Ser
 65                  70                  75                  80

Gly Phe Lys Gln Gly
                85

<210> SEQ ID NO 483
<211> LENGTH: 258
<212> TYPE: DNA
<213> ORGANISM: Escherichia coli

<400> SEQUENCE: 483
gtggagctaa agaaaagtat tggtgattac actgaaaccg aattcaaaaa aattattgaa    60
aacatcatca attgtgaagg tgatgaaaaa aacaggatg ataacctcga gcatttata    120 agtgttactg agcatcctag tggttctgat ctgatttatt acccagaagg taataatgat   180
ggtagccctg aagctgttat aaagagatt aaagaatggc gagctgctaa cggtaagtca   240
ggatttaaac agggctga                                                 258

<210> SEQ ID NO 484
<211> LENGTH: 86
<212> TYPE: PRT
<213> ORGANISM: Escherichia coli
```

-continued

<400> SEQUENCE: 484

Met Glu Leu Lys His Ser Ile Ser Asp Tyr Thr Glu Ala Glu Phe Leu
1               5                   10                  15

Gln Leu Val Thr Thr Ile Cys Asn Ala Asp Thr Ser Ser Glu Glu Glu
            20                  25                  30

Leu Val Lys Leu Val Thr His Phe Glu Glu Met Thr Glu His Pro Ser
        35                  40                  45

Gly Ser Asp Leu Ile Tyr Tyr Pro Lys Glu Gly Asp Asp Ser Pro
    50                  55                  60

Ser Gly Ile Val Asn Thr Val Lys Gln Trp Arg Ala Ala Asn Gly Lys
65                  70                  75                  80

Ser Gly Phe Lys Gln Gly
                85

<210> SEQ ID NO 485
<211> LENGTH: 261
<212> TYPE: DNA
<213> ORGANISM: Escherichia coli

<400> SEQUENCE: 485
atggaactga agcatagcat tagtgattat acagaagctg aattttaca acttgtaaca      60 acaatttgta atgcgaacac ttccagtgaa gaagaactgg ttaaattggt tacacacttt     120
gaggaaatga ctgagcaccc tagtggtagt gatttaatat attacccaaa agaaggtgat     180
gatgactcac cttcaggtat tgtaaacaca gtaaacaat ggcgagccgc taacggtaag      240
tcaggattta aacagggcta a                                               261

<210> SEQ ID NO 486
<211> LENGTH: 141
<212> TYPE: PRT
<213> ORGANISM: Escherichia coli

<400> SEQUENCE: 486

Met Leu Thr Leu Tyr Gly Tyr Ile Arg Asn Val Phe Leu Tyr Arg Met
1               5                   10                  15

Asn Asp Arg Ser Cys Gly Asp Phe Met Lys Val Ile Ser Met Lys Phe
            20                  25                  30

Ile Phe Ile Leu Thr Ile Ile Ala Leu Ala Ala Val Phe Phe Trp Ser
        35                  40                  45

Glu Asp Lys Gly Pro Ala Cys Tyr Gln Val Ser Asp Glu Gln Ala Arg
    50                  55                  60

Thr Phe Val Lys Asn Asp Tyr Leu Gln Arg Met Lys Arg Trp Asp Asn
65                  70                  75                  80

Asp Val Gln Leu Leu Gly Thr Glu Ile Pro Lys Ile Thr Trp Glu Lys
                85                  90                  95

Ile Glu Arg Ser Leu Thr Asp Val Glu Asp Glu Lys Thr Leu Leu Val
            100                 105                 110

Pro Phe Lys Ala Glu Gly Pro Asp Gly Lys Arg Met Tyr Tyr Gly Met
        115                 120                 125

Tyr His Cys Glu Glu Gly Tyr Val Glu Tyr Ala Asn Asp
    130                 135                 140

<210> SEQ ID NO 487
<211> LENGTH: 354
<212> TYPE: DNA
<213> ORGANISM: Escherichia coli

<400> SEQUENCE: 487

| | | | | |
|---|---|---|---|---|
| atgaaagtaa ttagcatgaa atttatttt attttaacga ttattgctct tgctgctgtt | 60 |
| ttttctggt ctgaagataa aggtccggca tgctatcagg tcagcgatga acaggccaga | 120 |
| acgtttgtaa aaaatgatta cctgcaaaga atgaaacgct gggacaacga tgtacaactt | 180 |
| cttggtacag aaatcccgaa aattacatgg gaaaagattg agagaagttt aacagatgtt | 240 |
| gaagatgaaa aaacacttct tgtcccattt aaagctgaag gcccggacgg taagagaatg | 300 |
| tattatggca tgtaccattg tgaggaggga tatgttgaat atgcgaatga ctaa | 354 |

<210> SEQ ID NO 488
<211> LENGTH: 175
<212> TYPE: PRT
<213> ORGANISM: Escherichia coli

<400> SEQUENCE: 488

```
Met Thr Ser Asn Lys Asp Lys Asn Lys Ala Asn Glu Ile Leu Tyr
1               5                   10                  15

Ala Phe Ser Ile Ile Gly Ile Ile Pro Leu Met Ala Ile Leu Ile Leu
            20                  25                  30

Arg Ile Asn Asp Pro Tyr Ser Gln Val Leu Tyr Tyr Leu Tyr Asn Lys
        35                  40                  45

Val Ala Phe Leu Pro Ser Ile Thr Ser Leu His Asp Pro Val Met Thr
    50                  55                  60

Thr Leu Met Ser Asn Tyr Asn Lys Thr Ala Pro Val Met Gly Ile Leu
65                  70                  75                  80

Val Phe Leu Cys Thr Tyr Lys Thr Arg Glu Ile Ile Lys Pro Val Thr
                85                  90                  95

Arg Lys Leu Val Val Gln Ser Cys Phe Trp Gly Pro Val Phe Tyr Ala
            100                 105                 110

Ile Leu Ile Tyr Ile Thr Leu Phe Tyr Asn Leu Glu Leu Thr Thr Ala
        115                 120                 125

Gly Gly Phe Phe Lys Leu Leu Ser His Asn Val Ile Thr Leu Phe Ile
    130                 135                 140

Leu Tyr Cys Ser Ile Tyr Phe Thr Val Leu Thr Met Thr Tyr Ala Ile
145                 150                 155                 160

Leu Leu Met Pro Leu Leu Val Ile Lys Tyr Phe Lys Gly Arg Gln
                165                 170                 175
```

<210> SEQ ID NO 489
<211> LENGTH: 528
<212> TYPE: DNA
<213> ORGANISM: Escherichia coli

<400> SEQUENCE: 489

| | | | | |
|---|---|---|---|---|
| atgaccagca ataaagataa gaacaagaaa gcaaacgaaa tattatatgc attttccata | 60 |
| atcgggatta ttccattaat ggctatatta tacttcgaa taaatgatcc atattctcaa | 120 |
| gtgctgtact acttatataa taaggtgcca tttctcccct ctattacatc attgcatgat | 180 |
| cccgtcatga caacacttat gtcaaactac aacaagacag cgccagttat gggtattctc | 240 |
| gttttctttt gcacatataa gacaagagaa atcataaagc cagtaacaag aaaacttgtt | 300 |
| gtgcaatcct gtttctgggg gccgtttttt tatgccattc tgatttatat cacactgttc | 360 |
| tataatctgg aactaacaac agcaggtggt ttttttaaat tattatctca taatgtcatc | 420 |
| actctgttta ttttatattg ctccatttac tttactgttt taaccatgac atatgcgatt | 480 |

```
ttactgatgc cattacttgt cattaaatat tttaaaggga ggcagtaa              528
```

```
<210> SEQ ID NO 490
<211> LENGTH: 78
<212> TYPE: PRT
<213> ORGANISM: Escherichia coli

<400> SEQUENCE: 490
```

```
Met Asp Arg Lys Arg Thr Lys Leu Glu Leu Leu Phe Ala Phe Ile Ile
1               5                   10                  15

Asn Ala Thr Ala Ile Tyr Ile Ala Leu Ala Ile Tyr Asp Cys Val Phe
            20                  25                  30

Arg Gly Lys Asp Phe Leu Ser Met His Thr Phe Cys Phe Ser Ala Leu
        35                  40                  45

Met Ser Ala Ile Cys Tyr Phe Val Gly Asp Asn Tyr Tyr Ser Ile Ser
    50                  55                  60

Asp Lys Ile Lys Arg Arg Ser Tyr Glu Asn Ser Asp Ser Lys
65                  70                  75
```

```
<210> SEQ ID NO 491
<211> LENGTH: 237
<212> TYPE: DNA
<213> ORGANISM: Escherichia coli

<400> SEQUENCE: 491
atggatagaa aagaacaaa attagagttg ttatttgcat ttataataaa tgccaccgca    60
atatatattg cattagctat atatgattgt gtttttagag gaaaggactt tttatccatg   120
catacatttt gcttctctgc attaatgtct gcaatatgtt actttgttgg tgataattat   180
tattcaatat ccgataagat aaaaaggaga tcatatgaga actctgactc taaatga     237
```

```
<210> SEQ ID NO 492
<211> LENGTH: 113
<212> TYPE: PRT
<213> ORGANISM: Shigella sonnei

<400> SEQUENCE: 492
```

```
Met Ser Leu Arg Tyr Tyr Ile Lys Asn Ile Leu Phe Gly Leu Tyr Cys
1               5                   10                  15

Ala Leu Ile Tyr Ile Tyr Leu Ile Thr Lys Asn Asn Glu Gly Tyr Tyr
            20                  25                  30

Phe Leu Ala Ser Asp Lys Met Leu Tyr Ala Ile Val Ile Ser Thr Ile
        35                  40                  45

Leu Cys Pro Tyr Ser Lys Tyr Ala Ile Glu His Ile Phe Phe Lys Phe
    50                  55                  60

Ile Lys Lys Asp Phe Phe Arg Lys Arg Lys Asn Leu Asn Lys Cys Pro
65                  70                  75                  80

Arg Gly Lys Ile Lys Pro Tyr Leu Cys Val Tyr Asn Leu Leu Cys Leu
                85                  90                  95

Val Leu Ala Ile Pro Phe Gly Leu Leu Gly Leu Val Tyr Ile Asn Lys
                100                 105                 110

Glu
```

```
<210> SEQ ID NO 493
<211> LENGTH: 342
<212> TYPE: DNA
<213> ORGANISM: Shigella sonnei

<400> SEQUENCE: 493
```

```
atgagtttaa gatactacat aaaaaatatt ttgtttggcc tatactgcgc acttatatat      60 atataccta taacaaaaaa caacgaaggg tattatttcc tagcgtcaga taagatgcta     120
tacgcaatag tgataagcac tattctatgc ccatattcaa aatatgctat tgaacacata     180
ttttttaagt tcataaagaa agattttttc agaaaaagaa aaaacctaaa taatgcccc     240 cgtggcaaaa ttaaaccgta tttatgcgta tacaatctac tttgtttggt cctagcaatc     300
ccatttggat tgctaggact tgtttatatc aataaagaat aa                        342
```

<210> SEQ ID NO 494
<211> LENGTH: 113
<212> TYPE: PRT
<213> ORGANISM: Escherichia coli

<400> SEQUENCE: 494

```
Met Ser Leu Arg Tyr Tyr Ile Lys Asn Ile Leu Phe Gly Leu Tyr Cys
1               5                   10                  15

Thr Leu Ile Tyr Ile Tyr Leu Ile Thr Lys Asn Ser Glu Glu Tyr Tyr
            20                  25                  30

Phe Leu Val Thr Asp Lys Met Leu Tyr Ala Ile Val Ile Ser Thr Ile
        35                  40                  45

Leu Cys Pro Tyr Ser Lys Tyr Ala Ile Glu His Ile Ala Phe Asn Phe
    50                  55                  60

Ile Lys Lys His Phe Phe Glu Arg Arg Lys Asn Leu Asn Asn Ala Pro
65                  70                  75                  80

Val Ala Lys Leu Asn Leu Phe Met Leu Tyr Asn Leu Leu Cys Leu Val
                85                  90                  95

Leu Ala Ile Pro Phe Gly Leu Leu Gly Leu Phe Ile Ser Ile Lys Asn
            100                 105                 110

Asn
```

<210> SEQ ID NO 495
<211> LENGTH: 342
<212> TYPE: DNA
<213> ORGANISM: Escherichia coli

<400> SEQUENCE: 495

```
atgagcttaa gatactacat aaaaaatatt ttatttggcc tgtactgcac acttatatat      60 atataccta taacaaaaaa cagcgaagag tattatttcc ttgtgacaga taagatgcta     120
tatgcaatag tgataagcac tattctatgt ccatattcaa aatatgctat tgaacacata     180
gcttttaact tcataaagaa acatttttc gaaagaagaa aaaacctaaa taacgccccc     240
gtagcaaaat taaacctatt tatgctatat aatctacttt gtttggtcct agcaatccca     300
tttggattgc taggactttt tatatcaata agaataatt aa                         342
```

<210> SEQ ID NO 496
<211> LENGTH: 113
<212> TYPE: PRT
<213> ORGANISM: Leuconostoc gelidum

<400> SEQUENCE: 496

```
Met Arg Lys Asn Asn Ile Leu Leu Asp Asp Ala Lys Ile Tyr Thr Asn
1               5                   10                  15

Lys Leu Tyr Leu Leu Leu Ile Asp Arg Lys Asp Asp Ala Gly Tyr Gly
            20                  25                  30

Asp Ile Cys Asp Val Leu Phe Gln Val Ser Lys Lys Leu Asp Ser Thr
```

```
                  35                  40                  45
Lys Asn Val Glu Ala Leu Ile Asn Arg Leu Val Asn Tyr Ile Arg Ile
 50                  55                  60

Thr Ala Ser Thr Asn Arg Ile Lys Phe Ser Lys Asp Glu Glu Ala Val
 65                  70                  75                  80

Ile Ile Glu Leu Gly Val Ile Gly Gln Lys Ala Gly Leu Asn Gly Gln
                 85                  90                  95

Tyr Met Ala Asp Phe Ser Asp Lys Ser Gln Phe Tyr Ser Ile Phe Glu
                100                 105                 110

Arg
```

<210> SEQ ID NO 497
<211> LENGTH: 342
<212> TYPE: DNA
<213> ORGANISM: Leuconostoc gelidum

<400> SEQUENCE: 497

```
ttgagaaaaa ataacatttt attggacgat gctaaaatat acacgaacaa actctatttg      60
ctattaatcg atagaaaaga tgacgctggg tatggagata tttgtgatgt tttgtttcag     120
gtatccaaaa aattagatag cacaaaaaat gtagaagcat tgattaaccg attggtcaat     180
tatatacgaa ttaccgcttc aacaaacaga attaagtttt caaaagatga agaggctgta     240
attatagaac ttggtgtaat tggtcagaag gctggattaa acggccaata catggctgat     300
ttttctgaca aatctcagtt ttatagtatc tttgaaagat aa                        342
```

<210> SEQ ID NO 498
<211> LENGTH: 91
<212> TYPE: PRT
<213> ORGANISM: Lactococcus lactis subsp. cremoris

<400> SEQUENCE: 498

```
Met Lys Lys Lys Val Asp Thr Glu Lys Gln Ile Thr Ser Trp Ala Ser
  1               5                  10                  15

Asp Leu Ala Ser Lys Asn Glu Thr Lys Val Gln Glu Lys Leu Ile Leu
                 20                  25                  30

Ser Ser Tyr Ile Gln Asp Ile Glu Asn His Val Tyr Phe Pro Lys Ala
                 35                  40                  45

Met Ile Ser Leu Glu Lys Lys Leu Arg Asp Gln Asn Asn Ile Cys Ala
 50                  55                  60

Leu Ser Lys Glu Val Asn Gln Phe Tyr Phe Lys Val Val Glu Val Asn
 65                  70                  75                  80

Gln Arg Lys Ser Trp Met Val Gly Leu Ile Val
                 85                  90
```

<210> SEQ ID NO 499
<211> LENGTH: 276
<212> TYPE: DNA
<213> ORGANISM: Lactococcus lactis subsp. cremoris

<400> SEQUENCE: 499

```
atgaaaaaaa aagttgatac agaaaaacaa attacttctt gggcatctga cttagcttcc      60
aaaaatgaaa caaaggttca gaaaaaatta atactgtctt cttatattca ggacatcgaa     120
aaccatgttt actttccaaa agcaatgatt tctttagaaa aaaaattacg agaccaaaat     180
aatatttgcg ctttatcaaa agaagtcaat cagttttatt ttaaagttgt tgaagtaaat     240
caaagaaaat cctggatggt aggtttgata gtttaa                              276
```

<210> SEQ ID NO 500
<211> LENGTH: 112
<212> TYPE: PRT
<213> ORGANISM: Pediococcus acidilactici

<400> SEQUENCE: 500

Met Asn Lys Thr Lys Ser Glu His Ile Lys Gln Gln Ala Leu Asp Leu
1               5                   10                  15

Phe Thr Arg Leu Gln Phe Leu Leu Gln Lys His Asp Thr Ile Glu Pro
            20                  25                  30

Tyr Gln Tyr Val Leu Asp Ile Leu Glu Thr Gly Ile Ser Lys Thr Lys
        35                  40                  45

His Asn Gln Gln Thr Pro Glu Arg Gln Ala Arg Val Val Tyr Asn Lys
    50                  55                  60

Ile Ala Ser Gln Ala Leu Val Asp Lys Leu His Phe Thr Ala Glu Glu
65                  70                  75                  80

Asn Lys Val Leu Ala Ala Ile Asn Glu Leu Ala His Ser Gln Lys Gly
                85                  90                  95

Trp Gly Glu Phe Asn Met Leu Asp Thr Thr Asn Thr Trp Pro Ser Gln
            100                 105                 110

<210> SEQ ID NO 501
<211> LENGTH: 339
<212> TYPE: DNA
<213> ORGANISM: Pediococcus acidilactici

<400> SEQUENCE: 501
atgaataaga ctaagtcgga acatattaaa caacaagctt tggacttatt tactaggcta     60
cagtttttac tacagaagca cgatactatc gaaccttacc agtacgtttt agatattctg    120
gagactggta tcagtaaaac taaacataac cagcaaacgc tgaacgaca agctcgtgta    180 gtctacaaca agattgccag ccaagcgtta gtagataagt tacattttac tgccgaagaa    240
aacaaagttc tagcagccat caatgaattg gcgcattctc aaaaagggtg gggcgagttt    300
aacatgctag atactaccaa tacgtggcct agccaatag                           339

<210> SEQ ID NO 502
<211> LENGTH: 88
<212> TYPE: PRT
<213> ORGANISM: Carnobacterium maltaromaticum

<400> SEQUENCE: 502

Met Ile Lys Asp Glu Lys Ile Asn Lys Ile Tyr Ala Leu Val Lys Ser
1               5                   10                  15

Ala Leu Asp Asn Thr Asp Val Lys Asn Asp Lys Lys Leu Ser Leu Leu
            20                  25                  30

Leu Met Arg Ile Gln Glu Thr Ser Ile Asn Gly Glu Leu Phe Tyr Asp
        35                  40                  45

Tyr Lys Lys Glu Leu Gln Pro Ala Ile Ser Met Tyr Ser Ile Gln His
    50                  55                  60

Asn Phe Arg Val Pro Asp Asp Leu Val Lys Leu Leu Ala Leu Val Gln
65                  70                  75                  80

Thr Pro Lys Ala Trp Ser Gly Phe
                85

<210> SEQ ID NO 503
<211> LENGTH: 267

```
<212> TYPE: DNA
<213> ORGANISM: Carnobacterium maltaromaticum

<400> SEQUENCE: 503
atgataaaag atgaaaaaat aaataaaatc tatgctttag ttaagagcgc acttgataat      60
acggatgtta agaatgataa aaactttct ttacttctta tgagaataca agaaacatca     120
attaatggag aactatttta cgattataaa aagaattac agccagctat tagtatgtac     180
tctattcaac ataactttcg ggttcctgac gatctagtaa aactgttagc attagttcaa     240
acacctaaag cttggtcagg gttttaa                                         267

<210> SEQ ID NO 504
<211> LENGTH: 111
<212> TYPE: PRT
<213> ORGANISM: Carnobacterium maltaromaticum

<400> SEQUENCE: 504

Met Asp Ile Lys Ser Gln Thr Leu Tyr Leu Asn Leu Ser Glu Ala Tyr
1               5                   10                  15

Lys Asp Pro Glu Val Lys Ala Asn Glu Phe Leu Ser Lys Leu Val Val
            20                  25                  30

Gln Cys Ala Gly Lys Leu Thr Ala Ser Asn Ser Glu Asn Ser Tyr Ile
        35                  40                  45

Glu Val Ile Ser Leu Leu Ser Arg Gly Ile Ser Ser Tyr Tyr Leu Ser
    50                  55                  60

His Lys Arg Ile Ile Pro Ser Ser Met Leu Thr Ile Tyr Thr Gln Ile
65                  70                  75                  80

Gln Lys Asp Ile Lys Asn Gly Asn Ile Asp Thr Glu Lys Leu Arg Lys
                85                  90                  95

Tyr Glu Ile Ala Lys Gly Leu Met Ser Val Pro Tyr Ile Tyr Phe
            100                 105                 110

<210> SEQ ID NO 505
<211> LENGTH: 336
<212> TYPE: DNA
<213> ORGANISM: Carnobacterium maltaromaticum

<400> SEQUENCE: 505
atggatataa agtctcaaac attatatttg aatctaagcg aggcatataa agaccctgaa      60
gtaaaagcta atgaattctt atcaaaatta gttgtacaat gtgctgggaa attaacagct     120
tcaaacagtg agaacagtta tattgaagta atatcattgc tatctagggg tatttctagt     180
tattatttat cccataaacg tataattcct tcaagtatgt taactatata tactcaaata     240
caaaaggata taaaaaacgg gaatattgac accgaaaaat taaggaaata tgagatagca     300
aaaggattaa tgtccgttcc ttatatatat ttctaa                               336

<210> SEQ ID NO 506
<211> LENGTH: 245
<212> TYPE: PRT
<213> ORGANISM: Lactococcus lactis subsp. lactis

<400> SEQUENCE: 506

Met Arg Arg Tyr Leu Ile Leu Ile Val Ala Leu Ile Gly Ile Thr Gly
1               5                   10                  15

Leu Ser Gly Cys Tyr Gln Thr Ser His Lys Lys Val Arg Phe Asp Glu
            20                  25                  30

Gly Ser Tyr Thr Asn Phe Ile Tyr Asp Asn Lys Ser Tyr Phe Val Thr
```

|   |   |   | 35 |   |   |   | 40 |   |   |   | 45 |   |   |
|---|---|---|---|---|---|---|---|---|---|---|---|---|---|

Asp Lys Glu Ile Pro Gln Glu Asn Val Asn Asn Ser Lys Val Lys Phe
50                      55                      60

Tyr Lys Leu Leu Ile Val Asp Met Lys Ser Glu Lys Leu Leu Ser Ser
65                      70                      75                      80

Ser Asn Lys Asn Ser Val Thr Leu Val Leu Asn Asn Ile Tyr Glu Ala
                85                      90                      95

Ser Asp Lys Ser Leu Cys Met Gly Ile Asn Asp Arg Tyr Tyr Lys Ile
                100                     105                     110

Leu Pro Glu Ser Asp Lys Gly Ala Val Lys Ala Leu Arg Leu Gln Asn
                115                     120                     125

Phe Asp Val Thr Ser Asp Ile Ser Asp Asp Asn Phe Val Ile Asp Lys
130                     135                     140

Asn Asp Ser Arg Lys Ile Asp Tyr Met Gly Asn Ile Tyr Ser Ile Ser
145                     150                     155                     160

Asp Thr Thr Val Ser Asp Glu Glu Leu Gly Glu Tyr Gln Asp Val Leu
                165                     170                     175

Ala Glu Val Arg Val Phe Asp Ser Val Ser Gly Lys Ser Ile Pro Arg
                180                     185                     190

Ser Glu Trp Gly Arg Ile Asp Lys Asp Gly Ser Asn Ser Lys Gln Ser
                195                     200                     205

Arg Thr Glu Trp Asp Tyr Gly Glu Ile His Ser Ile Arg Gly Lys Ser
210                     215                     220

Leu Thr Glu Ala Phe Ala Val Glu Ile Asn Asp Asp Phe Lys Leu Ala
225                     230                     235                     240

Thr Lys Val Gly Asn
                245

<210> SEQ ID NO 507
<211> LENGTH: 738
<212> TYPE: DNA
<213> ORGANISM: Lactococcus lactis subsp. lactis

<400> SEQUENCE: 507

```
atgagaagat atttaatact tattgtggcc ttaataggga taacaggttt atcagggtgt      60
tatcaaacaa gtcataaaaa ggtgaggttt gacgaaggaa gttatactaa ttttatttat     120
gataataaat cgtatttcgt aactgataag gagattcctc aggagaacgt taacaattcc     180
aaagtaaaat tttataagct gttgattgtt gacatgaaaa gtgagaaact tttatcaagt     240
agcaacaaaa atagtgtgac tttggtctta aataatattt atgaggcttc tgacaagtcg     300
ctatgtatgg gtattaacga cagatactat aagatacttc cagaaagtga taggggggcg     360
gtcaaagctt tgagattaca aaactttgat gtgacaagcg atatttctga tgataatttt     420
gttattgata aaaatgattc acgaaaaatt gactatatgg gaaatattta cagtatatcg     480
gacaccaccg tatctgatga agaattggga gaatatcagg atgttttagc tgaagtacgt     540
gtgtttgatt cagttagtgg caaaagtatc ccgaggtctg aatgggggag aattgataag     600
gatggttcaa attccaaaca gagtaggacg gaatgggatt atggcgaaat ccattctatt     660
agaggaaaat ctcttactga agcatttgcc gttgagataa atgatgattt taagcttgca     720
acgaaggtag gaaactag                                                   738
```

<210> SEQ ID NO 508
<211> LENGTH: 261
<212> TYPE: PRT

<213> ORGANISM: Rhizobium leguminosarum bv. trifolii

<400> SEQUENCE: 508

| | | | | | | | | | | | | | | |
|---|---|---|---|---|---|---|---|---|---|---|---|---|---|---|
| Met | Asn | Asp | Glu | Ile | Cys | Leu | Thr | Gly | Gly | Arg | Thr | Thr | Val | Thr |
| 1 | | | | 5 | | | | | 10 | | | | | 15 |
| Arg | Arg | Gly | Gly | Val | Val | Tyr | Arg | Glu | Gly | Pro | Trp | Ser | Ser | Thr |
| | | | 20 | | | | | 25 | | | | | 30 | |
| Val | Ile | Ser | Leu | Leu | Arg | His | Leu | Glu | Ala | Ser | Gly | Phe | Ala | Glu | Ala |
| | | | 35 | | | | | 40 | | | | | 45 | |
| Pro | Ser | Val | Val | Gly | Thr | Gly | Phe | Asp | Glu | Arg | Gly | Arg | Glu | Thr | Leu |
| | 50 | | | | | 55 | | | | | 60 | | | | |
| Ser | Phe | Ile | Glu | Gly | Glu | Phe | Val | His | Pro | Gly | Pro | Trp | Ser | Glu | Glu |
| 65 | | | | | 70 | | | | | 75 | | | | | 80 |
| Ala | Phe | Pro | Gln | Phe | Gly | Met | Met | Leu | Arg | Arg | Leu | His | Asp | Ala | Thr |
| | | | | 85 | | | | | 90 | | | | | 95 | |
| Ala | Ser | Phe | Lys | Pro | Pro | Glu | Asn | Ser | Met | Trp | Arg | Asp | Trp | Phe | Gly |
| | | | | 100 | | | | | 105 | | | | | 110 | |
| Arg | Asn | Leu | Gly | Glu | Gly | Gln | His | Val | Ile | Gly | His | Cys | Asp | Thr | Gly |
| | | | 115 | | | | | 120 | | | | | 125 | | |
| Pro | Trp | Asn | Ile | Val | Cys | Arg | Ser | Gly | Leu | Pro | Val | Gly | Leu | Ile | Asp |
| | 130 | | | | | 135 | | | | | 140 | | | | |
| Trp | Glu | Val | Ala | Gly | Pro | Val | Arg | Ala | Asp | Ile | Glu | Leu | Ala | Gln | Ala |
| 145 | | | | | 150 | | | | | 155 | | | | | 160 |
| Cys | Trp | Leu | Asn | Ala | Gln | Leu | Tyr | Asp | Asp | Ile | Ala | Glu | Arg | Val |
| | | | | 165 | | | | | 170 | | | | | 175 |
| Gly | Leu | Gly | Ser | Val | Thr | Met | Arg | Ala | His | Gln | Val | Arg | Leu | Leu | Leu |
| | | | 180 | | | | | 185 | | | | | 190 | | |
| Asp | Gly | Tyr | Gly | Leu | Ser | Arg | Lys | Gln | Arg | Gly | Gly | Phe | Val | Asp | Lys |
| | | | 195 | | | | | 200 | | | | | 205 | | |
| Leu | Ile | Thr | Phe | Ala | Val | His | Asp | Ala | Ala | Glu | Gln | Ala | Lys | Glu | Ala |
| | 210 | | | | | 215 | | | | | 220 | | | | |
| Ala | Val | Thr | Pro | Glu | Ser | Asn | Asp | Ala | Glu | Pro | Leu | Trp | Ala | Ile | Ala |
| 225 | | | | | 230 | | | | | 235 | | | | | 240 |
| Trp | Arg | Thr | Arg | Ser | Ala | Ser | Trp | Met | Leu | His | His | Arg | Gln | Thr | Leu |
| | | | | 245 | | | | | 250 | | | | | 255 | |
| Glu | Ala | Ala | Leu | Ala | | | | | | | | | | | |
| | | | | 260 | | | | | | | | | | | |

<210> SEQ ID NO 509
<211> LENGTH: 786
<212> TYPE: DNA
<213> ORGANISM: Rhizobium leguminosarum bv. trifolii

<400> SEQUENCE: 509

```
atgaatgatg agatttgcct gacaggtggc ggacgaacga ctgtcacgcg gcgcggcgga    60
gtcgtgtatc gcgaaggcgg cccgtggtca tcaaccgtca tttcgctcct gcggcatctg   120
gaagcctctg gcttcgctga agctccttcc gttgtcggca ccggtttcga tgagcgcggc   180
cgggagacat tatcgtttat cgagggtgag tttgttcacc caggcccttg gtcggaggag   240
gcttttccgc aatttggaat gatgttgcgg cgactgcacg atgccaccgc ctcgttcaaa   300
cctcccgaaa actcgatgtg gcgcgattgg ttcgggcgta acctcggtga gggtcaacac   360
gtaataggac actgcgacac aggcccatgg aacattgttt gccggtcagg attgcctgtc   420
gggttgatag attgggaggt ggctgggcct gtcagggcgg atatcgaatt ggcccaggct   480
```

-continued

```
tgttggctga atgcccagct ctacgatgac gacattgcgg agagggtcgg attaggctct      540
gtgaccatga gagcgcatca agttcgcctg ctgcttgacg gctatggtct gtctcggaag      600
caacgcggcg gcttcgtcga caagctaatc acgttcgcag ttcacgatgc ggccgagcag      660
gcgaaagagg cggctgtcac gccagagtcg aacgatgcgg aaccgctatg gcaattgcc       720 tggcgcacta gaagtgcctc ctggatgctc catcatcggc aaacactgga agcagcgctg      780
gcatag                                                                 786
```

<210> SEQ ID NO 510
<211> LENGTH: 436
<212> TYPE: PRT
<213> ORGANISM: Bacillus subtilis

<400> SEQUENCE: 510

| Met | Asn | Asn | Ile | Ile | Pro | Ile | Met | Ser | Leu | Leu | Phe | Lys | Gln | Leu | Tyr |
|---|---|---|---|---|---|---|---|---|---|---|---|---|---|---|---|
| 1 | | | | 5 | | | | | 10 | | | | | 15 | |

| Ser | Arg | Gln | Gly | Lys | Lys | Asp | Ala | Ile | Arg | Ile | Ala | Ala | Gly | Leu | Val |
|---|---|---|---|---|---|---|---|---|---|---|---|---|---|---|---|
| | | | 20 | | | | | 25 | | | | | 30 | | |

Ile Leu Ala Val Phe Glu Ile Gly Leu Ile Arg Gln Ala Gly Ile Asp
            35                  40                  45

Glu Ser Val Leu Arg Lys Thr Tyr Ile Ile Leu Ala Leu Leu Leu Met
 50                  55                  60

Asn Thr Tyr Met Val Phe Leu Ser Val Thr Ser Gln Trp Lys Glu Ser
 65                  70                  75                  80

Tyr Met Lys Leu Ser Cys Leu Leu Pro Ile Ser Ser Arg Ser Phe Trp
                85                  90                  95

Leu Ala Gln Ser Val Val Leu Phe Val Asp Thr Cys Leu Arg Arg Thr
            100                 105                 110

Leu Phe Phe Phe Ile Leu Pro Leu Phe Leu Phe Gly Asn Gly Thr Leu
        115                 120                 125

Ser Gly Ala Gln Thr Leu Phe Trp Leu Gly Arg Phe Ser Phe Phe Thr
    130                 135                 140

Val Tyr Ser Ile Ile Phe Gly Val Val Leu Ser Asn His Phe Val Lys
145                 150                 155                 160

Lys Lys Asn Leu Met Phe Leu Leu His Ala Ala Ile Phe Ala Cys Val
                165                 170                 175

Cys Ile Ser Ala Ala Leu Met Pro Ala Ala Thr Ile Pro Leu Cys Ala
            180                 185                 190

Val His Ile Leu Trp Ala Val Val Ile Asp Phe Pro Val Phe Leu Gln
        195                 200                 205

Ala Pro Pro Gln Gln Gly Lys Met His Ser Phe Met Arg Arg Ser Glu
    210                 215                 220

Phe Ser Phe Tyr Lys Arg Glu Trp Asn Arg Phe Ile Ser Ser Lys Ala
225                 230                 235                 240

Met Leu Leu Asn Tyr Ala Val Met Ala Val Phe Ser Gly Phe Ser
                245                 250                 255

Phe Gln Met Met Asn Thr Gly Ile Phe Asn Gln Gln Val Ile Tyr Ile
            260                 265                 270

Val Ile Ser Ala Leu Leu Leu Ile Cys Ser Pro Ile Ala Leu Leu Tyr
        275                 280                 285

Ser Ile Glu Lys Asn Asp Arg Met Leu Leu Ile Thr Leu Pro Ile Lys
    290                 295                 300

Arg Lys Thr Met Phe Trp Ala Lys Tyr Arg Phe Tyr Ser Gly Leu Leu
305                 310                 315                 320

```
Ala Gly Gly Phe Leu Leu Val Val Met Ile Val Gly Phe Ile Ser Gly
            325                 330                 335

Arg Ser Ile Ser Val Leu Thr Phe Leu Gln Cys Ile Glu Leu Leu Leu
            340                 345                 350

Ala Gly Ala Tyr Ile Arg Leu Thr Ala Asp Glu Lys Arg Pro Ser Phe
            355                 360                 365

Ser Trp Gln Thr Glu Gln Gln Leu Trp Ser Gly Phe Ser Lys Tyr Arg
            370                 375                 380

Ser Tyr Leu Phe Cys Leu Pro Leu Phe Leu Ala Ile Leu Ala Gly Thr
385                 390                 395                 400

Ala Val Ser Leu Ala Val Ile Pro Ile Ala Gly Leu Val Ile Val Tyr
            405                 410                 415

Tyr Leu Gln Lys Gln Asp Gly Gly Phe Phe Asp Thr Ser Lys Arg Glu
            420                 425                 430

Arg Leu Gly Ser
        435

<210> SEQ ID NO 511
<211> LENGTH: 1000
<212> TYPE: DNA
<213> ORGANISM: Bacillus subtilis

<400> SEQUENCE: 511
atgaataaca taatccctat catgtctttg ctgttcaaac agctttacag ccggcaaggg      60
aaaaaggacg ccatccgcat tgccgcaggc cttgtcattc tggccgtgtt tgaaatcggg     120
ctgatccgcc aggccggcat tgatgaatcg gtgttgcgca aaacgtatat catactcgcg     180
cttcttttga tgaacacata tatggtgttt ctttccgtga catcacaatg gaaggaatct     240
tatatgaagc tgagctgcct gctgccgatt tcttcacgga gcttttggct cgcccagagt     300
gtcgttttgt ttgtcgatac ctgtttgaga agaactttat tcttttttat tttaccgctg     360
ttcttatttg gaaacggaac gctgtcaggg gcgcaaacat tgttttggct cggcaggttt     420 tcgttttttta ccgtttactc cattattttc ggagttgtgc taagcaacca cttcgtcaaa     480
aagaagaact tgatgtttct gctgcatgcg gcgatattcg cctgtgtatg tatcagcgcc     540
gctttgatgc cggccgccac gattccgctt tgcgcggttc atatcctgtg ggcggtggtc     600
attgactttc ctgtctttct gcaggcgcct ccgcagcagg gcaagatgca ttcatttatg     660
cggcgatctg aattttcgtt ttacaaaaga gaatggaacc gatttatctc ttctaaagcg     720
atgctgttaa attacgcggt aatggcggta ttcagcggct tcttttcgtt ccagatgatg     780
aacaccggca tcttcaatca gcaagtgatt tatatcgtga tttccgcgct tttgctcatc     840
tgctcgccga tcgcccttttt gtattcgatt gaaaaaaatg accggatgct gctcatcacg     900
cttccgatca agcgaaaaac gatgtttttgg gcgaaatatc gctttttattc aggcctattg     960 gcaggcggat ttctccttgt cgtgatgatt gtgggtttca                            1000

<210> SEQ ID NO 512
<211> LENGTH: 239
<212> TYPE: PRT
<213> ORGANISM: Bacillus subtilis

<400> SEQUENCE: 512

Met Ser Ile Leu Asp Ile His Asp Val Ser Val Trp Tyr Glu Arg Asp
1               5                   10                  15

Asn Val Ile Leu Glu Gln Val Asp Leu His Leu Glu Lys Gly Ala Val
```

```
                 20                  25                  30
Tyr Gly Leu Leu Gly Val Asn Gly Ala Gly Lys Thr Thr Leu Ile Asn
             35                  40                  45

Thr Leu Thr Gly Val Asn Arg Asn Phe Ser Gly Arg Phe Thr Leu Cys
 50                  55                  60

Gly Ile Glu Ala Glu Ala Gly Met Pro Gln Lys Thr Ser Asp Gln Leu
 65                  70                  75                  80

Lys Thr His Arg Tyr Phe Ala Ala Asp Tyr Pro Leu Leu Phe Thr Glu
                 85                  90                  95

Ile Thr Ala Lys Asp Tyr Val Ser Phe Val His Ser Leu Tyr Gln Lys
            100                 105                 110

Asp Phe Ser Glu Gln Gln Phe Ala Ser Leu Ala Glu Ala Phe His Phe
            115                 120                 125

Ser Lys Tyr Ile Asn Arg Arg Ile Ser Glu Leu Ser Leu Gly Asn Arg
            130                 135                 140

Gln Lys Val Val Leu Met Thr Gly Leu Leu Leu Arg Ala Pro Leu Phe
145                 150                 155                 160

Ile Leu Asp Glu Pro Leu Val Gly Leu Asp Val Glu Ser Ile Glu Val
                165                 170                 175

Phe Tyr Gln Lys Met Arg Glu Tyr Cys Glu Ala Gly Gly Thr Ile Leu
            180                 185                 190

Phe Ser Ser His Leu Leu Asp Val Val Gln Arg Phe Cys Asp Tyr Ala
            195                 200                 205

Ala Ile Leu His Asn Lys Gln Ile Gln Lys Val Ile Pro Ile Gly Glu
            210                 215                 220

Glu Thr Asp Leu Arg Arg Glu Phe Phe Glu Val Ile Gly His Glu
225                 230                 235

<210> SEQ ID NO 513
<211> LENGTH: 716
<212> TYPE: DNA
<213> ORGANISM: Bacillus subtilis

<400> SEQUENCE: 513
gcattttgga tatacacgat gtatccgttt ggtatgaacg ggacaacgtc atcttagagc     60
acgtggactt acacttagaa aaaggcgccg tttacggatt gcttggggta acggtgccg    120 gcaaaacaac actgatcaat acgctgacag gagtgaaccg caattacagc gggggcttta    180
cgctgtgcgg cattgaagct gaggccggca tgccgcagaa aacatcagat caactgaaga    240
ttcaccgtta cttcgccgct gattatccgc tgctgtttac agaaattacg gcgaaggact    300
atgtgtcttt cgtccattcg ctttatcaaa aggatttttc agagcgacag tttgccagtt    360
tggctgaggc ctttcatttt tcaaaataca tcaacaggag aatctcggag ctgtccttgg    420
ggaacaggca aaaggttgtg ttgatgacag gattattgct gcgggctccc ctgtttattt    480
tggatgagcc gctcgtcggt ttggatgtgg aatcaataga ggtcttttat cagaaaatgc    540
gggagtactg tgaggaaggc ggaaccattt tgttttcttc ccatctgctc gatgtcgtgc    600
agagattttg tgattttgcg gccattctgc acaacaaaca gatccaaaag gtcattccga    660
ttggggagga gaccgatctg cggcgggaat tttttgaggt tatcggccat gaataa        716

<210> SEQ ID NO 514
<211> LENGTH: 53
<212> TYPE: PRT
<213> ORGANISM: Bacillus subtilis
```

```
<400> SEQUENCE: 514

Met Ser Pro Ala Gln Arg Arg Ile Leu Leu Tyr Ile Leu Ser Phe Ile
1               5                   10                  15

Phe Val Ile Gly Ala Val Val Tyr Phe Val Lys Ser Asp Tyr Leu Phe
            20                  25                  30

Thr Leu Ile Phe Ile Ala Ile Ala Ile Leu Phe Gly Met Arg Ala Arg
        35                  40                  45

Lys Ala Asp Ser Arg
    50

<210> SEQ ID NO 515
<211> LENGTH: 162
<212> TYPE: DNA
<213> ORGANISM: Bacillus subtilis

<400> SEQUENCE: 515
ttgtcaccag cacaaagaag aatttttactg tatatccttt cattatctt tgtcatcggc       60 gcagtcgtct attttgtcaa agcgattat ctgtttacgc tgattttcat tgccattgcc      120
attctgttcg ggatgcgcgc gcggaaggct gactcgcgat ga                        162

<210> SEQ ID NO 516
<211> LENGTH: 87
<212> TYPE: PRT
<213> ORGANISM: Escherichia coli

<400> SEQUENCE: 516

Met Glu Leu Lys Asn Ser Ile Ser Asp Tyr Thr Glu Ala Glu Phe Val
1               5                   10                  15

Gln Leu Leu Lys Glu Ile Glu Lys Glu Asn Val Ala Ala Thr Asp Asp
            20                  25                  30

Val Leu Asp Val Leu Leu Glu His Phe Val Lys Ile Thr Glu His Pro
        35                  40                  45

Asp Gly Thr Asp Leu Ile Tyr Tyr Pro Ser Asp Asn Arg Asp Asp Ser
    50                  55                  60

Pro Glu Gly Ile Val Lys Glu Ile Lys Glu Trp Arg Ala Ala Asn Gly
65                  70                  75                  80

Lys Pro Gly Phe Lys Gln Gly
                85

<210> SEQ ID NO 517
<211> LENGTH: 264
<212> TYPE: DNA
<213> ORGANISM: Escherichia coli

<400> SEQUENCE: 517
atggaactga aaaatagtat tagtgattac acagaggctg agtttgttca acttcttaag       60
gaaattgaaa aagagaatgt tgctgcaact gatgatgtgt tagatgtgtt actcgaacac      120
tttgtaaaaa ttactgagca tccagatgga acgatctga tttattatcc tagtgataat      180
agagacgata gccccgaagg gattgtcaag gaaattaaag aatggcgagc tgctaacggt      240
aagccaggat ttaaacaggg ctga                                            264

<210> SEQ ID NO 518
<211> LENGTH: 87
<212> TYPE: PRT
<213> ORGANISM: Pseudomonas aeruginosa

<400> SEQUENCE: 518
```

Met Lys Ser Lys Ile Ser Glu Tyr Thr Glu Lys Glu Phe Leu Glu Phe
1               5                   10                  15

Val Glu Asp Ile Tyr Thr Asn Asn Lys Lys Phe Pro Thr Glu Glu
            20                  25                  30

Ser His Ile Gln Ala Val Leu Glu Phe Lys Lys Leu Thr Glu His Pro
        35                  40                  45

Ser Gly Ser Asp Leu Leu Tyr Tyr Pro Asn Glu Asn Arg Glu Asp Ser
    50                  55                  60

Pro Ala Gly Val Val Lys Glu Val Lys Glu Trp Arg Ala Ser Lys Gly
65                  70                  75                  80

Leu Pro Gly Phe Lys Ala Gly
                85

<210> SEQ ID NO 519
<211> LENGTH: 264
<212> TYPE: DNA
<213> ORGANISM: Pseudomonas aeruginosa

<400> SEQUENCE: 519
atgaagtcca agatttccga atatacggaa aaagagtttc ttgagtttgt tgaagacata     60
tacacaaaca ataagaaaaa gttccctacc gaggagtctc atattcaagc cgtgcttgaa    120
tttaaaaaac taacggaaca cccaagcggc tcagaccttc tttactaccc caacgaaaat    180
agagaagata gcccagctgg agttgtaaag gaagttaaag aatggcgtgc ttccaagggg    240
cttcctggct ttaaggccgg ttag                                            264

<210> SEQ ID NO 520
<211> LENGTH: 87
<212> TYPE: PRT
<213> ORGANISM: Pseudomonas aeruginosa

<400> SEQUENCE: 520

Met Lys Ser Lys Ile Ser Glu Tyr Thr Glu Lys Glu Phe Leu Glu Phe
1               5                   10                  15

Val Lys Asp Ile Tyr Thr Asn Asn Lys Lys Phe Pro Thr Glu Glu
            20                  25                  30

Ser His Ile Gln Ala Val Leu Glu Phe Lys Lys Leu Thr Glu His Pro
        35                  40                  45

Ser Gly Ser Asp Leu Leu Tyr Tyr Pro Asn Glu Asn Arg Glu Asp Ser
    50                  55                  60

Pro Ala Gly Val Val Lys Glu Val Lys Glu Trp Arg Ala Ser Lys Gly
65                  70                  75                  80

Leu Pro Gly Phe Lys Ala Gly
                85

<210> SEQ ID NO 521
<211> LENGTH: 264
<212> TYPE: DNA
<213> ORGANISM: Pseudomonas aeruginosa

<400> SEQUENCE: 521
atgaagtcca agatttccga atatacggaa aaagagtttc ttgagtttgt taaagacata     60
tacacaaaca ataagaaaaa gttccctacc gaggagtctc atattcaagc cgtgcttgaa    120
tttaaaaaac taacggaaca cccaagcggc tcagaccttc tttactaccc caacgaaaat    180
agagaagata gcccagctgg agttgtaaag gaagttaaag aatggcgtgc ttccaagggg    240

```
cttcctggct ttaaggccgg ttag                                            264
```

<210> SEQ ID NO 522
<211> LENGTH: 95
<212> TYPE: PRT
<213> ORGANISM: Enterococcus hirae

<400> SEQUENCE: 522

```
Met Asp Phe Thr Lys Glu Glu Lys Leu Leu Asn Ala Ile Ser Lys Val
1               5                   10                  15

Tyr Asn Glu Ala Thr Ile Asp Asp Tyr Pro Asp Leu Lys Glu Lys Leu
            20                  25                  30

Phe Leu Tyr Ser Lys Glu Ile Ser Glu Gly Lys Ser Val Gly Glu Val
        35                  40                  45

Ser Met Lys Leu Ser Ser Phe Leu Gly Arg Tyr Ile Leu Lys His Lys
    50                  55                  60

Phe Gly Leu Pro Lys Ser Leu Ile Glu Leu Gln Glu Ile Val Ser Lys
65                  70                  75                  80

Glu Ser Gln Val Tyr Arg Gly Trp Ala Ser Ile Gly Ile Trp Ser
                85                  90                  95
```

<210> SEQ ID NO 523
<211> LENGTH: 288
<212> TYPE: DNA
<213> ORGANISM: Enterococcus hirae

<400> SEQUENCE: 523

```
atggatttta ctaaagaaga aaaacttta aatgcaatta gtaaagtata caatgaagca    60
actatagatg actatcctga cttaaaagaa aagctctttc tttattctaa agaaatcagt   120
gagggaaaaa gtgttggtga agttagtatg aaattagta gttttcttgg aagatatatt   180
ttaaaacata aatttggatt acctaaatct ttaatagaat acaagaaat tgttagtaag   240
gaatctcaag tatatagagg atgggcttct attggtattt ggagttaa                288
```

<210> SEQ ID NO 524
<211> LENGTH: 113
<212> TYPE: PRT
<213> ORGANISM: Leuconostoc mesenteroides

<400> SEQUENCE: 524

```
Met Lys Lys Lys Tyr Arg Tyr Leu Glu Asp Ser Lys Asn Tyr Thr Ser
1               5                   10                  15

Thr Leu Tyr Ser Leu Leu Val Asp Asn Val Asp Lys Pro Gly Tyr Ser
            20                  25                  30

Asp Ile Cys Asp Val Leu Leu Gln Val Ser Lys Lys Leu Asp Asn Thr
        35                  40                  45

Gln Ser Val Glu Ala Leu Ile Asn Arg Leu Val Asn Tyr Ile Arg Ile
    50                  55                  60

Thr Ala Ser Thr Tyr Lys Ile Ile Phe Ser Lys Lys Glu Glu Leu
65                  70                  75                  80

Ile Ile Lys Leu Gly Val Ile Gly Gln Lys Ala Gly Leu Asn Gly Gln
                85                  90                  95

Tyr Met Ala Asp Phe Ser Asp Lys Ser Gln Phe Tyr Ser Val Phe Asp
                100                 105                 110

Gln
```

<210> SEQ ID NO 525

```
<211> LENGTH: 342
<212> TYPE: DNA
<213> ORGANISM: Leuconostoc mesenteroides

<400> SEQUENCE: 525
ttgaaaaaaa agtatcggta tttagaagat agcaaaaatt acactagtac actctattct      60
ctgttagttg ataatgttga caaacctgga tactcagata tttgcgatgt tttgcttcaa     120
gtttctaaga agttggataa tactcaaagt gttgaagcgc taattaatcg attggttaat     180
tatattcgta ttactgcttc aacatacaaa attatttttt caaaaaaaga agaggaattg     240
attataaaac ttggtgttat tggacaaaaa gctggactta atggtcagta tatggctgat     300
ttttcagaca agtctcagtt ttacagcgtt ttcgatcagt aa                        342

<210> SEQ ID NO 526
<211> LENGTH: 93
<212> TYPE: PRT
<213> ORGANISM: Escherichia coli

<400> SEQUENCE: 526

Met Ser Phe Leu Asn Phe Ala Phe Ser Pro Val Phe Ser Ile Met
1               5                   10                  15

Ala Cys Tyr Phe Ile Val Trp Arg Asn Lys Arg Asn Glu Phe Val Cys
            20                  25                  30

Asn Arg Leu Leu Ser Ile Ile Ile Ser Phe Leu Ile Cys Phe Ile
        35                  40                  45

Tyr Pro Trp Leu Asn Tyr Lys Ile Glu Val Lys Tyr Tyr Ile Phe Glu
    50                  55                  60

Gln Phe Tyr Leu Phe Cys Phe Leu Ser Ser Leu Val Ala Val Val Ile
65                  70                  75                  80

Asn Leu Ile Val Tyr Phe Ile Leu Tyr Arg Arg Cys Ile
                85                  90

<210> SEQ ID NO 527
<211> LENGTH: 282
<212> TYPE: DNA
<213> ORGANISM: Escherichia coli

<400> SEQUENCE: 527
atgagttttc ttaattttgc attttctcct gtattcttct ccattatggc gtgttatttc      60
attgtatgga gaaataaacg aaacgaattt gtctgcaata gattgctatc aattataata     120
atatcttttt tgatatgctt catatatcca tggctaaatt acaaaatcga agttaaatat     180
tatatatttg aacagtttta tctttttttgt tttttatcgt cactcgtggc tgttgtaata     240
aacctaattg tatactttat attatacagg agatgtatat ga                       282

<210> SEQ ID NO 528
<211> LENGTH: 96
<212> TYPE: PRT
<213> ORGANISM: Escherichia coli

<400> SEQUENCE: 528

Met His Leu Lys Tyr Tyr Leu His Asn Leu Pro Glu Ser Leu Ile Pro
1               5                   10                  15

Trp Ile Leu Ile Leu Ile Phe Asn Asp Asn Asp Asn Thr Pro Leu Leu
            20                  25                  30

Phe Ile Phe Ile Ser Ser Ile His Val Leu Leu Tyr Pro Tyr Ser Lys
        35                  40                  45
```

```
Leu Thr Ile Ser Arg Tyr Ile Lys Glu Asn Thr Lys Leu Lys Lys Glu
    50                  55                  60

Pro Trp Tyr Leu Cys Lys Leu Ser Ala Leu Phe Tyr Leu Leu Met Ala
 65                  70                  75                  80

Ile Pro Val Gly Leu Pro Ser Phe Ile Tyr Tyr Thr Leu Lys Arg Asn
                85                  90                  95

<210> SEQ ID NO 529
<211> LENGTH: 291
<212> TYPE: DNA
<213> ORGANISM: Escherichia coli

<400> SEQUENCE: 529
atgcatttaa aatactacct acataattta cctgaatcac ttataccatg gattcttatt      60
ttaatattta acgacaatga taacactcct ttgttattta tatttatatc atcaatacat     120
gtattgctat atccatactc taaattaacc atatctagat atatcaaaga aaatacaaag     180
ttaaaaaaag aaccctggta cttatgcaag ttatctgcat tgtttttattt attaatggca     240 atcccagtag gattgccaag tttcatatat tacactctaa agagaaatta a              291

<210> SEQ ID NO 530
<211> LENGTH: 344
<212> TYPE: PRT
<213> ORGANISM: Escherichia coli

<400> SEQUENCE: 530

Met Met Ile Gln Ser His Pro Leu Ala Ala Pro Leu Ala Val Gly
 1               5                  10                  15

Asp Thr Ile Gly Phe Phe Ser Ser Ser Ala Pro Ala Thr Val Thr Ala
                20                  25                  30

Lys Asn Arg Phe Phe Arg Gly Val Glu Phe Leu Gln Lys Gly Phe
            35                  40                  45

Lys Leu Val Ser Gly Lys Leu Thr Gly Lys Thr Asp Phe Tyr Arg Ser
 50                  55                  60

Gly Thr Ile Lys Glu Arg Ala Gln Glu Phe Asn Glu Leu Val Tyr Asn
 65                  70                  75                  80

Pro Asp Ile Thr Cys Ile Met Ser Thr Ile Gly Gly Asp Asn Ser Asn
                85                  90                  95

Ser Leu Leu Pro Phe Leu Asp Tyr Asp Ala Ile Ile Ala Asn Pro Lys
               100                 105                 110

Ile Ile Ile Gly Tyr Ser Asp Thr Thr Ala Leu Leu Ala Gly Ile Tyr
           115                 120                 125

Ala Lys Thr Gly Leu Ile Thr Phe Tyr Gly Pro Ala Leu Ile Pro Ser
130                 135                 140

Phe Gly Glu His Pro Pro Leu Val Asp Ile Thr Tyr Glu Ser Phe Ile
145                 150                 155                 160

Lys Ile Leu Thr Arg Lys Gln Ser Gly Ile Tyr Thr Tyr Thr Leu Pro
                165                 170                 175

Glu Lys Trp Ser Asp Glu Ser Ile Asn Trp Asn Glu Asn Lys Ile Leu
                180                 185                 190

Arg Pro Lys Lys Leu Tyr Lys Asn Asn Cys Ala Phe Tyr Gly Ser Gly
            195                 200                 205

Lys Val Glu Gly Arg Val Ile Gly Gly Asn Leu Asn Thr Leu Thr Gly
        210                 215                 220

Ile Trp Gly Ser Glu Trp Met Pro Glu Ile Leu Asn Gly Asp Ile Leu
225                 230                 235                 240
```

```
Phe Ile Glu Asp Ser Arg Lys Ser Ile Ala Thr Ile Glu Arg Leu Phe
                245                 250                 255

Ser Met Leu Lys Leu Asn Arg Val Phe Asp Lys Val Ser Ala Ile Ile
            260                 265                 270

Leu Gly Lys His Glu Leu Phe Asp Cys Ala Gly Ser Lys Arg Arg Pro
        275                 280                 285

Tyr Glu Val Leu Thr Glu Val Leu Asp Gly Lys Gln Ile Pro Val Leu
    290                 295                 300

Asp Gly Phe Asp Cys Ser His Thr His Pro Met Leu Thr Leu Pro Leu
305                 310                 315                 320

Gly Val Lys Leu Ala Ile Asp Phe Asp Asn Lys Asn Ile Ser Ile Thr
                325                 330                 335

Glu Gln Tyr Leu Ser Thr Glu Lys
            340
```

<210> SEQ ID NO 531
<211> LENGTH: 1000
<212> TYPE: DNA
<213> ORGANISM: Escherichia coli

<400> SEQUENCE: 531

```
atgatgatac aatctcatcc actactggcc gctcccctgg cagtaggaga tacaattggt      60
ttcttttcat catctgctcc ggcaacagtt actgcaaaaa atcgtttttt tcggggagtt     120
gagtttcttc agagaaaggg atttaagctg gtatcaggga agcttaccgg taaaacagat     180
ttttatcgtt caggtactat taagaaaaga gctcaagaat taatgagtt agtctacaat     240
cctgatatta cctgtataat gtcaacgatc ggtggagata cagtaattc actactaccg     300
tttctggact atgatgctat cattgcaaac cccaaaatta tcataggtta ctcagataca     360
actgctttat tagcaggaat atatgcaaaa acagggttaa taacattcta tggaccagct     420
cttattcctt cgtttggtga acatccacct cttgtggata acatatgaa tcatttatt      480
aaaatactaa caagaaaaca atcaggaata tatacctaca cattacctga aaagtggagt     540
gatgagagca taaactggaa tgaaaacaag atattaaggc ctaagaagct atataaaaac     600
aactgtgcct tttatggttc cggaaaagtt gaggggcgtg taattggagg aaatctaaat     660
actttgacag gtatatgggg gagtgaatgg atgcctgaaa ttcttaatgg agatatattg     720
tttattgagg acagtcggaa aagcattgca acaattgaac gattattctc tatgctaaag     780
cttaatcgcg tgtttgataa agttagtgca ataatactcg ggaaacatga gcttttgat      840
tgtgcaggaa gtaaacgcag accatatgaa gtattaacag aggtattaga tgggaaacag     900
attcctgtac tggatggatt tgattgttca catacacatc caatgctaac tcttccactt     960
ggtgtaaaat tagctattga ctttgacaac aaaaatatat                          1000
```

<210> SEQ ID NO 532
<211> LENGTH: 90
<212> TYPE: PRT
<213> ORGANISM: Lactobacillus sakei

<400> SEQUENCE: 532

```
Met Lys Ala Asp Tyr Lys Lys Ile Asn Ser Ile Leu Thr Tyr Thr Ser
1               5                   10                  15

Thr Ala Leu Lys Asn Pro Lys Ile Ile Lys Asp Lys Asp Leu Val Val
            20                  25                  30

Leu Leu Thr Ile Ile Gln Glu Glu Ala Lys Gln Asn Arg Ile Phe Tyr
```

```
                35                  40                  45
Asp Tyr Lys Arg Lys Phe Arg Pro Ala Val Thr Arg Phe Thr Ile Asp
         50                  55                  60
Asn Asn Phe Glu Ile Pro Asp Cys Leu Val Lys Leu Leu Ser Ala Val
 65                  70                  75                  80
Glu Thr Pro Lys Ala Trp Ser Gly Phe Ser
                 85                  90
```

<210> SEQ ID NO 533
<211> LENGTH: 268
<212> TYPE: DNA
<213> ORGANISM: Lactobacillus sakei

<400> SEQUENCE: 533

```
ggcagattat aaaaaaataa attcaatact aacttacaca tctactgctt taaaaaaccc      60
taaaattata aaagataaag atttagtagt ccttctaact attattcaag aagaagccaa     120
acaaaataga atcttttatg attataaaag aaaatttcgt ccagcggtta ctcgctttac     180
aattgataat aattttgaga ttcctgattg tttggttaaa ctactgtcag ctgttgaaac     240
acctaaggcg tggtctggat ttagttag                                        268
```

<210> SEQ ID NO 534
<211> LENGTH: 83
<212> TYPE: PRT
<213> ORGANISM: Escherichia coli

<400> SEQUENCE: 534

```
Met Lys Leu Ser Pro Lys Ala Ala Ile Glu Val Cys Asn Glu Ala Ala
  1               5                  10                  15
Lys Lys Gly Leu Trp Ile Leu Gly Ile Asp Gly Gly His Trp Leu Asn
                 20                  25                  30
Pro Gly Phe Arg Ile Asp Ser Ser Ala Ser Trp Thr Tyr Asp Met Pro
             35                  40                  45
Glu Glu Tyr Lys Ser Lys Thr Pro Glu Asn Asn Arg Leu Ala Ile Glu
         50                  55                  60
Asn Ile Lys Asp Asp Ile Glu Asn Gly Tyr Thr Ala Phe Ile Ile Thr
 65                  70                  75                  80
Leu Lys Met
```

<210> SEQ ID NO 535
<211> LENGTH: 251
<212> TYPE: DNA
<213> ORGANISM: Escherichia coli

<400> SEQUENCE: 535

```
tgaagttatc accaaaagct gcaatagaag tttgtaatga agcagcgaaa aaaggcttat      60
ggatttgggg cattgatggt gggcattggc tgaatcctgg attcaggata gatagttcag     120
catcatggac atatgatatg ccggaggaat acaaatcaaa accccctgaa ataatagat     180
tggctattga aaatattaaa gatgatattg agaatggata cactgctttc attatcacgt     240
taaagatgta a                                                          251
```

<210> SEQ ID NO 536
<211> LENGTH: 436
<212> TYPE: PRT
<213> ORGANISM: Bacillus subtilis

<400> SEQUENCE: 536

```
Met Asn Asn Ile Phe Pro Ile Met Ser Leu Leu Phe Lys Gln Leu Tyr
1               5                   10                  15

Ser Arg Gln Gly Lys Lys Asp Ala Ile Arg Ile Ala Ala Gly Leu Val
            20                  25                  30

Ile Leu Ala Val Phe Glu Ile Gly Leu Ile Arg Gln Ala Gly Ile Asp
            35                  40                  45

Glu Ser Val Leu Gly Lys Thr Tyr Ile Ile Leu Ala Leu Leu Leu Met
        50                  55                  60

Asn Thr Tyr Met Val Phe Leu Ser Val Thr Ser Gln Trp Lys Glu Ser
65                  70                  75                  80

Tyr Met Lys Leu Ser Cys Leu Leu Pro Ile Ser Ser Arg Ser Phe Trp
                85                  90                  95

Leu Ala Gln Ser Val Val Leu Phe Val Asp Thr Cys Leu Arg Arg Thr
            100                 105                 110

Leu Phe Phe Phe Ile Leu Pro Leu Phe Leu Phe Gly Asn Gly Thr Leu
        115                 120                 125

Ser Gly Ala Gln Thr Leu Phe Trp Leu Gly Arg Phe Ser Phe Phe Thr
    130                 135                 140

Val Tyr Ser Ile Leu Phe Gly Val Met Leu Ser Asn His Phe Val Lys
145                 150                 155                 160

Lys Lys Asn Ser Met Phe Leu Leu His Ala Ala Val Phe Ala Phe Val
                165                 170                 175

Cys Leu Ser Ala Ala Phe Met Pro Ala Val Thr Ile Pro Leu Cys Ala
            180                 185                 190

Val His Met Leu Trp Ala Val Ile Ile Asp Phe Pro Val Phe Leu Gln
        195                 200                 205

Ala Pro Pro His Gln Ser Lys Met His Phe Phe Met Arg Arg Ser Glu
    210                 215                 220

Phe Ser Phe Tyr Lys Arg Glu Trp Asn Arg Phe Ile Ser Ser Lys Ala
225                 230                 235                 240

Met Leu Leu Asn Tyr Val Val Met Ala Ala Phe Ser Gly Phe Phe Ser
                245                 250                 255

Phe Gln Met Met Asn Thr Gly Ile Phe Asn Gln Gln Val Ile Tyr Ile
            260                 265                 270

Val Ile Ser Ala Leu Leu Leu Ile Cys Ser Pro Ile Ala Leu Leu Tyr
        275                 280                 285

Ser Ile Glu Lys Asn Asp Arg Met Leu Leu Ile Thr Leu Pro Ile Lys
    290                 295                 300

Arg Arg Thr Met Phe Trp Ala Lys Tyr Arg Phe Tyr Ser Gly Leu Leu
305                 310                 315                 320

Ala Gly Gly Phe Leu Leu Val Ala Ile Ile Val Gly Phe Ile Ser Gly
                325                 330                 335

Arg Pro Ile Ser Ala Leu Thr Phe Val Gln Cys Met Glu Leu Leu Leu
            340                 345                 350

Ala Gly Ala Phe Ile Arg Leu Thr Ala Asp Glu Lys Arg Pro Ser Phe
        355                 360                 365

Gly Trp Gln Thr Glu Gln Gln Leu Trp Ser Gly Phe Ser Lys Tyr Arg
    370                 375                 380

Ser Tyr Leu Phe Cys Leu Pro Leu Phe Leu Ala Thr Leu Ala Gly Thr
385                 390                 395                 400

Ala Val Ser Leu Ala Val Ile Pro Ile Ala Ala Leu Ile Ile Val Tyr
                405                 410                 415
```

Tyr Leu Gln Lys Gln Asp Gly Gly Phe Phe Asp Thr Ser Lys Arg Glu
                420                 425                 430

Arg Ile Gly Ser
        435

<210> SEQ ID NO 537
<211> LENGTH: 1000
<212> TYPE: DNA
<213> ORGANISM: Bacillus subtilis

<400> SEQUENCE: 537

```
ttggggagga gaccgatctg cggcgggaat ttttgaggt tatcggccat gaataacata      60
ttccccatca tgtcgttgct gttcaaacag ctgtacagcc ggcaagggaa aaaggacgct    120
atccgcattg ctgcagggct tgtgattctc gccgtgtttg aaatcgggct gatccgacaa    180
gccggcattg acgaatcggt gttgggaaaa acgtatatca tattggcgct tctcttaatg    240
aacacgtata tggtgtttct ttccgtgaca tcacaatgga aggaatctta tatgaagctg    300
agctgtctgc tgccgatttc atcacggagc ttttggctcg cccagagtgt cgttctgttt    360
gtcgataccl gtttgagaag aacgttattc ttttttattt taccgctgtt cttatttgga    420
aacgaaacgc tgtcagggc gcaaacattg ttttggcttg gcagattttc gttttttacc    480
gtttactcga ttctattcgg agttatgcta agcaaccatt tcgtcaaaaa gaagaactcg    540
atgtttctgc tgcatgcggc ggtattcgcc tttgtatgcc tcagtgccgc ttttatgccg    600
gccgtcacga tcccgctatg cgcggttcac atgctatggg cggtgatcat tgactttccg    660
gtctttctgc aggcgcctcc gcatcagagc aagatgcatt ttttatgcg gcgatctgaa    720
ttttcgtttt acaaaagaga atggaaccga tttatttctt ctaaagcgat gctgttaaat    780
tacgtggtga tggcggcgtt cagcggattc ttttcgttcc agatgatgaa cactggcatc    840
ttcaatcagc aagtgattta tattgtgatt ccgctctat gctgatttg ctcgccgatc    900
gccccttttgt actctattga aaaaaacgat cgcatgctgc tcatcacgct tccaattaaa    960
agaagaacga tgttttgggc gaaatatcgc ttttattcag                          1000
```

<210> SEQ ID NO 538
<211> LENGTH: 580
<212> TYPE: PRT
<213> ORGANISM: Escherichia coli

<400> SEQUENCE: 538

Met Glu Arg Lys Gln Lys Asn Ser Leu Phe Asn Tyr Ile Tyr Ser Leu
1               5                   10                  15

Met Asp Val Arg Gly Lys Phe Leu Phe Phe Ser Met Leu Phe Ile Thr
            20                  25                  30

Ser Leu Ser Ser Ile Ile Ile Ser Ile Ser Pro Leu Ile Leu Ala Lys
        35                  40                  45

Ile Thr Asp Leu Leu Ser Gly Ser Leu Ser Asn Phe Ser Tyr Glu Tyr
    50                  55                  60

Leu Val Leu Leu Ala Cys Leu Tyr Met Phe Cys Val Ile Ser Asn Lys
65                  70                  75                  80

Ala Ser Val Phe Leu Phe Met Ile Leu Gln Ser Ser Leu Arg Ile Asn
                85                  90                  95

Met Gln Lys Lys Met Ser Leu Lys Tyr Leu Arg Glu Leu Tyr Asn Glu
            100                 105                 110

Asn Ile Thr Asn Leu Ser Lys Asn Asn Ala Gly Tyr Thr Thr Gln Ser
        115                 120                 125

```
Leu Asn Gln Ala Ser Asn Asp Ile Tyr Ile Leu Val Arg Asn Val Ser
    130                 135                 140

Gln Asn Ile Leu Ser Pro Val Ile Gln Leu Ile Ser Thr Ile Val Val
145                 150                 155                 160

Val Leu Ser Thr Lys Asp Trp Phe Ser Ala Gly Val Phe Phe Leu Tyr
                165                 170                 175

Ile Leu Val Phe Val Ile Phe Asn Thr Arg Leu Thr Gly Ser Leu Ala
            180                 185                 190

Ser Leu Arg Lys His Ser Met Asp Ile Thr Leu Asn Ser Tyr Ser Leu
        195                 200                 205

Leu Ser Asp Thr Val Asp Asn Met Ile Ala Ala Lys Lys Asn Asn Ala
210                 215                 220

Leu Arg Leu Ile Ser Glu Arg Tyr Glu Asp Ala Leu Thr Gln Glu Asn
225                 230                 235                 240

Asn Ala Gln Lys Lys Tyr Trp Leu Leu Ser Ser Lys Val Leu Leu Leu
                245                 250                 255

Asn Ser Leu Leu Ala Val Ile Leu Phe Gly Ser Val Phe Ile Tyr Asn
            260                 265                 270

Ile Leu Gly Val Leu Asn Gly Val Val Ser Ile Gly His Phe Ile Met
        275                 280                 285

Ile Thr Ser Tyr Ile Ile Leu Leu Ser Thr Pro Val Glu Asn Ile Gly
290                 295                 300

Ala Leu Leu Ser Glu Ile Arg Gln Ser Met Ser Ser Leu Ala Gly Phe
305                 310                 315                 320

Ile Gln Arg His Ala Glu Asn Lys Ala Thr Ser Pro Ser Ile Pro Phe
                325                 330                 335

Leu Asn Met Glu Arg Lys Leu Asn Leu Ser Ile Arg Glu Leu Ser Phe
            340                 345                 350

Ser Tyr Ser Asp Asp Lys Lys Ile Leu Asn Ser Val Ser Leu Asp Leu
        355                 360                 365

Phe Thr Gly Lys Met Tyr Ser Leu Thr Gly Pro Ser Gly Ser Gly Lys
370                 375                 380

Ser Thr Leu Val Lys Ile Ile Ser Gly Tyr Tyr Lys Asn Tyr Phe Gly
385                 390                 395                 400

Asp Ile Tyr Leu Asn Asp Ile Ser Leu Arg Asn Ile Ser Asp Glu Asp
                405                 410                 415

Leu Asn Asp Ala Ile Tyr Tyr Leu Thr Gln Asp Asp Tyr Ile Phe Met
            420                 425                 430

Asp Thr Leu Arg Phe Asn Leu Arg Leu Ala Asn Tyr Asp Ala Ser Glu
        435                 440                 445

Asn Glu Ile Phe Lys Val Leu Lys Leu Ala Asn Leu Ser Val Val Asn
450                 455                 460

Asn Glu Pro Val Ser Leu Asp Thr His Leu Ile Asn Arg Gly Asn Asn
465                 470                 475                 480

Tyr Ser Gly Gly Gln Lys Gln Arg Ile Ser Leu Ala Arg Leu Phe Leu
                485                 490                 495

Arg Lys Pro Ala Ile Ile Ile Asp Glu Ala Thr Ser Ala Leu Asp
            500                 505                 510

Tyr Ile Asn Glu Ser Glu Ile Leu Ser Ser Ile Arg Thr His Phe Pro
        515                 520                 525

Asp Ala Leu Ile Ile Asn Ile Ser His Arg Ile Asn Leu Leu Glu Cys
530                 535                 540
```

Ser Asp Cys Val Tyr Val Leu Asn Glu Gly Asn Ile Val Ala Ser Gly
545                 550                 555                 560

His Phe Arg Asp Leu Met Val Ser Asn Glu Tyr Ile Ser Gly Leu Ala
                565                 570                 575

Ser Val Thr Glu
            580

<210> SEQ ID NO 539
<211> LENGTH: 1000
<212> TYPE: DNA
<213> ORGANISM: Escherichia coli

<400> SEQUENCE: 539
atggaaagaa aacagaaaaa ctcattattt aattatattt attcattaat ggatgtaaga      60
ggtaaatttt tattcttttc catgttattc attacatcat tatcatcgat aatcatatct     120
atttcaccat tgattcttgc aaagattaca gatttactgt ctggctcatt gtcaaatttt     180
agttatgaat atctggtttt acttgcctgt ttatacatgt tttgcgttat atctaataaa     240
gcaagtgttt ttttatttat gatactgcaa agtagtctac gtattaacat gcagaaaaaa     300
atgtcgctaa agtatttgag agaattgtat aacgaaaata taactaactt gagtaaaaat     360
aatgctggat atacaacgca aagtcttaac caggcttcaa atgacattta tattcttgtg     420
agaaatgttt cccagaatat cctgtcacct gttatacaac ttatttccac tattgttgtt     480
gttttatcta cgaaggactg gttttctgcc ggtgtgtttt ttctctatat tctggtatttt    540
gtaattttta ataccagact gactggcagt ttagcgtctc tcagaaaaca cagcatggat     600
atcactctta actcttatag tctgttatct gatactgttg ataacatgat agcagctaaa     660
aagaataatg cattaagact tatttctgaa cgttatgaag atgctctcac tcaggaaaac     720
aatgctcaga aaaatactg gttactcagt tctaaagttc ttttattgaa ctctttactt     780
gctgtaatat tatttggttc tgtattcata tataatattt taggtgtgct gaatggtgta     840
gttagtatcg gccacttcat tatgattaca tcatatatca ttcttctttc aacgccagtg     900
gaaaatatag gggcattgct aagtgagatc aggcagtcaa tgtctagcct ggcaggtttt     960
attcaacgtc atgccgagaa taaagccaca ctctccttcaa                         1000

<210> SEQ ID NO 540
<211> LENGTH: 95
<212> TYPE: PRT
<213> ORGANISM: Klebsiella pneumoniae

<400> SEQUENCE: 540

Met Thr Leu Leu Ser Phe Gly Phe Ser Pro Val Phe Ser Val Met
1               5                   10                  15

Ala Phe Cys Ile Ile Ser Arg Ser Lys Phe Tyr Pro Gln Arg Thr Arg
                20                  25                  30

Asn Lys Val Ile Val Leu Ile Leu Thr Phe Phe Ile Cys Phe Leu
            35                  40                  45

Tyr Pro Leu Thr Lys Val Tyr Leu Val Gly Ser Tyr Gly Ile Phe Asp
        50                  55                  60

Lys Phe Tyr Leu Phe Cys Phe Ile Ser Thr Leu Ile Ala Ile Ala Ile
65                  70                  75                  80

Asn Val Val Ile Leu Thr Ile Asn Gly Ala Lys Asn Glu Arg Asn
                85                  90                  95

<210> SEQ ID NO 541

```
<211> LENGTH: 288
<212> TYPE: DNA
<213> ORGANISM: Klebsiella pneumoniae

<400> SEQUENCE: 541
atgacattac tttcatttgg attttctcct gttttctttt cagtcatggc gttctgtatc    60
atttcacgta gtaaattcta tccgcagaga acgcgaaaca aagttattgt tctgatttta   120
ctaacttttt ttatttgttt tttatatcca ttaacaaaag tgtatctggt gggaagttac   180
ggtatatttg acaaattcta cctcttttgc tttatttcta cgttaattgc aatagcaatt   240
aacgtagtga tacttacaat aaatggagct aagaatgaga gaaattag               288

<210> SEQ ID NO 542
<211> LENGTH: 13
<212> TYPE: RNA
<213> ORGANISM: Artificial Sequence
<220> FEATURE:
<223> OTHER INFORMATION: Kozak sequence
<220> FEATURE:
<221> NAME/KEY: misc_feature
<222> LOCATION: (7)..(7)
<223> OTHER INFORMATION: n = a or g

<400> SEQUENCE: 542
gccgccrcca ugg                                                      13

<210> SEQ ID NO 543
<211> LENGTH: 6
<212> TYPE: RNA
<213> ORGANISM: Artificial Sequence
<220> FEATURE:
<223> OTHER INFORMATION: Shine-Delgarno sequence

<400> SEQUENCE: 543 ggaggu                                                               6

<210> SEQ ID NO 544
<211> LENGTH: 30
<212> TYPE: DNA
<213> ORGANISM: Artificial Sequence
<220> FEATURE:
<223> OTHER INFORMATION: Lead promoter

<400> SEQUENCE: 544
gaaaaccttg tcaatgaaga gcgatctatg                                    30

<210> SEQ ID NO 545
<211> LENGTH: 30
<212> TYPE: DNA
<213> ORGANISM: Artificial Sequence
<220> FEATURE:
<223> OTHER INFORMATION: FecA promoter

<400> SEQUENCE: 545
ttctcgttcg actcatagct gaacacaaca                                    30

<210> SEQ ID NO 546
<211> LENGTH: 16
<212> TYPE: DNA
<213> ORGANISM: Artificial Sequence
<220> FEATURE:
<223> OTHER INFORMATION: Cu-sensitive promoter

<400> SEQUENCE: 546
atgacaaaat tgtcat                                                   16
```

```
<210> SEQ ID NO 547
<211> LENGTH: 30
<212> TYPE: DNA
<213> ORGANISM: Artificial Sequence
<220> FEATURE:
<223> OTHER INFORMATION: Fe promoter

<400> SEQUENCE: 547
accaatgctg ggaacggcca gggcacctaa                                          30

<210> SEQ ID NO 548
<211> LENGTH: 30
<212> TYPE: DNA
<213> ORGANISM: Artificial Sequence
<220> FEATURE:
<223> OTHER INFORMATION: Fe and UV promoters

<400> SEQUENCE: 548
ctgaaagcgc ataccgctat ggaggggggtt                                         30

<210> SEQ ID NO 549
<211> LENGTH: 30
<212> TYPE: DNA
<213> ORGANISM: Artificial Sequence
<220> FEATURE:
<223> OTHER INFORMATION: PrFe (PI + PII rus operon)

<400> SEQUENCE: 549
tagatatgcc tgaaagcgca taccgctatg                                          30

<210> SEQ ID NO 550
<211> LENGTH: 30
<212> TYPE: DNA
<213> ORGANISM: Artificial Sequence
<220> FEATURE:
<223> OTHER INFORMATION: Lux cassette right promoter

<400> SEQUENCE: 550
tgttatagtc gaatacctct ggcggtgata                                          30

<210> SEQ ID NO 551
<211> LENGTH: 30
<212> TYPE: DNA
<213> ORGANISM: Artificial Sequence
<220> FEATURE:
<223> OTHER INFORMATION: P(Las) TetO

<400> SEQUENCE: 551
ttttggtaca ctccctatca gtgatagaga                                          30

<210> SEQ ID NO 552
<211> LENGTH: 30
<212> TYPE: DNA
<213> ORGANISM: Artificial Sequence
<220> FEATURE:
<223> OTHER INFORMATION: P(Las) CIO

<400> SEQUENCE: 552 cttttggta cactacctct ggcggtgata                                           30

<210> SEQ ID NO 553
<211> LENGTH: 30
<212> TYPE: DNA
<213> ORGANISM: Artificial Sequence
<220> FEATURE:
```

```
<223> OTHER INFORMATION: P(Rhl)

<400> SEQUENCE: 553
tacgcaagaa aatggtttgt tatagtcgaa                                       30

<210> SEQ ID NO 554
<211> LENGTH: 30
<212> TYPE: DNA
<213> ORGANISM: Artificial Sequence
<220> FEATURE:
<223> OTHER INFORMATION: Double Promoter (LuxR/HSL, positive / cI,
      negative)

<400> SEQUENCE: 554
cgtgcgtgtt gataacaccg tgcgtgttga                                       30

<210> SEQ ID NO 555
<211> LENGTH: 30
<212> TYPE: DNA
<213> ORGANISM: Artificial Sequence
<220> FEATURE:
<223> OTHER INFORMATION: P2 promoter in agr operon from S. aureus

<400> SEQUENCE: 555
agattgtact aaatcgtata atgacagtga                                       30

<210> SEQ ID NO 556
<211> LENGTH: 30
<212> TYPE: DNA
<213> ORGANISM: Artificial Sequence
<220> FEATURE:
<223> OTHER INFORMATION: plux-cI hybrid promoter

<400> SEQUENCE: 556
gtgttgatgc ttttatcacc gccagtggta                                       30

<210> SEQ ID NO 557
<211> LENGTH: 30
<212> TYPE: DNA
<213> ORGANISM: Artificial Sequence
<220> FEATURE:
<223> OTHER INFORMATION: plux-lac hybrid promoter

<400> SEQUENCE: 557
agtgtgtgga attgtgagcg gataacaatt                                       30

<210> SEQ ID NO 558
<211> LENGTH: 30
<212> TYPE: DNA
<213> ORGANISM: Artificial Sequence
<220> FEATURE:
<223> OTHER INFORMATION: CinR, CinL and glucose controlled promotor

<400> SEQUENCE: 558
acatcttaaa agttttagta tcatattcgt                                       30

<210> SEQ ID NO 559
<211> LENGTH: 30
<212> TYPE: DNA
<213> ORGANISM: Artificial Sequence
<220> FEATURE:
<223> OTHER INFORMATION: RhlR promoter repressible by CI

<400> SEQUENCE: 559
tacgcaagaa aatggtttgt tatagtcgaa                                       30
```

<210> SEQ ID NO 560
<211> LENGTH: 30
<212> TYPE: DNA
<213> ORGANISM: Artificial Sequence
<220> FEATURE:
<223> OTHER INFORMATION: Reverse Lux Promoter

<400> SEQUENCE: 560
tcttgcgtaa acctgtacga tcctacaggt                                    30

<210> SEQ ID NO 561
<211> LENGTH: 30
<212> TYPE: DNA
<213> ORGANISM: Artificial Sequence
<220> FEATURE:
<223> OTHER INFORMATION: rhlI promoter

<400> SEQUENCE: 561
atcctccttt agtcttcccc ctcatgtgtg                                    30

<210> SEQ ID NO 562
<211> LENGTH: 30
<212> TYPE: DNA
<213> ORGANISM: Artificial Sequence
<220> FEATURE:
<223> OTHER INFORMATION: lasI promoter

<400> SEQUENCE: 562
taaaattatg aaatttgcat aaattcttca                                    30

<210> SEQ ID NO 563
<211> LENGTH: 30
<212> TYPE: DNA
<213> ORGANISM: Artificial Sequence
<220> FEATURE:
<223> OTHER INFORMATION: LuxR+3OC6HSL independent R0065

<400> SEQUENCE: 563
gtgttgacta ttttacctct ggcggtgata                                    30

<210> SEQ ID NO 564
<211> LENGTH: 30
<212> TYPE: DNA
<213> ORGANISM: Artificial Sequence
<220> FEATURE:
<223> OTHER INFORMATION: LasR/LasI Inducible & RHLR/RHLI repressible
      Promoter

<400> SEQUENCE: 564
gaaatctggc agttttggt acacgaaagc                                     30

<210> SEQ ID NO 565
<211> LENGTH: 30
<212> TYPE: DNA
<213> ORGANISM: Artificial Sequence
<220> FEATURE:
<223> OTHER INFORMATION: pLux/cI Hybrid Promoter

<400> SEQUENCE: 565
acaccgtgcg tgttgatata gtcgaataaa                                    30

<210> SEQ ID NO 566
<211> LENGTH: 30
<212> TYPE: DNA
<213> ORGANISM: Artificial Sequence
<220> FEATURE:

-continued

<223> OTHER INFORMATION: pLas promoter

<400> SEQUENCE: 566
aaaattatga aatttgtata aattcttcag					30

<210> SEQ ID NO 567
<211> LENGTH: 30
<212> TYPE: DNA
<213> ORGANISM: Artificial Sequence
<220> FEATURE:
<223> OTHER INFORMATION: pLas/cI Hybrid Promoter

<400> SEQUENCE: 567
ggttcttttt ggtacctctg gcggtgataa					30

<210> SEQ ID NO 568
<211> LENGTH: 30
<212> TYPE: DNA
<213> ORGANISM: Artificial Sequence
<220> FEATURE:
<223> OTHER INFORMATION: pLas/Lux Hybrid Promoter

<400> SEQUENCE: 568
tgtaggatcg tacaggtata aattcttcag					30

<210> SEQ ID NO 569
<211> LENGTH: 30
<212> TYPE: DNA
<213> ORGANISM: Artificial Sequence
<220> FEATURE:
<223> OTHER INFORMATION: pLux

<400> SEQUENCE: 569
caagaaaatg gtttgttata gtcgaataaa					30

<210> SEQ ID NO 570
<211> LENGTH: 30
<212> TYPE: DNA
<213> ORGANISM: Artificial Sequence
<220> FEATURE:
<223> OTHER INFORMATION: pLux/Las Hybrid Promoter

<400> SEQUENCE: 570
ctatctcatt tgctagtata gtcgaataaa					30

<210> SEQ ID NO 571
<211> LENGTH: 30
<212> TYPE: DNA
<213> ORGANISM: Artificial Sequence
<220> FEATURE:
<223> OTHER INFORMATION: Hybrid promoter: HSL-LuxR activated, P22 C2
      repressed

<400> SEQUENCE: 571
tagtttataa tttaagtgtt ctttaatttc					30

<210> SEQ ID NO 572
<211> LENGTH: 30
<212> TYPE: DNA
<213> ORGANISM: Artificial Sequence
<220> FEATURE:
<223> OTHER INFORMATION: PAI+LasR -> LuxI (AI)

<400> SEQUENCE: 572
caccttcggg tgggcctttc tgcgttata					30

<210> SEQ ID NO 573
<211> LENGTH: 30
<212> TYPE: DNA
<213> ORGANISM: Artificial Sequence
<220> FEATURE:
<223> OTHER INFORMATION: PAI+LasR -> LasI & AI+LuxR --[\m]LasI

<400> SEQUENCE: 573
aataactctg atagtgctag tgtagatctc                                          30

<210> SEQ ID NO 574
<211> LENGTH: 30
<212> TYPE: DNA
<213> ORGANISM: Artificial Sequence
<220> FEATURE:
<223> OTHER INFORMATION: PAI+LasR -> LasI+GFP & AI+LuxR --[\m]LasI+GFP

<400> SEQUENCE: 574
caccttcggg tgggcctttc tgcgtttata                                          30

<210> SEQ ID NO 575
<211> LENGTH: 30
<212> TYPE: DNA
<213> ORGANISM: Artificial Sequence
<220> FEATURE:
<223> OTHER INFORMATION: Complex QS -> LuxI & LasI circuit

<400> SEQUENCE: 575
caccttcggg tgggcctttc tgcgtttata                                          30

<210> SEQ ID NO 576
<211> LENGTH: 30
<212> TYPE: DNA
<213> ORGANISM: Artificial Sequence
<220> FEATURE:
<223> OTHER INFORMATION: position 3 mutated promoter lux pR-3 (luxR &
      HSL regulated)

<400> SEQUENCE: 576
caagaaaatg gtttgttata gtcgaataaa                                          30

<210> SEQ ID NO 577
<211> LENGTH: 30
<212> TYPE: DNA
<213> ORGANISM: Artificial Sequence
<220> FEATURE:
<223> OTHER INFORMATION: position 5 mutated promoter lux pR-5 (luxR &
      HSL regulated)

<400> SEQUENCE: 577
caagaaaatg gtttgttata gtcgaataaa                                          30

<210> SEQ ID NO 578
<211> LENGTH: 30
<212> TYPE: DNA
<213> ORGANISM: Artificial Sequence
<220> FEATURE:
<223> OTHER INFORMATION: position 3&5 mutated promoter lux pR-3/5
      (luxR & HSL regulated)

<400> SEQUENCE: 578
caagaaaatg gtttgttata gtcgaataaa                                          30

<210> SEQ ID NO 579
<211> LENGTH: 30
<212> TYPE: DNA

<213> ORGANISM: Artificial Sequence
<220> FEATURE:
<223> OTHER INFORMATION: Promoter (HSL-mediated luxR repressor)

<400> SEQUENCE: 579
ttgacacctg taggatcgta caggtataat                                    30

<210> SEQ ID NO 580
<211> LENGTH: 30
<212> TYPE: DNA
<213> ORGANISM: Artificial Sequence
<220> FEATURE:
<223> OTHER INFORMATION: Promoter (luxR & HSL regulated -- lux pR)

<400> SEQUENCE: 580
caagaaaatg gtttgttata gtcgaataaa                                    30

<210> SEQ ID NO 581
<211> LENGTH: 30
<212> TYPE: DNA
<213> ORGANISM: Artificial Sequence
<220> FEATURE:
<223> OTHER INFORMATION: Promoter (luxR & HSL regulated -- lux pL)

<400> SEQUENCE: 581
cacgcaaaac ttgcgacaaa caataggtaa                                    30

<210> SEQ ID NO 582
<211> LENGTH: 30
<212> TYPE: DNA
<213> ORGANISM: Artificial Sequence
<220> FEATURE:
<223> OTHER INFORMATION: Promoter (RhlR & C4-HSL regulated)

<400> SEQUENCE: 582
gttagctttc gaattggcta aaaagtgttc                                    30

<210> SEQ ID NO 583
<211> LENGTH: 30
<212> TYPE: DNA
<213> ORGANISM: Artificial Sequence
<220> FEATURE:
<223> OTHER INFORMATION: Promoter (cinR and HSL regulated)

<400> SEQUENCE: 583
ccattctgct ttccacgaac ttgaaaacgc                                    30

<210> SEQ ID NO 584
<211> LENGTH: 30
<212> TYPE: DNA
<213> ORGANISM: Artificial Sequence
<220> FEATURE:
<223> OTHER INFORMATION: Promoter (LasR & PAI regulated)

<400> SEQUENCE: 584
ggccgcgggt tcttttggt acacgaaagc                                     30

<210> SEQ ID NO 585
<211> LENGTH: 30
<212> TYPE: DNA
<213> ORGANISM: Artificial Sequence
<220> FEATURE:
<223> OTHER INFORMATION: Promoter, Standard (luxR and HSL regulated --
      lux pR)

<400> SEQUENCE: 585
aagaaaatgg tttgttgata ctcgaataaa                               30

<210> SEQ ID NO 586
<211> LENGTH: 30
<212> TYPE: DNA
<213> ORGANISM: Artificial Sequence
<220> FEATURE:
<223> OTHER INFORMATION: P(Bla)

<400> SEQUENCE: 586
gtttatacat aggcgagtac tctgttatgg                               30

<210> SEQ ID NO 587
<211> LENGTH: 30
<212> TYPE: DNA
<213> ORGANISM: Artificial Sequence
<220> FEATURE:
<223> OTHER INFORMATION: P(Cat)

<400> SEQUENCE: 587
agaggttcca actttcacca taatgaaaca                               30

<210> SEQ ID NO 588
<211> LENGTH: 30
<212> TYPE: DNA
<213> ORGANISM: Artificial Sequence
<220> FEATURE:
<223> OTHER INFORMATION: P(Kat)

<400> SEQUENCE: 588
taaacaacta acggacaatt ctacctaaca                               30

<210> SEQ ID NO 589
<211> LENGTH: 30
<212> TYPE: DNA
<213> ORGANISM: Artificial Sequence
<220> FEATURE:
<223> OTHER INFORMATION: Template for Building Primer Family Member

<400> SEQUENCE: 589
acatcaagcc aaattaaaca ggattaacac                               30

<210> SEQ ID NO 590
<211> LENGTH: 30
<212> TYPE: DNA
<213> ORGANISM: Artificial Sequence
<220> FEATURE:
<223> OTHER INFORMATION: Reverse lambda cI-regulated promoter

<400> SEQUENCE: 590
gaggtaaaat agtcaacacg cacggtgtta                               30

<210> SEQ ID NO 591
<211> LENGTH: 30
<212> TYPE: DNA
<213> ORGANISM: Artificial Sequence
<220> FEATURE:
<223> OTHER INFORMATION: Key Promoter absorbs 3

<400> SEQUENCE: 591
caggccggaa taactcccta taatgcgcca                               30

<210> SEQ ID NO 592
<211> LENGTH: 30
<212> TYPE: DNA
<213> ORGANISM: Artificial Sequence

```
<220> FEATURE:
<223> OTHER INFORMATION: constitutive promoter family member

<400> SEQUENCE: 592
ggctagctca gtcctaggta cagtgctagc                                              30

<210> SEQ ID NO 593
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 593
agctagctca gtcctaggta ttatgctagc                                              30

<210> SEQ ID NO 594
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 594
agctagctca gtcctaggta ctgtgctagc                                              30

<210> SEQ ID NO 595
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 595
agctagctca gtcctaggga ttatgctagc                                              30

<210> SEQ ID NO 596
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 596
agctagctca gtcctaggta ttgtgctagc                                              30

<210> SEQ ID NO 597
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 597
ggctagctca gtcctaggta ctatgctagc                                              30

<210> SEQ ID NO 598
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 598
ggctagctca gtcctaggta tagtgctagc                                              30
```

```
<210> SEQ ID NO 599
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 599
ggctagctca gccctaggta ttatgctagc                                    30

<210> SEQ ID NO 600
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 600
agctagctca gtcctaggta taatgctagc                                    30

<210> SEQ ID NO 601
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 601
agctagctca gtcctaggga ctgtgctagc                                    30

<210> SEQ ID NO 602
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 602
ggctagctca gtcctaggta caatgctagc                                    30

<210> SEQ ID NO 603
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 603
ggctagctca gtcctaggta tagtgctagc                                    30

<210> SEQ ID NO 604
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 604
agctagctca gtcctaggga ttatgctagc                                    30

<210> SEQ ID NO 605
<211> LENGTH: 30
<212> TYPE: DNA
<213> ORGANISM: Artificial Sequence
<220> FEATURE:
<223> OTHER INFORMATION: constitutive promoter family member
```

```
<400> SEQUENCE: 605
ggctagctca gtcctaggga ttatgctagc                                          30

<210> SEQ ID NO 606
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 606
ggctagctca gtcctaggta caatgctagc                                          30

<210> SEQ ID NO 607
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 607
agctagctca gcccttggta caatgctagc                                          30

<210> SEQ ID NO 608
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 608
agctagctca gtcctaggga ctatgctagc                                          30

<210> SEQ ID NO 609
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 609
agctagctca gtcctaggga ttgtgctagc                                          30

<210> SEQ ID NO 610
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 610
ggctagctca gtcctaggta ttgtgctagc                                          30

<210> SEQ ID NO 611
<211> LENGTH: 30
<212> TYPE: DNA
<213> ORGANISM: Artificial Sequence
<220> FEATURE:
<223> OTHER INFORMATION: constitutive promoter family member

<400> SEQUENCE: 611
agctagctca gtcctaggta taatgctagc                                          30

<210> SEQ ID NO 612
```

```
<211> LENGTH: 30
<212> TYPE: DNA
<213> ORGANISM: Artificial Sequence
<220> FEATURE:
<223> OTHER INFORMATION: 1bp mutant from J23107

<400> SEQUENCE: 612
ggctagctca gtcctaggta ttatgctagc                                    30

<210> SEQ ID NO 613
<211> LENGTH: 30
<212> TYPE: DNA
<213> ORGANISM: Artificial Sequence
<220> FEATURE:
<223> OTHER INFORMATION: 1bp mutant from J23114

<400> SEQUENCE: 613
ggctagctca gtcctaggta caatgctagc                                    30

<210> SEQ ID NO 614
<211> LENGTH: 30
<212> TYPE: DNA
<213> ORGANISM: Artificial Sequence
<220> FEATURE:
<223> OTHER INFORMATION: pBAD reverse

<400> SEQUENCE: 614
aaagtgtgac gccgtgcaaa taatcaatgt                                    30

<210> SEQ ID NO 615
<211> LENGTH: 30
<212> TYPE: DNA
<213> ORGANISM: Artificial Sequence
<220> FEATURE:
<223> OTHER INFORMATION: NikR promoter, a protein of the ribbon helix-
      helix family of trancription factors that repress expre

<400> SEQUENCE: 615
gacgaatact taaaatcgtc atacttattt                                    30

<210> SEQ ID NO 616
<211> LENGTH: 30
<212> TYPE: DNA
<213> ORGANISM: Artificial Sequence
<220> FEATURE:
<223> OTHER INFORMATION: lacq_Promoter

<400> SEQUENCE: 616
aaacctttcg cggtatggca tgatagcgcc                                    30

<210> SEQ ID NO 617
<211> LENGTH: 30
<212> TYPE: DNA
<213> ORGANISM: Artificial Sequence
<220> FEATURE:
<223> OTHER INFORMATION: lacIQ - promoter sequence

<400> SEQUENCE: 617
tgatagcgcc cggaagagag tcaattcagg                                    30

<210> SEQ ID NO 618
<211> LENGTH: 30
<212> TYPE: DNA
<213> ORGANISM: Artificial Sequence
<220> FEATURE:
<223> OTHER INFORMATION: E. Coli CreABCD phosphate sensing operon
      promoter
```

<400> SEQUENCE: 618
ttatttaccg tgacgaacta attgctcgtg                                                30

<210> SEQ ID NO 619
<211> LENGTH: 30
<212> TYPE: DNA
<213> ORGANISM: Artificial Sequence
<220> FEATURE:
<223> OTHER INFORMATION: GlnRS promoter

<400> SEQUENCE: 619
catacgccgt tatacgttgt ttacgctttg                                                30

<210> SEQ ID NO 620
<211> LENGTH: 30
<212> TYPE: DNA
<213> ORGANISM: Artificial Sequence
<220> FEATURE:
<223> OTHER INFORMATION: Constitutive weak promoter of lacZ

<400> SEQUENCE: 620
ttatgcttcc ggctcgtatg ttgtgtggac                                                30

<210> SEQ ID NO 621
<211> LENGTH: 30
<212> TYPE: DNA
<213> ORGANISM: Artificial Sequence
<220> FEATURE:
<223> OTHER INFORMATION: Mutated LacZ promoter

<400> SEQUENCE: 621
ttatgcttcc ggctcgtatg gtgtgtggac                                                30

<210> SEQ ID NO 622
<211> LENGTH: 30
<212> TYPE: DNA
<213> ORGANISM: Artificial Sequence
<220> FEATURE:
<223> OTHER INFORMATION: constitutive promoter with (TA)10 between -10
    and -35 elements

<400> SEQUENCE: 622
atatatatat atatataatg gaagcgtttt                                                30

<210> SEQ ID NO 623
<211> LENGTH: 30
<212> TYPE: DNA
<213> ORGANISM: Artificial Sequence
<220> FEATURE:
<223> OTHER INFORMATION: constitutive promoter with (TA)9 between -10
    and -35 elements

<400> SEQUENCE: 623
atatatatat atatataatg gaagcgtttt                                                30

<210> SEQ ID NO 624
<211> LENGTH: 30
<212> TYPE: DNA
<213> ORGANISM: Artificial Sequence
<220> FEATURE:
<223> OTHER INFORMATION: constitutive promoter with (C)10 between -10
    and -35 elements

<400> SEQUENCE: 624
ccccgaaagc ttaagaatat aattgtaagc                                                30

<210> SEQ ID NO 625
<211> LENGTH: 30
<212> TYPE: DNA
<213> ORGANISM: Artificial Sequence
<220> FEATURE:
<223> OTHER INFORMATION: constitutive promoter with (C)12 between -10
    and -35 elements

<400> SEQUENCE: 625
ccccgaaagc ttaagaatat aattgtaagc                                30

<210> SEQ ID NO 626
<211> LENGTH: 30
<212> TYPE: DNA
<213> ORGANISM: Artificial Sequence
<220> FEATURE:
<223> OTHER INFORMATION: optimized (TA) repeat constitutive promoter
    with 13 bp between -10 and -35 elements

<400> SEQUENCE: 626
tgacaatata tatatatata taatgctagc                                30

<210> SEQ ID NO 627
<211> LENGTH: 30
<212> TYPE: DNA
<213> ORGANISM: Artificial Sequence
<220> FEATURE:
<223> OTHER INFORMATION: optimized (TA) repeat constitutive promoter
    with 15 bp between -10 and -35 elements

<400> SEQUENCE: 627
acaatatata tatatatata taatgctagc                                30

<210> SEQ ID NO 628
<211> LENGTH: 30
<212> TYPE: DNA
<213> ORGANISM: Artificial Sequence
<220> FEATURE:
<223> OTHER INFORMATION: optimized (TA) repeat constitutive promoter
    with 17 bp between -10 and -35 elements

<400> SEQUENCE: 628
aatatatata tatatatata taatgctagc                                30

<210> SEQ ID NO 629
<211> LENGTH: 30
<212> TYPE: DNA
<213> ORGANISM: Artificial Sequence
<220> FEATURE:
<223> OTHER INFORMATION: optimized (TA) repeat constitutive promoter
    with 19 bp between -10 and -35 elements

<400> SEQUENCE: 629
tatatatata tatatatata taatgctagc                                30

<210> SEQ ID NO 630
<211> LENGTH: 30
<212> TYPE: DNA
<213> ORGANISM: Artificial Sequence
<220> FEATURE:
<223> OTHER INFORMATION: optimized (TA) repeat constitutive promoter
    with 21 bp between -10 and -35 elements

<400> SEQUENCE: 630
tatatatata tatatatata taatgctagc                                30

-continued

<210> SEQ ID NO 631
<211> LENGTH: 30
<212> TYPE: DNA
<213> ORGANISM: Artificial Sequence
<220> FEATURE:
<223> OTHER INFORMATION: optimized (A) repeat constitutive promoter with
      17 bp between -10 and -35 elements

<400> SEQUENCE: 631
aaaaaaaaaa aaaaaaaata taatgctagc                                       30

<210> SEQ ID NO 632
<211> LENGTH: 30
<212> TYPE: DNA
<213> ORGANISM: Artificial Sequence
<220> FEATURE:
<223> OTHER INFORMATION: optimized (A) repeat constitutive promoter with
      18 bp between -10 and -35 elements

<400> SEQUENCE: 632
aaaaaaaaaa aaaaaaaata taatgctagc                                       30

<210> SEQ ID NO 633
<211> LENGTH: 30
<212> TYPE: DNA
<213> ORGANISM: Artificial Sequence
<220> FEATURE:
<223> OTHER INFORMATION: J23101:GFP

<400> SEQUENCE: 633
caccttcggg tgggcctttc tgcgtttata                                       30

<210> SEQ ID NO 634
<211> LENGTH: 30
<212> TYPE: DNA
<213> ORGANISM: Artificial Sequence
<220> FEATURE:
<223> OTHER INFORMATION: J23119:IFP

<400> SEQUENCE: 634
caccttcggg tgggcctttc tgcgtttata                                       30

<210> SEQ ID NO 635
<211> LENGTH: 30
<212> TYPE: DNA
<213> ORGANISM: Artificial Sequence
<220> FEATURE:
<223> OTHER INFORMATION: J23119:HO1

<400> SEQUENCE: 635
caccttcggg tgggcctttc tgcgtttata                                       30

<210> SEQ ID NO 636
<211> LENGTH: 30
<212> TYPE: DNA
<213> ORGANISM: Artificial Sequence
<220> FEATURE:
<223> OTHER INFORMATION: Infrared signal reporter
      (J23119:IFP:J23119:HO1)

<400> SEQUENCE: 636
caccttcggg tgggcctttc tgcgtttata                                       30

<210> SEQ ID NO 637
<211> LENGTH: 30
<212> TYPE: DNA

```
<213> ORGANISM: Artificial Sequence
<220> FEATURE:
<223> OTHER INFORMATION: Double terminator + constitutive promoter

<400> SEQUENCE: 637
ggctagctca gtcctaggta cagtgctagc                                          30

<210> SEQ ID NO 638
<211> LENGTH: 30
<212> TYPE: DNA
<213> ORGANISM: Artificial Sequence
<220> FEATURE:
<223> OTHER INFORMATION: Double terminator + Constitutive promoter +
      Strong RBS

<400> SEQUENCE: 638
tgctagctac tagagattaa agaggagaaa                                          30

<210> SEQ ID NO 639
<211> LENGTH: 30
<212> TYPE: DNA
<213> ORGANISM: Artificial Sequence
<220> FEATURE:
<223> OTHER INFORMATION: IPTG inducible Lac promoter cassette

<400> SEQUENCE: 639
ttgtgagcgg ataacaagat actgagcaca                                          30

<210> SEQ ID NO 640
<211> LENGTH: 30
<212> TYPE: DNA
<213> ORGANISM: Artificial Sequence
<220> FEATURE:
<223> OTHER INFORMATION: IPTG inducible Lac promoter cassette

<400> SEQUENCE: 640
ttgtgagcgg ataacaagat actgagcaca                                          30

<210> SEQ ID NO 641
<211> LENGTH: 30
<212> TYPE: DNA
<213> ORGANISM: Artificial Sequence
<220> FEATURE:
<223> OTHER INFORMATION: IPTG inducible Lac promoter cassette

<400> SEQUENCE: 641
ttgtgagcgg ataacaagat actgagcaca                                          30

<210> SEQ ID NO 642
<211> LENGTH: 30
<212> TYPE: DNA
<213> ORGANISM: Artificial Sequence
<220> FEATURE:
<223> OTHER INFORMATION: M13K07 gene I promoter

<400> SEQUENCE: 642
cctgttttta tgttattctc tctgtaaagg                                          30

<210> SEQ ID NO 643
<211> LENGTH: 30
<212> TYPE: DNA
<213> ORGANISM: Artificial Sequence
<220> FEATURE:
<223> OTHER INFORMATION: M13K07 gene II promoter

<400> SEQUENCE: 643
```

```
aaatatttgc ttatacaatc ttcctgtttt                                       30

<210> SEQ ID NO 644
<211> LENGTH: 30
<212> TYPE: DNA
<213> ORGANISM: Artificial Sequence
<220> FEATURE:
<223> OTHER INFORMATION: M13K07 gene III promoter

<400> SEQUENCE: 644
gctgataaac cgatacaatt aaaggctcct                                       30

<210> SEQ ID NO 645
<211> LENGTH: 30
<212> TYPE: DNA
<213> ORGANISM: Artificial Sequence
<220> FEATURE:
<223> OTHER INFORMATION: M13K07 gene IV promoter

<400> SEQUENCE: 645
ctcttctcag cgtcttaatc taagctatcg                                       30

<210> SEQ ID NO 646
<211> LENGTH: 30
<212> TYPE: DNA
<213> ORGANISM: Artificial Sequence
<220> FEATURE:
<223> OTHER INFORMATION: M13K07 gene V promoter

<400> SEQUENCE: 646
atgagccagt tcttaaaatc gcataaggta                                       30

<210> SEQ ID NO 647
<211> LENGTH: 30
<212> TYPE: DNA
<213> ORGANISM: Artificial Sequence
<220> FEATURE:
<223> OTHER INFORMATION: M13K07 gene VI promoter

<400> SEQUENCE: 647
ctattgattg tgacaaaata aacttattcc                                       30

<210> SEQ ID NO 648
<211> LENGTH: 30
<212> TYPE: DNA
<213> ORGANISM: Artificial Sequence
<220> FEATURE:
<223> OTHER INFORMATION: M13K07 gene VIII promoter

<400> SEQUENCE: 648
gtttcgcgct tggtataatc gctggggtc                                        30

<210> SEQ ID NO 649
<211> LENGTH: 30
<212> TYPE: DNA
<213> ORGANISM: Artificial Sequence
<220> FEATURE:
<223> OTHER INFORMATION: M13110

<400> SEQUENCE: 649
ctttgcttct gactataata gtcagggtaa                                       30

<210> SEQ ID NO 650
<211> LENGTH: 30
<212> TYPE: DNA
<213> ORGANISM: Artificial Sequence
```

```
<220> FEATURE:
<223> OTHER INFORMATION: Modified promoter sequence of g3.

<400> SEQUENCE: 650
aaaccgatac aattaaaggc tcctgctagc                                           30

<210> SEQ ID NO 651
<211> LENGTH: 30
<212> TYPE: DNA
<213> ORGANISM: Artificial Sequence
<220> FEATURE:
<223> OTHER INFORMATION: Constitutive Promoter I

<400> SEQUENCE: 651
caccacactg atagtgctag tgtagatcac                                           30

<210> SEQ ID NO 652
<211> LENGTH: 30
<212> TYPE: DNA
<213> ORGANISM: Artificial Sequence
<220> FEATURE:
<223> OTHER INFORMATION: Constitutive Promoter II

<400> SEQUENCE: 652
gccggaataa ctccctataa tgcgccacca                                           30

<210> SEQ ID NO 653
<211> LENGTH: 30
<212> TYPE: DNA
<213> ORGANISM: Artificial Sequence
<220> FEATURE:
<223> OTHER INFORMATION: --Specify Parts List--

<400> SEQUENCE: 653
ttgacaagct tttcctcagc tccgtaaact                                           30

<210> SEQ ID NO 654
<211> LENGTH: 30
<212> TYPE: DNA
<213> ORGANISM: Artificial Sequence
<220> FEATURE:
<223> OTHER INFORMATION: Full-length stationary phase osmY promoter

<400> SEQUENCE: 654
ggtttcaaaa ttgtgatcta tatttaacaa                                           30

<210> SEQ ID NO 655
<211> LENGTH: 30
<212> TYPE: DNA
<213> ORGANISM: Artificial Sequence
<220> FEATURE:
<223> OTHER INFORMATION: Minimal stationary phase osmY promoter

<400> SEQUENCE: 655
ggtttcaaaa ttgtgatcta tatttaacaa                                           30

<210> SEQ ID NO 656
<211> LENGTH: 30
<212> TYPE: DNA
<213> ORGANISM: Artificial Sequence
<220> FEATURE:
<223> OTHER INFORMATION: htpG Heat Shock Promoter

<400> SEQUENCE: 656
tctattccaa taaagaaatc ttcctgcgtg                                           30
```

<210> SEQ ID NO 657
<211> LENGTH: 30
<212> TYPE: DNA
<213> ORGANISM: Artificial Sequence
<220> FEATURE:
<223> OTHER INFORMATION: Promoter veg a constitutive promoter for B.
      subtilis

<400> SEQUENCE: 657
aaaaatgggc tcgtgttgta caataaatgt                                      30

<210> SEQ ID NO 658
<211> LENGTH: 30
<212> TYPE: DNA
<213> ORGANISM: Artificial Sequence
<220> FEATURE:
<223> OTHER INFORMATION: Promoter 43 a constitutive promoter for B.
      subtilis

<400> SEQUENCE: 658
aaaaaaagcg cgcgattatg taaaatataa                                      30

<210> SEQ ID NO 659
<211> LENGTH: 30
<212> TYPE: DNA
<213> ORGANISM: Artificial Sequence
<220> FEATURE:
<223> OTHER INFORMATION: Strong constitutive promoter for Bacillus
      subtilis

<400> SEQUENCE: 659
aattgcagta ggcatgacaa aatggactca                                      30

<210> SEQ ID NO 660
<211> LENGTH: 30
<212> TYPE: DNA
<213> ORGANISM: Artificial Sequence
<220> FEATURE:
<223> OTHER INFORMATION: PliaG

<400> SEQUENCE: 660
caagcttttc ctttataata gaatgaatga                                      30

<210> SEQ ID NO 661
<211> LENGTH: 30
<212> TYPE: DNA
<213> ORGANISM: Artificial Sequence
<220> FEATURE:
<223> OTHER INFORMATION: PlepA

<400> SEQUENCE: 661
tctaagctag tgtattttgc gtttaatagt                                      30

<210> SEQ ID NO 662
<211> LENGTH: 30
<212> TYPE: DNA
<213> ORGANISM: Artificial Sequence
<220> FEATURE:
<223> OTHER INFORMATION: Pveg

<400> SEQUENCE: 662
aatgggctcg tgttgtacaa taaatgtagt                                      30

<210> SEQ ID NO 663
<211> LENGTH: 30
<212> TYPE: DNA

```
<213> ORGANISM: Artificial Sequence
<220> FEATURE:
<223> OTHER INFORMATION: Promoter ctc for B. subtilis

<400> SEQUENCE: 663
atccttatcg ttatgggtat tgtttgtaat                                30

<210> SEQ ID NO 664
<211> LENGTH: 30
<212> TYPE: DNA
<213> ORGANISM: Artificial Sequence
<220> FEATURE:
<223> OTHER INFORMATION: Promoter gsiB for B. subtilis

<400> SEQUENCE: 664
taaaagaatt gtgagcggga atacaacaac                                30

<210> SEQ ID NO 665
<211> LENGTH: 30
<212> TYPE: DNA
<213> ORGANISM: Artificial Sequence
<220> FEATURE:
<223> OTHER INFORMATION: Promoter 43 a constitutive promoter for B.
      subtilis

<400> SEQUENCE: 665
aaaaaaagcg cgcgattatg taaaatataa                                30

<210> SEQ ID NO 666
<211> LENGTH: 30
<212> TYPE: DNA
<213> ORGANISM: Artificial Sequence
<220> FEATURE:
<223> OTHER INFORMATION: Pspv2 from Salmonella

<400> SEQUENCE: 666
tacaaaataa ttccctgca aacattatca                                 30

<210> SEQ ID NO 667
<211> LENGTH: 30
<212> TYPE: DNA
<213> ORGANISM: Artificial Sequence
<220> FEATURE:
<223> OTHER INFORMATION: Pspv from Salmonella

<400> SEQUENCE: 667
tacaaaataa ttccctgca aacattatcg                                 30

<210> SEQ ID NO 668
<211> LENGTH: 30
<212> TYPE: DNA
<213> ORGANISM: Artificial Sequence
<220> FEATURE:
<223> OTHER INFORMATION: T7 promoter (strong promoter from T7
      bacteriophage)

<400> SEQUENCE: 668
agggaataca agctacttgt tcttttttgca                               30

<210> SEQ ID NO 669
<211> LENGTH: 23
<212> TYPE: DNA
<213> ORGANISM: Artificial Sequence
<220> FEATURE:
<223> OTHER INFORMATION: T7 Promoter

<400> SEQUENCE: 669
```

```
taatacgact cactataggg aga                                           23

<210> SEQ ID NO 670
<211> LENGTH: 28
<212> TYPE: DNA
<213> ORGANISM: Artificial Sequence
<220> FEATURE:
<223> OTHER INFORMATION: T7 Promoter

<400> SEQUENCE: 670
gaatttaata cgactcacta tagggaga                                      28

<210> SEQ ID NO 671
<211> LENGTH: 19
<212> TYPE: DNA
<213> ORGANISM: Artificial Sequence
<220> FEATURE:
<223> OTHER INFORMATION: T7 consensus -10 and rest

<400> SEQUENCE: 671
taatacgact cactatagg                                                19

<210> SEQ ID NO 672
<211> LENGTH: 30
<212> TYPE: DNA
<213> ORGANISM: Artificial Sequence
<220> FEATURE:
<223> OTHER INFORMATION: overlapping T7 promoter

<400> SEQUENCE: 672
gagtcgtatt aatacgactc actatagggg                                    30

<210> SEQ ID NO 673
<211> LENGTH: 30
<212> TYPE: DNA
<213> ORGANISM: Artificial Sequence
<220> FEATURE:
<223> OTHER INFORMATION: more overlapping T7 promoter

<400> SEQUENCE: 673
agtgagtcgt actacgactc actatagggg                                    30

<210> SEQ ID NO 674
<211> LENGTH: 30
<212> TYPE: DNA
<213> ORGANISM: Artificial Sequence
<220> FEATURE:
<223> OTHER INFORMATION: weaken overlapping T7 promoter

<400> SEQUENCE: 674
gagtcgtatt aatacgactc tctatagggg                                    30

<210> SEQ ID NO 675
<211> LENGTH: 23
<212> TYPE: DNA
<213> ORGANISM: Artificial Sequence
<220> FEATURE:
<223> OTHER INFORMATION: T7 Consensus Promoter Sequence

<400> SEQUENCE: 675
taatacgact cactataggg aga                                           23

<210> SEQ ID NO 676
<211> LENGTH: 23
<212> TYPE: DNA
```

```
<213> ORGANISM: Artificial Sequence
<220> FEATURE:
<223> OTHER INFORMATION: T7 RNAP promoter

<400> SEQUENCE: 676
ttatacgact cactataggg aga                                    23

<210> SEQ ID NO 677
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 677
gaatacgact cactataggg aga                                    23

<210> SEQ ID NO 678
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 678
taatacgtct cactataggg aga                                    23

<210> SEQ ID NO 679
<211> LENGTH: 23
<212> TYPE: DNA
<213> ORGANISM: Artificial Sequence
<220> FEATURE:
<223> OTHER INFORMATION: T7 RNAP promoter

<400> SEQUENCE: 679
tcatacgact cactataggg aga                                    23

<210> SEQ ID NO 680
<211> LENGTH: 30
<212> TYPE: DNA
<213> ORGANISM: Artificial Sequence
<220> FEATURE:
<223> OTHER INFORMATION: T7 strong promoter

<400> SEQUENCE: 680
taatacgact cactataggg agaccacaac                             30

<210> SEQ ID NO 681
<211> LENGTH: 30
<212> TYPE: DNA
<213> ORGANISM: Artificial Sequence
<220> FEATURE:
<223> OTHER INFORMATION: T7 weak binding and processivity

<400> SEQUENCE: 681
taattgaact cactaaaggg agaccacagc                             30

<210> SEQ ID NO 682
<211> LENGTH: 30
<212> TYPE: DNA
<213> ORGANISM: Artificial Sequence
<220> FEATURE:
<223> OTHER INFORMATION: T7 weak binding promoter

<400> SEQUENCE: 682
cgaagtaata cgactcacta ttagggaaga                             30
```

<210> SEQ ID NO 683
<211> LENGTH: 30
<212> TYPE: DNA
<213> ORGANISM: Artificial Sequence
<220> FEATURE:
<223> OTHER INFORMATION: pCyc (Medium) Promoter

<400> SEQUENCE: 683
acaaacacaa atacacacac taaattaata                    30

<210> SEQ ID NO 684
<211> LENGTH: 30
<212> TYPE: DNA
<213> ORGANISM: Artificial Sequence
<220> FEATURE:
<223> OTHER INFORMATION: pAdh (Strong) Promoter

<400> SEQUENCE: 684
ccaagcatac aatcaactat ctcatataca                    30

<210> SEQ ID NO 685
<211> LENGTH: 30
<212> TYPE: DNA
<213> ORGANISM: Artificial Sequence
<220> FEATURE:
<223> OTHER INFORMATION: pSte5 (Weak) Promoter

<400> SEQUENCE: 685
gatacaggat acagcggaaa caacttttaa                    30

<210> SEQ ID NO 686
<211> LENGTH: 30
<212> TYPE: DNA
<213> ORGANISM: Artificial Sequence
<220> FEATURE:
<223> OTHER INFORMATION: yeast ADH1 promoter

<400> SEQUENCE: 686
tttcaagcta taccaagcat acaatcaact                    30

<210> SEQ ID NO 687
<211> LENGTH: 30
<212> TYPE: DNA
<213> ORGANISM: Artificial Sequence
<220> FEATURE:
<223> OTHER INFORMATION: cyc100 minimal promoter

<400> SEQUENCE: 687
cctttgcagc ataaattact atacttctat                    30

<210> SEQ ID NO 688
<211> LENGTH: 30
<212> TYPE: DNA
<213> ORGANISM: Artificial Sequence
<220> FEATURE:
<223> OTHER INFORMATION: cyc70 minimal promoter

<400> SEQUENCE: 688
cctttgcagc ataaattact atacttctat                    30

<210> SEQ ID NO 689
<211> LENGTH: 30
<212> TYPE: DNA
<213> ORGANISM: Artificial Sequence
<220> FEATURE:

<223> OTHER INFORMATION: cyc43 minimal promoter

<400> SEQUENCE: 689
cctttgcagc ataaattact atacttctat                                30

<210> SEQ ID NO 690
<211> LENGTH: 30
<212> TYPE: DNA
<213> ORGANISM: Artificial Sequence
<220> FEATURE:
<223> OTHER INFORMATION: cyc28 minimal promoter

<400> SEQUENCE: 690
cctttgcagc ataaattact atacttctat                                30

<210> SEQ ID NO 691
<211> LENGTH: 30
<212> TYPE: DNA
<213> ORGANISM: Artificial Sequence
<220> FEATURE:
<223> OTHER INFORMATION: cyc16 minimal promoter

<400> SEQUENCE: 691
cctttgcagc ataaattact atacttctat                                30

<210> SEQ ID NO 692
<211> LENGTH: 30
<212> TYPE: DNA
<213> ORGANISM: Artificial Sequence
<220> FEATURE:
<223> OTHER INFORMATION: pPGK1

<400> SEQUENCE: 692
ttatctactt tttacaacaa atataaaaca                                30

<210> SEQ ID NO 693
<211> LENGTH: 30
<212> TYPE: DNA
<213> ORGANISM: Artificial Sequence
<220> FEATURE:
<223> OTHER INFORMATION: pCYC Yeast Promoter

<400> SEQUENCE: 693
acaaacacaa atacacacac taaattaata                                30

<210> SEQ ID NO 694
<211> LENGTH: 30
<212> TYPE: DNA
<213> ORGANISM: Artificial Sequence
<220> FEATURE:
<223> OTHER INFORMATION: Yeast GPD (TDH3) Promoter

<400> SEQUENCE: 694
gtttcgaata aacacacata aacaaacaaa                                30

<210> SEQ ID NO 695
<211> LENGTH: 30
<212> TYPE: DNA
<213> ORGANISM: Artificial Sequence
<220> FEATURE:
<223> OTHER INFORMATION: yeast mid-length ADH1 promoter

<400> SEQUENCE: 695
ccaagcatac aatcaactat ctcatataca                                30

```
<210> SEQ ID NO 696
<211> LENGTH: 30
<212> TYPE: DNA
<213> ORGANISM: Artificial Sequence
<220> FEATURE:
<223> OTHER INFORMATION: Yeast CLB1 promoter region, G2/M cell cycle
      specific

<400> SEQUENCE: 696
accatcaaag gaagctttaa tcttctcata                                        30

<210> SEQ ID NO 697
<211> LENGTH: 30
<212> TYPE: DNA
<213> ORGANISM: Artificial Sequence
<220> FEATURE:
<223> OTHER INFORMATION: CMV promoter

<400> SEQUENCE: 697
agaacccact gcttactggc ttatcgaaat                                        30

<210> SEQ ID NO 698
<211> LENGTH: 30
<212> TYPE: DNA
<213> ORGANISM: Artificial Sequence
<220> FEATURE:
<223> OTHER INFORMATION: Ubc Promoter

<400> SEQUENCE: 698
ggccgttttt ggcttttttg ttagacgaag                                        30

<210> SEQ ID NO 699
<211> LENGTH: 564
<212> TYPE: DNA
<213> ORGANISM: Escherichia coli
<220> FEATURE:
<221> NAME/KEY: gene
<222> LOCATION: (1)..(564)
<223> OTHER INFORMATION: McbG gene

<400> SEQUENCE: 699
atggatataa tagaaaaaag aatcacaaaa cgacacctca gtgaaagtga attatcaggt        60
gtaaattatt acaattgtat atttgaacga atacagcttg acaactttaa ctttcgcgat       120
tgtgagttcg aaaaatgtcg cttcgtaaac tgctcaataa agaatttaaa acttaatttt       180
tttaaactta ttgactgtga attcaaagat tgtttattac aaggagtaaa tgcagcagac       240
attatgtttc cctgtacttt ttctcttgta aattgtgatt tgagatttgt tgattttatt       300
agtttacggt tacagaaatc tattttttta tcctgtcgct tccgtgattg tttatttgag       360
gaaacagacc ttcgtaaatc tgattttact ggttcggagt ttaataatac agagttcaga       420
cattctgatt tgtctcactg tgatttttca atgacagaag gtctcgatat aaatcctgag       480
ataaacagga tcttatctat aaagatacca caggaagcag gtttaaaaat acttaaacga       540
atgggagtgg ttgtagggg  atga                                             564

<210> SEQ ID NO 700
<211> LENGTH: 1770
<212> TYPE: DNA
<213> ORGANISM: Escherichia coli
<220> FEATURE:
<221> NAME/KEY: gene
<222> LOCATION: (1)..(1770)
<223> OTHER INFORMATION: MccE gene

<400> SEQUENCE: 700
```

-continued

```
atggcgcaaa aaataacacc atctaaaatt gttaaacatg cccgggagtt aattattaag      60
gggattgaat cggcgataa ctcatttgtc attttgatg tagatggagc tctggagcgt       120
ctggaacatt acaggtgtca acttaagagt tttttcccca acagcagtat cgcatattca     180
tataagtcaa ataatctggc acaatggtgc cagattatct caggtaaagg tttgtatgca    240
gaggtgtgct ctgttgatga aatgaacctc gctaaaagag acggttttaa ccggattgtt    300
tttgatggcc ctttaaaaaa aacgagtgaa ctattaaagg caatagagat tggggcatta    360
attgaagttg acaatattga tgaatgtaaa agacttaatg aactatgtaa attgcataag    420
ttgacatgta gaattcattt gagattatcg cattactatg atgataattt atcaagattt    480
ggcttatctg aaagtgaggc tattaattta ctggagatgt tgatcagtaa gtcagagtat    540
ctcattttag acgggttcca tttacatgtt ggctctaatc tacccaatgc ggaaaaaata    600
tgtaaagctg ttatacagta tcatgagttg attcttaggt atatgccaga tgatggcact    660
cttaatcttg gtagtgggat acctgcagat tctttctcag catccagtga taacccaact    720
ccatgtccgg aggtattttt ctcatcgata tatgatacaa taaaaaattg cttcggtact    780
gtatgtgata aatggaacta tattttgaa cctgggagac atctggtcga agactttggc     840
tactttatag ggaaagttat tagtactaaa aacaggtatg gtgttaaagt tgctcaaact    900
aacattggta taaactggat accttcgatc agaaattggg accattcatt tacattgttt    960
cataatcata accatatttc agatgataaa tctgatgagt atattattgc tggattcaat    1020
tgctttgaat gtgattgctt gtttccttca gttattcttc ccagtaactt atctgattat    1080 ttatttctg ttcgagggtg tggtgcttat gatatgcaaa caggaaacca gtggacgcgt     1140
aatctttatg ctgtatatac cataacaaat gatgttgtta atatatcaag gattcacaga    1200
agagaacttg atttccggaa gtatgatgta tctcttacgc catcaggaat aaaagtaaat    1260
gatgagatta cattattgta tccagcgtta aaatacgctg aagagttata tttgctcatt    1320
aatcaaaaca aaataaattt cattaaaagc atggcatggc cagcgtttgt taataacatt    1380
tctgattctg tttctttcat tgagcaatca atgattgata accagaatga aaaagcatta    1440 atcctctta ttaaatacaa aactaagata gctggcgttg tatcttttaa tattattgac     1500
catgccaata aaacagcata tattggctat tggttaggcg ctaactttca gggaaagggg   1560
attgtaacca atgctataaa taaactgata caggagtatg gggattcggg cgttataaaa    1620
agatttgtta taaaatgtat tgttgataat aaaaaagta atgccacggc attgaggtgt     1680
ggcttcacct tagagggtgt tctgcaaaaa gcagaaatac tcaacggtgt atcatacgat   1740 caaaatatt attcgaaagt aattggttaa                                      1770
```

<210> SEQ ID NO 701
<211> LENGTH: 561
<212> TYPE: DNA
<213> ORGANISM: Artificial sequence
<220> FEATURE:
<223> OTHER INFORMATION: C-terminal part of MccE gene

<400> SEQUENCE: 701

```
atgttccgga agtatgatgt atctcttacg ccatcaggaa taaaagtaaa tgatgagatt      60
acattattgt atccagcgtt aaaatacgct gaagagttat atttgctcat taatcaaaac    120
aaaataaatt tcattaaaag catggcatgg ccagcgtttg ttaataacat ttctgattct    180
gtttctttca ttgagcaatc aatgattgat aaccagaatg aaaaagcatt aatcctcttt    240
```

| | |
|---|---|
| attaaataca aaactaagat agctggcgtt gtatctttta atattattga ccatgccaat | 300 |
| aaaacagcat atattggcta ttggttaggc gctaactttc agggaaaggg gattgtaacc | 360 |
| aatgctataa ataaactgat acaggagtat ggggattcgg gcgttataaa aagatttgtt | 420 |
| ataaaatgta ttgttgataa taaaaaaagt aatgccacgg cattgaggtg tggcttcacc | 480 |
| ttagagggtg ttctgcaaaa agcagaaata ctcaacggtg tatcatacga tcaaaatatt | 540 |
| tattcgaaag taattggtta a | 561 |

<210> SEQ ID NO 702
<211> LENGTH: 6904
<212> TYPE: DNA
<213> ORGANISM: Artificial Sequence
<220> FEATURE:
<223> OTHER INFORMATION: pSyn2-McbG

<400> SEQUENCE: 702

| | |
|---|---|
| atggatataa tagaaaaaag aatcacaaaa cgacacctca gtgaaagtga attatcaggt | 60 |
| gtaaattatt acaattgtat atttgaacga atacagcttg acaactttaa ctttcgcgat | 120 |
| tgtgagttcg aaaaatgtcg cttcgtaaac tgctcaataa agaatttaaa acttaatttt | 180 |
| tttaaactta ttgactgtga attcaaagat tgtttattac aaggagtaaa tgcagcagac | 240 |
| attatgtttc cctgtacttt ttctcttgta aattgtgatt tgagatttgt tgatttatt | 300 |
| agtttacggt tacagaaatc tattttttta tcctgtcgct tccgtgattg tttatttgag | 360 |
| gaaacagacc ttcgtaaatc tgattttact ggttcggagt ttaataatac agagttcaga | 420 |
| cattctgatt tgtctcactg tgattttca atgacagaag gtctcgatat aaatcctgag | 480 |
| ataaacagga tcttatctat aaagatacca caggaagcag gtttaaaaat acttaaacga | 540 |
| atgggagtgg ttgtaggggg atgacttctg ttttggcgga tgagagaaga ttttcagcct | 600 |
| gatacagatt aaatcagaac gcagaagcgg tctgataaaa cagaatttgc ctggcggcag | 660 |
| tagcgcggtg gtcccacctg accccatgcc gaactcagaa gtgaaacgcc gtagcgccga | 720 |
| tggtagtgtg gggtctcccc atgcgagagt agggaactgc caggcatcaa ataaaacgaa | 780 |
| aggctcagtc gaaagactgg gccttttcgtt ttatctgttg tttgtcggtg aacgctctcc | 840 |
| tgagtaggac aaatccgccg ggagcggatt tgaacgttgc gaagcaacgg cccggagggt | 900 |
| ggcgggcagg acgcccgcca taaactgcca ggcatcaaat taagcagaag gccatcctga | 960 |
| cggatggcct ttttgcgttt ctacaaactc ttttgttat ttttctaaat acattcaaat | 1020 |
| atgtatccgc tcatgagaca ataaccctga taaatgcttc aataatattg aaaaaggaag | 1080 |
| agtatgagta ttcaacattt ccgtgtcgcc cttattccct tttttgcggc attttgcctt | 1140 |
| cctgtttttg ctcacccaga aacgctggtg aaagtaaaag atgctgaaga tcagttgggt | 1200 |
| gcacgagtgg gttacatcga actggatctc aacagcggta agatccttga gttttcgc | 1260 |
| cccgaagaac gttttccaat gatgagcact tttaaagttc tgctatgtgg cgcggtatta | 1320 |
| tcccgtgttg acgccgggca agagcaactc ggtcgccgca tacactattc tcagaatgac | 1380 |
| ttggttgagt actcaccagt cacagaaaag catcttacgg atggcatgac agtaagagaa | 1440 |
| ttatgcagtg ctgccataac catgagtgat aacactgcgg ccaacttact tctgacaacg | 1500 |
| atcggaggac cgaaggagct aaccgctttt ttgcacaaca tgggggatca tgtaactcgc | 1560 |
| cttgatcgtt gggaaccgga gctgaatgaa gccataccaa acgacgagcg tgacaccacg | 1620 |
| atgcctgtag caatggcaac aacgttgcgc aaactattaa ctggcgaact acttactcta | 1680 |
| gcttcccggc aacaattaat agactggatg gaggcggata aagttgcagg accacttctg | 1740 |

```
cgctcggccc ttccggctgg ctggtttatt gctgataaat ctggagccgg tgagcgtggg    1800
tctcgcggta tcattgcagc actggggcca gatggtaagc cctcccgtat cgtagttatc    1860
tacacgacgg ggagtcaggc aactatggat gaacgaaata gacagatcgc tgagataggt    1920
gcctcactga ttaagcattg gtaactgtca gaccaagttt actcatatat actttagatt    1980
gatttaaaac ttcattttta atttaaaagg atctaggtga agatccttttt tgataatctc    2040 atgaccaaaa tcccttaacg tgagttttcg ttccactgag cgtcagaccc cgtagaaaag    2100
atcaaaggat cttcttgaga tccttttttt ctgcgcgtaa tctgctgctt gcaaacaaaa    2160
aaaccaccgc taccagcggt ggtttgtttg ccggatcaag agctaccaac tcttttttccg    2220 aaggtaactg gcttcagcag agcgcagata ccaaatactg tccttctagt gtagccgtag    2280
ttaggccacc acttcaagaa ctctgtagca ccgcctacat acctcgctct gctaatcctg    2340
ttaccagtgg ctgctgccag tggcgataag tcgtgtctta ccgggttgga ctcaagacga    2400
tagttaccgg ataaggcgca gcggtcgggc tgaacggggg gttcgtgcac acagcccagc    2460
ttggagcgaa cgacctacac cgaactgaga tacctacagc gtgagctatg agaaagcgcc    2520
acgcttcccg aagggagaaa ggcggacagg tatccggtaa gcggcagggt cggaacagga    2580
gagcgcacga gggagcttcc aggggggaaac gcctggtatc tttatagtcc tgtcgggttt    2640
cgccacctct gacttgagcg tcgatttttg tgatgctcgt caggggggcg agcctatgg    2700 aaaaacgcca gcaacgcggc cttttttacgg ttcctggcct tttgctggcc ttttgctcac    2760
atgttctttc ctgcgttatc ccctgattct gtggataacc gtattaccgc ctttgagtga    2820
gctgataccg ctcgccgcag ccgaacgacc gagcgcagcg agtcagtgag cgaggaagcg    2880
gaagagcgcc tgatgcggta ttttctcctt acgcatctgt gcggtatttc acaccgatta    2940
ccgacctttg agtgagcatc gatggcagct cgcgttgcat tttcggaagc gctcgttttc    3000
ggaaacgctt tgaagttcct attccgaagt tcctattctc tagctagaaa gtataggaac    3060
ttcagagcgc ttttgaaaac caaaagcgct ctgaagacgc actttcaaaa aaccaaaaac    3120
gcaccggact gtaacgagct actaaaatat tgcgaatacc gcttccacaa acattgctca    3180
aaagtatctc tttgctatat atctctgtgc tatatcccta taaacctac ccatccacct    3240 ttcgctcctt gaacttgcat ctaaactcga cctctacatt ttttatgttt atctctagta    3300
ttactcttta gacaaaaaaa ttgtagtaag aactattcat agagtgaatc gaaaacaata    3360
cgaaaatgta acatttcct atacgtagta tatagagaca aaatagaaga aaccgttcat    3420
aattttctga ccaatgaaga atcatcaacg ctatcacttt ctgttcacaa agtatgcatc    3480
gatgctgata ccgctcgccg cagccgaacg accgagcgca gcgagtcagt gagcgaggaa    3540
gcggaagagc gcccaatacg caaaccgcct ctccccgcgc gttggccgat tcattaatgc    3600
agcagatctg gcttttcaat tcatcatttt ttttttattc tttttttga tttcggtttc    3660 tttgaaattt ttttgattcg gtaatctccg aacagaagga agaacgaagg aaggagcaca    3720
gacttagatt ggtatatata cgcatatgta gtgttgaaga acatgaaat tgcccagtat    3780 tcttaaccca actgcacaga acaaaaaccg gaaacgaaga taatcatgt cgaaagctac    3840 atataaggaa cgtgctgcta ctcatcctag tcctgttgct gccaagctat ttaatatcat    3900
gcacgaaaag caaacaaact tgtgtgcttc attggatgtt cgtaccacca aggaattact    3960
ggagttagtt gaagcattag gtcccaaaat ttgtttacta aaaacacatg tggatatctt    4020
gactgatttt tccatggagg gcacagttaa gccgctaaag gcattatccg ccaagtacaa    4080
```

-continued

```
tttttttactc ttcgaagaca gaaaatttgc tgacattggt aatacagtca aattgcagta   4140
ctctgcgggt gtatacagaa tagcagaatg ggcagacatt acgaatgcac acggtgtggt   4200
gggcccaggt attgttagcg gtttgaagca ggcggcagaa gaagtaacaa aggaacctag   4260
aggccttttg atgttagcag aattgtcatg caagggctcc ctatctactg gagaatatac   4320
taagggtact gttgacattg cgaagagcga caaagatttt gttatcggct ttattgctca   4380
aagagacatg ggtggaagag atgaaggtta cgattggttg attatgacac ccggtgtggg   4440
tttagatgac aagggagacg cattgggtca acagtataga accgtggatg atgtggtctc   4500
tacaggatct gacattatta ttgttggaag aggactattt gcaaagggaa gggatgctaa   4560
ggtagagggt gaacgttaca gaaaagcagg ctgggaagca tatttgagaa gatgcggcca   4620
gcaaaactaa aaaactgtat tataagtaaa tgcatgtata ctaaactcac aaaaaaaaaa   4680
aattggaaag aaaaagctca gatctgctgg cacgacaggt ttcccgtggt gcactctcag   4740
tacaatctgc tctgatgccg catagttaag ccagtataca ctccgctatc gctacgtgac   4800
tgggtcatgg ctgcgcccg acaccgcca cacccgctg acgcgcctg acgggcttgt   4860
ctgctcccgg catccgctta cagacaagct gtgaccgtct ccgggagctg catgtgtcag   4920
aggttttcac cgtcatcacc gaaacgcgcg aggcagctgc ggtaaagctc atcagcgtgg   4980
tcgtgaagcg attcacagat gtctgcctgt tcatccgcgt ccagctcgtt gagtttctcc   5040
agaagcgtta atgtctggct tctgataaag cgggccatgt taagggcggt ttttttcctgt   5100
ttggtcactt gatgcctccg tgtaaggggg aatttctgtt catgggggta atgataccga   5160
tgaaacgaga gaggatgctc acgatacggg ttactgatga tgaacatgcc cggttactgg   5220
aacgttgtga gggtaaacaa ctggcggtat ggatgcggcg ggaccagaga aaatcactc   5280
agggtcaatg ccagcgcttc gttaatacag atgtaggtgt tccacagggt agccagcagc   5340
atcctgcgat gcagatccgg aacataatgg tgcagggcgc tgacttccgc gtttccagac   5400
tttacgaaac acgaaaccg aagaccattc atgttgttgc tcaggtcgca gacgttttgc   5460
agcagcagtc gcttcacgtt cgctcgcgta tcggtgattc attctgctaa ccagtaaggc   5520
aaccccgcca gcctagccgg gtcctcaacg acaggagcac gatcatgcgc acccgtggcc   5580
aggacccaac gctgcccgag atgcgccgcg tgcggctgct ggagatggcg gacgcgatgg   5640
atatgttctg ccaagggttg gtttgcgcat tcacagttct ccgcaagaat tgattggctc   5700
caattcttgg agtggtgaat ccgttagcga ggtgccgccg gcttccattc aggtcgaggt   5760
ggcccggctc catgcaccgc gacgcaacgc ggggaggcag acaaggtata gggcggcgcc   5820
tacaatccat gccaacccgt tccatgtgct cgccgaggcg cataaatcg ccgtgacgat   5880
cagcggtcca gtgatcgaag ttaggctggt aagagccgcg agcgatcctt gaagctgtcc   5940
ctgatggtcg tcatctacct gcctggacag catggcctgc aacgcgggca tcccgatgcc   6000
gccggaagcg agaagaatca taatgggaa ggccatccag cctcgcgtcg cgaacgccag   6060
caagacgtag cccagcgcgt cggccgccat gccggcgata atggcctgct tctcgccgaa   6120
acgtttggtg gcgggaccag tgacgaaggc ttgagcgagg gcgtgcaaga ttccgaatac   6180
cgcaagcgac aggccgatca tcgtcgcgct ccagcgaaag cggtcctcgc cgaaaatgac   6240
ccagagcgct gccggcacct gtcctacgag ttgcatgata agaagacag tcataagtgc   6300
ggcgacgata gtcatgcccc gcgcccaccg gaaggagctg actgggttga aggctctcaa   6360
gggcatcggt cgacgctctc ccttatgcga ctcctgcatt aggaagcagc ccagtagtag   6420
gttgaggccg ttgagcaccg ccgccgcaag gaatggtgca tgcaaggaga tggcgcccaa   6480
```

```
cagtccccg gccacggggc ctgccaccat acccacgccg aaacaagcgc tcatgagccc    6540
gaagtggcga gcccgatctt ccccatcggt gatgtcggcg atataggcgc cagcaaccgc    6600
acctgtggcg ccggtgatgc cggccacgat gcgtccggcg tagaggatcc ggagcttatc    6660
gactgcacgg tgcaccaatg cttctggcgt caggcagcca tcggaagctg tggtatggct    6720
gtgcaggtcg taaatcactg cataattcgt gtcgctcaag gcgcactccc gttctggata    6780 atgtttttg cgccgacatc ataacggttc tggcaaatat tctgaaatga gctgttgaca    6840
attaatcatc ggctcgtata atgtgtggaa ttgtgagcgg ataacaattt cacacaggaa    6900
acag                                                                6904
```

<210> SEQ ID NO 703  
<211> LENGTH: 7807  
<212> TYPE: DNA  
<213> ORGANISM: Artificial Sequence  
<220> FEATURE:  
<223> OTHER INFORMATION: pSyn2-McbE/F

<400> SEQUENCE: 703

```
atggttacat taaaaatggc gataattttt ctgatggaac aaatcagaac ccctttcagc      60
ttaatatgga caattatgtc acctacagtg ttgttctttt tccttcattt caatgaaatt     120
gaacttcatt atggtgatac agcatggctc ggaaaacaaa tatcatggtt tgtaggctac     180
atttcttttt ctgttgttct gtttaattac tgtctgtatc tggtcggaag aagagaaagt     240
ggttttattg ctaccttcgt gcataatatg gatggtcgac tattatttat tcgttctcaa     300
ttaatagcct cacttatcat gtctattttg tatgtgtttt ttttcatttt agtcgtacta     360
acaggattcc aggcaagtcc agattatcaa atagtaatga ttattttaaa atcgatatac     420
ataaatgcat ttatgatggt ttcactcact ttcatggcat cgttcagagt cacattccaa     480
acagccagca ctatctattc tgtattaata actgtctgta tggtatcagg aattgtatca     540
ttaaaatata atgaggggat cgtttactgg ataaatcagg ttaatcctat cgccatctat     600
tctacaatac tccagtcaga ccaggagttg tctctgatga cgatattttt ctatagtata     660
atgttaatca taagtattat ttcagcacta accttcaaaa ctgagccagt ctggagttct     720
caatgaccat acctcttta gaaatcaact ctctgagctt tcatataaa gtaaatttac       780 cccctgtttt caataatctg tcgcttaaga ttgagcaggg agagttgata ggtctgcttg     840
gagaaaatgg agccgggaag accactcttt ttaaccttat caggggcgga gtcagtaatt     900
atgaagggac cctcaagcga aatttctctg gtggagaatt agtaagtcta cctcaagtca     960
taaatctttc aggtacacta aggaatgagg aggttcttga tttgatttgc tgcttcaata    1020
agttaactaa aaaacaggca tggacagagc ttaatcataa atggaatgat aattttttca    1080
ttcgctatga taaaataaga cgtaaaagga cttacacggt aagttatgga gagaagcgtt    1140
ggcttatcat atctttgatg ctaacgcttt gcaaaaatgc ccgttatttt ttactggatg    1200
aaccaactgt aggcattgat attcagtaca gaatgatgtt atgggaactg ataaataaga    1260
tcaccgctga cgggaaaacg gtattttct caactcatat tttttgatgaa ttaacaagag    1320 ataaaatccc cttctatatg ctttcaaaaa atagtataaa tcgttattct gatatgagtg    1380 atttttattca atccaataat gaaacaactc cagaaaaggc atttattaaa gaagttatgg    1440
gaacaggaga ctgacacatg gatataactt ctgttttggc ggatgagaga agatttttcag    1500 cctgatacag attaaatcag aacgcagaag cggtctgata aaacagaatt tgcctggcgg    1560
```

```
cagtagcgcg gtggtccac ctgaccccat gccgaactca gaagtgaaac gccgtagcgc    1620
cgatggtagt gtgggtctc cccatgcgag agtagggaac tgccaggcat caaataaaac    1680
gaaaggctca gtcgaaagac tgggcctttc gttttatctg ttgtttgtcg gtgaacgctc    1740
tcctgagtag gacaaatccg ccgggagcgg atttgaacgt tgcgaagcaa cggcccggag    1800
ggtggcgggc aggacgcccg ccataaactg ccaggcatca aattaagcag aaggccatcc    1860
tgacggatgg ccttttttgcg tttctacaaa ctcttttgtt tattttttcta aatacattca    1920 aatatgtatc cgctcatgag acaataaccc tgataaatgc ttcaataata ttgaaaaagg    1980
aagagtatga gtattcaaca tttccgtgtc gcccttattc ccttttttgc ggcattttgc    2040
cttcctgttt ttgctcaccc agaaacgctg gtgaaagtaa agatgctga agatcagttg    2100 ggtgcacgag tgggttacat cgaactggat ctcaacagcg gtaagatcct tgagagtttt    2160
cgccccgaag aacgttttcc aatgatgagc acttttaaag ttctgctatg tggcgcggta    2220
ttatcccgtg ttgacgccgg gcaagagcaa ctcggtcgcc gcatacacta ttctcagaat    2280
gacttggttg agtactcacc agtcacagaa aagcatctta cggatggcat gacagtaaga    2340
gaattatgca gtgctgccat aaccatgagt gataacactg cggccaactt acttctgaca    2400
acgatcggag gaccgaagga gctaaccgct tttttgcaca acatggggga tcatgtaact    2460
cgccttgatc gttgggaacc ggagctgaat gaagccatac caaacgacga gcgtgacacc    2520
acgatgcctg tagcaatggc aacaacgttg cgcaaactat taactggcga actacttact    2580
ctagcttccc ggcaacaatt aatagactgg atggaggcgg ataaagttgc aggaccactt    2640
ctgcgctcgg cccttccggc tggctggttt attgctgata atctggagc cggtgagcgt    2700 gggtctcgcg gtatcattgc agcactgggg ccagatggta agccctcccg tatcgtagtt    2760
atctacacga cggggagtca ggcaactatg gatgaacgaa atagacagat cgctgagata    2820
ggtgcctcac tgattaagca ttggtaactg tcagaccaag tttactcata tatactttag    2880
attgatttaa aacttcattt ttaatttaaa aggatctagg tgaagatcct ttttgataat    2940
ctcatgacca aaatccctta acgtgagttt tcgttccact gagcgtcaga ccccgtagaa    3000
aagatcaaag gatcttcttg agatcctttt tttctgcgcg taatctgctg cttgcaaaca    3060
aaaaaaccac cgctaccagc ggtggtttgt ttgccggatc aagagctacc aactcttttt    3120
ccgaaggtaa ctggcttcag cagagcgcag ataccaaata ctgtccttct agtgtagccg    3180
tagttaggcc accacttcaa gaactctgta gcaccgccta catcctcgc tctgctaatc    3240 ctgttaccag tggctgctgc cagtggcgat aagtcgtgtc ttaccgggtt ggactcaaga    3300
cgatagttac cggataaggc gcagcggtcg ggctgaacgg ggggttcgtg cacacagccc    3360
agcttggagc gaacgaccta caccgaactg agatacctac agcgtgagct atgagaaagc    3420
gccacgcttc ccgaagggag aaaggcggac aggtatccgg taagcggcag gtcggaaca    3480 ggagagcgca cgagggagct tccagggga aacgcctggt atctttatag tcctgtcggg    3540
tttcgccacc tctgacttga gcgtcgattt ttgtgatgct cgtcaggggg gcggagccta    3600
tggaaaaacg ccagcaacgc ggcctttta cggttcctgg ccttttgctg gccttttgct    3660
cacatgttct ttcctgcgtt atcccctgat tctgtggata accgtattac cgcctttgag    3720
tgagctgata ccgctcgccg cagccgaacg accgagcgca gcgagtcagt gagcgaggaa    3780
gcggaagagc gcctgatgcg gtattttctc cttacgcatc tgtgcggtat tcacaccga    3840 ttaccgcct ttgagtgagc atcgatgca gctcgcgttg cattttcgga agcgctcgtt    3900
ttcggaaacg cttttgaagtt cctattccga agttcctatt ctctagctag aaagtatagg    3960
```

```
aacttcagag cgcttttgaa aaccaaaagc gctctgaaga cgcactttca aaaaaccaaa    4020
aacgcaccgg actgtaacga gctactaaaa tattgcgaat accgcttcca caaacattgc    4080
tcaaaagtat ctctttgcta tatatctctg tgctatatcc ctatataacc tacccatcca    4140
cctttcgctc cttgaacttg catctaaact cgacctctac atttttatg tttatctcta    4200 gtattactct ttagacaaaa aaattgtagt aagaactatt catagagtga atcgaaaaca    4260
atacgaaaat gtaaacattt cctatacgta gtatatagag acaaaataga agaaaccgtt    4320
cataattttc tgaccaatga agaatcatca acgctatcac tttctgttca caaagtatgc    4380
atcgatgctg ataccgctcg ccgcagccga acgaccgagc gcagcgagtc agtgagcgag    4440
gaagcggaag agcgcccaat acgcaaaccg cctctccccg cgcgttggcc gattcattaa    4500
tgcagcagat ctggcttttc aattcatcat tttttttta ttcttttttt tgatttcggt    4560
ttctttgaaa ttttttttgat tcggtaatct ccgaacagaa ggaagaacga aggaaggagc    4620
acagacttag attggtatat atacgcatat gtagtgttga agaaacatga aattgcccag    4680
tattcttaac ccaactgcac agaacaaaaa ccggaaacga agataaatca tgtcgaaagc    4740
tacatataag gaacgtgctg ctactcatcc tagtcctgtt gctgccaagc tatttaatat    4800
catgcacgaa aagcaaacaa acttgtgtgc ttcattggat gttcgtacca ccaaggaatt    4860
actggagtta gttgaagcat taggtcccaa aatttgttta ctaaaaacac atgtggatat    4920
cttgactgat ttttccatgg agggcacagt taagccgcta aaggcattat ccgccaagta    4980
caatttttta ctcttcgaag acagaaaatt tgctgacatt ggtaatacag tcaaattgca    5040
gtactctgcg ggtgtataca gaatagcaga atgggcagac attacgaatg cacacggtgt    5100
ggtgggccca ggtattgtta gcggtttgaa gcaggcggca gaagaagtaa caaaggaacc    5160
tagaggcctt ttgatgttag cagaattgtc atgcaagggc tccctatcta ctggagaata    5220
tactaagggt actgttgaca ttgcgaagag cgacaaagat tttgttatcg gctttattgc    5280
tcaaagagac atgggtggaa gagatgaagg ttacgattgg ttgattatga cacccggtgt    5340
gggtttagat gacaagggag acgcattggg tcaacagtat agaaccgtgg atgatgtggt    5400
ctctacagga tctgacatta ttattgttgg aagaggacta tttgcaaagg gaagggatgc    5460
taaggtagag ggtgaacgtt acagaaaagc aggctgggaa gcatatttga aagatgcgg    5520 ccagcaaaac taaaaaactg tattataagt aaatgcatgt atactaaact cacaaaaaaa    5580
aaaaattgga agaaaaagc tcagatctgc tggcacgaca ggtttcccgt ggtgcactct    5640
cagtacaatc tgctctgatg ccgcatagtt aagccagtat acactccgct atcgctacgt    5700
gactgggtca tggctgcgcc ccgacacccg ccaacacccg ctgacgcgcc ctgacgggct    5760
tgtctgctcc cggcatccgc ttacagacaa gctgtgaccg tctccgggag ctgcatgtgt    5820
cagaggtttt caccgtcatc accgaaacgc gcgaggcagc tgcggtaaag ctcatcagcg    5880
tggtcgtgaa gcgattcaca gatgtctgcc tgttcatccg cgtccagctc gttgagtttc    5940
tccagaagcg ttaatgtctg gcttctgata aagcgggcca tgttaagggc ggttttttcc    6000
tgtttggtca cttgatgcct ccgtgtaagg gggaatttct gttcatgggg gtaatgatac    6060
cgatgaaacg agagaggatg ctcacgatac gggttactga tgatgaacat gcccggttac    6120
tggaacgttg tgagggtaaa caactggcgg tatggatgcg gcgggaccag agaaaaatca    6180
ctcagggtca atgccagcgc ttcgttaata cagatgtagg tgttccacag ggtagccagc    6240
agcatcctgc gatgcagatc cggaacataa tggtgcaggg cgctgacttc cgcgtttcca    6300
```

```
gactttacga aacacggaaa ccgaagacca ttcatgttgt tgctcaggtc gcagacgttt    6360
tgcagcagca gtcgcttcac gttcgctcgc gtatcggtga ttcattctgc taaccagtaa    6420
ggcaaccccg ccagcctagc cgggtcctca acgacaggag cacgatcatg cgcacccgtg    6480
gccaggaccc aacgctgccc gagatgcgcc gcgtgcggct gctggagatg gcggacgcga    6540
tggatatgtt ctgccaaggg ttggtttgcg cattcacagt tctccgcaag aattgattgg    6600
ctccaattct tggagtggtg aatccgttag cgaggtgccg ccggcttcca ttcaggtcga    6660
ggtggcccgg ctccatgcac cgcgacgcaa cgcggggagg cagacaaggt atagggcggc    6720
gcctacaatc catgccaacc cgttccatgt gctcgccgag gcggcataaa tcgccgtgac    6780
gatcagcggt ccagtgatcg aagttaggct ggtaagagcc gcgagcgatc cttgaagctg    6840
tccctgatgg tcgtcatcta cctgcctgga cagcatggcc tgcaacgcgg gcatcccgat    6900
gccgccggaa gcgagaagaa tcataatggg gaaggccatc cagcctcgcg tcgcgaacgc    6960
cagcaagacg tagcccagcg cgtcggccgc catgccggcg ataatggcct gcttctcgcc    7020
gaaacgtttg gtggcgggac cagtgacgaa ggcttgagcg agggcgtgca agattccgaa    7080
taccgcaagc gacaggccga tcatcgtcgc gctccagcga aagcggtcct cgccgaaaat    7140
gacccagagc gctgccggca cctgtcctac gagttgcatg ataaagaaga cagtcataag    7200
tgcggcgacg atagtcatgc cccgcgccca ccggaaggag ctgactgggt tgaaggctct    7260
caagggcatc ggtcgacgct ctcccttatg cgactcctgc attaggaagc agcccagtag    7320
taggttgagg ccgttgagca ccgccgccgc aaggaatggt gcatgcaagg agatggcgcc    7380
caacagtccc ccgccacgg ggcctgccac catacccacg ccgaaacaag cgctcatgag    7440
cccgaagtgg cgagcccgat cttccccatc ggtgatgtcg gcgatatagg cgccagcaac    7500
cgcacctgtg gcgccggtga tgccggccac gatgcgtccg gcgtagagga tccggagctt    7560
atcgactgca cggtgcacca atgcttctgg cgtcaggcag ccatcggaag ctgtggtatg    7620
gctgtgcagg tcgtaaatca ctgcataatt cgtgtcgctc aaggcgcact cccgttctgg    7680
ataatgtttt ttgcgccgac atcataacgg ttctggcaaa tattctgaaa tgagctgttg    7740
acaattaatc atcggctcgt ataatgtgtg gaattgtgag cggataacaa tttcacacag    7800
gaaacag                                                              7807
```

<210> SEQ ID NO 704
<211> LENGTH: 4916
<212> TYPE: DNA
<213> ORGANISM: Artificial Sequence
<220> FEATURE:
<223> OTHER INFORMATION: pMcbG 1.0

<400> SEQUENCE: 704

```
catatgcgaa ttcgcggccg caaagcttgc ccgggatccc accaccacca ccaccactga      60
gatccggctg ctaacaaagc ccgaaaggaa gctgagttgg ctgctgccac cgctgagcaa     120
taactagcat aaccccttgg ggcctctaaa cgggtcttga gggttttttt gctgaaagga     180
ggaactatat ccggattcag gagagcgttc accgacaaac aacagataaa acgaaaggcc     240
cagtctttcg actgagcctt tcgttttatt tgatgcctgg cagttcccta ctctcgcatg     300
gggagacccc acactaccat cggcgctacg gcgtttcact tctgagttcg gcatggggtc     360
aggtgggacc accgcgctac tgccgccagg caaattctgt tttatcagac cgcttctgcg     420
ttctgattta atctgtatca ggctgaaaat cttctctcat ccgccaaaac agaagtcatc     480
cccctacaac cactcccatt cgtttaagta tttttaaacc tgcttcctgt ggtatcttta     540
```

```
tagataagat cctgtttatc tcaggattta tatcgagacc ttctgtcatt gaaaaatcac    600
agtgagacaa atcagaatgt ctgaactctg tattattaaa ctccgaacca gtaaaatcag    660
atttacgaag gtctgtttcc tcaaataaac aatcacggaa gcgacaggat aaaaaaatag   720
atttctgtaa ccgtaaacta ataaaatcaa caaatctcaa atcacaattt acaagagaaa    780
aagtacaggg aaacataatg tctgctgcat ttactccttg taataaacaa tctttgaact    840
cacagtcaat aagtttaaaa aaattaagtt ttaaattctt tattgagcag tttacgaagc    900 gacattttc gaactcacaa tcgcgaaagt taaagttgtc aagctgtatt cgttcaaata    960
tacaattgta ataatttaca cctgataatt cactttcact gaggtgtcgt tttgtgattc   1020
ttttttctat tatatccatc tgtttcctgt gtgaaattgt tatccgctca caaaggaat   1080 tatagtttca acagatcttg atgcaatggg ctcatttcag aatatttgcc agaaccgtta   1140
tgatgtcggc gcaaaaaaca ttatccagaa cgggagtgcg ccttgagcga cacgaattat   1200
gcagtgattt acgacctgca cagccatacc acagcttccg atggctgcct gacgccagaa   1260
gcattggtgc accgtgcagt cgataagccc ggatcgttcc actgagcgtc agaccccgta   1320
gaaaagatca aggatcttc ttgagatcct tttttctgc gcgtaatctg ctgcttgcaa   1380
acaaaaaaac caccgctacc agcggtggtt tgtttgccgg atcaagagct accaactctt   1440
tttccgaagg taactggctt cagcagagcg cagataccaa atactgtcct tctagtgtag   1500
ccgtagttag gccaccactt caagaactct gtagcaccgc ctacatacct cgctctgcta   1560
atcctgttac cagtggctgc tgccagtggc gataagtcgt gtcttaccgg gttggactca   1620
agacgatagt taccggataa ggcgcagcgg tcgggctgaa cggggggttc gtgcacacag   1680
cccagcttgg agcgaacgac ctacaccgaa ctgagatacc tacagcgtga gctatgagaa   1740
agcgccacgc ttcccgaagg gagaaaggcg gacaggtatc cggtaagcgg cagggtcgga   1800
acaggagagc gcacgaggga gcttccaggg ggaaacgcct ggtatcttta tagtcctgtc   1860
gggtttcgcc acctctgact tgagcgtcga ttttgtgat gctcgtcagg gggcggagc   1920 ctatggaaaa acgccagcaa cgcggccttt ttacggttcc tggccttttg ctggccttt   1980 gctcacatgt tctttcctgc gttatcccct gattctgtgg ataaccgtat taccgccttt   2040
gagtgagctg ataccgctcg ccgcagccga cgaccgagc gcagcgagtc agtgagcgag   2100
gaagcggaag agcgcctgat gcggtatttt ctccttacgc atctgtgcgg tatttcacac   2160
cgcatatatg gtgcactctc agtacaatct gctctgatgc cgcatagtta agccagtata   2220
cactccgcta tcgctacgtg actgggtcat ggctgcgccc cgacacccgc caacacccgc   2280
tgacgcgccc tgacgggctt gtctgctccc ggcatccgct tacagacaag ctgtgaccgt   2340
ctccgggagc tgcatgtgtc agaggttttc accgtcatca ccgaaacgcg cgaggcagct   2400
gcggtaaagc tcatcagcgt ggtcgtgaag cgattcacag atgtctgcct gttcatccgc   2460
gtccagctcg ttgagtttct ccagaagcgt taatgtctgg cttctgataa agcgggccat   2520
gttaagggcg gttttttcct gtttggtcac tgatgcctcc gtgtaagggg gatttctgtt   2580
catgggggta atgataccga tgaaacgaga gaggatgctc acgatacggg ttactgatga   2640
tgaacatgcc cggttactgg aacgttgtga gggtaaacaa ctggcggtat ggatctgcag   2700
ggcgggacca gagaaaaatc actcagggtc aatgccagcg cttcgttaat acagatgtag   2760
gtgttccaca gggtagccag cagcatcctg cgatgcagat ccggaacata atggtgcagg   2820
gcgctgactt ccgcgtttcc agactttacg aaacacggaa accgaagacc attcatgttg   2880
```

```
ttgctcaggt cgcagacgtt ttgcagcagc agtcgcttca cgttcgctcg cgtatcggtg    2940
attcattctg ctaaccagta aggcaacccc gccagcctag ccgggtcctc aacgacagga    3000
gcacgatcat gcgcacccgt ggggccgcca tgccggcgat aatggcctgc ttctcgccga    3060
aacgtttggt ggcgggacca gtgacgaagg cttgagcgag ggcgtgcaag attccgaata    3120
ccgcaagcga caggccgatc atcgtcgcgc tccagcgaaa gcggtcctcg ccgaaaatga    3180
cccagagcgc tgccggcacc tgtcctacga gttgcatgat aaagaagaca gtcataagtg    3240
cggcgacgat agtcatgccc cgcgcccacc ggaaggagct gactgggttg aaggctctca    3300
agggcatcgg tcgagatccc ggtgcctaat gagtgagcta acttacatta attgcgttgc    3360
gctcactgcc cgctttccag tcgggaaacc tgtcgtgcca gctgcattaa tgaatcggcc    3420
aacgcgcggg gagaggcggt ttgcgtattg ggcgccaggg tggtttttct tttcaccagt    3480
gagacgggca acagctgatt gcccttcacc gcctggccct gagagagttg cagcaagcgg    3540
tccacgctgg tttgccccag caggcgaaaa tcctgtttga tggtggttaa cggcgggata    3600
taacatgagc tgtcttcggt atcgtcgtat cccactaccg agatatccgc accaacgcgc    3660
agcccggact cggtaatggc gcgcattgcg cccagcgcca tctgatcgtt ggcaaccagc    3720
atcgcagtgg gaacgatgcc ctcattcagc atttgcatgg tttgttgaaa ccggacatg    3780
gcactccagt cgccttcccg ttccgctatc ggctgaattt gattgcgagt gagatattta    3840
tgccagccag ccagacgcag acgcgccgag acagaactta atgggcccgc taacagcgcg    3900
atttgctggt gacccaatgc gaccagatgc tccacgccca gtcgcgtacc gtcttcatgg    3960
gagaaaataa tactgttgat gggtgtctgg tcagagacat caagaaataa cgccggaaca    4020
ttagtgcagg cagcttccac agcaatggca tcctggtcat ccagcggata gttaatgatc    4080
agcccactga cgcgttgcgc gagaagattg tgcaccgccg cttttacaggc ttcgacgccg    4140
cttcgttcta ccatcgacac caccacgctg gcacccagtt gatcggcgcg agatttaatc    4200
gccgcgacaa tttgcgacgg cgcgtgcagg ccagactgg aggtggcaac gccaatcagc    4260
aacgactgtt tgcccgccag ttgttgtgcc acgcggttgg gaatgtaatt cagctccgcc    4320
atcgccgctt ccacttttc ccgcgttttc gcagaaacgt ggctggcctg gttcaccacg    4380
cgggaaacgg tctgataaga gacaccggca tactctgcga catcgtataa cgttactggt    4440
ttcacattca cccctgaa ttgactctct tccgggcgct atcatgccat accgcgaaag    4500
gttttgcgcc attcgatggt gtccgggatc tcgacgctct cccttatgcg actcctgcat    4560
taggaagcag cccagtagta ggttgaggcc gttgagcacc gccgccgcaa ggaatggtgc    4620
atgcaaggag atggcgccca acagtccccc ggccacgggg cctgccacca tacccacgcc    4680
gaaacaagcg ctcatgagcc cgaagtggcg agcccgatct tccccatcgg tgatgtcggc    4740
gatataggcg ccagcaaccg cacctgtggc gccggtgatg ccggccacga tgcgtccggc    4800
gtagaggatc gagatctcga tcccgcgaaa ttaatacgac tcactatagg ggaattgtga    4860
gcggataaca attcccctct agaaataatt ttgtttaact ttaagaagga gatata        4916
```

<210> SEQ ID NO 705
<211> LENGTH: 4892
<212> TYPE: DNA
<213> ORGANISM: Artificial Sequence
<220> FEATURE:
<223> OTHER INFORMATION: pMcbG 1.1

<400> SEQUENCE: 705

```
catatgcgaa ttcgcggccg caaagcttgc ccgggatccc accaccacca ccaccactga      60
```

```
gatccggctg ctaacaaagc ccgaaaggaa gctgagttgg ctgctgccac cgctgagcaa    120
taactagcat aaccccttgg ggcctctaaa cgggtcttga ggggtttttt gctgaaagga    180
ggaactatat ccggattcag gagagcgttc accgacaaac aacagataaa acgaaaggcc    240
cagtctttcg actgagcctt tcgttttatt tgatgcctgg cagttcccta ctctcgcatg    300
gggagacccc acactaccat cggcgctacg gcgtttcact tctgagttcg catggggtc     360 aggtgggacc accgcgctac tgccgccagg caaattctgt tttatcagac cgcttctgcg    420
ttctgattta atctgtatca ggctgaaaat cttctctcat ccgccaaaac agaagtcatc    480
cccctacaac cactcccatt cgtttaagta ttttaaacc tgcttcctgt ggtatcttta     540
tagataagat cctgtttatc tcaggattta tatcgagacc ttctgtcatt gaaaaatcac    600
agtgagacaa atcagaatgt ctgaactctg tattattaaa ctccgaacca gtaaaatcag    660
atttacgaag gtctgtttcc tcaaataaac aatcacggaa gcgacaggat aaaaaaatag    720
atttctgtaa ccgtaaacta ataaaatcaa caaatctcaa atcacaattt acaagagaaa    780
aagtacaggg aaacataatg tctgctgcat ttactccttg taataaacaa tctttgaact    840
cacagtcaat aagtttaaaa aaattaagtt ttaaattctt tattgagcag tttacgaagc    900
gacatttttc gaactcacaa tcgcgaaagt taaagttgtc aagctgtatt cgttcaaata    960
tacaattgta ataatttaca cctgataatt cactttcact gaggtgtcgt tttgtgattc   1020
ttttttctat tatatccatc tgtttcctga aggaattata gtttcaacag atcttgatgc   1080
aatgggctca tttcagaata tttgccagaa ccgttatgat gtcggcgcaa aaaacattat   1140
ccagaacggg agtgcgcctt gagcgacacg aattatgcag tgatttacga cctgcacagc   1200
cataccacag cttccgatgg ctgcctgacg ccagaagcat tggtgcaccg tgcagtcgat   1260
aagcccggat cgttccactg agcgtcagac cccgtagaaa agatcaaagg atcttcttga   1320
gatccttttt ttctgcgcgt aatctgctgc ttgcaaacaa aaaaaccacc gctaccagcg   1380
gtggtttgtt tgccggatca agagctacca actcttttc cgaaggtaac tggcttcagc   1440
agagcgcaga taccaaatac tgtccttcta gtgtagccgt agttaggcca ccacttcaag   1500
aactctgtag caccgcctac atacctcgct ctgctaatcc tgttaccagt ggctgctgcc   1560
agtggcgata gtcgtgtct taccggggttg gactcaagac gatagttacc ggataaggcg   1620
cagcggtcgg gctgaacggg gggttcgtgc acacagccca gcttggagcg aacgacctac   1680
accgaactga gatacctaca gcgtgagcta tgagaaagcg ccacgcttcc gaagggaga    1740 aaggcggaca ggtatccggt aagcggcagg gtcggaacag gagagcgcac gagggagctt   1800 ccaggggaa acgcctggta tctttatagt cctgtcgggt ttcgccacct ctgacttgag    1860
cgtcgatttt tgtgatgctc gtcagggggg cggagcctat ggaaaaacgc cagcaacgcg   1920 gccttttac ggttcctggc cttttgctgg ccttttgctc acatgttctt tcctgcgtta    1980
tcccctgatt ctgtggataa ccgtattacc gcctttgagt gagctgatac cgctcgccgc   2040
agccgaacga ccgagcgcag cgagtcagtg agcgaggaag cggaagagcg cctgatgcgg   2100
tattttctcc ttacgcatct gtgcggtatt tcacaccgca tatatggtgc actctcagta   2160
caatctgctc tgatgccgca tagttaagcc agtatacact ccgctatcgc tacgtgactg   2220
ggtcatggct gcgccccgac acccgccaac acccgctgac gcgccctgac gggcttgtct   2280
gctcccggca tccgcttaca dacaagctgt gaccgtctcc gggagctgca tgtgtcagag   2340
gttttcaccg tcatcaccga aacgcgcgag gcagctgcgg taaagctcat cagcgtggtc   2400
```

```
gtgaagcgat tcacagatgt ctgcctgttc atccgcgtcc agctcgttga gtttctccag    2460
aagcgttaat gtctggcttc tgataaagcg ggccatgtta agggcggttt tttcctgttt    2520
ggtcactgat gcctccgtgt aagggggatt tctgttcatg ggggtaatga taccgatgaa    2580
acgagagagg atgctcacga tacgggttac tgatgatgaa catgcccggt tactggaacg    2640
ttgtgagggt aaacaactgg cggtatggat ctgcagggcg ggaccagaga aaaatcactc    2700
agggtcaatg ccagcgcttc gttaatacag atgtaggtgt tccacagggt agccagcagc    2760
atcctgcgat gcagatccgg aacataatgg tgcagggcgc tgacttccgc gtttccagac    2820
tttacgaaac acggaaaccg aagaccattc atgttgttgc tcaggtcgca gacgttttgc    2880
agcagcagtc gcttcacgtt cgctcgcgta tcggtgattc attctgctaa ccagtaaggc    2940
aaccccgcca gcctagccgg gtcctcaacg acaggagcac gatcatgcgc acccgtgggg    3000
ccgccatgcc ggcgataatg gcctgcttct cgccgaaacg tttggtggcg ggaccagtga    3060
cgaaggcttg agcgagggcg tgcaagattc cgaataccgc aagcgacagg ccgatcatcg    3120
tcgcgctcca gcgaaagcgg tcctcgccga aaatgaccca gagcgctgcc ggcacctgtc    3180
ctacgagttg catgataaag aagacagtca taagtgcggc gacgatagtc atgccccgcg    3240
cccaccggaa ggagctgact gggttgaagg ctctcaaggg catcggtcga gatcccggtg    3300
cctaatgagt gagctaactt acattaattg cgttgcgctc actgcccgct ttccagtcgg    3360
gaaacctgtc gtgccagctg cattaatgaa tcggccaacg cgcggggaga gcggtttgc    3420 gtattgggcg ccagggtggt ttttcttttc accagtgaga cgggcaacag ctgattgccc    3480
ttcaccgcct ggccctgaga gagttgcagc aagcggtcca cgctggtttg ccccagcagg    3540
cgaaaatcct gtttgatggt ggttaacggc gggatataac atgagctgtc ttcggtatcg    3600
tcgtatccca ctaccgagat atccgcacca acgcgcagcc cggactcggt aatggcgcgc    3660
attgcgccca gcgccatctg atcgttggca accagcatcg cagtgggaac gatgccctca    3720
ttcagcattt gcatggtttg ttgaaaaccg gacatggcac tccagtcgcc ttcccgttcc    3780
gctatcggct gaatttgatt gcgagtgaga tatttatgcc agccagccag acgcagacgc    3840
gccgagacag aacttaatgg gcccgctaac agcgcgattt gctggtgacc caatgcgacc    3900
agatgctcca cgcccagtcg cgtaccgtct tcatgggaga aaataatact gttgatgggt    3960
gtctggtcag agacatcaag aaataacgcc ggaacattag tgcaggcagc ttccacagca    4020
atggcatcct ggtcatccag cggatagtta atgatcagcc cactgacgcg ttgcgcgaga    4080
agattgtgca ccgccgcttt acaggcttcg acgccgcttc gttctaccat cgacaccacc    4140
acgctggcac ccagttgatc ggcgcgagat ttaatcgccg cgacaatttg cgacggcgcg    4200
tgcagggcca gactggaggt ggcaacgcca atcagcaacg actgtttgcc cgccagttgt    4260
tgtgccacgc ggttgggaat gtaattcagc tccgccatcg ccgcttccac ttttttcccgc    4320 gttttcgcag aaacgtggct ggcctggttc accacgcggg aaacggtctg ataagagaca    4380
ccggcatact ctgcgacatc gtataacgtt actggtttca cattcaccac cctgaattga    4440
ctctcttccg ggcgctatca tgccataccg cgaaaggttt tgcgccattc gatggtgtcc    4500
gggatctcga cgctctccct tatgcgactc ctgcattagg aagcagccca gtagtaggtt    4560
gaggccgttg agcaccgccg ccgcaaggaa tggtgcatgc aaggagatgg cgcccaacag    4620 tccccggcc acggggcctg ccaccatacc cacgccgaaa caagcgctca tgagcccgaa    4680
gtggcgagcc cgatcttccc catcggtgat gtcggcgata taggcgccag caaccgcacc    4740
tgtggcgccg gtgatgccgg ccacgatgcg tccggcgtag aggatcgtga tctcgatccc    4800
```

```
gcgaaattaa tacgactcac tatagggaa ttgtgagcgg ataacaattc ccctctagaa      4860 ataatttgt ttaactttaa gaaggagata ta                                    4892
```

<210> SEQ ID NO 706
<211> LENGTH: 185
<212> TYPE: PRT
<213> ORGANISM: Artificial Sequence
<220> FEATURE:
<223> OTHER INFORMATION: C-terminal part of McсE protein

<400> SEQUENCE: 706

```
Phe Arg Lys Tyr Asp Val Ser Leu Thr Pro Ser Gly Ile Lys Val Asn
1               5                   10                  15

Asp Glu Ile Thr Leu Leu Tyr Pro Ala Leu Lys Tyr Ala Glu Glu Leu
            20                  25                  30

Tyr Leu Leu Ile Asn Gln Asn Lys Ile Asn Phe Ile Lys Ser Met Ala
        35                  40                  45

Trp Pro Ala Phe Val Asn Asn Ile Ser Asp Ser Val Ser Phe Ile Glu
    50                  55                  60

Gln Ser Met Ile Asp Asn Gln Asn Glu Lys Ala Leu Ile Leu Phe Ile
65                  70                  75                  80

Lys Tyr Lys Thr Lys Ile Ala Gly Val Val Ser Phe Asn Ile Ile Asp
                85                  90                  95

His Ala Asn Lys Thr Ala Tyr Ile Gly Tyr Trp Leu Gly Ala Asn Phe
            100                 105                 110

Gln Gly Lys Gly Ile Val Thr Asn Ala Ile Asn Lys Leu Ile Gln Glu
        115                 120                 125

Tyr Gly Asp Ser Gly Val Ile Lys Arg Phe Val Ile Lys Cys Ile Val
    130                 135                 140

Asp Asn Lys Lys Ser Asn Ala Thr Ala Leu Arg Cys Gly Phe Thr Leu
145                 150                 155                 160

Glu Gly Val Leu Gln Lys Ala Glu Ile Leu Asn Gly Val Ser Tyr Asp
                165                 170                 175

Gln Asn Ile Tyr Ser Lys Val Ile Gly
            180                 185
```

<210> SEQ ID NO 707
<211> LENGTH: 247
<212> TYPE: DNA
<213> ORGANISM: Artificial Sequence
<220> FEATURE:
<223> OTHER INFORMATION: P24 promoter

<400> SEQUENCE: 707

```
ttatcgactg cacggtgcac caatgcttct ggcgtcaggc agccatcgga agctgtggta      60
tggctgtgca ggtcgtaaat cactgcataa ttcgtgtcgc tcaaggcgca ctcccgttct     120
ggataatgtt ttttgcgccg acatcataac ggttctggca aatattctga atgagcccta    180
ttgcatcaag atctgttgaa actataattc cttttgtgag cggataacaa tttcacacag    240
gaaacag                                                               247
```

<210> SEQ ID NO 708
<211> LENGTH: 152
<212> TYPE: DNA
<213> ORGANISM: Artificial Sequence
<220> FEATURE:
<223> OTHER INFORMATION: Proc promoter

<400> SEQUENCE: 708

```
cacagctaac accacgtcgt ccctatctgc tgccctaggt ctatgagtgg ttgctggata    60
actttacggg catggataag gctcgtatga tatattcagg gagaccacaa cggtttccct   120
ctacaaataa ttttgtttaa cttttactag ag                                 152
```

<210> SEQ ID NO 709
<211> LENGTH: 237
<212> TYPE: DNA
<213> ORGANISM: Escherichia coli
<220> FEATURE:
<221> NAME/KEY: gene
<222> LOCATION: (1)..(237)
<223> OTHER INFORMATION: Cvi

<400> SEQUENCE: 709

```
atggatagaa aagaacaaa attagagttg ttatttgcat ttataataaa tgccaccgca    60
atatatattg cattagctat atatgattgt gttttagag gaaaggactt tttatccatg   120
catacatttt gcttctctgc attaatgtct gcaatatgtt actttgttgg tgataattat   180
tattcaatat ccgataagat aaaaaggaga tcatatgaga actctgactc taaatga     237
```

<210> SEQ ID NO 710
<211> LENGTH: 1328
<212> TYPE: DNA
<213> ORGANISM: Artificial Sequence
<220> FEATURE:
<223> OTHER INFORMATION: proC-McbG-C-terminal MccE

<400> SEQUENCE: 710

```
agatctcaca gctaacacca cgtcgtccct atctgctgcc ctaggtctat gagtggttgc    60
tggataactt tacgggcatg gataaggctc gtatgatata ttcagggaga ccacaacggt   120
ttccctctac aaataatttt gtttaacttt tactagagaa agaggagaaa gctagcatgg   180
atataataga aaaagaatc acaaaacgac acctcagtga agtgaatta tcaggtgtaa    240
attattacaa ttgtatattt gaacgaatac agcttgacaa ctttaacttt cgcgattgtg   300
agttcgaaaa atgtcgcttc gtaaactgct caataaagaa tttaaaactt aatttttta   360
aacttattga ctgtgagttc aaagattgtt tattacaagg agtaaatgca gcagacatta   420
tgtttccctg tacttttcct cttgtaaatt gtgatttgag atttgttgat tttattagtt   480
tacggttaca gaaatctatt ttttatcct gtcgcttccg tgattgttta tttgaggaaa   540
cagaccttcg taaatctgat tttactggtt cggagtttaa taatacagag ttcagacatt   600
ctgatttgtc tcactgtgat ttttcaatga cagaaggtct cgatataaat cctgagataa   660
acaggatctt atctataaag ataccacagg aagcaggttt aaaaatactt aaacgaatgg   720
gagtggttgt aggggatga cacgtgaagg aggagctaga tgttccggaa gtatgatgta   780
tctcttacgc catcaggaat aaagtaaat gatgagatta cattattgta tccagcgtta   840
aaatacgctg aagagttata tttgctcatt aatcaaaaca aaataaattt cattaaaagc   900
atggcatggc cagcgtttgt taataacatt tctgattctg tttctttcat tgagcaatca   960
atgattgata accagaatga aaagcatta atcctcttta ttaaatacaa actaagata   1020
gctggcgttg tatcttttaa tattattgac catgccaata aacagcata tattggctat  1080
tggttaggcg ctaactttca gggaaagggg attgtaacca atgctataaa taaactgata  1140
caggagtatg gggattcggg cgttataaaa agatttgtta taaatgtat tgttgataat  1200
aaaaaagta atgccacggc attgaggtgt ggcttcacct tagagggtgt tctgcaaaaa  1260
```

```
gcagaaatac tcaacggtgt atcatacgat caaaatattt attcgaaagt aattggttaa   1320
gtttaaac                                                            1328

<210> SEQ ID NO 711
<211> LENGTH: 1002
<212> TYPE: DNA
<213> ORGANISM: Artificial Sequence
<220> FEATURE:
<223> OTHER INFORMATION: proC-Cvi-C-terminal MccE

<400> SEQUENCE: 711
agatctcaca gctaacacca cgtcgtccct atctgctgcc ctaggtctat gagtggttgc     60
tggataactt tacgggcatg ataaggctc gtatgatata ttcagggaga ccacaacggt    120
ttccctctac aaataatttt gtttaacttt tactagagaa agaggagaaa gctagcatgg    180
atagaaaaag aacaaaatta gagttgttat ttgcatttat aataaatgcc accgcaatat    240
atattgcatt agctatatat gattgtgttt ttagaggaaa ggacttttta tccatgcata    300
cattttgctt ctctgcatta atgtctgcaa tatgttactt tgttggtgat aattattatt    360
caatatccga taagataaaa aggagatcct acgagaactc tgactctaaa taagtttgtg    420
aaggaggagc tagatgttcc ggaagtatga tgtatctctt acgccatcag gaataaaagt    480
aaatgatgag attacattat tgtatccagc gttaaaatac gctgaagagt tatatttgct    540
cattaatcaa aacaaaataa atttcattaa aagcatggca tggccagcgt tgttaataa     600 catttctgat tctgtttctt tcattgagca atcaatgatt gataaccaga atgaaaaagc    660
attaatcctc tttattaaat acaaaactaa gatagctggc gttgtatctt ttaatattat    720
tgaccatgcc aataaaacag catatattgg ctattggtta ggcgctaact ttcagggaaa    780
ggggattgta accaatgcta taaataaact gatacaggag tatggggatt cgggcgttat    840
aaaaagattt gttataaaat gtattgttga ataataaaaa agtaatgcca cggcattgag    900
gtgtggcttc accttagagg gtgttctgca aaaagcagaa atactcaacg gtgtatcata    960
cgatcaaaat atttattcga agtaattgg ttaagtttaa ac                      1002

<210> SEQ ID NO 712
<211> LENGTH: 5290
<212> TYPE: DNA
<213> ORGANISM: Artificial Sequence
<220> FEATURE:
<223> OTHER INFORMATION: Vector pBACT5.0

<400> SEQUENCE: 712
catatgcgaa ttcgcggccg caaagcttgc ccgggatccc accaccacca ccaccactga     60
gatccggctg ctaacaaagc ccgaaaggaa gctgagttgg ctgctgccac cgctgagcaa    120
taactagcat aaccccttgg ggcctctaaa cgggtcttga ggggttttt gctgaaagga    180 ggaactatat ccggattcag gagagcgttc accgacaaac aacagataaa acgaaaggcc    240
cagtctttcg actgagcctt tcgttttatt tgatgcctgg cagttcccta ctctcgcatg    300 gggagaccc acactaccat cggcgctacg gcgtttcact tctgagttcg gcatggggtc    360
aggtgggacc accgcgctac tgccgccagg caaattctgt tttatcagac cgcttctgcg    420
ttctgattta atctgtatca ggctgaaaat cttctctcat ccgccaaaac agtttaaact    480
taaccaatta ctttcgaata aatattttga tcgtatgata caccgttgag tatttctgct    540
ttttgcagaa caccctctaa ggtgaagcca cacctcaatg ccgtggcatt acttttttta    600
```

```
ttatcaacaa tacattttat aacaaatctt tttataacgc ccgaatcccc atactcctgt    660
atcagtttat ttatagcatt ggttacaatc ccctttccct gaaagttagc gcctaaccaa    720
tagccaatat atgctgtttt attggcatgg tcaataatat taaaagatac aacgccagct    780
atcttagttt tgtatttaat aaagaggatt aatgcttttt cattctggtt atcaatcatt    840
gattgctcaa tgaaagaaac agaatcagaa atgttattaa caaacgctgg ccatgccatg    900
cttttaatga aatttatttt gttttgatta atgagcaaat ataactcttc agcgtatttt    960
aacgctggat acaataatgt aatctcatca tttactttta ttcctgatgg cgtaagagat   1020
acatcatact tccggaacat ctagctcctc cttcacaaac ttatttagag tcagagttct   1080
cgtaggatct ccttttate ttatcggata ttgaataata attatcacca acaaagtaac   1140
atattgcaga cattaatgca gagaagcaaa atgtatgcat ggataaaaag tccttcctc    1200 taaaaacaca atcatatata gctaatgcaa tatatattgc ggtggcattt attataaatg   1260
caaataacaa ctctaatttt gttcttttc tatccatgct agctttctcc tctttctcta   1320
gtaaaagtta aacaaaatta tttgtagagg gaaaccgttg tggtctccct gaatatatca   1380
tacgagcctt atccatgccc gtaaagttat ccagcaacca ctcatagacc tagggcagca   1440
gatagggacg acgtggtgtt agctgtgaga tcttgatgca atgggctcat ttcagaatat   1500
ttgccagaac cgttatgatg tcggcgcaaa aacattatc cagaacggga gtgcgccttg   1560
agcgacacga attatgcagt gatttacgac ctgcacagcc ataccacagc ttccgatggc   1620
tgcctgacgc cagaagcatt ggtgcaccgt gcagtcgata agcccggatc gttccactga   1680
gcgtcagacc ccgtagaaaa gatcaaagga tcttcttgag atcctttttt tctgcgcgta   1740
atctgctgct tgcaaacaaa aaaaccaccg ctaccagcgg tggtttgttt gccggatcaa   1800
gagctaccaa ctctttttcc gaaggtaact ggcttcagca gagcgcagat accaaatact   1860
gtccttctag tgtagccgta gttaggccac cacttcaaga actctgtagc accgcctaca   1920
tacctcgctc tgctaatcct gttaccagtg gctgctgcca gtggcgataa gtcgtgtctt   1980
accgggttgg actcaagacg atagttaccg gataaggcgc agcggtcggg ctgaacgggg   2040
ggttcgtgca cacagcccag cttggagcga acgacctaca ccgaactgag atacctacag   2100
cgtgagctat gagaaagcgc cacgcttccc gaagggagaa aggcggacag gtatccggta   2160
agcggcaggg tcgaacagg agagcgcacg agggagcttc caggggggaaa cgcctggtat   2220 ctttatagtc ctgtcgggtt tcgccacctc tgacttgagc gtcgattttt gtgatgctcg   2280 tcagggggc ggagcctatg gaaaaacgcc agcaacgcgg cctttttacg gttcctggcc   2340
ttttgctggc cttttgctca catgttcttt cctgcgttat cccctgattc tgtggataac   2400
cgtattaccg cctttgagtg agctgatacc gctcgccgca gccgaacgac cgagcgcagc   2460
gagtcagtga gcgaggaagc ggaagagcgc ctgatgcggt attttctcct tacgcatctg   2520
tgcggtattt cacaccgcat atatggtgca ctctcagtac aatctgctct gatgccgcat   2580
agttaagcca gtatacactc cgctatcgct acgtgactgg gtcatggctg cgccccgaca   2640
cccgccaaca cccgctgacg cgccctgacg ggcttgtctg ctcccggcat ccgcttacag   2700
acaagctgtg accgtctccg ggagctgcat gtgtcagagg ttttcaccgt catcaccgaa   2760
acgcgcgagg cagctgcggt aaagctcatc agcgtggtcg tgaagcgatt cacagatgtc   2820
tgcctgttca tccgcgtcca gctcgttgag tttctccaga agcgttaatg tctggcttct   2880
gataaagcgg gccatgttaa gggcggtttt ttcctgtttg gtcactgatg cctccgtgta   2940
agggggattt ctgttcatgg ggtaatgat accgatgaaa cgagagagga tgctcacgat   3000
```

```
acgggttact gatgatgaac atgcccggtt actggaacgt tgtgagggta aacaactggc    3060
ggtatggatc tgcagggcgg gaccagagaa aaatcactca gggtcaatgc cagcgcttcg    3120
ttaatacaga tgtaggtgtt ccacagggta gccagcagca tcctgcgatg cagatccgga    3180
acataatggt gcagggcgct gacttccgcg tttccagact ttacgaaaca cggaaaccga    3240
agaccattca tgttgttgct caggtcgcag acgttttgca gcagcagtcg cttcacgttc    3300
gctcgcgtat cggtgattca ttctgctaac cagtaaggca accccgccag cctagccggg    3360
tcctcaacga caggagcacg atcatgcgca cccgtggggc cgccatgccg gcgataatgg    3420
cctgcttctc gccgaaacgt ttggtggcgg gaccagtgac gaaggcttga gcagggcgt     3480
gcaagattcc gaataccgca agcgacaggc cgatcatcgt cgcgctccag cgaaagcggt    3540
cctcgccgaa aatgacccag agcgctgccg gcacctgtcc tacgagttgc atgataaaga    3600
agacagtcat aagtgcggcg acgatagtca tgccccgcgc ccaccggaag gagctgactg    3660
ggttgaaggc tctcaagggc atcggtcgag atcccggtgc ctaatgagtg agctaactta    3720
cattaattgc gttgcgctca ctgcccgctt tccagtcggg aaacctgtcg tgccagctgc    3780
attaatgaat cggccaacgc gcggggagag gcggtttgcg tattgggcgc cagggtggtt    3840
tttcttttca ccagtgagac gggcaacagc tgattgccct tcaccgcctg gccctgagag    3900
agttgcagca agcggtccac gctggtttgc cccagcaggc gaaaatcctg tttgatggtg    3960
gttaacggcg ggatataaca tgagctgtct tcggtatcgt cgtatcccac taccgagata    4020
tccgcaccaa cgcgcagccc ggactcggta atggcgcgca ttgcgcccag cgccatctga    4080
tcgttggcaa ccagcatcgc agtgggaacg atgccctcat tcagcatttg catggtttgt    4140
tgaaaaccgg acatggcact ccagtcgcct tcccgttccg ctatcggctg aatttgattg    4200
cgagtgagat atttatgcca gccagccaga cgcagacgcg ccgagacaga acttaatggg    4260
cccgctaaca gcgcgatttg ctggtgaccc aatgcgacca gatgctccac gcccagtcgc    4320
gtaccgtctt catgggagaa aataatactg ttgatgggtg tctggtcaga gacatcaaga    4380
aataacgccg gaacattagt gcaggcagct tccacagcaa tggcatcctg gtcatccagc    4440
ggatagttaa tgatcagccc actgacgcgt tgcgcgagaa gattgtgcac cgccgcttta    4500
caggcttcga cgccgcttcg ttctaccatc gacaccacca cgctggcacc cagttgatcg    4560
gcgcgagatt taatcgccgc gacaatttgc gacggcgcgt gcagggccag actggaggtg    4620
gcaacgccaa tcagcaacga ctgtttgccc gccagttgtt gtgccacgcg gttgggaatg    4680
taattcagct ccgccatcgc cgcttccact ttttcccgcg ttttcgcaga acgtggctg     4740
gcctggttca ccacgcggga aacggtctga taagagacac cggcatactc tgcgacatcg    4800
tataacgtta ctggtttcac attcaccacc ctgaattgac tctcttccgg cgctatcat     4860
gccataccgc gaaaggtttt gcgccattcg atggtgtccg ggatctcgac gctctccctt    4920
atgcgactcc tgcattagga agcagcccag tagtaggttg aggccgttga gcaccgccgc    4980
cgcaaggaat ggtgcatgca aggagatggc gcccaacagt cccccggcca cggggcctgc    5040
caccataccc acgccgaaac aagcgctcat gagcccgaag tggcgagccc gatcttcccc    5100
atcggtgatg tcgcgatat aggcgccagc aaccgcacct gtggcgccgg tgatgccggc     5160
cacgatgcgt ccggcgtaga ggatcggatc tcgatcccgc gaaattaata cgactcacta    5220
tagggggaatt gtgagcggat aacaattccc ctctagaaat aattttgttt aactttaaga   5280
aggagatata                                                           5290
```

<210> SEQ ID NO 713
<211> LENGTH: 5616
<212> TYPE: DNA
<213> ORGANISM: Artificial Sequence
<220> FEATURE:
<223> OTHER INFORMATION: Vector pBACT2.0

<400> SEQUENCE: 713

| | | | | | |
|---|---|---|---|---|---|
| catatgcgaa | ttcgcggccg | caaagcttgc | ccgggatccc | accaccacca | ccaccactga | 60 |
| gatccggctg | ctaacaaagc | ccgaaaggaa | gctgagttgg | ctgctgccac | cgctgagcaa | 120 |
| taactagcat | aaccccttgg | ggcctctaaa | cgggtcttga | ggggttttt | gctgaaagga | 180 |
| ggaactatat | ccggattcag | gagagcgttc | accgacaaac | aacagataaa | acgaaaggcc | 240 |
| cagtctttcg | actgagcctt | tcgttttatt | tgatgcctgg | cagttcccta | ctctcgcatg | 300 |
| gggagacccc | acactaccat | cggcgctacg | gcgtttcact | tctgagttcg | gcatggggtc | 360 |
| aggtgggacc | accgcgctac | tgccgccagg | caaattctgt | tttatcagac | cgcttctgcg | 420 |
| ttctgattta | atctgtatca | ggctgaaaat | cttctctcat | ccgccaaaac | agtttaaact | 480 |
| taaccaatta | ctttcgaata | aatattttga | tcgtatgata | caccgttgag | tatttctgct | 540 |
| ttttgcagaa | caccctctaa | ggtgaagcca | cacctcaatg | ccgtggcatt | acttttttta | 600 |
| ttatcaacaa | tacattttat | aacaaatctt | tttataacgc | ccgaatcccc | atactcctgt | 660 |
| atcagtttat | ttatagcatt | ggttacaatc | ccctttccct | gaaagttagc | gcctaaccaa | 720 |
| tagccaatat | atgctgtttt | attggcatgg | tcaataatat | taaaagatac | aacgccagct | 780 |
| atcttagttt | tgtatttaat | aaagaggatt | aatgcttttt | cattctggtt | atcaatcatt | 840 |
| gattgctcaa | tgaaagaaac | agaatcagaa | atgttattaa | caaacgctgg | ccatgccatg | 900 |
| ctttaatga | aatttatttt | gttttgatta | atgagcaaat | ataactcttc | agcgtatttt | 960 |
| aacgctggat | acaataatgt | aatctcatca | tttactttta | ttcctgatgg | cgtaagagat | 1020 |
| acatcatact | tccggaacat | ctagctcctc | cttcacgtgt | catcccccta | caaccactcc | 1080 |
| cattcgttta | agtatttta | aacctgcttc | ctgtggtatc | tttatagata | agatcctgtt | 1140 |
| tatctcagga | tttatatcga | gaccttctgt | cattgaaaaa | tcacagtgag | acaaatcaga | 1200 |
| atgtctgaac | tctgtattat | taaactccga | accagtaaaa | tcagatttac | gaaggtctgt | 1260 |
| ttcctcaaat | aaacaatcac | ggaagcgaca | ggataaaaaa | atagatttct | gtaaccgtaa | 1320 |
| actaataaaa | tcaacaaatc | tcaaatcaca | atttacaaga | gaaaaagtac | agggaaacat | 1380 |
| aatgtctgct | gcatttactc | cttgtaataa | acaatctttg | aactcacagt | caataagttt | 1440 |
| aaaaaaatta | agttttaaat | tctttattga | gcagtttacg | aagcgacatt | tttcgaactc | 1500 |
| acaatcgcga | aagttaaagt | tgtcaagctg | tattcgttca | aatatacaat | tgtaataatt | 1560 |
| tacacctgat | aattcacttt | cactgaggtg | tcgttttgtg | attcttttt | ctattatatc | 1620 |
| catgctagct | ttctcctctt | tctctagtaa | aagttaaaca | aaattatttg | tagagggaaa | 1680 |
| ccgttgtggt | ctccctgaat | atatcatacg | agccttatcc | atgcccgtaa | agttatccag | 1740 |
| caaccactca | tagacctagg | gcagcagata | gggacgacgt | ggtgttagct | gtgagatctt | 1800 |
| gatgcaatgg | gctcatttca | gaatatttgc | cagaaccgtt | atgatgtcgg | cgcaaaaaac | 1860 |
| attatccaga | acgggagtgc | gccttgagcg | acacgaatta | tgcagtgatt | tacgacctgc | 1920 |
| acagccatac | cacagcttcc | gatggctgcc | tgacgccaga | agcattggtg | caccgtgcag | 1980 |
| tcgataagcc | cggatcgttc | cactgagcgt | cagaccccgt | agaaaagatc | aaaggatctt | 2040 |
| cttgagatcc | ttttttctg | cgcgtaatct | gctgcttgca | aacaaaaaaa | ccaccgctac | 2100 |

```
cagcggtggt tgtttgccg gatcaagagc taccaactct tttccgaag gtaactggct   2160 tcagcagagc gcagatacca aatactgtcc ttctagtgta gccgtagtta ggccaccact   2220
tcaagaactc tgtagcaccg cctacatacc tcgctctgct aatcttgtta ccagtggctg   2280
ctgccagtgg cgataagtcg tgtcttaccg ggttggactc aagacgatag ttaccggata   2340
aggcgcagcg gtcgggctga acgggggggtt cgtgcacaca gcccagcttg gagcgaacga   2400
cctacaccga actgagatac ctacagcgtg agctatgaga aagcgccacg cttcccgaag   2460
ggagaaaggc ggacaggtat ccggtaagcg gcagggtcgg aacaggagag cgcacgaggg   2520
agcttccagg gggaaacgcc tggtatcttt atagtcctgt cgggtttcgc cacctctgac   2580
ttgagcgtcg atttttgtga tgctcgtcag ggggcggag cctatggaaa aacgccagca   2640
acgcggcctt tttacggttc ctggcctttt gctggccttt tgctcacatg ttctttcctg   2700
cgttatcccc tgattctgtg gataaccgta ttaccgcctt tgagtgagct gataccgctc   2760
gccgcagccg aacgaccgag cgcagcgagt cagtgagcga ggaagcggaa gagcgcctga   2820 tgcggtatt tctccttacg catctgtgcg gtatttcaca ccgcatatat ggtgcactct   2880
cagtacaatc tgctctgatg ccgcatagtt aagccagtat acactccgct atcgctacgt   2940
gactgggtca tggctgcgcc ccgacacccg ccaacacccg ctgacgcgcc ctgacgggct   3000
tgtctgctcc cggcatccgc ttacagacaa gctgtgaccg tctccgggag ctgcatgtgt   3060
cagaggtttt caccgtcatc accgaaacgc gcgaggcagc tgcggtaaag ctcatcagcg   3120
tggtcgtgaa gcgattcaca gatgtctgcc tgttcatccg cgtccagctc gttgagtttc   3180
tccagaagcg ttaatgtctg gcttctgata aagcgggcca tgttaagggc ggttttttcc   3240
tgtttggtca ctgatgcctc cgtgtaaggg ggatttctgt tcatggggggt aatgataccg   3300 atgaaacgag agaggatgct cacgatacgg gttactgatg atgaacatgc ccggttactg   3360
gaacgttgtg agggtaaaca actggcggta tggatctgca gggcgggacc agagaaaaat   3420
cactcagggt caatgccagc gcttcgttaa tacagatgta ggtgttccac agggtagcca   3480
gcagcatcct gcgatgcaga tccggaacat aatggtgcag ggcgctgact tccgcgtttc   3540
cagactttac gaaacacgga aaccgaagac cattcatgtt gttgctcagg tcgcagacgt   3600
tttgcagcag cagtcgcttc acgttcgctc gcgtatcggt gattcattct gctaaccagt   3660
aaggcaaccc cgccagccta gccgggtcct caacgacagg agcacgatca tgcgcacccg   3720
tggggccgcc atgccggcga taatggcctg cttctcgccg aaacgtttgg tggcgggacc   3780
agtgacgaag gcttgagcga gggcgtgcaa gattccgaat accgcaagcg acaggccgat   3840
catcgtcgcg ctccagcgaa agcggtcctc gccgaaaatg acccagagcg ctgccggcac   3900
ctgtcctacg agttgcatga taagaagac agtcataagt gcggcgacga tagtcatgcc   3960
ccgcgcccac cggaaggagc tgactgggtt gaaggctctc aagggcatcg gtcgagatcc   4020
cggtgcctaa tgagtgagct aacttacatt aattgcgttg cgctcactgc ccgctttcca   4080
gtcgggaaac ctgtcgtgcc agctgcatta atgaatcggc caacgcgcgg ggagaggcgg   4140
tttgcgtatt gggcgccagg gtggttttc ttttcaccag tgagacgggc aacagctgat   4200
tgcccttcac cgcctggccc tgagagagtt gcagcaagcg gtccacgctg gtttgcccca   4260
gcaggcgaaa atcctgtttg atggtggtta acggcgggat ataacatgag ctgtcttcgg   4320
tatcgtcgta tccccactacc gagatatccg caccaacgcg cagcccggac tcggtaatgg   4380
cgcgcattgc gcccagcgcc atctgatcgt tggcaaccag catcgcagtg ggaacgatgc   4440
```

```
cctcattcag catttgcatg gtttgttgaa aaccggacat ggcactccag tcgccttccc    4500
gttccgctat cggctgaatt tgattgcgag tgagatattt atgccagcca gccagacgca    4560
gacgcgccga gacagaactt aatgggcccg ctaacagcgc gatttgctgg tgacccaatg    4620
cgaccagatg ctccacgccc agtcgcgtac cgtcttcatg ggagaaaata atactgttga    4680
tgggtgtctg gtcagagaca tcaagaaata acgccggaac attagtgcag gcagcttcca    4740
cagcaatggc atcctggtca tccagcggat agtaatgat cagcccactg acgcgttgcg    4800
cgagaagatt gtgcaccgcc gctttacagg cttcgacgcc gcttcgttct accatcgaca    4860
ccaccacgct ggcacccagt tgatcggcgc gagatttaat cgccgcgaca atttgcgacg    4920
gcgcgtgcag ggccagactg gaggtggcaa cgccaatcag caacgactgt ttgcccgcca    4980
gttgttgtgc cacgcggttg ggaatgtaat tcagctccgc catcgccgct tccactttt    5040 cccgcgtttt cgcagaaacg tggctggcct ggttcaccac gcgggaaacg gtctgataag    5100
agacaccggc atactctgcg acatcgtata acgttactgg tttcacattc accaccctga    5160
attgactctc ttccgggcgc tatcatgcca taccgcgaaa ggttttgcgc cattcgatgg    5220
tgtccgggat ctcgacgctc tcccttatgc gactcctgca ttaggaagca gcccagtagt    5280
aggttgaggc cgttgagcac cgccgccgca aggaatggtg catgcaagga gatggcgccc    5340
aacagtcccc cggccacggg gcctgccacc atacccacgc cgaaacaagc gctcatgagc    5400
ccgaagtggc gagcccgatc ttccccatcg gtgatgtcgg cgatataggc gccagcaacc    5460
gcacctgtgg cgccggtgat gccggccacg atgcgtccgg cgtagaggat cggatctcga    5520
tcccgcgaaa ttaatacgac tcactatagg ggaattgtga gcggataaca attcccctct    5580
agaaataatt ttgtttaact ttaagaagga gatata                              5616

<210> SEQ ID NO 714
<211> LENGTH: 5988
<212> TYPE: DNA
<213> ORGANISM: Artificial Sequence
<220> FEATURE:
<223> OTHER INFORMATION: Vector pBACT5.0-mCherry

<400> SEQUENCE: 714
aataattttg tttaacttta agaaggagat ataccatggt gagcaagggc gaggaggata      60
acatggctat cattaaagag ttcatgcgct tcaaagttca catggagggt tctgttaacg     120
gtcacgagtt cgagatcgaa ggcgaaggcg agggccgtcc gtatgaaggc acccagaccg     180
ccaaactgaa agtgactaaa ggcggccccgc tgccttttgc gtgggacatc ctgagcccgc     240
aatttatgta cggttctaaa gcttatgtta aacacccagc ggatatcccg gactatctga     300
agctgtcttt tccggaaggt ttcaagtggg aacgcgtaat gaattttgaa gatggtggtg     360
tcgtgaccgt cactcaggac tcctccctgc aggatggcga gttcatctat aaagttaaac     420
tgcgtggtac taattttcca tctgatggcc cggtgatgca aagaagacg atgggttggg     480 aggcgtctag cgaacgcatg tatccggaag atggtgcgct gaaaggcgaa attaaacagc     540
gcctgaaact gaaagatggc ggccattatg acgctgaagt gaaaaccacg tacaaagcca     600
agaaacctgt gcagctgcct ggcgcgtaca atgtgaatat taaactggac atcacctctc     660
ataatgaaga ttatacgatc gtagagcaat atgagcgcgc ggagggtcgt cattctaccg     720
gtggcatgga cgagctgtac aagcaccacc accaccacca ctgaggatcc caccaccacc     780
accaccactg agatccggct gctaacaaag cccgaaagga agctgagttg gctgctgcca     840
ccgctgagca ataactagca taaccccttg gggcctctaa acgggtcttg aggggtttt     900
```

-continued

```
tgctgaaagg aggaactata tccggattca ggagagcgtt caccgacaaa caacagataa      960
aacgaaaggc ccagtctttc gactgagcct ttcgttttat ttgatgcctg gcagttccct     1020
actctcgcat ggggagaccc cacactacca tcggcgctac ggcgtttcac ttctgagttc     1080
ggcatggggt caggtgggac caccgcgcta ctgccgccag gcaaattctg ttttatcaga     1140
ccgcttctgc gttctgattt aatctgtatc aggctgaaaa tcttctctca tccgccaaaa     1200
cagtttaaac ttaaccaatt actttcgaat aaatattttg atcgtatgat acaccgttga     1260
gtatttctgc ttttgcaga acaccctcta aggtgaagcc acacctcaat gccgtggcat     1320
tacttttttt attatcaaca atacatttta taacaaatct ttttataacg cccgaatccc     1380
catactcctg tatcagttta tttatagcat tggttacaat ccccttttccc tgaaagttag     1440 cgcctaacca atagccaata tatgctgttt tattggcatg gtcaataata ttaaaagata     1500
caacgccagc tatcttagtt ttgtatttaa taaagaggat taatgctttt tcattctggt     1560
tatcaatcat tgattgctca atgaaagaaa cagaatcaga aatgttatta acaaacgctg     1620
gccatgccat gcttttaatg aaatttattt tgttttgatt aatgagcaaa tataactctt     1680
cagcgtattt taacgctgga tacaataatg taatctcatc atttacttttt attcctgatg     1740 gcgtaagaga tacatcatac ttccggaaca tctagctcct ccttcacaaa cttatttaga     1800
gtcagagttc tcgtaggatc tcctttttat cttatcggat attgaataat aattatcacc     1860
aacaaagtaa catattgcag acattaatgc agagaagcaa aatgtatgca tggataaaaa     1920
gtcctttcct ctaaaaacac aatcatatat agctaatgca atatatattg cggtggcatt     1980
tattataaat gcaaataaca actctaattt tgttcttttt ctatccatgc tagctttctc     2040
ctctttctct agtaaaagtt aaacaaaatt atttgtagag ggaaaccgtt gtggtctccc     2100
tgaatatatc atacgagcct tatccatgcc cgtaaagtta tccagcaacc actcatagac     2160
ctagggcagc agatagggac gacgtggtgt tagctgtgag atcttgatgc aatgggctca     2220
tttcagaata tttgccagaa ccgttatgat gtcggcgcaa aaaacattat ccagaacggg     2280
agtgcgcctt gagcgacacg aattatgcag tgatttacga cctgcacagc cataccacag     2340
cttccgatgg ctgcctgacg ccagaagcat tggtgcaccg tgcagtcgat aagcccggat     2400
cgttccactg agcgtcagac cccgtagaaa agatcaaagg atcttcttga gatccttttt     2460
ttctgcgcgt aatctgctgc ttgcaaacaa aaaaaccacc gctaccagcg gtggtttgtt     2520
tgccggatca agagctacca actcttttc cgaaggtaac tggcttcagc agagcgcaga     2580
taccaaatac tgtccttcta gtgtagccgt agttaggcca ccacttcaag aactctgtag     2640
caccgcctac atacctcgct ctgctaatct tgttaccagt ggctgctgcc agtggcgata     2700
agtcgtgtct taccggggttg gactcaagac gatagttacc ggataaggcg cagcggtcgg     2760
gctgaacggg gggttcgtgc acacagccca gcttggagcg aacgacctac accgaactga     2820
gatacctaca gcgtgagcta tgagaaagcg ccacgcttcc cgaagggaga aaggcggaca     2880
ggtatccggt aagcggcagg gtcggaacag gagagcgcac gagggagctt ccaggggggaa     2940 acgcctggta tctttatagt cctgtcgggt ttcgccacct ctgacttgag cgtcgatttt     3000
tgtgatgctc gtcagggggg cggagccyat ggaaaaacgc cagcaacgcg ccttttttac     3060
ggttcctggc cttttgctgg ccttttgctc acatgttctt tcctgcgtta tcccctgatt     3120
ctgtggataa ccgtattacc gcctttgagt gagctgatac cgctcgccgc agccgaacga     3180
ccgagcgcag cgagtcagtg agcgaggaag cggaagagcg cctgatgcgg tatttttctcc     3240
```

```
ttacgcatct gtgcggtatt tcacaccgca tatatggtgc actctcagta caatctgctc    3300
tgatgccgca tagttaagcc agtatacact ccgctatcgc tacgtgactg ggtcatggct    3360 gcgcccgac acccgccaac acccgctgac gcgccctgac gggcttgtct gctcccggca    3420
tccgcttaca gacaagctgt gaccgtctcc gggagctgca tgtgtcagag gttttcaccg    3480
tcatcaccga aacgcgcgag gcagctgcgg taaagctcat cagcgtggtc gtgaagcgat    3540
tcacagatgt ctgcctgttc atccgcgtcc agctcgttga gtttctccag aagcgttaat    3600
gtctggcttc tgataaagcg ggccatgtta agggcggttt tttcctgttt ggtcactgat    3660
gcctccgtgt aagggggatt tctgttcatg ggggtaatga taccgatgaa acgagagagg    3720
atgctcacga tacgggttac tgatgatgaa catgcccggt tactggaacg ttgtgagggt    3780
aaacaactgg cggtatggat ctgcagggcg ggaccagaga aaaatcactc agggtcaatg    3840
ccagcgcttc gttaatacag atgtaggtgt tccacagggt agccagcagc atcctgcgat    3900
gcagatccgg aacataatgg tgcagggcgc tgacttccgc gtttccagac tttacgaaac    3960
acggaaaccg aagaccattc atgttgttgc tcaggtcgca gacgttttgc agcagcagtc    4020
gcttcacgtt cgctcgcgta tcggtgattc attctgctaa ccagtaaggc aaccccgcca    4080
gcctagccgg gtcctcaacg acaggagcac gatcatgcgc acccgtgggg ccgccatgcc    4140
ggcgataatg gcctgcttct cgccgaaacg tttggtggcg ggaccagtga cgaaggcttg    4200
agcgagggcg tgcaagattc cgaataccgc aagcgacagg ccgatcatcg tcgcgctcca    4260
gcgaaagcgg tcctcgccga aaatgaccca gagcgctgcc ggcacctgtc ctacgagttg    4320
catgataaag aagacagtca taagtgcggc gacgatagtc atgccccgcg cccaccggaa    4380
ggagctgact gggttgaagg ctctcaaggg catcggtcga gatcccggtg cctaatgagt    4440
gagctaactt acattaattg cgttgcgctc actgcccgct ttccagtcgg gaaacctgtc    4500
gtgccagctg cattaatgaa tcggccaacg cgcgggggaga ggcggtttgc gtattgggcg    4560
ccagggtggt ttttcttttc accagtgaga cgggcaacag ctgattgccc ttcaccgcct    4620
ggccctgaga gagttgcagc aagcggtcca cgctggtttg ccccagcagg cgaaaatcct    4680
gtttgatggt ggttaacggc gggatataac atgagctgtc ttcggtatcg tcgtatccca    4740
ctaccgagat atccgcacca acgcgcagcc cggactcggt aatggcgcgc attgcgccca    4800
gcgccatctg atcgttggca accagcatcg cagtgggaac gatgccctca ttcagcattt    4860
gcatggtttg ttgaaaaccg gacatggcac tccagtcgcc ttcccgttcc gctatcggct    4920
gaatttgatt gcgagtgaga tatttatgcc agccagccag acgcagacgc gccgagacag    4980
aacttaatgg gcccgctaac agcgcgattt gctggtgacc caatgcgacc agatgctcca    5040
cgcccagtcg cgtaccgtct tcatgggaga aaataatact gttgatgggt gtctggtcag    5100
agacatcaag aaataacgcc ggaacattag tgcaggcagc ttccacagca atggcatcct    5160
ggtcatccag cggatagtta atgatcagcc cactgacgcg ttgcgcgaga agattgtgca    5220
ccgccgcttt acaggcttcg acgccgcttc gttctaccat cgacaccacc acgctggcac    5280
ccagttgatc ggcgcgagat ttaatcgccg cgacaatttg cgacggcgcg tgcagggcca    5340
gactggaggt ggcaacgcca atcagcaacg actgtttgcc cgccagttgt tgtgccacgc    5400
ggttgggaat gtaattcagc tccgccatcg ccgcttccac ttttttcccgc gttttcgcag    5460 aaacgtggct ggcctggttc accacgcggg aaacggtctg ataagagaca ccggcatact    5520
ctgcgacatc gtataacgtt actggtttca cattcaccac cctgaattga ctctcttccg    5580
ggcgctatca tgccataccg cgaaaggttt tgcgccattc gatggtgtcc gggatctcga    5640
```

-continued

| | |
|---|---|
| cgctctccct tatgcgactc ctgcattagg aagcagccca gtagtaggtt gaggccgttg | 5700 |
| agcaccgccg ccgcaaggaa tggtgcatgc aaggagatgg cgcccaacag tcccccggcc | 5760 |
| acggggcctg ccaccatacc cacgccgaaa caagcgctca tgagcccgaa gtggcgagcc | 5820 |
| cgatcttccc catcggtgat gtcggcgata taggcgccag caaccgcacc tgtggcgccg | 5880 |
| gtgatgccgg ccacgatgcg tccggcgtag aggatcggat ctcgatcccg cgaaattaat | 5940 |
| acgactcact ataggggaat tgtgagcgga taacaattcc cctctaga | 5988 |

<210> SEQ ID NO 715
<211> LENGTH: 2353
<212> TYPE: DNA
<213> ORGANISM: Artificial Sequence
<220> FEATURE:
<223> OTHER INFORMATION: McbG-MccE

<400> SEQUENCE: 715

| | |
|---|---|
| atggatataa tagaaaaaag aatcacaaaa cgacacctca gtgaaagtga attatcaggt | 60 |
| gtaaattatt acaattgtat atttgaacga atacagcttg acaactttaa ctttcgcgat | 120 |
| tgtgagttcg aaaaatgtcg cttcgtaaac tgctcaataa agaatttaaa acttaatttt | 180 |
| tttaaactta ttgactgtga attcaaagat tgtttattac aaggagtaaa tgcagcagac | 240 |
| attatgtttc cctgtacttt ttctcttgta aattgtgatt tgagatttgt tgatttattt | 300 |
| agtttacggt tacagaaatc tatttttta tcctgtcgct tccgtgattg tttatttgag | 360 |
| gaaacagacc ttcgtaaatc tgattttact ggttcggagt ttaataatac agagttcaga | 420 |
| cattctgatt tgtctcactg tgattttca atgacagaag gtctcgatat aaatcctgag | 480 |
| ataaacagga tcttatctat aaagatacca caggaagcag gtttaaaaat acttaaacga | 540 |
| atgggagtgg ttgtaggggg atgacacgtg aaggaggagc tagatggcgc aaaaaataac | 600 |
| accatctaaa attgttaaac atgcccggga gttaattatt aaggggattg aatcgggcga | 660 |
| taactcattt gtcattttg atgtagatgg agctctggag cgtctggaac attacaggtg | 720 |
| tcaacttaag agttttttcc ccaacagcag tatcgcatat tcatataagt caaataatct | 780 |
| ggcacaatgg tgccagatta tctcaggtaa aggtttgtat gcagaggtgt gctctgttga | 840 |
| tgaaatgaac ctcgctaaaa gagacggttt taaccggatt gttttgatg gccctttaaa | 900 |
| aaaaacgagt gaactattaa aggcaataga gattggggca ttaattgaag ttgacaatat | 960 |
| tgatgaatgt aaaagactta atgaactatg taaattgcat aagttgacat gtagaattca | 1020 |
| tttgagatta tcgcattact atgatgataa tttatcaaga tttggcttat ctgaaagtga | 1080 |
| ggctattaat ttactggaga tgttgatcag taagtcagag tatctcattt tagacgggtt | 1140 |
| ccatttacat gttggctcta atctacccaa tgcggaaaaa atatgtaaag ctgttataca | 1200 |
| gtatcatgag ttgattctta ggtatatgcc agatgatggc actcttaatc ttggtagtgg | 1260 |
| gataccctgca gattctttct cagcatccag tgataaccca actccatgtc cggaggtatt | 1320 |
| tttctcatcg atatatgata caataaaaaa ttgcttcggt actgtatgtg ataaatggaa | 1380 |
| ctatattttt gaacctggga gacatctggt cgaagacttt ggctacttta tagggaaagt | 1440 |
| tattagtact aaaaacaggt atggtgttaa agttgctcaa actaacattg gtataaactg | 1500 |
| gataccttcg atcagaaatt gggaccattc atttacattg tttcataatc ataaccatat | 1560 |
| ttcagatgat aaatctgatg agtatattat tgctggattc aattgctttg aatgtgattg | 1620 |
| cttgtttcct tcagttattc ttcccagtaa cttatctgat tatttatttt ctgttcgagg | 1680 |

```
gtgtggtgct tatgatatgc aaacaggaaa ccagtggacg cgtaatcttt atgctgtata   1740
taccataaca aatgatgttg ttaatatatc aaggattcac agaagagaac ttgatttccg   1800
gaagtatgat gtatctctta cgccatcagg aataaaagta aatgatgaga ttacattatt   1860
gtatccagcg ttaaaatacg ctgaagagtt atatttgctc attaatcaaa acaaaataaa   1920
tttcattaaa agcatggcat ggccagcgtt tgttaataac atttctgatt ctgtttcttt   1980
cattgagcaa tcaatgattg ataaccagaa tgaaaaagca ttaatcctct ttattaaata   2040
caaaactaag atagctggcg ttgtatcttt taatattatt gaccatgcca ataaaacagc   2100
atatattggc tattggttag gcgctaactt tcagggaaag gggattgtaa ccaatgctat   2160
aaataaactg atacaggagt atggggattc gggcgttata aaaagatttg ttataaaatg   2220
tattgttgat aataaaaaaa gtaatgccac ggcattgagg tgtggcttca ccttagaggg   2280
tgttctgcaa aaagcagaaa tactcaacgg tgtatcatac gatcaaaata tttattcgaa   2340
agtaattggt taa                                                     2353

<210> SEQ ID NO 716
<211> LENGTH: 1144
<212> TYPE: DNA
<213> ORGANISM: Artificial sequence
<220> FEATURE:
<223> OTHER INFORMATION: McbG-Cter part MccE

<400> SEQUENCE: 716
atggatataa tagaaaaaag aatcacaaaa cgacacctca gtgaaagtga attatcaggt     60
gtaaattatt acaattgtat atttgaacga atacagcttg acaactttaa ctttcgcgat    120
tgtgagttcg aaaaatgtcg cttcgtaaac tgctcaataa agaatttaaa acttaatttt    180
tttaaactta ttgactgtga attcaaagat tgtttattac aaggagtaaa tgcagcagac    240
attatgtttc cctgtacttt ttctcttgta aattgtgatt tgagatttgt tgattttatt    300
agtttacggt tacagaaatc tattttttta tcctgtcgct tccgtgattg tttatttgag    360
gaaacagacc ttcgtaaatc tgattttact ggttcggagt ttaataatac agagttcaga    420
cattctgatt tgtctcactg tgattttttca atgacagaag gtctcgatat aaatcctgag    480
ataaacagga tcttatctat aaagatacca caggaagcag gtttaaaaat acttaaacga    540
atgggagtgg ttgtagggg  atgacacgtg aaggaggagc tagatgttcc ggaagtatga    600
tgtatctctt acgccatcag gaataaaagt aaatgatgag attacattat tgtatccagc    660
gttaaaatac gctgaagagt tatatttgct cattaatcaa acaaaataa atttcattaa    720 aagcatggca tggccagcgt tgttaataa catttctgat tctgtttctt tcattgagca    780
atcaatgatt gataaccaga tgaaaaagc attaatcctc tttattaaat acaaaactaa    840
gatagctggc gttgtatctt ttaatattat tgaccatgcc aataaaacag catatattgg    900
ctattggtta ggcgctaact ttcagggaaa ggggattgta accaatgcta taaataaact    960
gatacaggag tatggggatt cgggcgttat aaaaagattt gttataaaat gtattgttga   1020
taataaaaaa agtaatgcca cggcattgag gtgtggcttc accttagagg gtgttctgca   1080
aaagcagaaa atactcaacg gtgtatcata cgatcaaaat atttattcga agtaattgg    1140 ttaa                                                               1144

<210> SEQ ID NO 717
<211> LENGTH: 2026
<212> TYPE: DNA
<213> ORGANISM: Artificial sequence
```

<220> FEATURE:
<223> OTHER INFORMATION: Cvi-MccE

<400> SEQUENCE: 717

```
atggatagaa aaagaacaaa attagagttg ttatttgcat ttataataaa tgccaccgca      60
atatatattg cattagctat atatgattgt gttttagag gaaaggactt tttatccatg     120
catacatttt gcttctctgc attaatgtct gcaatatgtt actttgttgg tgataattat    180
tattcaatat ccgataagat aaaaaggaga tcctacgaga actctgactc taaataacac    240
gtgaaggagg agctagatgg cgcaaaaaat aacaccatct aaaattgtta aacatgcccg    300
ggagttaatt attaagggga ttgaatcggg cgataactca tttgtcattt ttgatgtaga    360
tggagctctg gagcgtctgg aacattacag gtgtcaactt aagagttttt tccccaacag    420
cagtatcgca tattcatata agtcaaataa tctggcacaa tggtgccaga ttatctcagg    480
taaaggtttg tatgcagagg tgtgctctgt tgatgaaatg aacctcgcta aaagagacgg    540
ttttaaccgg attgttttg atggccctt aaaaaaaacg agtgaactat taaaggcaat    600
agagattggg gcattaattg aagttgacaa tattgatgaa tgtaaaagac ttaatgaact    660
atgtaaattg cataagttga catgtagaat tcatttgaga ttatcgcatt actatgatga    720
taatttatca agatttggct tatctgaaag tgaggctatt aatttactgg agatgttgat    780
cagtaagtca gagtatctca ttttagacgg gttccattta catgttggct ctaatctacc    840
caatgcggaa aaaatatgta agctgttat acagtatcat gagttgattc ttaggtatat    900
gccagatgat ggcactctta atcttggtag tgggatacct gcagattctt tctcagcatc    960
cagtgataac ccaactccat gtccggaggt atttttctca tcgatatatg atacaataaa   1020
aaattgcttc ggtactgtat gtgataaatg gaactatatt tttgaacctg ggagacatct   1080
ggtcgaagac tttggctact ttataggga agttattagt actaaaaaca ggtatggtgt   1140
taaagttgct caaactaaca ttggtataaa ctggatacct tcgatcagaa attgggacca   1200
ttcatttaca ttgtttcata atcataacca tatttcagat gataaatctg atgagtatat   1260
tattgctgga ttcaattgct ttgaatgtga ttgcttgttt ccttcagtta ttcttcccag   1320
taacttatct gattatttat tttctgttcg agggtgtggt gcttatgata tgcaaacagg   1380
aaaccagtgg acgcgtaatc tttatgctgt ataccata acaaatgatg ttgttaatat    1440
atcaaggatt cacagaagag aacttgattt ccgaagtat gatgtatctc ttacgccatc   1500
aggaataaaa gtaatgatg agattacatt attgtatcca gcgttaaaat acgctgaaga   1560
gttatatttg ctcattaatc aaaacaaat aaatttcatt aaaagcatgg catggccagc   1620
gtttgttaat aacatttctg attctgtttc tttcattgag caatcaatga ttgataacca   1680
gaatgaaaaa gcattaatcc tctttattaa atacaaaact aagatagctg gcgttgtatc   1740
ttttaatatt attgaccatg ccaataaaac agcatatatt ggctattggt taggcgctaa   1800
ctttcaggga aaggggattg taaccaatgc tataaataaa ctgatacagg agtatgggga   1860
ttcgggcgtt ataaaaagat ttgttataaa atgtattgtt gataataaaa aagtaatgc    1920
cacggcattg aggtgtggct tcaccttaga gggtgttctg caaaaagcag aaatactcaa   1980
cggtgtatca tacgatcaaa atatttattc gaaagtaatt ggttaa                 2026
```

<210> SEQ ID NO 718
<211> LENGTH: 817
<212> TYPE: DNA
<213> ORGANISM: Artificial sequence
<220> FEATURE:

<223> OTHER INFORMATION: Cvi-Cter part MccE

<400> SEQUENCE: 718

```
atggatagaa aaagaacaaa attagagttg ttatttgcat ttataataaa tgccaccgca    60
atatatattg cattagctat atatgattgt gtttttagag gaaaggactt tttatccatg   120
catacatttt gcttctctgc attaatgtct gcaatatgtt actttgttgg tgataattat   180
tattcaatat ccgataagat aaaaaggaga tcctacgaga actctgactc taaataacac   240
gtgaaggagg agctagatgt tccggaagta tgatgtatct cttacgccat caggaataaa   300
agtaaatgat gagattacat tattgtatcc agcgttaaaa tacgctgaag agttatattt   360
gctcattaat caaaacaaaa taaatttcat taaaagcatg gcatggccag cgtttgttaa   420
taacatttct gattctgttt ctttcattga gcaatcaatg attgataacc agaatgaaaa   480
agcattaatc ctctttatta aatacaaaac taagatagct ggcgttgtat ctttttaatat  540
tattgaccat gccaataaaa cagcatatat tggctattgg ttaggcgcta actttcaggg   600
aaagggggatt gtaaccaatg ctataaataa actgatacag gagtatgggg attcgggcgt   660
tataaaaaga tttgttataa aatgtattgt tgataataaa aaaagtaatg ccacggcatt   720
gaggtgtggc ttcaccttag agggtgttct gcaaaaagca gaaatactca acggtgtatc   780
atacgatcaa aatatttatt cgaaagtaat tggttaa                            817
```

<210> SEQ ID NO 719
<211> LENGTH: 9521
<212> TYPE: DNA
<213> ORGANISM: Artificial sequence
<220> FEATURE:
<223> OTHER INFORMATION: Vector pUC-ColV

<400> SEQUENCE: 719

```
gcgatcgcgg ctcccgacat cttggaccat tagctccaca ggtatcttct tccctctagt    60
ggtcataaca gcagcttcag ctacctctca attcaaaaaa ccccctcaaga cccgtttaga   120
ggccccaagg ggttatgcta tcaatcgttg cgttacacac acaaaaaacc aacacacatc   180
catcttcgat ggatagcgat tttattatct aactgctgat cgagtgtagc cagatctttg   240
tcgatcctac catccactcg acacacccgc cagcggccgc tgccaagctt ccgagctctg   300
cccttcccta gagaatcctg ccaggcttgc cacactgata tatcttgact ttatgtaaac   360
gatatgacac tttaacatga taatgattac cattctcttt taatatacag agaaactagg   420
aaatagatga atgagttatg ttactttaat attctctgac aataacctaa atcagttaga   480
ttattgtcat ttaataaata atgacattct ttcatcataa ataaaaagac tattgtttat   540
aatattgttc tcagcattat atgattattt atcctgataa ctctcctatg ttgtatgttt   600
atgatttt ccttgaaaca tataatgcaa atttcgatt tattttccat cattaatcca      660
gataaacaac aaactaatag tatgcaagga gacattattt gtttcgccat gatgctttag   720
aaaacagaaa aatgaagtgg cagggacggg caatattact tcccggaata ccactgtggt   780
taatcatgct gggaagcatt gtgtttatta cggcatttct gatgttcatt attgttggta   840
cctatagccg ccgtgttaat gtcagtggtg aggtcacaac ctggccaaga gctgtcaata   900
tatattcagg tgtacaggga tttgttgtca ggcagtttgt tcatgaaggg cagttgataa   960
aaaaagggga tcctgtttat ctgattgaca tcagtaaaag tacacgcaat ggtattgtca  1020
ctgataatca tcgccgggat atagaaaacc agctggttcg tgtggacaac attatttccc  1080
gtctggaaga aagtaaaaaa ataacgctag ataccctgga aaaacaacgt ctgcaataca  1140
```

-continued

```
cagatgcgtt ccgtcgctca tcagacatta tacagcgtgc agaggaaggg ataaaaataa    1200
tgaaaaataa tatggagaat tacagatact atcagtcaaa aggactgatt aataaagatc    1260
aattaactaa ccaagttgca ttatattatc aacaacaaaa caaccttctc agtctgagcg    1320
gacaaaatga acaaaatgcc ctgcagataa ccactctgga gagtcagatt cagactcagg    1380
cagcagattt tgataatcgt atctatcaga tggaactgca acgactcgaa ttgcagaaag    1440
aactggttaa cactgatgtg gaaggcgaaa tcattatccg ggcgttgtct gacgggaaag    1500
ttgactccct gagtgtcact gtagggcaaa tggtcaatac cggagacagc cttctgcagg    1560
ttattcctga gaacattgaa aactattatc ttattctctg ggtcccgaat gatgctgttc    1620
cttatatttc ggctggtgac aaagtgaata ttcgttatga agccttcccc tcagaaaaat    1680
ttgggcagtt ctctgctacg gttaaaacta tatccaggac tcctgcgtca acacaggaaa    1740
tgttgaccta aagggagca cctcaaaata cgccgggtgc ctctgttccc tggtataaag    1800
tcattgcgac gcctgaaaag cagataatca ggtatgacga aaaataccct cctctggaaa    1860
atggaatgaa agccgaaagt acactatttc tggaaaaaag gcgtatttac cagtggatgc    1920
tttctccttt ctatgacatg aaacacagtg caacaggacc gatcaatgac taacaggaat    1980
ttcagacaaa ttataaatct gcttgatttg cgctggcaac gtcgtgttcc ggttattcat    2040
cagacggaga ccgctgaatg tggactggcc tgcctagcaa tgatatgcgg tcattttggt    2100
aagaatattg acctgatata tcttcgccgg aagtttaatc tctctgcccg tggagcaacc    2160
cttgcaggaa tcaatggaat agcggagcaa ctggggatgg ccacccgggc tctttcactg    2220
gagttggatg aacttcgagt cctcaaaacg ccgtgtattc tccactggga tttcagtcac    2280
ttcgtcgttc tggtcagcgt aaagcgtaac cgttatgtac tgcatgatcc ggccaggggc    2340
ataagatata tcagccggga ggaaatgagc cgatatttta caggcgttgc acttgaggtc    2400
tggcccggaa gtgaattcca gtcggaaacc ctgcagaccc gcataagtct tcgttcactg    2460
attaacagta tttacggtat taaaagaacg ctggcgaaaa ttttctgtct gtcagttgta    2520
attgaagcaa tcaatctgct aatgccggtg gggacacagc tggttatgga tcatgctatt    2580
cctgcggggg acagagggct actgacgcta atttctgctg ctcttatgtt ttttatatta    2640
ctcaaagctg caacgagtac gctgcgcgca tggtcttcac tggttatgag cacgctcatc    2700
aatgtacagt ggcagtcggg gctgttcgat catcttctca gactaccgct ggcgtttttt    2760
gaacgccgaa aattaggtga tatccagtca cgttttgact cccttgacac attgagggcc    2820
acatttacca ccagtgtgat cgggttcata atggacagca ttatggttgt cggtgtttgt    2880
gtgatgatgc tgttatacgg aggatatctc acctggatag ttctctgctt taccacaatt    2940 tacatttta ttcgactggt gacatacggc aattaccgac agatatcaga agaatgtctt    3000
gtcagggagg cccgtgccgc ctcctatttt atggaaacat tatatggtat tgccacggta    3060
aaaatccagg ggatggtcgg aattcggggg gcacactggc ttaatatgaa aatagatgcg    3120
ataaattcgg gtattaagct aaccaggatg gatttgctct tcggaggaat aaataccttt    3180
gttaccgcct gtgatcagat tgtaatttta tggctgggag caggccttgt gatcgataat    3240
cagatgacaa taggaatgtt tgtagcgttt agttcttttc gtgggcagtt ttcggaaaga    3300
gttgcctctc tgaccagttt tcttcttcag ctaagaataa tgagtctgca caatgagcgc    3360
attgcagata ttgcattaca tgaaaaggag gaaaagaaac ctgaaattga aatcgttgct    3420
gatatggggc caatatccct ggaaaccaat ggtttaagct atcgttatga cagtcagtca    3480
```

```
gcaccgatat tcagtgctct gagtttatct gtagctccgg gggaaagtgt ggctataact    3540
ggtgcttccg gtgcgggaaa aaccacatta atgaaagtac tatgtggact atttgaacct    3600
gatagcggga gggtactgat aaatggtata gatatacgcc aaattggaat aaataattat    3660
caccggatga tagcctgtgt tatgcaggat gaccggctat tttcaggctc aattcgtgaa    3720
aatatctgtg gttttgcaga ggaaatggat gaagagtgga tggtagaatg tgccagagca    3780
agtcatattc atgatgttat aatgaatatg ccaatgggat atgaaacatt aataggtgaa    3840
cttggggaag gtcttctctgg cggtcaaaaa cagcgtatat ttattgcacg agccttatac    3900
cggaaaccag gaatattatt tatggatgag gcaaccagtg ctcttgattc agagagtgaa    3960
catttcgtga atgttgccat aaaaaacatg aatatcacca gggtaattat tgcacacaga    4020
gaaacaacgt tgagaactgt tgatagagtt atttctattt aaaccataga ggaattacaa    4080
gcgtatgagg aatatttctt cctgttataa ttcctcgtta tgctcagata tctgttggag    4140
gtggaatgga agatagacaa tccaccaaga agaaatatca ttctgtgtgg attgtccaat    4200
aactgttctt tcttatatta aataaactga tttataaaca aacatcacta agattatttg    4260
gactccaatt acacaatctt cccgcagcat agttccatgc ttctgaaggt atcccttcgg    4320 gttttgctt aattgttccc cctaaaccgg atggagacat tgcaggatta ggtttgtgag    4380
tggatgcata gtcatatatt gcacctccag ccacaccccc agcagctgct ccaattcctc    4440
ctgcaacaaa ttgcccggat agtgttccta tagccatcgc aatatcacgc cctgaagcac    4500
caccagaaac agaatctaat tcatttagag tcagagttct catatgatct cctttttatc    4560
ttatcggata ttgaataata attatcacca acaaagtaac atattgcaga cattaatgca    4620
gagaagcaaa atgtatgcat ggataaaaag tcctttcctc taaaaacaca atcatatata    4680
gctaatgcaa tatatattgc ggtggcattt attataaatg caaataacaa ctctaattt    4740 gttcttttc tatccattac ttttatccc attactttct atcccattac cacacaaaca    4800
ctaacgataa tgattatcgt taacatagtc aagagtgaag ggtaggaggc cctcaacccc    4860
ctataagggg tccgcttgga aaacggattt ccccacgtca agagaattga tttgaacgag    4920
tggcttcgct acaaacagct cccgtttgtg tgtgaaaaac ccctctcaac agatctcaac    4980
tctgcacgat atctacagga gattgctcca aaaggcagta tcgtgtcttt taactaccga    5040
tataaccccg tcatcgacat gataatgcgt ctgagaaatg agaagaaatt aggtgaactg    5100
catttcttct cagcagaatt taataaaaat tctgcactga cccgtctaga agttgtctcc    5160
tcctgcactg actgactgat acaatcgatt tctggatccg caggcctctg ctagcttgac    5220
tgactgagat acagcgtacc ttcagctcac agacatgata agatacattg atgagtttgg    5280
acaaaccaca actagaatgc agtgaaaaaa atgctttatt tgtgaaattt gtgatgctat    5340
tgctttattt gtaaccatta aagctgcaa taaacaagtt aacaacaaca attgcattca    5400
ttttatgttt caggttcagg gggaggtgtg ggaggttttt taaagcaagt aaaacctcta    5460
caaatgtggt attggcccat ctctatcggt atcgtagcat aaccccttgg ggcctctaaa    5520
cgggtcttga ggggtttttt gtgcccctcg gccggattg ctatctaccg gcattggcgc    5580
agaaaaaaat gcctgatgcg acgctgcgcg tcttatactc ccacatatgc cagattcagc    5640
aacggatacg gcttccccaa cttgcccact tccatacgtg tcctccttac cagaaattta    5700
tccttaaggt cgtcagctat cctgcaggcg atctctcgat ttcgatcaag acattccttt    5760
aatggtcttt tctggacacc actaggggtc agaagtagtt catcaaactt tcttccctcc    5820
ctaatctcat tggttacctt gggctatcga aacttaatta accagtcaag tcagctactt    5880
```

```
ggcgagatcg acttgtctgg gtttcgacta cgctcagaat tgcgtcagtc aagttcgatc    5940
tggtccttgc tattgcaccc gttctccgat tacgagtttc atttaaatca tgtgagcaaa    6000
aggccagcaa aaggccagga accgtaaaaa ggccgcgttg ctggcgtttt tccataggct    6060
ccgcccccct gacgagcatc acaaaaatcg acgctcaagt cagaggtggc gaaacccgac    6120
aggactataa agataccagg cgtttccccc tggaagctcc ctcgtgcgct ctcctgttcc    6180
gaccctgccg cttaccggat acctgtccgc ctttctccct tcgggaagcg tggcgctttc    6240
tcatagctca cgctgtaggt atctcagttc ggtgtaggtc gttcgctcca agctgggctg    6300
tgtgcacgaa ccccccgttc agcccgaccg ctgcgcctta ccggtaact atcgtcttga    6360
gtccaacccg gtaagacacg acttatcgcc actggcagca gccactggta acaggattag    6420
cagagcgagg tatgtaggcg gtgctacaga gttcttgaag tggtggccta actacggcta    6480
cactagaaga acagtatttg gtatctgcgc tctgctgaag ccagttacct tcggaaaaag    6540
agttggtagc tcttgatccg gcaaacaaac caccgctggt agcggtggtt ttttgtttg    6600
caagcagcag attacgcgca gaaaaaaagg atctcaagaa gatcctttga tcttttctac    6660
ggggtctgac gctcagtgga acgaaaactc acgttaaggg attttggtca tgagattatc    6720
aaaaaggatc ttcacctaga tccttttaaa ttaaaaatga agttttaaat caatctaaag    6780
tatatatgag taaacttggt ctgacagtta ccaatgctta atcagtgagg cacctatctc    6840
agcgatctgt ctatttcgtt catccatagt tgcatttaaa tttccgaact ctccaaggcc    6900
ctcgtcggaa atcttcaaa cctttcgtcc gatccatctt gcaggctacc tctcgaacga    6960
actatcgcaa gtctcttggc cggccttgcg ccttggctat tgcttggcag cgcctatcgc    7020
caggtattac tccaatcccg aatatccgag atcgggatca cccgagagaa gttcaaccta    7080
catcctcaat cccgatctat ccgagatccg aggaatatcg aaatcggggc gcgccaagct    7140
gttgtgaccg cttgctctag ccagctatcg agttgtgaac cgatccatct agcaattggt    7200
ctcgatctag cgataggctt cgatctagct atgtagaaac gccgtgtgct cgatcgcttg    7260
ataaggtcca cgtagctgct ataattgctt caacagaaca tattgactat ccggtattac    7320
ccggcaaagg aggtagccaa catgacagct ctgacagagg gagcgaaact gttcgagaag    7380
gagatcccgt acatcacaga gttggaagga gatgtcgaag gatgaaatt catcatcaag    7440
ggagaaggaa cgggtgacgc aacgaccgga acgatcaagg ccaaatacat tgtaccacg    7500
ggcgatttgc ctgtcccctg ggcgacgctt gtaagcacgc tctcgtatgg tgtccagtgc    7560
ttcgcgaaat atccatcgca cattaaggac ttttttcaagt cggccatgcc agaaggttac    7620
acacaagaac gaaccatctc ctttgagggg gacggagtgt ataagacacg cgcgatggta    7680
acgtacgagc gcgggtccat ctacaacagg gtaactctta ctgggagaa ctttaagaag    7740
gacgggcata tcttgcggaa aaacgtggca tttcaatgtc cgccctcgat tctgtatatt    7800
ctcccggaca cggtgaataa tgggatcaga gtggagttca accaggcata cgatattgag    7860
ggtgtgactg aaaagctcgt caccaaatgc agccagatga atcgccccct tgcgggatca    7920
gcagccgtcc atatccccg gtatcaccat attacctacc acacaaaact ctcaaaagac    7980
agagatgaga gaagggacca tatgtgcctg gtcgaagtag tgaaggcggt ggatcttgat    8040
acataccagt aggctagcca ttggcgcaga aaaaaatgcc tgatgcgacg ctgcgcgtct    8100
tatactccca catatgccag attcagcaac ggatacggct tccccaactt gcccacttcc    8160
atacgtgtcc tccttaccag aaatttatcc ttaagggcgc gcctggtgta ccgagaacga    8220
```

-continued

```
tcctctcagt gcgagtctcg acgatccata tcgttgcttg gcagtcagcc agtcggaatc    8280
cagcttggga cccaggaagt ccaatcgtca gatattgtac tcaagcctgg tcacggcagc    8340
gtaccgatct gtttaaacct agatattgat agtctgatcg gtcaacgtat aatcgagtcc    8400
tagcttttgc aaacatctat caagagacag gatcagcagg aggctttcgc atgattgaac    8460
aagatggatt gcacgcaggt tctccggcgg cttgggtgga gaggctattc ggctatgact    8520
gggcacaaca gacaatcggc tgctctgatg ccgccgtgtt ccggctgtca gcgcaggggc    8580
gtccggttct ttttgtcaag accgacctgt ccggtgccct gaatgaactg caagacgagg    8640
cagcgcggct atcgtggctg gcgacgacgg gcgttccttg cgcggctgtg ctcgacgttg    8700
tcactgaagc gggaagggac tggctgctat tgggcgaagt gccggggcag gatctcctgt    8760
catctcacct tgctcctgcc gagaaagtat ccatcatggc tgatgcaatg cggcggctgc    8820
atacgcttga tccggctacc tgcccattcg accaccaagc gaaacatcgc atcgagcgag    8880
cacgtactcg gatggaagcc ggtcttgtcg atcaggatga tctggacgaa gagcatcagg    8940
ggctcgcgcc agccgaactg ttcgccaggc tcaaggcgtc tatgcccgac ggcgaggatc    9000
tcgtcgtgac ccacggcgat gcctgcttgc cgaatatcat ggtggaaaat ggccgctttt    9060
ctggattcat cgactgtggc cgtctgggtg tggcggaccg ctatcaggac atagcgttgg    9120
ctacccgtga tattgctgaa gagcttggcg gcgaatgggc tgaccgcttc cttgtgcttt    9180
acggtatcgc cgcgcccgat cgcagcgca tcgccttcta tcgccttctt gacgagttct    9240
tctgaccgat tctaggtgca ttggcgcaga aaaaaatgcc tgatgcgacg ctgcgcgtct    9300
tatactccca catatgccag attcagcaac ggatacggct tccccaactt gcccacttcc    9360
atacgtgtcc tccttaccag aaatttatcc ttaaggtcgt ttaaactcga ctctggctct    9420
atcgaatctc cgtcgtttcg agcttacgcg aacagccgtg gcgctcattt gctcgtcggg    9480
catcgaatct cgtcagctat cgtcagctta ccttttggc a                          9521
```

<210> SEQ ID NO 720
<211> LENGTH: 9
<212> TYPE: PRT
<213> ORGANISM: Lactobacillus curvatus

<400> SEQUENCE: 720

Asn Ile Pro Gln Leu Thr Pro Thr Pro
1               5

<210> SEQ ID NO 721
<211> LENGTH: 27
<212> TYPE: DNA
<213> ORGANISM: Lactobacillus curvatus

<400> SEQUENCE: 721
aacattccgc agctgacccc gaccccg                                          27

<210> SEQ ID NO 722
<211> LENGTH: 18
<212> TYPE: PRT
<213> ORGANISM: Bacillus thuringiensis
<220> FEATURE:
<221> NAME/KEY: VARIANT
<222> LOCATION: (4)..(4)
<223> OTHER INFORMATION: Xaa = any amino acid
<220> FEATURE:
<221> NAME/KEY: VARIANT
<222> LOCATION: (7)..(7)
<223> OTHER INFORMATION: Xaa = any amino acid
<220> FEATURE:

<221> NAME/KEY: VARIANT
<222> LOCATION: (10)..(10)
<223> OTHER INFORMATION: Xaa = any amino acid

<400> SEQUENCE: 722

Asp Trp Thr Xaa Trp Ser Xaa Leu Val Xaa Ala Ala Cys Ser Val Glu
1 5 10 15

Leu Leu

<210> SEQ ID NO 723
<211> LENGTH: 54
<212> TYPE: DNA
<213> ORGANISM: Bacillus thuringiensis
<220> FEATURE:
<221> NAME/KEY: misc_feature
<222> LOCATION: (10)..(12)
<223> OTHER INFORMATION: n = A,T,C or G
<220> FEATURE:
<221> NAME/KEY: misc_feature
<222> LOCATION: (19)..(21)
<223> OTHER INFORMATION: n = A,T,C or G
<220> FEATURE:
<221> NAME/KEY: misc_feature
<222> LOCATION: (28)..(30)
<223> OTHER INFORMATION: n = A,T,C or G

<400> SEQUENCE: 723
gattggaccn nntggagcnn nctggtgnnn gcggcgtgca gcgtggaact gctg 54

<210> SEQ ID NO 724
<211> LENGTH: 30
<212> TYPE: PRT
<213> ORGANISM: Lactobacillus curvatus L442

<400> SEQUENCE: 724

Ala Tyr Pro Gly Asn Gly Val His Cys Gly Lys Tyr Ser Cys Thr Val
1 5 10 15

Asp Lys Gln Thr Ala Ile Gly Asn Ile Gly Asn Asn Ala Ala
20 25 30

<210> SEQ ID NO 725
<211> LENGTH: 90
<212> TYPE: DNA
<213> ORGANISM: Lactobacillus curvatus L442

<400> SEQUENCE: 725
gcgtatccgg gcaacggcgt gcattgcggc aaatatagct gcaccgtgga taaacagacc 60
gcgattggca acattggcaa caacgcggcg 90

<210> SEQ ID NO 726
<211> LENGTH: 43
<212> TYPE: PRT
<213> ORGANISM: Carnobacterium divergens

<400> SEQUENCE: 726

Thr Lys Tyr Tyr Gly Asn Gly Val Tyr Cys Asn Ser Lys Lys Cys Trp
1 5 10 15

Val Asp Trp Gly Thr Ala Gln Gly Cys Ile Asp Val Val Ile Gly Gln
20 25 30

Leu Gly Gly Gly Ile Pro Gly Lys Gly Lys Cys
35 40

<210> SEQ ID NO 727
<211> LENGTH: 129

```
<212> TYPE: DNA
<213> ORGANISM: Carnobacterium divergens

<400> SEQUENCE: 727
accaaatatt atggcaacgg cgtgtattgc aacagcaaaa aatgctgggt ggattggggc    60
accgcgcagg gctgcattga tgtggtgatt ggccagctgg cggcggcat tccgggcaaa   120 ggcaaatgc                                                          129

<210> SEQ ID NO 728
<211> LENGTH: 24
<212> TYPE: PRT
<213> ORGANISM: Microbispora sp. (strain 107891

<400> SEQUENCE: 728

Val Thr Ser Trp Ser Leu Cys Thr Pro Gly Cys Thr Ser Pro Gly Gly
 1               5                  10                  15

Gly Ser Asn Cys Ser Phe Cys Cys
             20

<210> SEQ ID NO 729
<211> LENGTH: 72
<212> TYPE: DNA
<213> ORGANISM: Microbispora sp. (strain 107891

<400> SEQUENCE: 729
gtgaccagct ggagcctgtg caccccgggc tgcaccagcc cgggcggcgg cagcaactgc    60
agcttttgct gc                                                       72

<210> SEQ ID NO 730
<211> LENGTH: 62
<212> TYPE: PRT
<213> ORGANISM: Enterococcus sp.

<400> SEQUENCE: 730

Asn Arg Trp Tyr Cys Asn Ser Ala Ala Gly Gly Val Gly Gly Ala Ala
 1               5                  10                  15

Val Cys Gly Leu Ala Gly Tyr Val Gly Glu Ala Lys Glu Asn Ile Ala
             20                  25                  30

Gly Glu Val Arg Lys Gly Trp Gly Met Ala Gly Gly Phe Thr His Asn
         35                  40                  45

Lys Ala Cys Lys Ser Phe Pro Gly Ser Gly Trp Ala Ser Gly
     50                  55                  60

<210> SEQ ID NO 731
<211> LENGTH: 186
<212> TYPE: DNA
<213> ORGANISM: Enterococcus sp.

<400> SEQUENCE: 731
aaccgctggt attgcaacag cgcggcgggc ggcgtgggcg gcgcggcggt gtgcggcctg    60
gcgggctatg tgggcgaagc gaaagaaaac attgcgggcg aagtgcgcaa aggctggggc   120
atggcgggcg gctttaccca taacaaagcg tgcaaaagct ttccgggcag cggctgggcg   180
agcggc                                                             186

<210> SEQ ID NO 732
<211> LENGTH: 39
<212> TYPE: PRT
<213> ORGANISM: Enterococcus faecium
```

-continued

<400> SEQUENCE: 732

Thr Thr Lys Asn Tyr Gly Asn Gly Val Cys Asn Ser Val Asn Trp Cys
1               5                   10                  15

Gln Cys Gly Asn Val Trp Ala Ser Cys Asn Leu Ala Thr Gly Cys Ala
            20                  25                  30

Ala Trp Leu Cys Lys Leu Ala
        35

<210> SEQ ID NO 733
<211> LENGTH: 117
<212> TYPE: DNA
<213> ORGANISM: Enterococcus faecium

<400> SEQUENCE: 733
accaccaaaa actatggcaa cggcgtgtgc aacagcgtga actggtgcca gtgcggcaac    60
gtgtgggcga gctgcaacct ggcgaccggc tgcgcggcgt ggctgtgcaa actggcg      117

<210> SEQ ID NO 734
<211> LENGTH: 30
<212> TYPE: PRT
<213> ORGANISM: Paenibacillus polymyxa

<400> SEQUENCE: 734

Ala Ser Ile Ile Lys Thr Thr Ile Lys Val Ser Lys Ala Val Cys Lys
1               5                   10                  15

Thr Leu Thr Cys Ile Cys Thr Gly Ser Cys Ser Asn Cys Lys
            20                  25                  30

<210> SEQ ID NO 735
<211> LENGTH: 90
<212> TYPE: DNA
<213> ORGANISM: Paenibacillus polymyxa

<400> SEQUENCE: 735
gcgagcatta ttaaaaccac cattaaagtg agcaaagcgg tgtgcaaaac cctgacctgc    60
atttgcaccg gcagctgcag caactgcaaa                                    90

<210> SEQ ID NO 736
<211> LENGTH: 31
<212> TYPE: PRT
<213> ORGANISM: Staphylococcus epidermidis

<400> SEQUENCE: 736

Ser Ala Ser Ile Val Lys Thr Thr Ile Lys Ala Ser Lys Leu Cys
1               5                   10                  15

Arg Gly Phe Thr Leu Thr Cys Gly Cys His Phe Thr Gly Lys Lys
            20                  25                  30

<210> SEQ ID NO 737
<211> LENGTH: 93
<212> TYPE: DNA
<213> ORGANISM: Staphylococcus epidermidis

<400> SEQUENCE: 737
agcgcgagca ttgtgaaaac caccattaaa gcgagcaaaa aactgtgccg cggctttacc    60
ctgacctgcg gctgccattt taccggcaaa aaa                                93

<210> SEQ ID NO 738
<211> LENGTH: 58
<212> TYPE: PRT

<213> ORGANISM: Enterococcus faecium

<400> SEQUENCE: 738

```
Met Glu Lys Leu Thr Val Lys Glu Met Ser Gln Val Val Gly Gly Lys
1               5                   10                  15
Tyr Tyr Gly Asn Gly Val Ser Cys Asn Lys Lys Gly Cys Ser Val Asp
                20                  25                  30
Trp Gly Lys Ala Ile Gly Ile Ile Gly Asn Asn Ala Ala Ala Asn Leu
            35                  40                  45
Thr Thr Gly Gly Lys Ala Gly Trp Lys Gly
        50                  55
```

<210> SEQ ID NO 739
<211> LENGTH: 178
<212> TYPE: DNA
<213> ORGANISM: Enterococcus faecium

<400> SEQUENCE: 739

```
atggaaaaat taactgtgaa agaaatgtcg caagtagttg gcggaaagta ctatggtaac        60
ggagtatcat gtaataaaaa gggatgtagt gttgattggg gaaaagctat tggtattatt       120
ggaaataatg ctgctgctaa tttaactact ggcggaaaag cagggtggaa aggttaac         178
```

<210> SEQ ID NO 740
<211> LENGTH: 39
<212> TYPE: PRT
<213> ORGANISM: Paenibacillus polymyxa

<400> SEQUENCE: 740

```
Ala Thr Tyr Tyr Gly Asn Gly Leu Tyr Cys Asn Lys Gln Lys His Tyr
1               5                   10                  15
Thr Trp Val Asp Trp Asn Lys Ala Ser Arg Glu Ile Gly Lys Ile Thr
                20                  25                  30
Val Asn Gly Trp Val Gln His
            35
```

<210> SEQ ID NO 741
<211> LENGTH: 93
<212> TYPE: DNA
<213> ORGANISM: Paenibacillus polymyxa

<400> SEQUENCE: 741

```
agcgcgagca ttgtgaaaac caccattaaa gcgagcaaaa aactgtgccg cggctttacc        60
ctgacctgcg gctgccattt taccggcaaa aaa                                     93
```

<210> SEQ ID NO 742
<211> LENGTH: 35
<212> TYPE: PRT
<213> ORGANISM: Bacillus circulans

<400> SEQUENCE: 742

```
Val Asn Tyr Gly Asn Gly Val Ser Cys Ser Lys Thr Lys Cys Ser Val
1               5                   10                  15
Asn Trp Gly Ile Ile Thr His Gln Ala Phe Arg Val Thr Ser Gly Val
                20                  25                  30
Ala Ser Gly
        35
```

<210> SEQ ID NO 743
<211> LENGTH: 105

```
<212> TYPE: DNA
<213> ORGANISM: Bacillus circulans

<400> SEQUENCE: 743
gtgaactatg caacggcgt gagctgcagc aaaaccaaat gcagcgtgaa ctggggcatt    60
attacccatc aggcgtttcg cgtgaccagc ggcgtggcga gcggc                  105

<210> SEQ ID NO 744
<211> LENGTH: 30
<212> TYPE: PRT
<213> ORGANISM: Paenibacillus polymyxa

<400> SEQUENCE: 744
```

Phe Val Tyr Gly Asn Gly Val Thr Ser Ile Leu Val Gln Ala Gln Phe
1               5                   10                  15

Leu Val Asn Gly Gln Arg Arg Phe Phe Tyr Thr Pro Asp Lys
            20                  25                  30

```
<210> SEQ ID NO 745
<211> LENGTH: 90
<212> TYPE: DNA
<213> ORGANISM: Paenibacillus polymyxa

<400> SEQUENCE: 745
tttgtgtatg caacggcgt gaccagcatt ctggtgcagg cgcagtttct ggtgaacggc    60
cagcgccgct tttttatac cccggataaa                                     90

<210> SEQ ID NO 746
<211> LENGTH: 13
<212> TYPE: PRT
<213> ORGANISM: Lactobacillus rhamnosus

<400> SEQUENCE: 746
```

Ala Val Pro Ala Val Arg Lys Thr Asn Glu Thr Leu Asp
1               5                   10

```
<210> SEQ ID NO 747
<211> LENGTH: 39
<212> TYPE: DNA
<213> ORGANISM: Lactobacillus rhamnosus

<400> SEQUENCE: 747
gcggtgccgg cggtgcgcaa aaccaacgaa accctggat                          39

<210> SEQ ID NO 748
<211> LENGTH: 60
<212> TYPE: PRT
<213> ORGANISM: Bacillus licheniformis

<400> SEQUENCE: 748
```

Met Lys Asn Ser Ala Ala Arg Glu Ala Phe Lys Gly Ala Asn His Pro
1               5                   10                  15

Ala Gly Met Val Ser Glu Glu Glu Leu Lys Ala Leu Val Gly Gly Asn
            20                  25                  30

Asp Val Asn Pro Glu Thr Thr Pro Ala Thr Thr Ser Ser Trp Thr Cys
            35                  40                  45

Ile Thr Ala Gly Val Thr Val Ser Ala Ser Leu Cys
        50                  55                  60

```
<210> SEQ ID NO 749
<211> LENGTH: 180
```

<212> TYPE: DNA
<213> ORGANISM: Bacillus licheniformis

<400> SEQUENCE: 749

```
atgaaaaaca gcgcggcgcg cgaagcgttt aaaggcgcga accatccggc gggcatggtg      60
agcgaagaag aactgaaagc gctggtgggc ggcaacgatg tgaacccgga accaccccg      120
gcgaccacca gcagctggac ctgcattacc gcgggcgtga ccgtgagcgc gagcctgtgc    180
```

<210> SEQ ID NO 750
<211> LENGTH: 689
<212> TYPE: PRT
<213> ORGANISM: Pseudomonas aeruginosa

<400> SEQUENCE: 750

```
Met Ala Val Asn Asp Tyr Glu Pro Gly Ser Met Val Ile Thr His Val
1               5                   10                  15

Gln Gly Gly Gly Arg Asp Ile Ile Gln Tyr Ile Pro Ala Arg Ser Ser
            20                  25                  30

Tyr Gly Thr Pro Pro Phe Val Pro Gly Pro Ser Pro Tyr Val Gly
        35                  40                  45

Thr Gly Met Gln Glu Tyr Arg Lys Leu Arg Ser Thr Leu Asp Lys Ser
    50                  55                  60

His Ser Glu Leu Lys Lys Asn Leu Lys Asn Glu Thr Leu Lys Glu Val
65                  70                  75                  80

Asp Glu Leu Lys Ser Glu Ala Gly Leu Pro Gly Lys Ala Val Ser Ala
                85                  90                  95

Asn Asp Ile Arg Asp Glu Lys Ser Ile Val Asp Ala Leu Met Asp Ala
            100                 105                 110

Lys Ala Lys Ser Leu Lys Ala Ile Glu Asp Arg Pro Ala Asn Leu Tyr
        115                 120                 125

Thr Ala Ser Asp Phe Pro Gln Lys Ser Glu Ser Met Tyr Gln Ser Gln
    130                 135                 140

Leu Leu Ala Ser Arg Lys Phe Tyr Gly Glu Phe Leu Asp Arg His Met
145                 150                 155                 160

Ser Glu Leu Ala Lys Ala Tyr Ser Ala Asp Ile Tyr Lys Ala Gln Ile
                165                 170                 175

Ala Ile Leu Lys Gln Thr Ser Gln Glu Leu Glu Asn Lys Ala Arg Ser
            180                 185                 190

Leu Glu Ala Glu Ala Gln Arg Ala Ala Glu Val Glu Ala Asp Tyr
        195                 200                 205

Lys Ala Arg Lys Ala Asn Val Glu Lys Val Gln Ser Glu Leu Asp
    210                 215                 220

Gln Ala Gly Asn Ala Leu Pro Gln Leu Thr Asn Pro Thr Pro Glu Gln
225                 230                 235                 240

Trp Leu Glu Arg Ala Thr Gln Leu Val Thr Gln Ala Ile Ala Asn Lys
                245                 250                 255

Lys Lys Leu Gln Thr Ala Asn Asn Ala Leu Ile Ala Lys Ala Pro Asn
            260                 265                 270

Ala Leu Glu Lys Gln Lys Ala Thr Tyr Asn Ala Asp Leu Leu Val Asp
        275                 280                 285

Glu Ile Ala Ser Leu Gln Ala Arg Leu Asp Lys Leu Asn Ala Glu Thr
    290                 295                 300

Ala Arg Arg Lys Glu Ile Ala Arg Gln Ala Ala Ile Arg Ala Ala Asn
305                 310                 315                 320
```

```
Thr Tyr Ala Met Pro Ala Asn Gly Ser Val Val Ala Thr Ala Ala Gly
            325                 330                 335

Arg Gly Leu Ile Gln Val Ala Gln Gly Ala Ala Ser Leu Ala Gln Ala
        340                 345                 350

Ile Ser Asp Ala Ile Ala Val Leu Gly Arg Val Leu Ala Ser Ala Pro
    355                 360                 365

Ser Val Met Ala Val Gly Phe Ala Ser Leu Thr Tyr Ser Ser Arg Thr
370                 375                 380

Ala Glu Gln Trp Gln Asp Gln Thr Pro Asp Ser Val Arg Tyr Ala Leu
385                 390                 395                 400

Gly Met Asp Ala Ala Lys Leu Gly Leu Pro Pro Ser Val Asn Leu Asn
                405                 410                 415

Ala Val Ala Lys Ala Ser Gly Thr Val Asp Leu Pro Met Arg Leu Thr
            420                 425                 430

Asn Glu Ala Arg Gly Asn Thr Thr Thr Leu Ser Val Val Ser Thr Asp
        435                 440                 445

Gly Val Ser Val Pro Lys Ala Val Pro Val Arg Met Ala Ala Tyr Asn
    450                 455                 460

Ala Thr Thr Gly Leu Tyr Glu Val Thr Val Pro Ser Thr Thr Ala Glu
465                 470                 475                 480

Ala Pro Pro Leu Ile Leu Thr Trp Thr Pro Ala Ser Pro Pro Gly Asn
                485                 490                 495

Gln Asn Pro Ser Ser Thr Pro Val Val Pro Lys Pro Val Pro Val
            500                 505                 510

Tyr Glu Gly Ala Thr Leu Thr Pro Val Lys Ala Thr Pro Glu Thr Tyr
        515                 520                 525

Pro Gly Val Ile Thr Leu Pro Glu Asp Leu Ile Ile Gly Phe Pro Ala
    530                 535                 540

Asp Ser Gly Ile Lys Pro Ile Tyr Val Met Phe Arg Asp Pro Arg Asp
545                 550                 555                 560

Val Pro Gly Ala Ala Thr Gly Lys Gly Gln Pro Val Ser Gly Asn Trp
                565                 570                 575

Leu Gly Ala Ala Ser Gln Gly Glu Gly Ala Pro Ile Pro Ser Gln Ile
            580                 585                 590

Ala Asp Lys Leu Arg Gly Lys Thr Phe Lys Asn Trp Arg Asp Phe Arg
        595                 600                 605

Glu Gln Phe Trp Ile Ala Val Ala Asn Asp Pro Glu Leu Ser Lys Gln
    610                 615                 620

Phe Asn Pro Gly Ser Leu Ala Val Met Arg Asp Gly Gly Ala Pro Tyr
625                 630                 635                 640

Val Arg Glu Ser Glu Gln Ala Gly Gly Arg Ile Lys Ile Glu Ile His
                645                 650                 655

His Lys Val Arg Ile Ala Asp Gly Gly Val Tyr Asn Met Gly Asn
            660                 665                 670

Leu Val Ala Val Thr Pro Lys Arg His Ile Glu Ile His Lys Gly Gly
        675                 680                 685

Lys

<210> SEQ ID NO 751
<211> LENGTH: 2070
<212> TYPE: DNA
<213> ORGANISM: Pseudomonas aeruginosa

<400> SEQUENCE: 751
```

```
atggctgtca atgattacga acctggttcg atggttatta cacatgtgca gggtggtggg      60
cgtgacataa tccagtatat tcctgctcga tcaagctacg gtactccacc atttgtccca     120
ccaggaccaa gtccgtatgt cggtactgga atgcaggagt acaggaagct aagaagtacg     180
cttgataagt cccattcaga actcaagaaa aacctgaaaa atgaaaccct gaaggaggtt     240
gatgaactca agagtgaagc ggggttgcca ggtaaagcgg tcagtgccaa tgacatccgc     300
gatgaaaaga gtatcgttga tgcactcatg gatgccaaag caaaatcgct aaaggccatt     360
gaggatcgcc cggccaatct ttatacggct tcagactttc ctcagaagtc agagtcgatg     420
taccagagtc agttgctggc cagccgaaaa ttctatggag agttcctgga tcgccatatg     480
agtgagctgg ccaaagcgta cagcgccgat atctataagg cgcaaatcgc tatcttgaaa     540
caaacgtctc aagagctgga gaataaagcc cggtcattgg aagcagaagc ccagcgagcc     600
gctgctgagg tggaggcgga ctacaaggcc aggaaggcaa atgtcgagaa aaaagtgcag     660
tccgagcttg accaggctgg gaatgctttg cctcaactga ccaatccaac gccagagcag     720
tggcttgaac gcgctactca actggttacg caggcgatcg ccaataagaa gaaattgcag     780
actgcaaaca atgccttgat tgccaaggca cccaatgcac tggagaaaca aaaggcaacc     840
tacaacgccg atctcctagt ggatgaaatc gccagcctgc aagcacggct ggacaagctg     900
aacgccgaaa cggcaaggcg caaggaaatc gctcgtcaag cggcgatcag ggctgccaat     960
acttatgcca tgccagccaa tggcagcgtt gtcgccaccg ccgcaggccg gggtctgatc    1020
caggtcgcac aaggcgccgc atcccttgct caagcgatct ccgatgcgat tgccgtcctg    1080
ggccgggtcc tggcttcagc cccctcggtg atggccgtgg gctttgccag tctgacctac    1140
tcctcccgga ctgccgagca atggcaggac caaacgcccg atagcgttcg ttacgccctg    1200
ggcatggatg ccgctaaatt ggggcttccc ccaagcgtaa acctgaacgc ggttgcaaaa    1260
gccagcggta ccgtcgatct gccgatgcgc ctgaccaacg aggcacgagg caacacgacg    1320
acccttttcgg tggtcagcac cgatggtgtg agcgttccga agcgttcc ggtccggatg    1380
gcggcctaca atgccacgac aggcctgtac gaggttacgg ttccctctac gaccgcagaa    1440
gcgccgccac tgatcctgac ctggacgccg gcgagtcctc caggaaacca gaaccctccg    1500
agtaccactc cggtcgtacc gaagccggtg ccggtatatg agggagcgac ccttacaccg    1560
gtgaaggcta cccccgaaac ctatcctggg gtgattacac taccggaaga cctgatcatc    1620
ggcttcccgg ccgactcggg gatcaagccg atctatgtga tgttcaggga tccgcgggat    1680
gtacctggtg ctgcgactgg caagggacag cccgtcagcg gtaattggct cggcgccgcc    1740
tctcaaggtg agggggctcc aattccaagc cagattgcgg ataaactacg tggtaagaca    1800
ttcaaaaact ggcgggactt tcgggaacaa ttctggatag ctgtggctaa tgatcctgag    1860
ttaagtaaac agtttaatcc tggtagttta gctgtaatga gagatggagg ggctccttat    1920
gtcagagagt cagaacaggc tggcgggaga ataaagatcg aaatccacca caaggttcga    1980
atagcagatg gaggcggcgt ttacaatatg gggaaccttg ttgcagtaac gccaaaacgt    2040
catatagaaa tccacaaggg agggaagtga                                     2070
```

<210> SEQ ID NO 752
<211> LENGTH: 36
<212> TYPE: PRT
<213> ORGANISM: Lactobacillus plantarum

<400> SEQUENCE: 752

Lys Tyr Tyr Gly Asn Gly Leu Ser Cys Ser Lys Lys Gly Cys Thr Val

```
1               5                   10                  15
Asn Trp Gly Gln Ala Phe Ser Cys Gly Val Asn Arg Val Ala Thr Ala
                20                  25                  30
Gly His Gly Lys
            35

<210> SEQ ID NO 753
<211> LENGTH: 108
<212> TYPE: DNA
<213> ORGANISM: Lactobacillus plantarum

<400> SEQUENCE: 753
aaatattatg gcaacggcct gagctgcagc aaaaaaggct gcaccgtgaa ctggggccag      60
gcgtttagct gcggcgtgaa ccgcgtggcg accgcgggcc atggcaaa                 108

<210> SEQ ID NO 754
<211> LENGTH: 30
<212> TYPE: PRT
<213> ORGANISM: Lactococcus lactis

<400> SEQUENCE: 754

Met Lys Thr Ile Leu Arg Phe Val Ala Gly Tyr Asp Ile Ala Ser His
1               5                   10                  15
Lys Lys Lys Thr Gly Gly Tyr Pro Trp Glu Arg Gly Lys Ala
                20                  25                  30

<210> SEQ ID NO 755
<211> LENGTH: 93
<212> TYPE: DNA
<213> ORGANISM: Lactococcus lactis

<400> SEQUENCE: 755
atgaaaacaa tcctacgttt tgttgctggc tacgatattg ctagtcataa aaagaaaact      60
ggcggctatc catgggaacg tggaaaagct taa                                   93

<210> SEQ ID NO 756
<211> LENGTH: 24
<212> TYPE: PRT
<213> ORGANISM: Lactobacillus acidophilus

<400> SEQUENCE: 756

Gly Asn Pro Lys Val Ala His Cys Ala Ser Gln Ile Gly Arg Ser Thr
1               5                   10                  15
Ala Trp Gly Ala Val Ser Gly Ala
                20

<210> SEQ ID NO 757
<211> LENGTH: 72
<212> TYPE: DNA
<213> ORGANISM: Lactobacillus acidophilus

<400> SEQUENCE: 757
ggcaacccga aagtggcgca ttgcgcgagc cagattggcc gcagcaccgc gtggggcgcg      60
gtgagcggcg cg                                                          72

<210> SEQ ID NO 758
<211> LENGTH: 53
<212> TYPE: PRT
<213> ORGANISM: Lactobacillus salivarius cp400

<400> SEQUENCE: 758
```

```
Met Phe Phe Asn Phe Met Lys Lys Val Asp Val Lys Asn Phe Gly
1               5                   10                  15

Tyr Lys Glu Val Ser Arg Lys Asp Leu Ala Lys Val Asn Gly Gly Lys
            20                  25                  30

Arg Lys Lys His Arg Cys Arg Val Tyr Asn Asn Gly Met Pro Thr Gly
            35                  40                  45

Met Tyr Arg Trp Cys
    50

<210> SEQ ID NO 759
<211> LENGTH: 162
<212> TYPE: DNA
<213> ORGANISM: Lactobacillus salivarius cp400

<400> SEQUENCE: 759
atgtttttta attttatgaa aaaagtagat gtgaagaaga attttggata taaagaagtt        60
tctagaaaag atctagctaa agtaaatggt ggaaagagaa agaaacatcg ttgcagagtt       120
tataataatg gaatgcctac aggaatgtat cgttggtgct aa                          162
```